United States Patent
Bonafoux et al.

(10) Patent No.: US 9,567,339 B2
(45) Date of Patent: Feb. 14, 2017

(54) PRIMARY CARBOXAMIDES AS BTK INHIBITORS

(71) Applicant: AbbVie Inc., North Chicago, IL (US)

(72) Inventors: Dominique Bonafoux, Winthrop, MA (US); Heather M. Davis, Oxford, MA (US); Kristine E. Frank, Grayslake, IL (US); Michael M. Friedman, Brookline, MA (US); J. Martin Herold, Cambridge, MA (US); Michael Z. Hoemann, Shrewsbury, MA (US); Raymond Huntley, Worcester, MA (US); Augustine Osuma, Lindenhurst, IL (US); George Sheppard, Wilmette, IL (US); Gagandeep K. Somal, Ashland, MA (US); Jennifer Van Camp, Lake Forest, IL (US); Stacy A. Van Epps, Ashland, MA (US); Anil Vasudevan, Union Grove, WI (US); Grier A. Wallace, Sterling, MA (US); Lu Wang, Westborough, MA (US); Lu Wang, Northborough, MA (US); Zhi Wang, Libertyville, IL (US); Noel S. Wilson, Kenosha, WI (US); Xiangdong Xu, Buffalo Grove, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/315,504

(22) Filed: Jun. 26, 2014

(65) Prior Publication Data

US 2015/0005279 A1 Jan. 1, 2015

Related U.S. Application Data

(60) Provisional application No. 61/897,577, filed on Oct. 30, 2013, provisional application No. 61/839,729, filed on Jun. 26, 2013.

(51) Int. Cl.

| | | |
|---|---|---|
| *C07D 487/04* | (2006.01) | |
| *C07D 417/12* | (2006.01) | |
| *C07D 471/04* | (2006.01) | |
| *C07D 209/08* | (2006.01) | |
| *C07D 417/14* | (2006.01) | |
| *C07D 401/14* | (2006.01) | |
| *C07D 403/14* | (2006.01) | |
| *C07D 231/56* | (2006.01) | |
| *C07D 401/12* | (2006.01) | |

(52) U.S. Cl.
CPC ........... *C07D 487/04* (2013.01); *C07D 209/08* (2013.01); *C07D 231/56* (2013.01); *C07D 401/12* (2013.01); *C07D 401/14* (2013.01); *C07D 403/14* (2013.01); *C07D 417/12* (2013.01); *C07D 417/14* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 7,087,637 B2 | 8/2006 | Grandel et al. | |
| 7,858,796 B2 * | 12/2010 | Kerns ................. | C07D 401/04 |
| | | | 546/201 |
| 8,338,439 B2 | 12/2012 | Singh et al. | |
| 8,354,406 B2 | 1/2013 | Deng et al. | |
| 8,362,065 B2 | 1/2013 | Liu et al. | |
| 2004/0097485 A1 | 5/2004 | Burkitt et al. | |
| 2008/0269193 A1 | 10/2008 | Huang et al. | |
| 2008/0269200 A1 * | 10/2008 | Baldwin ............. | C07D 209/08 |
| | | | 514/217.08 |
| 2012/0040958 A1 | 2/2012 | Boehm et al. | |
| 2012/0282262 A1 | 11/2012 | Okun et al. | |
| 2013/0096118 A1 | 4/2013 | Liu et al. | |

FOREIGN PATENT DOCUMENTS

| | | | |
|---|---|---|---|
| CN | 101481380 A | 7/2009 | |
| WO | WO-2005/012283 A1 | 2/2005 | |
| WO | WO 2006034317 A2 * | 3/2006 | ........... C07D 401/04 |

(Continued)

OTHER PUBLICATIONS

Michelotti et. al. "Two classes of p38a MAP kinase inhibitors having a common diphenylether core but exhibiting divergent binding modes" 2005, 15, 5274-5279.*
Jiang et. al. "3,5-Disubstituted quinolines as novel c-Jun N-terminal kinase inhibitors." Bioorganic & Medicinal Chemistry Letters 2007, 17, 6378-6382.*
Liu et. al. "Synthesis and SAR of 1,9-dihydro-9-hydroxypyrazolo[3,4-b]quinolin-4-ones as novel, selective c-Jun N-terminal kinase inhibitors" Bioorganic & Medicinal Chemistry Letters 2006, 16, 2590-2594.*
Miyazaki et. al. "Design and effective synthesis of novel templates, 3,7-diphenyl-4-amino-thieno and furo-[3,2-c]pyridines as protein kinase inhibitors and in vitro evaluation targeting angiogenetic kinases" Bioorganic & Medicinal Chemistry Letters 2007, 17, 250-254.*
Mulvihill et. al. "Novel 2-phenylquinolin-7-yl-derived imidazo[1,5-a]pyrazines as potent insulin-like growth factor-I receptor (IGF-IR) inhibitors" Bioorganic & Medicinal Chemistry 2008, 16, 1359-1375.*
Wolff, Manfred E. "Burger's Medicinal Chemistry, 5ed, Part I", John Wiley & Sons, 1995, pp. 975-977.*

(Continued)

*Primary Examiner* — David K O'Dell
(74) *Attorney, Agent, or Firm* — McCarter & English, LLP; Elizabeth A. Hanley; Yu Lu

(57) ABSTRACT

The invention provides compounds of Formula (I)

Formula (I)

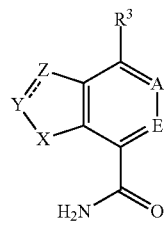

pharmaceutically acceptable salts, pro-drugs, biologically active metabolites, stereoisomers and isomers thereof wherein the variable are defined herein. The compounds of the invention are useful for treating immunological and oncological conditions.

20 Claims, No Drawings

(56) References Cited

FOREIGN PATENT DOCUMENTS

| WO | WO-2006/106326 | A1 | | 10/2006 | |
| WO | WO 2006106326 | A1 | * | 10/2006 | ........... C07D 401/12 |
| WO | WO-2011/090760 | A1 | | 7/2011 | |
| WO | WO-2011/144585 | A1 | | 11/2011 | |
| WO | WO-2012/009649 | A1 | | 1/2012 | |
| WO | WO-2012/142498 | A2 | | 10/2012 | |
| WO | WO-2013/148603 | A1 | | 10/2013 | |

OTHER PUBLICATIONS

Banker, G.S. et al, "Modern Pharmaceutics, 3ed.", Marcel Dekker, New York, 1996, pp. 451 and 596.*

Rautio et. al. "Prodrugs: design and clinical Applications" Nature Reviews Drug Discovery 2008, 7, 255-270.*

Beaumont "Design of Ester Prodrugs to Enhance Oral Absorption of Poorly Permeable Compounds: Challenges to the Discovery Scientist" Current Drug Metabolism, 2003, 4, 461-485.*

Bernard Testa "Predicting drug metabolism: Concepts and challenges" Pure and Applied Chemistry 2004, vol. 76, No. 5, pp. 907-914.*

Henry R. Henze and Charles M. Blair "The Number of Structurally Isomeric Alcohols of the Methanol Series" Journal of the American Chemical Society 1931, 3042.*

Georg Pilz, "Modern multiple sclerosis treatment—what is approved, what is on the horizon" Drug Discovery Today Dec. 2008, vol. 13, Nos. 23/24 1013-1025.*

STN-Chemical database registry # 1253792-04-9 Nov. 19, 2010.*

Online "http://web.archive.org/web/20100328065929/http://www.apacpharma.com/catalogue.html" dated Mar. 28, 2010, accessed May 11, 2015.*

Online "http://web.archive.org/web/20070630171813/http://www.enamine.net/index.php?option=com_content&task=view&id=22&menuid=51& PhPSESSID=64a4f248f69d671a413f487bb62c4d90" dated Jun. 30, 2007, accessed Nov. 9, 2011.*

Regueiro-Ren, Alicia, et al., "Inhibitors of Human Immunodeficiency Virus Type 1 (HIV-1) Attachment. 12. Structure-Activity Relationships Associated with 4-Fluoro-6-azaindole Derivatives Leading to the Indentification of 1-(4-Benzoylpiperazin-1-yl)-2-(4-fluoro-7-[1,2,3]triazol-1-yl-1 H-pyrrolo[2,3- c]pyridin-3-yl)ethane-1,2-dion", Journal of Medicinal Chemistry, 56(4)1656-1669, Feb. 28, 2013.

* cited by examiner

PRIMARY CARBOXAMIDES AS BTK INHIBITORS

RELATED APPLICATIONS

This application claims, under 35 U.S.C. §119(e), the benefit of the filing date of U.S. Provisional Application No. 61/839,729, filed on Jun. 26, 2013, and that of U.S. Provisional Application No. 61/897,577, filed on Oct. 30, 2013, the entire content of each of which is incorporated herein by reference.

BACKGROUND OF THE INVENTION

The protein kinases represent a large family of proteins that play a central role in the regulation of a wide variety of cellular processes and maintenance of cellular function. A partial, non-limiting, list of these kinases include: non-receptor tyrosine kinases such as the Tec family (BTK, ITK, Tec, ETK/BMX & RLK/TXK), Janus kinase family (Jak1, Jak2, Jak3 and Tyk2); the fusion kinases, such as BCR-Abl, focal adhesion kinase (FAK), Fes, Lck and Syk; receptor tyrosine kinases such as epidermal growth factor receptor (EGFR), the platelet-derived growth factor receptor kinase (PDGF-R), the receptor kinase for stem cell factor, c-kit, the hepatocyte growth factor receptor, c-Met, and the fibroblast growth factor receptor, FGFR3; and serine/threonine kinases such as b-RAF, mitogen-activated protein kinases (e.g., MKK6) and SAPK2β. Aberrant kinase activity has been observed in many disease states including benign and malignant proliferative disorders as well as diseases resulting from inappropriate activation of the immune and nervous systems. The novel compounds of this invention inhibit the activity of one or more protein kinases and are, therefore, expected to be useful in the treatment of kinase-mediated diseases.

Bruton's tyrosine kinase (BTK) is a non-receptor tyrosine kinase with a key role in immunoreceptor signaling (BCR, FcεR, FcγR, DAP12, Dectin-1, GPVI, etc.) in a host of hematopoietic cells including B cells, platelets, mast cells, basophils, eosinophils, macrophages and neutrophils as well as osteoclasts involved in bone destruction (for reviews, see Brunner et al., 2005 *Histol. Histopathol.*, 20:945, Mohamed et al., 2009 *Immunol. Rev.*, 228:58). Mutations in BTK are known to lead to X-linked agammaglobulinemia (XLA) in humans and X-linked immunodeficiency (Xid) in mice, which are characterized by limited B-cell production & reduced antibody titers (Lindvall et al., 2005 *Immunol. Rev.*, 203:200). The combined action of BTK in multiple cell types makes it an attractive target for autoimmune disease. BTK is related with sequence homology to other Tec family kinases (ITK, Tec, ETK/BMX & RLK/TXK).

In B-lymphocytes, BTK is required for B-cell development and for $Ca^{2+}$ mobilization following of B-cell receptor (BCR) engagement (Khan et al., 1995 *Immunity* 3:283; Genevier et al., 1997 *Clin. Exp. Immun.*, 110:286) where it is believed to downstream of Src family kinases (such as Lyn), Syk & PI3K. BTK has been shown to be important for both thymus-dependent and thymus-independent type 2 responses to antigens (Khan et al., *Immunity* 1995, 3:283). In mast cells, studies using BTK mouse knock-outs (Hata et al., 1998 *J. Exp. Med.*, 187:1235; Schmidt et al., 2009 *Eur. J. Immun.*, 39:3228) indicate a role for BTK in FcεRI induced signaling, histamine release & production of cytokines such as TNF, IL-2, & IL-4. In platelets, BTK is important for signaling through the glycoprotein VI (GPVI) receptor that responds to collagen and has been shown to promote platelet aggregation and contribute to cytokine production from fibroblast-like synoviocytes (Hsu et al., 2013 *Immun. Letters*, 150:97). In monocytes and macrophages, the action of BTK in invoked in FcγRI induced signaling and may also have role in Toll-Like Receptor-induced cytokine responses including TLR2, TLR4, TLR8 & TLR9 (Horwood et al., 2003 *J. Exp. Med.*, 197:1603; Horwood et al., 2006 *J. Immunol.*, 176:3635; Perez de Diego et al., 2006 *Allerg. Clin. Imm.*, 117:1462; Doyle et al., 2007 *J. Biol. Chem.*, 282:36959, Hasan et al., 2007 *Immunology*, 123:239; Sochorava et al., 2007 *Blood*, 109:2553; Lee et al., 2008, *J. Biol. Chem.*, 283:11189).

Therefore, inhibition of BTK is expected to intervene at several critical junctions of the inflammatory reactions resulting in an effective suppression of autoimmune response. As such diseases involving B-cell receptor activation, antibody-Fc receptor interactions & GPVI receptor signaling may be modulated by treatment with BTK inhibitors. BTK inhibition is likely to act on both the initiation of autoimmune disease by blocking BCR signaling and the effector phase by abrogation of FcR signaling on macrophages, neutrophils, basophils, and mast cells. Furthermore, blocking BTK would provide additional benefit via inhibition of osteoclast maturation and therefore attenuate the bone erosions & overall joint destruction associated with rheumatoid arthritis Inhibiting BTK may be useful in treating a host of inflammatory and allergic diseases—for example (but not limited to), rheumatoid arthritis (RA), systemic lupus erythematosus (SLE), multiple sclerosis (MS) and type I hypersensitivity reactions such as allergic rhinitis, allergic conjunctivitis, atopic dermatitis, allergic asthma and systemic anaphylaxis. For a review on targeting BTK as a treatment for inflammatory disorders and autoimmunity as well as leukemias and lymphomas, see Uckun & Qazi, 2010 *Expert Opin. Ther. Pat.*, 20:1457. Because BTK is highly expressed in cancers of the hematopoietic system & BTK-dependent signaling in believed to be disregulated there, BTK inhibitors are expected to be useful treatments for B-cell lymphomas/leukemias & other oncologic disease—for example (but not limited to) acute lymphoblastic leukemia (ALL), chronic lymphocytic leukemia (CLL), non-Hodgkin's lymphoma (NHL), small lymphocytic lymphoma (SLL), and acute myeloid leukemia (for review, see Buggy & Elias 2012 *Int. Rev. Immunol.* 31:119). Taken together, BTK inhibitors provide a strong method to treat a host of inflammatory diseases and immunological disorders as well as hematologic cancers.

SUMMARY OF THE INVENTION

In a first embodiment the invention provides a compound of Formula (I):

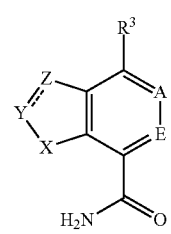

Formula (I)

or a pharmaceutically acceptable salt, pro-drug, biologically active metabolite, isomer, or stereoisomer thereof, wherein:

X is $NR^2$ or S;

Y is N or $CR^1$, and Z is N or $CR^1$; or, Y is $CR^1R^2$ and Z is $CR^1R^2$;

A is N or $CR^4$;

E is N or $CR^5$;

$R^1$ is independently H, deuterium, CN, halogen, $CF_3$, $NR^cR^c$, —$N(R^a)C(O)R^b$, optionally substituted ($C_1$-$C_6$)alkyl, optionally substituted ($C_2$-$C_6$)alkenyl, optionally substituted aryl, optionally substituted ($C_3$-$C_6$)cycloalkyl, optionally substituted ($C_3$-$C_6$)cycloalkenyl, optionally substituted heteroaryl, or optionally substituted saturated or partially saturated heterocyclyl;

$R^2$ is independently H, deuterium, or optionally substituted ($C_1$-$C_3$)alkyl;

$R^3$ is halogen, —$N(R^a)_2$, optionally substituted aryl, optionally substituted ($C_3$-$C_7$)cycloalkyl, optionally substituted saturated or partially saturated heterocyclyl, or optionally substituted heteroaryl; or $R^3$ is —$R^{301}$-L-$R^{302}$ wherein
  $R^{301}$ is a bond, —O—, —$OCH_2$—, —$NR^d$—, or optionally substituted ($C_1$-$C_3$)alkylene, and
  L is optionally substituted phenyl, optionally substituted ($C_3$-$C_6$)cycloalkyl, optionally substituted heteroaryl or a saturated or partially saturated heterocyclyl containing one or more heteroatoms, at least one of which is nitrogen; or
  L is -$L^1$-$L^2$ wherein $L^1$ is attached to $R^{301}$ and
    $L^1$ is optionally substituted phenyl, optionally substituted heteroaryl or optionally substituted saturated or partially saturated carbocycle or a saturated or partially saturated heterocyclyl; and
    $L^2$ is a bond, $CH_2$, $NR^d$, $CH_2N(H)$, $S(O)_2N(H)$, or —O—;
  $R^{302}$ is CN, —$CH_2CN$, optionally substituted —C(=O)$R^{302a}$, $(CH_2)_n$— optionally substituted saturated or partly saturated heterocyclyl or optionally substituted —$S(O)_2(C_2)$alkenyl;
  wherein $R^{302a}$ is optionally substituted ($C_1$-$C_4$)alkyl, optionally substituted ($C_2$-$C_4$)alkenyl, ($C_2$-$C_4$)alkynyl, —C(O)—($C_1$-$C_4$)alkyl, optionally substituted saturated or partially unsaturated ($C_3$-$C_6$)cycloalkyl, optionally substituted aryl, optionally substituted heteroaryl, —N(H)— optionally substituted heteroaryl or $(CH_2)_n$— optionally substituted unsaturated or partly saturated heterocyclyl;

$R^4$ is H, deuterium, CN, optionally substituted ($C_1$-$C_3$)alkyl, optionally substituted ($C_3$-$C_6$) cycloalkyl or optionally substituted saturated or partially saturated heterocyclyl, or optionally substituted heteroaryl;
  wherein the optionally substituted saturated or partially saturated heterocyclyl; and optionally substituted heteroaryl contain at least one nitrogen atom; or $R^3$ and $R^4$, together with the carbon atoms to which they are attached, form an optionally substituted, saturated, unsaturated or partially unsaturated 5 or 6 membered carbocyclic ring or an optionally substituted, saturated, or partially unsaturated 5 or 6 membered heterocyclic ring containing one or more heteroatoms selected from N, S and O;

$R^5$ is H, deuterium, halogen, or optionally substituted ($C_1$-$C_3$)alkyl;

$R^a$ is independently selected from H, —C(O)— optionally substituted ($C_2$-$C_6$)alkenyl, optionally substituted ($C_1$-$C_6$)alkyl, —$(CH_2)_n$— optionally substituted ($C_3$-$C_6$)cycloalkyl, —$(CH_2)_n$— optionally substituted heterocyclyl, or —$(CH_2)_n$— optionally substituted heteroaryl;

$R^b$ is H, optionally substituted ($C_1$-$C_6$)alkyl, optionally substituted ($C_2$-$C_6$)alkenyl, optionally substituted ($C_2$-$C_6$)alkynyl, —$CH_2$—O— optionally substituted aryl, or —$CH_2$—O— optionally substituted heteroaryl;

$R^c$ is independently H, optionally substituted ($C_1$-$C_6$) alkyl, optionally substituted ($C_3$-$C_6$)cycloalkyl, optionally substituted saturated or partially saturated heterocyclyl, optionally substituted aryl or optionally substituted heteroaryl;

$R^d$ is H, optionally substituted heterocyclyl, —$(CH_2)$— optionally substituted ($C_3$-$C_6$)cycloalkyl, —$(CH_2)$— optionally substituted heteroaryl or optionally substituted ($C_1$-$C_3$)alkyl;

$R^f$ is optionally substituted ($C_1$-$C_3$)alkyl, optionally substituted ($C_2$-$C_4$)alkenyl or optionally substituted ($C_2$-$C_4$)alkynyl; and n is independently 0 or 1.

In a second embodiment the invention provides a compound according to the first embodiment, wherein Y is $CR^1$ and $R^1$ of Y is H, optionally substituted ethenyl, optionally substituted ethyl, optionally substituted methyl, optionally substituted 2,3-dihydrobenzofuranyl, optionally substituted 1,4-dioxanyl, optionally substituted 3,4-dihydro-2H-benzo[b][1,4]oxazinyl, optionally substituted 6,7-dihydro-4H-pyrazolo[5,1-c][1,4]oxazinyl, optionally substituted chromanyl, optionally substituted cyclohexenyl, optionally substituted cyclopropyl, optionally substituted tetrahydrofuranyl, optionally substituted isochromanyl, optionally substituted 1,2,3,4-tetrahydro-isoquinolinyl, optionally substituted isoxazolyl, optionally substituted morpholinyl, optionally substituted oxetanyl, optionally substituted phenyl, optionally substituted piperidinyl, optionally substituted piperazinyl, optionally substituted 3,6-dihydro-2H-pyranyl, optionally substituted pyrano[4,3-b]pyridinyl, optionally substituted pyrazolyl, optionally substituted pyridinyl, optionally substituted 3H-pyridin-1-one, optionally substituted 1,2,3,6-tetrahydropyridinyl, optionally substituted pyrimidinyl, optionally substituted pyrrolidinyl, optionally substituted 2,5-dihydropyrrolyl, optionally substituted tetrahydropyranyl or optionally substituted tetrahydro-2H-thiopyranyl.

In a third embodiment the invention provides a compound according to any of the foregoing embodiments wherein $R^1$ is H or $R^1$ is optionally substituted by one or more substituents independently selected from the group consisting of CN, OH, =O, halogen, ($C_1$-$C_4$)alkyl, ($C_1$-$C_4$)alkoxy, —$CH_2CH_2OH$, —$CH_2C(CH_3)_2OH$, —$CH_2CH(OH)CH_2OH$, —CH=$CH_2$, —$CH_2NH_2$, —$CH_2N(H)C(O)R^e$, —C(O)($C_1$-$C_4$)alkyl, —C(O)($C_1$-$C_4$)alkoxy, —C(O)$NH_2$, —C(O)N($CH_3$)$_2$, —C(O)— optionally substituted heterocyclyl, —N(H)C(O)$CH_3$, N($CH_3$)$_2$, —$S(O)_2$($C_1$-$C_4$)alkyl, —$S(O)_2$-pyrrolidinyl, ($C_1$-$C_4$)alkoxy, —$CH_2$-morpholinyl, —$CH_2CH_2$-morpholinyl, morpholinyl, tetrahydropyranyl;
  wherein $R^e$ is ($C_1$-$C_3$)alkyl, —$CH_2Cl$, —C≡CH, —C≡$CCH_3$, —CH=$CH_2$, —CH=$CHCH_3$, —C(=$CH_2$)$CH_3$, —$CH_2CN$, —$CH_2CH_2N(CH_3)_2$, —$CH_2CH_2$-piperidinyl, —$CH_2O$— optionally substituted phenyl.

In a fourth embodiment the invention provides a compound according to any of the foregoing embodiments wherein $R^3$ is —N(H)C(O)CH=$CH_2$, optionally substituted isoxazolyl, optionally substituted phenyl, optionally substituted pyrazolyl, optionally substituted pyridinyl, optionally substituted pyrimidinyl, optionally substituted thiazolyl, or optionally substituted thienyl.

In a fifth embodiment the invention provides a compound according to any of the foregoing embodiments according to claim 4, wherein $R^3$ is optionally substituted by one or more substituents independently selected from —NH$_2$, —NHCH$_3$, (C$_1$-C$_4$)alkyl and —C(O)(C$_2$-C$_4$)alkenyl.

In a sixth embodiment the invention provides a compound according to any of the foregoing embodiments wherein X is NR$^2$ and R$^2$ is H.

In a seventh embodiment the invention provides a compound according to any of the foregoing embodiments wherein Y is CR$^1$ and R$^1$ of Y is H, optionally substituted phenyl, optionally substituted piperazinyl, optionally substituted pyrazolyl, or optionally substituted 1,2,3,6-tetrahydropyridinyl.

In an eighth embodiment the invention provides a compound according to any of the foregoing embodiments wherein Y is CR$^1$ and R$^1$ of Y is optionally substituted by one or more substituents independently selected from halogen, (C$_1$-C$_4$)alkyl, —C(O)(C$_1$-C$_4$)alkyl, and —S(O)$_2$(C$_1$-C$_4$)alkyl.

In a ninth embodiment the invention provides a compound according to any of the foregoing embodiments wherein
  Z is N or Z is CR$^1$ and R$^1$ of Z is H; and
  A is CR$^4$ and R$^4$ is H or azetidinyl substituted with C(O)CH=CH$_2$.

In a tenth embodiment the invention provides a compound according to any of the foregoing embodiments wherein the compound is
4-(3-amino-2-methylphenyl)-2-(1-(methylsulfonyl)-1,2,3,6-tetrahydropyridin-4-yl)-1H-indole-7-carboxamide;
2-(4-fluorophenyl)-4-(pyridin-3-yl)-1H-indole-7-carboxamide;
4-(pyridin-3-yl)-2-p-tolyl-1H-indole-7-carboxamide;
2-(4-fluorophenyl)-4-(pyridin-4-yl)-1H-indole-7-carboxamide;
2-(4-fluorophenyl)-4-(1H-pyrazol-5-yl)-1H-indole-7-carboxamide;
4-(3,5-dimethylisoxazol-4-yl)-2-p-tolyl-1H-indole-7-carboxamide;
2-(1-acetylpiperidin-4-yl)-4-(3-amino-2-methylphenyl)-1H-indole-7-carboxamide;
4-(pyridin-4-yl)-2-p-tolyl-1H-indole-7-carboxamide;
4-(thiophen-2-yl)-2-p-tolyl-1H-indole-7-carboxamide;
4-(2-aminophenyl)-1H-indole-7-carboxamide;
4-(3-amino-2-methylphenyl)-1H-indole-7-carboxamide;
4-(5-aminopyridin-3-yl)-1H-indole-7-carboxamide;
4-(2-aminopyridin-4-yl)-1H-indole-7-carboxamide;
4-(2-aminoethylamino)-2-(4-fluorophenyl)-1H-indole-7-carboxamide;
4-(2-aminoethylamino)-2-p-tolyl-1H-indole-7-carboxamide;
4-(pyrimidin-5-yl)-2-p-tolyl-1H-indole-7-carboxamide;
4-(1H-pyrazol-4-yl)-2-p-tolyl-1H-indole-7-carboxamide;
4-(1H-pyrazol-5-yl)-2-p-tolyl-1H-indole-7-carboxamide;
2-(4-fluorophenyl)-4-(pyrimidin-5-yl)-1H-indole-7-carboxamide;
4-(thiazol-2-yl)-2-p-tolyl-1H-indole-7-carboxamide;
4-(pyridin-2-yl)-2-p-tolyl-1H-indole-7-carboxamide;
4-(thiophen-3-yl)-2-p-tolyl-1H-indole-7-carboxamide;
4-(1-methyl-1H-pyrazol-4-yl)-2-p-tolyl-1H-indole-7-carboxamide;
4-(1H-pyrazol-3-yl)-2-p-tolyl-1H-indole-7-carboxamide;
4-(2-aminophenyl)-2-(1-(methylsulfonyl)-1,2,3,6-tetrahydropyridin-4-yl)-1H-indole-7-carboxamide;
2-(1-(methylsulfonyl)-1,2,3,6-tetrahydropyridin-4-yl)-4-phenyl-1H-indole-7-carboxamide;
4-(3-amino-2-methylphenyl)-2-(4,4-difluorocyclohex-1-enyl)1H-indole-7-carboxamide;
4-(3-amino-2-methylphenyl)-1H-pyrrolo[2,3-c]pyridine-7-carboxamide;
4-(1-acryloylpiperidin-3-yl)-1H-indole-7-carboxamide;
4-(1-acryloylpiperidin 3-yl)-2-(1-methyl-1H-pyrazol-4-yl)-1H-indole-7-carboxamide;
4-(2-aminoethylamino)-2-p-tolyl-1H-indole-7-carboxamide;
4-((1R,2R)-2-aminocyclohexylamino)-2-(4-fluorophenyl)-1H-indole-7-carboxamide*;
4-(1-methyl-1H-pyrazol-5-ylamino)-2-p-tolyl-1H-indole-7-carboxamide;
4-iodo-2-(pyridin-3-yl)-1H-indole-7-carboxamide;
4-(3-amino-2-methylphenyl)-2-(1-(methylsulfonyl)-1,2,3,6-tetrahydropyridin-4-yl)-1H-indole-7-carboxamide;
4-(3,5-dimethylisoxazol-4-yl)-2-(4-fluorophenyl)-1H-indole-7-carboxamide;
4-(2-aminophenyl)-2-(1-(methylsulfonyl)-1,2,3,6-tetrahydropyridin-4-yl)-1H-indole-7-carboxamide; or
2-(1-Acetylpiperidin-4-yl)-4-(3-amino-2-methylphenyl)-1H-indole-7-carboxamide.

In an eleventh embodiment the invention provides a compound according to any of the first through third embodiments wherein $R^3$ is —$R^{301}$-L-$R^{302}$, and $R^{301}$ is a bond, N(H), N(CH$_3$), CH$_2$, C(H)(optionally substituted (C$_1$-C$_3$)alkyl), O, or OCH$_2$.

In an twelfth embodiment the invention provides a compound according to the any of the first through third or eleventh embodiments wherein
  L is optionally substituted azetidinyl, optionally substituted cyclopentyl, optionally substituted 3,6-diazabicyclo[3.2.0]heptanyl, optionally substituted 1,4-dioxanyl, optionally substituted morpholinyl, optionally substituted [1,4]oxepanyl, optionally substituted phenyl, optionally substituted piperidinyl, or optionally substituted pyrrolidinyl; or
  L is L$^1$-L$^2$ wherein
    L$^1$ is optionally substituted cyclohexyl, optionally substituted cyclopentyl optionally substituted phenyl, optionally substituted piperidinyl, optionally substituted pyridinyl;
    L$^2$ is N(H), N(CH$_3$), N(CH$_2$CH$_2$OH), N(CH$_2$CH(CH$_3$)$_2$), N(oxetanyl), N(CH$_2$-cyclopentyl), N(CH$_2$-thiazolyl), O, S(O)$_2$N(H), or CH$_2$N(H).

In an thirteenth embodiment the invention provides a compound according to any of the first through third and eleventh and twelfth embodiments wherein L or L$^1$ is optionally substituted with one or more substituents independently selected from halogen, CN, OH, (C$_1$-C$_4$)alkoxy, (C$_1$-C$_4$)alkyl, —CH$_2$OH, —N(H)CH$_2$-heteroaryl, benzyloxy, and —OCH$_2$-heteroaryl.

In an fourteenth embodiment the invention provides a compound according to any of the first through third and eleventh through thirteenth embodiments wherein $R^{302}$ is —C(O)CH$_3$, —C(O)C(O)CH$_3$, —C(O)CF$_2$(Cl), —CH(CH$_3$)$_2$, —CH$_2$Cl, —CH$_2$CN, —C(O)CH$_2$CN, —C(O)CH$_2$CH$_3$, —C(O)CH$_2$F, —C(O)CH(CH$_3$)$_2$, —C(O)—CH$_2$CH(CH$_3$)$_2$, —C(O)CH(CH$_3$)(Cl), —C(O)CH$_2$CH(CH$_3$)CH$_3$, —C(O)CH(Cl)CH$_2$CH$_3$, —CH$_2$CH$_2$OH, —C(O)CH$_2$N(CH$_3$)$_2$, —C(O)CH=CH$_2$, —C(O)C≡CH, —C(O)CH=CHCl, —C(O)CH=CHCH$_3$, —C(O)C(=CH$_2$)CH$_3$, —C(O)C(CH$_2$CH$_3$)=CH$_2$, —C(O)CH=CHCH(CH$_3$)$_2$, —C(O)CH=CHC(O)OH, —C(O)

CH=CHC(O)N(H)CH$_2$CH$_3$, —C(O)CH=CHCH$_2$N(CH$_3$)$_2$, —C(O)CH=CHC(O)OCH$_3$, —C(O)CH=CHC(O)OCH$_2$CH$_3$, —C(O)CH=CHC(O)N(H)CH$_3$, —C(O)CH=CHC(O)CH$_2$CH$_2$OCH$_3$, —C(O)CH=CHC(O)N(CH$_3$)$_2$, —C(O)CH=CHC(O)N(H)CH$_2$CH$_3$, —C(O)CH=CHC(O)N(H)CH$_2$CH$_2$OCH$_3$, —C(O)CH=CHCH$_2$N(H)CH$_2$CH$_2$OCH$_3$, —C(O)C(CN)=C(OH)(CH$_3$), —C(O)CH=CH— optionally substituted pyrazolyl —C(O)CH=CHCH$_2$N(H)— optionally substituted cyclopropyl, —C(O)CH=CHCH$_2$N(H)CH$_2$— optionally substituted tetrahydrofuranyl, —C(O)CH=CHC(O)NH$_2$, —C(O)CH=CHC(O)N(H)— optionally substituted cyclopropyl, —C(O)C(CH$_3$)=CHCH$_3$, —C(O)C(CH$_3$)=CHCH$_2$CH$_3$, —C(O)C(=CH$_2$)CH$_2$N(CH$_3$)$_2$, —C(O)C(=CH$_2$)CH$_2$NH$_2$, —C(O)C(=CH$_2$)CH$_2$N(H)(CH$_3$), —C(O)C(=CH$_2$)CH$_3$, —C(O)C(=CH$_2$)CH$_2$— optionally substituted morpholinyl, —C(O)C(=CH$_2$)— optionally substituted phenyl, —CH$_2$— optionally substituted benzo[d]isothiazolyl, —C(O)—CH$_2$—O— optionally substituted phenyl, —CH$_2$— optionally substituted thiazolyl, —CH$_2$CH$_2$— optionally substituted morpholinyl, —C(O)CH$_2$O— optionally substituted phenyl, —C(O)CH$_2$CH$_2$— optionally substituted piperazinyl, —C(O)CH$_2$CH$_2$— optionally substituted piperidinyl, —C(O)CH$_2$O— optionally substituted pyridinyl, —C(O)CH$_2$CH$_2$ optionally substituted pyrrolidinyl, —C(O)CH=CH optionally substituted cyclopropyl, —C(O)CH=CHCH$_2$— optionally substituted morpholinyl, —C(O)CH=CHCH$_2$— optionally substituted piperidinyl, —C(O)CH=CH— optionally substituted pyrazolyl, —C(O)CH=CH— optionally substituted pyridinyl, —C(O)CH=CH— optionally substituted thiazolyl, —C(O)— optionally substituted cyclohexenyl, —C(=O)— optionally substituted cyclohexyl, —C(O)— optionally substituted cyclopentenyl, —C(O)-cyclopentyl, optionally substituted imidazo[1,2-c]pyrazinyl, optionally substituted tetrahydroimidazo[1,2-c]pyrazinyl, optionally substituted dihydroisoindolyl, optionally substituted 1,2,3,4-tetrahydro-isoquinolinyl, optionally substituted isoquinolinyl, —C(O)— optionally substituted isoxazolyl, —C(O)— optionally substituted oxazolyl, optionally substituted oxetanyl, —C(=O)— optionally substituted phenyl, optionally substituted piperidinyl, —C(O)— optionally substituted piperidinyl, optionally substituted pyrazolyl, —C(O)CH$_2$O— optionally substituted pyridazinyl, —C(O)— optionally substituted pyridinyl, optionally substituted pyrimidinyl, optionally substituted quinazolinyl, optionally substituted dihydroquinolinyl, optionally substituted —C(O)-tetrahydrobenzo[b]thiophenyl, —C(O)— optionally substituted tetrahydropyranyl, —C(O)— optionally substituted tetrahydropyridinyl, —C(O)-thiazolyl, —C(O)N(H)-thiazolyl, —C(O)NHCH$_2$CN, or —S(O)$_2$CH=CH$_2$.

In a fifteenth embodiment the invention provides a compound according to any of the first through third or thirteenth through fourteenth embodiments wherein X is NR$^2$ and R$^2$ is H.

In a sixteenth embodiment the invention provides a compound according to any of the first through third or thirteenth through fifteenth embodiments wherein Y is CR$^1$ and R$^1$ of Y is optionally substituted with one or more substituents independently selected from halogen, CN, =O, (C$_1$-C$_4$)alkyl, (C$_2$-C$_4$)alkenyl, —CH$_2$NH$_2$, —CH$_2$CH$_2$OH, —CH$_2$CH(OH)CH$_2$CH$_3$, —CH$_2$CH(OH)CH$_2$OH, —CH$_2$CH$_2$OCH$_2$CH$_3$, —CH$_2$C(OH)(CH$_3$)$_2$, —CH$_2$NHC(O)(C$_1$-C$_4$)alkyl, —CH$_2$NHC(O)CH$_2$Cl, —CH$_2$NHC(O)CH$_2$CN, —CH$_2$NHC(O)CH$_2$CH$_2$N(CH$_3$)$_2$, —CH$_2$NHC(O)C(=CH$_2$)CH$_3$, —CH$_2$NHC(O)(C$_2$-C$_4$)alkynyl, —CH$_2$NHC(O)CH$_2$CH$_2$-piperidinyl, —(C$_1$-C$_4$)alkyl-morpholinyl, —CH$_2$NHC(O)CH$_2$O-phenyl wherein the phenyl is optionally substituted with halogen, (C$_1$-C$_4$)alkoxy, —C(O)(C$_1$-C$_4$)alkyl, —C(O)(C$_1$-C$_4$)alkoxy, —C(O)N(H)$_2$, —C(O)N(CH$_3$)$_2$, —C(O)-morpholinyl, —C(O)-pyrrolidinyl, —N(CH$_3$)$_2$, —NHC(O)(C$_1$-C$_4$)alkyl, —NHC(O)(C$_2$-C$_4$)alkenyl, —NHC(O)CH$_2$CN, —S(O)$_2$(C$_1$-C$_4$)alkyl, —S(O)$_2$-pyrrolidinyl, morpholinyl, tetrahydropyranyl, or 4-methylpiperazinecarbonyl.

In a seventeenth embodiment the invention provides a compound according to any of the first through third or thirteenth through sixteenth embodiments wherein Z is CR$^1$ and R$^1$ of Z is H, (C$_1$-C$_4$)alkyl, —NHC(O)CH$_2$Cl, —NHC(O)CH$_2$CN, —NHC(O)(C$_2$-C$_4$)alkenyl, —NHC(O)(C$_2$-C$_4$)alkynyl, —NHC(O)C(=CH$_2$)CH$_3$, —NHC(O)CH$_2$-phenyl wherein the phenyl is optionally substituted with halogen, or pyrazolyl substituted with CH$_3$.

In a eighteenth embodiment the invention provides a compound according to any of the first through third or thirteenth through seventeenth embodiments wherein R$^{302}$ is optionally substituted with one or more substituents independently selected from halogen, CF$_3$, OCF$_3$, =O, CHF$_2$, CN, C(O)OH, OH, (C$_1$-C$_4$)alkyl, (C$_1$-C$_4$)alkoxy, (C$_3$-C$_6$)cycloalkyl, —(C$_1$-C$_4$)alkylCN, —(C$_1$-C$_4$)alkylC(O)NH$_2$, —C(O)NH$_2$, —C(O)N(H)(C$_1$-C$_4$)alkyl, —C(O)N(C$_1$-C$_4$)alkyl)$_2$, —C(O)N(H)cyclopropyl, —C(O)(C$_1$-C$_4$)alkoxy, NH$_2$, N(H)CH$_3$, N(CH$_3$)$_2$, or optionally substituted benzyl.

In a nineteenth embodiment the invention provides a compound according to any of the first through third or thirteenth through eighteenth embodiments wherein X is NR$^2$ wherein R$^2$ is H;

Y is CR$^1$ wherein R$^1$ is H, CH$_3$, substituted pyrazolyl, 6,7-dihydro-4H-pyrazolo[5,1-c][1,4]oxazinyl or tetrahydrofuranyl;

Z is CR$^1$ wherein R$^1$ is H;

E is CR$^5$ wherein R$^5$ is H;

R$^3$ is —R$^{301}$-L-R$^{302}$ wherein

R$^{301}$ is a bond, —O—, —N(H)—, —N(CH$_3$)— or —C(H)(CH$_3$)—;

L is azetidinyl, 3,6-diazabicyclo[3.2.0]heptanyl, morpholinyl, [1,4]oxepanyl, piperidinyl, or pyrrolidinyl;
wherein the azetidinyl is optionally substituted with CH$_3$; and
wherein the piperidinyl is optionally substituted with —CH$_2$OH; and R$^{302}$ is —C(O)CH=CH$_2$ or —C(O)C=CH.

In a twentieth embodiment the invention provides a compound according to any of the first through third or thirteenth through nineteenth embodiments wherein the compound is:

4-((1-acryloylazetidin-3-yl)(methyl)amino)-1H-indole-7-carboxamide;

4-(5-acetylthiophen-2-yl)-2-p-tolyl-1H-indole-7-carboxamide;

4-(1-(4-methoxybenzyl)-1H-pyrazol-5-ylamino)-2-p-tolyl-1H-indole-7-carboxamide;

4-(3-(6-fluoro-4-oxoquinazolin-3(4H)-yl)-2-methylphenyl)-2-(pyridin-3-yl)-1H-indole-7-carboxamide;

4-(3-(6-fluoro-4-oxoquinazolin-3(4H)-yl)-2-methylphenyl)-2-(pyridin-3-yl)-1H-indole-7-carboxamide;

4-(2-methyl-3-(4-oxoquinazolin-3(4H)-yl)phenyl)-2-(pyridin-3-yl)-1H-indole-7-carboxamide;

4-(2-methyl-3-(4,5,6,7-tetrahydrobenzo[b]thiophene-2-carboxamido)phenyl)-2-(pyridin-3-yl)-1H-indole-7-carboxamide;

4-(2-methyl-3-(1-oxoisoindolin-2-yl)phenyl)-2-(pyridin-3-yl)-1H-indole-7-carboxamide;

4-(2-methyl-3-(6-methyl-1-oxoisoindolin-2-yl)phenyl)-2-(pyridin-3-yl)-1H-indole-7-carboxamide;

4-(3-(6-fluoro-1-oxoisoindolin-2-yl)-2-methylphenyl)-2-(pyridin-3-yl)-1H-indole-7-carboxamide;
4-(3-(6-fluoro-1-oxoisoindolin-2-yl)-2-methylphenyl)-2-(4-fluorophenyl)-1H-indole-7-carboxamide;
2-(4-fluorophenyl)-4-(2-methyl-3-(4,5,6,7-tetrahydrobenzo[b]thiophene-2-carboxamido)phenyl)-1H-indole-7-carboxamide;
N-(3-(7-carbamoyl-2-(pyridin-3-yl)-1H-indol-4-yl)-4-methylphenyl)thiazole-2-carboxamide 2,2,2-trifluoroacetate;
N-(3-(7-carbamoyl-2-(pyridin-3-yl)-1H-indol-4-yl)-2-methylphenyl)thiazole-2-carboxamide;
(R)-4-(3-(4-oxoquinazolin-3(4H)-yl)piperidin-1-yl)-1H-indole-7-carboxamide*;
(R)-2-(4-fluorophenyl)-4-(3-(4-oxoquinazolin-3(4H)-yl)piperidin-1-yl)-1H-indole-7-carboxamide*;
(R)-4-(3-(4-oxoquinazolin-3(4H)-yl)piperidin-1-yl)-2-(pyridin-3-yl)-1H-indole-7-carboxamide*;
(R)-2-(1-methyl-1H-pyrazol-4-yl)-4-(3-(4-oxoquinazolin-3(4H)-yl)piperidin-1-yl)-1H-indole-7-carboxamide*;
(R)-4-(3-(6-fluoro-4-oxoquinazolin-3(4H)-yl)piperidin-1-yl)-2-(4-fluorophenyl)-1H-indole-7-carboxamide*;
2-(1-methyl-1H-pyrazol-4-yl)-4-(2-methyl-3-(4-oxoquinazolin-3(4H)-yl)phenyl)-1H-indole-7-carboxamide;
4-(2-methyl-3-(4-oxoquinazolin-3(4H)-yl)phenyl)-1H-indole-7-carboxamide;
2-(1-acetyl-1,2,3,6-tetrahydropyridin-4-yl)-4-(2-methyl-3-(4-oxoquinazolin-3(4H)-yl)phenyl)-1H-indole-7-carboxamide;
(R)-4-(3-(4-tert-butylbenzamido)piperidin-1-yl)-2-(pyridin-3-yl)-1H-indole-7-carboxamide*;
(R)-4-(3-(4-tert-butylbenzamido)piperidin-1-yl)-1H-indole-7-carboxamide*;
(R)—N-(1-(7-carbamoyl-1H-indol-4-yl)piperidin-3-yl)-2-methyloxazole-4-carboxamide*;
(R)-4-(3-(3-thiazol-2-ylureido)piperidin-1-yl)-1H-indole-7-carboxamide*;
4-(3-(4-tert-butylbenzamido)-2-methylphenyl)-1H-indole-7-carboxamide;
4-(3-(7-cyclopropyl-5-fluoro-4-oxoquinazolin-3(4H)-yl)piperidin-1-yl)-1H-indole-7-carboxamide;
(R)-4-(3-(4-tert-butylbenzamido)piperidin-1-yl)-2-(1-methyl-1H-pyrazol-4-yl)-1H-indole-7-carboxamide*;
(R)-4-(3-(4-methoxybenzamido)piperidin-1-yl)-2-(1-methyl-1H-pyrazol-4-yl)-1H-indole-7-carboxamide*;
(R)-5-tert-butyl-N-(1-(7-carbamoyl-1H-indol-4-yl)piperidin-3-yl)isoxazole-3-carboxamide*;
(R)-2-(1-methyl-1H-pyrazol-4-yl)-4-(3-(4-(trifluoromethyl)benzamido)piperidin-1-yl)-1H-indole-7-carboxamide*;
(R)-4-(3-(4-methoxybenzamido)piperidin-1-yl)-1H-indole-7-carboxamide*;
(R)-4-(3-(4-(trifluoromethyl)benzamido)piperidin-1-yl)-1H-indole-7-carboxamide*;
(R)-4-(3-(4-(difluoromethyl)benzamido)piperidin-1-yl)-2-(1-methyl-1H-pyrazol-4-yl)-1H-indole-7-carboxamide*;
4-(3-(6-fluoro-4-oxoquinazolin-3(4H)-yl)-2-methylphenyl)-2-(1-methyl-1H-pyrazol-4-yl)-1H-indole-7-carboxamide;
2-(3,6-dihydro-2H-pyran-4-yl)-4-(2-methyl-3-(4-oxoquinazolin-3(4H)-yl)phenyl)-1H-indole-7-carboxamide;
2-(4-fluorophenyl)-4-(2-methyl-3-(4-oxoquinazolin-3(4H)-yl)phenyl)-1H-indole-7-carboxamide;
(R)-4-(3-(4-(1-amino-2-methyl-1-oxopropan-2-yl)benzamido)piperidin-1-yl)-2-(1-methyl-1H-pyrazol-4-yl)-1H-indole-7-carboxamide;
(R)-2-(1-methyl-1H-pyrazol-4-yl)-4-(3-(4-(trifluoromethoxy)benzamido)piperidin-1-yl)-1H-indole-7-carboxamide*;
2-(1-(2-hydroxyethyl)-1H-pyrazol-4-yl)-4-(2-methyl-3-(4-oxoquinazolin-3(4H)-yl)phenyl)-1H-indole-7-carboxamide;
(R)-4-(3-(6-fluoro-1-oxoisoindolin-2-yl)piperidin-1-yl)-2-(1-methyl-1H-pyrazol-4-yl)-1H-indole-7-carboxamide*;
2-(3,6-dihydro-2H-pyran-4-yl)-4-(3-(6-fluoro-4-oxoquinazolin-3(4H)-yl)-2-methylphenyl)-1H-indole-7-carboxamide;
2-(1-acetyl-1,2,3,6-tetrahydropyridin-4-yl)-4-(3-(6-fluoro-4-oxoquinazolin-3(4H)-yl)-2-methylphenyl)-1H-indole-7-carboxamide;
N-(3-(7-carbamoyl-2-(1-methyl-1H-pyrazol-4-yl)-1H-indol-4-yl)-2-methylphenyl)thiazole-2-carboxamide;
4-(3-(6-fluoro-4-oxoquinazolin-3(4H)-yl)-2-(hydroxymethyl)phenyl)-2-(1-methyl-1H-pyrazol-4-yl)-1H-indole-7-carboxamide;
2-(1-methyl-1H-pyrazol-4-yl)-4-(2-methyl-3-(4,5,6,7-tetrahydrobenzo[b]thiophene-2-carboxamido)phenyl)-1H-indole-7-carboxamide;
(R)-4-(3-(4-cyclopropylbenzamido)piperidin-1-yl)-2-(1-methyl-1H-pyrazol-4-yl)-1H-indole-7-carboxamide*;
2-(2,5-dihydro-1H-pyrrol-3-yl)-4-(2-methyl-3-(4-oxoquinazolin-3(4H)-yl)phenyl)-1H-indole-7-carboxamide;
4-(2-methyl-3-(4-oxoquinazolin-3(4H)-yl)phenyl)-2-(1,2,3,6-tetrahydropyridin-4-yl)-1H-indole-7-carboxamide;
2-(1-((R)-2,3-dihydroxypropyl)-1H-pyrazol-4-yl)-4-(2-methyl-3-(4-oxoquinazolin-3(4H)-yl)phenyl)-1H-indole-7-carboxamide*;
N-(3-(7-carbamoyl-2-(1-methyl-1H-pyrazol-4-yl)-1H-indol-4-yl)-2-(hydroxymethyl)phenyl)thiazole-2-carboxamide;
2-(1-acetyl-1,2,3,6-tetrahydropyridin-4-yl)-4-(3-(4-tert-butylbenzamido)-2-methylphenyl)-1H-indole-7-carboxamide;
N-(3-(2-(1-acetyl-1,2,3,6-tetrahydropyridin-4-yl)-7-carbamoyl-1H-indol-4-yl)-2-methylphenyl)thiazole-2-carboxamide;
2-(1-acetyl-1,2,3,6-tetrahydropyridin-4-yl)-4-(2-methyl-3-(4,5,6,7-tetrahydrobenzo[b]thiophene-2-carboxamido)phenyl)-1H-indole-7-carboxamide;
2-(1-acetyl-1,2,3,6-tetrahydropyridin-4-yl)-4-(3-(4-cyclopropylbenzamido)-2-methylphenyl)-1H-indole-7-carboxamide;
4-(2-methyl-3-(1-oxo-3,4-dihydroisoquinolin-2(1H)-yl)phenyl)-2-(1-(methylsulfonyl)-1,2,3,6-tetrahydropyridin-4-yl)-1H-indole-7-carboxamide;
2-(1-methyl-2,5-dihydro-1H-pyrrol-3-yl)-4-(2-methyl-3-(4-oxoquinazolin-3(4H)-yl)phenyl)-1H-indole-7-carboxamide;
2-(1-acetyl-2,5-dihydro-1H-pyrrol-3-yl)-4-(2-methyl-3-(4-oxoquinazolin-3(4H)-yl)phenyl)-1H-indole-7-carboxamide;
ethyl 3-(7-carbamoyl-4-(2-methyl-3-(4-oxoquinazolin-3(4H)-yl)phenyl)-1H-indol-2-yl)-2,5-dihydro-1H-pyrrole-1-carboxylate;
2-(1-methyl-1,2,3,6-tetrahydropyridin-4-yl)-4-(2-methyl-3-(4-oxoquinazolin-3(4H)-yl)phenyl)-1H-indole-7-carboxamide;
4-(2-methyl-3-(4-oxoquinazolin-3(4H)-yl)phenyl)-2-(1-(methylsulfonyl)-1,2,3,6-tetrahydropyridin-4-yl)-1H-indole-7-carboxamide;
N-(3-(7-carbamoyl-2-(1-(methylsulfonyl)-1,2,3,6-tetrahydropyridin-4-yl)-1H-indol-4-yl)-2-methylphenyl)thiazole-2-carboxamide;
N-(3-(7-carbamoyl-2-(1-(methylsulfonyl)-1,2,3,6-tetrahydropyridin-4-yl)-1H-indol-4-yl)-2-methylphenyl)thiazole-2-carboxamide;

2-(1-((S)-2,3-dihydroxypropyl)-1H-pyrazol-4-yl)-4-(2-methyl-3-(4-oxoquinazolin-3(4H)-yl)phenyl)-1H-indole-7-carboxamide;
N-(3-(7-carbamoyl-2-(1-methyl-1H-pyrazol-4-yl)-1H-indol-4-yl)-2-methylphenyl)-N-methylthiazole-2-carboxamide;
N-(3-(7-carbamoyl-2-(1-methyl-1H-pyrazol-4-yl)-1H-indol-4-yl)-2-methylphenyl)-N-(oxetan-3-yl)thiazole-2-carboxamide;
2-(1-acetyl-1,2,3,6-tetrahydropyridin-4-yl)-4-(3-(4-(2-cyanopropan-2-yl)benzamido)-2-methylphenyl)-1H-indole-7-carboxamide;
4-(2-methyl-3-(4-oxoquinazolin-3(4H)-yl)phenyl)-2-(pyrimidin-5-yl)-1H-indole-7-carboxamide;
4-(3-(6-fluoro-4-oxoquinazolin-3(4H)-yl)-2-methylphenyl)-2-(pyrimidin-5-yl)-1H-indole-7-carboxamide;
4-(3-(4-(difluoromethyl)benzamido)-2-methylphenyl)-2-(pyrimidin-5-yl)-1H-indole-7-carboxamide;
4-(3-(4-cyclopropylbenzamido)-2-methylphenyl)-2-(pyrimidin-5-yl)-1H-indole-7-carboxamide;
4-(3-(6-fluoro-4-oxoquinazolin-3(4H)-yl)-2-methylphenyl)-2-(1-(2-hydroxy-2-methylpropyl)-1H-pyrazol-4-yl)-1H-indole-7-carboxamide;
(R)-2-(1-(methylsulfonyl)-1,2,3,6-tetrahydropyridin-4-yl)-4-(3-(8-oxo-5,6-dihydroimidazo[1,2-c]pyrazin-7(8H)-yl)piperidin-1-yl)-1H-indole-7-carboxamide*;
(R)-2-(1-(methylsulfonyl)-1,2,3,6-tetrahydropyridin-4-yl)-4-(3-(8-oxoimidazo[1,2-c]pyrazin-7(8H)-yl)piperidin-1-yl)-1H-indole-7-carboxamide*;
4-(2-methyl-3-(oxetan-3-ylamino)phenyl)-2-(1-(methylsulfonyl)-1,2,3,6-tetrahydropyridin-4-yl)-1H-indole-7-carboxamide;
4-(2-methyl-3-(1-oxo-3,4-dihydroisoquinolin-2(1H)-yl)phenyl)-2-(1-(methylsulfonyl)-1,2,3,6-tetrahydropyridin-4-yl)-1H-indole-7-carboxamide;
4-(3-(4-(difluoromethyl)benzamido)-2-methylphenyl)-2-(1-(methylsulfonyl)-1,2,3,6-tetrahydropyridin-4-yl)-1H-indole-7-carboxamide;
4-(3-(4-hydroxy-4-(trifluoromethyl)cyclohexanecarboxamido)-2-methylphenyl)-2-(1-(methylsulfonyl)-1,2,3,6-tetrahydropyridin-4-yl)-1H-indole-7-carboxamide;
(R)-2-(1-(methylsulfonyl)-1,2,3,6-tetrahydropyridin-4-yl)-4-(3-(1-oxo-3,4-dihydroisoquinolin-2(1H)-yl)piperidin-1-yl)-1H-indole-7-carboxamide*;
2-(1-acetylpiperidin-4-yl)-4-(3-(4-cyclopropylbenzamido)-2-methylphenyl)-1H-indole-7-carboxamide;
(R)—N-(1-(7-carbamoyl-2-(1-(methylsulfonyl)-1,2,3,6-tetrahydropyridin-4-yl)-1H-indol-4-yl)piperidin-3-yl)-2-methyloxazole-4-carboxamide*;
(R)-2-(1-(methylsulfonyl)-1,2,3,6-tetrahydropyridin-4-yl)-4-(2-oxo-1,3'-bipiperidin-1'-yl)-1H-indole-7-carboxamide*;
2-(1-methyl-1H-pyrazol-4-yl)-4-(2-methyl-3-(4-oxoquinazolin-3(4H)-yl)phenyl)-1H-benzo[d]imidazole-7-carboxamide;
4-(3-(4-(difluoromethyl)-N-(oxetan-3-yl)benzamido)-2-methylphenyl)-2-(1-(methylsulfonyl)-1,2,3,6-tetrahydropyridin-4-yl)-1H-indole-7-carboxamide;
4-(2-methyl-3-(oxetan-3-ylamino)phenyl)-1H-indole-7-carboxamide;
4-(3-(4-(difluoromethyl)benzamido)-2-methylphenyl)-1H-indole-7-carboxamide;
4-(3-(2-hydroxyethylamino)-2-methylphenyl)-2-(1-(methylsulfonyl)-1,2,3,6-tetrahydropyridin-4-yl)-1H-indole-7-carboxamide;
(R)—N-(1-(7-carbamoyl-2-(1-(methylsulfonyl)-1,2,3,6-tetrahydropyridin-4-yl)-1H-indol-4-yl)piperidin-3-yl)thiazole-2-carboxamide*;
4-(3-(cyclohexanecarboxamido)-2-methylphenyl)-2-(1-(methylsulfonyl)-1,2,3,6-tetrahydropyridin-4-yl)-1H-indole-7-carboxamide;
4-(3-(4-(difluoromethyl)-N-(2-hydroxyethyl)benzamido)-2-methylphenyl)-2-(1-(methylsulfonyl)-1,2,3,6-tetrahydropyridin-4-yl)-1H-indole-7-carboxamide;
N-(3-(7-carbamoyl-2-(1-(methylsulfonyl)-1,2,3,6-tetrahydropyridin-4-yl)-1H-indol-4-yl)-2-methylphenyl)isothiazole-4-carboxamide;
4-(2-methyl-3-(tetrahydro-2H-pyran-4-carboxamido)phenyl)-2-(1-(methylsulfonyl)-1,2,3,6-tetrahydropyridin-4-yl)-1H-indole-7-carboxamide;
4-(2-methyl-3-(1-methylpiperidine-3-carboxamido)phenyl)-2-(1-(methylsulfonyl)-1,2,3,6-tetrahydropyridin-4-yl)-1H-indole-7-carboxamide;
4-(2-methyl-3-(1-methylpiperidine-4-carboxamido)phenyl)-2-(1-(methylsulfonyl)-1,2,3,6-tetrahydropyridin-4-yl)-1H-indole-7-carboxamide;
4-(3-(cyclopentanecarboxamido)-2-methylphenyl)-2-(1-(methylsulfonyl)-1,2,3,6-tetrahydropyridin-4-yl)-1H-indole-7-carboxamide;
N-(3-(7-carbamoyl-2-(1-(methylsulfonyl)-1,2,3,6-tetrahydropyridin-4-yl)-1H-indol-4-yl)-2-methylphenyl)-2-methylthiazole-4-carboxamide;
4-(3-(3-methoxycyclohexanecarboxamido)-2-methylphenyl)-2-(1-(methylsulfonyl)-1,2,3,6-tetrahydropyridin-4-yl)-1H-indole-7-carboxamide;
4-(2-methyl-3-(3-methylbutanamido)phenyl)-2-(1-(methylsulfonyl)-1,2,3,6-tetrahydropyridin-4-yl)-1H-indole-7-carboxamide;
4-(3-isobutyramido-2-methylphenyl)-2-(1-(methylsulfonyl)-1,2,3,6-tetrahydropyridin-4-yl)-1H-indole-7-carboxamide;
4-(2-methyl-3-(nicotinamido)phenyl)-2-(1-(methylsulfonyl)-1,2,3,6-tetrahydropyridin-4-yl)-1H-indole-7-carboxamide;
4-(3-acrylamido-2-methylphenyl)-2-(1-(methylsulfonyl)-1,2,3,6-tetrahydropyridin-4-yl)-1H-indole-7-carboxamide;
N-(3-(7-carbamoyl-2-(1-(methylsulfonyl)-1,2,3,6-tetrahydropyridin-4-yl)-1H-indol-4-yl)-2-methylphenyl)-5-methylthiazole-2-carboxamide;
N-(3-(7-carbamoyl-2-(1-methyl-6-oxo-1,6-dihydropyridin-3-yl)-1H-indol-4-yl)-2-methylphenyl)thiazole-2-carboxamide;
N-((3R,4R)-1-(7-carbamoyl-2-(1-(methylsulfonyl)-1,2,3,6-tetrahydropyridin-4-yl)-1H-indol-4-yl)-4-hydroxypiperidin-3-yl)thiazole-2-carboxamide;
(R)-4-(3-acrylamidopiperidin-1-yl)-2-(1-(methylsulfonyl)-1,2,3,6-tetrahydropyridin-4-yl)-1H-indole-7-carboxamide*;
4-(2-methyl-3-(thiazol-2-ylmethylamino)phenyl)-2-(1-(methylsulfonyl)-1,2,3,6-tetrahydropyridin-4-yl)-1H-indole-7-carboxamide;
4-(2-methyl-3-(N-(thiazol-2-ylmethyl)acrylamido)phenyl)-2-(1-(methylsulfonyl)-1,2,3,6-tetrahydropyridin-4-yl)-1H-indole-7-carboxamide;
(Z)-4-(2-methyl-3-(2-methylbut-2-enamido)phenyl)-2-(1-(methylsulfonyl)-1,2,3,6-tetrahydropyridin-4-yl)-1H-indole-7-carboxamide;
(E)-4-(3-(4-(dimethylamino)but-2-enamido)-2-methylphenyl)-2-(1-(methylsulfonyl)-1,2,3,6-tetrahydropyridin-4-yl)-1H-indole-7-carboxamide;

4-(2-methyl-3-(3-(piperidin-1-yl)propanamido)phenyl)-2-(1-(methylsulfonyl)-1,2,3,6-tetrahydropyridin-4-yl)-1H-indole-7-carboxamide;
4-(3-(2-cyano acetamido)-2-methylphenyl)-2-(1-(methylsulfonyl)-1,2,3,6-tetrahydropyridin-4-yl)-1H-indole-7-carboxamide;
4-(2-methyl-3-propionamidophenyl)-2-(1-(methylsulfonyl)-1,2,3,6-tetrahydropyridin-4-yl)-1H-indole-7-carboxamide;
4-(3-methacrylamido-2-methylphenyl)-2-(1-(methylsulfonyl)-1,2,3,6-tetrahydropyridin-4-yl)-1H-indole-7-carboxamidel;
4-(3-(2-chloro-2,2-difluoro acetamido)-2-methylphenyl)-2-(1-(methylsulfonyl)-1,2,3,6-tetrahydropyridin-4-yl)-1H-indole-7-carboxamide;
4-(3-(2-chloropropanamido)-2-methylphenyl)-2-(1-(methylsulfonyl)-1,2,3,6-tetrahydropyridin-4-yl)-1H-indole-7-carboxamide;
(E)-4-(3-but-2-enamido-2-methylphenyl)-2-(1-(methylsulfonyl)-1,2,3,6-tetrahydropyridin-4-yl)-1H-indole-7-carboxamide;
N1-(3-(7-carbamoyl-2-(1-(methylsulfonyl)-1,2,3,6-tetrahydropyridin-4-yl)-1H-indol-4-yl)-2-methylphenyl);
4-(3-(2-(4-fluorophenoxy)acetamido)-2-methylphenyl)-2-(1-(methylsulfonyl)-1,2,3,6-tetrahydropyridin-4-yl)-1H-indole-7-carboxamide;
4-(2-methyl-3-(3-(pyrrolidin-1-yl)propanamido)phenyl)-2-(1-(methylsulfonyl)-1,2,3,6-tetrahydropyridin-4-yl)-1H-indole-7-carboxamide;
4-(3-(2-(4-cyanophenoxy)acetamido)-2-methylphenyl)-2-(1-(methylsulfonyl)-1,2,3,6-tetrahydropyridin-4-yl)-1H-indole-7-carboxamide;
4-(2-methyl-3-(2-(pyridin-3-yloxy)acetamido)phenyl)-2-(1-(methylsulfonyl)-1,2,3,6-tetrahydropyridin-4-yl)-1H-indole-7-carboxamide;
4-(3-(cyclopent-1-enecarboxamido)-2-methylphenyl)-2-(1-(methylsulfonyl)-1,2,3,6-tetrahydropyridin-4-yl)-1H-indole-7-carboxamide;
(E)-4-(2-methyl-3-(2-methylpent-2-enamido)phenyl)-2-(1-(methylsulfonyl)-1,2,3,6-tetrahydropyridin-4-yl)-1H-indole-7-carboxamide;
(Z)-4-(3-(3-chloroacrylamido)-2-methylphenyl)-2-(1-(methylsulfonyl)-1,2,3,6-tetrahydropyridin-4-yl)-1H-indole-7-carboxamide;
(E)-methyl 4-(3-(7-carbamoyl-2-(1-(methylsulfonyl)-1,2,3,6-tetrahydropyridin-4-yl)-1H-indol-4-yl)-2-methylphenylamino)-4-oxobut-2-enoate;
4-(3-(cyclohex-1-enecarboxamido)-2-methylphenyl)-2-(1-(methylsulfonyl)-1,2,3,6-tetrahydropyridin-4-yl)-1H-indole-7-carboxamide;
(E)-ethyl 4-(3-(7-carbamoyl-2-(1-(methylsulfonyl)-1,2,3,6-tetrahydropyridin-4-yl)-1H-indol-4-yl)-2-methylphenylamino)-4-oxobut-2-enoate;
4-(2-methyl-3-(2-phenoxyacetamido)phenyl)-2-(1-(methylsulfonyl)-1,2,3,6-tetrahydropyridin-4-yl)-1H-indole-7-carboxamide;
4-(3-(2-fluoroacetamido)-2-methylphenyl)-2-(1-(methylsulfonyl)-1,2,3,6-tetrahydropyridin-4-yl)-1H-indole-7-carboxamide;
4-(3-acrylamido-2-methylphenyl)-2-(4,4-difluorocyclohex-1-enyl)-1H-indole-7-carboxamide;
4-(2-(acrylamidomethyl)phenyl)-2-(1-(methylsulfonyl)-1,2,3,6-tetrahydropyridin-4-yl)-1H-indole-7-carboxamide;
4-(3-(3-(dimethylamino)propanamido)-2-methylphenyl)-2-(1-(methylsulfonyl)-1,2,3,6-tetrahydropyridin-4-yl)-1H-indole-7-carboxamide;
4-(2-acrylamidophenyl)-2-(1-(methylsulfonyl)-1,2,3,6-tetrahydropyridin-4-yl)-1H-indole-7-carboxamide;
4-(3-(acrylamidomethyl)phenyl)-2-(1-(methylsulfonyl)-1,2,3,6-tetrahydropyridin-4-yl)-1H-indole-7-carboxamide;
4-(3-(acrylamidomethyl)phenyl)-2-(1-(methylsulfonyl)-1,2,3,6-tetrahydropyridin-4-yl)-1H-indole-7-carboxamide;
4-(3-(2-cyanopyrimidin-4-ylamino)phenyl)-2-(1-(methylsulfonyl)-1,2,3,6-tetrahydropyridin-4-yl)-1H-indole-7-carboxamide;
4-(3-(6-cyclopropyl-8-fluoro-1-oxoisoquinolin-2(1H)-yl)-2-(hydroxymethyl)phenyl)-2-(1-methyl-1H-pyrazol-4-yl)-1H-indole-7-carboxamide;
4-(3-acrylamidophenyl)-1H-indole-7-carboxamide;
4-(3-acrylamido-2-methylphenyl)-1H-indole-7-carboxamide;
4-(3-acrylamido-2-methylphenyl)-2-(2-methoxypyridin-3-yl)-1H-indole-7-carboxamide;
4-(2-methyl-3-(2-(pyridin-2-yloxy)acetamido)phenyl)-2-(1-(methylsulfonyl)-1,2,3,6-tetrahydropyridin-4-yl)-1H-indole-7-carboxamide;
N1-(3-(7-carbamoyl-2-(1-(methylsulfonyl)-1,2,3,6-tetrahydropyridin-4-yl)-1H-indol-4-yl)-2-methylphenyl)fumaramide;
4-(3-(2-chlorobutanamido)-2-methylphenyl)-2-(1-(methylsulfonyl)-1,2,3,6-tetrahydropyridin-4-yl)-1H-indole-7-carboxamide;
4-(2-methyl-3-(3-(4-methylpiperazin-1-yl)propanamido)phenyl)-2-(1-(methylsulfonyl)-1,2,3,6-tetrahydropyridin-4-yl)-1H-indole-7-carboxamide;
4-(2-methyl-3-(2-(pyridazin-3-yloxy)acetamido)phenyl)-2-(1-(methylsulfonyl)-1,2,3,6-tetrahydropyridin-4-yl)-1H-indole-7-carboxamide;
2-(1-(methylsulfonyl)-1,2,3,6-tetrahydropyridin-4-yl)-4-(3-(thiazol-2-ylmethoxy)phenyl)-1H-indole-7-carboxamide;
methyl 3-(4-(3-acrylamido-2-methylphenyl)-7-carbamoyl-1H-indol-2-yl)benzoate;
4-(3-acrylamido-2-methylphenyl)-2-(3-methoxyphenyl)-1H-indole-7-carboxamide;
4-(3-acrylamido-2-methylphenyl)-2-(4-methoxyphenyl)-1H-indole-7-carboxamide;
4-(3-acrylamido-2-methylphenyl)-2-(6-methylpyridin-3-yl)-1H-indole-7-carboxamide;
4-(3-acrylamido-2-methylphenyl)-2-(3-carbamoylphenyl)-1H-indole-7-carboxamide;
N-(3-(7-carbamoyl-3-methyl-1H-indol-4-yl)-2-methylphenyl)thiazole-2-carboxamide;
4-(3-acrylamido-2-methylphenyl)-2-(3,5-dimethylisoxazol-4-yl)-1H-indole-7-carboxamide;
4-(3-acrylamido-2-methylphenyl)-2-(1-(tetrahydro-2H-pyran-2-yl)-1H-pyrazol-5-yl)-1H-indole-7-carboxamide;
4-(3-acrylamido-2-methylphenyl)-2-(3,5-dimethyl-1H-pyrazol-4-yl)-1H-indole-7-carboxamide;
4-(3-acrylamido-2-methylphenyl)-2-(1-isopropyl-1H-pyrazol-4-yl)-1H-indole-7-carboxamide;
4-(3-acrylamido-2-methylphenyl)-2-(1,3-dimethyl-1H-pyrazol-4-yl)-1H-indole-7-carboxamide;
4-(3-acrylamido-2-methylphenyl)-2-(1-ethyl-1H-pyrazol-4-yl)-1H-indole-7-carboxamide;
4-(3-acrylamido-2-methylphenyl)-2-(1-isobutyl-1H-pyrazol-4-yl)-1H-indole-7-carboxamide;
(E)-N-(3-(3-but-2-enamido-7-carbamoyl-1H-indol-4-yl)-2-methylphenyl)thiazole-2-carboxamide;
N-(3-(7-carbamoyl-3-methacrylamido-1H-indol-4-yl)-2-methylphenyl)thiazole-2-carboxamide;
N-(3-(3-but-2-ynamido-7-carbamoyl-1H-indol-4-yl)-2-methylphenyl)thiazole-2-carboxamide;

N-(3-(7-carbamoyl-3-(2-(4-fluorophenoxy)acetamido)-1H-indol-4-yl)-2-methylphenyl)thiazole-2-carboxamide;
4-(3-acrylamido-2-methylphenyl)-2-(2-fluoropyridin-3-yl)-1H-indole-7-carboxamide;
4-(3-acrylamido-2-methylphenyl)-2-(1-ethyl-1H-pyrazol-4-yl)-1H-indole-7-carboxamide;
2-(3-acetamidophenyl)-4-(3-acrylamido-2-methylphenyl)-1H-indole-7-carboxamide;
4-(3-acrylamido-2-methylphenyl)-2-(2-methoxypyridin-4-yl)-1H-indole-7-carboxamide;
4-(3-acrylamido-2-methylphenyl)-2-(3-cyanophenyl)-1H-indole-7-carboxamide;
methyl 4-(4-(3-acrylamido-2-methylphenyl)-7-carbamoyl-1H-indol-2-yl)benzoate;
4-(3-acrylamido-2-methylphenyl)-2-(2,3-dihydrobenzofuran-5-yl)-1H-indole-7-carboxamide;
4-(3-acrylamido-2-methylphenyl)-2-(3-fluorophenyl)-1H-indole-7-carboxamide;
4-(3-acrylamido-2-methylphenyl)-2-(3-(dimethylamino)phenyl)-1H-indole-7-carboxamide;
4-(2-(2-chloroacetamido)phenyl)-2-(1-(methylsulfonyl)-1,2,3,6-tetrahydropyridin-4-yl)-1H-indole-7-carboxamide;
4-(2-acetamidophenyl)-2-(1-(methylsulfonyl)-1,2,3,6-tetrahydropyridin-4-yl)-1H-indole-7-carboxamide;
4-(3-acrylamido-2-methylphenyl)-2-(2-methyl-5-(pyrrolidin-1-ylsulfonyl)phenyl)-1H-indole-7-carboxamide;
4-(3-acrylamido-2-methylphenyl)-2-(2-fluorophenyl)-1H-indole-7-carboxamide;
N-(3-(3-acrylamido-7-carbamoyl-1H-indol-4-yl)-2-methylphenyl)thiazole-2-carboxamide;
N-(3-(7-carbamoyl-3-(2-chloroacetamido)-1H-indol-4-yl)-2-methylphenyl)thiazole-2-carboxamide;
4-(3-acrylamido-2-methylphenyl)-2-(1-methyl-1H-pyrazol-5-yl)-1H-indole-7-carboxamide;
4-(3-acrylamido-2-methylphenyl)-2-(pyridin-4-yl)-1H-indole-7-carboxamide;
4-(3-acrylamido-2-methylphenyl)-2-(1-(2-morpholinoethyl)-1H-pyrazol-4-yl)-1H-indole-7-carboxamide;
4-(3-acrylamido-2-methylphenyl)-2-(6-morpholinopyridin-3-yl)-1H-indole-7-carboxamide;
4-(3-acrylamido-2-methylphenyl)-2-(3-(4-methylpiperazine-1-carbonyl)phenyl)-1H-indole-7-carboxamide;
N-(3-(2-(2-(acrylamidomethyl)phenyl)-7-carbamoyl-1H-indol-4-yl)-2-methylphenyl)thiazole-2-carboxamide;
N-(3-(2-(2-(acetamidomethyl)phenyl)-7-carbamoyl-1H-indol-4-yl)-2-methylphenyl)thiazole-2-carboxamide;
N-(3-(7-carbamoyl-2-(2-(propionamidomethyl)phenyl)-1H-indol-4-yl)-2-methylphenyl)thiazole-2-carboxamide;
N-(3-(2-(2-(butyramidomethyl)phenyl)-7-carbamoyl-1H-indol-4-yl)-2-methylphenyl)thiazole-2-carboxamide;
(E)-N-(3-(2-(2-(but-2-enamidomethyl)phenyl)-7-carbamoyl-1H-indol-4-yl)-2-methylphenyl)thiazole-2-carboxamide;
N-(3-(7-carbamoyl-2-(2-(methacrylamidomethyl)phenyl)-1H-indol-4-yl)-2-methylphenyl)thiazole-2-carboxamide;
N-(3-(7-carbamoyl-2-(2-(propiolamidomethyl)phenyl)-1H-indol-4-yl)-2-methylphenyl)thiazole-2-carboxamide;
N-(3-(2-(2-(but-2-ynamidomethyl)phenyl)-7-carbamoyl-1H-indol-4-yl)-2-methylphenyl)thiazole-2-carboxamide;
N-(3-(7-carbamoyl-2-(2-(((2-cyano acetamido)methyl)phenyl)-1H-indol-4-yl)-2-methylphenyl)thiazole-2-carboxamide;
N-(3-(7-carbamoyl-2-(2-((3-(dimethylamino)propanamido)methyl)phenyl)-1H-indol-4-yl)-2-methylphenyl)thiazole-2-carboxamide;
N-(3-(7-carbamoyl-2-(2-((3-(piperidin-1-yl)propanamido)methyl)phenyl)-1H-indol-4-yl)-2-methylphenyl)thiazole-2-carboxamide;
N-(3-(7-carbamoyl-2-(2-((2-phenoxyacetamido)methyl)phenyl)-1H-indol-4-yl)-2-methylphenyl)thiazole-2-carboxamide;
N-(3-(7-carbamoyl-2-(24(2-(4-fluorophenoxy)acetamido)methyl)phenyl)-1H-indol-4-yl)-2-methylphenyl)thiazole-2-carboxamide;
N-(3-(7-carbamoyl-2-(2-((2-chloro acetamido)methyl)phenyl)-1H-indol-4-yl)-2-methylphenyl)thiazole-2-carboxamide;
N-(3-(2-(2-(aminomethyl)phenyl)-7-carbamoyl-1H-indol-4-yl)-2-methylphenyl)thiazole-2-carboxamide;
4-(3-acrylamido-2-methylphenyl)-2-(4-fluorophenyl)-1H-indole-7-carboxamide;
4-(3-acrylamido-2-methylphenyl)-2-phenyl-1H-indole-7-carboxamide;
4-(3-acrylamido-2-methylphenyl)-2-(2-(methylsulfonyl)phenyl)-1H-indole-7-carboxamide;
4-(3-acrylamido-2-methylphenyl)-2-(4-(dimethylcarbamoyl)phenyl)-1H-indole-7-carboxamide;
4-(3-acrylamido-2-methylphenyl)-2-(pyrimidin-5-yl)-1H-indole-7-carboxamide;
4-(3-acrylamido-2-methylphenyl)-2-(pyridin-3-yl)-1H-indole-7-carboxamide;
4-(3-acrylamido-2-methylphenyl)-2-(4-(morpholine-4-carbonyl)phenyl)-1H-indole-7-carboxamide;
4-(3-acrylamido-2-methylphenyl)-2-(4-(pyrrolidine-1-carbonyl)phenyl)-1H-indole-7-carboxamide;
4-(3-acrylamido-2-methylphenyl)-2-(4-(4-methylpiperazine-1-carbonyl)phenyl)-1H-indole-7-carboxamide;
4-(3-acrylamido-2-methylphenyl)-2-(4-(methylsulfonyl)phenyl)-1H-indole-7-carboxamide;
4-(3-acrylamido-2-methylphenyl)-2-(6-methoxypyridin-3-yl)-1H-indole-7-carboxamide;
4-(3-acrylamido-2-methylphenyl)-2-(4-cyanophenyl)-1H-indole-7-carboxamide;
4-(3-acrylamido-2-methylphenyl)-2-(2-methoxyphenyl)-1H-indole-7-carboxamide;
N-(3-(7-carbamoyl-3-(2-cyanoacetamido)-1H-indol-4-yl)-2-methylphenyl)thiazole-2-carboxamide;
4-(2-acrylamidophenyl)-1H-indole-7-carboxamide;
4-(3-acrylamido-2-methylphenyl)-2-(4-(morpholinomethyl)phenyl)-1H-indole-7-carboxamide;
4-(3-acrylamido-2-methylphenyl)-2-(4-carbamoylphenyl)-1H-indole-7-carboxamide;
4-(3-acrylamido-5-(thiazol-2-ylmethylamino)phenyl)-2-(1-(methylsulfonyl)-1,2,3,6-tetrahydropyridin-4-yl)-1H-indole-7-carboxamide;
4-(2-methyl-3-(N-methylacrylamido)phenyl)-1H-indole-7-carboxamide;
4-(3-(methylamino)phenyl)-1H-indole-7-carboxamide;
4-(3-(N-methylacrylamido)phenyl)-1H-indole-7-carboxamide;
4-(2-methyl-3-(2-methylenebutanamido)phenyl)-1H-indole-7-carboxamide;
4-(2-methyl-3-(3-(pyrrolidin-1-yl)propanamido)phenyl)-1H-indole-7-carboxamide;
4-(3-methacrylamido-2-methylphenyl)-1H-indole-7-carboxamide;
(E)-4-(3-(3-cyclopropylacrylamido)-2-methylphenyl)-1H-indole-7-carboxamide;
(E)-4-(2-methyl-3-(3-(pyridin-2-yl)acrylamido)phenyl)-1H-indole-7-carboxamide;
(E)-4-(2-methyl-3-(3-(1-methyl-1H-pyrazol-4-yl)acrylamido)phenyl)-1H-indole-7-carboxamide;

(E)-ethyl 4-(3-(7-carbamoyl-1H-indol-4-yl)-2-methylphenylamino)-4-oxobut-2-enoate;
(E)-4-(3-(4-(dimethylamino)but-2-enamido)-2-methylphenyl)-1H-indole-7-carboxamide;
(E)-4-(2-methyl-3-(3-(pyridin-3-yl)acrylamido)phenyl)-1H-indole-7-carboxamide;
(E)-4-(2-methyl-3-(4-methylpent-2-enamido)phenyl)-1H-indole-7-carboxamide;
N1-(3-(7-carbamoyl-1H-indol-4-yl)-2-methylphenyl)-N4-ethylmaleamide;
4-(3-acetamido-2-methylphenyl)-1H-indole-7-carboxamide;
(E)-4-(3-but-2-enamido-2-methylphenyl)-1H-indole-7-carboxamide;
4-(2-methyl-3-(3-morpholinopropan amido)phenyl)-1H-indole-7-carboxamide;
(E)-4-(2-methyl-3-(3-(thiazol-2-yl)acrylamido)phenyl)-1H-indole-7-carboxamide;
4-(2-methyl-3-(2-phenylacrylamido)phenyl)-1H-indole-7-carboxamide;
(E)-4-(2-methyl-3-(4-(piperidin-1-yl)but-2-enamido)phenyl)-1H-indole-7-carboxamide;
(E)-4-(2-methyl-3-(4-((tetrahydrofuran-2-yl)methylamino)but-2-enamido)phenyl)-1H-indole-7-carboxamide;
(E)-4-(3-(4-(2-methoxyethylamino)but-2-enamido)-2-methylphenyl)-1H-indole-7-carboxamide;
(E)-4-(3-(4-(cyclopropylamino)but-2-enamido)-2-methylphenyl)-1H-indole-7-carboxamide;
(E)-4-(2-methyl-3-(4-morpholinobut-2-enamido)phenyl)-1H-indole-7-carboxamide;
(E)-4-(2-methyl-3-(4-(4-methylpiperazin-1-yl)but-2-enamido)phenyl)-1H-indole-7-carboxamide;
4-(3-acrylamido-4-(benzyloxy)phenyl)-1H-indole-7-carboxamide;
4-(3-acrylamido-5-(benzyloxy)phenyl)-1H-indole-7-carboxamide;
4-(3-acrylamido-4-(thiazol-2-ylmethoxy)phenyl)-1H-indole-7-carboxamide;
4-(3-acrylamido-5-(thiazol-2-ylmethoxy)phenyl)-1H-indole-7-carboxamide;
4-(2-acrylamido-4-(thiazol-2-ylmethoxy)phenyl)-1H-indole-7-carboxamide;
4-(3-acrylamido-2-methylphenyl)-1H-pyrrolo[2,3-c]pyridine-7-carboxamide;
4-(2-acrylamido-4-(benzyloxy)phenyl)-1H-indole-7-carboxamide;
4-(5-acrylamidopyridin-3-yl)-1H-indole-7-carboxamide;
4-(2-acrylamidopyridin-4-yl)-1H-indole-7-carboxamide;
N1-(3-(7-carbamoyl-1H-indol-4-yl)phenyl)-N4-(2-methoxyethyl)maleamide;
N1-(3-(7-carbamoyl-1H-indol-4-yl)phenyl)-N4-ethylmaleamide;
4-(3-(1-methyl-1,2,5,6-tetrahydropyridine-3-carboxamido)phenyl)-1H-indole-7-carboxamide;
4-(3-(vinylsulfonamido)phenyl)-1H-indole-7-carboxamide;
4-(3-(2-oxopropanamido)phenyl)-1H-indole-7-carboxamide;
(E)-methyl 4-(3-(7-carbamoyl-1H-indol-4-yl)phenylamino)-4-oxobut-2-enoate;
4-(3-(cyanomethylcarbamoyl)phenyl)-1H-indole-7-carboxamide;
N-(3-(7-carbamoyl-1H-indol-4-yl)phenyl)-5-methylisoxazole-4-carboxamide;
N1-(3-(7-carbamoyl-1H-indol-4-yl)phenyl)-N4-methylfumaramide;
N1-(3-(7-carbamoyl-1H-indol-4-yl)phenyl)-N4,N4-dimethylfumaramide;
N1-(3-(7-carbamoyl-1H-indol-4-yl)phenyl)-N4-ethylfumaramide;
N1-(3-(7-carbamoyl-1H-indol-4-yl)phenyl)-N4-cyclopropylfumaramide;
(E)-4-(3-(7-carbamoyl-1H-indol-4-yl)phenylamino)-4-oxobut-2-enoic acid;
4-(3-(N-isobutylacrylamido)phenyl)-1H-indole-7-carboxamide;
1-Acryloyl-1,2,3,6-tetrahydro-pyrrolo[2,3-e]indole-5-carboxylic acid amide;
4-acrylamido-1H-indole-7-carboxamide;
4-(3-(N-(cyanomethyl)sulfamoyl)phenyl)-1H-indole-7-carboxamide;
4-(3-acrylamidophenyl)-1H-pyrrolo[3,2-c]pyridine-7-carboxamide;
4-(3-acrylamido-2-methylphenyl)-1H-pyrrolo[3,2-c]pyridine-7-carboxamide;
4-(3((2-oxopropanamido)methyl)phenyl)-1H-indole-7-carboxamide;
4-(3-acrylamidophenyl)-1H-indazole-7-carboxamide;
4-(3-acrylamido-2-methoxyphenyl)-1H-indole-7-carboxamide;
4-(3-acrylamido-2-fluorophenyl)-1H-indole-7-carboxamide;
4-(5-acrylamido-2-fluorophenyl)-1H-indole-7-carboxamide;
4-(3-acrylamido-4-fluorophenyl)-1H-indole-7-carboxamide;
4-(5-acrylamido-2-chlorophenyl)-1H-indole-7-carboxamide;
4-(5-acrylamido-2,4-difluorophenyl)-1H-indole-7-carboxamide;
4-(3-acrylamido-4-cyanophenyl)-1H-indole-7-carboxamide;
4-(3-acrylamido-2,6-difluorophenyl)-1H-indole-7-carboxamide;
4-(3-acrylamido-5-methylphenyl)-1H-indole-7-carboxamide;
4-(3-acrylamido-4-methylphenyl)-1H-indole-7-carboxamide;
4-(3-acrylamido-4-methoxyphenyl)-1H-indole-7-carboxamide;
4-(3-acrylamido-5-methoxyphenyl)-1H-indole-7-carboxamide;
4-(3-acrylamido-4-chlorophenyl)-1H-indole-7-carboxamide;
4-(5-acrylamido-2,3-difluorophenyl)-1H-indole-7-carboxamide;
4-(3-acrylamido-5-cyanophenyl)-1H-indole-7-carboxamide;
4-(3-acrylamido-2-cyanophenyl)-1H-indole-7-carboxamide;
4-(3-acrylamidophenyl)-2-vinyl-1H-indole-7-carboxamide;
4-(3-acrylamidophenyl)-2-ethyl-1H-indole-7-carboxamide;
4-(3-(2-(morpholinomethyl)acrylamido)phenyl)-1H-indole-7-carboxamide;
4-(3-(2-((dimethylamino)methyl)acrylamido)phenyl)-1H-indole-7-carboxamide;
(E)-4-(3-(4-(dimethylamino)but-2-enamido)-2-methylphenyl)-1H-pyrrolo[2,3-c]pyridine-7-carboxamide;
4-((1R,3S)-3-acrylamidocyclohexyl)-1H-indole-7-carboxamide;
4-(cis-3-acrylamidocyclohexyl)-1H-indole-7-carboxamide;
4-((1S,3S)-3-acrylamidocyclohexyl)-1H-indole-7-carboxamide;
4-(trans-3-acrylamidocyclohexyl)-1H-indole-7-carboxamide;

4-(cis-3-acrylamidocyclohexyl)-1H-indole-7-carboxamide;
4-(3-(2-(aminomethyl)acrylamido)phenyl)-1H-indole-7-carboxamide;
4-((1R,3S)-3-acrylamidocyclopentyl)-1H-indole-7-carboxamide;
4-(3-(2-((methylamino)methyl)acrylamido)phenyl)-1H-indole-7-carboxamide;
4-(3-acrylamidophenyl)-2-methyl-1H-indole-7-carboxamide;
4-((1S,3S)-3-acrylamidocyclopentyl)-1H-indole-7-carboxamide;
4-(3-acrylamidophenyl)-2-(2-ethoxyethyl)-1H-indole-7-carboxamide;
4-(3-acrylamidophenyl)-2-(2-hydroxyethyl)-1H-indole-7-carboxamide;
4-(1-acryloylpiperidin 3-yl)-2-(1-methyl-1H-pyrazol-4-yl)-1H-indole-7-carboxamide;
4-(3-acrylamido-2-methylphenyl)-2-(1-isopropyl-1H-pyrazol-4-yl)-1H-indole-7-carboxamide;
4-(3-(4-cyclopropylbenzamido)-2-methylphenyl)-2-(1-(methylsulfonyl)-1,2,3,6-tetrahydropyridin-4-yl)-1H-indole-7-carboxamide;
4-(2-methyl-3-(1-methylpiperidine-4-carboxamido)phenyl)-2-(1-(methylsulfonyl)-1,2,3,6-tetrahydropyridin-4-yl)-1H-indole-7-carboxamide;
4-(3-(N-(cyclopentylmethyl)acrylamido)phenyl)-1H-indole-7-carboxamide;
ethyl 4-(7-carbamoyl-4-(2-methyl-3-(4-oxoquinazolin-3(4H)-yl)phenyl)-1H-indol-2-yl)5,6-dihydropyridine-1(2H)-carboxylate;
(R)-4-(3-(4-oxoquinazolin-3(4H)-yl)piperidin-1-yl)-1H-indole-7-carbonitrile;
4-(2,6-dichlorobenzyl)-2-(p-tolyl)-1H-indole-7-carboxamide;
(E)-4-(3-(2-cyano-3-hydroxybut-2-enamido)phenyl)-1H-indole-7-carboxamide;
4-(cis-3-acrylamidocyclopentyl)-1H-indole-7-carboxamide;
4-(trans-3-acrylamidocyclopentyl)-1H-indole-7-carboxamide;
4-(trans-3-acrylamidocyclopentyl)-1H-indole-7-carboxamide;
4-((1-acryloylazetidin-3-yl)oxy)-1H-indole-7-carboxamide;
(S)-4-(1-(1-acryloylazetidin-3-yl)ethyl)-1H-indole-7-carboxamide;
(R)-4-(1-(1-acryloylazetidin-3-yl)ethyl)-1H-indole-7-carboxamide*;
4-((1-acryloylazetidin-3-yl)(methyl)amino)-1H-pyrrolo[2,3-c]pyridine-7-carboxamide;
(R)-4-(1-acryloylpiperidin-3-yl)-1H-indole-7-carboxamide*;
(S)-4-(1-acryloylpiperidin-3-yl)-1H-indole-7-carboxamide*;
(S)-4-(1-acryloylpiperidin-3-yl)-2-methyl-1H-indole-7-carboxamide;
(R)-4-(1-acryloylpiperidin-3-yl)-2-methyl-1H-indole-7-carboxamide;
(R)-4-(4-acryloylmorpholin-2-yl)-2-(1-methyl-1H-pyrazol-4-yl)-1H-indole-7-carboxamide;
(S)-4-(4-acryloylmorpholin-2-yl)-2-(1-methyl-1H-pyrazol-4-yl)-1H-indole-7-carboxamide;
(R)-4-(1-acryloylpyrrolidin-3-yl)-2-(6,7-dihydro-4H-pyrazolo[5,1-c][1,4]oxazin-2-yl)-1H-indole-7-carboxamide;
2-methyl-4-(methyl(1-propioloylazetidin-3-yl)amino)-1H-indole-7-carboxamide;
(S)-4-(1-acryloylpyrrolidin-3-yl)-2-(6,7-dihydro-4H-pyrazolo[5,1-c][1,4]oxazin-2-yl)-1H-indole-7-carboxamide;
(R)-4-(4-acryloyl-1,4-oxazepan-6-yl)-1H-pyrrolo[3,2-c]pyridine-7-carboxamide;
(S)-4-(4-acryloyl-1,4-oxazepan-6-yl)-1H-pyrrolo[3,2-c]pyridine-7-carboxamide;
(R)-4-(1-acryloylpiperidin-3-yl)-1H-pyrrolo[3,2-c]pyridine-7-carboxamide;
(S)-4-(1-acryloylpiperidin-3-yl)-1H-pyrrolo[3,2-c]pyridine-7-carboxamide;
(R)-7-(1-acryloylppiperidin-3-yl)-2-(1-methyl-1H-pyrazol-4-yl)thiazolo[5,4-c]pyridine-4-carboxamide;
(S)-7-(1-acryloylpiperidin-3-yl)-2-(1-methyl-1H-pyrazol-4-yl)thiazolo[5,4-c]pyridine-4-carboxamide;
(S)-4-(4-acryloyl-1,4-oxazepan-6-yl)-1H-indole-7-carboxamide;
4-((3S,5R)-1-acryloyl-5-(hydroxymethyl)piperidin-3-yl)-1H-indole-7-carboxamide;
4-((3S,5S)-1-acryloyl-5-(hydroxymethyl)piperidin-3-yl)-1H-indole-7-carboxamide;
4-((3R,5S)-1-acryloyl-5-(hydroxymethyl)piperidin-3-yl)-1H-indole-7-carboxamide;
4-((3R,5R)-1-acryloyl-5-(hydroxymethyl)piperidin-3-yl)-1H-indole-7-carboxamide;
(R)-4-(1-acryloylpyrrolidin-3-yl)-2-(1-methyl-1H-pyrazol-4-yl)-1H-indole-7-carboxamide;
(S)-4-(1-acryloylpyrrolidin-3-yl)-2-(1-methyl-1H-pyrazol-4-yl)-1H-indole-7-carboxamide;
4-((1R,3R)-3-acrylamido cyclopentyl)-1H-indole-7-carboxamide;
(S)-4-(1-acryloylpiperidin-3-yl)-1H-pyrrolo[2,3-c]pyridine-7-carboxamide;
(R)-4-(1-acryloylpiperidin-3-yl)-1H-pyrrolo[2,3-c]pyridine-7-carboxamide;
(R)-2-methyl-4-(1-propionylpyrrolidin-3-yl)-1H-indole-7-carboxamide;
(S)-2-methyl-4-(1-propionylpyrrolidin-3-yl)-1H-indole-7-carboxamide;
4-((1-acryloylazetidin-3-yl)(methyl)amino)-2-(isochroman-7-yl)-1H-indole-7-carboxamide;
4-((1-acryloylazetidin-3-yl)(methyl)amino)-2-(6,7-dihydro-4H-pyrazolo[5,1-c][1,4]oxazin-2-yl)-1H-indole-7-carboxamide;
4-((1-acryloylazetidin-3-yl)(methyl)amino)-2-(4,4-difluorocyclohex-1-en-1-yl)-1H-indole-7-carboxamide;
4-((1-acryloylazetidin-3-yl)(methyl)amino)-2-(4-(methylsulfonyl)cyclohex-1-en-1-yl)-1H-indole-7-carboxamide;
4-((1-acryloylazetidin-3-yl)(methyl)amino)-2-(6-morpholinopyridin-3-yl)-1H-indole-7-carboxamide;
4-((1-acryloylazetidin-3-yl)(methyl)amino)-2-(7,8-dihydro-5H-pyrano[4,3-b]pyridin-3-yl)-1H-indole-7-carboxamide;
4-((1-acryloylazetidin-3-yl)(methyl)amino)-2-(chroman-7-yl)-1H-indole-7-carboxamide;
4-((1-acryloylazetidin-3-yl)(methyl)amino)-2-(5-(morpholino methyl)pyridin-2-yl)-1H-indole-7-carboxamide;
4-((1-acryloylazetidin-3-yl)(methyl)amino)-2-(1-methyl-1H-pyrazol-4-yl)-1H-indole-7-carboxamide;
4-((1-acryloylazetidin-3-yl)(methyl)amino)-2-(3,4-dihydro-2H-benzo[b][1,4]oxazin-6-yl)-1H-indole-7-carboxamide;
4-((1-acryloylazetidin-3-yl)(methyl)amino)-2-(1-methyl-1H-pyrazol-5-yl)-1H-indole-7-carboxamide;
4-((1-acryloylazetidin-3-yl)(methyl)amino)-2-(2-ethyl-1,2,3,4-tetrahydroisoquinolin-6-yl)-1H-indole-7-carboxamide;
4-((1-acryloylazetidin-3-yl)(methyl)amino)-2-(1,3-dimethyl-1H-pyrazol-4-yl)-1H-indole-7-carboxamide;

4-((1-acryloylazetidin-3-yl)(methyl)amino)-2-(1,1-dioxido-tetrahydro-2H-thiopyran-4-yl)-1H-indole-7-carboxamide;

4-((1-acryloylazetidin-3-yl)(methyl)amino)-2-(1-propylpiperidin-4-yl)-1H-indole-7-carboxamide;

4-((1-acryloylazetidin-3-yl)(methyl)amino)-2-(tetrahydrofuran-3-yl)-1H-indole-7-carboxamide;

4-((1-acryloylazetidin-3-yl)(methyl)amino)-2-(3-hydroxyoxetan-3-yl)-1H-indole-7-carboxamide;

4-((1-acryloylazetidin-3-yl)(methyl)amino)-2-methyl-1H-indole-7-carboxamide;

(R)-4-(4-acryloyl-1,4-oxazepan-6-yl)-1H-indole-7-carboxamide;

(S)-4-(1-acryloylpyrrolidin-3-yl)-2-methyl-1H-indole-7-carboxamide*;

(R)-4-(1-acryloylpyrrolidin-3-yl)-2-methyl-1H-indole-7-carboxamide*;

4-((1R,5S)-6-acryloyl-3,6-diazabicyclo [3.2.0]heptan-3-yl)-1H-indole-7-carboxamide;

4-((1S,5R)-6-acryloyl-3,6-diazabicyclo [3.2.0]heptan-3-yl)-1H-indole-7-carboxamide;

(R)-4-(1-(1-acryloylazetidin-3-yl)ethyl)-1H-pyrrolo[3,2-c]pyridine-7-carboxamide;

(S)-4-(1-(1-acryloylazetidin-3-yl)ethyl)-1H-pyrrolo[3,2-c]pyridine-7-carboxamide;

4-((1-acryloylazetidin-3-yl)amino)-1H-pyrrolo[2,3-c]pyridine-7-carboxamide;

4-((1-acryloyl-3-methylazetidin-3-yl)(methyl)amino)-1H-indole-7-carboxamide;

4-((1-cyanoazetidin-3-yl)(methyl)amino)-2-methyl-1H-indole-7-carboxamide;

4-(2-chloro-6-fluorobenzyl)-2-p-tolyl-1H-indole-7-carboxamide;

(S)-4-((1-acryloylazetidin-3-yl)(methyl)amino)-2-(tetrahydrofuran-3-yl)-1H-indole-7-carboxamide;

(R)-4-((1-acryloylazetidin-3-yl)(methyl)amino)-2-(tetrahydrofuran-3-yl)-1H-indole-7-carboxamide;

(S)-4-(4-acryloyl-1,4-oxazepan-6-yl)-1H-pyrrolo[2,3-c]pyridine-7-carboxamide;

(R)-4-(4-acryloyl-1,4-oxazepan-6-yl)-1H-pyrrolo[2,3-c]pyridine-7-carboxamide;

(S)-4-(1-acryloylpiperidin-3-yl)-2-(1-methyl-1H-pyrazol-4-yl)-1H-indole-7-carboxamide; or (R)-4-(1-acryloylpiperidin-3-yl)-2-(1-methyl-1H-pyrazol-4-yl)-1H-indole-7-carboxamide.

In a twenty-first embodiment the invention provides a method of treating a disease comprising administering a therapeutically effective amount of a compound of claim 1 to a patient in need thereof.

In a twenty-second embodiment the invention provides a compound according to any of foregoing embodiments, wherein the disease is rheumatoid arthritis, juvenile rheumatoid arthritis, osteoarthritis, Crohn's disease, inflammatory bowel disease, ulcerative colitis, psoriatic arthritis, psoriasis, ankylosing spondylitis, interstitial cystitis, asthma, systemic lupus erythematosus, lupus nephritis, B cell chronic lymphocytic lymphoma, multiple sclerosis, chronic lymphocytic leukemia, small lymphocytic lymphoma, mantle cell lymphoma, B-cell non-Hodgkin's lymphoma, activated B-cell like diffuse large B-cell lymphoma, multiple myeloma, diffuse large B-cell lymphoma, follicular lymphoma, hairy cell leukemia or Lymphoblastic lymphoma.

In a twenty-third embodiment the invention provides kit comprising a packaged product comprising components with which to administer a compound a compound according to any of foregoing embodiments for treatment of an autoimmune disorder.

In a twenty-fourth embodiment the invention provides a kit according to the twenty-third embodiment, wherein the packaged product comprises a compound of claim 1 and instructions for use.

In a twenty-fifth embodiment the invention provides a pharmaceutical composition comprising a compound according to any of the first through twentieth embodiments and one or more pharmaceutically acceptable excipients.

DETAILED DESCRIPTION OF THE INVENTION

Protein kinases are a broad and diverse class, of over 500 enzymes, that include oncogenes, growth factors receptors, signal transduction intermediates, apoptosis related kinases and cyclin dependent kinases. They are responsible for the transfer of a phosphate group to specific tyrosine, serine or threonine amino acid residues, and are broadly classified as tyrosine and serine/threonine kinases as a result of their substrate specificity.

The protein kinases represent a large family of proteins that play a central role in the regulation of a wide variety of cellular processes and maintenance of cellular function. A partial, non-limiting, list of these kinases include: non-receptor tyrosine kinases such as the Tec family (BTK, ITK, Tec, ETK/BMX & RLK/TXK), Janus kinase family (Jak1, Jak2, Jak3 and Tyk2); the fusion kinases, such as BCR-Abl, focal adhesion kinase (FAK), Fes, Lck and Syk; receptor tyrosine kinases such as epidermal growth factor receptor (EGFR), the platelet-derived growth factor receptor kinase (PDGF-R), the receptor kinase for stem cell factor, c-kit, the hepatocyte growth factor receptor, c-Met, and the fibroblast growth factor receptor, FGFR3; and serine/threonine kinases such as b-RAF, mitogen-activated protein kinases (e.g., MKK6) and SAPK2β. Aberrant kinase activity has been observed in many disease states including benign and malignant proliferative disorders as well as diseases resulting from inappropriate activation of the immune and nervous systems. The novel compounds of this invention inhibit the activity of one or more protein kinases and are, therefore, expected to be useful in the treatment of kinase-mediated diseases.

Bruton's tyrosine kinase (BTK) is a non-receptor tyrosine kinase with a key role in immunoreceptor signaling (BCR, FcεR, FcγR, DAP12, Dectin-1, GPVI, etc.) in a host of hematopoietic cells including B cells, platelets, mast cells, basophils, eosinophils, macrophages and neutrophils as well as osteoclasts involved in bone destruction (for reviews, see Brunner et al., 2005 *Histol. Histopathol.*, 20:945; Mohamed et al., 2009 *Immunol. Rev.*, 228:58). Mutations in BTK are known to lead to X-linked agammaglobulinemia (XLA) in humans and X-linked immunodeficiency (Xid) in mice, which are characterized by limited B-cell production & reduced antibody titers (Lindvall et al., 2005 *Immunol. Rev.*, 203:200). The combined action of BTK in multiple cell types makes it an attractive target for autoimmune disease. BTK is related with sequence homology to other Tec family kinases (ITK, Tec, ETK/BMX & RLK/TXK).

In B-lymphocytes, BTK is required for B-cell development and for Ca2+ mobilization following B-cell receptor (BCR) engagement (Khan et al., 1995 *Immunity* 3:283; Genevier et al., 1997 *Clin. Exp. Immun.*, 110:286) where it is believed to be downstream of Src family kinases (such as Lyn), Syk & PI3K. BTK has been shown to be important for both thymus-dependent and thymus-independent type 2 responses to antigens (Khan et al., *Immunity* 1995; 3:283). In mast cells, studies using BTK mouse knock-outs (Hata et al., 1998 *J. Exp. Med.,* 187:1235; Schmidt et al., 2009 *Eur. J. Immun.,* 39:3228) indicate a role for BTK in FcεRI induced signaling, histamine release & production of cytokines such as TNF, IL-2, & IL-4. In platelets, BTK is important for signaling through the glycoprotein VI (GPVI) receptor that responds to collagen and has been shown to promote platelet aggregation and contribute to cytokine production from fibroblast-like synoviocytes (Hsu et al., 2013 *Immun. Letters* 150:97). In monocytes and macrophages, the action of BTK is invoked in FcγRI induced signaling and may also have role in Toll-Like Receptor-induced cytokine responses including TLR2, TLR4, TLR8 & TLR9 (Horwood et al., 2003 *J. Exp. Med.,* 197:1603; Horwood et al., 2006 *J. Immunol.,* 176:3635; Perez de Diego et al., 2006 *Allerg. Clin. Imm.,* 117:1462; Doyle et al., 2007 *J. Biol. Chem.,* 282:36959, Hasan et al., 2007 *Immunology,* 123:239; Sochorava et al., 2007 *Blood,* 109:2553; Lee et al., 2008, *J. Biol. Chem.,* 283:11189).

Therefore, inhibition of BTK is expected to intervene at several critical junctions of the inflammatory reactions resulting in an effective suppression of autoimmune response. As such diseases involving B-cell receptor activation, antibody-Fc receptor interactions & GPVI receptor signaling may be modulated by treatment with BTK inhibitors. BTK inhibition is likely to act on both the initiation of autoimmune disease by blocking BCR signaling and the effector phase by abrogation of FcR signaling on macrophages, neutrophils, basophils, and mast cells. Furthermore, blocking BTK would provide additional benefit via inhibition of osteoclast maturation and therefore attenuate the bone erosions & overall joint destruction associated with rheumatoid arthritis Inhibiting BTK may be useful in treating a host of inflammatory and allergic diseases for example (but not limited to), rheumatoid arthritis (RA), systemic lupus erythematosus (SLE), multiple sclerosis (MS) and type I hypersensitivity reactions such as allergic rhinitis, allergic conjunctivitis, atopic dermatitis, allergic asthma and systemic anaphylaxis. For a review on targeting BTK as a treatment for inflammatory disorders and autoimmunity as well as leukemias and lymphomas, see Uckun & Qazi 2010 *Expert Opin Ther Pat* 20:1457. Because BTK is highly expressed in cancers of the hematopoietic system & BTK-dependent signaling in believed to be disregulated there, BTK inhibitors are expected to be useful treatments for B-cell lymphomas/leukemias & other oncologic disease— for example (but not limited to) acute lymphoblastic leukemia (ALL), chronic lymphocytic leukemia (CLL), non-Hodgkin's lymphoma (NHL), small lymphocytic lymphoma (SLL), and acute myeloid leukemia (for review, see Buggy & Elias 2012 *Int Rev Immunol.* 31:119). Taken together, BTK inhibitors provide a strong method to treat a host of inflammatory diseases and immunological disorders as well as hematologic cancers.

All kinases bind a common molecule, ATP, and therefore have structurally similar binding pockets. Therefore, one of the challenges for any kinase inhibitor is that they are prone to inhibit more than one kinase due to the homology of the binding pocket. For example, staurosporine, a well characterized promiscuous kinase inhibitor, has been shown to inhibit at least 253 with a $k_d$ of <3 μM kinases from the human kinome (see Nature Biotechnology, 208, 26, p. 127). Additionally, several marketed kinase inhibitors are known to inhibit more than one intended kinase, for example Imatinib (Gleevec®) targets ABL, ARG, PDGFR-α/β and c-KIT kinases, sorafenib (Nexavar®) targets B-RAF, VEG-FRs, PDGFR-α/β, FLT3 and c-KIT and sunitinib (Sutent®) targets VEGFR, PDGFR, CSF1R, FLT3 and c-KIT (Nature Reviews Drug Discovery 2011, 10, 111).

Inhibition of certain kinases in the human kinome are known to have undesired effects when used as pharmaceutical treatment. For instance, a number of kinase targets have been implicated in playing a role in the cardiotoxicity profiles for kinase inhibitors that are currently on the market. These kinases can include, but not limited to, VEGFR2, PI3K, AKT, PDGFR-α/β, AMPK, GSK3, ERKs, CDK2, Aurora, PLK, INK, CAMKII<PDK1, mTOR, LKB1, CAMKKβ, MEK1/2, PKA, PKCα, RAF1, B-RAF, EGFR, ERBB2, c-K1t, ABL, ARG, JAK2, FAK, DMPK, LTK, ROCK, LKB1, LDB3, PIM, GRK2, GRK5, ASK1, and PTEN (see *Nature Reviews Drug Discovery* 2011, 10:111). One example from a marketed kinase inhibitor is that in clinical trials with sunitinib, patients were found to be at increased risk for hypertension (see *The Lancet* 2006, 368: 1329; and *J. Clin. Oncol.* 2009, 27:3584). Subsequent research on the mechanism for the increased hypertension suggest that while PDGFR and VEGFR may be playing a role, off-target kinase inhibition, such as AMPK, may also be contributing to sunitinib's increased risk for hypertension (*Curr. Hypertens. Rep.* 2011, 13:436). Additionally, there is a patent application, US 2011/0212461, that has been filed that is a method for the prediction of cardiotoxicity based on the activity versus a list of kinases including CSF1R, KIT, FYN, PDGFR beta, FGR, LCK, Ephrin Receptor B2, FRK, ABL1, PDGFR1 alpha, HCK, ABL2, LYN, ZAK, YES1, MAP4K4, PKN1, BRAF, DDR2, MAP4K5 and STK24. Therefore, identification of kinase inhibitors with a selective profile Btk kinase are desirable. The compounds of this invention are selective for the inhibition of Btk over other kinases.

Many of the kinases, whether a receptor or non-receptor tyrosine kinase or a S/T kinase have been found to be involved in cellular signaling pathways involved in numerous pathogenic conditions, including immunomodulation, inflammation, or proliferative disorders such as cancer.

Many autoimmune diseases and disease associated with chronic inflammation, as well as acute responses, have been linked to excessive or unregulated production or activity of one or more cytokines.

The compounds of the invention are also useful in the treatment of rheumatoid arthritis, asthma, allergic asthma, osteoarthritis, juvenile arthritis, lupus, lupus nephritis, systemic lupus erythematosus (SLE), ankylosing spondylitis, an ocular condition, interstitial cystitis, a cancer, a solid tumor, a sarcoma, fibrosarcoma, osteoma, melanoma, retinoblastoma, a rhabdomyosarcoma, glioblastoma, neuroblastoma, teratocarcinoma, hypersensitivity reactions, hyperkinetic movement disorders, hypersensitivity pneumonitis, hypertension, hypokinetic movement disorders, aordic and peripheral aneuryisms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile spinal muscular atrophy, lymphoma, myeloma, leukaemia, malignant ascites, hematopoietic cancers, a diabetic condition such as insulin-dependent diabetes mellitus glaucoma, diabetic retinopathy or microangiopathy, sickle cell anaemia, chronic inflammation, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, progressive supranucleo palsy, primary pulmonary hypertension, radiation therapy, Raynaud's phenomenon, Raynaud's disease, Refsum's disease, regular narrow QRS tachycardia, renovascular hypertension, restrictive cardiomyopathy, sarcoma, senile chorea, senile dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, inflammatory bowel disease, diabetes, diabetes mellitus, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, *yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, H is bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, *pneumocystis carinii* pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthritis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, or age-related macular degeneration. In addition, these compounds can be used as active agents against hyperproliferative disorders such as thyroid hyperplasia (especially Grave's disease), and cysts (such as hypervascularity of ovarian stroma characteristic of polycystic ovarian syndrome (Stein- Leventhal syndrome) and polycystic kidney disease since such diseases require a proliferation of blood vessel cells for growth and/or metastasis.

In yet other embodiments, the compounds described herein can be used to treat a cancer, e.g., B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplamacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt's lymphoma/leukemia, lymphomatoid granulomatosis, pancreatic cancer, solid or hematological tumors, a benign or malignant tumor, carcinoma of the brain, kidney (e.g., renal cell carcinoma (RCC)), squamous cell carcinoma, salivary gland carcinoma, liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia.

In yet other embodiments, the compounds described herein can be used to treat Behcet's disease, osteoporosis, bone cancer, and bone metastasis, systemic sclerosis, contact dermatitis and other eczematous dermatitis, seborrhoetic dermatitis, lichen planus, epidermolysis bullosa, angiodermas, vasculitides, cutaneous eosinophilias, or vernal conjunctivitis.

In yet other embodiments, the compounds described herein can be used to treat those conditions characterized by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung, and idiopathic interstitial pneumonia.

Compounds of Formula (I) of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the compounds of this invention. Non-limiting examples of therapeutic agents for rheumatoid arthritis with which a compound of Formula (I) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, MMP-13 and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (U.S. Pat. No. 6,090,382, HUMIRA™), CA2 (REMICADE™), SIMPONI™ (golimumab), CIMZIA™, ACTEMRA™, CDP 571, and soluble p55 or p75 TNF receptors, derivatives, thereof, (p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination is non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (I) of the invention may also be combined with agents, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, JAK1, JAK2, JAK3, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™) and p55TNFRIgG (Lenercept), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. Preferred combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, p38 or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-IRI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, D2E7 (U.S. Pat. No. 6,090,382, HUMIRA™), CA2 (REMICADE™), CDP 571, TNFR-Ig constructs, (p75TNFRIgG (ENBREL™) and p55TNFRIgG (LENERCEPT™) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

Preferred examples of therapeutic agents for multiple sclerosis in which a compound of Formula (I) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of Formula (I) may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/ Biogen), interferon gamma antagonists and IL-4 agonists.

Non-limiting examples of therapeutic agents for ankylosing spondylitis with which a compound of Formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™).

Non-limiting examples of therapeutic agents for asthma with which a compound of Formula (I) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/ pseudoephed, phenylephrine/cod/promethazine, codeine/ promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/ chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for HCV with which a compound of Formula (I) can be combined include the following: Interferon-alpha-2α, Interferon-alpha-2β, Interferon-alpha con1, Interferon-alpha-n1, pegylated interferon-alpha-2α, pegylated interferon-alpha-2β, ribavirin, peginterferon alfa-2b+ribavirin, ursodeoxycholic acid, glycyrrhizic acid, thymalfasin, Maxamine, VX-497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of Formula (I) (can be combined include the following: prednisone, azathioprine, albuterol, colchicine, albuterol sulfate, digoxin, gamma interferon, methylprednisolone sodium succinate, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for myocardial infarction with which a compound of Formula (I) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hydrochloride/magnesium carbonate, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of Formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (U.S. Pat. No. 6,090,382, HUMIRA™), and efalizumab.

Non-limiting examples of therapeutic agents for restenosis with which a compound of Formula (I) can be combined include the following: sirolimus, paclitaxel, everolimus, tacrolimus, ABT-578, and acetaminophen.

Non-limiting examples of therapeutic agents for sciatica with which a compound of Formula (I) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol HCl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene n-pap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, and temazepam.

Preferred examples of therapeutic agents for SLE (Lupus) with which a compound of Formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) (can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™).

In this invention, the following definitions are applicable:

A "therapeutically effective amount" is an amount of a compound of Formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula (I) which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of Formula (I) and their salts may exist in more than one crystal form and the present invention includes each crystal form and mixtures thereof.

Certain compounds of Formula (I) and their salts may also exist in the form of solvates, for example hydrates, and the present invention includes each solvate and mixtures thereof.

Certain compounds of Formula (I) may contain one or more chiral centers, and exist in different optically active forms. When compounds of Formula (I) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of Formula (I) (and mixtures thereof.

Certain compounds of Formula (I) may exist in different tautomeric forms or as different geometric isomers, and the present invention includes each tautomer and/or geometric isomer of compounds of Formula (I) and mixtures thereof.

Certain compounds of Formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) and mixtures thereof.

Certain compounds of Formula (I) may exist in zwitterionic form and the present invention includes each zwitterionic form of compounds of Formula (I) (and mixtures thereof.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents wherein the free hydrogen is replaced by $(C_1-C_4)$alkyl, $(C_1-C_{12})$ alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as (β-dimethylaminoethyl), carbamoyl-$(C_1-C_2)$alkyl, N,N-di$(C_1-C_2)$-alkylcarbamoyl-$(C_1-C_2)$alkyl and piperidino-, pyrrolidino- or morpholino$(C_2-C_3)$alkyl.

Other exemplary pro-drugs release an alcohol of Formula (I) wherein the free hydrogen of the hydroxyl substituent (e.g., $R^1$ contains hydroxyl) is replaced by $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_{12})$alkoxycarbonyloxymethyl, N—$(C_1-C_6)$alkoxycarbonylamino-methyl, succinoyl, $(C_1-C_6)$alkanoyl, α-amino$(C_1-C_4)$alkanoyl, arylactyl and α-aminoacyl, or α-aminoacyl-α-aminoacyl wherein said α-aminoacyl moieties are independently any of the naturally occurring L-amino acids found in proteins, $P(O)(OH)_2$, —$P(O)(O(C_1-C_6)alkyl)_2$ or glycosyl (the radical resulting from detachment of the hydroxyl of the hemiacetal of a carbohydrate).

As used herein, the term "bridged $(C_5-C_{12})$ cycloalkyl group" means a saturated or unsaturated, bicyclic or polycyclic bridged hydrocarbon group having two or three $C_3-C_{10}$ cycloalkyl rings. Non bridged cycloalkyls are excluded. Bridged cyclic hydrocarbon may include, such as bicyclo [2.1.1]hexyl, bicyclo [2.2.1]heptyl, bicyclo [2.2.2] octyl, bicyclo [3.2.1]octyl, bicyclo [4.3.1]decyl, bicyclo [3.3.1]nonyl, bornyl, bornenyl, norbornyl, norbornenyl, 6,6-dimethylbicyclo [3.1.1]heptyl, tricyclobutyl, and adamantyl.

As used herein the term "bridged $(C_2-C_{10})$ heterocyclyl" means bicyclic or polycyclic aza-bridged hydrocarbon groups and may include azanorbornyl, quinuclidinyl, isoquinuclidinyl, tropanyl, azabicyclo [3.2.1]octanyl, azabicyclo [2.2.1]heptanyl, 2-azabicyclo [3.2.1]octanyl, azabicyclo [3.2.1]octanyl, azabicyclo [3.2.2]nonanyl, azabicyclo [3.3.0]nonanyl, and azabicyclo [3.3.1]nonanyl.

The term "heterocyclic," "heterocyclyl" or "heterocyclylene," as used herein, include non-aromatic, ring systems, including, but not limited to, monocyclic, bicyclic, tricyclic and spirocyclic rings, which can be completely saturated or which can contain one or more units of unsaturation, for the avoidance of doubt, the degree of unsaturation does not result in an aromatic ring system) and have 5 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, indolinyl, isoindolinyl, morpholinyl, piperazinyl, piperidinyl, pyrrolidinyl, quinuclidinyl, thiomorpholinyl, tetrahydropyranyl, tetrahydrofuranyl, tetrahydroindolyl, thiomorpholinyl and tropanyl.

The term "heteroaryl" or "heteroarylene" as used herein, include aromatic ring systems, including, but not limited to, monocyclic, bicyclic and tricyclic rings, and have 5 to 12 atoms including at least one heteroatom, such as nitrogen, oxygen, or sulfur. For purposes of exemplification, which should not be construed as limiting the scope of this invention: azaindolyl, benzo[b]thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indazolyl, isoxazolyl, isothiazolyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo [3,4-d]pyrimidinyl, quinolinyl, quinazolinyl, triazolyl, thiazolyl, thiophenyl, tetrazolyl, thiadiazolyl, thienyl, 6H-pyrrolo[2,3-e][1,2,4]triazolo[4,3-a]pyrazinyl, 6H-imidazo[1,5-a]pyrrolo[2,3-e]pyrazinyl, 1,6-dihydropyrazolo[3,4-d] pyrrolo[2,3-b]pyridine, 3H-3,4,6,8a-tetraaza-asindacenyl, 3H-imidazo[1,2-a]pyrrolo[2,3-e]pyrazinyl, pyrazolo[3,4-d] pyrrolo[2,3-b]pyridinyl, 1,6-dihydro-1,2,5,6-tetraaza-as-indacenyl, 3H-3,4,8a-triaza-as-indacenyl, 6H-3-oxa-2,5,6-triaza-as-indacenyl, 3,6-dihydro-2,3,6-tetraaza-as-indacenyl, 1,6-dihydro-dipyrrolo[2,3-b;2'3'-d]pyridinyl, 6H-3-thia-2,5, 6-triaza-as-indacenyl or 1,6-dihydroimidazo[4,5-d]pyrrolo [2,3-b]pyridine.

As used herein, "alkyl," "alkylene" or notations such as "$(C_1-C_8)$" include straight chained or branched hydrocarbons which are completely saturated. Examples of alkyls are methyl, ethyl, propyl, isopropyl, butyl, pentyl, hexyl and isomers thereof. As used herein, "alkenyl," "alkenylene," "alkynylene" and "alkynyl" means $C_2-C_8$ and includes straight chained or branched hydrocarbons which contain one or more units of unsaturation, one or more double bonds for alkenyl and one or more triple bonds for alkynyl.

As used herein, "aromatic" groups (or "aryl" or "arylene" groups) include aromatic carbocyclic ring systems (e.g.

phenyl) and fused polycyclic aromatic ring systems (e.g. naphthyl, biphenyl and 1,2,3,4-tetrahydronaphthyl).

As used herein, "cycloalkyl" or "cycloalkylene" means $C_3$-$C_{12}$ monocyclic or multicyclic (e.g., bicyclic, tricyclic, spirocyclic, etc.) hydrocarbons that is completely saturated. Examples of a cycloalkyl group are cyclopropyl, cyclobutyl, cyclopentyl, and cyclohexyl.

As used herein, "cycloalkenyl" means $C_3$-$C_{12}$ monocyclic or multicyclic (e.g., bicyclic, tricyclic, spirocyclic, etc.) hydrocarbons that has one or more unsaturated bonds but does not amount to an aromatic group. Examples of a cycloalklenyl group are cyclopentenyl and cyclohexenyl.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: $(C_1$-$C_8)$alkyl groups, $(C_2$-$C_8)$alkenyl groups, $(C_2$-$C_8)$alkynyl groups, $(C_3$-$C_{10})$cycloalkyl groups, halogen (F, Cl, Br or I), halogenated $(C_1$-$C_8)$alkyl groups (for example but not limited to —$CF_3$), —O—$(C_1$-$C_8)$alkyl groups, =O, =$CH_2$, —OH, —$CH_2OH$, —$CH_2NH_2$, $(C_1$-$C_4)$alkyl-OH, —$CH_2CH_2OCH_2CH_3$, —S—$(C_1$-$C_8)$alkyl groups, —SH, $(C_1$-$C_8)$alkyl groups, —N$((C_1$-$C_8)$alkyl$)_2$ groups, —$NH_2$, —C(O)$NH_2$, —$CH_2NHC(O)(C_1$-$C_4)$alkyl, —$CH_2NHC(O)$$CH_2Cl$, —$CH_2NHC(O)CH_2CN$, —$CH_2NHC(O)CH_2CH_2N(CH_3)_2$, —$CH_2NHC(O)C(=CH_2)CH_3$, —$CH_2NHC(O)(C_2$-$C_4)$alkynyl, —$CH_2NHC(O)CH_2CH_2$-piperidinyl, —$(C_1$-$C_4)$alkyl-morpholinyl, —$CH_2NHC(O)CH_2O$-phenyl wherein the phenyl is optionally substituted with halogen, $(C_1$-$C_4)$alkoxy, —C(O)$(C_1$-$C_4)$alkyl, —C(O)$(C_1$-$C_4)$alkoxy, —C(O)N(H)$_2$, —C(O)N$(CH_3)_2$, —C(O)$(C_1$-$C_6)$hetero aryl, —N$(CH_3)_2$, —NHC(O) $(C_1$-$C_4)$ alkyl, —NHC(O)$(C_2$-$C_4)$alkenyl, —NHC(O)$CH_2CN$, —S(O)$_2(C_1$-$C_4)$ alkyl, —S(O)$_2$ $(C_1$-$C_6)$hetero aryl, —S(O)$_2(C_1$-$C_6)$ $(C_1$-$C_6)$heterocyclyl, 4-methylpiperazinecarbonyl, —$(C_1$-$C_4)$alkylC(O)$NH_2$, —C(O)NH$(C_1$-$C_8)$alkyl groups, —C(O)N$((C_1$-$C_8)$alkyl$)_2$, —C(O)N(H) $(C_3$-$C_8)$ cyclo alkyl groups, —C(O)$(C_1$-$C_4)$ alkoxy, —NHC(O)H, —NHC(O)$(C_1$-$C_8)$ alkyl groups, —NHC(O) $(C_3$-$C_8)$ cyclo alkyl groups, —N$((C_1$-$C_8)$ alkyl) C(O)H, —N$((C_1$-$C_8)$ alkyl)C(O)$(C_1$-$C_8)$ alkyl groups, —NHC(O)$NH_2$, —NHC(O)NH$(C_1$-$C_8)$ alkyl groups, —N$((C_1$-$C_8)$alkyl)C(O)$NH_2$ groups, —NHC(O)N$((C_1$-$C_8)$ alkyl)$_2$ groups, —N$((C_1$-$C_8)$ alkyl)C(O)N$((C_1$-$C_8)$ alkyl)$_2$ groups, —N$((C_1$-$C_8)$alkyl)C(O)NH$((C_1$-$C_8)$alkyl), —NHCH$_2$-heteroaryl, benzyl, —OCH$_2$-heteroaryl, —C(O)H, —C(O) $(C_1$-$C_8)$alkyl groups, —CN, —NO$_2$, —S(O)$(C_1$-$C_8)$ alkyl groups, S(O)$_2(C_1$-$C_8)$alkyl groups, —S(O)$_2$N$((C_1$-$C_8)$alkyl)$_2$ groups, —S(O)$_2$NH$(C_1$-$C_8)$alkyl groups, —S(O)$_2$ NH$(C_3$-$C_8)$cyclo alkyl groups, —S(O)$_2NH_2$ groups, —NHS(O)$_2(C_1$-$C_8)$alkyl groups, —N$((C_1$-$C_8)$alkyl)S(O)$_2(C_1$-$C_8)$alkyl groups, —$(C_1$-$C_8)$alkyl-O—$(C_1$-$C_8)$ alkyl groups, —O—$(C_1$-$C_8)$alkyl-O—$(C_1$-$C_8)$alkyl groups, —C(O)OH, —C(O)O$(C_1$-$C_8)$alkyl groups, NHOH, NHO$(C_1$-$C_8)$alkyl groups, —O-halogenated $(C_1$-$C_8)$alkyl groups (for example but not limited to —OCF$_3$), —S(O)$_2$-halogenated $(C_1$-$C_8)$alkyl groups (for example but not limited to —S(O)$_2CF_3$), —S-halogenated $(C_1$-$C_8)$alkyl groups (for example but not limited to —SCF$_3$), —$(C_1$-$C_6)$heterocyclyl (for example but not limited to pyrrolidine, tetrahydrofuran, pyran or morpholine), —$(C_1$-$C_6)$heteroaryl (for example but not limited to tetrazole, imidazole, furan, pyrazine or pyrazole),-phenyl, optionally substituted benzyl, —NHC(O)O—$(C_1$-$C_6)$alkyl groups, —N$((C_1$-$C_6)$alkyl)C(O)O—$(C_1$-$C_6)$ alkyl groups, —C(=NH)—$(C_1$-$C_6)$alkyl groups, —C(=NOH)—$(C_1$-$C_6)$alkyl groups, or —C(=N—O—$(C_1$-$C_6)$alkyl)-$(C_1$-$C_6)$alkyl groups.

The term "kit" as used herein refers to a packaged product comprising components with which to administer a compound of Formula (I) of the invention for treatment of an autoimmune disorder. The kit preferably comprises a box or container that holds the components of the kit. The box or container is affixed with a label or a Food and Drug Administration approved protocol. The box or container holds components of the invention which are preferably contained within plastic, polyethylene, polypropylene, ethylene, or propylene vessels. The vessels can be capped-tubes or bottles. The kit can also include instructions for administering a compound of Formula (I).

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counter ions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (e.g., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see, e.g., Fingl et al., 1975, in *The Pharmacological Basis of Therapeutics*, Ch. 1, p. 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

In some formulations it may be beneficial to use the compounds of the present invention in the form of particles of very small size, for example as obtained by fluid energy milling The use of compounds of the present invention in the manufacture of pharmaceutical compositions is illustrated by the following description. In this description the term "active compound" denotes any compound of the invention but particularly any compound which is the final product of one of the following Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

| Parts by weight | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of Formula (I) as a medicament.

A further aspect of the present invention provides the use of a compound of Formula (I) or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of Formula (I) to a mammal, particularly a human being, in need thereof.

ABBREVIATIONS

Ac Acetyl
AcOH Glacial acetic acid
Bn Benzyl
BnBr Benzyl bromide
Boc t-Butoxycarbonyl
Boc$_2$O Di-tert-butyl dicarbonate
BPO Benzoyl peroxide
br broad
t-BuOH tert-Butanol
$(CH_2O)_n$ paraformaldehyde
d Doublet
dba Dibenzylideneacetone
DCAD (E)-Bis(4-chlorobenzyl) diazene-1,2-dicarboxylate
DCE 1,2-Dichloroethane
DCM Dichloromethane (methylene chloride)
dd Doublet of doublets
DIEA N,N-Diisopropylethylamine
DMA Dimethylacetamide
DMAP 4-Dimethylaminopyridine
DME 1,2-Dimethoxyethane
DMF N,N-Dimethylformamide
DMSO Dimethyl sulfoxide
dppf 1,1'-Bis(diphenylphosphino)ferrocene
EDC 1-(3-dimethylaminopropyl)-3-ethylcarbodiimide
EDC.HCl N1-((ethylimino)methylene)-N3,N3-dimethyl-propane-1,3-diamine hydrochloride
equiv Equivalent(s) EtOAc Ethyl acetate
Et$_2$O Diethyl ether
EtOH Ethanol
Fmoc Fluorenylmethyloxycarbonyl
g Gram(s)
h Hour(s)
HATU 4-(3-Acrylamidophenyl)-2-ethyl-1H-indole-7-carboxamide
HOBt 1H-Benzo[d][1,2,3]triazol-1-ol hydrate
HPLC High-pressure liquid chromatography
IPA Isopropyl alcohol
KHMDS Potassium bis(trimethylsilyl)amide
KOAc Potassium acetate
KOt-Bu Potassium ter t-butoxide
LC/MS Liquid chromatography/mass spectrometry
LDA Lithium diisopropylamide
LiHMDS Lithium bis(trimethylsilyl)amide
m Multiplet
M Molar
MeCN Acetonitrile
MeOH Methyl alcohol
min Minute(s)
mmol Millimole
MS Mass spectrometry
MsCl Methanesulfonyl chloride
MTBE tert-Butyl methyl ether
n- Normal (nonbranched)
N Normal
NaBH(OAc)$_3$ Sodium triacetoxyhydroborate
NaHMDS Sodium bis(trimethylsilyl)amide
n-BuLi n-Butyl lithium
NaOt-Bu Sodium tert-butoxide
NBS N-bromosuccinimide
NCS N-chlorosuccinimide
NH$_4$OAc Ammonium acetate
NMP N-Methylpyrrolidinone
NMR Nuclear magnetic resonance
Pd$_2$dba$_3$ Tris(dibenzylideneacetone)dipalladium(0)
Pd(OAc)$_2$ Palladium(II) acetate
Pet ether petroleum ether
pH −log [H$^+$]
Pd(PPh$_3$)$_4$ Tetrakis(triphenylphosphine)palladium(0)
Pd(PPh$_3$)$_2$Cl$_2$ Bis(triphenylphosphine)palladium(II) chloride
PMB para-Methoxybenzyl
PPh$_3$ Triphenylphosphine
ppm Parts per million
PrOH Propanol
psi Pounds per square inch PyBOP ((1H-benzo[d][1,2,3]triazol-1-yl)oxy)tri(pyrrolidin-1-yl)phosphonium hexafluorophosphate(V)
$R_t$ Retention time
rt Room temperature
s Singlet
SEM 2-(Trimethylsilyl)ethoxymethyl
SEMCl 2-(Trimethylsilyl)ethoxymethyl chloride
SFC Supercritical fluid chromatography
SPE Solid phase extraction
t Triplet
t- Tertiary
TBAF tetrabutylammonium fluoride
TBME tert-Butyl methyl ether
TBDMS tert-Butyldimethylsilane
TBSCl tert-Butyldimethylsilyl chloride
TBTU 2-(1H-Benzo[d][1,2,3]triazol-1-yl)-1,1,3,3-tetramethylisouronium tetrafluoroborate
TEA Triethylamine
tert- Tertiary
tert-Butyl X-Phos 2-Di-tert-butylphosphino-2',4',6'-triisopropylbiphenyl
TFA Trifluoroacetic acid
THF Tetrahydrofuran
TLC Thin layer chromatography
TMS Trimethylsilyl
TMSCl Trimethylsilyl chloride
TMSI Trimethylsilyl iodide
TsCl p-Toluenesulfonyl chloride
UV Ultraviolet
wt % Weight percent
X-Phos 2-Dicyclohexylphosphino-2',4',6'-triisopropylbiphenyl General Synthetic Schemes Compounds of the invention may be prepared using the synthetic transformations illustrated in Schemes I-XVIII. Starting materials are commercially available, may be prepared by the procedures described herein, by literature procedures, or by procedures that would be well known to one skilled in the art of organic chemistry.

Methods for preparing 1H-indole-7-carboxamide compounds 9 of the invention are illustrated in Scheme I. In Scheme I, step a, commercially available 4-bromo-2-nitrobenzoic acid 1 is reacted with vinylmagnesium bromide via a Bartoli indole synthesis using methods known to one skilled in the art (for example Preparation #1, step A) to give indole 2. Indole 2 can be alkylated with methyl iodide (Scheme I, step b) to provide methyl 1H-indole-7-carboxylate 3 using methods known to one skilled in the art (for example Preparation #1, step B). The resulting indole 3 may be tosyl (Ts) protected (Scheme I, step c) using conditions such as those described in Preparation #1, step C or those described in Greene, T. W. and Wuts, P. G. M. "Protective Groups in Organic Synthesis, 3rd Edition", 1999, Wiley-Interscience; Larock, R. C. "Comprehensive Organic Transformations: A Guide to Functional Group Preparations, $2^{nd}$ edition", 1999, Wiley-VCH. In step d, directed lithiation of methyl 4-bromo-1-tosyl-1H-indole-7-carboxylate 4 followed by trapping of the anion with iodine yields methyl 4-bromo-2-iodo-1H-indole-7-carboxylates 5 using conditions such as those described in Preparation #1 step D. Tosyl protected methyl 4-bromo-2-iodo-1H-indole-7-carboxylates 5 may be hydrolyzed and deprotected under aqueous base conditions in one step e to give 4-bromo-2-iodo-1H-indole-7-carboxylic acid 6 using conditions such as those described in Preparation #1, step E or known to one skilled in the art (for example, the books from Larock, R. C. or Greene, T. W. and Wuts, P. G. M. referenced above). In step f, 4-bromo-2-iodo-1H-indole-7-carboxylic acid 6 may be converted to a primary amide 7 as shown using conditions such as those described in General Procedure D. The 4-bromo-2-iodo-1H-indole-7-carboxamide 7 may undergo a variety of reactions known to one skilled in the art (for example, Larock, R. C. referenced above) including, but not limited to, Suzuki or Stille coupling reactions such as those described in General Procedure A and Example #22, step A. Alternatively, in step i, the tosyl protected indoles 5 may undergo a variety of reactions known to one skilled in the art (for example, Larock, R. C. referenced above) including, but not limited to, Suzuki or Stille coupling reactions described by General Procedure A (for example Preparation #15 step A). Hydrolysis of esters 10 gives acids 11 (Scheme I, step j) using well known conditions such as those described in Preparation #15, step B or General Procedure C. In step k, carboxylic acid 11 may be coverted to primary amides 12 as shown using conditions such as those described in General Procedure D. Removal of the sulfonamide protecting group of indoles 12 may be accomplished using conditions such as those described in General Procedure N, or by methods known to one skilled in the art (for example, Larock, R. C. or Greene, T. W. and Wuts, P. G. M. referenced above) to give indoles 8 (Scheme I, step 1). Indoles 8 are reacted with a boronate ester or boronic acid, either commercially available or prepared by methods known to one skilled in the art (see, for example, Larock, R. C. "Comprehensive Organic Transformations: A Guide to Functional Group Preparations, $2^{nd}$ edition", 1999, Wiley-VCH or General Procedure P), using Suzuki coupling conditions, such as those described by General Procedure A, to give 1H-indole-7-carboxamide compounds 9. Alternatively, in step h, indoles 8 may undergo a variety of reactions known to one skilled in the art (for example, Larock, R. C. referenced above) including, but not limited to, Buchwald or Negishi coupling conditions as described by General Procedures T and U. Further functionalization of the R" group in indoles 9 can be performed, if desired, using reactions known to one skilled in the art (for example, Larock, R. C. referenced above). For example, indoles 9 containing a double bond may be reduced to saturated systems using hydrogenation conditions such as those described in General Procedure L. Ethers can be prepared from indoles 9 containing an alcohol using condition such as those described in General Procedure Q. In addition amides, ureas, sulfonamides, aryl amines, heteroaryl amines, or sulfonyl ureas can be prepared from indoles 9 containing a primary or secondary amine (for example General Procedures D, E, I, H, and J). Also, deprotection of indoles 9 containing a protecting group in either R' or R" can be performed using conditions such as those described in Greene, T. W. and Wuts, P. G. M. referenced above or in General Procedures G, M, or N. For example, for R" containing a TBDMS-protected alcohol, the protecting group can be removed to yield an unprotected alcohol (for example General Procedure M) and the deprotected compounds 9 may then be reacted further as described above. Alternatively, compound 4 may first undergo a coupling reaction in step m, including but not limited to, such as Suzuki, Buchwald, or Negishi using conditions as described b General Procedures A, T and U to give compounds 107 followed by an iodination reaction as illustrated in General Procedure Y to give compounds 108 (step n). Indoles 108 may undergo a variety of reactions known to one skilled in the art (for example, Larock, R. C. referenced above) including, but not limited to, Suzuki or Stille coupling reactions such as those described in General Procedure A to give compounds 109. One can then envisage that compounds 109 can undergo hydrolysis, amidation and de-tosylation reactions similar to steps j, k and I to arrive at compounds 9.

step h, indole 14 may undergo a variety of reactions known to one skilled in the art including, but not limited to, Suzuki or Stille coupling reactions such as those described in Scheme I

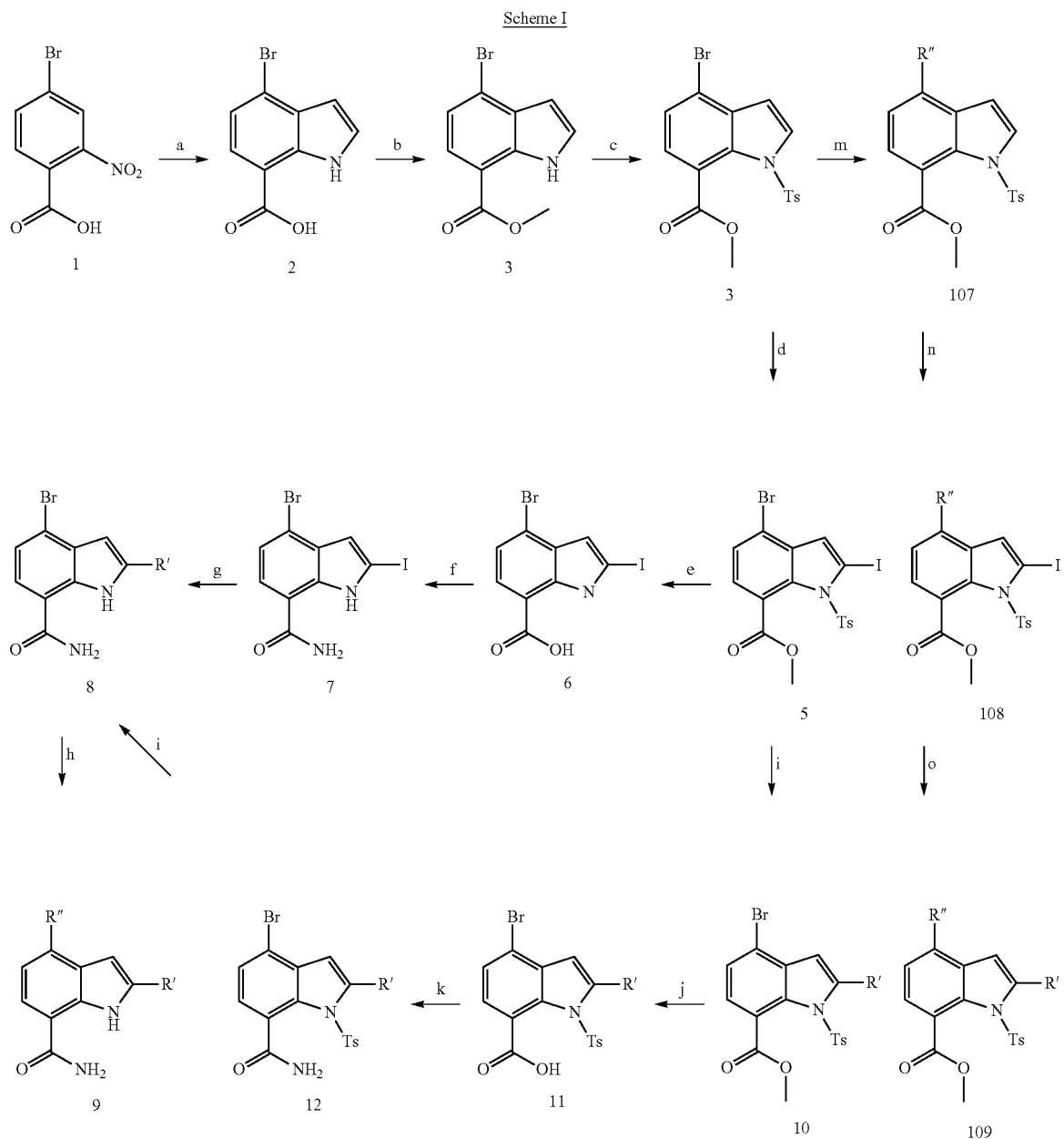

An alternative method preparing 1H-indole-7-carboxamide compounds 9 of the invention are illustrated in Scheme II. In step a, indole 3 from Scheme I may be protected with a SEM group using conditions known in the literature such as those found in Greene, T. W. and Wuts, P. G. M. referenced above or as those described in Preparation #10, step A. The resulting SEM protected indole 13 can undergo directed lithiation followed by trapping of the anion with an electrophile (for example iodomethane) yielding indole 14 as shown in step b using conditions described in Example #19, step A or trapping the anion with iodine as shown in step g yielding methyl 4-bromo-2-iodo-14(2-(trimethylsilyl) ethoxy)methyl)-1H-indole-7-carboxylate 17 using conditions such as those described in Preparation #10, step B). In Larock, R. C. referenced above, General Procedure A, and Preparation #10, step C. Hydrolysis of esters 14 gives acids 15 (step c) using well known conditions such as those described in Preparation #10, step D, or General Procedure C. Indole carboxylic acids 15 may be converted to primary amides 16 as shown using conditions such as those described in General Procedure D. The SEM protecting group of 1H-indole-7-carboxamide compounds 16 may be removed by methods such as those described in Preparation #10, step E or using conditions such as described in Greene, T. W. and Wuts, P. G. M. referenced above to give 1H-indole-7-carboxamides 8. Indoles 8 may then be reacted further as described above (Scheme I) to give the targeted 1H-indole-7-carboxamide compounds 9.

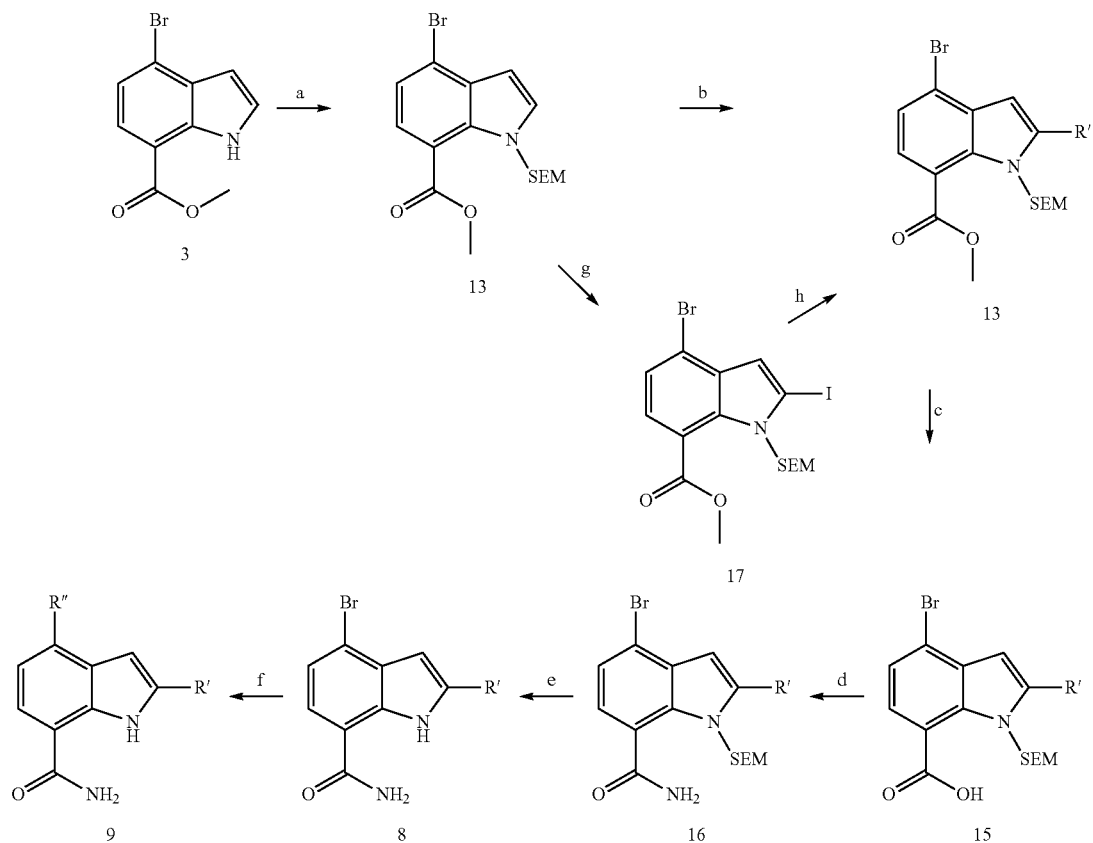

An additional method preparing indole-7-carboxamide compounds 9 of the invention is illustrated in Scheme III. Hydrolysis of ester 17 gives acid 18 (step a) using well known conditions such as those described in Preparation #10, step D or General Procedure C. Acid 18 may be coverted to a primary amide 19 as shown using conditions such as those described in General Procedure D. The SEM protecting group of indole 19 may be removed by methods such as those described in Example #19, step D or using conditions such as described in Greene, T. W. and Wuts, P. G. M. referenced above to give 1H-indole-7-carboxamides 7. Indoles 7 may then be reacted further as described above to give the targeted 1H-indole-7-carboxamide compounds 9.

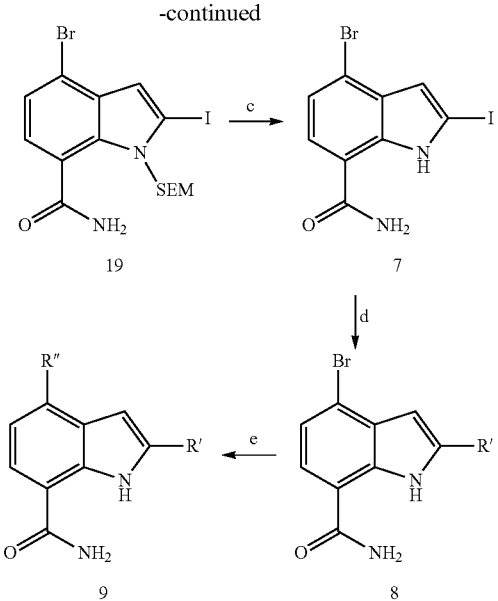

An alternative method preparing 1H-indole-7-carboxamide compounds 9 of the invention is illustrated in Scheme IV. Indole 19 may undergo a variety of reactions known to one skilled in the art (for example, Larock, R. C. referenced above) including, but not limited to, Stille coupling reactions such as those described in Example #22, step A or Suzuki coupling reaction as those described in General Procedure A. In step b, indole-7-carboxamides 16 are reacted with a boronate ester or boronic acid either commercially available or can be prepared by methods known to one skilled in the art (see, for example, Example #22, step B; Larock, R. C. "Comprehensive Organic Transformations: A Guide to Functional Group Preparations, 2$^{nd}$ edition", 1999, Wiley-VCH; or General Procedure A) using Suzuki coupling conditions (for example, Example #19 or General Procedure A). The SEM protecting group of indoles 20 may be removed by methods such as those described in Example #22, step D or using conditions such as described in Greene, T. W. and Wuts, P. G. M. referenced above to give 1H-indole-7-carboxamides 9. Indoles 9 may then be reacted further as described above.

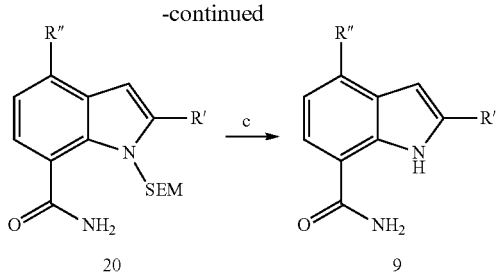

Indole-7-carboxamide compounds 9 of the invention can also be prepared using the route illustrated in Scheme V. In step a, methyl ester 21 is prepared using standard condition such as those described in General Procedure F, or Larock, R. C. referenced above. Enolizable ketones 23 react with m-nitroaniline 22 to give 4-nitroindoles 24 (step b) using standard conditions such as those described in General Procedure F, or *Tetrahedron*, 2004, 60(2), 347. In step c, acids 24 may be converted to primary amides 25 as shown using conditions such as those described in General Procedure D or F. Amino indoles 26 are prepared by reduction of the nitro group of primary amides 25 using methods known to one skilled in the art (for example, General Procedure F, or Larock, R. C. referenced above). Diazotization of 26 followed by iodination gives 27 using standard condition such as those described in General Procedure F, or Larock, R. C. referenced above. In step f, indoles 27 may undergo a variety of reactions known to one skilled in the art (for example, Larock, R. C. referenced above) including, but not limited to, Suzuki, Buchwald, or Negishi coupling conditions as described by General Procedures A, T and U. Indoles 9 may then be reacted further as described above.

Scheme IV

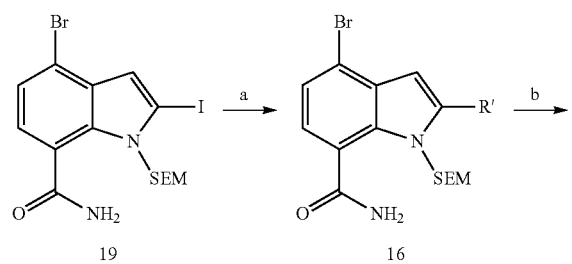

Scheme V

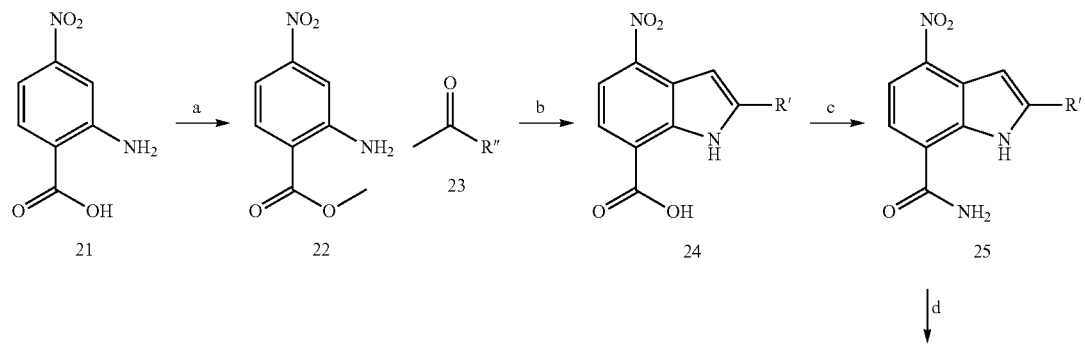

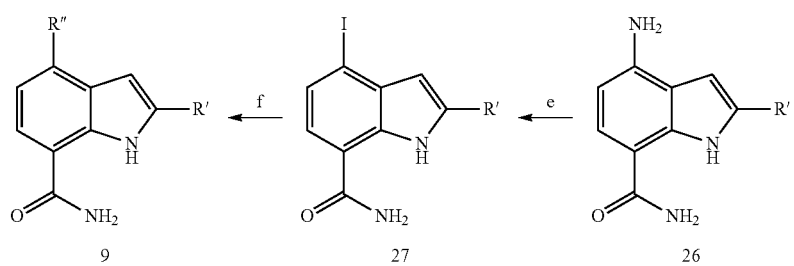

Methods for preparing 1H-indole-7-carboxamide compounds 30 of the invention are illustrated in Scheme VI. In Scheme VI, step a, commercially available 4-bromo-1H-indole-7-carbonitrile [Sinova] 28 is hydrolyzed to give primary amide 29 using conditions such as those described in Preparation #2 or known to one skilled in the art (for example, the books from Larock, R. C. or Greene, T. W. and Wuts, P. G. M. referenced above). In step b, indole 29 may undergo a variety of reactions known to one skilled in the art (for example, Larock, R. C. referenced above) including, but not limited to, Suzuki, Buchwald, or Negishi coupling conditions as described by General Procedures A, T and U. Alternatively, indole 29 can be converted to the boronate ester 31 using reactions such as those described in General Procedure P. Indole 31 may undergo a Suzuki coupling using conditions such as those described in General Procedure A or known to one skilled in the art (for example, Larock, R. C. referenced above). Further functionalization of the R' group in indoles 30 can be performed, if desired, using reactions known to one skilled in the art (for example, Larock, R. C. referenced above). For example, indoles 30 containing a double bond may be reduced to saturated systems using hydrogenation conditions such as those described in General Procedure L. Ethers can be prepared from indoles 30 containing an alcohol using condition such as those described in General Procedure Q. In addition amides, ureas, sulfonamides, aryl amines, heteroaryl amines, or sulfonyl ureas can be prepared from indoles 30 with an R' containing a primary or secondary amine (for example General Procedures D, E, I, H, and J). Also, deprotection of the R' group in 1H-indole-7-carboxamide compounds 30 to yield an unprotected compound can be performed using conditions such as those described in Greene, T. W. and Wuts, P. G. M. referenced above or in General Procedures G, M, or N. For example, a protecting group such as a Boc group can be removed from a protected amine to yield the unprotected amine (for example General Procedure G) and the deprotected compounds 30 may then be reacted further as described above.

Scheme VI

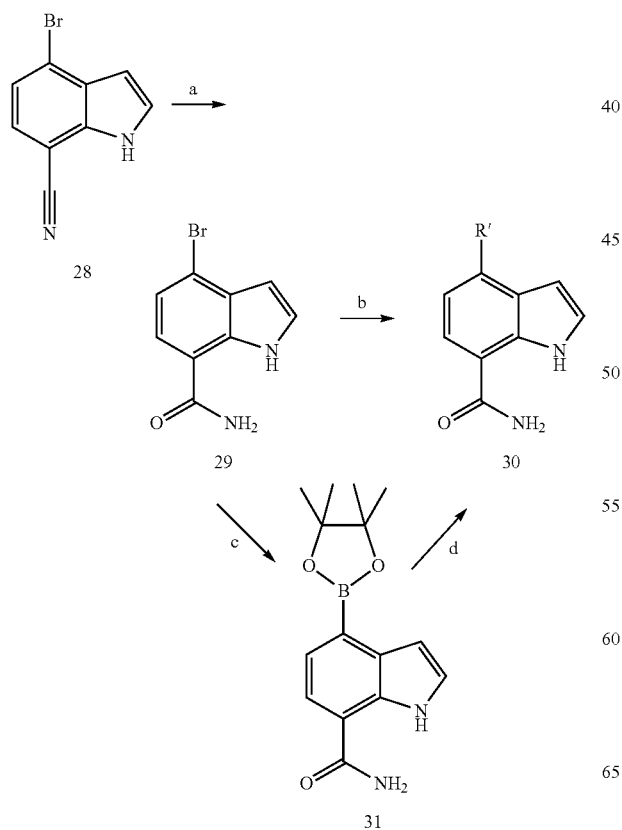

Methods for preparing 1H-indole-7-carboxamide compounds 35 of the invention are illustrated in Scheme VII. Nitration of indole 29 (Scheme VII step a) can be performed using conditions such as those described in Preparation #7, step C or known to one skilled in the art (for example, Larock, R. C. referenced above). In step b, indole 32 may undergo a variety of reactions known to one skilled in the art (for example, Larock, R. C. referenced above) including, but not limited to, Suzuki, Buchwald, or Negishi coupling conditions as described by General Procedures A, T and U Amino indoles 34 are prepared from the reduction of nitroindoles 33 using methods known to one skilled in the art (for example, Preparation #7, step E, or Larock, R. C. referenced above). The amino indoles 34 may be coverted to give amides 35 as shown in step d using conditions such as those described in General Procedure D or E.

Scheme VII

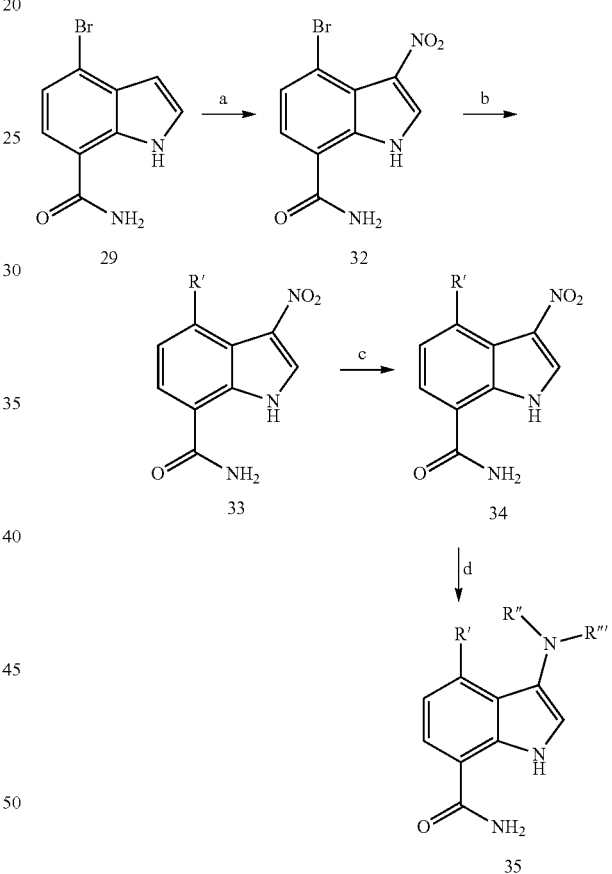

Methods for preparing 1H-pyrrolo[3,2-c]pyridine-7-carboxamides 39 of the invention are illustrated in Scheme VIII. In Scheme VIII, step a, 6-bromo-4-nitronicotinic acid [*European Journal of Medicinal Chemistry* 1977, 12(6), 541] 36 is reacted with vinylmagnesium bromide via a Bartoli indole synthesis using methods known to one skilled in the art (for example Preparation #9, step A) to give pyrrolo[3,2-c]pyridine 37. In step b, the acid of compounds 37 may be converted to primary amides 38 as shown using conditions such as those described in General Procedure D. Pyrrolo[3,2-c]pyridine 38 may undergo a variety of reactions known to one skilled in the art (for example, Larock, R. C. referenced above) including, but not limited to, Suzuki, Buchwald, or Negishi coupling conditions as described by General Procedures A, T and U. Further functionalization of the R' group in pyrrolo[3,2-c]pyridines 39 can be performed, if desired, using reactions known to one skilled in the art (for example, Larock, R. C. referenced above). For example, indoles 39 containing a double bond may be reduced to saturated systems using hydrogenation conditions such as those described in General Procedure L. Ethers can be prepared from indoles 39 containing an alcohol using condition such as those described in General Procedure Q. In addition amides, ureas, sulfonamides, aryl amines, heteroaryl amines, or sulfonyl ureas can be prepared from indoles 39 containing a primary or secondary amine (for example General Procedures D, E, I, H, and J). Also, deprotection of indoles 39 containing a protecting group in R' can be performed using conditions such as those described in Greene, T. W. and Wuts, P. G. M. referenced above or in General Procedures G, M, or N. For example, for R" containing a TBDMS-protected alcohol, the protecting group can be removed to yield an unprotected alcohol (for example General Procedure M) and the deprotected compounds 39 may then be reacted further as described above.

in the art (for example, Larock, R. C. referenced above). For example, indoles 44 containing a double bond may be reduced to saturated systems using hydrogenation conditions such as those described in General Procedure L. Ethers can be prepared from indoles 44 containing an alcohol using condition such as those described in General Procedure Q. Also, deprotection of indoles 44 containing a protected alcohol can be performed using conditions such as those described in Greene, T. W. and Wuts, P. G. M. referenced above or in General Procedures M. In addition amides, ureas, sulfonamides, aryl amines, heteroaryl amines, or sulfonyl ureas can be prepared from indoles 44 with an R' containing a primary or secondary amine (for example General Procedures D, E, I, H, and J). Also, deprotection of the R' group in 1H-indole-7-carboxamide compounds 44 to yield an unprotected compound can be performed using conditions such as those described in Greene, T. W. and Wuts, P. G. M. referenced above or in General Procedures G, M, or N. For example, a protecting group such as a Boc group can be removed from a protected amine to yield the unprotected amine (for example General Procedure G) and the deprotected compounds 44 may then be reacted further as described above.

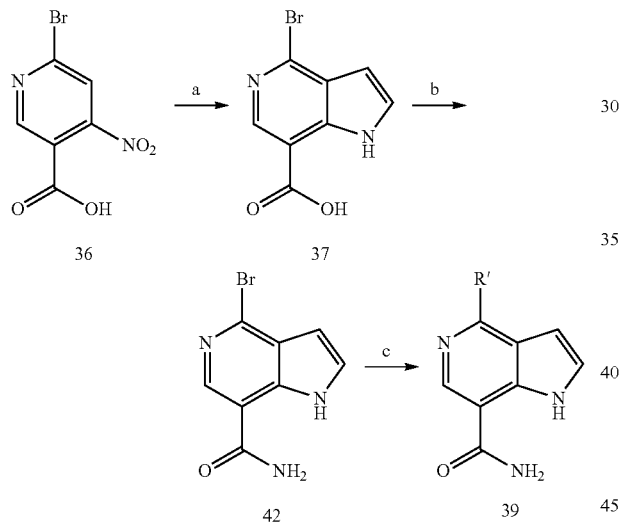

Scheme VIII

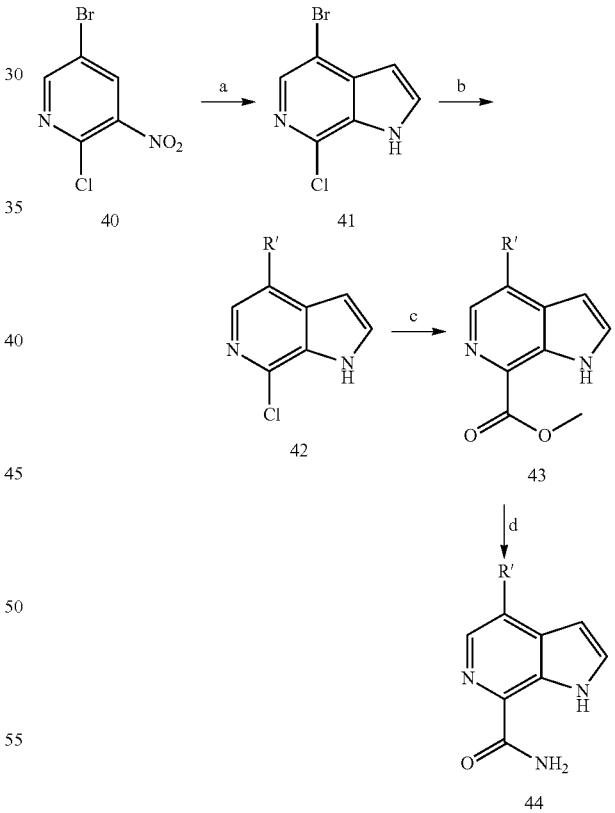

Scheme IX

Methods for preparing 1H-pyrrolo[2,3-c]pyridine-7-carboxamides 44 of the invention are illustrated in Scheme IX. In Scheme IX, step a, 5-bromo-2-chloro-3-nitropyridine 40 is reacted with vinylmagnesium bromide via a Bartoli indole synthesis using methods known to one skilled in the art (for example, Example #2, step A) to give pyrrolo[2,3-c]pyridine 41. In step b, pyrrolo[2,3-c]pyridine 41 may undergo a variety of reactions known to one skilled in the art (for example, Larock, R. C. referenced above) including, but not limited to, Suzuki, Buchwald, or Negishi coupling conditions as described by General Procedures A, T and U to give pyrrolo[2,3-c]pyridines 42. In step c, Pd-mediated carbonylation of pyrrolo[2,3-c]pyridines 42 gives esters 43 using methods known to one skilled in the art such as those described in Example #2, step C. Esters 43 may undergo ammonolysis such as those described in Example #2, step D or known to one skilled in the art (for example, Larock, R. C. referenced above) give compounds 44. Further functionalization of the R' group in pyrrolo[2,3-c]pyridines 44 can be performed, if desired, using reactions known to one skilled in the art (for example, Larock, R. C. referenced above). For Methods for preparing 1H-indole-7-carboxamides 51 of the invention are illustrated in Scheme X. In Scheme X, step a, indole 45 under goes a Vilsmeier-Haack reaction using methods known to one skilled in the art (for example, Example #3, step A) to give aldehyde 46. The reductive amination of aldehyde 46 with 4-methoxybenzylamine (PMB) using conditions such as those described in General Procedure H gives amine 47 (Scheme X, step b). Hydrolysis of ester 47 gives acid 48 (step c) using well known conditions such as those described in Example #3, step C or General Procedure C. Acid 48 may be converted to a primary amide 49 as shown using conditions such as those described in General Procedure D. Indole 49 may undergo a variety of reactions known to one skilled in the art (for example, Larock, R. C. referenced above) including, but not limited to, Suzuki, Buchwald, or Negishi coupling conditions as described by General Procedures A, T and U. Indoles 50 may be converted to give methyl indoles 51 using conditions such as those described in Example #3, step F.

Scheme X

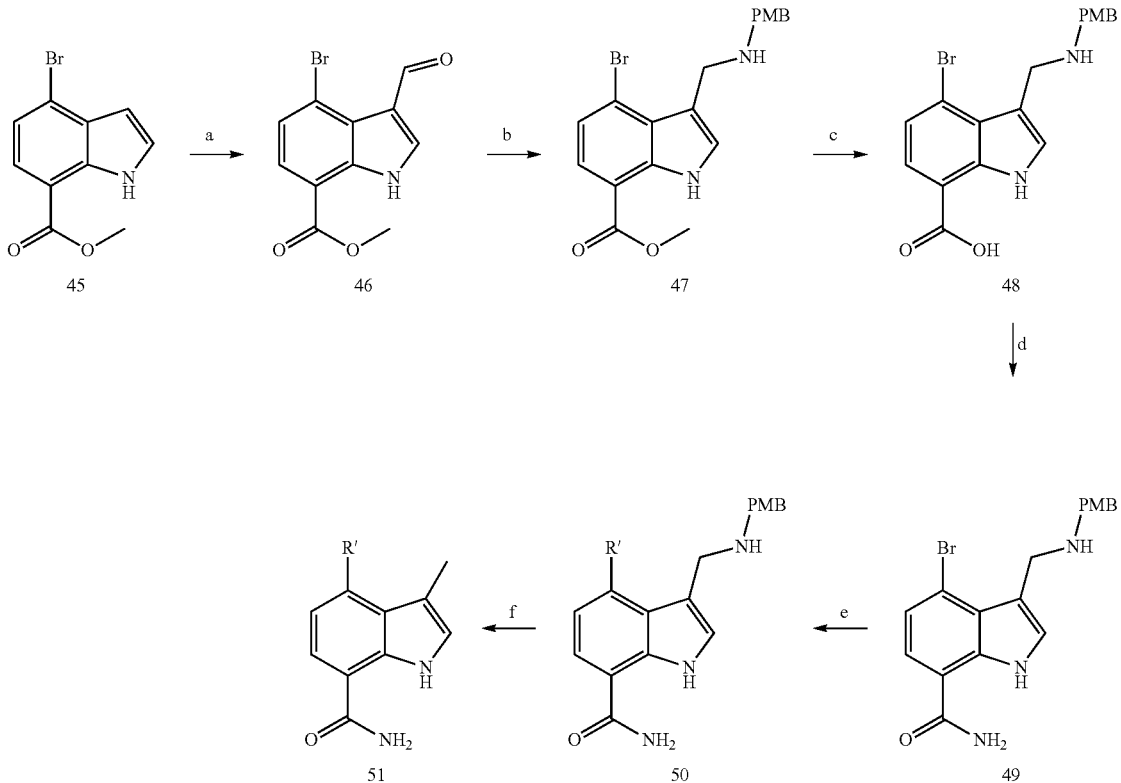

Methods for preparing 1,2,3,6-tetrahydropyrrolo[2,3-e]indole-5-carboxamides 58 of the invention are illustrated in Scheme XI. Nitration of 5-bromoindoline 52 (Scheme XI, step a) can be performed using conditions such as those described in Example #4, step A or known to one skilled in the art (for example, Larock, R. C. referenced above). The resulting indoline 53 may be protected (Scheme XI, step b) using conditions described in Greene, T. W. and Wuts, P. G. M. referenced above (for example, a Boc protecting group using conditions such as those described in Example #4, step B or those described in Greene, T. W. and Wuts, P. G. M. referenced above). In Scheme XI, step c, indoline 54 is reacted with vinylmagnesium bromide via a Bartoli indole synthesis using methods known to one skilled in the art to give indole 55 using conditions described in Example #4, step C. In step d, Pd-mediated cyanation of bromide 55 gives the corresponding nitrile 56 (for example, Example #4, step D or *Tetrahedron Letters* 1999, 40(47), 8193-8195). Subsequent hydrolysis of nitrile 56 gives a primary amide 57 (Scheme XI, step e) using methods known to one skilled in the art (for example, General Procedure O). The primary amide 57 may be converted to give amides 58 as shown in step f using conditions such as those described in General Procedure D or E.

Scheme XI

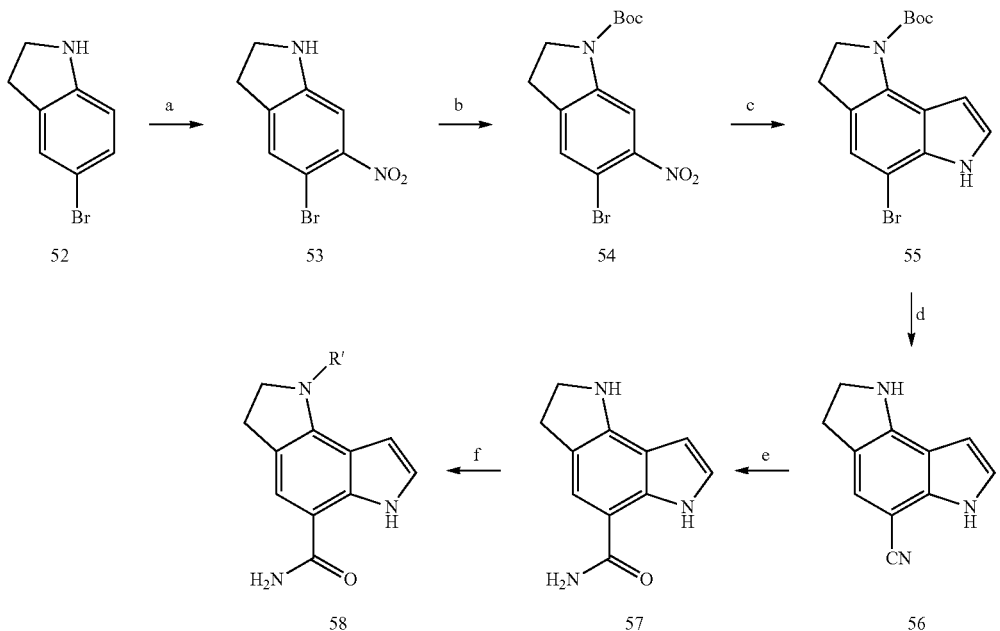

Methods for preparing benzimidazoles 64 of the invention are illustrated in Scheme XII. In step a, 4,7-dibromobenzo[c][1,2,5]thiadiazole 59 may undergo a variety of reactions known to one skilled in the art (for example, Larock, R. C. referenced above) including, but not limited to, Suzuki, Buchwald, or Negishi coupling conditions as described by General Procedures A, T and U. In step b, Pd-mediated cyanation of bromide 60 gives the corresponding nitriles 61 (for example *Tetrahedron Letters* 1999, 40(47), 8193-8195). Nitriles 61 can undergo ring opening to give diamine 62 using conditions such as those described in Example #14, step C. As shown in Scheme XII, step d, the cyclization of the diamine 62 can be accomplished by reacting with aldehydes (for example, Example #14, step D). Hydrolysis of nitrile 63 gives benzimidazoles 64 (Scheme XII, step e) using methods known to one skilled in the art such as those described in General Procedure O.

Scheme XII

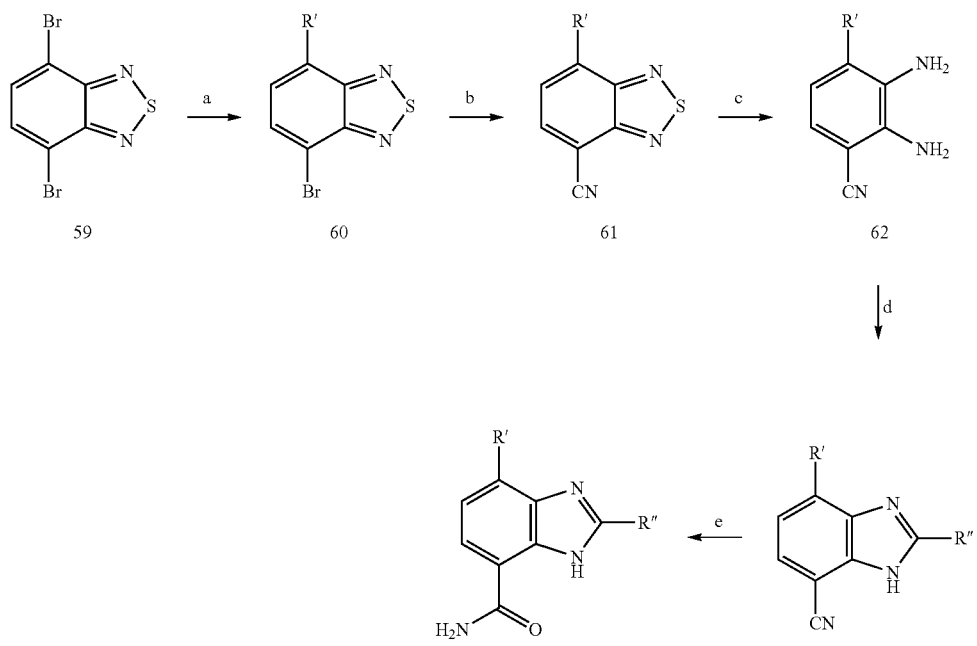

Methods for preparing indazoles 70 of the invention are illustrated in Scheme XIII. In Scheme XIII, step a, 2-amino-4-chloro-3-methylbenzoic acid [Enamine] 65 is esterified using standard conditions such as those described in General Procedure F or Larock, R. C. referenced above. In step b, the cyclization of ester 66 gives indazole 67 using methods known to one skilled in the art (for example, Example #18, step B or WO2007/113596). Hydrolysis of ester 67 gives acid 68 (Scheme XIII, step c) using well known conditions such as those described in General Procedure C. The acid 68 may be coverted to amide 69 as shown in step d using conditions such as those described in General Procedure D. Indole 69 may undergo a variety of reactions known to one skilled in the art (for example, Larock, R. C. referenced above) including, but not limited to, Suzuki, Buchwald, or Negishi coupling conditions as described by General Procedures A, T and U. Further functionalization of the R' group in indoles 70 can be performed, if desired, using reactions known to one skilled in the art (for example, Larock, R. C. referenced above). For example, indoles 70 containing a double bond may be reduced to saturated systems using hydrogenation conditions such as those described in General Procedure L. Ethers can be prepared from indoles 70 containing an alcohol using conditions such as those described in General Procedure Q. In addition amides, ureas, sulfonamides, aryl amines, heteroaryl amines, or sulfonyl ureas can be prepared from indoles 70 with an R' containing a primary or secondary amine (for example General Procedures D, E, I, H, and J). Also, deprotection of the R' group in 1H-indole-7-carboxamide compounds 70 to yield an unprotected compound can be performed using conditions such as those described in Greene, T. W. and Wuts, P. G. M. referenced above or in General Procedures G, M, or N. For example, a protecting group such as a Boc group can be removed from a protected amine to yield the unprotected amine (for example General Procedure G) and the deprotected compounds 70 may then be reacted further as described above.

Scheme XIII

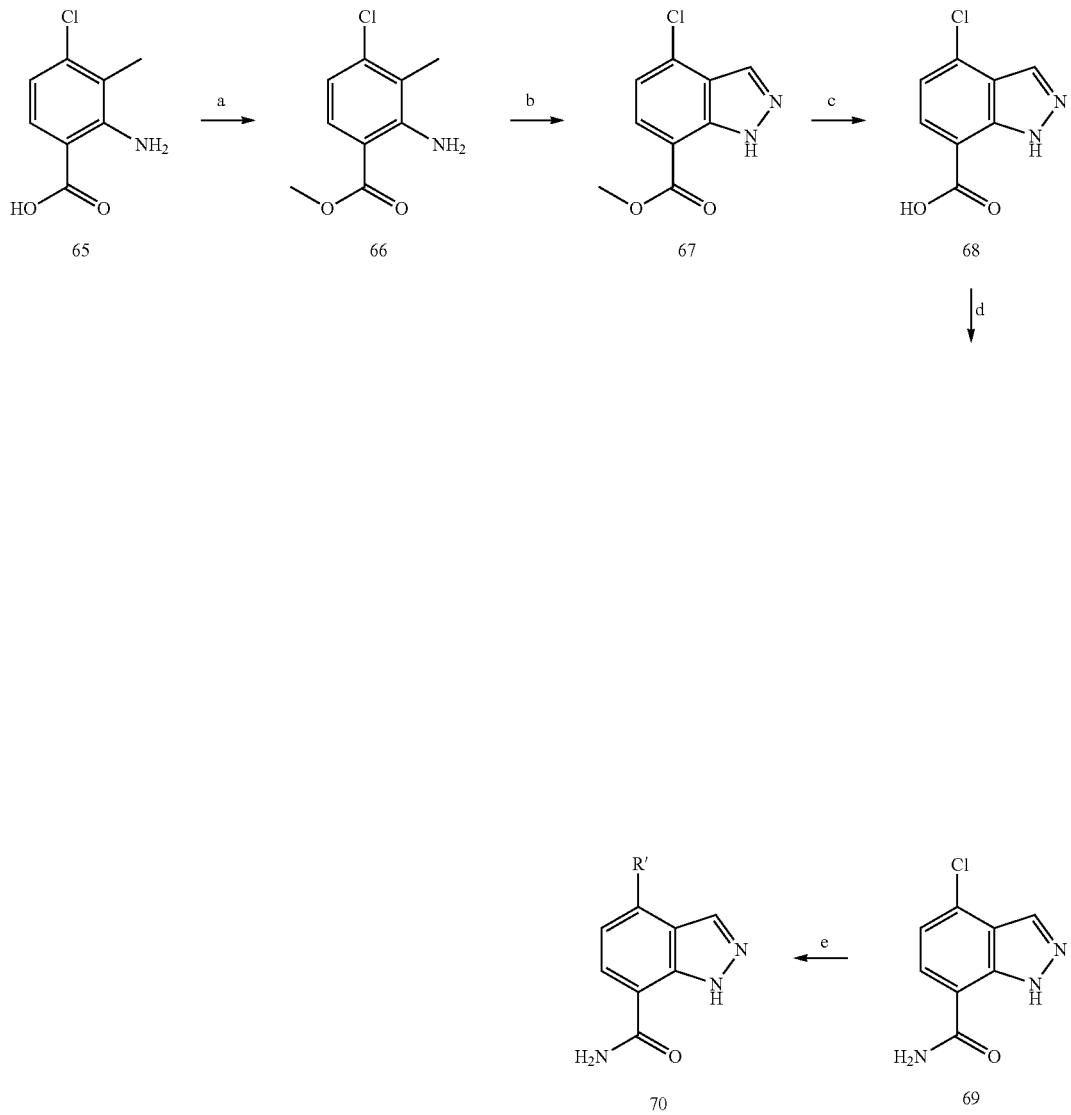

Methods for preparing 1H-indole-7-carboxamide compounds 77 of the invention are illustrated in Scheme XIV. In Scheme XIV, step a, indole 71 may be tosyl (Ts) protected (Scheme I, step c) using conditions such as those described in Preparation #1 step C or those described in Greene, T. W. and Wuts, P. G. M. or Larock, R. C. referenced above). In step b, directed lithiation of 4-fluoro-1-tosyl-1H-indole-7-carbonitrile 72 followed by trapping of the anion with iodine yields indole 73 using conditions such as those described in Preparation #1, step D. The 4-fluoro-2-iodo-1-tosyl-1H-indole-7-carbonitrile 73 may undergo a variety of reactions known to one skilled in the art (for example, Larock, R. C. referenced above) including, but not limited to, Suzuki coupling reactions such as those described in General Procedure A. Further functionalization of the R' group in tosyl protected carbonitriles 74 can be performed, if desired, using reactions known to one skilled in the art (for example, Larock, R. C. referenced above). For example, formation of amides, ethers, ureas, sulfonamides, aryl amines, heteroaryl amines, or sulfonyl ureas can be prepared from compounds one skilled in the art (for example, the books from Larock, R. C. or Greene, T. W. and Wuts, P. G. M. referenced above). In step f, 1H-indole-7-carbonitriles 76 hydrolyzed to give primary amide 77 using conditions such as those described in Preparation #2 or known to one skilled in the art (for example, the books from Larock, R. C. or Greene, T. W. and Wuts, P. G. M. referenced above). In addition, amides, carbamates, ureas, or substituted amines can be prepared from 1H-indole-7-carboxamide compounds 77 containing a primary or secondary amine (for example General Procedures). Also, deprotection of 1H-indole-7-carboxamide compounds 77 containing a protected primary or secondary amine can be performed using conditions such as those described in Greene, T. W. and Wuts, P. G. M. referenced above or in General Procedures. For example, for R'' or R''' containing a protecting group (for example a Boc group), the protecting group can be removed to yield the unprotected amine (for example General Procedure G) and the deprotected compounds 3 may then be reacted further as described above.

Scheme XIV

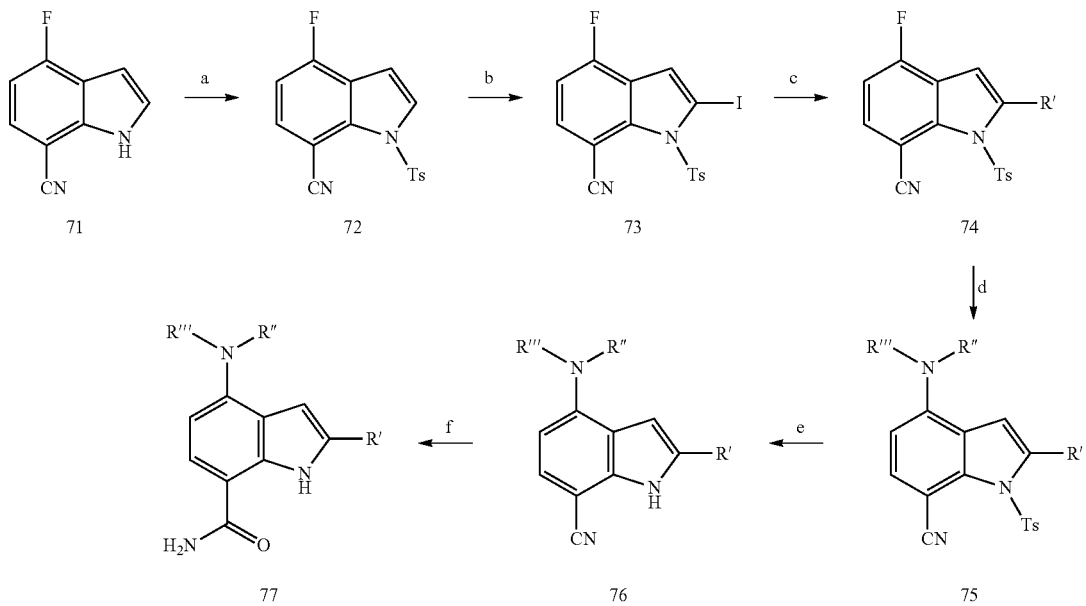

74 with an R' containing a primary or secondary amine (for example General Procedures D, E, I, H, and J). Also, deprotection of the R' group in compounds 74 to yield an unprotected compound can be performed using conditions such as those described in Greene, T. W. and Wuts, P. G. M. referenced above or in General Procedures G, M, or N. For example, a protecting group such as a Boc group can be removed from a protected amine to yield the unprotected amine (for example Preparation #27, Step D or General Procedure G) and the deprotected compounds 74 may then be reacted further as described above amine Indole carbonitriles 74 shown in step d can be reacted with amines via displacement chemistry using conditions known to one skilled in the art such as those described in General Procedure B to give compounds 75. Tosyl protected 1H-indole-7-carbonitriles 75 may be deprotected under aqueous base conditions in one step to give compound 76 using conditions such as those described in Example #12, step B or known to Methods for preparing 7-chlorothiazolo[5,4-c]pyridine-4-carboxamides 87 of the invention are illustrated in Scheme XV. Wittig reaction of an aldehyde 78 (step a) is performed with a triphenyl phosphonium ylide using standard conditions known to on skilled in the art, such as those described in Preparation #46, step A or Larock, R. C. referenced above, to give α,β unsaturated methyl ester 79. This intermediate is reacted with a boronate or boronic acid via a Suzuki reaction in step b, using conditions such as those illustrated in Preparation #46, step B. Intermediate 80 is hydrolyzed to give an acid as shown in Preparation #46, step B (step c). In step d, the acid is converted to an acyl azide via in situ formation of an acyl chloride using standard conditions such as those described Preparation #46, step D or WO 2012/035039. The acyl azide intermediate can then undergo a Curtius rearrangement and cyclize to give a pyridone 83 in step e, under high temperatures (For example, Preparation #46, step E or WO 2012/035039). On treatment with POCl₃, in step f, pyridine-2-chloride is formed (for example, Preparation #46, step F or WO 2012/035039), which can subsequently be treated with NCS in step g, to afford a 4-bromo-7-chlorothiazolo[5,4-c]pyridine intermediate 85, as illustrated in Preparation #46, step G. Conversion of the bromo group in 85 to a cyano functionality is performed via Pd-catalyzed cyanation reaction and subsequent hydrolysis of the cyano group yields a 7-chlorothiazolo[5,4-c]pyridine-4-carboxamide as illustrated in Preparation #46, step H. In step j, thiazolo[5,4-c]pyridine-4-carboxamide 87 may undergo a variety of reactions known to one skilled in the art (for example, Larock, R. C. referenced above) including, but not limited to, Suzuki, Buchwald, or Negishi coupling conditions as described by General Procedures A, T and U to give thiazolo[5,4-c]pyridine-4-carboxamides 88.

Scheme XV

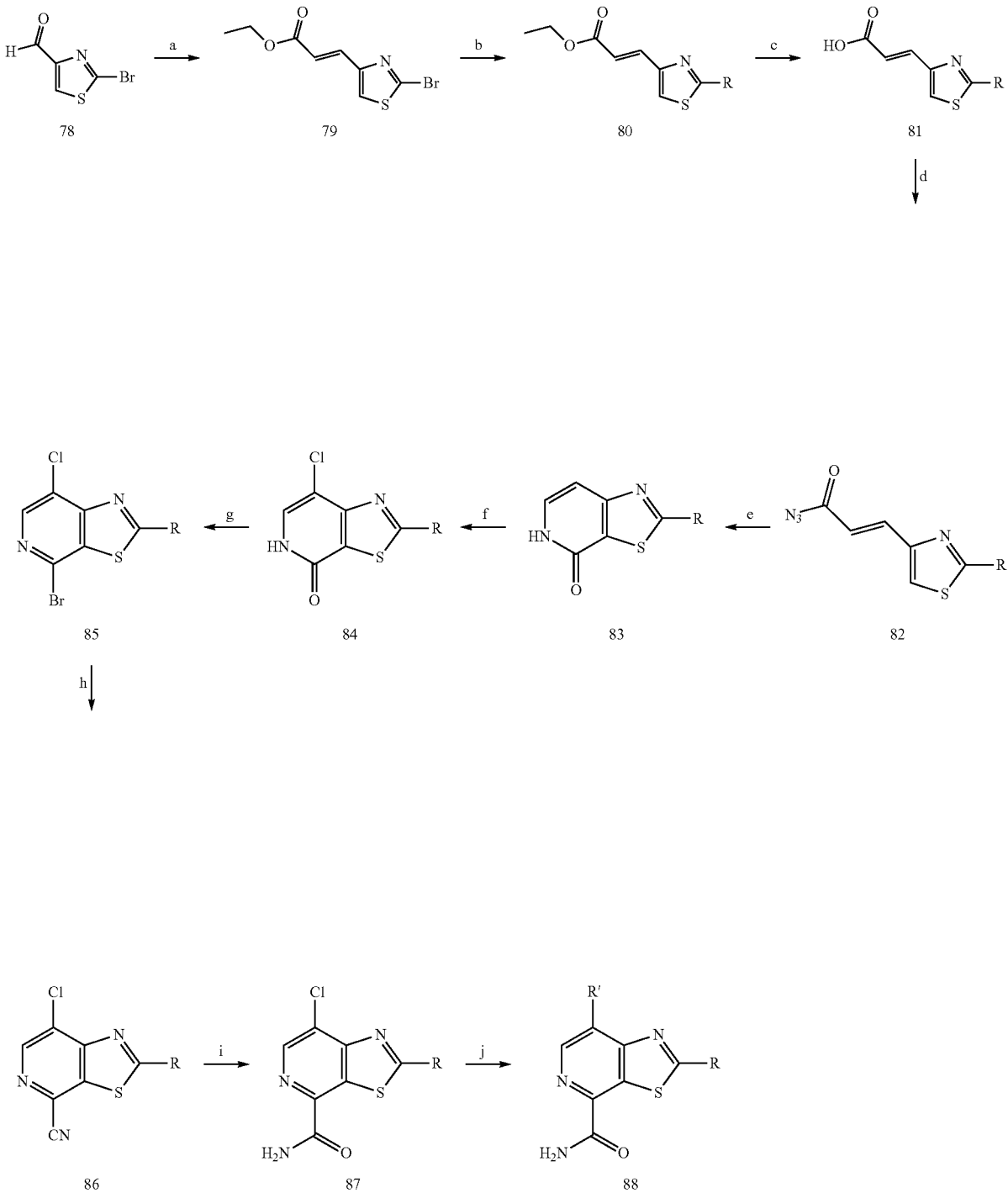

A second alternative for the preparation of 1H-pyrrolo[3,2-c]pyridine-7-carboxamides 39 to the route shown in scheme VIII is shown in scheme XVI, wherein 1H-pyrrolo[3,2-c]pyridine-7-carboxamides 39 can also be prepared from commercially available methyl 1H-pyrrolo[3,2-c]pyridine-7-carboxylate 89, which is first tosylated in step a, using standard conditions known to one skilled in the art, as shown in General Procedure AH. The tosylated intermediate 90 is then oxidized (step b) using conditions such as those described in General Procedure AC to give an N-oxide intermediate 91. In step c the material is halogenated as illustrated in Preparation #45, step C, followed by hydrolysis using a base, to both remove the tosyl group and hydrolyze the ester to an acid using conditions such as those described in General Procedure X. The acid can then undergo a standard amine coupling reaction as illustrated in General Procedure D, to give the amide in step e. The pyrrolo[3,2-c]pyridine 94 may undergo a variety of reactions known to one skilled in the art (for example, Larock, R. C. referenced above) including, but not limited to, Suzuki, Buchwald, or Negishi coupling conditions as described by General Procedures A, T and U to give compounds 39. Further functionalization of the R' group in pyrrolo[3,2-c]pyridines 39 can be performed, if desired, using reactions known to one skilled in the art (for example, Larock, R. C. referenced above). For example, pyrrolo[3,2-c]pyridines 39 containing a double bond may be reduced to saturated systems using hydrogenation conditions such as those described in General Procedure L. Ethers can be prepared from indoles 39 containing an alcohol using condition such as those described in General Procedure Q. In addition amides, ureas, sulfonamides, aryl amines, heteroaryl amines, or sulfonyl ureas can be prepared from indoles 39 containing a primary or secondary amine (for example General Procedures D, E, I, H, and J). Also, deprotection of indoles 39 containing a protecting group in R' can be performed using conditions such as those described in Greene, T. W. and Wuts, P. G. M. referenced above or in General Procedures G, M, or N. For example, for R" containing a TBDMS-protected alcohol, the protecting group can be removed to yield an unprotected alcohol (for example General Procedure M) and the deprotected compounds 39 may then be reacted further as described above.

Scheme XVI

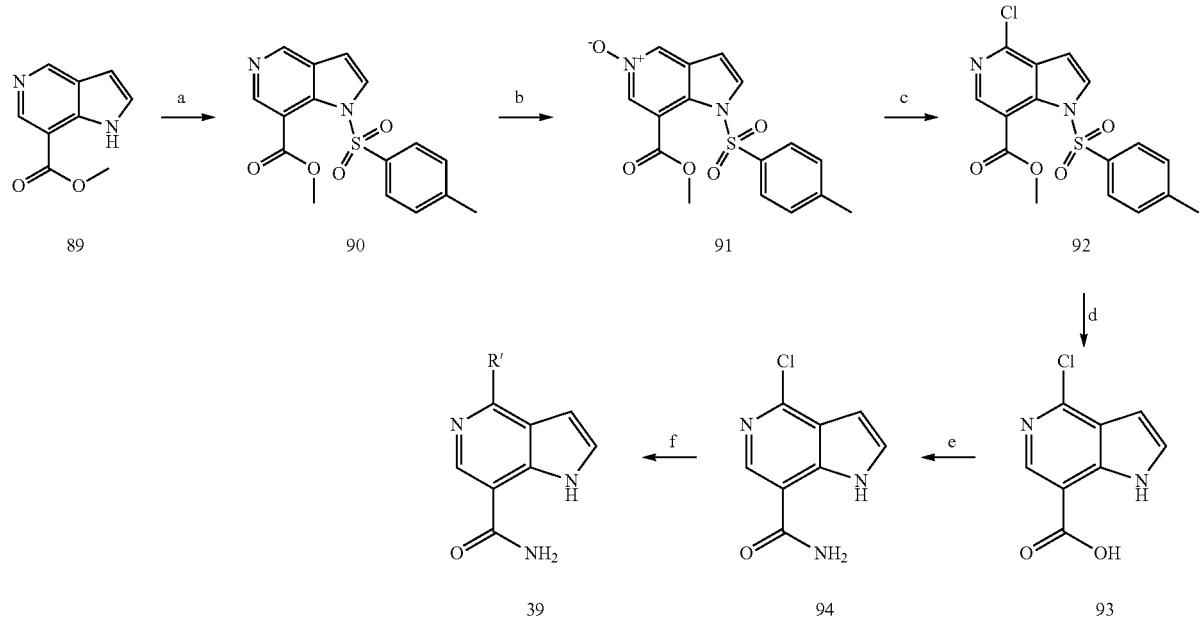

A third alternative to routes shown in schemes VIII and XVI for the preparation of 1H-pyrrolo[3,2-c]pyridine-7-carboxamides 39 is shown in scheme XVII. In step a, (4-methoxyphenyl)methanamine is treated with dimethyl 3-oxopentanedioate to give intermediate 96, which is not isolated. In step b, it is cyclized in situ via treatment with chloroacetaldehye using conditions such as those illustrated in Preparation #37, step A or WO 2005121140. De-protonation of the acidic hydrogen of 97 and reaction with methylformate, in step c, is accomplished using methods known to one skilled in the art (for example Preparation #37, step B, or WO 2005121140) to give intermediate 98. In step d, cyclization of intermediate 98 is performed using conditions such as those illustrated in Preparation #37, step C or WO 2005121140 to give the pyridinone intermediate 99. Subsequent aromatization and halogenation of pyridinone intermediate 99 in step e is done using well known conditions (for example Preparation #37, step D or WO 2005121140) to give pyrrolo[3,2-c]pyridine 100. Hydrolysis of the ester functionality in 100 gives acid 93 (step f) using standard conditions such as those described in General Procedure C. The acid can then undergo an amine coupling reaction as illustrated in General Procedure D, to give the amide in step e. The pyrrolo[3,2-c]pyridine 94 may undergo a variety of reactions known to one skilled in the art (for example, Larock, R. C. referenced above) including, but not limited to, Suzuki, Buchwald, or Negishi coupling conditions as described by General Procedures A, T and U to give compounds 39. Further functionalization of the R' group in pyrrolo[3,2-c]pyridines 39 can be performed, if desired, using reactions known to one skilled in the art (for example, Larock, R. C. referenced above). For example, pyrrolo[3,2- c]pyridines 39 containing a double bond may be reduced to saturated systems using hydrogenation conditions such as those described in General Procedure L. Ethers can be prepared from indoles 39 containing an alcohol using condition such as those described in General Procedure Q. In addition amides, ureas, sulfonamides, aryl amines, heteroaryl amines, or sulfonyl ureas can be prepared from indoles 39 containing a primary or secondary amine (for example General Procedures D, E, I, H, and J). Also, deprotection of indoles 39 containing a protecting group in R' can be performed using conditions such as those described in Greene, T. W. and Wuts, P. G. M. referenced above or in General Procedures G, M, or N. For example, for R" containing a TBDMS-protected alcohol, the protecting group can be removed to yield an unprotected alcohol (for example General Procedure M) and the deprotected compounds 39 may then be reacted further as described above.

yield compounds 44. Alternatively the carbonitrile 103 may first be hydrolyzed as shown in step c to give the amide 104 when subjected to known conditions (for example General Procedure O). The amide 104 may then undergo a variety of reactions known to one skilled in the art (for example, Larock, R. C. referenced above) including, but not limited to, Suzuki, Buchwald, or Negishi coupling conditions as described by General Procedures A, T and U to give compounds 44. Further functionalization of the R' group in pyrrolo[2,3-c]pyridines 44 can be performed, if desired, using reactions known to one skilled in the art (for example, Larock, R. C. referenced above). For example, pyrrolo[2,3-c]pyridines 44 containing a double bond may be reduced to saturated systems using hydrogenation conditions such as those described in General Procedure L. Ethers can be prepared from pyrrolo[2,3-c]pyridines 44 containing an alcohol using condition such as those described in General

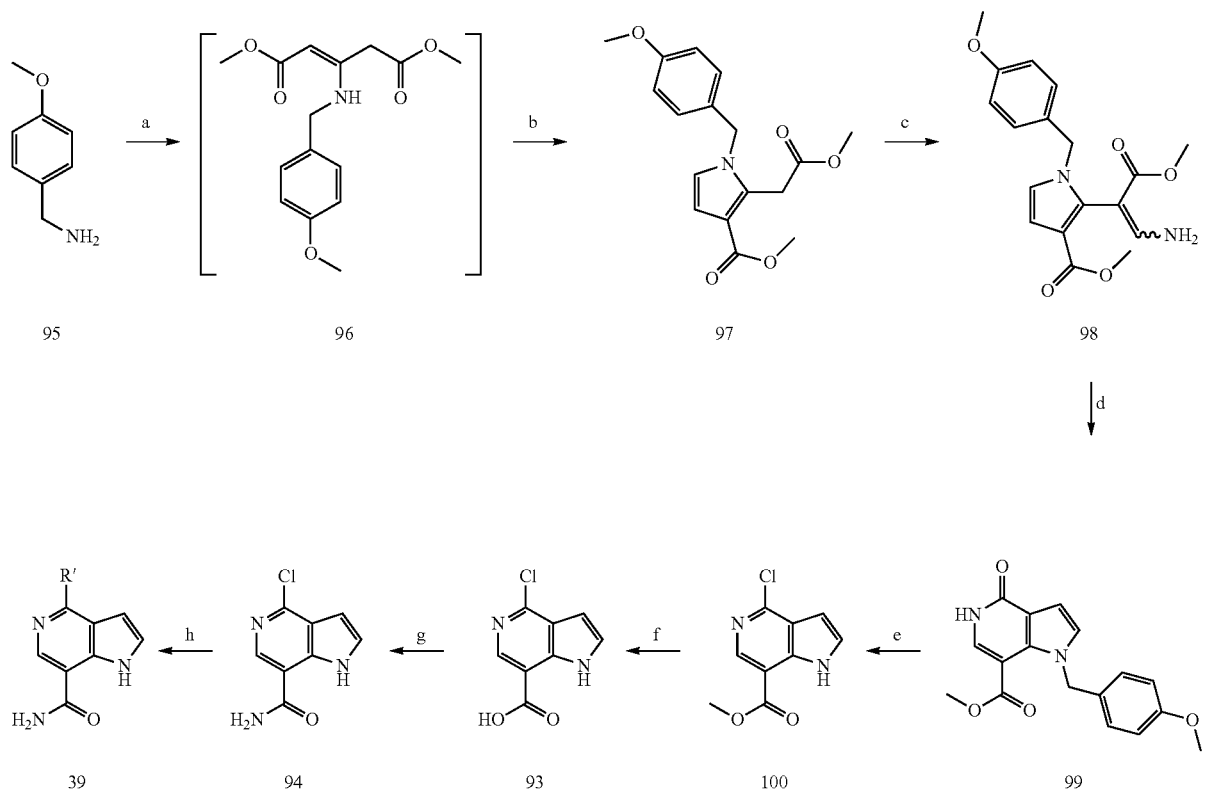

Scheme XVII

Alternative methods for preparing 1H-pyrrolo[2,3-c]pyridine-7-carboxamides 44 of the invention are illustrated in Scheme XVIII. 4-Bromo-1H-pyrrolo[2,3-c]pyridine 101 is oxidized to the N-oxide intermediate using methods known to one skilled in the art (for example General Procedure AC). Cyanation of the N-oxide 102 in step b is accomplished using conditions such as those illustrated in General Procedure AD to give the carbonitrile 103. The carbonitrile 103 may undergo a variety of reactions known to one skilled in the art (for example, Larock, R. C. referenced above) including, but not limited to, Suzuki, Buchwald, or Negishi coupling conditions as described by General Procedures A, T and U to give pyrrolo[2,3-c]pyridines 106. Subsequent hydrolysis of pyrrolo[2,3-c]pyridines 106 in step f, using standard conditions (for example General Procedure O) will Procedure Q. In addition amides, ureas, sulfonamides, aryl amines, heteroaryl amines, or sulfonyl ureas can be prepared from pyrrolo[2,3-c]pyridines 44 containing a primary or secondary amine (for example General Procedures D, E, I, H, and J). Also, deprotection of pyrrolo[2,3-c]pyridines 44 containing a protecting group in R' can be performed using conditions such as those described in Greene, T. W. and Wuts, P. G. M. referenced above or in General Procedures G, M, or N. For example, for R" containing a TBDMS-protected alcohol, the protecting group can be removed to yield an unprotected alcohol (for example General Procedure M) and the deprotected compounds 44 may then be reacted further as described above.

Scheme XVIII

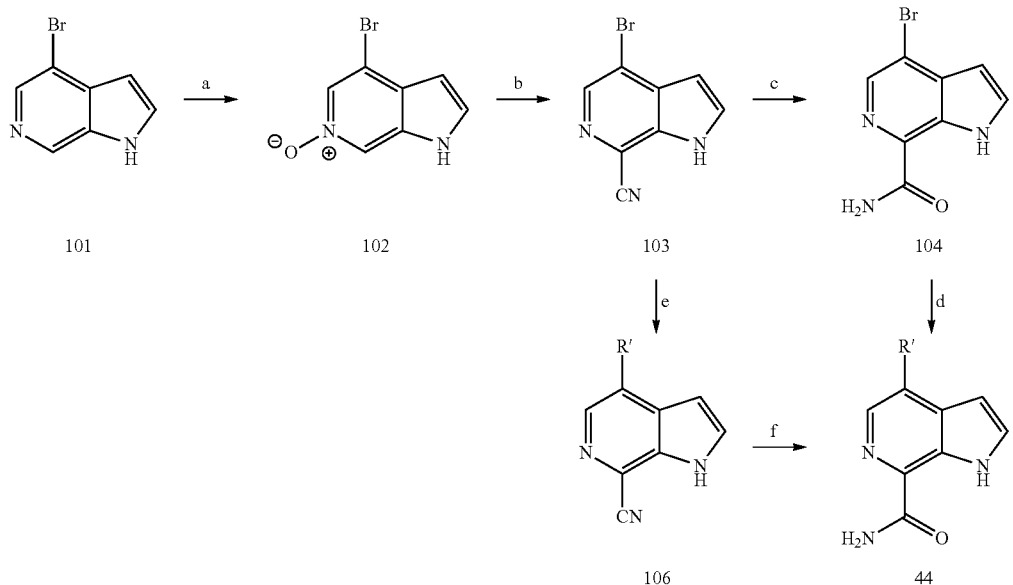

If desired, chiral separation of any of the chiral compounds in Schemes IXVIII may be done using methods known to one skilled in the art such as chiral preparative HPLC, chiral SFC or crystallization of diastereomeric salts.

GENERAL PROCEDURES AND EXAMPLES

The general synthetic schemes that were utilized to construct the majority of compounds disclosed in this application are described below in Schemes 1-34. These schemes are provided for illustrative purposes only and are not to be construed as limiting the scope of the invention.

Scheme 1. Suzuki Reaction of an aryl or hereroaryl halide with an aryl or heteroaryl boronic acid or boronate (General Procedure A)

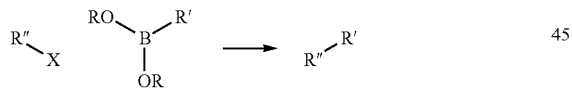

Scheme 2. Nucleophilic displacement of an aryl halide with an amine (General Procedure B)

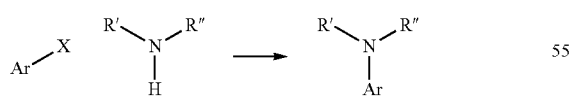

Scheme 3. Hydrolysis of an ester to a carboxylic acid (General Procedure C)

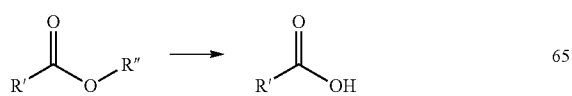

Scheme 4.
Formation of an amide from an amine and a carboxylic acid (General Procedure D)

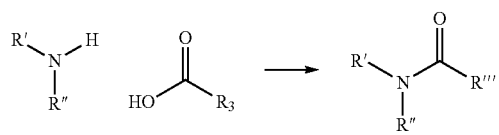

Scheme 5. Formation of an amide from an amine and an acid halide or anhydride (General Procedure E)

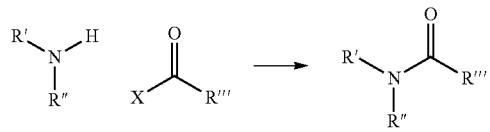

Scheme 6. Formation of a 4-iodoindole-7-carboxamide (General Procedure F)

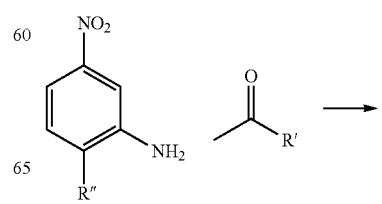

-continued

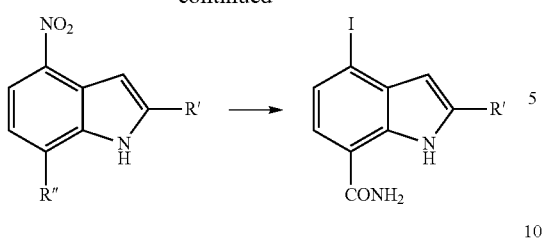

Scheme 7. Acidic cleavage of a Boc-protected amine (General Procedure G)

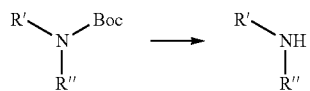

Scheme 8. Reductive amination of an aldehyde or ketone with primary or secondary amine (General Procedure H)

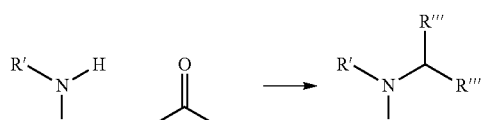

Scheme 9. Formation of a sulfonamide from an amine and a sulfonyl chloride (General Procedure I)

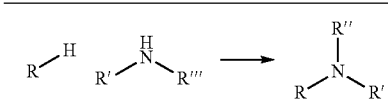

Scheme 10. Substitution of an alkyl halide with an amine nucleophile (General Procedure J)

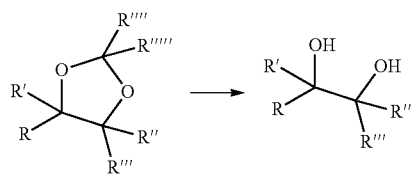

Scheme 11. Hydrolysis of an acetonide (General Procedure K)

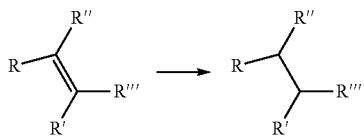

Scheme 12. Hydrogenation of an alkene (General Procedure L)

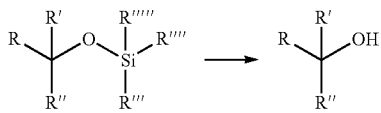

Scheme 13. Removal of a silyl group from an O-silyl ether (General Procedure M)

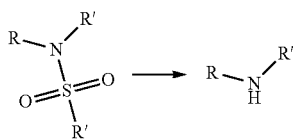

Scheme 14. Hydrolysis of a sulfonamide (General Procedure N)

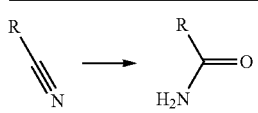

Scheme 15. Hydrolysis of a nitrile to a primary amide (General Procedure O)

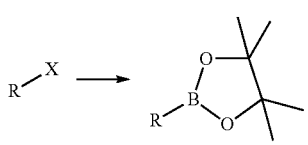

Scheme 16. Formation of a boronate from an aryl halide or heteroaryl halide (General Procedure P)

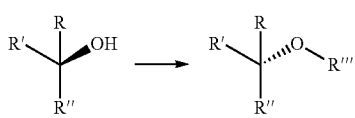

Scheme 17. Mitsunobu reaction of an alcohol (General Procedure Q)

Scheme 18. Reduction of a nitro group to an amine using Fe (General Procedure R)

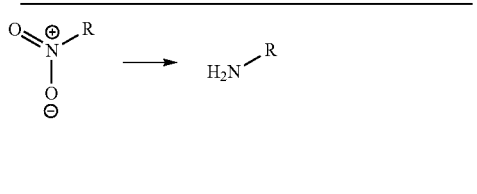

Scheme 19. Demethylation of aryl methyl ether (General Procedure S)

Scheme 20. Buchwald reaction of an aryl halide or a heteroaryl halide with an amine (General Procedure T)

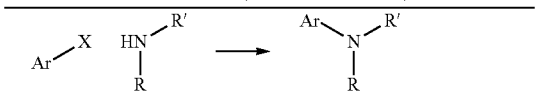

Scheme 21. Negishi cross-coupling reaction of an aryl halide or a heteroaryl halide with an organozine (General Procedure U)

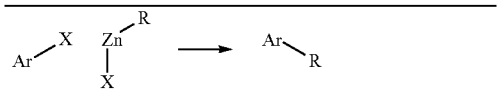

Scheme 22. Formation of an amide from a Boc-protected amine and a carboxylic acid (General Procedure V)

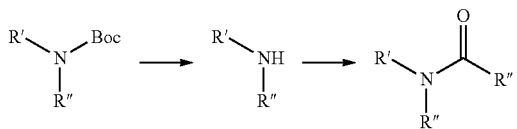

Scheme 23. Conversion of a vinyl triflate to a vinyl boronate or boronic acid (General procedure W)

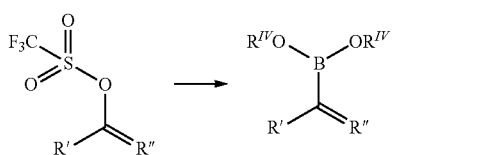

Scheme 24. Hydrolysis of an ester to a carboxylic acid under basic conditions and removal of a tosyl group from an N-tosyl protected heteroaryl ring (General Procedure X)

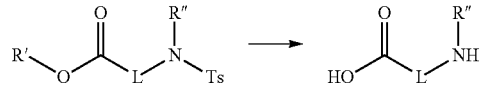

Scheme 25. Iodination of a 1H-indole or a 1H-aza indole ring to give a 2-iodo-1H-indole or a 2-iodo-1H-azaindole ring (General Procedure Y)

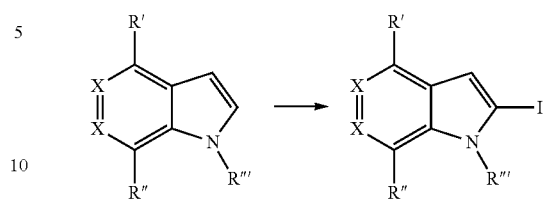

Scheme 26. Formation of an N-Boc protected amine (General Procedure Z)

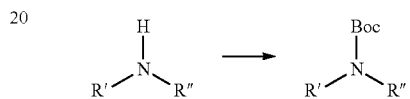

Scheme 27. Conversion of a ketone to a vinyl triflate (General Procedure AA)

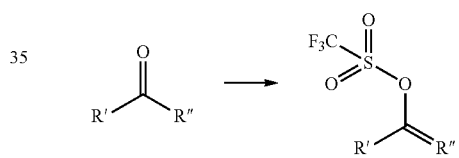

Scheme 28. Reduction of a double bond and removal of a CBZ group from a CBZ protected amine (General Procedure AB)

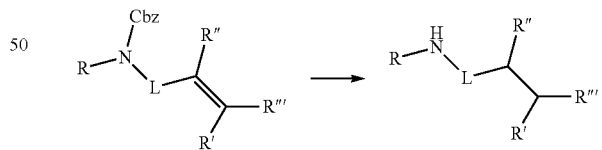

Scheme 29. N-Oxidation of an N containing hetero aromatic ring (General Procedure AC)

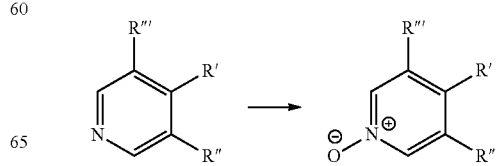

Scheme 30. Cyanation of a N-oxide containing heteroaryl ring (General Procedure AD)

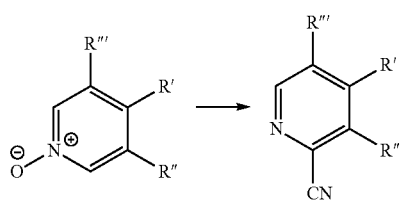

Scheme 31. Reduction of an ester to form an alcohol (General Procedure AE)

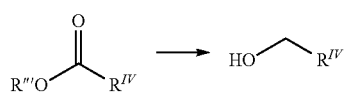

Scheme 32. Reduction of a pyridine ring to a piperidine ring (General Procedure AF)

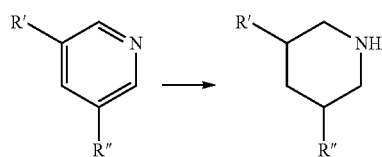

Scheme 33. Borylation of a vinyl triflate and Suzuki reaction of the in situ formed boronate with an aryl halide (General Procedure AG)

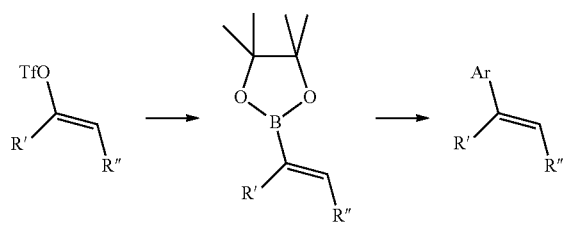

Scheme 34. Formation of an N-tosyl protected heteroaromic ring (General Procedure AH)

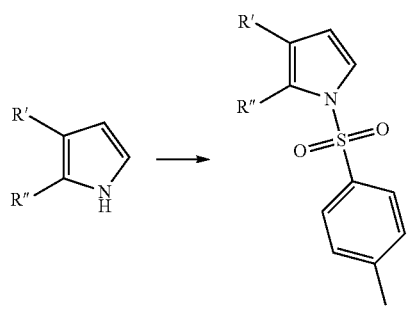

List of General Procedures

General Procedure A Suzuki Reaction of an aryl or heteroaryl halide with an aryl or heteroaryl boronic acid or boronate General Procedure B Nucleophilic displacement of an aryl halide with an amine General Procedure C Hydrolysis of an ester to a carboxylic acid General Procedure D Formation of an amide from an amine and a carboxylic acid General Procedure E Formation of an amide from an amine and an acid halide or anhydride General Procedure F Formation of a 4-iodoindole-7-carboxamide General Procedure G Acidic cleavage of a Boc-protected amine General Procedure H Reductive amination of an aldehyde or ketone with a primary or secondary amine General Procedure I Formation of a sulfonamide from an amine and a sulfonyl chloride General Procedure J Substitution of an alkyl halide with an amine nucleophile General Procedure K Hydrolysis of an acetonide General Procedure L Hydrogenation of an alkene General Procedure M Removal of a silyl group from an O-silyl ether General Procedure N Hydrolysis of a sulfonamide General Procedure O Hydrolysis of a nitrile to a primary amide General Procedure P Formation of a boronate from an aryl halide or heteroaryl halide General Procedure Q Mitsunobu reaction of an alcohol General Procedure R Reduction of a nitro group to an amine using Fe General Procedure S Demethylation of aryl methyl ether General Procedure T Buchwald reaction of an aryl halide or an heteroaryl halide with an amine General Procedure U Negishi cross-coupling reaction of an aryl halide or a heteroaryl halide with an organozinc General Procedure V Formation of an amide from a Boc-protected amine and a carboxylic acid General Procedure W Conversion of a vinyl triflate to a vinyl boronate or boronic acid General Procedure X Hydrolysis of an ester to a carboxylic acid under basic conditions and removal of a tosyl group from an N-tosyl protected heteroaryl ring General Procedure Y Iodination of a 1H-indole or a 1H-aza indole ring to give a 2-iodo-1H-indole or a 2-iodo-1H-azaindole ring General Procedure Z Formation of an N-Boc protected amine General Procedure AA Conversion of a ketone to a vinyl triflate General Procedure AB Reduction of a double bond and removal of a CBZ group from a CBZ protected amine General Procedure AC N-Oxidation of an N containing hetero aromatic ring General Procedure AD Cyanation of an N-oxide containing heteroaryl ring General Procedure AE Reduction of an ester to form an alcohol General Procedure AF Reduction of a pyridine ring to a piperidine ring General Procedure AG Borylation of a vinyl triflate and Suzuki reaction of the newly formed boronate with an aryl halide General Procedure AH Formation of an N-tosyl protected heteroaromatic ring The following examples are ordered according to the final general procedure used in their Preparation. The synthetic routes to any novel intermediates are detailed by sequentially listing the general procedure (letter codes) in parentheses after their name with additional reactants or reagents as appropriate. A worked example of this protocol is given below using Example #A.3.7 as a non-limiting illustration. Example #A.3.7 is 2-(1-acetyl-1,2,3,6-tetrahydropyridin-4-yl)-4-(3-(4-(difluoromethyl)benzamido)-2-methylphenyl)-1H-indole-7-carboxamide, which was prepared from 2-(1-acetyl-1,2,3,6-tetrahydropyridin-4-yl)-4-bromo-1H-indole-7-carboxamide using General Procedure A with 4-(difluoromethyl)-N-(2-methyl-3-(4,4,5,5-tetramethyl-1,3,2-dioxaborolan-2-yl)phenyl)benzamide as represented in Scheme A.

The precursor to Example #A.3.7, 2-(1-acetyl-1,2,3,6-tetrahydropyridin-4-yl)-4-bromo-1H-indole-7-carboxamide, was prepared (as shown in Scheme B) by reacting 4-bromo-2-iodo-1H-indole-7-carboxamide (Preparation #1) with 1-(4-(4,4,5,5-tetramethyl-1,3,2-dioxaborolan-2-yl)-5,6-dihydropyridin-1(2H)-yl)ethanone, commercially available Combi-Blocks, following the conditions given in General Procedure A. Hence the Example #A.3.7 would be written as: Example #A.3.7 was prepared from 4-(difluoromethyl)-N-(2-methyl-3-(4,4,5,5-tetramethyl-1,3,2-dioxaborolan-2-yl)phenyl)benzamide (Preparation #29) and 2-(1-acetyl-1,2,3,6-tetrahydropyridin-4-yl)-4-bromo-1H-indole-7-carboxamide (prepared using A with 4-bromo-2-iodo-1H-indole-7-carboxamide [Preparation #1] and 1-(4-(4,4,5,5-tetramethyl-1,3,2-dioxaborolan-2-yl)-5,6-dihydropyridin-1(2H)-yl)ethanone [Combi-Blocks]) using General Procedure A. In the tables after a General Procedure, this is represented by having one reactant in the title of the table and one in a separate column in the same row as the product.

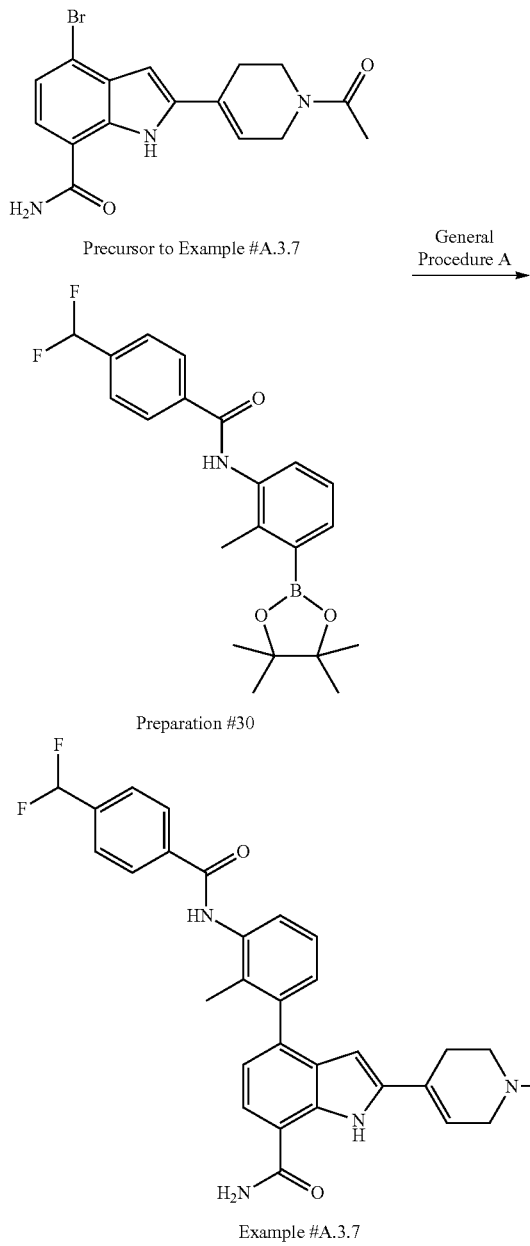

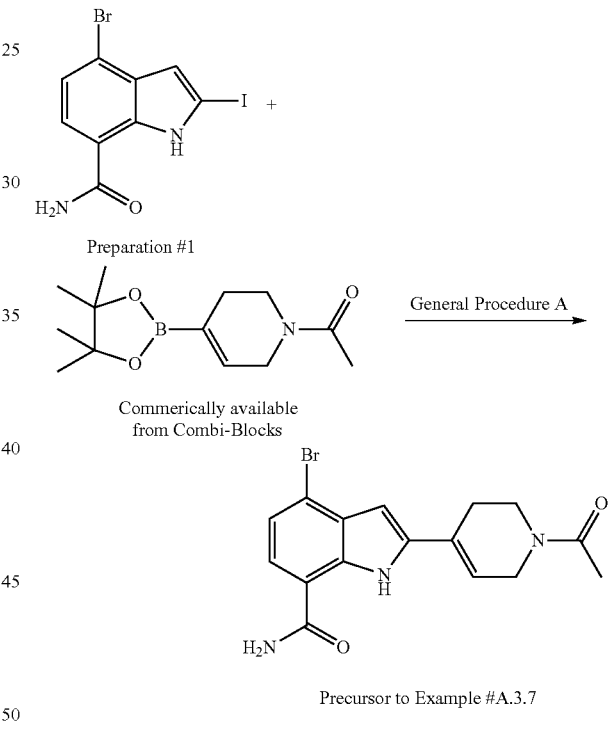

In Vitro BTK Kinase Activity Measured by Time-Resolved Fluorescence Resonance Energy Transfer (trFRET)

The in-house BTK corresponds to recombinant human catalytic domain (aa 393-659), which was expressed in SF9 cells with an N-terminal his tag and purified by immobilized metal affinity chromatography. BTK was mixed with peptide substrate (biotin-TYR1, Sequence: Biotin-(Ahx)-GAEEEI-YAAFFA-COOH, 0.2 μM final) at varying inhibitor concentrations in reaction buffer: 50 mM MOPSO pH 6.5, 10 mM $MgCl_2$, 2 mM $MnCl_2$, 2.5 mM DTT, 0.01% BSA, 0.1 mM $Na_3VO_4$ and 0.001 mM ATP. After about 60 mM incubation at room temperature, the reaction was quenched by addition of EDTA (final concentration: 100 mM) and developed by addition of detection reagents (final approximate concentrations: 30 mM HEPES pH 7.0, 0.06% BSA, 0.006% Tween-20, 0.24 M KF, 80 ng/mL PT66K (europium labeled anti-phosphotyrosine antibody cat #61T66KLB Cisbio, Bedford, Mass.) and 0.6 μg/mL SAXL (Phycolink streptavidin-allophycocyanin acceptor, cat #PJ25S, Prozyme, San Leandro, Calif.). The developed reaction was incubated in the dark for about 60 mM at room temperature, then read via a time-resolved fluorescence detector (Rubystar, BMG) using a 337 nm laser for excitation and monitoring emission wavelength at 665 nm. Within the linear range of the assay, the observed signal at 665 nm was directly related to phosphorylated product and can be used to calculate the $IC_{50}$ values.

For the purpose of the Tables and Examples below, the Btk $IC_{50}$ of each compound is expressed as follows: A=a compound with $IC_{50}$ less than 0.1 μM, B=a compound with $IC_{50}$ within the range of 0.1 μM to 1 μM, and C=a compound with a Btk $IC_{50}$ within the range of 1 μM to 10 μM.

Analytical Methods

Analytical data was included within the procedures below, in the illustrations of the general procedures, or in the tables of examples. Unless otherwise stated, all $^1$H NMR data were collected on a Varian 400 MHz Mercury Plus, Inova, or 400-MR instrument and chemical shifts are quoted in parts per million (ppm). LC/MS and HPLC data are referenced to the table of LC/MS and HPLC conditions using the lower case method letter provided in Table 1.

TABLE 1

LC/MS and HPLC methods

| Method | Conditions |
|---|---|
| a | LC/MS: The gradient was 5-60% B in 1.5 min then 60-95% B to 2.5 min with a hold at 95% B for 1.2 min (1.3 mL/min flow rate). Mobile phase A was 10 mM NH$_4$OAc, mobile phase B was HPLC grade MeCN. The column used for the chromatography is a 4.6 × 50 mm MAC-MOD Halo C18 column (2.7 μm particles). Detection methods are diode array (DAD) and evaporative light scattering (ELSD) detection as well as positive/negative electrospray ionization. |
| b | LC/MS: The gradient was 30-60% B in 1.50 min then 60-95% B to 2.5 min with a hold at 95% B for 1.2 min (1.3 mL/min flow rate). Mobile phase A was 10 mM NH$_4$OAc, mobile phase B was HPLC grade MeCN. The column used for the chromatography was a 4.6 × 50 mm MAC-MOD Halo C8 column (2.7 μm particles). Detection methods were diode array (DAD) and evaporative light scattering (ELSD) detection as well as positive/negative electrospray ionization. |
| c | LC/MS: The gradient was 5% B for 0.1 min, 5-100% B in 5.1 min with a hold at 100% B for 0.5 min then 100-5% B in 0.3 min (2.0 mL/min flow rate). Mobile phase A was 0.1% TFA in water, mobile phase B was HPLC grade MeCN. The column used for the chromatography was a 2.1 × 50 mm Phenomenex Luna Combi-HTS C8(2) column (5 μm particles) at a temperature of 55° C. Detection methods are diode array (DAD) and evaporative light scattering (ELSD) detection under positive APCI ionization conditions. |
| d | LC/MS: The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% TFA in water, mobile phase B was 0.018% TFA in MeCN. The column used for the chromatography was a 2.1 × 50 mm Venusil XBP-C18 column (5 μm particles). Detection methods are diode array (DAD) and evaporative light scattering (ELSD) detection as well as positive/negative electrospray ionization. |
| e | LC/MS: The gradient was 10% B for 0.1 min, 10-100% B in 1.0 min with a hold at 100% B for 0.2 min then 100-10% B in 0.1 min (1.0 mL/min flow rate). Mobile phase A was 0.1% TFA in water, mobile phase B was HPLC grade MeOH. The column used for the chromatography was a 2.1 × 30 mm Waters BEH C8 column (1.7 μm particles) at a temperature of 55° C. Detection methods are diode array (DAD) and evaporative light scattering (ELSD) detection under positive APCI ionization conditions. |
| f | LC/MS: The gradient was 5% B for 0.1 min, 5-100% B in 2.5 min with a hold at 100% B for 0.3 min then 100-5% B in 0.1 min (2.0 mL/min flow rate). Mobile phase A was 0.1% TFA in water, mobile phase B was HPLC grade MeCN. The column used for the chromatography was a 2.1 mm × 50 mm Phenomenex Luna Combi-HTS C8(2) column (5 μm particles) at a temperature of 55° C. Detection methods are diode array (DAD) and evaporative light scattering (ELSD) detection under positive APCI ionization conditions. |
| g | LC/MS: The gradient was 5% B for 0.1 min, 5-100% B in 2.5 min with a hold at 100% B for 0.3 min then 100-5% B in 0.1 min (2.0 mL/min flow rate). Mobile phase A was 0.1% TFA in water, mobile phase B was HPLC grade MeCN. The column used for the chromatography was a 2.1 × 50 mm Phenomenex Luna Combi-HTS C8(2) column (5 μm particles) at a temperature of 65° C. Detection methods are diode array (DAD) and evaporative light scattering (ELSD) detection under positive APCI ionization conditions. |
| h | LC/MS: The gradient was 10-100% MeCN (A) and 10 mM ammonium acetate in water (B) was used, at a flow rate of 1.0 mL/min (0-0.1 min 10% A, 0.1-1.1 min 10-100% A, 1.1-1.3 min 100% A, 1.3-1.4 min 100-10% A). The column used for the chromatography was a 2.1 × 30 mm Waters BEH C8 column (1.7 μm particles) at a temperature of 55° C. Detection methods are diode array (DAD) and evaporative light scattering (ELSD) detection under positive APCI ionization conditions. |
| i | HPLC: The gradient was 5-95% B over about 10 min (25 mL/min flow rate). Mobile phase A was 0.1% TFA in water, mobile phase B was HPLC grade MeCN. The column used for the chromatography was a 250 × 21.2 mm Phenomenex Luna C18(2) 100 Å AXIA column (10 μm particles). Detection method is UV at wavelengths of 220 nM and 254 nM. |

TABLE 1-continued

LC/MS and HPLC methods

| Method | Conditions |
|---|---|
| j | LC/MS: The gradient was 5-100% B in 3.4 min with a hold at 100% B for 0.45 min, 100-5% B in 0.01 min, and then held at 5% B for 0.65 min (0.8 mL/min flow rate). Mobile phase A was 10 mM $NH_4HCO_3$, mobile phase B was HPLC grade MeCN. The column used for the chromatography is a 2.1 × 50 mm Xbridge Shield RPC18 column (5 μm particles). Detection methods are diode array (DAD) and evaporative light scattering (ELSD) detection as well as positive/negative electrospray ionization. |
| k | LC/MS: The gradient was 0-60% B in 2.1 min then 60-100% B to 2.5 min, finally changed to 0% B in 0.02 min under this condition for 0.5 min (1 mL/min flow rate). Mobile phase A was $H_2O$ containing 0.0375% TFA, mobile phase B was MeCN containing 0.018% TFA. The column used for the chromatography is a 2.1 × 30 mm Halo C18 column (2.7 μm particles). Detection methods are diode array (DAD) and evaporative light scattering (ELSD) detection as well as positive/negative electrospray ionization.) |
| l | LC/MS: The gradient was 10-90% B in 1.15 min with a hold at 90% B for 0.4 min, 90-10% B in 0.01 min and then held at 10% B for 0.54 min (1 mL/min flow rate). Mobile phase A 0.0375% TFA in water, mobile phase B was 0.018% TFA in MeCN. The column used for the chromatography is a 2.1 × 30 mm Halo C18 column (2.7 μm particles). Detection methods are diode array (DAD) and positive/negative electrospray ionization. |
| m | LC/MS: The gradient was 10-80% B in 2.0 min then 80-80% B in 0.48 min, finally changed to 10% B in 0.02 min under this condition for 0.5 min (1.0 mL/min flow rate). Mobile phase A was $H_2O$ containing 0.0375% TFA, mobile phase B was MeCN containing 0.018% TFA. The column used for the chromatography is a 2.1 × 30 mm Halo C18 column (2.7 μm particles). Detection methods are diode array (DAD) and positive/negative electrospray ionization. |
| n | HPLC: The gradient was 0-30% B over 25 min (80 mL/min flow rate). Mobile phase A was 0.09% TFA in water, mobile phase B was MeCN. The column used for the chromatography was a 50 × 250 mm Luna(2) C18 column (10 μm particles). Detection method is UV. |
| o | LC/MS: The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% TFA in water, mobile phase B was 0.018% TFA in MeCN. The column used for the chromatography was a 2.1 × 50 mm Venusil XBP-C18 column (5 μm particles). Detection methods are diode array (DAD) and evaporative light scattering (ELSD) detection as well as positive/negative electrospray ionization. |
| p | LC/MS: The gradient was 5-100% B in 3.4 min with a hold at 100% B for 0.45 min, 100-5% B in 0.01 min, and then held at 5% B for 0.65 min (0.8 mL/min flow rate). Mobile phase A was 10 mM $NH_4HCO_3$, mobile phase B was HPLC grade MeCN. The column used for the chromatography was a 2.1 × 50 mm Xbridge Shield RPC18 column (5 μm particles). Detection methods are diode array (DAD) and evaporative light scattering (ELSD) detection as well as positive/negative electrospray ionization. |
| q | HPLC: The gradient was a hold at 21% B for 1 min and then 21-51% B over 7 min with a hold at 51% B for 4 min (25.0 mL/min flow rate). Mobile phase A was 0.075% TFA in water, mobile phase B was 0.075% TFA in MeCN. The column used for the chromatography was a 30 × 100 mm Luna C18 column (5 μm particles). Detection method is UV at wavelengths of 220 nm and 254 nm. |
| r | HPLC: The gradient was a hold at 25% B for 2 min and then 25-55% B over 12 min (25.0 mL/min flow rate). Mobile phase A was 0.075% TFA in water, mobile phase B was 0.075% TFA in MeCN. The column used for the chromatography was a 30 × 100 mm Luna C18 column (5 μm particles). Detection method is UV at wavelengths of 220 nm and 254 nm. |
| s | HPLC: The gradient was 10-38% B over 20 min (80 mL/min flow rate). Mobile phase A was 0.09% TFA in water, mobile phase B was MeCN. The column used for the chromatography was a 50 × 250 mm Luna(2) C18 column (10 μm particles). Detection method is UV. |
| t | HPLC: The gradient was a hold at 5% B for 1 min and then 5-35% B over 12 min (25.0 mL/min flow rate). Mobile phase A was 0.075% TFA in water, mobile phase B was MeCN. The column used for the chromatography was a 30 × 100 mm Luna C18 column (5 μm particles). Detection method is UV at wavelengths of 220 nm and 254 nm. |
| u | HPLC: The gradient was 7-37% B over 8 min with a hold at 37% B for 2 min (25.0 mL/min flow rate). Mobile phase A was 0.04% $NH_3 \cdot H_2O$ in water, mobile phase B was MeCN. The column used for the chromatography was a 25 × 150 mm Waters Xbridge column (5 μm particles). Detection method is UV at wavelengths of 220 nm and 254 nm. |
| v | LC/MS: The gradient was 0-80% B in 3.4 min, 80-100% B in 0.45 min, 100-0% B in 0.01 min, and then held at 0% B for 0.65 min (0.8 mL/min flow rate). Mobile phase A was 0.0375% TFA in water, mobile phase B was 0.018% TFA in MeCN. The column used for the chromatography was a 2.1 × 50 mm Venusil XBP-C18 column (5 μm particles). Detection methods are diode array (DAD) and evaporative light scattering (ELSD) detection as well as positive/negative electrospray ionization. |

TABLE 1-continued

LC/MS and HPLC methods

| Method | Conditions |
|---|---|
| w | HPLC: The gradient was a hold at 18% B for 1 min and then 18-48% B over 12 min (25.0 mL/min flow rate). Mobile phase A was 0.075% TFA in water, mobile phase B was MeCN. The column used for the chromatography was a 30 × 100 mm Luna C18 column (5 μm particles). Detection method is UV at wavelengths of 220 nm and 254 nm. |
| x | HPLC: The gradient was a hold at 23% B for 1 min and then 23-53% B over 12 min (25.0 mL/min flow rate). Mobile phase A was 0.075% TFA in water, mobile phase B was MeCN. The column used for the chromatography was a 30 × 100 mm Luna C18 column (5 μm particles). Detection method is UV at wavelengths of 220 nm and 254 nm. |
| y | HPLC: The gradient was a hold at 20% B for 1 min and then 20-35% B over 12 min (25.0 mL/min flow rate). Mobile phase A was 0.075% TFA in water, mobile phase B was MeCN. The column used for the chromatography was a 30 × 100 mm Luna C18 column (5 μm particles). Detection method is UV at wavelengths of 220 nm and 254 nm. |
| z | HPLC: The gradient was a hold at 15% B for 1 min and then 15-45% B over 12 min (25.0 mL/min flow rate). Mobile phase A was 0.075% TFA in water, mobile phase B was MeCN. The column used for the chromatography was a 30 × 100 mm Luna C18 column (5 μm particles). Detection method is UV at wavelengths of 220 nm and 254 nm. |
| aa | HPLC: The gradient was a hold at 5% B for 0.2 min, 5-95% B over 1.7 min with a hold at 95% B for 1.3 min (2.5 mL/min flow rate). Mobile phase A was 0.01% TFA in water, mobile phase B was 0.01% TFA in MeCN. The column used for the chromatography was a 4.6 × 50 mm SunFire C18 column (3.5 μm particles) at a temperature of 50° C. Detection method is UV. |
| ab | HPLC: The gradient was a hold at 5% B for 0.2 min, 5-95% B over 1.7 min with a hold at 95% B for 1.4 min (2.1 mL/min flow rate). Mobile phase A was 0.01% TFA in water, mobile phase B was 0.01% TFA in MeCN. The column used for the chromatography was a 4.6 × 50 mm XBridge C18 column (3.5 μm particles) at a temperature of 50° C. Detection method is UV. |
| ac | HPLC: The gradient was a hold at 5% B for 0.2 min, 5-95% B over 1.7 min with a hold at 95% B for 1.4 min (2.1 mL/min flow rate). Mobile phase A was 10 mM $NH_4HCO_3$, mobile phase B was MeCN. The column used for the chromatography was a 4.6 × 50 mm XBridge C18 column (3.5 μm particles) at 50° C. Detection method is UV. |
| ad | HPLC: The gradient was 37-67% B over 23 min (80 mL/min flow rate). Mobile phase A was 0.04% $NH_3\cdot H_2O$ in water, mobile phase B was MeCN. The column used for the chromatography was a 50 × 300 mm Gemini column (10 μm particles). Detection method is UV at wavelengths of 220 nm and 254 nm. |
| ae | LC/MS: The gradient was 10% B for 0.1 min, 10-100% B in 1.0 min with a hold at 100% B for 0.2 min then 100-10% B in 0.1 min (1.0 mL/min flow rate). Mobile phase A was 0.1% TFA in water, mobile phase B was HPLC grade MeCN. The column used for the chromatography was a 2.1 × 30 mm Waters BEH C8 column (1.7 μm particles) at a temperature of 55° C. Detection methods are diode array (DAD) and evaporative light scattering (ELSD) detection under positive APCI ionization conditions. |
| af | HPLC: The gradient was a hold at 10% B for 0.5 min, 20-100% B over 6.5 min, 95% B for 3 min, and then 95-10% B over 2 min (50.0 mL/min flow rate). Mobile phase A was 0.1% TFA in water and mobile phase B was HPLC grade MeCN. The column used for the chromatography was a 30 × 75 mm Phenomenex Luna C8(2) 100 Å AXIA column (5 μm particle). Detection methods were Waters 996 diode-array detector and Alltech Varex III evaporative light-scattering detector. |
| ag | HPLC: The gradient was a hold at 10% B for 0.5 min, 40-75% B over 6.5 min, 95% B for 3 min, and then 95-10% B over 2 min (50.0 mL/min flow rate). Mobile phase A was 0.1% TFA in water and mobile phase B was HPLC grade MeCN. The column used for the chromatography was a 30 × 75 mm Phenomenex Luna C8(2) 100 Å AXIA column (5 μm particle). Detection methods were Waters 996 diode-array detector and Alltech Varex III evaporative light-scattering detector. |
| ah | Instrument: Gilson 281 semi-preparative HPLC system<br>Mobile phase: A: 15 mL TFA in 20 L $H_2O$; B: MeCN<br>Column: Luna 100 × 30.0 mm, 5μ; Flow rate: 25 mL/min;<br>Monitor wavelength: 220&254 nm<br>Gradient: an initial hold at 21% B for 1 min, a gradient of 21% to 51% B in 12 min |
| ai | Instrument: Shimadzu LC-20AP preparative HPLC<br>Column: Synergi Max-RP C18 250 × 80 mm i.d. 10 u<br>Mobile phase: A for $H_2O$(0.09% TFA) and B for $CH_3CN$<br>Gradient: B from 15% to 43% in 25 min<br>Flow rate: 40 mL/min<br>Injection amount: 50 mg per injection |
| aj | Instrument: Gilson 281 semi-preparative HPLC system<br>Mobile phase: A: TFA/$H_2O$ = 0.075% v/v; B: MECN<br>Column: Luna C18 100 × 30.0 mm, 5μ |

TABLE 1-continued

LC/MS and HPLC methods

| Method | Conditions |
|---|---|
|  | Flow rate: 25 mL/min<br>Monitor wavelength: 220&254 nm<br>Gradient:<br><br>| Time | B % |<br>|---|---|<br>| 0.00 | 10 |<br>| 12.0 | 40 |<br>| 14.0 | 40 |<br>| 14.2 | 100 |<br>| 16.2 | 100 |<br>| 16.4 | 10 |<br>| 18.0 | 10 | |
| ak | Instrument: Gilson 281 semi-preparative HPLC system<br>Mobile phase: A: TFA/H$_2$O = 0.075% v/v; B: MeCN<br>Column:<br>Luna C18 200 × 21.2 mm, 5μ<br>Flow rate: 25 mL/min<br>Monitor wavelength: 220&254 nm<br>Gradient:<br><br>| Time | B % |<br>|---|---|<br>| 0.00 | 1 |<br>| 12.0 | 8 |<br>| 14.0 | 8 |<br>| 14.2 | 100 |<br>| 16.2 | 100 |<br>| 16.4 | 1 |<br>| 18.0 | 1 | |
| al | Instrument: Gilson 281 semi-preparative HPLC system<br>Mobile phase: A: 15 mL TFA in 20 L H$_2$O; B: MeCN<br>Column: Luna 100 × 30.0 mm, 5μ<br>Flow rate: 25 mL/min<br>Monitor wavelength: 220&254 nm<br>Gradient: an initial hold at 8% B for 1 min, a gradient of 8% to 38% B in 12 min |
| am | Instrument: Gilson 281 semi-preparative HPLC system<br>Mobile phase: A: TFA/H$_2$O = 0.075% v/v; B: MeCN<br>Column: Luna C18 100 × 30.0 mm, 5μ<br>Flow rate: 25 mL/min<br>Monitor wavelength: 220&254 nm<br>Gradient:<br><br>| Time | B % |<br>|---|---|<br>| 0.00 | 18 |<br>| 8.00 | 48 |<br>| 12.0 | 48 |<br>| 12.1 | 100 |<br>| 13.6 | 100 |<br>| 13.7 | 18 |<br>| 14.7 | 18 | |
| an | Instrument: Gilson 281 semi-preparative HPLC system<br>Mobile phase: A: 8 mL NH$_3$•H$_2$O in 20 L H$_2$O; B: MeCN<br>Column: waters Xbridge130 × 21.2 mm, 5μ<br>Flow rate: 25 mL/min<br>Monitor wavelength: 220&254 nm<br>Gradient: an initial hold at 27% B for 1 min, a gradient of 27% to 57% B in 12 min |
| ao | Instrument: Shimadzu LC-8A preparative HPLC<br>Column: Luna(2) C18 250 × 50 mm i.d. 10 u<br>Mobile phase: A for H$_2$O (0.09% TFA) and B for CH$_3$CN<br>Gradient: B from 82% to 82%<br>Flow rate: 100 mL/min<br>Injection amount: 0.7 g per injection |
| ap | HPLC: The gradient was a hold at 10% B for 0.5 min, 10-50% B over 6.5 min,<br>50-80% over 5 min, 80-100% over 0.5 min, with a hold at 100% B for 0.5 min (40 mL/min<br>flow rate). Mobile phase A was 0.01% TFA in water, mobile phase B<br>was MeCN. The column used for the chromatography was a 30 × 75 mm SunFire<br>C8 column (5 μm particles) at ambient temperature. Detection method is UV. |
| aq | HPLC: The gradient was a hold at 10% B for 0.5 min, 10-50% B over 3.5 min,<br>50-80% over 4 min, 80-100% over 1.0 min, with a hold at 100% B for 2.0 min (40 mL/min<br>flow rate). Mobile phase A was 0.01% TFA in water, mobile phase B<br>was MeCN. The column used for the chromatography was a 30 × 75 mm SunFire<br>C8 column (5 μm particles) at ambient temperature. Detection method is UV. |
| ar | LC/MS: The gradient was a hold at 5% B for 0.2 min, 5-95% B over 1.7 min with<br>a hold at 95% B for 1.3 min (2.3 mL/min flow rate). Mobile phase A was 0.01% |

TABLE 1-continued

LC/MS and HPLC methods

| Method | Conditions |
|---|---|
|  | TFA in water, mobile phase B was 0.01% TFA in MeCN. The column used for the chromatography was a 4.6 × 50 mm XBridge C18 column (3.5 μm particles) at a temperature of 50° C. Detection methods are diode array (DAD) under positive APCI ionization conditions. |
| as | LC/MS: The gradient was 5-60% B in 1.50 min then 60-95% B to 2.5 min with a hold at 95% B for 1.2 min (1.3 mL/min flow rate). Mobile phase A was 10 mM NH₄OAc, mobile phase B was HPLC grade MeCN. The column used for the chromatography was a 4.6 × 50 mm MAC-MOD Halo C8 column (2.7 μm particles). Detection methods were diode array (DAD) and evaporative light scattering (ELSD) detection as well as positive/negative electrospray ionization. |
| at | LC/MS: The gradient was 5-95% B over 1.2 min, with a hold at 95% for 1.3 min, back to 5% over 0.01 min (2.0 mL/min flow rate). Mobile phase A was 0.01% TFA in water, mobile phase B was 0.01% TFA in MeCN. The column used for the chromatography was a 4.6 × 50 mm SunFire C18 column (3.5 μm particles) at 50 C. Detection method is UV |
| au | LC/MS: The gradient was 5-95% B over 1.3 min, with a hold at 95% for 1.5 min, back to 5% over 0.01 min (1.8 mL/min flow rate). Mobile phase A was 0.01% ammonium acetate in water, mobile phase B was MeCN. The column used for the chromatography was a 4.6 × 50 mm Xbridge C18 column (3.5 μm particles) at 50 C. Detection method is UV |
| av | LC/MS: The gradient was 5-100% B over 1.2 min, with a hold at 100% for 1.3 min (2.0 mL/min flow rate). Mobile phase A was 0.01% TFA in water, mobile phase B was 0.01% TFA in MeCN. The column used for the chromatography was a 4.6 × 50 mm Sunfire C18 column (3.5 μm particles) at 50 C. Detection method is UV and MS |
| aw | LC/MS: The gradient was 5-95% B over 1.3 min, with a hold at 95% for 1.5 min (1.8 mL/min flow rate). Mobile phase A was 0.01% ammonium acetate in water, mobile phase B was MeCN. The column used for the chromatography was a 4.6 × 50 mm Xbridge C18 column (3.5 μm particles) at 50 C. Detection method is UV and MS |
| ax | LC/MS: The gradient was 5-100% B over 1.3 min (2.0 mL/min flow rate). Mobile phase A was 0.01% TFA in water, mobile phase B was 0.01% TFA in MeCN. The column used for the chromatography was a 4.6 × 50 mm Sunfire C18 column (3.5 μm particles) at 45 C. Detection method is UV and MS |
| ay | LC/MS: The gradient was 5-100% B over 1.2 min, with a hold at 95% for 1.3 min (2.0 mL/min flow rate). Mobile phase A was 0.01% TFA in water, mobile phase B was 0.01% TFA in MeCN. The column used for the chromatography was a 4.6 × 50 mm Sunfire C18 column (3.5 μm particles) at 50 C. Detection method is UV and MS |
| az | LC/MS: The gradient was 5-100% B over 1.2 min, with a hold at 100% for 1.3 min (2.0 mL/min flow rate), then down to 95% over 0.01 min. Mobile phase A was 0.01% TFA in water, mobile phase B was 0.01% TFA in MeCN. The column used for the chromatography was a 4.6 × 50 mm Sunfire C18 column (3.5 μm particles) at 50 C. Detection method is UV and MS |
| ba | LC/MS: The gradient was 5-60% B in 1.50 min then 60-95% B to 2.5 min with a hold at 95% B for 1.2 min (1.3 mL/min flow rate). Mobile phase A was 0.1% formic acid in water, mobile phase B was HPLC grade MeCN. The column used for the chromatography was a 4.6 × 50 mm MAC-MOD Halo C18 column (2.7 μm particles). Detection methods were diode array (DAD) and evaporative light scattering (ELSD) detection as well as positive/negative electrospray ionization. |
| bb | LC/MS: The gradient was 5-60% B in 0.60 min then 60-95% B to 1.00 min with a hold at 95% B for 0.30 min (1.3 mL/min flow rate). Mobile phase A was 10 mM ammonium acetate, mobile phase B was HPLC grade MeCN. The column used for the chromatography was a 2.1 × 50 mm ACE Excel 2 UHPLC C18 column (2.0 μm particles). Detection methods were diode array (DAD) and evaporative light scattering (ELSD) detection as well as positive/negative electrospray ionization. |
| bc | Instrument Gilson 281(PHG008)<br>Column: waters X-bridge ODS C 18 19 × 250 mm, 10 μm<br>Mobile Phase: A: water (10 ppM NH₄HC0₃); B: ACN<br>Flow Rate: 30 mL/min<br>Monitor wavelength: 220 & 254 nm<br>Gradient: 10-60% B in 8 min, stop at 15 min |
| bd | HPLC: The column used for the chromatography was a 21.2 × 250 mm Hypersil C18 HS column (8 mm particles). The gradient was 40% B for 4 min, 40-65% B over 30 min (21 mL/min flow rate). Mobile phase A was 0.05N aqueous NH₄OAc buffer (pH 4.5) and mobile phase B was HPLC grade MeCN. Detection method is UV, l = 254 nm |
| be | LC/MS: The gradient was 5-100% B over 1.2 min, with a hold at 100% for 1.3 min, then back down to 5% over 0.01 min (2.0 mL/min flow rate). Mobile phase A was 0.01% TFA in water, mobile phase B was 0.01% TFA in MeCN. The column used for the chromatography was a 4.6 × 50 mm Sunfire C18 column (3.5 μm particles) at 50 C. Detection method is UV and MS |

TABLE 2

Chiral HPLC methods

| Method | Conditions |
|---|---|
| 1 | The gradient was 20% B in 15.25 min then 20-65% B in 0.05 min and held at 65% B for 6.70 min Then equilibrated back down to 20% and held for 4 min (20 mL/min flow rate). Mobile phase B was 1:1 EtOH/MeOH and mobile phase A was HPLC grade heptane with 0.12% diethylamine added. The column used for the chromatography was a Daicel IA, 20 × 250 mm column (5 μm particles). Detection method was UV ($\lambda$ = 264 nm) |
| 2 | The method was isocratic 25% B for 25 min (20 mL/min flow rate). Mobile phase B was EtOH and Mobile phase A was HPLC grade heptane with no modifier added. The column used for the chromatography was a Daicel IA, 20 × 250 mm column (5 μm particles). Detection methods were evaporative light scattering (ELSD) detection and UV ($\lambda$ = 312 nm) |
| 3 | (LC) The gradient was 40-65% B in 14.75 min then step to 98% B and hold for 5.2 min (20 mL/min flow rate). Mobile phase B was EtOH (200 proof), mobile phase A was HPLC grade heptane with 0.2% diethylamine added. The column used for the chromatography was a WhelkO1 R,R 21 × 250 mm column from Regis Technologies (5 μm particles). |
| 4 | (SFC) Isocratic, 50% co-solvent B (80 mL/min, 100 bar system pressure, 40° C.). Co-solvent B was 1:1 HPLC grade EtOh:MeCN with 0.1% triethylamine added. Solvent A was SFC grade $CO_2$. The column used for the chromatography was a 30 × 250 mm Daicel Chiralpak AS-H (5 μm particles). |
| 5 | (LC) Isocratic 18% B for 20 min then 18-30% B in 7 min and hold at 30% B for 6 min (20 mL/min flow rate). Mobile phase B was EtOH (200 proof), mobile phase A was HPLC grade heptane with 0.2% diethylamine added. The column used for the chromatography was a WhelkO1 R,R 21 × 250 mm column from Regis Technologies (5 μm particles). |
| 6 | (LC) Isocratic 9% B for 37.5 min then step to 40% B to elute second stereoisomer (20 mL/min flow rate). Mobile phase B was EtOH (200 proof), mobile phase A was HPLC grade heptane with 0.2% diethylamine added. The chromatography used a Daicel IA, 21 × 250 mm column (5 μm particles). |
| 7 | (LC) Isocratic 22% B for 19 min then step to 35% B and hold for 3 min (20 mL/min flow rate). Mobile phase B was EtOH (200 proof), mobile phase A was HPLC grade heptane with 0.2% diethylamine added. The chromatography used a Daicel IE, 20 × 250 mm column (5 μm particles). |
| 8 | (LC) Isocratic 30% B for 15 min then 30-33% B in 9 min then step to 45% B and hold for 4 min (20 mL/min flow rate). Mobile phase B was EtOH (200 proof), mobile phase A was HPLC grade heptane with 0.2% diethylamine added. The chromatography used a Daicel IE, 20 × 250 mm column (5 μm particles). |
| 9 | (LC) Isocratic 15% B for 17 min then step to 55% B and hold for 11 min (20 mL/min flow rate). Mobile phase B was EtOH (200 proof), mobile phase A was HPLC grade heptane with 0.2% diethylamine added. The chromatography used a Daicel IC, 20 × 250 mm column (5 μm particles). |
| 10 | (LC) Isocratic 20% B for 42 min (20 mL/min flow rate). Mobile phase B was EtOH (200 proof), mobile phase A was HPLC grade heptane with 0.2% diethylamine added. The chromatography used a Daicel IC, 20 × 250 mm column (5 μm particles). |
| 11 | (LC) Isocratic 25% B for 18.5 min then step to 60% B and hold for 4 min (20 mL/min flow rate). Mobile phase B was 200 proof EtOH, mobile phase A was HPLC grade heptane with 0.2% diethylamine added. The column used for the chromatography was a WhelkO1 S,S 21 × 250 mm column from Regis Technologies (5 μm particles). |
| 12 | LC) Isocratic 25% B for 15 min then step to 45% B and hold for 12 min (20 mL/min flow rate). Mobile phase B was HPLC grade IPA, mobile phase A was HPLC grade heptane with 0.2% diethylamine added. The column used for the chromatography was a Daciel IC 20 × 250 mm column (5 μm particles). |
| 13 | LC) Isocratic 30% B for 15.5 min then step to 35% B and hold for 20 min (20 mL/min flow rate). Mobile phase B was HPLC grade IPA, mobile phase A was HPLC grade heptane with 0.2% diethylamine added. The column used for the chromatography was a Daicel IF 20 × 250 mm column (5 μm particles). |
| 14 | (LC) Isocratic 25% B for 25 min (20 mL/min flow rate). Mobile phase B was EtOH (200 proof), mobile phase A was HPLC grade heptane with 0.2% diethylamine added. The chromatography used a Daicel IB, 20 × 250 mm column (5 μm particles). |
| 15 | (LC) 40-45% B in 5 min, hold at 45% B for 23 min then step to 65% B and hold for 10 min (20 mL/min flow rate). Mobile phase B was EtOH (200 proof), mobile phase A was HPLC grade heptane with no modifier added. The column used for the chromatography was a WhelkO1 S,S 21 × 250 mm column from Regis Technologies (5 μm particles). |
| 16 | (LC) Isocratic 19% B for 35 min (25 mL/min flow rate). Mobile phase B was HPLC grade MeCN, mobile phase A was HPLC grade water with no modifier added. The chromatography used an Astec, Chirobiotic T 21.2 × 250 mm column (5 μm particles). |
| 17 | (LC) Isocratic 25% B for 18.5 min then step to 50% B and hold for 5.5 min (20 mL/min flow rate). Mobile phase B was 200 proof EtOH, mobile phase A was HPLC grade heptane with 0.2% diethylamine added. The column used for the chromatography was a Daicel IF, 20 × 250 mm column (5 μm particles). |

TABLE 2-continued

Chiral HPLC methods

| Method | Conditions |
|---|---|
| 18 | (LC) Isocratic 5% B for 37.5 min (20 mL/min flow rate). Mobile phase B was 200 proof EtOH, mobile phase A was HPLC grade heptane with 0.2% diethylamine added. The column used for the chromatography was a Daicel IB, 20 × 250 mm column (5 μm particles). |
| 19 | (LC) Isocratic 20% B for 30 min (20 mL/min flow rate). Mobile phase B was 200 proof EtOH, mobile phase A was HPLC grade heptane with 0.2% diethylamine added. The column used for the chromatography was a Daicel IF, 20 × 250 mm column (5 μm particles). |

General Purification Methods

For the general procedures, the final compounds may be purified by any technique or combination of techniques known to one skilled in the art. Some examples that are not limiting include column chromatography with a solid phase (i.e. silica gel, alumina, etc.) and a solvent (or combination of solvents) that elutes the desired compounds (I.e. hexanes, heptane, EtOAc, DCM, MeOH, EtOH, MeCN, water, etc.); preparatory TLC with a solid phase (i.e. silica gel, alumina etc.) and a solvent (or combination of solvents) that elutes the desired compounds (I.e. hexanes, heptane, EtOAc, DCM, MeOH, EtOH, MeCN, water, etc.); reverse phase HPLC (see Table 1 for some non-limiting conditions); recrystallization from an appropriate solvent (i.e. MeOH, EtOH, IPA, EtOAc, toluene, etc.) or combination of solvents (i.e. EtOAc/heptane, EtOAc/MeOH, etc.); chiral LC with a solid phase and an appropriate solvent (i.e. EtOH/heptane, MeOH/heptane, IPA/heptane, etc. with or without a modifier such as diethylamine, TFA, etc.) to elute the desired compound; chiral SFC with a solid phase and $CO_2$ with an appropriate modifier (i.e. MeOH, EtOH, IPA with or without additional modifier such as diethylamine, TFA, etc.); precipitation from a combination of solvents (i.e. DMF/water, DMSO/DCM, EtOAc/heptane, etc.); trituration with an appropriate solvent (i.e. EtOAc, DCM, MeCN, MeOH, EtOH, IPA, n-PrOH, etc.); extractions by dissolving a compound in a liquid and washing with an appropriately immiscible liquid (i.e. DCM/water, EtOAc/water, DCM/saturated $NaHCO_3$, EtOAc/saturated $NaHCO_3$, DCM/10% aqueous HCl, EtOAc/10% aqueous HCl, etc.); distillation (i.e. simple, fractional, Kugelrohr, etc.); gas chromatography using an appropriate temperature, carrier gas and flow rate; sublimation at an appropriate temperature and pressure; filtration through a media (i.e. Florosil®, alumina, Celite®, silica gel, etc.) with a solvent (i.e. heptane, hexanes, EtOAc, DCM, MeOH, etc.) or combination of solvents; salt formation with solid support (resin based, i.e. ion exchange) or without. Some descriptions of these techniques can be found in the following references, Gordon, A. J. and Ford, R. A. "The Chemist's Companion", 1972; Palleros, D. R. "Experimental Organic Chemistry", 2000; Still, W. C., Kahn, M. and Mitra, A. J. Org. Chem. 1978, 43, 2923; Yan, B. "Analysis and Purification Methods in Combinatorial Chemistry" 2003; Harwood, L. M., Moody, C. J. and Percy, J. M. "Experimental Organic Chemistry: Standard and Microscale, 2nd Edition", 1999; Stichlmair, J. G. and Fair, J. R. "Distillation; Principles and Practices" 1998; Beesley T. E. and Scott, R. P. W. "Chiral Chromatography", 1999; Landgrebe, J. A. "Theory and Practice in the Organic Laboratory, 4th Edition", 1993; Skoog, D. A. and Leary, J. J. "Principles of Instrumental Analysis, 4th Edition" 1992; Subramanian, G. "Chiral Separation Techniques 3rd Edition" 2007; Kazakevich, Y. and Lobrutto, R. "HPLC for Pharmaceutical Scientists" 2007. Final or intermediate compounds prepared via any of the following General Procedures can be optionally purified using one or more of the purification methods described above.

Preparations and Examples

The general synthetic methods used in each General Procedure follow and include an illustration of a compound that was synthesized using the designated General Procedure. None of the specific conditions and reagents noted herein are to be construed as limiting the scope of the invention and are provided for illustrative purposes only. All starting materials are commercially available from Sigma-Aldrich (including Fluka and Discovery CPR) unless otherwise noted after the chemical name. Reagent/reactant names given are as named on the commercial bottle or as generated by IUPAC conventions, CambridgeSoft® ChemDraw Ultra 9.0.7, CambridgeSoft® Chemistry E-Notebook v9.0.127 or v11.0.3.68, or AutoNom 2000. Compounds designated as salts (e.g. hydrochloride, acetate) may contain more than one molar equivalent of the salt. Compounds of the invention where the absolute stereochemistry has been determined by the use of a commercially available enantiomerically pure starting material or a stereochemically defined intermediate, or by X-ray diffraction are denoted by an asterisk after the example number.

Preparation #1.
4-Bromo-2-iodo-1H-indole-7-carboxamide

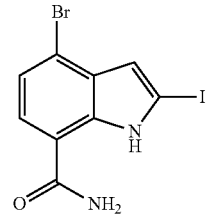 [SMILES: NC(=O)c1ccc(Br)c2cc(I)[nH]c12]

Step A: 4-Bromo-1H-indole-7-carboxylic acid

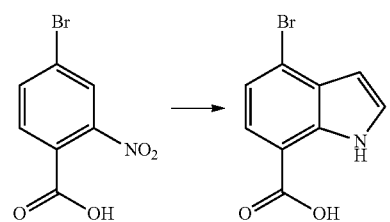 [SMILES: O=C(O)c1ccc(Br)cc1[N+](=O)[O-] ; O=C(O)c1ccc(Br)c2cc[nH]c12]

To a solution of 4-bromo-2-nitrobenzoic acid (30 g, 122 mmol) in anhydrous THF (500 mL), a solution of vinylmagnesium bromide (51.2 mL, 512 mmol, 1 N) in THF was added dropwise at about −30 to −50° C. The reaction mixture was stirred at about −30 to −40° C. for about 2 h. Then the reaction mixture was poured into saturated aqueous NH₄Cl solution and the mixture was extracted with EtOAc (200 mL×2). The combined organic layers were washed with brine, dried over andydrous Na₂SO₄, filtered and concentrated under reduced pressure to provide 4-bromo-1H-indole-7-carboxylic acid (33 g crude), which was used directly for next step without further purification. $^1$H NMR (400 MHz, DMSO-d₆) δ 11.42 (m, 1H), 8.11 (bs, 1H), 7.63 (dd, J=17.4, 8.0 Hz, 1H), 7.45 (dt, J=14.2, 2.8 Hz, 1H), 7.32 (dd, J=21.9, 8.0 Hz, 1H), 6.47 (ddd, J=25.5, 3.1, 2.1 Hz, 1H).

Step B: Methyl 4-bromo-1H-indole-7-carboxylate

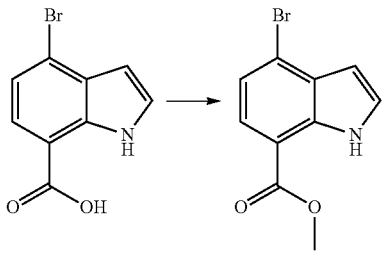

To a solution of 4-bromo-1H-indole-7-carboxylic acid (33 g, 137 mmol) in DMF (300 mL), Cs₂CO₃ (90 g, 276 mmol) was added and stirred at rt for 1 h. Then iodomethane (29.3 g, 206 mmol) was added dropwise at about 0° C. The reaction mixture was warmed to rt for about 3 h. The mixture was poured into water and extracted with EtOAc (200 mL×2). The combined organic layers were washed with brine, dried over anhydrous Na₂SO₄, filtered and concentrated under reduced pressure and the residue was purified by silica gel column chromatography to provide methyl 4-bromo-1H-indole-7-carboxylate (13.8 g, 20%): $^1$H NMR (CDCl₃) δ 9.98 (s, 1H), 7.76-7.74 (d, J=8, 1H), 7.39-7.34 (m, 2H), 6.68-6.66 (m, 1H), 4.00 (s, 3H).

Step C: Methyl 4-bromo-1-tosyl-1H-indole-7-carboxylate

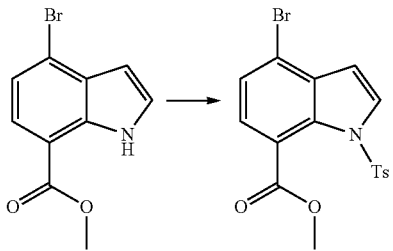 [SMILES: COC(=O)c1ccc(Br)c2cc[nH]c12 ; COC(=O)c1ccc(Br)c2ccn(S(=O)(=O)c3ccc(C)cc3)c12]

To a solution of methyl 4-bromo-1H-indole-7-carboxylate (130 g, 512 mmol) in anhydrous THF (1500 mL) was added NaH (18.4 g, 767 mmol) in portions at about 0° C. and stirred for about 1 h at 0° C. Then TsCl (117 g, 614 mmol) was added in portions at about 0° C. The reaction mixture was warmed to rt for about 2 h. The reaction mixture was poured into ice water and extracted with EtOAc (1000 mL×2). The combined organic layers were washed with brine, dried over anhydrous Na₂SO₄, filtered and concentrated under reduced pressure and the residue was purified by silica gel column chromatography to provide methyl 4-bromo-1-tosyl-1H-indole-7-carboxylate (150 g, 72%): $^1$H NMR (CDCl₃) δ 7.60-7.58 (d, J=8.4, 2H), 7.54-7.53 (d, J=3.6, 1H), 7.46-7.44 (d, J=8, 1H), 7.37-7.35 (d, J=8.4, 1H), 7.21-7.18 (d, J=8.4, 2H), 6.77-6.76 (m, 1H), 3.93 (s, 3H), 2.35 (s, 3H).

Step D: Methyl 4-bromo-2-iodo-1-tosyl-1H-indole-7-carboxylate

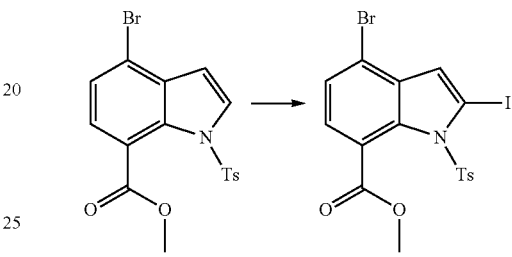

To a solution of diisopropylamine (6.2 g, 61.2 mmol) in anhydrous THF (100 mL), stirred in t-BuLi (3.92 g, 61.2 mmol) in pentane was added at about 0° C. under N₂ atmosphere, and the mixture was stirred for about 10 min. The solution of methyl 4-bromo-1-tosyl-1H-indole-7-carboxylate (10 g, 24.49 mmol) in anhydrous THF (100 mL) was added at about −70° C. under N₂ atmosphere. After about 30 min, a solution of I₂ (9.33 g, 36.7 mmol) in anhydrous THF (50 mL) was added. After about 30 min, the cooling bath was removed and the mixture was stirred for about another hour. The mixture was quenched with saturated aqueous Na₂S₂O₃. Water and EtOAc were added to the mixture. The layers were separated and the aqueous layer was extracted with EtOAc (300 mL×2). The combined organic layers were washed with brine, dried with anhydrous Na₂SO₄, filtered, concentrated under reduced pressure and the residue was purified by silica gel column chromatography to provide methyl 4-bromo-2-iodo-1-tosyl-1H-indole-7-carboxylate (7.5 g, 38%): $^1$H NMR (CDCl₃): δ 7.64-7.59 (m, 2H), 7.55-7.53 (m, 2H), 7.30-7.27 (m, 2H), 7.17-7.17 (m, 1H), 4.06-4.05 (d, J=1.2, 3H), 2.49 (s, 3H).

Step E: 4-Bromo-2-iodo-1H-indole-7-carboxylic acid

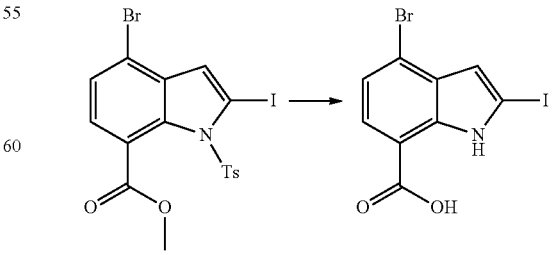

To a solution of methyl 4-bromo-2-iodo-1-tosyl-1H-indole-7-carboxylate (75 g, 23.4 mmol) in MeOH (750 mL), THF (1500 mL) and water (750 mL), LiOH (67 g, 280 mmol) was added the reaction mixture was heated at about 45° C. for about 3 h. The resulting solution was concentrated under reduced pressure to remove MeOH and THF, then the solution was adjusted to pH=6 to 7 with HCl (1 N), the precipitate was filtered and dried by high vacuum to provide 4-bromo-2-iodo-1H-indole-7-carboxylic acid (45 g, 88%): $^1$H NMR (DMSO-d6) δ 11.60 (s, 1H), 7.56 (d, J=8.0, 1H), 7.31 (m, J=8.0, 1H), 6.72 (s, 1H).

Step F: 4-bromo-2-iodo-1H-indole-7-carboxamide

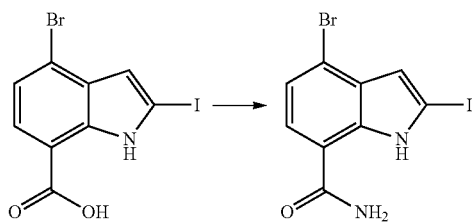 [SMILES: O=C(O)c1ccc(Br)c2cc(I)[nH]c12 ; NC(=O)c1ccc(Br)c2cc(I)[nH]c12]

To a solution of 4-bromo-2-iodo-1H-indole-7-carboxylic acid (45 g, 123 mmol) in DMF (450 mL) was added HOBt (28.2 g, 184 mmol), PyBOP (96 g, 184 mmol), NH$_4$Cl (10 g, 184.5 mmol) and DIEA (63.6 g, 492 mmol). The reaction mixture was stirred at rt for about 2 h. Water was added, the reaction mixture was extracted with EtOAc (1000 mL×2), the organic phase was dried with anhydrous Na$_2$SO$_4$ and concentrated under reduced pressure and the residue was purified by column chromatography with Pet ether:EtOAc (20:1 to 1:1) to provide 4-bromo-2-iodo-1H-indole-7-carboxamide (25 g, 56%): $^1$H NMR (DMSO-d6) δ 11.62 (s, 1H), 8.24 (s, 1H), 7.62-7.60 (d, J=8, 2H), 7.38-7.36 (d, J=8, 1H), 6.77 (s, 1H): LC/MS (Table 1, Method d) R$_t$=3.07 min; MS m/z: 366 (M–H)$^-$.

Preparation #2. 4-Bromo-1H-indole-7-carboxamide

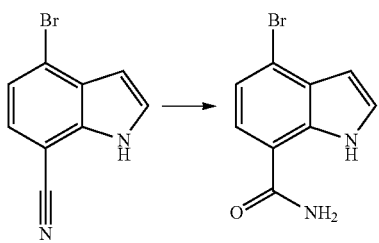 [SMILES: N#Cc1ccc(Br)c2cc[nH]c12 ; NC(=O)c1ccc(Br)c2cc[nH]c12]

To a solution of 4-bromo-1H-indole-7-carbonitrile (3 g, 13.57 mmol, Sinova) in EtOH (36.2 mL)/DMSO (9.05 mL) was slowly added hydrogen peroxide (28.0 mL, 274 mmol) and NaOH (28.0 mL, 28.0 mmol). The reaction mixture was stirred at rt for about 1 h. Water was added and the precipitate was collected by filtration, washed with water, and dried under vacuum to provide 4-bromo-1H-indole-7-carboxamide (2.85 g, 88%). LC/MS (Table 1, Method f) R$_t$=1.42 min; MS m/z: 280 (M+MeCN)$^+$.

Preparation #3. 2-(2-Methyl-3-(4,4,5,5-tetramethyl-1,3,2-dioxaborolan-2-yl)phenyl)-3,4-dihydroisoquinolin-1(2H)-one

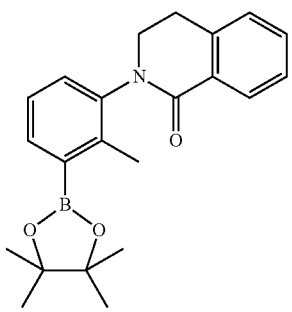 [SMILES: Cc1c(B2OC(C)(C)C(C)(C)O2)cccc1N1CCc2ccccc2C1=O]

Step A: 3,4-Dihydroisoquinolin-1(2H)-one

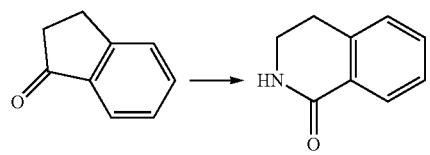 [SMILES: O=C1CCc2ccccc21 ; O=C1NCCc2ccccc21]

To a solution of 2,3-dihydro-1H-inden-1-one (30 g, 227 mmol) in DCM (300 mL) was added methanesulfonic acid (300 mL) and the solution was cooled to about 0° C. Sodium azide (30 g, 461 mmol) was added to the solution in portions at about 0° C. and the reaction mixture was stirred overnight at rt. The reaction mixture was neutralized with 20% aqueous NaOH and extracted with DCM (2×1 L). The organic phase was dried with anhydrous Na$_2$SO$_4$ and concentrated to give a residue, which was purified by column chromatography on silica gel to provide 3,4-dihydroisoquinolin-1(2H)-one (5 g, 15%): $^1$H NMR (MeOD) δ 7.93-7.91 (m, 1H), 7.49-7.45 (m, 1H), 7.36-7.45 (m, 1H), 7.28-7.26 (d, 1H), 3.50-3.46 (t, 2H), 2.97-2.94 (t, 2H).

Step B: 2-(3-Bromo-2-methylphenyl)-3,4-dihydroisoquinolin-1(2H)-one

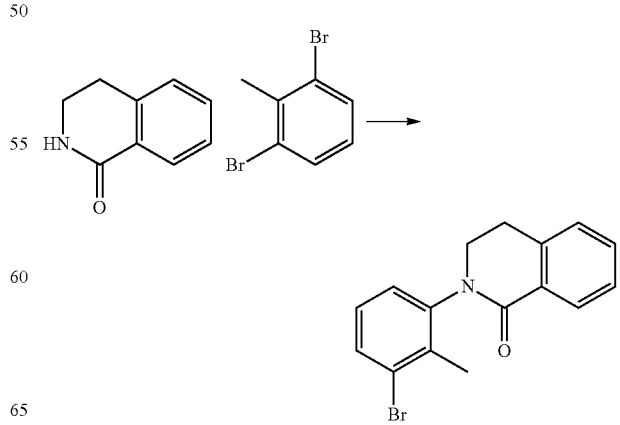

A mixture of 3,4-dihydroisoquinolin-1(2H)-one (3.5 g, 13.6 mmol), 1,3-dibromo-2-methylbenzene (17.5 g, 70.5 mmol) and K₂CO₃ (9.85 g, 71.3 mmol) in DMSO (40 mL) was purged with N₂, treated with CuI (1.75 g, 9 mmol) and heated to about 160° C. for about 4 h. The reaction mixture was diluted with DCM and filtered through Celite®. The filtrate was washed with 5% ammonia hydroxide, dried and concentrated. The residue was purified by column chromatography on silica gel to provide 2-(3-bromo-2-methylphenyl)-3,4-dihydroisoquinolin-1(2H)-one (6 g, 80%): $^1$H NMR (CDCl₃) δ 8.16-8.14 (d, 1H), 7.56-7.54 (d, 2H), 7.49-7.41 (t, 1H), 7.26 (d, 1H), 7.25-7.18 (d, 1H), 7.15-7.13 (d, 1H), 3.98-3.92 (m, 1H), 3.76-3.70 (m, 1H), 3.30-3.22 (m, 1H), 3.13-3.07 (m, 1H) 2.36 (s, 3H).

Step C: 2-(2-Methyl-3-(4,4,5,5-tetramethyl-1,3,2-dioxaborolan-2-yl)phenyl)-3,4-dihydroisoquinolin-1(2H)-one

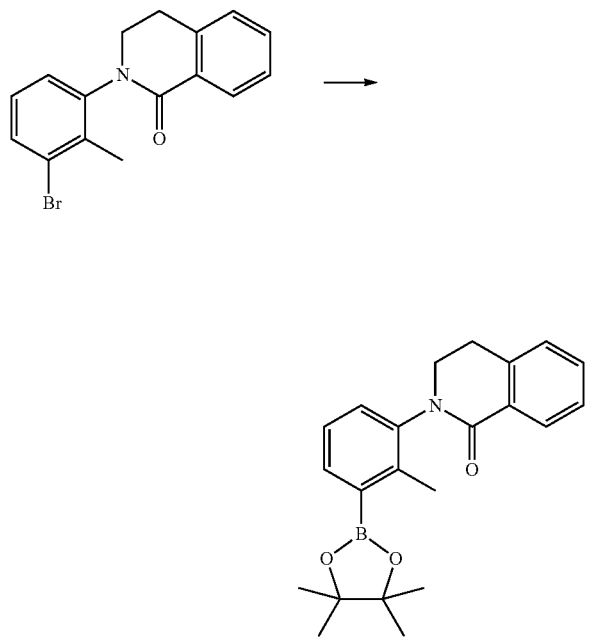

To a mixture of 2-(3-bromo-2-methylphenyl)-3,4-dihydroisoquinolin-1(2H)-one (4.6 g, 14.6 mmol), bis(pinacolato)diboron (8.8 g, 34.6 mmol) and CH₃COOK (9 g, 91.8 mmol) in 1,4-dioxane (100 mL) and DMSO (20 mL), PdCl₂(dppf) (1 g, 1.4 mmol) was added. The reaction mixture was heated at about 120° C. overnight under N₂ protection. After cooling to ambient temperature, the reaction mixture was filtered through Celite® the solid was washed with EtOAc, and the filtrate was washed with water and brine, dried over Na₂SO₄, concentrated and the residue was purified by column chromatography on silica gel to provide 2-(2-methyl-3-(4,4,5,5-tetramethyl-1,3,2-dioxaborolan-2-yl)phenyl)-3,4-dihydroisoquinolin-1(2H)-one (1.5 g, 28%): $^1$H NMR (CDCl₃) δ 8.19-8.17 (dd, 1H), 7.80-7.78 (dd, 1H), 7.51-7.47 (t, 1H), 7.42-7.38 (t, 1H), 7.32-7.25 (m, 3H), 3.96-3.89 (m, 1H), 3.77-3.71 (m, 1H), 3.27-3.23 m, 1H), 3.14-3.08 (m, 1H), 2.50 (s, 3H), 1.36 (s, 12H); LC/MS (Table 1, Method o) R$_t$=3.34 min; MS m/z: 364 (M+H)$^+$.

Preparation #4. N-(2-Methyl-3-(4,4,5,5-tetramethyl-1,3,2-dioxaborolan-2-yl)phenyl)thiazole-2-carboxamide

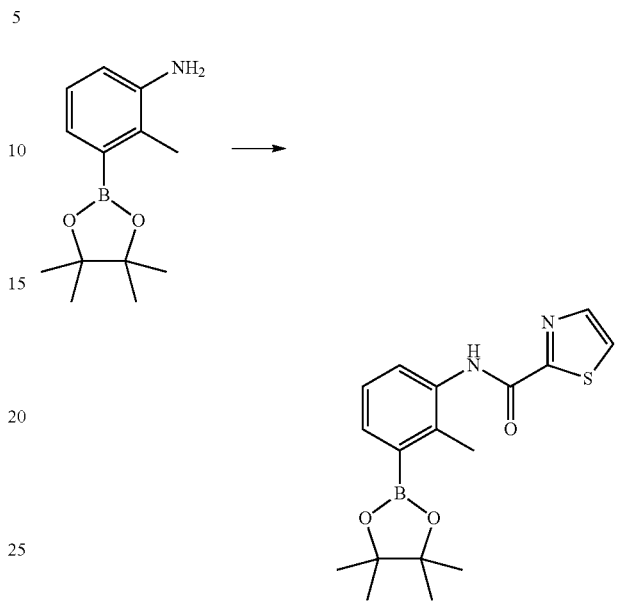

To a solution of 2-methyl-3-(4,4,5,5-tetramethyl-1,3,2-dioxaborolan-2-yl)aniline (1.9 g, 8.15 mmol, CombiBlocks) in DCM (50 mL), DIEA (2.1 g, 16.3 mmol) and HATU (4.03 g, 10.6 mmol) were added at rt. After about 5 min, thiazole-2-carboxylic acid (1.9 g, 8.15 mmol) was added and the solution was stirred for about 3 h at rt. The reaction mixture was poured into water, extracted with DCM (100 mL×2) and the organic phase was washed with brine, dried with anhydrous Na₂SO₄ and concentrated under reduced pressure and the residue was purified by column chromatography on silica gel (eluted with Pet ether:EtOAc=10:1 to 3:1) to provide N-(2-methyl-3-(4,4,5,5-tetramethyl-1,3,2-dioxaborolan-2-yl)phenyl)thiazole-2-carboxamide (1 g, 36%): $^1$H NMR (CDCl₃) δ 9.07 (s, 1H), 8.16-8.14 (d, J=8 Hz, 1H), 7.87-7.86 (t, J=3.2 Hz, 1H), 7.57-7.55 (m, 2H), 7.20-7.18 (m, 1H), 2.53 (s, 3H), 1.29 (s, 12H).

Preparation #5. 1-Methyl-5-(4,4,5,5-tetramethyl-1,3,2-dioxaborolan-2-yl)pyridin-2(1H)-one

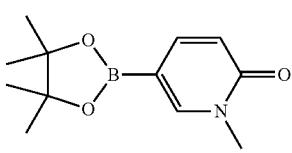 [SMILES: Cn1cc(B2OC(C)(C)C(C)(C)O2)ccc1=O]

Step A: 5-Bromo-1-methylpyridin-2(1H)-one

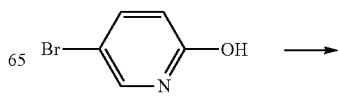

-continued

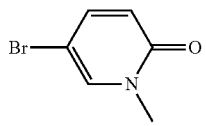

To a solution of 5-bromopyridin-2-ol (4 g, 23 mmol) in THF (200 mL) at about 0° C. was added NaH (0.83 g, 34.7 mmol) in portions. The reaction mixture was stirred at rt for about 15 min followed by addition of iodomethane (9.8 g, 69 mmol). The mixture was stirred overnight at rt. After the completion of the reaction (TLC monitoring), the reaction mixture was cooled to about 0° C., water was added, extracted with EtOAc (100 mL×2). The organic layer was washed with brine, dried with anhydrous $Na_2SO_4$, filtered and concentrated under reduced pressure to provide 5-bromo-1-methylpyridin-2-(1H)-one (3 g, 69%): $^1$H NMR (MeOD) δ 7.87 (s, 1 H), 7.58-7.55 (m, 1 H), 6.47 (d, J=9.6 Hz, 1 H), 3.53 (s, 3 H).

Step B: 1-Methyl-5-(4,4,5,5-tetramethyl-1,3,2-dioxaborolan-2-yl)pyridin-2(1H)-one

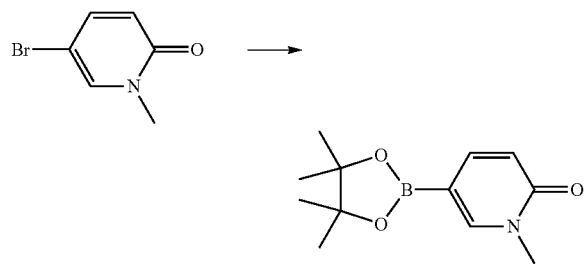

To a mixture of 5-bromo-1-methylpyridin-2(1H)-one (1.0 g, 5.32 mmol), KOH (0.78 g, 7.98 mmol) and bis(pinacolato)diboron (0.162 g, 6.38 mmol) in 1,4-dioxane (20 mL), tricyclohexylphosphine (149 mg, 0.532 mmol), $Pd_2$ $dba_3$ (487 mg, 0.532 mmol) were added under $N_2$ atmosphere. The mixture was stirred at about 80° C. for about 5 h. Then water was added, the aqueous layer was extracted with EtOAc (50 mL×2), and the organic layer was dried over anhydrous $Na_2SO_4$, concentrated under reduced pressure and the residue was purified by column chromatograph on silica gel to provide 1-methyl-5-(4,4,5,5-tetramethyl-1,3,2-dioxaborolan-2-yl)pyridin-2(1H)-one (0.80 g, 64%): $^1$H NMR (CDCl$_3$) δ 7.70 (s, 1 H), 7.54 (d, J=8.8 Hz, 1 H), 6.47 (d, J=8.8 Hz, 1 H), 3.49 (s, 3 H), 1.24 (s, 12 H).

Preparation #6. 4-(3-(4,4,5,5-Tetramethyl-1,3,2-dioxaborolan-2-yl)phenylamino)pyrimidine-2-carbonitrile

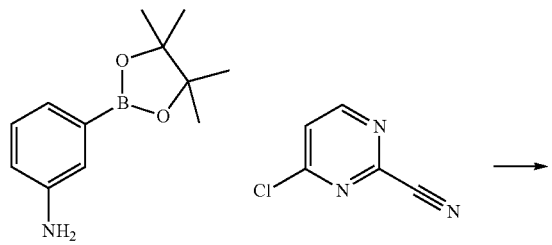

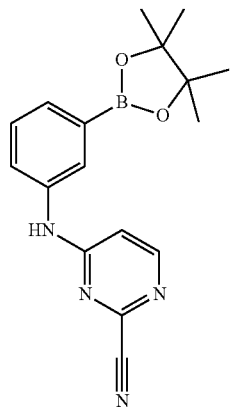

To a microwave vial was added 4-chloropyrimidine-2-carbonitrile (100 mg, 0.717 mmol, CombiPhos), 3-(4,4,5,5-tetramethyl-1,3,2-dioxaborolan-2-yl)aniline (314 mg, 1.433 mmol), and N-ethyl-N-isopropylpropan-2-amine (0.250 mL, 1.433 mmol) in MeCN (7 mL). The vial was sealed and heated in a microwave at about 150° C. for about 20 min with stirring. The reaction mixture was cooled to rt and the solvent removed under a warm stream of nitrogen. The residue was dissolved in DCM (10 mL) and washed with water (10 mL). The mixture was separated using a Biotage phase separator and the organics were concentrated in vacuo to afford the crude product. The crude product was added to a silica gel column and was eluted with 10-60% EtAcO/heptane to provide 4-(3-(4,4,5,5-tetramethyl-1,3,2-dioxaborolan-2-yl)phenylamino)pyrimidine-2-carbonitrile (0.11 g, 48%): LC/MS (Table 1, Method f) $R_t$=1.89 min; MS m/z: 323 (M+H)$^+$.

Preparation #7. N-(3-(3-amino-7-carbamoyl-1H-indol-4-yl)-2-methylphenyl)thiazole-2-carboxamide

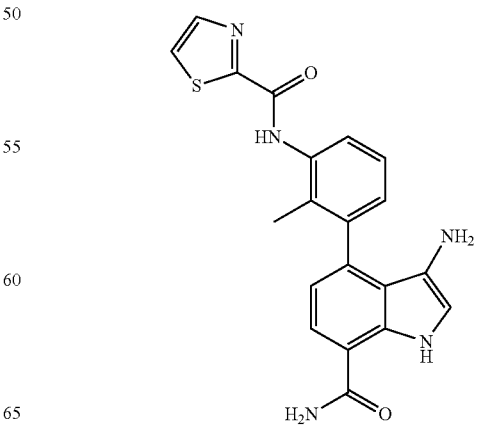

Step A: 4-Bromo-1H-indole-7-carboxylic acid

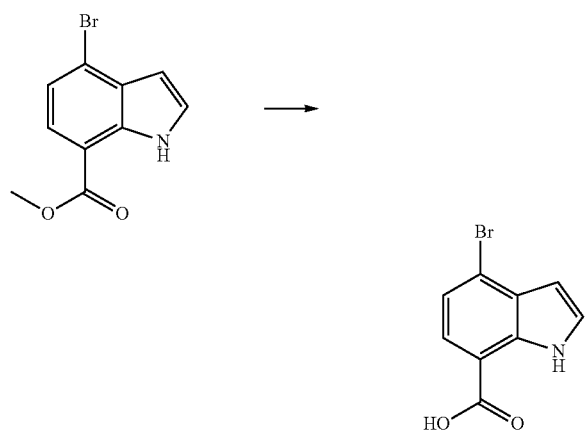

To a solution of methyl 4-bromo-1H-indole-7-carboxylate (6 g, 23 mmol, Preparation #1 step B) in THF (300 mL), water (60 mL) and MeOH (60 mL) was added lithium hydroxide (2.83 g, 118 mmol). Then the mixture was heated to reflux overnight. After cooling to rt, the solvent was removed under reduced pressure, the aqueous layer was acidified by addition of 4 N HCl to about pH 6. The precipitate was filtered, and the solid was dried to provide 4-bromo-1H-indole-7-carboxylic acid (5.5 g, 97%): $^1$H NMR (DMSO-d6) δ 11.39 (br, 1H), 7.65-7.63 (d, J=8.0 Hz, 1H), 7.46-7.44 (m, 1H), 7.33-7.31 (d, J=8.0 Hz, 1H), 6.49-6.48 (m, 1H).

Step B: 4-Bromo-1H-indole-7-carboxamide

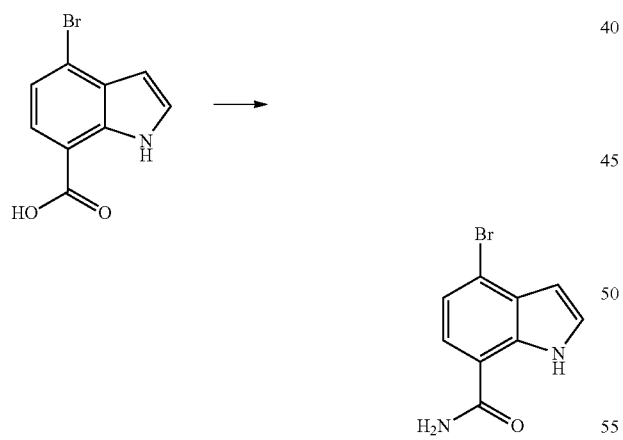

A solution of 4-bromo-1H-indole-7-carboxylic acid (5.5 g, 22.91 mmol) EDC (6.59 g, 34.4 mmol) and HOBt (5.26 g, 34.4 mmol) in THF (150 mL) and DCM (180 mL) was stirred at rt for 1 h. The mixture was then bubbled with NH$_3$ gas for about 15 min and the resulting mixture was stirred at rt overnight. The mixture was diluted by addition of water and extracted with DCM. The organic phase was washed with brine, dried and concentrated to give a residue, which was suspended in ether and filtered to provide 4-bromo-1H-indole-7-carboxamide (5.3 g, 97%): $^1$H NMR (DMSO-d6) δ 11.40 (br, 1H), 8.08 (br, 1H), 7.29-7.57 (d, J=7.6 Hz, 1H), 7.43-7.42 (m, 2H), 7.28-7.26 (d, J=7.6 Hz, 1H), 6.43-6.42 (m, 1H).

Step C: 4-Bromo-3-nitro-1H-indole-7-carboxamide

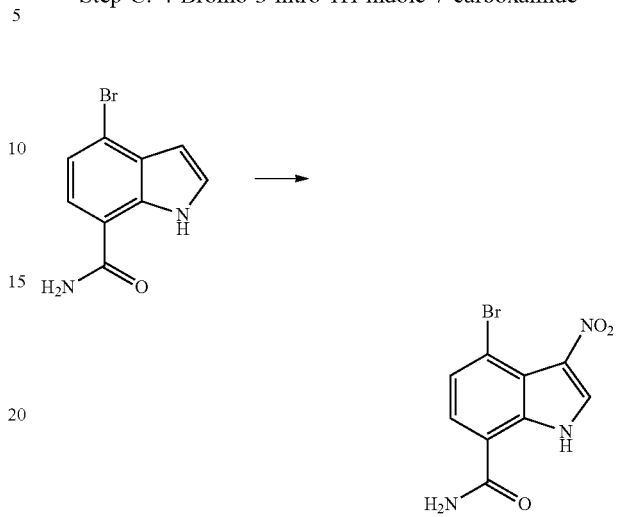

To a solution of 4-bromo-1H-indole-7-carboxamide (5.3 g, 22.17 mmol) and AgNO$_3$ (11.30 g, 66.5 mmol) in CH$_3$CN (100 mL) was added benzoyl chloride (9.35 g, 66.5 mmol) in CH$_3$CN (20 mL) at about 0° C. and the mixture was stirred at about 0° C. for 1 h in the dark. Water and EtOAc was added. The organic phase was concentrated to give a residue which was washed with DCM to provide 4-bromo-3-nitro-1H-indole-7-carboxamide (2.6 g, 41%): $^1$H NMR (DMSO-d6) δ 12.46 (br, 1H), 8.39-8.38 (d, J=3.6 Hz, 1H), 8.33 (br, 1H), 7.77-7.73 (m, 2H), 7.67-7.62 (m, 1H). LC/MS (Table 1, Method I) R$_t$=2.41 min; MS m/z: 285 (M+H)$^+$.

Step D: N-(3-(7-Carbamoyl-3-nitro-1H-indol-4-yl)-2-methylphenyl)thiazole-2-carboxamide

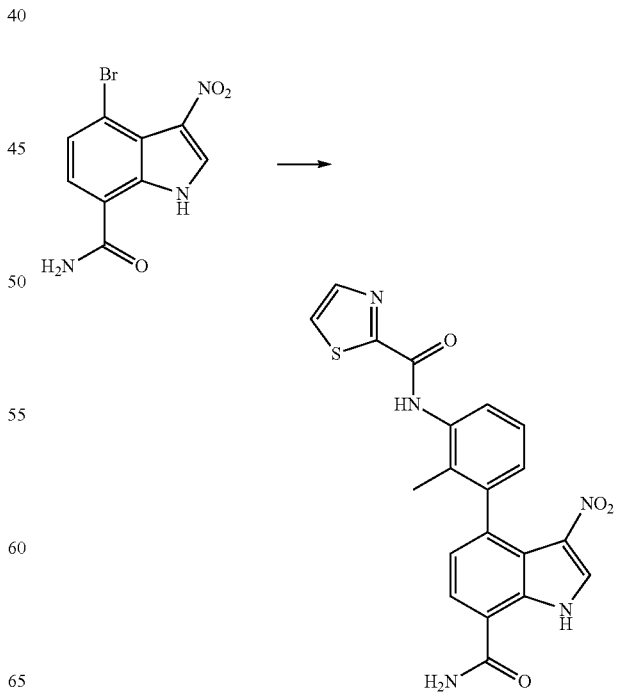

To a solution of 4-bromo-3-nitro-1H-indole-7-carboxamide (4 g, 14 mmol), N-(2-methyl-3-(4,4,5,5-tetramethyl-1,3,2-dioxaborolan-2-yl)phenyl)thiazole-2-carboxamide (5.8 g, 16.9 mmol, Preparation #4) in 1,4-dioxane (100 mL) and water (25 mL) was added Pd(PPh$_3$)$_4$ (0.81 g, 0.7 mmol) and CsF (6.4 g, 42 mmol) and the mixture was stirred at about 120° C. overnight under N$_2$. After cooling to rt, the mixture was diluted by addition of water and extracted with EtOAc. The organic phase was dried and concentrated under reduced pressure to give a residue, which was purified by prep-HPLC (Table 1, Method ah) to provide crude N-(3-(7-carbamoyl-3-nitro-1H-indol-4-yl)-2-methylphenyl)thiazole-2-carboxamide (2 g, 33%): LC/MS (Table 1, Method I) R$_t$=1.44 min; MS m/z: 422 (M+H)$^+$.

Step E: N-(3-(3-Amino-7-carbamoyl-1H-indol-4-yl)-2-methylphenyl)thiazole-2-carboxamide

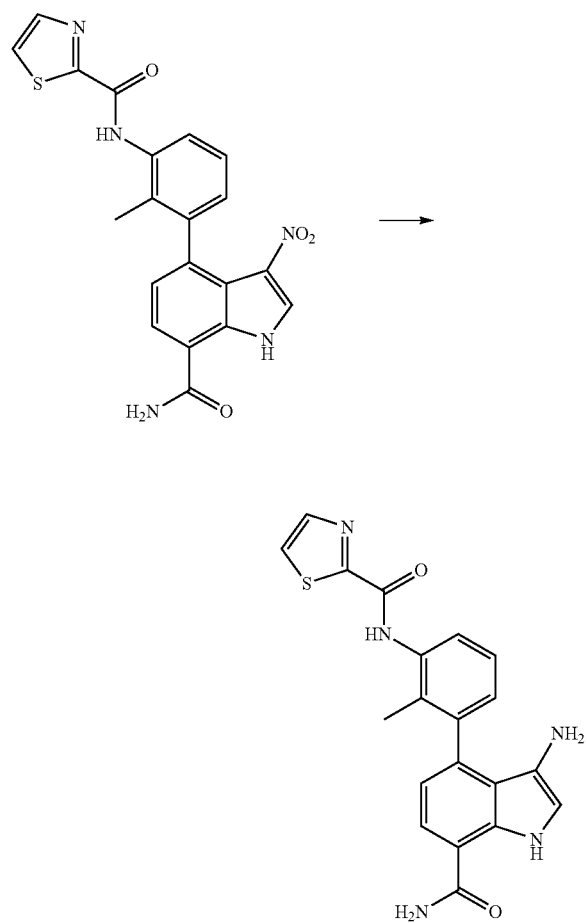

To a solution of N-(3-(7-carbamoyl-3-nitro-1H-indol-4-yl)-2-methylphenyl)thiazole-2-carboxamide (0.20 g, 0.48 mmol) in EtOH (20 mL) was added Raney Ni (0.10 g) and the mixture was stirred at rt under H$_2$ 50 psi for about 6 h. The mixture was filtered and the filtrate was concentrated under reduced pressure to provide crude N-(3-(3-amino-7-carbamoyl-1H-indol-4-yl)-2-methylphenyl)thiazole-2-carboxamide (0.11 g, 59%) which was used without further purification: LC/MS (Table 1, Method I) R$_t$=1.54 min; MS m/z: 392 (M+H)$^+$.

Preparation #8. 4-Hydroxy-N-(2-methyl-3-(4,4,5,5-tetramethyl-1,3,2-dioxaborolan-2-yl)phenyl)-4-(trifluoromethyl)cyclohexanecarboxamide

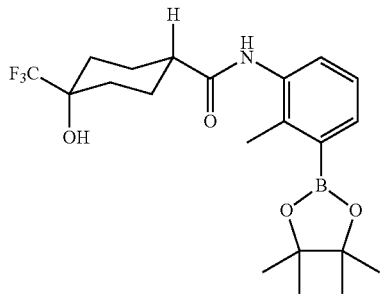 [SMILES: Cc1c(NC(=O)C2CCC(O)(C(F)(F)F)CC2)cccc1B1OC(C)(C)C(C)(C)O1]

Step A: Ethyl 4-hydroxy-4-(trifluoromethyl)cyclohexanecarboxylate

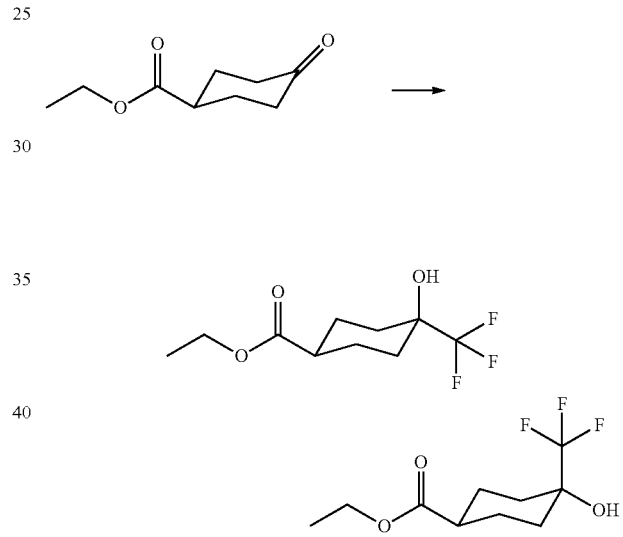

A round bottom flask was charged with ethyl 4-oxocyclohexanecarboxylate (10.0 g, 58.8 mmol) and CsF (8.92 g, 58.8 mmol) in DME (100 mL) at about 23° C. The reaction was cooled in an ice bath to about 5° C., then trimethyl (trifluoromethyl)silane (8.35 g, 58.8 mmol) was added dropwise at such a rate as to maintain reaction temperature below 8° C. The reaction was stirred about 18 h at about 23° C. TBAF (19.4 mL, 1M solution in THF, 19.39 mmol) was added drop wise and the mixture was stirred about 20 min. The mixture was diluted with EtOAc (200 mL) and washed with water (3×200 mL). The organic layer was dried over Na$_2$SO$_4$, filtered and concentrated under reduced pressure. The residue was purified on silica gel using a gradient 10 to 50% EtOAc in heptaneto give ethyl 4-hydroxy-4-(trifluoromethyl)cyclohexanecarboxylate (9.27 g, 67%). The product was taken as a mixture of isomers to the next step without further purification: $^1$H NMR (DMSO-d6) δ 5.73 (s, 0.5H), 5.72 (s, 0.5H), 4.13-4.01 (m, 2H), 2.70-2.64 (m, 0.55H), 2.37-2.27 (m, 0.45H), 1.90-1.45 (m, 8H), 1.21-1.14 (m, 3H).

Step B: (1s,4s)-4-Hydroxy-4-(trifluoromethyl)cyclohexanecarboxylic acid

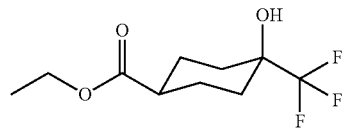

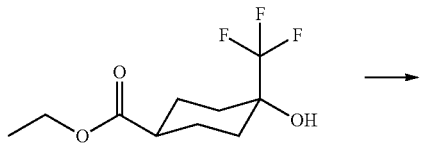

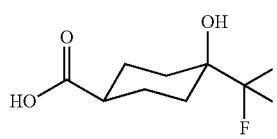

Dry EtOH (90 mL) was treated with sodium (1.03 g, 45.0 mmol) at rt and the mixture was stirred until the sodium dissolved. A solution of ethyl 4-hydroxy-4-(trifluoromethyl)cyclohexanecarboxylate (9.00 g, 37.5 mmol) in EtOH (90 mL) was added and the mixture was heated at about 70° C. under nitrogen for about 18 h. To the mixture was added 2N aqueous NaOH (18.7 mL, 37.5 mmol) and the mixture was stirred with heating at about 70° C. for about 4 h. The reaction was cooled to rt and concentrated to remove most of the EtOH. The resulting suspension was diluted with water (50 mL) to give a clear solution. The solution was acidified with conc. HCl to pH=2. The solution was concentrated to a volume of about 50 mL and the precipitated product was collected by filtration. The precipitate was rinsed with water (2×8 mL) and dried for about 18 h under reduced pressure to give (1s,4s)-4-hydroxy-4-(trifluoromethyl)cyclohexanecarboxylic acid as a white solid (5.99 g, 75%): LC/MS (Table 1, Method a) $R_t$=1.35 min; MS m/z 211 (M−H)$^-$, $^1$H NMR (DMSO-d6) δ 12.10 (s, 1H), 5.69 (s, 1H), 2.26-2.16 (m, 1H), 1.79-1.69 (m, 4H), 1.69-1.56 (m, 2H), 1.55-1.44 (m, 2H).

Step C: (1s,4s)-4-Hydroxy-N-(2-methyl-3-(4,4,5,5-tetramethyl-1,3,2-dioxaborolan-2-yl)phenyl)-4-(trifluoromethyl)cyclohexanecarboxamide

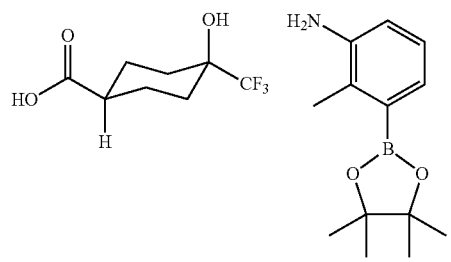

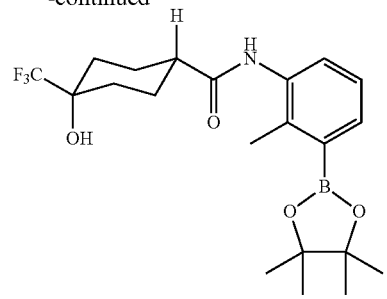

A solution containing (1s,4s)-4-hydroxy-4-(trifluoromethyl)cyclohexanecarboxylic acid (100 mg, 0.471 mmol) and 2-methyl-3-(4,4,5,5-tetramethyl-1,3,2-dioxaborolan-2-yl)aniline (110 mg, 0.471 mmol, CombiBlocks) in DMF (2.0 mL) was treated with DIEA (0.082 mL, 0.471 mmol) and 2-(3H-[1,2,3]triazolo[4,5-b]pyridin-3-yl)-1,1,3,3-tetramethylisouronium hexafluorophosphate(V) (179 mg, 0.471 mmol) and the mixture was stirred at rt for about 1 h. The mixture was diluted with water (5 mL), triturated and the supernatant decanted. The residue was dissolved in EtOAc (10 mL), dried over Na$_2$SO$_4$, filtered and concentrated. The residue was purified on silica gel using a gradient of 25-75% EtOAc in heptane. Product fractions were combined, concentrated and dried to solids under reduced pressure to give (1s,4s)-4-hydroxy-N-(2-methyl-3-(4,4,5,5-tetramethyl-1,3,2-dioxaborolan-2-yl)phenyl)-4-(trifluoromethyl)cyclohexanecarboxamide as a solid (135 mg, 67%): LC/MS (Table 1, Method b) $R_t$=1.56 min; MS m/z 428 (M+H)$^+$, $^1$H NMR (DMSO-d6) δ 9.23 (s, 1H), 7.46 (dd, J=7.4, 1.4 Hz, 1H), 7.35 (dd, J=7.9, 1.4 Hz, 1H), 7.14 (t, J=7.6 Hz, 1H), 5.74 (s, 1H), 2.44-2.34 (m, 1H), 2.32 (s, 3H), 1.90-1.67 (m, 6H), 1.60-1.42 (m, 2H), 1.30 (s, 12H).

Preparation #9: 4-Bromo-1H-pyrrolo[3,2-c]pyridine-7-carboxamide

Step A: 4-Bromo-1H-pyrrolo[3,2-c]pyridine-7-carboxylic acid

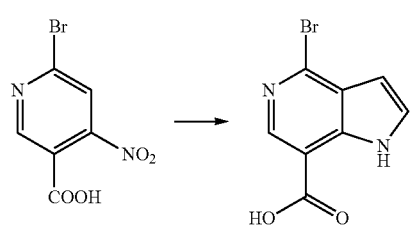 [SMILES: O=C(O)c1cnc(Br)cc1[N+](=O)[O-] ; O=C(O)c1cnc(Br)c2cc[nH]c12]

A solution of 6-bromo-4-nitronicotinic acid (3.8 g, 15.4 mmol, Eur. J. Med. Chem. 1977, 12(6), 541) in anhydrous THF (100 mL) was stirred between about −40 and −50° C. for about 5 min. Then vinylmagnesium bromide (1N in THF, 69.2 mL, 69.2 mmol) was added dropwise. The mixture was stirred between about −40 and −50° C. for about 4 h. The mixture was quenched with saturated aqueous NH$_4$Cl (2 mL). The solvent was removed under reduced pressure to get a residue, which was purified by prep-HPLC (Table 1, Method w) to provide 4-bromo-1H-pyrrolo[3,2-c]pyridine-7-carboxylic acid (1 g, 27%): $^1$H NMR (DMSO-d6) δ 11.90 (br. s, 1H), 8.46 (s, 1H), 7.54 (t, J=2.65 Hz, 1H), 6.56 (br, 1H).

Step B:
4-Bromo-1H-pyrrolo[3,2-c]pyridine-7-carboxamide

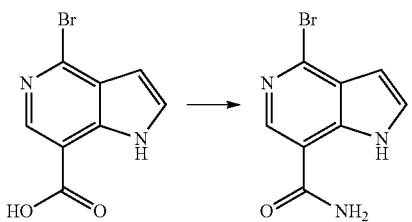 [SMILES: O=C(O)c1cnc(Br)c2cc[nH]c12 ; NC(=O)c1cnc(Br)c2cc[nH]c12]

To a solution of 4-bromo-1H-pyrrolo[3,2-c]pyridine-7-carboxylic acid (100 mg, 0.42 mmol) in DMF (2 mL) was added HOBt (95 mg, 0.62 mmol) and EDCI (119 mg, 0.62 mmol). After the reaction mixture was stirred at rt for about 1 h, NH$_3$/THF (10 mL) was added and the resulting mixture was stirred at rt overnight. Then the suspension was filtered and the filtrate was concentrated under reduced pressure. Water was added and extracted with EtOAc. The combined organic phase was washed with brine, dried over Na$_2$SO$_4$, filtered and concentrated under reduced pressure to provide 4-bromo-1H-pyrrolo[3,2-c]pyridine-7-carboxamide (60 mg, 42%). The product was used without further purification: $^1$H NMR (DMSO-d6) δ 11.89 (br, 1H), 8.51 (s, 1H), 8.27 (br, 1H), 7.68 (br, 1H), 7.52-7.51 (d, J=2.8 Hz, 1H), 6.52-6.51 (d, J=3.2 Hz, 1H).

Preparation #10. 4-Bromo-2-(1-methyl-1H-pyrazol-4-yl)-1H-indole-7-carboxamide

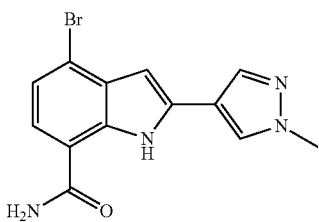 [SMILES: Cn1cc(-c2cc3c(Br)ccc(C(N)=O)c3[nH]2)cn1]

Step A: Methyl 4-bromo-1-((2-(trimethylsilyl)ethoxy)methyl)-1H-indole-7-carboxylate

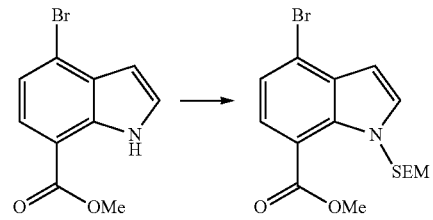 [SMILES: COC(=O)c1ccc(Br)c2cc[nH]c12 ; COC(=O)c1ccc(Br)c2ccn(COCC[Si](C)(C)C)c12]

To a solution of methyl 4-bromo-1H-indole-7-carboxylate (35 g, 138 mmol, Preparation #1 step B) in anhydrous THF (1500 mL) was added NaH (10 g, 250 mmol) in portions at about 0° C. and stirred for 1 h at about 0° C. Then SEMCl (31.9 mL, 180 mmol) was added in portions at about 0° C. The reaction mixture was allowed to warm up to rt and stirred for about 12 h. Then to the reaction mixture was added saturated aqueous NH$_4$Cl and extracted with EtOAc. The combined organic layers were washed with brine, dried over anhydrous Na$_2$SO$_4$, filtered and concentrated under reduced pressure to give the residue, which was purified by column chromatography on silica gel to give methyl 4-bromo-1-((2-(trimethylsilyl)ethoxy)methyl)-1H-indole-7-carboxylate (32 g, 60%): $^1$H NMR (CDCl$_3$) δ 7.62-7.60 (d, J=8.4 Hz, 1H), 7.46-7.44 (d, J=8.0 Hz, 1H), 7.36-7.35 (d, J=3.2 Hz, 1H), 6.77-6.76 (d, J=3.6 Hz, 1H), 5.80 (s, 2H), 4.06 (s, 3H), 3.32-3.28 (t, J=8.0 Hz, 2H), 0.89-0.85 (t, J=8.0 Hz, 2H), 0.00 (s, 9H).

Step B: Methyl 4-bromo-2-iodo-1-((2-(trimethylsilyl)ethoxy)methyl)-1H-indole-7-carboxylate

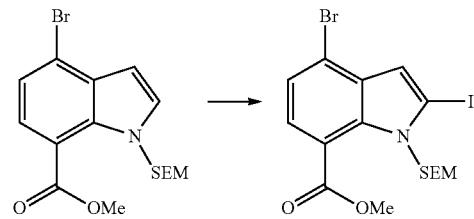 [SMILES: COC(=O)c1ccc(Br)c2ccn(COCC[Si](C)(C)C)c12 ; COC(=O)c1ccc(Br)c2cc(I)n(COCC[Si](C)(C)C)c12]

To a solution of methyl 4-bromo-1-((2-(trimethylsilyl)ethoxy)methyl)-1H-indole-7-carboxylate (10 g, 26 mmol, Preparation #1 step B) in anhydrous THF (200 mL) was added lithium diisopropylamide (18 mL, 36 mmol) at about −70° C. and stirred for about 2 h. Then a solution of I$_2$ (10 g, 39 mmol) in anhydrous THF (50 mL) was added to above solution dropwise at about −70° C. and then stirred for about 2 h. The mixture was poured into aqueous Na$_2$S$_2$O$_3$ solution and extracted with EtOAc. The combined organic phases were washed with brine, dried over Na$_2$SO$_4$, filtered and concentrated under pressure to get a residue, which was purified by column chromatography (eluted with Pet ether:EtOAc=200:1) to provide methyl 4-bromo-2-iodo-1-((2-(trimethylsilyl)ethoxy)methyl)-1H-indole-7-carboxylate (6.2 g, 47%): $^1$H NMR (CDCl$_3$) δ 7.50-7.48 (d, J=8.0 Hz, 1H), 7.42-7.40 (d, J=8.0 Hz, 1H), 7.10 (s, 1H), 5.90 (s, 2H), 4.06 (s, 3H), 3.29-3.25 (t, J=8.0 Hz, 2H), 0.87-0.83 (t, J=8.0 Hz, 2H), 0.00 (s, 9H).

Step C: Methyl 4-bromo-2-iodo-1-((2-(trimethylsilyl)ethoxy)methyl)-1H-indole-7-carboxylate

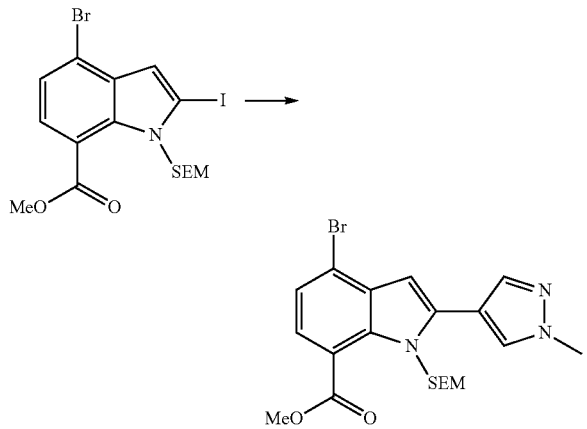

To a solution of methyl 4-bromo-2-iodo-14(2-(trimethylsilyl)ethoxy)methyl)-1H-indole-7-carboxylate (1.1 g, 2.2 mmol) in DME (20 mL) and water (5 mL) was added 1-methyl-4-(4,4,5,5-tetramethyl-1,3,2-dioxaborolan-2-yl)-1H-pyrazole (0.49 g, 2.37 mmol), PdCl$_2$(dppf) (0.176 g, 0.216 mmol) and Na$_2$CO$_3$ (0.894 g, 6.47 mmol). The mixture was heated to reflux for about 3 h. After cooling to rt, water (20 mL) was added to the solution and extracted with EtOAc (50 mL). The organic phase was dried over Na$_2$SO$_4$ and concentrated in vacuo to get a crude product, which was purified by column chromatography on silica gel (eluted with Pet ether:EtOAc=10:1) to provide methyl 4-bromo-2-iodo-1-((2-(trimethylsilyl)ethoxy)methyl)-1H-indole-7-carboxylate (0.65 g, 65%): $^1$H NMR (CDCl$_3$) δ 7.84 (s, 1H), 7.77 (s, 1H), 7.61-7.59 (d, J=7.2 Hz, 1H), 7.49-7.40 (d, J=8.0 Hz, 1H), 6.79 (s 1H), 5.84 (s, 2H), 4.14 (s, 3H), 4.11 (s, 3H), 3.20-3.16 (t, J=8.4 Hz, 2H), 0.82-0.78 (t, J=8.4 Hz, 2H), 0.00 (s, 9H).

Step D: 4-Bromo-2-(1-methyl-1H-pyrazol-4-yl)-1-((2-(trimethylsilyl)ethoxy) methyl)-1H-indole-7-carboxylic acid

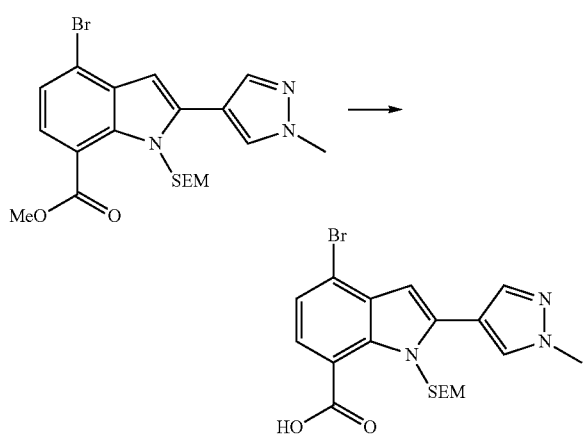

To a solution of methyl 4-bromo-2-iodo-14(2-(trimethylsilyl)ethoxy)methyl)-1H-indole-7-carboxylate (0.65 mg, 1.41 mmol) in THF (10 mL), MeOH (2 mL) and water (2 mL) was added LiOH (0.17 mg, 7.04 mmol). The mixture was heated to reflux for about 4 h. After cooling to rt, the solvent was removed under reduced pressure and the aqueous layer was acidified with aqueous HCl (1N) to pH=4, extracted with EtOAc (10 mL), dried over Na$_2$SO$_4$, and concentrated under reduced pressure to provide 4-bromo-2-(1-methyl-1H-pyrazol-4-yl)-1-((2-(trimethylsilyl)ethoxy)methyl)-1H-indole-7-carboxylic acid (0.63 g, 99%): $^1$H NMR (CDCl$_3$) δ 7.90 (s, 1H), 7.81 (s, 1H), 7.80-7.79 (d, J=2.4 Hz, 1H), 7.54-7.52 (d, J=8.0 Hz, 1H), 6.84 (s, 1H), 5.95 (s, 2H), 4.18 (s, 3H), 3.25-3.20 (t, J=7.2 Hz, 2H), 0.82-0.78 (t, J=7.2 Hz, 2H), 0.00 (s, 9H).

Step E: 4-Bromo-2-(1-methyl-1H-pyrazol-4-yl)-1-((2-(trimethylsilyl)ethoxy)methyl)-1H-indole-7-carboxamide

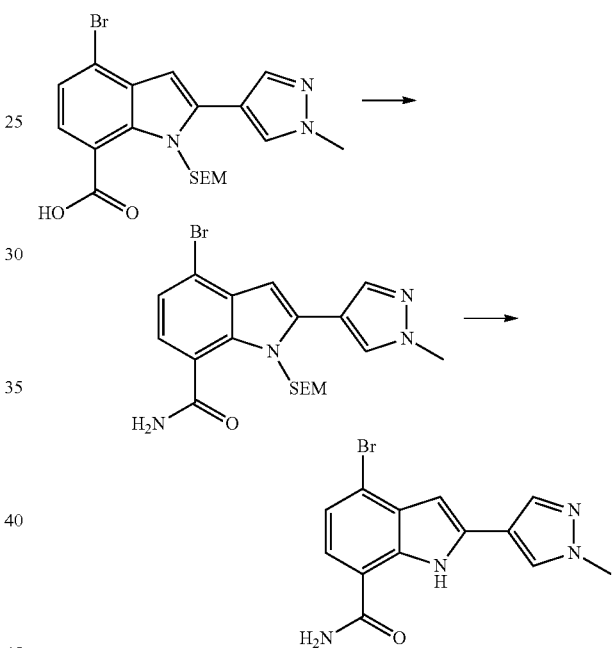

To a solution of 4-bromo-2-(1-methyl-1H-pyrazol-4-yl)-1-((2-(trimethylsilyl)ethoxy)methyl)-1H-indole-7-carboxylic acid (0.63 g, 1.4 mmol) in DMF (10 mL) was added PyBOP (1.46 g, 2.80 mmol), HOBt (0.43 g, 2.80 mmol), NH$_4$Cl (0.11 g, 2.10 mmol) and DIEA (0.72 g, 5.60 mmol). The mixture was stirred at rt for about 2 h. Water (20 mL) was added to the mixture and extracted with EtOAc (30 mL). The organic phase was dried over Na$_2$SO$_4$ and concentrated under reduced pressure to get a crude product, which was purified by column chromatography on silica gel (eluted with Pet ether:EtOAc=3:1) to provide crude 4-bromo-2-(1-methyl-1H-pyrazol-4-yl)-1-((2-(trimethylsilyl)ethoxy)methyl)-1H-indole-7-carboxamide. It was dissolved in anhydrous THF (10 mL) was added (2.02 g, 12.2 mmol) and ethane-1,2-diamine (2.20 g, 36.7 mmol) and heated to about 100° C. for about 2 h. After cooling to rt, water was added to dilute the mixture, extracted with EtOAc, the organic phase was dried over Na$_2$SO$_4$, and concentrated under reduced pressure to give a residue, which was purified by column chromatography on silica gel (eluted with Pet ether:EtOAc=3:1) to provide 4-bromo-2-(1-methyl-1H-pyrazol-4- yl)-1H-indole-7-carboxamide (0.20 g, 51%): $^1$H NMR (CDCl$_3$) δ 10.40 (br, 1 H), 7.87 (s, 1 H), 7.75 (s, 1 H), 7.30-7.28 (d, J=8, 1 H), 7.20-7.18 (d, J=8, 1 H), 6.64 (s, 1 H), 6.05 (br, 2 H), 3.99 (s, 3 H).

Preparation #11. 3-(2-(((tert-Butyldimethylsilyl)oxy)methyl)-3-(4,4,5,5-tetramethyl-1,3,2-dioxaborolan-2-yl)phenyl)-6-fluoroquinazolin-4(3H)-one

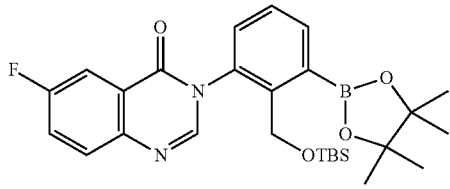 [SMILES: CC1(C)OB(c2cccc(-n3cnc4ccc(F)cc4c3=O)c2CO[Si](C)(C)C(C)(C)C)OC1(C)C]

Step A: (2-Amino-6-bromophenyl)methanol

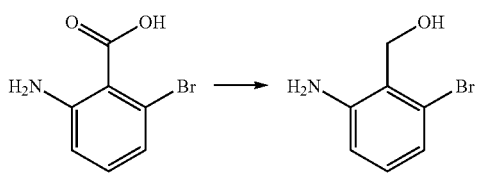 [SMILES: Nc1cccc(Br)c1C(=O)O ; Nc1cccc(Br)c1CO]

The solution of 2-amino-6-bromobenzoic acid (19.8 g, 91.7 mmol) in THF (190 mL) was added to the suspension of LiAlH$_4$ (7.00 g, 183 mmol) in THF (190 mL) dropwise at about 0° C. After the addition was complete, the mixture was stirred at rt for about 4 h. Then the mixture was quenched with EtOAc (180 mL). The mixture was poured into H$_2$O (1.1 L) and filtered. The filtrate was extracted with EtOAc (3×900 mL). The combined organic layer was dried over Na$_2$SO$_4$, filtered and concentrated. The residue was purified by column chromatography on silica gel (eluted with Pet ether:EtOAc=50:1-5:1) to provide (2-amino-6-bromophenyl)methanol (10 g, 54%): $^1$H NMR (CDCl$_3$) δ 1.77 (s, 1H), 4.34 (s, 2H), 4.92 (s, 2H), 6.64 (m, 1H), 6.95 (m, 2H).

Step B: 3-Bromo-2-(((tert-butyldimethylsilyl)oxy)methyl)aniline

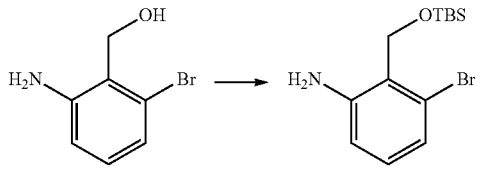 [SMILES: Nc1cccc(Br)c1CO ; CC(C)(C)[Si](C)(C)OCc1c(N)cccc1Br]

To the solution of (2-amino-6-bromophenyl)methanol (3.02 g, 15 mmol) and imidazole (1.83 g, 27 mmol) in DMF (40 mL) was added TBSCl (3.39 g, 22.5 mmol) in portions at about 0° C. Then the resulting mixture was stirred at rt overnight. The mixture was poured into H$_2$O (80 mL), extracted with MTBE (3×80 mL). The combined organic phase was washed with brine, dried over Na$_2$SO$_4$, filtered and concentrated under reduced pressure. The residue was purified by column chromatography on silica gel (eluted with Pet ether:EtOAc=15:1) to give 3-bromo-2-(((tert-butyldimethylsilyl)oxy)methyl)aniline (4.2 g, 89%): $^1$H NMR (CDCl$_3$) δ 0.00 (s, 6H), 0.80 (s, 9H), 4.38 (s, 2H), 4.85 (s, 2H), 6.48 (m, 1H), 6.79 (m, 2H).

Step C: 3-(3-Bromo-2-(((tert-butyldimethylsilyl)oxy)methyl)phenyl)-6-fluoroquinazolin-4(3H)-one

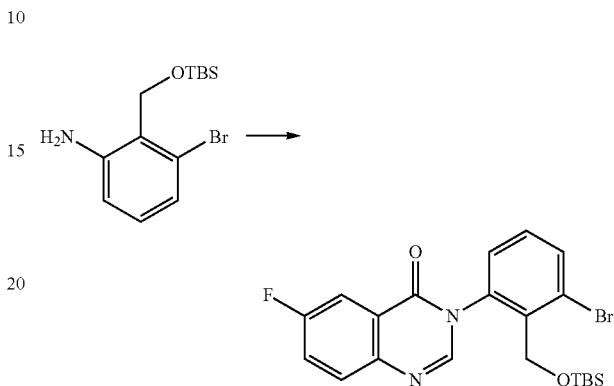

The mixture of 3-bromo-2-(((tert-butyldimethylsilyl)oxy)methyl)aniline (3.5 g, 11 mmol), 2-amino-5-fluoro-benzoic acid (1.7 g, 11 mmol) and CH(OMe)$_3$ (1.8 g, 16.5 mmol) in THF (30 mL) was heated at about 120° C. in a sealed tube overnight. The mixture was cooled to rt and concentrated under reduced pressure. The residue was washed with EtOAc to afford 3-(3-bromo-2-(((tert-butyldimethylsilyl)oxy)methyl)phenyl)-6-fluoroquinazolin-4(3H)-one (1.3 g, 25%): $^1$H NMR (CDCl$_3$) δ 0.00 (d, J=8 Hz, 6H), 0.85 (s, 9H), 4.57 (d, J=11.6 Hz, 1H), 4.98 (d, J=11.6 Hz, 1H), 7.35 (m, 1H), 7.43 (t, J=8 Hz, 1H), 7.62 (m, 1H), 7.83 (m, 2H), 8.06 (m, 2H).

Step D: 3-(2-4(tert-Butyldimethylsilyl)oxy)methyl)-3-(4,4,5,5-tetramethyl-1,3,2-dioxaborolan-2-yl)phenyl)-6-fluoroquinazolin-4(3H)-one

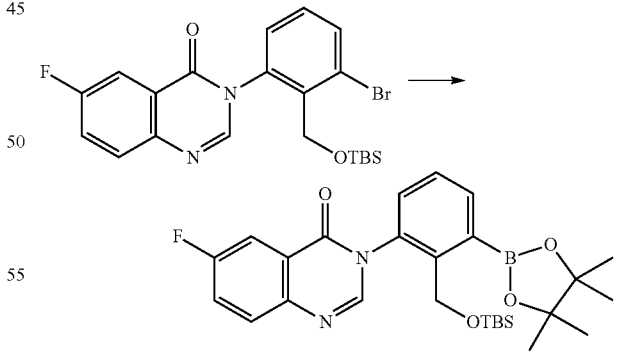

The mixture of 3-(3-bromo-2-(((tert-butyldimethylsilyl)oxy)methyl)phenyl)-6-fluoroquinazolin-4(3H)-one (4 g, 8.6 mmol), dioxaborolanyl (2.6 g, 10.4 mmol), KOAc (1.7 g, 17.2 mmol) and Pd(dppf)Cl$_2$ (0.8 g) in DMSO/1,4-dioxane (8 mL: 40 mL) was heated to about 110° C. under N$_2$ atmosphere for about 2 h. The mixture was cooled to rt, diluted with EtOAc (100 mL), filtered and the filtrate was washed with H$_2$O (30 mL) and brine (30 mL) successively.

The organic phase was dried over Na$_2$SO$_4$, filtered and concentrated to afford the crude product which was purified by column chromatography on silica gel (Pet ether/EtOAc, 30:1 to 5:1) to provide 3-(2-(((tert-butyldimethylsilyl)oxy)methyl)-3-(4,4,5,5-tetramethyl-1,3,2-dioxaborolan-2-yl)phenyl)-6-fluoroquinazolin-4(3H)-one (1.7 g, 38%): $^1$H NMR (CDCl$_3$) δ 0.00 (d, J=2 Hz, 6H), 0.92 (s, 9H), 1.52 (s, 12H), 4.70 (d, J=1.6 Hz, 1H), 5.43 (d, J=1.6 Hz, 1H), 7.63 (m, 1H), 7.70 (m, 2H), 7.93 (m, 1H), 8.16 (m, 3H).

Preparation #12: (R)-7-(Piperidin-3-yl)imidazol-[1,2-a]pyrazin-8(7H)-one hydrochloride

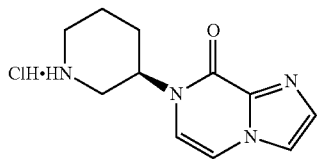

Step A: (R)-tert-Butyl (1-benzylpiperidin-3-yl)carbamate

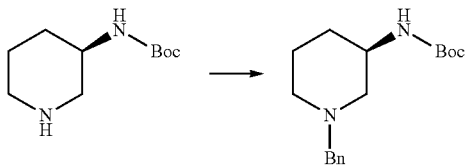 [SMILES: CC(C)(C)OC(=O)N[C@@H]1CCCNC1 ; CC(C)(C)OC(=O)N[C@@H]1CCCN(Cc2ccccc2)C1]

To a solution of (R)-tert-butyl piperidin-3-ylcarbamate (40.0 g, 0.2 mol, 1.0 equiv) and TEA (22.22 g, 0.22 mol, 1.1 equiv) in DCM (500 mL) was added dropwise bromomethyl-benzene (37.62 g, 0.22 mol, 1.1 equiv) at 0° C. After stirring overnight at about 25° C., the solution was diluted with DCM and washed with water. The organic layer was dried and evaporated to afford (R)-tert-butyl (1-benzylpiperidin-3-yl)carbamate (58.0 g, 100%), which was used to the next step without further purification: $^1$H NMR (CDCl$_3$) 7.15-7.26 (m, 5H), 4.92 (s, 1H), 3.67 (s, 1H), 3.39 (s, 2H), 2.16-2.45 (m, 4H), 1.41-1.61 (m, 4H), 1.37 (s, 9H)

Step B: (R)-1-Benzylpiperidin-3-amine hydrochloride

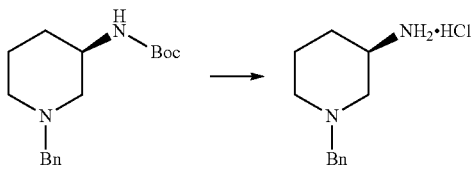

To a solution of (R)-tert-butyl (1-benzylpiperidin-3-yl) carbamate (58.0 g, 0.2 mol, 1.0 equiv) in MeOH (200 mL) was added HCl/MeOH (4.0 M, 200 mL) and the mixture was stirred for about 2 h. The solvent was removed by vacuum to provide (R)-1-benzylpiperidin-3-amine hydrochloride (50 g): $^1$H NMR (MeOD) δ 7.64 (d, J=2.4 Hz, 2H), 7.50 (s, 3H), 4.42-4.52 (q, 2H), 3.64-3.66 (d, J=10.8 Hz, 2H), 3.51-3.54 (d, J=12 Hz, 1H), 3.01-3.16 (m, 2H), 2.20-2.22 (d, J=11.2 Hz, 1H), 2.00-2.11 (m, 2H), 1.66-1.74 (m, 1H)

Step C: (R)—N-(1-Benzylpiperidin-3-yl)-1H-imidazole-2-carboxamide

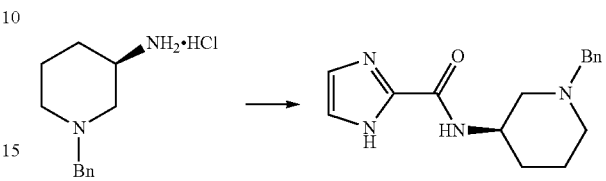

To a solution of 1H-imidazole-2-carboxylic acid (16.8 g, 0.15 mol) in DMF (500 mL) was added HATU (57 g, 0.15 mol) and the mixture was stirred for about 2 h at rt. Then (R)-tert-butyl (1-benzylpiperidin-3-yl)carbamate (39.45 g, 0.15 mol) was added to the solution and the mixture was stirred overnight. Additional 1H-imidazole-2-carboxylic acid (5.2 g, 46 mmol) and HATU (17.6 g, 46 mmol, 0.3 equiv) was added and the mixture was stirred at rt for 3 days. The solvent was removed and the residue was dissolved in EtOAc, washed with water, dried and concentrated. The residue was purified by column chromatograph on silica gel to provide crude (R)—N-(1-benzylpiperidin-3-yl)-1H-imidazole-2-carboxamide (50 g): LC/MS (Table 1, Method k) R$_t$=1.15 min; MS m/z: 285 (M+H)$^+$.

Step D: (R)—N-(1-Benzylpiperidin-3-yl)-1-(2,2-diethoxyethyl)-1H-imidazole-2-carboxamide

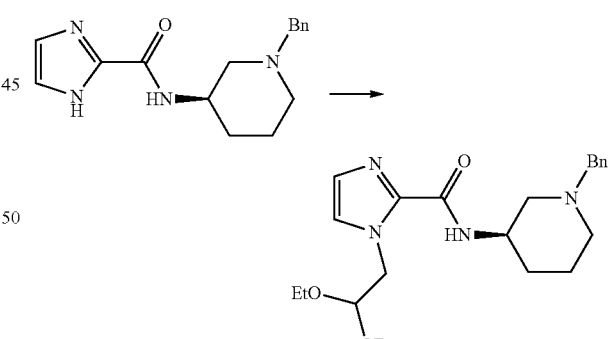

A mixture of (R)-7-(1-benzylpiperidin-3-yl)imidazol-[1,2-a]pyrazin-8(7H)-one (73.0 g, 150 mmol, crude), 2-bromo-1,1-diethoxy-ethane (30 g, 150 mmol), K$_2$CO$_3$ (41.4 g, 300 mmol) and KI (1 g) in DMF (500 mL) was heated to about 120° C. for 3 days. The solvent was removed. The residue was dissolved in DCM, washed with water, dried and evaporated to afford (R)—N-(1-benzylpiperidin-3-yl)-1-(2,2-diethoxyethyl)-1H-imidazole-2-carboxamide (30 g, 75 mmol) as an oil: LC/MS (Table 1, Method k) R$_t$=1.81 min; MS m/z: 401 (M+H)$^+$.

Step E: (R)-7-(1-Benzylpiperidin-3-yl)imidazol-[1,2-a]pyrazin-8(7H)-one

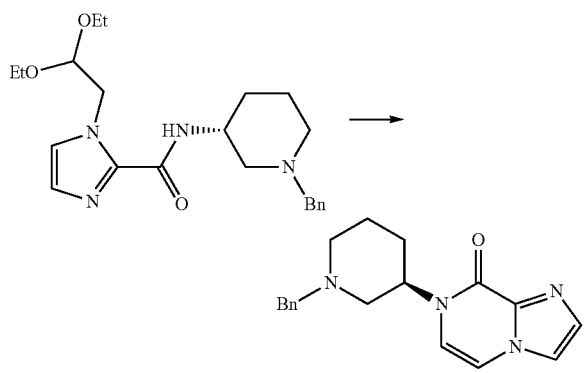

A mixture of (R)—N-(1-benzylpiperidin-3-yl)-1-(2,2-diethoxyethyl)-1H-imidazole-2-carboxamide (30.0 g, 75 mmol, crude) in 2N HCl (200 mL) was heated to reflux overnight. The solvent was removed and the residue was diluted with water (50 mL) which was basified by saturated Na$_2$CO$_3$ to pH 10. The aqueous phase was extracted with DCM, dried and evaporated. The residue was purified by column chromatograph on silica gel to afford (R)-7-benzylpiperidin-3-yl)imidazo[1,2-a]pyrazin-8(7H)-one (3.0 g, 9.7 mmol): $^1$H NMR (CDCl$_3$) δ 7.44 (s, 1H), 7.17-7.24 (m, 7H), 7.01-7.02 (d, J=6 Hz, 1H), 5.00-5.05 (m, 1H), 3.45-3.47 (d, J=5.6 Hz, 2H), 2.78-2.80 (m, 1H), 2.55-2.58 (m, 1H), 2.31-2.36 (m, 1H), 2.25 (s, 1H), 1.81 (s, 1H), 1.16-1.69 (m, 3H)

Step F: (R)-tert-Butyl 3-(8-oxoimidazo[1,2-a]pyrazin-7(8H)-yl)piperidine-1-carboxylate

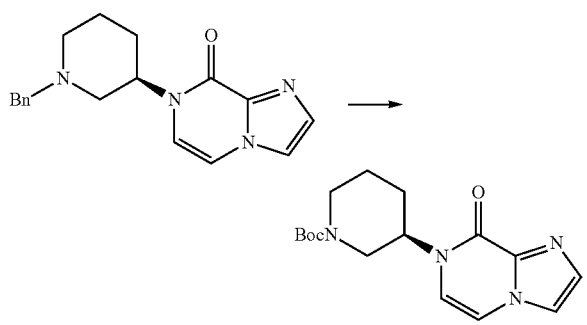

To a solution of (R)-7-(1-benzylpiperidin-3-yl)imidazo[1,2-a]pyrazin-8(7H)-one (2.13 g, 6.9 mmol) in MeOH (40 mL) was added (Boc)$_2$O (3.09 g, 13.8 mmol) and Pd/C (1.5 g). The mixture was hydrogenated under H$_2$ balloon overnight and then filtrated. The filtrate was concentrated and purified by column chromatograph on silica gel to afford (R)-tert-butyl 3-(8-oxoimidazo[1,2-a]pyrazin-7(8H)-yl)piperidine-1-carboxylate (1.4 g, 64%): $^1$H NMR (MeOD) δ 7.69-7.70 (d, J=1.2 Hz, 1H), 7.52-7.54 (d, J=6.4 Hz, 1H), 7.50 (s, 1H), 7.12-7.14 (d, J=6 Hz, 1H), 4.74-4.82 (m, 1H), 4.12-4.15 (d, J=11.6 Hz, 1H), 4.04-4.05 (m, 1H), 3.05-3.11 (m, 1H), 2.83 (s, 1H), 1.91-2.02 (m, 2H), 1.86-1.90 (m, 1H), 1.60-1.71 (m, 1H), 1.46 (s, 9H)

Step G: (R)-7-(Piperidin-3-yl)imidazo[1,2-a]pyrazin-8(7H)-one hydrochloride

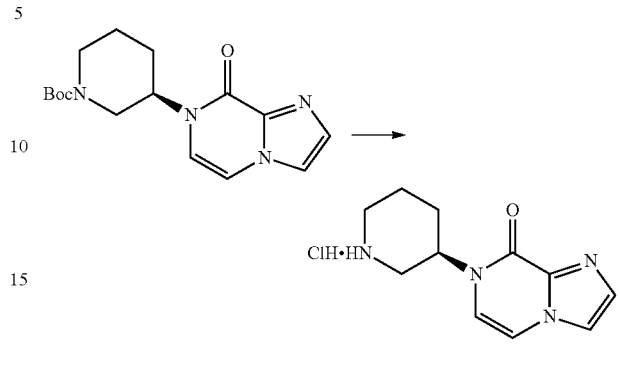

To a solution of (R)-tert-butyl 3-(8-oxoimidazo[1,2-c]pyrazin-7(8H)-yl)piperidine-1-carboxylate (1.4 g, 4.4 mmol) in MeOH (10 mL) was added HCl/MeOH (4 M, 10 mL) and the mixture was stirred for about 1 h at rt. The solvent was removed to afford (R)-7-(piperidin-3-yl)imidazo[1,2-a]pyrazin-8(7H)-one hydrochloride (1.35 g, 100%): $^1$H NMR (DMSO-d6) δ 10.06 (s, 1H), 9.67 (s, 1H), 8.18-8.21 (m, 1H), 8.00-8.03 (m, 1H), 7.89-7.93 (m, 1H), 7.69-7.74 (m, 1H), 5.12-5.18 (m, 1H), 3.20-3.34 (m, 3H), 2.82-2.90 (m, 1H), 2.02-2.08 (m, 1H), 1.84-1.93 (m, 3H)

Preparation #13: (R)-7-(Piperidin-3-yl)-6,7-dihydroimidazo[1,2-a]pyrazin-8(5H)-one hydrochloride

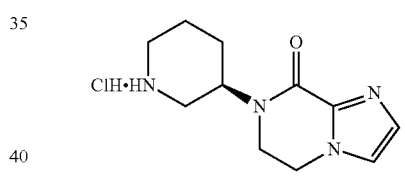

Step A: (R)-tert-Butyl 3-(8-oxo-5,6-dihydroimidazo[1,2-a]pyrazin-7(8H)-yl)piperidine-1-carboxylate

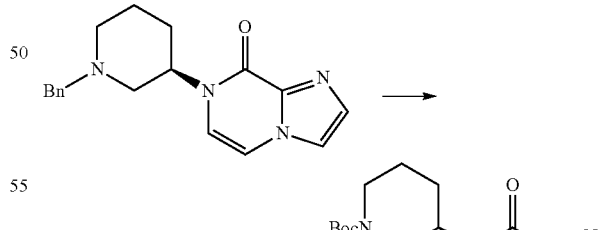

To a solution of (R)-7-(1-benzylpiperidin-3-yl)imidazo[1,2-a]pyrazin-8(7H)-one (0.77 g, 2.5 mmol) in MeOH (20 mL) was added (Boc)$_2$O (1.09 g, 5.0 mmol) and Pd(OH)$_2$ (0.5 g). The mixture was hydrogenated under H$_2$ balloon overnight and then filtrated. The filtrate was evaporated and purified by column chromatograph on silica gel to afford (R)-tert-butyl 3-(8-oxo-5,6-dihydroimidazo[1,2-a]pyrazin-7(8H)-yl)piperidine-1-carboxylate (0.5 g, 60%): ¹H NMR (MeOD) δ 7.16 (s, 1H), 7.06 (s, 1H), 4.22-4.33 (m, 1H), 4.19-4.20 (m, 2H), 3.93-3.96 (m, 2H), 3.64-3.78 (m, 2H), 2.86-2.89 (m, 1H), 2.61 (s, 1H), 168-1.79 (m, 3H), 1.47-1.53 (m, 1H), 1.46 (s, 9H).

Step B: (R)-7-(Piperidin-3-yl)-6,7-dihydroimidazol-[1,2-a]pyrazin-8(5H)-one hydrochloride

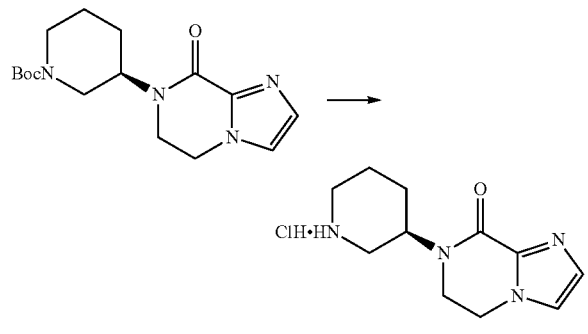

To a solution of (R)-tert-butyl 3-(8-oxo-5,6-dihydroimidazo[1,2-c]pyrazin-7(8H)-yl)piperidine-1-carboxylate (0.5 g, 1.5 mmol, 1 equiv) in MeOH (5 mL) was added HCl/MeOH (4.0 M, 5 mL) and the mixture was stirred for 1 h at rt. The solvent was removed to afford (R)-7-(piperidin-3-yl)-6,7-dihydroimidazo[1,2-a]pyrazin-8(5H)-one hydrochloride (0.45 g, 100%): ¹H NMR (MeOD) δ 7.75-7.78 (q, J=9.6 Hz, 2H), 4.66-4.74 (m, 1H), 4.56-4.59 (q, J=7.2 Hz, 2H), 3.99-4.03 (t, J=6 Hz, 2H), 3.32-3.45 (m, 3H), 2.96-3.03 (m, 1H), 1.85-2.14 (m, 4H).

Preparation #14: (Z)-4-((3-(7-carbamoyl-1H-indol-4-yl)phenyl)amino)-4-oxobut-2-enoic acid

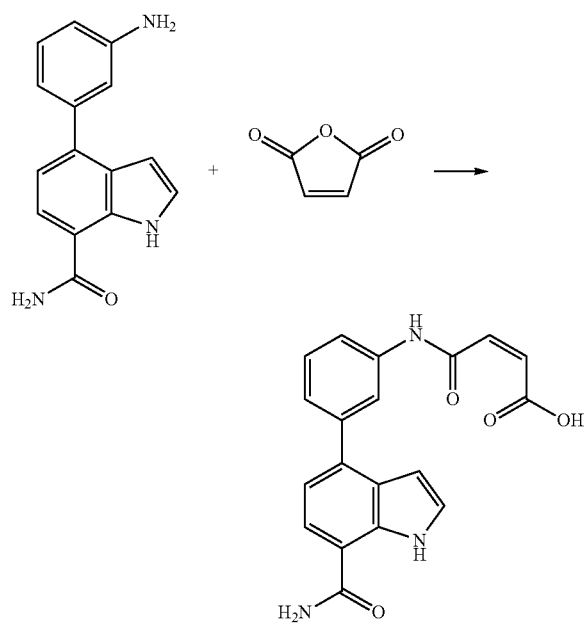

To a solution of 4-(3-aminophenyl)-1H-indole-7-carboxamide (0.25 g, 0.995 mmol, Preparation #A.1), furan-2,5-dione (0.117 g, 1.19 mmol), and N-ethyl-N-isopropylpropan-2-amine (0.521 mL, 2.98 mmol) in DMF (10.0 mL) was added. The mixture is stirred at rt overnight. Solvent was removed under high vacuum and the residue was purified by prep HPLC (Table 2, Method y) to provide (Z)-4-((3-(7-carbamoyl-1H-indol-4-yl)phenyl)amino)-4-oxobut-2-enoic acid (0.32 g, 92%) as a solid. LC/MS (Table 1, Method g) R$_f$=1.37 min; MS m/z 350 (M+H)⁺.

Preparation #15. tert-Butyl 3-(7-carbamoyl-4-(2-methyl-3-(4-oxoquinazolin-3(4H)-yl)phenyl)-1H-indol-2-yl)-2,5-dihydro-1H-pyrrole-1-carboxylate

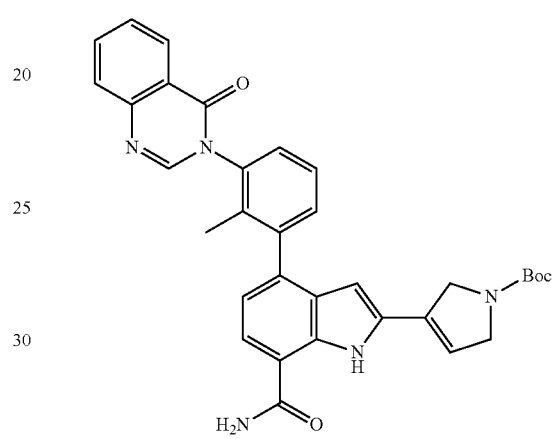

Step A. Methyl 4-bromo-2-(1-(tert-butoxycarbonyl)-2,5-dihydro-1H-pyrrol-3-yl)-1-tosyl-1H-indole-7-carboxylate

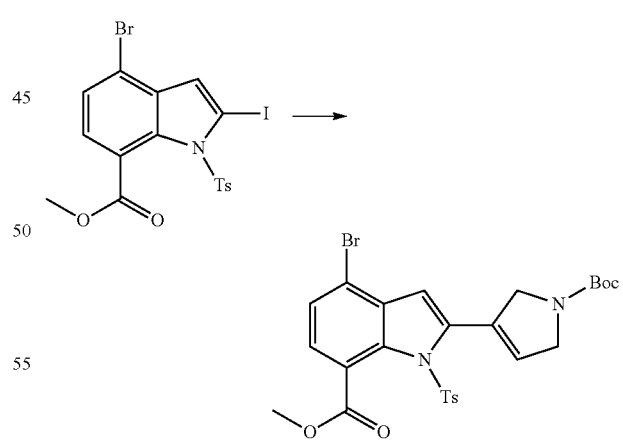

To a mixture of methyl 4-bromo-2-iodo-1-tosyl-1H-indole-7-carboxylate (1 g, 1.9 mmol, Preparation #1, Step D) in DME (20 mL)/water (5 mL) was added tert-butyl 3-(4,4,5,5-tetramethyl-1,3,2-dioxaborolan-2-yl)-2,5-dihydro-1H-pyrrole-1-carboxylate (0.72 g, 2.4 mmol), Na$_2$CO$_3$ (0.6 g, 5.6 mmol) and Pd(dppf)Cl$_2$ (0.2 g, 0.28 mmol). The reaction mixture was stirred at rt for 10 h under N$_2$ atmosphere. After filtering, the filtrate was concentrated under reduced pressure to give a residue, which was purified by column chromatography on silica gel (eluted with hexanes: EtOAc=5:1) to give methyl 4-bromo-2-(1-(tert-butoxycarbonyl)-2,5-dihydro-1H-pyrrol-3-yl)-1-tosyl-1H-indole-7-carboxylate (0.6 g, 56%) as yellow solid: $^1$H NMR (CDCl$_3$) δ 7.68-7.56 (d, J=8.22 Hz, 1H), 7.55-7.54 (m, 1H), 7.14-7.05 (m, 4H), 6.45-6.37 (m, 2H), 4.37-4.31 (m, 2H), 4.05 (s, 3H), 3.89-3.84 (m, 2H), 2.38-2.34 (m, 3H), 1.53 (m, 9H).

Step B: 4-Bromo-2-(1-(tert-butoxycarbonyl)-2,5-dihydro-1H-pyrrol-3-yl)-1H-indole-7-carboxylic acid

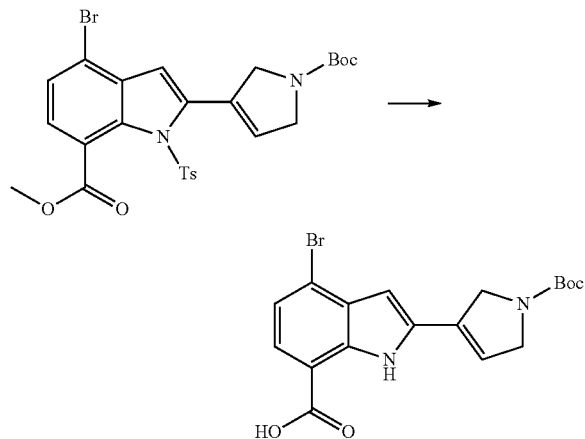

To a solution of methyl 4-bromo-2-(1-(tert-butoxycarbonyl)-2,5-dihydro-1H-pyrrol-3-yl)-1-tosyl-1H-indole-7-carboxylate (2.5 g, 4.34 mmol) in THF (20 mL)/MeOH (5 mL)/water (5 mL) was added LiOH.H$_2$O (2.5 g, 59.5 mmol) at rt. The reaction mixture was stirred at rt for about 3 h. The reaction was concentrated and residue was acidified by addition of 2N HCl to about pH 5 and extracted with EtOAc (3×50 mL). The combined organic layer was dried and concentrated to give a solid, which was washed with EtOAc and MTBE to give 4-bromo-2-(1-(tert-butoxycarbonyl)-2,5-dihydro-1H-pyrrol-3-yl)-1H-indole-7-carboxylic acid (1 g, 56.5%) as white solid: $^1$H NMR (CDCl$_3$) δ 9.84 (m, 1 H), 7.77-7.75 (t, J=5.6 Hz, 1H), 7.34-7.32 (d, J=8 Hz, 1H), 6.54-6.49 (d, J=16.8 Hz, 1H), 6.18-6.14 (d, J=18 Hz, 1H), 4.58-4.51 (d, J=30.4 Hz, 2H), 4.38-4.32 (d, J=22 Hz, 2H), 1.54 (s, 9H).

Step C: tert-Butyl 3-(4-bromo-7-carbamoyl-1H-indol-2-yl)-2,5-dihydro-1H-pyrrole-1-carboxylate

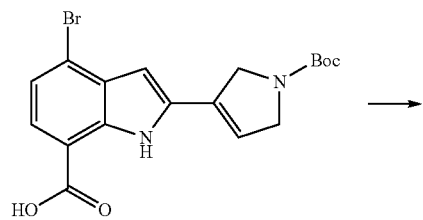

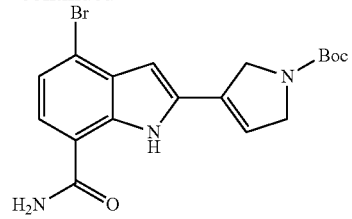

To a solution of 4-bromo-2-(1-(tert-butoxycarbonyl)-2,5-dihydro-1H-pyrrol-3-yl)-1H-indole-7-carboxylic acid (1 g, 2. 5 mmol) in DMF (6 mL) was added PyBOP (2.6 g, 4.9 mmol), HOBt (0.75 g, 4.91 mmol), DIEA (1.7 mL, 9.82 mmol) and NH$_4$Cl (0.2 g, 3.7 mmol). The reaction mixture was stirred at rt overnight. After quenching with water, the aqueous layer was extracted with EtOAc (3×25 mL). The combined organic layers were dried and concentrated under reduced pressure to give a residue, which was purified by prep-HPLC (Table 1, Method ad) to give tert-butyl 3-(4-bromo-7-carbamoyl-1H-indol-2-yl)-2,5-dihydro-1H-pyrrole-1-carboxylate (0.6 g, 54%) as white solid: $^1$H NMR (CDCl$_3$) δ 10.42 (s, 1H), 7.26-7.25 (m, 2H), 6.48 (s, 1H), 6.19-6.13 (d, J=22.4 Hz, 1H), 4.55-4.51 (d, J=16 Hz, 2H), 4.37-4.32 (d, J=18 Hz, 2H), 1.54 (s, 9H).

Step D: tert-Butyl 3-(7-carbamoyl-4-(2-methyl-3-(4-oxoquinazolin-3(4H)-yl)phenyl)-1H-indol-2-yl)-2,5-dihydro-1H-pyrrole-1-carboxylate

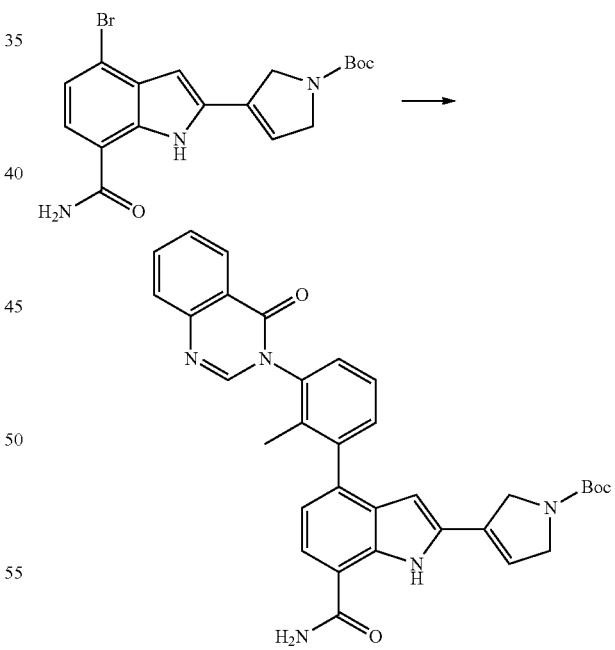

A solution of tert-butyl 3-(4-bromo-7-carbamoyl-1H-indol-2-yl)-2,5-dihydro-1H-pyrrole-1-carboxylate (0.6 g, 1.48 mmol), 3-(2-methyl-3-(4,4,5,5-tetramethyl-1,3,2-dioxaborolan-2-yl)-phenyl)quinazolin-4(3H)-one (1 g, 2.95 mmol, WO 2011159857), K$_2$CO$_3$ (0.816 g, 5.91 mmol) and Pd(dppf)Cl$_2$ (0.22 g, 0.3 mmol) in THF (20 mL)/MeOH (5 mL)/water (5 mL) was stirred at about 60° C. for about 2 h under N$_2$ atmosphere. The solvent was removed to give a residue, which was purified by column chromatography on silica gel (eluted with hexanes:EtOAc=2:1) to give tert-butyl 3-(7-carbamoyl-4-(2-methyl-3-(4-oxoquinazolin-3(4H)-yl)phenyl)-1H-indol-2-yl)-2,5-dihydro-1H-pyrrole-1-carboxylate (0.6 g, 72%) as a solid: $^1$H NMR (MeOD) δ 10.44 (s, 1H), 8.40-8.38 (d, J=8 Hz, 1H), 8.15-8.10 (s, J=21.6 Hz, 1H), 7.83-7.81 (m, 2H), 7.59-7.35 (m, 5H), 7.09-6.98 (m, 1H), 6.31-6.11 (m, 4H), 4.49-4.36 (m, 4H), 2.04 (s, 3H), 1.51 (s, 9H).

Preparation #16. tert-Butyl 4-(7-carbamoyl-4-(2-methyl-3-(4-oxoquinazolin-3(4H)-yl)phenyl)-1H-indol-2-yl)-5,6-dihydropyridine-1(2H)-carboxylate

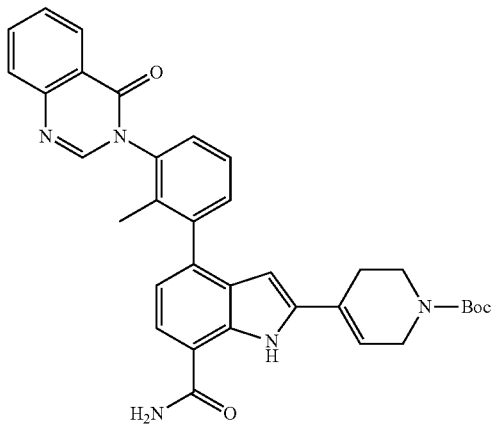 [SMILES: Cc1c(-c2ccc(C(N)=O)c3[nH]c(C4=CCN(C(=O)OC(C)(C)C)CC4)cc23)cccc1-n1cnc2ccccc2c1=O]

Step A: tert-Butyl 2-(4-bromo-7-carbamoyl-1H-indol-2-yl)benzylcarbamate

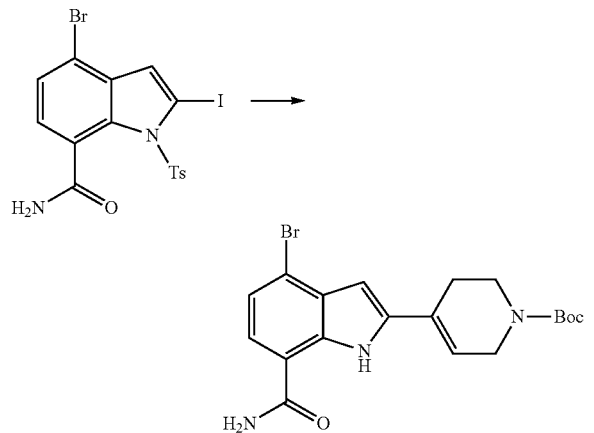

To a solution of compound methyl 4-bromo-2-iodo-1-tosyl-1H-indole-7-carboxylate (2.4 g, 6.58 mmol, Preparation #1) and tert-butyl 4-(4,4,5,5-tetramethyl-1,3,2-dioxaborolan-2-yl)-5,6-dihydropyridine-1(2H)-carboxylate (2.0 g, 6.58 mmol) in THF (50 mL), MeOH (10 mL) and water (10 mL) were added Na$_2$CO$_3$ (2.1 g, 19.73 mmol) and Pd(dppf)Cl$_2$ (0.481 g, 0.658 mmol), the mixture was heated to about 80° C. for about 3 h. The resulting solution was diluted with EtOAc (100 mL), and washed with water (30 mL). The organic phase was dried over Na$_2$SO$_4$, and concentrated under reduced pressure to give a crude product, which was purified by column chromatography on silica gel (eluted with Pet ether:EtOAc=1:1) to give tert-butyl 4-(4-bromo-7-carbamoyl-1H-indol-2-yl)-5,6-dihydropyridine-1(2H)-carboxylate (2 g, 72%) as a solid: $^1$H NMR (DMSO-d6) δ 10.87 (s, 1H), 8.15 (s, 1H), 7.59-7.57 (d, J=8.0 Hz, 1H), 7.52 (s, 1H), 7.27-7.25 (d, J=8.0 Hz, 1H), 6.47 (s, 1H), 6.42 (s, 1H), 4.03 (s, 2H), 3.55 (s, 2H), 2.52 (s, 2H), 1.41 (s, 9H).

Step B: tert-Butyl 4-(7-carbamoyl-4-(2-methyl-3-(4-oxoquinazolin-3(4H)-yl)phenyl)-1H-indol-2-yl)-5,6-dihydropyridine-1(2H)-carboxylate

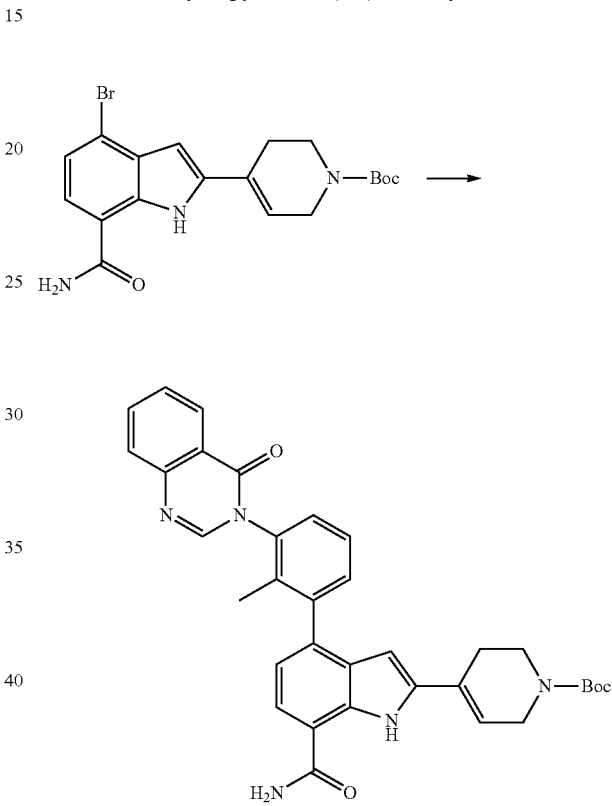

To a solution of tert-butyl 4-(4-bromo-7-carbamoyl-1H-indol-2-yl)-5,6-dihydropyridine-1(2H)-carboxylate (2 g, 4.76 mmol) and 3-(2-methyl-3-(4,4,5,5-tetramethyl-1,3,2-dioxaborolan-2-yl)phenyl)quinazolin-4(3H)-one (2.59 g, 7.14 mmol, WO 2011159857) in THF (40 mL), MeOH (10 mL) and water (10 mL) were added Na$_2$CO$_3$ (1.513 g, 14.28 mmol) and Pd(dppf)Cl$_2$ (0.348 g, 0.476 mmol). The mixture was heated to about 80° C. for about 4 h. The resulting solution was diluted with EtOAc (100 mL), and washed with water and brine (30 mL each). The organic phase was dried over Na$_2$SO$_4$, and concentrated to give a crude product, which was purified by column chromatography on silica gel (eluted with Pet ether:EtOAc=1:1) to give tert-butyl 4-(7-carbamoyl-4-(2-methyl-3-(4-oxoquinazolin-3(4H)-yl)phenyl)-1H-indol-2-yl)-5,6-dihydropyridine-1(2H)— carboxylate (1.4 g, 51%) as a solid: $^1$H NMR (CDCl$_3$) 10.43 (s, 1H), 8.42-8.40 (d, J=7.6 Hz, 1H), 8.15 (s, 1H), 7.85-7.83 (m, 2H), 7.61-7.59 (m, 1H), 7.49-7.45 (m, 3H), 7.37-7.34 (m, 1H), 7.04-7.01 (m, 1H), 6.20 (s, 2H), 3.65 (s, 2H), 2.55 (s, 2H), 2.00 (s, 3H), 1.76 (s, 2H), 1.50 (s, 9H).

Preparation #17: 1-(Methylsulfonyl)-4-(4,4,5,5-tetramethyl-1,3,2-dioxaborolan-2-yl)-1,2,3,6-tetrahydropyridine

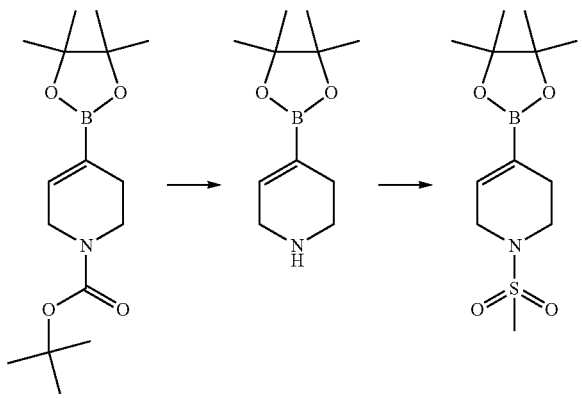

A solution of tert-butyl 4-(4,4,5,5-tetramethyl-1,3,2-dioxaborolan-2-yl)-5,6-dihydropyridine-1(2H)-carboxylate (4.03 g, 13.03 mmol, Carbocore) in HCl (4 M in dioxane, 19.55 mL, 78 mmol) was stirred at ambient temperature for about 2 h. The solution was concentrated under reduced pressure then dissolved in DCM (20.05 mL) and TEA added (12.72 mL, 91 mmol). The mixture was cooled to about 0° C. and methanesulfonyl chloride (1.83 mL, 23.5 mmol) added dropwise. The mixture was stirred at ambient temperature for about 2 h. To the mixture was added 1N HCl (60 mL) and the organic layer was extracted. The organic layer was with saturated aqueous sodium bicarbonate (60 mL), dried over MgSO$_4$, filtered, and concentrated under reduced pressure. The residue was triturated with a mixture of EtOAc and heptanes, filtered and dried (1.477 g). The filtrate was concentrated and residue was triturated with a mixture of EtOAc and heptanes, filtered and dried to get second lot (0.940 g). Lots were combined to obtain 1-(methylsulfonyl)-4-(4,4,5,5-tetramethyl-1,3,2-dioxaborolan-2-yl)-1,2,3,6-tetrahydropyridine (2.41 g, 64%). LC/MS (Table 1, Method a) R$_t$=2.18 min MS m/z: 288 (M+H)$^+$.

Preparation #18: 4-Bromo-2-(1-(methylsulfonyl)-1,2,3,6-tetrahydropyridin-4-yl)-1H-indole-7-carboxamide

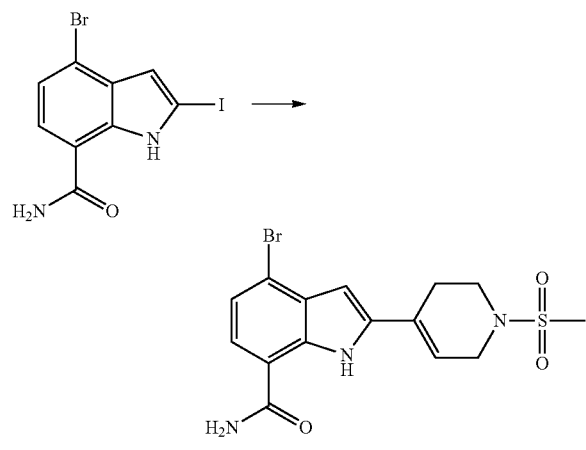

A flask containing 1-(methylsulfonyl)-4-(4,4,5,5-tetramethyl-1,3,2-dioxaborolan-2-yl)-1,2,3,6-tetrahydropyridine (0.446 g, 1.55 mmol, Preparation #17), 4-bromo-2-iodo-1H-indole-7-carboxamide (0.54 g, 1.48 mmol, Preparation #1), sodium carbonate (0.470 g, 4.44 mmol) and 1,1'-bis(diphenylphosphino)ferrocene]dichloropalladium(II) (0.108 g, 0.148 mmol) was purged with nitrogen. A mixture of THF (15.0 mL), MeOH (2.10 mL), and water (2.10 mL) was added. The mixture was stirred for about 2 h at about 70° C. The mixture was filtered through Celite®, rinsing with EtOAc and concentrated under reduced pressure. The residue was triturated with DCM, filtered, washed with DCM and EtOAc to afford a solid (0.315 g). The filtrate was concentrated and purified by column chromatography on silica gel (40-100% EtOAc/heptane). The resulting residue was triturated with DCM, filtered and dried to afford a solid (0.125 g). The solids were combined to obtain 4-bromo-2-(1-(methylsulfonyl)-1,2,3,6-tetrahydropyridin-4-yl)-1H-indole-7-carboxamide (0.44 g, 75%). LC/MS (Table 1, Method a) R$_t$=1.92 min MS m/z: 400 (M+H)$^+$.

Preparation #19: N-Methyl-N-(2-methyl-3-(4,4,5,5-tetramethyl-1,3,2-dioxaborolan-2-yl)phenyl)thiazole-2-carboxamide

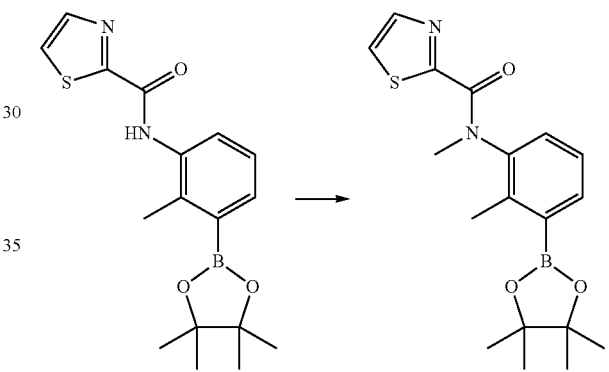

To N-(2-methyl-3-(4,4,5,5-tetramethyl-1,3,2-dioxaborolan-2-yl)phenyl)thiazole-2-carboxamide (502 mg, 1.46 mmol, Preparation #4) in THF (10 mL) was added sodium hydride (70.0 mg, 1.75 mmol) at about 0° C. and stirred for about 25 min. To the mixture was added iodomethane (0.363 mL, 5.83 mmol) at about 0° C. The reaction mixture was brought to rt and then stirred at rt for about 18 h. To mixture was added water, extracted twice with DCM and layers separated. Combined organic layers were evaporated and the residue was purified using normal phase chromatography to provide N-methyl-N-(2-methyl-3-(4,4,5,5-tetramethyl-1,3,2-dioxaborolan-2-yl)phenyl)thiazole-2-carboxamide (0.406 g, 59%). LC/MS (Table 1, Method f) R$_t$=1.97 min MS m/z: 359 (M+H)$^+$.

Preparation #20. (R)-1-((2,2-Dimethyl-1,3-dioxolan-4-yl)methyl)-4-(4,4,5,5-tetramethyl-1,3,2-dioxaborolan-2-yl)-1H-pyrazole

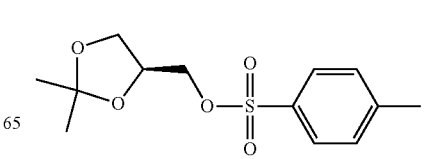

-continued

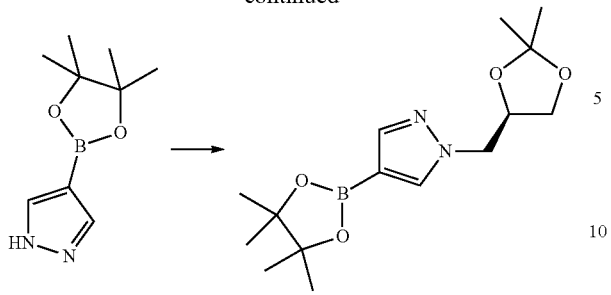

To a mixture of 4-(4,4,5,5-tetramethyl-1,3,2-dioxaborolan-2-yl)-1H-pyrazole (1 g, 5.15 mmol) in DMF (25.8 mL) was added sodium hydride (0.206 g, 5.15 mmol). The mixture was stirred at rt for about 10 min under nitrogen. (S)-(+)-2,2-dimethyl-1,3-dioxolan-4-ylmethyl p-toluenesulfonate (1.62 g, 5.67 mmol) was added and the mixture was stirred at about 90° C. overnight under an nitrogen atmosphere. The reaction was cooled to rt, and partitioned between EtOAc and water. The aqueous layer was re-extracted with EtOAc (2×) and the organics were combined, washed with water, brine, dried over anhydrous MgSO₄, filtered and concentrated under reduced pressure. The residue was purified by column chromatography on silica gel with EtOAc/hexanes (30-75%) to provide (R)-1-((2,2-dimethyl-1,3-dioxolan-4-yl)methyl)-4-(4,4,5,5-tetramethyl-1,3,2-dioxaborolan-2-yl)-1H-pyrazole (0.66 g, 42%): LC/MS (Table 1, Method f) R$_t$=1.41 min; MS m/z: 309 (M+H)$^+$.

Preparation #21. (S)-1-((2,2-Dimethyl-1,3-dioxolan-4-yl)methyl)-4-(4,4,5,5-tetramethyl-1,3,2-dioxaborolan-2-yl)-1H-pyrazole

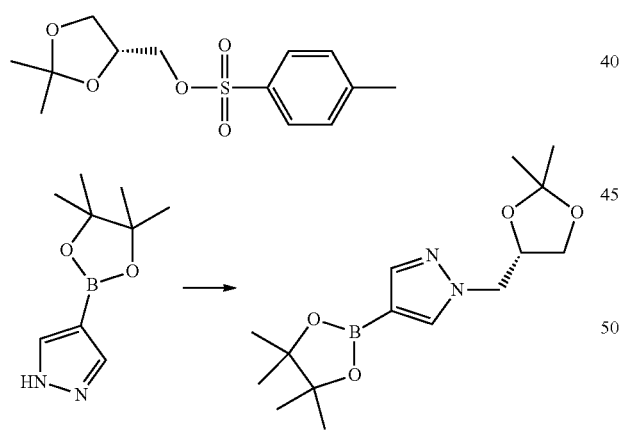

To a mixture of 4-(4,4,5,5-tetramethyl-1,3,2-dioxaborolan-2-yl)-1H-pyrazole (1.0 g, 5.2 mmol) in DMF (25.8 mL) was added sodium hydride (0.206 g, 5.15 mmol). The mixture was stirred at rt for about 10 min under nitrogen. (R)-(2,2-dimethyl-1,3-dioxolan-4-yl)methyl 4-methylbenzenesulfonate (1.62 g, 5.67 mmol) was added and the mixture was stirred at about 90° C. overnight under an nitrogen atmosphere. The reaction was cooled to rt, partitioned between EtOAc and water. The aqueous layer was re-extracted with EtOAc (2×) and the organics were combined, washed with water, brine, dried over anhydrous MgSO₄, filtered and concentrated under reduced pressure. The residue was purified by was column chromatography on silica gel with EtOAc/hexanes (30-75%) to provide (S)-1-((2,2-dimethyl-1,3-dioxolan-4-yl)methyl)-4-(4,4,5,5-tetramethyl-1,3,2-dioxaborolan-2-yl)-1H-pyrazole (0.83 g, 52%): LC/MS (Table 1, Method f) R$_t$=1.35 min; MS m/z: 251 (M-(CH₃)₂CHO+H)$^+$.

Preparation #22: N-(3-(4,4,5,5-Tetramethyl-1,3,2-dioxaborolan-2-yl)phenyl)acrylamide

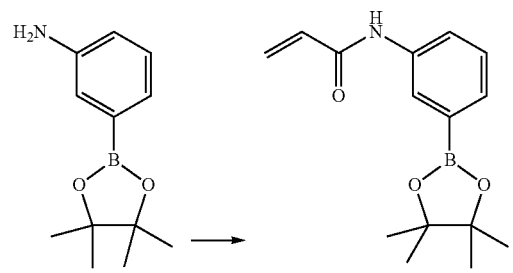 [SMILES: CC1(C)OB(c2cccc(N)c2)OC1(C)C ; C=CC(=O)Nc1cccc(B2OC(C)(C)C(C)(C)O2)c1]

To a vial was added 3-(4,4,5,5-tetramethyl-1,3,2-dioxaborolan-2-yl)aniline (0.30 g, 1.37 mmol) in DCM (10 mL), and DIEA (0.72 mL, 4.11 mmol). The mixture was cooled to about 0° C. and acryloyl chloride (0.122 mL, 1.51 mmol) was added while stirring. The mixture was stirred for about 20 min while warming to rt. The mixture was diluted with and additional DCM (10 mL) washed with water (2×10 mL), filtered through a Biotage phase separator and concentrated under a warm stream of nitrogen to provide N-(3-(4,4,5,5-tetramethyl-1,3,2-dioxaborolan-2-yl)phenyl)acrylamide (0.375 g, 100%): LC/MS (Table 1, Method f) R$_t$=1.70 min; MS m/z: 274 (M+H)$^+$.

Preparation #23: N-(trans-4-Hydroxypiperidin-3-yl)thiazole-2-carboxamide

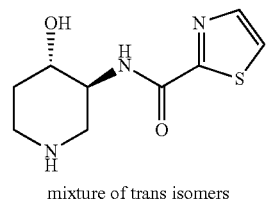 [SMILES: O=C(N[C@H]1CNCC[C@@H]1O)c1nccs1]

mixture of trans isomers

Step A. Benzyl 4-(hydroxyimino)piperidine-1-carboxylate

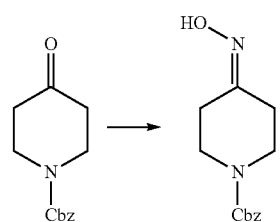 [SMILES: O=C1CCN(C(=O)OCc2ccccc2)CC1 ; O=C(OCc1ccccc1)N1CCC(=NO)CC1]

A mixture of benzyl 4-oxopiperidine-1-carboxylate (10 g, 42.9 mmol), NH$_2$OH HCl (5.9 g, 86 mmol) and K$_2$CO$_3$ (11.8 g, 86 mmol) in EtOH (45 mL) was heated at about 50° C. for about 0.5 h. Then the solvent was removed under reduced pressure. Water and EtOAc were added to the residue. The aqueous phase was extracted with EtOAc (3×75 mL). The organic layer was washed with brine and dried over Na$_2$SO$_4$, filtered and concentrated to provide benzyl 4-(hydroxyimino)piperidine-1-carboxylate (10 g, 94%). $^1$H NMR (CDCl$_3$) δ 2.36 (br, 2H), 2.63 (br, 2H), 3.63-3.58 (m, 4H), 5.15 (s, 2H), 7.36-7.35 (m, 5H), 9.05 (br, 1H).

Step B. Benzyl 4-((tosyloxy)imino)piperidine-1-carboxylate

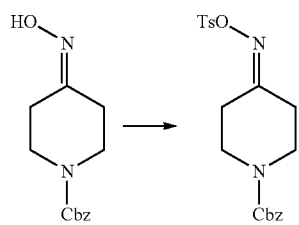 [SMILES: O=C(OCc1ccccc1)N1CCC(=NO)CC1 ; Cc1ccc(S(=O)(=O)ON=C2CCN(C(=O)OCc3ccccc3)CC2)cc1]

To a solution of benzyl 4-(hydroxyimino)piperidine-1-carboxylate (12.2 g, 49.1 mmol) in pyridine (75 mL) was added TsCl (12.2 g, 64 mmol) slowly at about 0° C. The reaction mixture was stirred at this temperature for about 0.5 h and stirred at rt for another 2 h. Then the solvent was removed under reduced pressure. Water and EtOAc were added to the residue. The aqueous phase was extracted with EtOAc (3×125 mL). The organic layer was washed with brine and dried over Na$_2$SO$_4$. The solvent was concentrated to give the crude product which was purified by column chromatography on silica gel (Pet ether:EtOAc=15:1) to provide benzyl 4-((tosyloxy)imino)piperidine-1-carboxylate (5 g, 25.3%): $^1$H NMR (CDCl$_3$) δ 2.37 (br, 2H), 2.44 (s, 3H), 2.63 (br, 2H), 3.62-3.55 (m, 4H), 5.13 (s, 2H), 7.35-7.32 (m, 7H), 7.85 (d, J=8.0 Hz, 2H).

Step C. Benzyl 3-amino-4-oxopiperidine-1-carboxylate hydrochloride

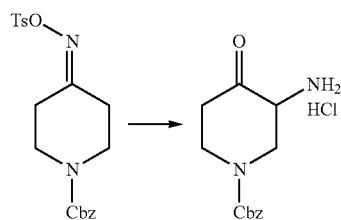 [SMILES: Cc1ccc(S(=O)(=O)ON=C2CCN(C(=O)OCc3ccccc3)CC2)cc1 ; NC1CN(C(=O)OCc2ccccc2)CCC1=O ; Cl]

Na (28.6 mg, 1.243 mmol) was added to EtOH (6.5 mL) and the mixture was stirred until the Na was completely dissolved. MgSO$_4$ (0.98 g) was added to the solution, then benzyl 4-((tosyloxy)imino)piperidine-1-carboxylate (0.5 g, 1.242 mmol) was added to the solution at about 0° C. After the reaction mixture was heated at about 30° C. for about 2 h, the mixture was filtered and 1 N HCl (6.5 mL) was added to the filtration. The filtration was stirred at rt for about 0.5 h and concentrated. The residue was mixed with EtOH (3 mL) and filtered. The filtration was concentrated to give crude benzyl 3-amino-4-oxopiperidine-1-carboxylate hydrochloride (200 mg, 0.702 mmol): $^1$H NMR (MeOD) δ=7.33 (m, 5H), 5.12 (br. s., 2H), 3.75-3.95 (m, 1H), 3.6-3.7 (m, 1H), 3.5 (m, 2H), 3.1-3.2 (m, 1H), 1.95-2.10 (m, 1H), 1.7-1.8 (m, 1H).

Step D. Benzyl 4-oxo-3-(thiazole-2-carboxamido)piperidine-1-carboxylate

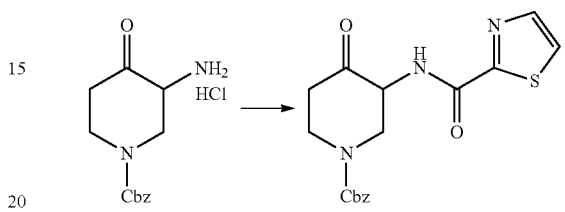

A solution of thiazole-2-carboxylic acid (189 mg, 14.6 mmol) and HATU (723 mg, 1.9 mmol) in DMF (20 mL) was stirred at rt for 0.5 h, then DIEA (945 mg, 7.31 mmol) and benzyl 3-amino-4-oxopiperidine-1-carboxylate hydrochloride (500 mg, 1.76 mmol) was added to the mixture. The reaction solution was stirred at rt for about 4 h. Water was added to the mixture, extracted with EtOAc (3×45 mL). The combined organic layer was washed with brine several times, dried over Na$_2$SO$_4$, filtered and concentrated to give the crude product which was purified by Prep-HPLC (Table 1, Method ai) to provide benzyl 4-oxo-3-(thiazole-2-carboxamido)piperidine-1-carboxylate (82 mg, 12%). $^1$H NMR (CDCl$_3$) δ 2.68-2.62 (br, 2H), 2.93-2.86 (m, 1H), 3.16 (br, 1H), 4.7-5.9 (br, 2H), 5.08-5.05 (m, 1H), 5.31-5.22 (m, 2H), 7.43-7.38 (m, 5H), 7.60 (q, J=1.2 Hz, 1H), 7.92-7.90 (m, 1H), 8.08 (s, 1H).

Step E. trans-Benzyl 4-hydroxy-3-(thiazole-2-carboxamido)piperidine-1-carboxylate

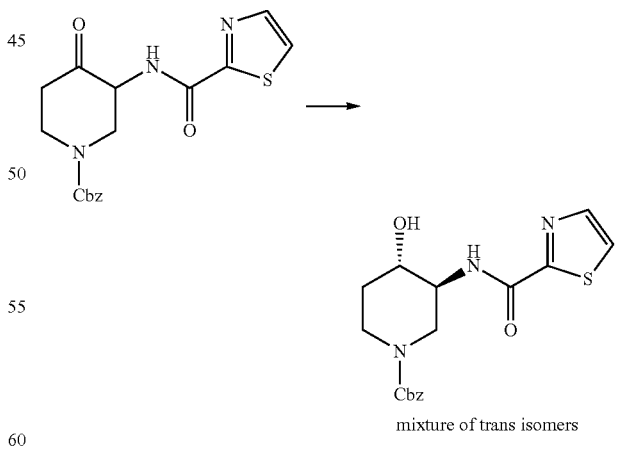

mixture of trans isomers

To a solution of benzyl 4-oxo-3-(thiazole-2-carboxamido)piperidine-1-carboxylate (6.9 g, 19.2 mmol) in MeOH (50 mL) was added NaBH$_4$ (0.726 g, 0.019 mmol) in batches and the mixture was stirred at rt for about 0.5 h. Then water (50 mL) was added to the reaction mixture and extracted with DCM (3×60 mL). The organic layer was washed with brine and dried over Na₂SO₄, filtered and concentrated under reduced pressure to give the crude product which was purified by column chromatography on silica gel to provide trans-benzyl 4-hydroxy-3-(thiazole-2-carboxamido)piperidine-1-carboxylate (3 g, 43%). ¹H NMR (MeOD) δ 1.56-1.51 (m, 1H), 2.00 (t, J=5.2 Hz, 1H), 3.10-2.97 (m, 2H), 3.85-3.75 (m, 2H), 4.16-3.99 (m, 1H), 4.21-4.20 (m, 1H), 5.12 (s, 2H), 7.34-7.31 (m, 5H), 7.85 (q, J=3.2 Hz, 1H), 7.94 (t, J=3.2 Hz, 1H).

Step F. N-(trans-4-Hydroxypiperidin-3-yl)thiazole-2-carboxamide

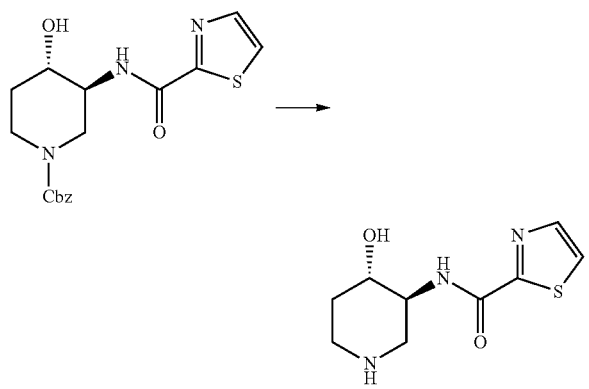

To a stirred solution of trans-benzyl 4-hydroxy-3-(thiazole-2-carboxamido)piperidine-1-carboxylate (0.7 g, 1.937 mmol) in MeCN (15 mL) was added TMSI (1.55 g, 775 mmol) slowly at about 0° C., then the mixture was stirred at rt for about 1 h. Water was poured into the mixture and MeCN was removed under reduced pressure. 1 N HCl was added to the residue and the mixture was extracted with MTBE (3×30 mL). Then the aqueous phase was basified with NaOH (3 N) to about pH=12 and extracted with DCM (6×45 mL). The organic phase was washed with brine and dried over Na₂SO₄, filtered and concentrated to give the crude product which was purified by Prep-TLC (1:1 MeOH/DCM) to provide N-(trans-4-hydroxypiperidin-3-yl)thiazole-2-carboxamide (50 mg, 11%): ¹H NMR (MeOD) δ 1.86-1.77 (m, 1H), 2.28-2.22 (m, 1H), 3.29-309 (m, 2H), 3.56-3.44 (m, 2H), 4.84-3.90 (m, 2H), 7.88 (q, J=3.2 Hz, 1H), 7.97 (q, J=3.2 Hz, 1H).

Preparation #24: 4-Bromo-2-iodo-14(2-(trimethylsilyl)ethoxy)methyl)-1H-indole-7-carboxamide

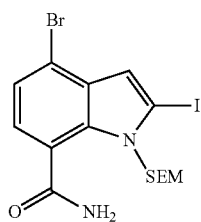 [SMILES: C[Si](C)(C)CCOCn1c(I)cc2c(Br)ccc(C(N)=O)c21]

Step A. 4-Bromo-2-iodo-1-((2-(trimethylsilyl)ethoxy)methyl)-1H-indole-7-carboxylic acid

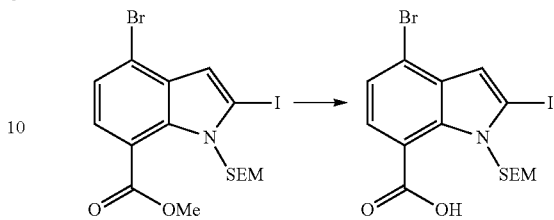

To a solution of methyl 4-bromo-2-iodo-14(2-(trimethylsilyl)ethoxy)methyl)-1H-indole-7-carboxylate (10 g, 19.6 mmol, Preparation #10, step B) in MeOH (150 mL), THF (300 mL) and water (150 mL) was added lithium hydroxide hydrate (12 g, 286 mmol). The resulting mixture was heated at about 45° C. for about 3 h. Then the mixture was concentrated under reduced pressure to remove most solvent, the residue was dissolved in water. The aqueous mixture was acidified by addition of aqueous HCl (1N) to about pH 6. The precipitate was filtered, and the solid was dried to give 4-bromo-2-iodo-1-((2-(trimethylsilyl)ethoxy)methyl)-1H-indole-7-carboxylic acid (9.1 g, 94%) as a solid: ¹H NMR (CDCl₃) δ 13.44 (br, 1H), 7.57-7.51 (m, 2H), 7.09 (s, 1H), 5.95 (s, 2H), 3.35-3.11 (t, J=8.0 Hz, 2H), 0.87-0.83 (t, J=8.0 Hz, 2H), 0.00 (s, 9H).

Step B. 4-Bromo-2-iodo-1-((2-(trimethylsilyl)ethoxy)methyl)-1H-indole-7-carboxamide

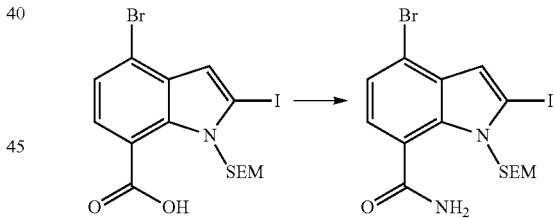

A solution of 4-bromo-2-iodo-14(2-(trimethylsilyl)ethoxy)methyl)-1H-indole-7-carboxylic acid (8 g, 16 mmol), EDCI (4.6 g, 24 mmol) and HOBt (3.7 g, 24 mmol) in THF (240 mL) and DCM (280 mL) was stirred at rt for about 1 h. The reaction mixture was then bubbled with NH₃ gas for 15 min and stirred at rt overnight. Then the mixture was concentrated and partitioned between aqueous NaHCO₃ and EtOAc. The organic phase was washed with brine, dried and concentrated to give a residue, which was suspended in Pet ether and the solid was collected by filtration to provide 4-bromo-2-iodo-142-(trimethylsilyl)ethoxy)methyl)-1H-indole-7-carboxamide (7.2 g, 90%) as a white solid: ¹H NMR (CDCl₃) δ 7.36-7.33 (m, 1H), 7.26-7.24 (d, J=8.0 Hz, 1H), 7.05 (s, 1H), 6.08 (br, 1H), 5.82 (br, 1H) 5.82 (s, 2H), 3.48-3.41 (m, 2H), 0.90-0.86 (m, 2H), 0.00 (s, 9H).

Preparation #25: 4-(Difluoromethyl)-N-(2-methyl-3-(4,4,5,5-tetramethyl-1,3,2-dioxaborolan-2-yl)phenyl)-N-(oxetan-3-yl)benzamide

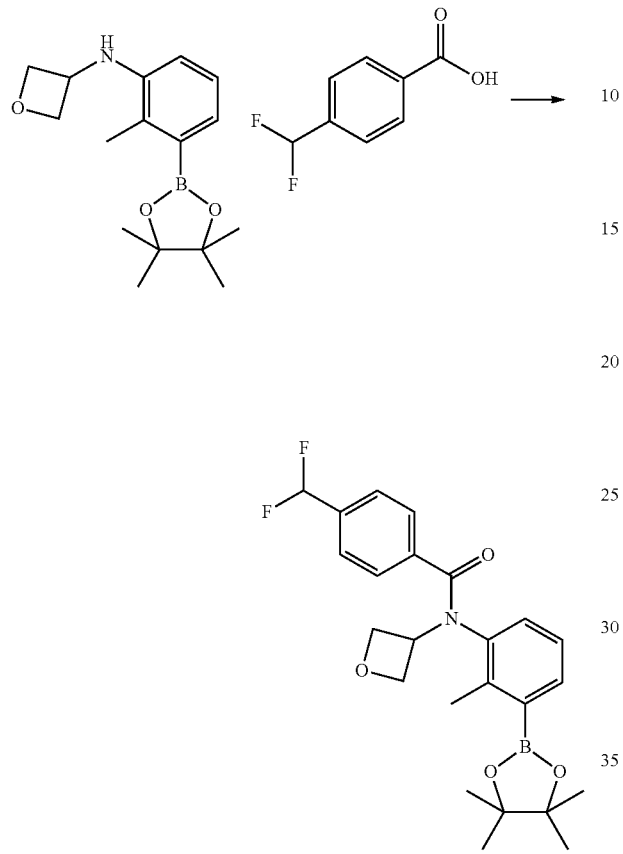

A solution of 4-(difluoromethyl)benzoic acid (0.089 g, 0.519 mmol, Oakwood) in DCM (3.46 mL) under nitrogen was treated with sulfurous dichloride (0.075 mL, 1.037 mmol) and 1 drop DMF. The mixture was stirred at about 35° C. for about 16 h. The reaction was concentrated under reduced pressure, triturated residue with heptane, and concentrated. The residue was dissolved in DCM (3.46 mL) and added N-(2-methyl-3-(4,4,5,5-tetramethyl-1,3,2-dioxaborolan-2-yl)phenyl)oxetan-3-amine (0.100 g, 0.346 mmol, prepared using H from 2-methyl-3-(4,4,5,5-tetramethyl-1,3,2-dioxaborolan-2-yl)aniline [Combi-Blocks] and 3-oxetanone [(Molbridge]) and TEA (0.193 mL, 1.383 mmol). The mixture was stirred at ambient temperature for about 4 h then diluted with DCM (10 mL) and quenched with saturated aqueous sodium bicarbonate (10 mL). The organics were combined and washed with 30 mL saturated aqueous sodium bicarbonate. The organic layer was dried over MgSO$_4$, filtered and concentrated under reduced pressure to give the crude product which was purified by column chromatography on silica gel (0-40% EtOAc/heptane) to provide a yellow oil that solidified upon standing to afford 4-(difluoromethyl)-N-(2-methyl-3-(4,4,5,5-tetramethyl-1,3,2-dioxaborolan-2-yl)phenyl)-N-(oxetan-3-yl)benzamide (0.092 g, 60%). LCMS (Table 1, Method a) R$_t$=2.51 min MS m/z: 444 (M+H)$^+$.

Preparation #26: 2-Methyl-1-(4-(4,4,5,5-tetramethyl-1,3,2-dioxaborolan-2-yl)-1H-pyrazol-1-yl)propan-2-ol

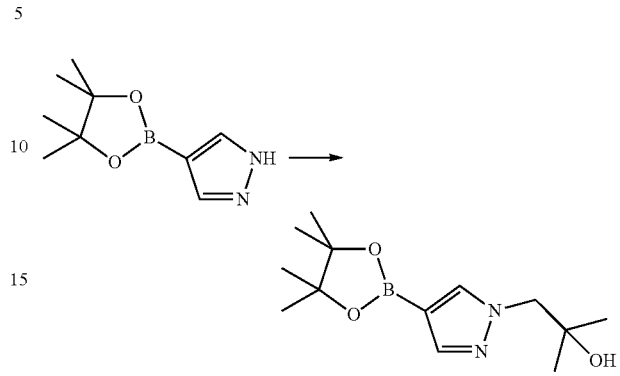

To a solution of 4-(4,4,5,5-tetramethyl-1,3,2-dioxaborolan-2-yl)-1H-pyrazole (2.0 g, 10.31 mmol) in 2,2-dimethyloxirane (11.96 mL, 134 mmol) in a 30 mL microwave vial was added cesium carbonate (0.521 g, 1.60 mmol). The mixture was heated in a microwave oven at about 120° C. for about 30 min. The reaction was cooled and filtered. The resulting solution was evaporated to dryness to give 2-methyl-1-(4-(4,4,5,5-tetramethyl-1,3,2-dioxaborolan-2-yl)-1H-pyrazol-1-yl)propan-2-ol as a white solid. (2.7 g, 99%); (Table 1, Method g) R$_t$=1.34 min; MS m/z: 267 (M+H)$^+$

Preparation #27: 4-Fluoro-2-iodo-1-tosyl-1H-indole-7-carbonitrile

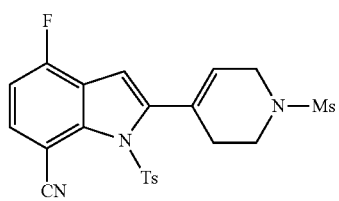 [SMILES: Cc1ccc(S(=O)(=O)n2c(C3=CCN(S(C)(=O)=O)CC3)cc3c(F)ccc(C#N)c32)cc1]

Step A. 4-Fluoro-1-tosyl-1H-indole-7-carbonitrile

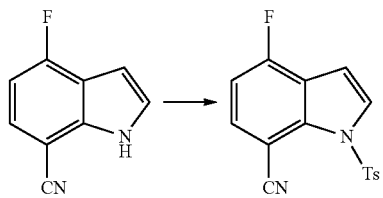 [SMILES: N#Cc1ccc(F)c2cc[nH]c12 ; Cc1ccc(S(=O)(=O)n2ccc3c(F)ccc(C#N)c32)cc1]

To a solution of 4-fluoro-1H-indole-7-carbonitrile (5.3 g, 33.1 mmol, Sinova) in DMF (92 mL) was added NaH (2.0 g, 49.6 mmol) at 0° C. under N$_2$ atmosphere and stirred for about 30 min. Then TsCl (9.46 g, 49.6 mmol) was added to the above mixture and stirred at rt for about 5 h. The mixture was poured into saturated aqueous NH$_4$Cl solution (200 mL), extracted with EtOAc (100 mL×3). The combined organic phase was washed with brine, dried over Na$_2$SO$_4$, filtered and concentrated to afford the crude product which was washed with MTBE to provide 4-fluoro-1-tosyl-1H-indole-7-carbonitrile (7 g, 67.3%) as a solid: ¹H NMR (CDCl₃) δ 2.39 (s, 3H), 6.86 (d, J=4 Hz, 1H), 6.99 (t, J=8.4 Hz, 1H), 7.33 (d, J=8.4 Hz, 2H), 7.62 (m, 1H), 7.84 (d, J=3.6 Hz, 1H), 7.92 (d, J=8.4 Hz, 2H).

Step B.
4-Fluoro-2-iodo-1-tosyl-1H-indole-7-carbonitrile

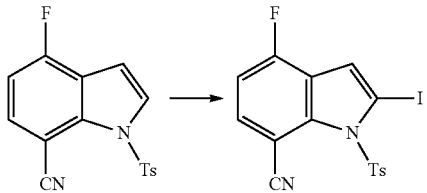 [SMILES: Cc1ccc(S(=O)(=O)n2ccc3c(F)ccc(C#N)c32)cc1 ; Cc1ccc(S(=O)(=O)n2c(I)cc3c(F)ccc(C#N)c32)cc1]

Freshly prepared LDA (67 mL, 38.2 mmol) was added dropwise to a solution of 4-fluoro-1-tosyl-1H-indole-7-carbonitrile (10 g, 31.8 mmol) in THF (50 mL) at about −78° C. After the addition was complete, the mixture was stirred for another 45 min. Then a solution of I₂ (9.69 g, 38.2 mmol) in THF (50 mL) was added dropwise to the mixture at about −78° C. After the addition, the mixture was stirred for about another 1 h. The solution was poured into saturated aqueous Na₂S₂O₃ (400 mL), extracted with EtOAc (100 mL×3). The combined organic phase was washed with brine, dried over Na₂SO₄, filtered and concentrated to afford the crude product which was washed with EtOAc to give 4-fluoro-2-iodo-1-tosyl-1H-indole-7-carbonitrile (8.5 g, 61%) as a solid: ¹H NMR (CDCl₃) δ 2.45 (s, 3H), 7.01 (t, J=8.4 Hz, 1H), 7.20 (s, 1H), 7.33 (d, J=8.4 Hz, 2H), 7.64 (m, 1H), 8.05 (d, J=8.4 Hz, 2H).

Step C. tert-Butyl 4-(7-cyano-4-fluoro-1-tosyl-1H-indol-2-yl)-5,6-dihydropyridine-1(2H)-carboxylate

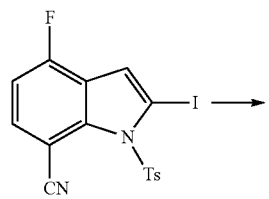

To a solution of 4-fluoro-2-iodo-1-tosyl-1H-indole-7-carbonitrile (2.92 g, 6.63 mmol) and tert-butyl 4-(4,4,5,5-tetramethyl-1,3,2-dioxaborolan-2-yl)-5,6-dihydropyridine-1(2H)-carboxylate (2.05 g, 6.63 mmol) in the mixture of THF (20 mL), MeOH (4 mL) and water (4 mL) was added Na₂CO₃ (2.108 g, 19.89 mmol) and PdCl₂(dppf) DCM (0.541 g, 0.663 mmol). The mixture was heated at about 80° C. for about 3 h. Then the reaction was cooled and diluted with EtOAc (30 mL) and washed with water (3×10 mL). The organic phase was dried over Na₂SO₄, filtered and concentrated under reduced pressure to give crude product which was purified by column chromatography on silica gel (eluted with Pet ether:EtOAc=10:1) to give tert-butyl 4-(7-cyano-4-fluoro-1-tosyl-1H-indol-2-yl)-5,6-dihydropyridine-1(2H)-carboxylate (2.5 g, 76%): ¹H NMR (CDCl₃) δ 1.25 (s, 2H), 1.52 (s, 9H), 2.38 (s, 3H), 3.63 (t, J=5.6 Hz, 2H), 4.09 (d, J=2.8 Hz, 2H), 5.83 (d, J=2.8 Hz, 1H), 6.56 (s, 1H), 7.04 (t, J=8.4 Hz, 1H), 7.20 (d, J=8.0 Hz, 2H), 7.48 (s, 2H), 7.68 (q, J=5.2 Hz, 1H).

Step D. 4-Fluoro-2-(1,2,3,6-tetrahydropyridin-4-yl)-1-tosyl-1H-indole-7-carbonitrile hydrochloride

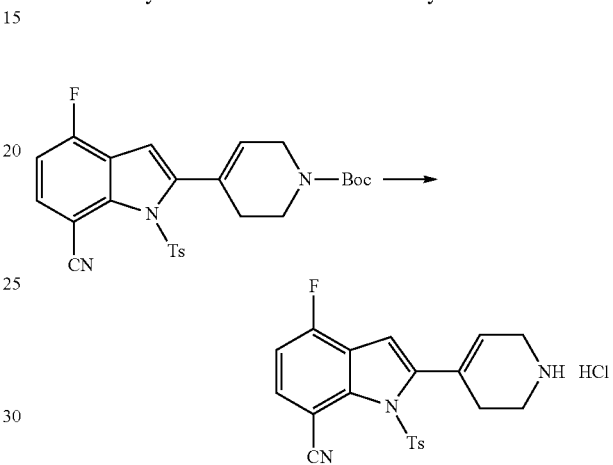

To a solution of tert-butyl 4-(7-cyano-4-fluoro-1-tosyl-1H-indol-2-yl)-5,6-dihydropyridine-1(2H)-carboxylate (2.7 g, 5.45 mmol) in EtOAc (30 mL) was added dropwise HCl/EtOAc (30 mL) at about 0° C., then the reaction was stirred at rt for about 3 h. The mixture was filtered and the filter cake was washed with EtOAc to give 4-fluoro-2-(1,2,3,6-tetrahydropyridin-4-yl)-1-tosyl-1H-indole-7-carbonitrile hydrochloride (1.96 g, 83%): ¹H NMR (MeOD) δ 2.35 (s, 3H), 2.78 (s, 2H), 3.48 (t, J=5.6 Hz, 2H), 3.94 (s, 2H), 6.04 (s, 1H), 6.86 (s, 1H), 7.23-7.29 (m, 3H), 7.43 (d, J=8.0 Hz, 2H), 7.84 (t, J=5.2 Hz, 1H).

Step E. 4-Fluoro-2-(1-(methylsulfonyl)-1,2,3,6-tetrahydropyridin-4-yl)-1-tosyl-1H-indole-7-carbonitrile

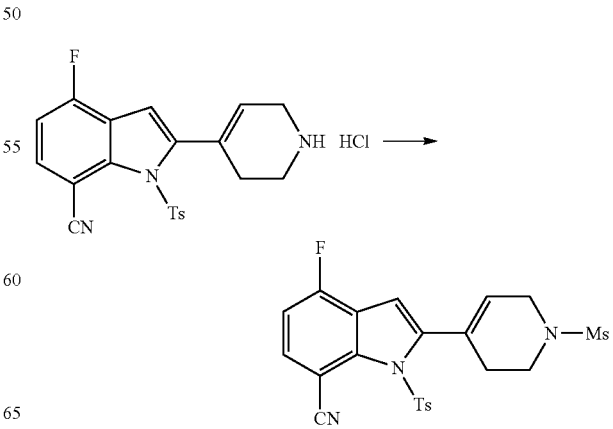

To a solution of tert-butyl 4-(7-cyano-4-fluoro-1-tosyl-1H-indol-2-yl)-5,6-dihydropyridine-1(2H)-carboxylate (1.96 g, 4.54 mmol) and TEA (1.84 g, 18.2 mmol) in DCM (30 mL) was added MsCl (0.623 g, 5.44 mmol), then the mixture was stirred at rt for about 24 h. Then water was added to the mixture and the reaction mixture was extracted with DCM (3×30 mL). The combined organic layer was washed with brine and dried over Na$_2$SO$_4$, filtered and concentrated under reduced pressure to give 4-fluoro-2-(1-(methylsulfonyl)-1,2,3,6-tetrahydropyridin-4-yl)-1-tosyl-1H-indole-7-carbonitrile (1.35 g, 63%) which was used in the next step without any further purification. LC/MS (Table 1, Method f) R$_t$=2.15 min; MS m/z: 474 (M+H)$^+$.

Preparation #28:
3-Bromo-N-(cyanomethyl)benzenesulfonamide

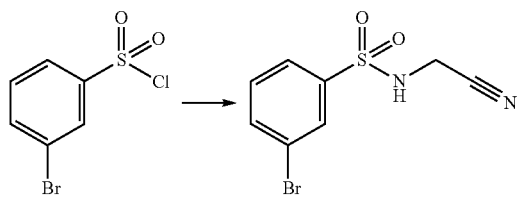 [SMILES: O=S(=O)(Cl)c1cccc(Br)c1 ; N#CCNS(=O)(=O)c1cccc(Br)c1]

To a cooled (0° C.) solution of 2-aminoacetonitrile hydrochloride (0.50 g, 5.40 mmol) in pyridine (27.0 mL) was slowly added 3-bromobenzene-1-sulfonyl chloride (0.779 mL, 5.40 mmol). The mixture was slowly warmed to rt and stirred for about 16 h. The mixture was concentrated under reduced pressure and the residue was dissolved in DCM and washed with 1N HCl, saturated sodium bicarbonate, brine and filtered through a Biotage Phase separator after each wash step. The organics were concentrated under reduced pressure afford the crude product. The crude product was purified by column chromatography on silica gel eluted EtOAc/heptane (0-40%) to provide 3-bromo-N-(cyanomethyl)benzenesulfonamide (0.61 g, 41%): $^1$H NMR (DMSO-d6): δ 8.73 (br, 1H), 7.98 (t, J=1.79, 1H), 7.91 (d, J=8.02, 1H), 7.84 (d, J=8.02, 1H), 7.60 (t, J=7.92, 1H), 4.18 (s, 2H).

Preparation #29: 4-Cyclopropyl-N-(2-methyl-3-(4,4,5,5-tetramethyl-1,3,2-dioxaborolan-2-yl)phenyl)benzamide

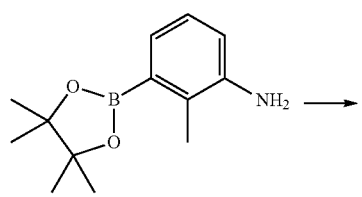

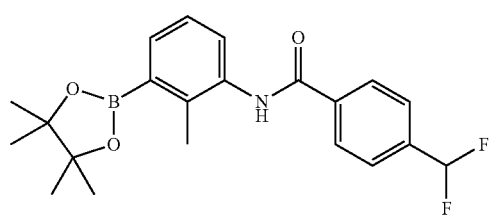

To a solution of 2-methyl-3-(4,4,5,5-tetramethyl-1,3,2-dioxaborolan-2-yl)aniline (0.350 g, 1.501 mmol) and HATU (0.856 g, 2.252 mmol) in DCM (2 mL) was added TEA (0.628 mL, 4.50 mmol) and 4-(difluoromethyl)benzoic acid (0.336 g, 1.952 mmol). The mixture was stirred at about rt for about 18 h. The mixture was evaporated and the resulting residue was purified by silica gel chromatography eluting with a gradient of 30-50% EtOAc in hexane to give 4-cyclopropyl-N-(2-methyl-3-(4,4,5,5-tetramethyl-1,3,2-dioxaborolan-2-yl)phenyl)benzamide (0.52, 89%); LC/MS (Table 1, Method c) R$_t$=2.10 min; MS m/z: 388 (M+H)$^+$ Preparation #30: (R)-6-Fluoro-2-(piperidin-3-yl)isoindolin-1-one hydrochloride

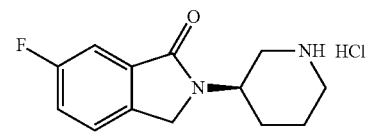 [SMILES: O=C1c2cc(F)ccc2CN1[C@@H]1CCCNC1 ; Cl]

Step A: Methyl 5-fluoro-2-methylbenzoate

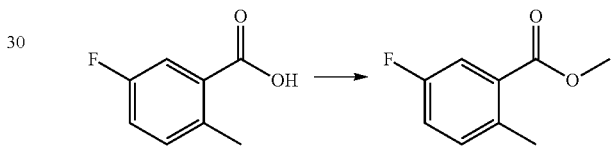

To a solution of 5-fluoro-2-methylbenzoic acid (20 g, 0.13 mol) in anhydrous MeOH (200 mL) was added SOCl$_2$ (38.9 g, 0.33 mol) dropwise. The resulting mixture was stirred at rt overnight. The solvent was evaporated to dryness to give methyl 5-fluoro-2-methylbenzoate (24 g, 99%) as an oil. $^1$H NMR (CDCl$_3$): δ 7.62-7.59 (d, J=9.6 Hz, 1H), 7.21-7.18 (d, J=8.4 Hz, 1H), 7.12-7.09 (d, J=8.0 Hz, 1H), 3.89 (s, 3H), 2.55 (s, 3H).

Step B: Methyl 2-(bromomethyl)-5-fluorobenzoate

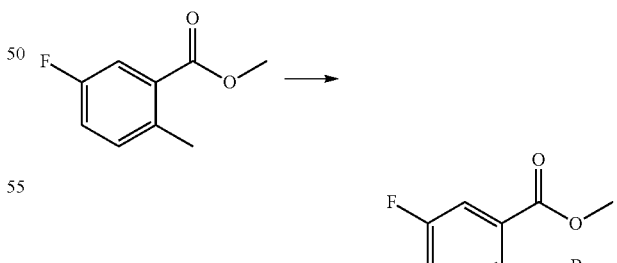

To a solution of methyl 5-fluoro-2-methylbenzoate (24 g, 0.14 mol) in CCl$_4$ (250 mL) was added NBS (28 g, 0.16 mol) and BPO (1.7 g, 7.2 mmol). The reaction mixture was heated to reflux for about 18 h. The hot reaction mixture was filtered and the filtrate was concentrated in vacuo to give methyl 2-(bromomethyl)-5-fluorobenzoate (35 g, crude), which was used in next step reaction directly without further purification. ¹H NMR (DMSO-d6): δ 7.67-7.60 (m, 2H), 7.48-7.45 (d, J=8.4 Hz, 1H), 4.98 (s, 2H), 3.86 (s, 3H).

Step C: (R)-tert-Butyl 3-(6-fluoro-1-oxoisoindolin-2-yl)piperidine-1-carboxylate

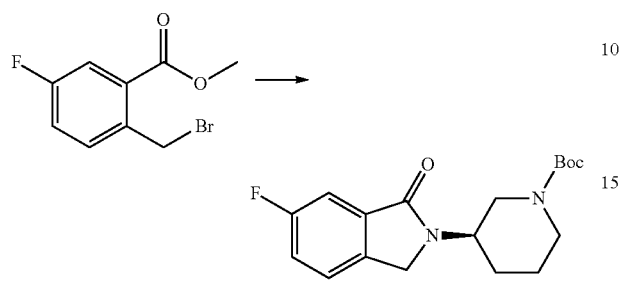

To a solution of methyl 2-(bromomethyl)-5-fluorobenzoate (35 g) in MeCN (400 mL) was added K₂CO₃ (39 g, 0.29 mol) and 3-(R)-amino-piperidine-1-carboxylic acid tert-butyl ester (20 g, 0.10 mol). The reaction mixture was heated to reflux for about 3 h and then stirred at rt overnight. The resulting suspension was filtered and the filtrate was concentrated under vacuum to give the residue which was dissolved in EtOAc (300 mL) and washed with brine (2×100 mL). The organic phase was dried over Na₂SO₄ and concentrated. The resulting residue was purified by column chromatography on silica gel (eluting with 15:1 petroleum ether: EtOAc) to give (R)-tert-butyl 3-(6-fluoro-1-oxoisoindolin-2-yl)piperidine-1-carboxylate (12 g, 25%) as a solid: ¹H NMR (CDCl₃): δ 7.46-7.43 (d, J=7.6 Hz, 1H), 7.35-7.32 (d, J=8.0 Hz, 1H), 7.20-7.14 (m, 1H), 4.36-4.26 (m, 2H), 4.18 (m, 1H), 4.06-3.89 (m, 2H), 2.99-2.93 (m, 1H), 2.75 (s, 1H), 1.95-1.92 (m, 1H), 1.74-1.65 (m, 2H), 1.56-1.54 (m, 1H), 1.39 (s, 9H).

Step D: (R)-6-Fluoro-2-(piperidin-3-yl)isoindolin-1-one hydrochloride

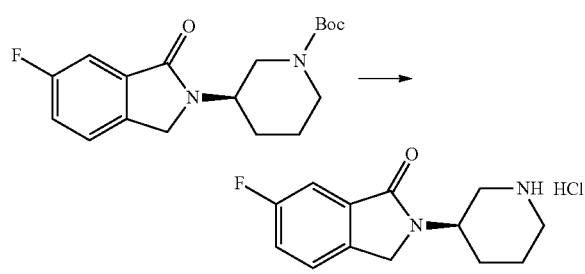

To a solution of (R)-tert-butyl 3-(6-fluoro-1-oxoisoindolin-2-yl)piperidine-1-carboxylate (12 g, 0.036 mol) in DCM (100 mL) was added 1M HCl in MeOH (150 mL). The resulting mixture was stirred at rt overnight. The reaction mixture was concentrated under vacuum to give (R)-6-fluoro-2-(piperidin-3-yl)isoindolin-1-one hydrochloride B (9.0 g, 100%) as a solid. LCMS (ESI+): m/z 235 (M+H)⁺, R$_t$: 1.90 min; ¹H NMR (D₂O): δ 7.43-7.40 (m, 1H), 7.28-7.21 (m, 2H), 4.39-4.37 (d, J=5.6 Hz, 1H), 4.33-4.31 (m, 1H), 3.38-3.34 (m, 2H), 3.12-3.06 (t, J=12.0 Hz, 1H), 2.88-2.85 (m, 1H), 2.00-1.95 (m, 2H), 1.87-1.77 (m, 2H).

Preparation #31: (R)-3-(Piperidin-3-yl)quinazolin-4(3H)-one

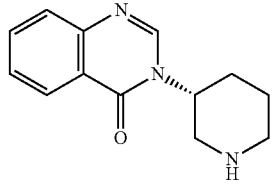 [SMILES: O=c1c2ccccc2ncn1[C@@H]1CCCNC1]

Step A: (R)-tert-Butyl 3-(4-oxoquinazolin-3(4H)-yl)piperidine-1-carboxylate

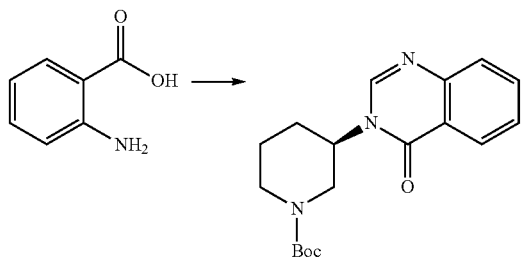 [SMILES: Nc1ccccc1C(=O)O ; CC(C)(C)OC(=O)N1CCC[C@@H](n2cnc3ccccc3c2=O)C1]

To a solution of 2-aminobenzoic acid (7.5 g, 54.7 mmol) and 3-(R)-amino-piperidine-1-carboxylic acid tert-butyl ester (10.9 g, 54.7 mmol) in THF (20 mL) was added triethyl orthoformate (8.1 g, 54.7 mmol). The reaction mixture was heated to about 110° C. in a sealed tube overnight. After cooling to rt, the mixture was diluted with water and extracted with EtOAc. The combined organic phase was washed with brine, dried over anhydrous Na₂SO₄ and concentrated under reduced pressure to give a residue, which was purified by column chromatography on silica gel (eluting with 10:1 petroleum ether: EtOAc) to give (R)-tert-butyl 3-(4-oxoquinazolin-3(4H)-yl)piperidine-1-carboxylate (7.5 g, 42%) as a yellow solid. ¹H NMR (CDCl₃): δ 8.34-8.32 (m, 1H), 8.11 (s, 1H), 7.80-7.71 (m, 2H), 7.55-7.51 (m, 1H), 4.75 (br, 1H), 4.23-4.11 (br, 2H), 3.24-3.18 (t, 1H), 2.87 (br, 1H), 2.18-1.98 (m, 2H), 1.91-1.87 (br, 1H), 1.77-1.71 (m, 1H), 1.48 (s, 9H).

Step B: (R)-3-(Piperidin-3-yl)quinazolin-4(3H)-one

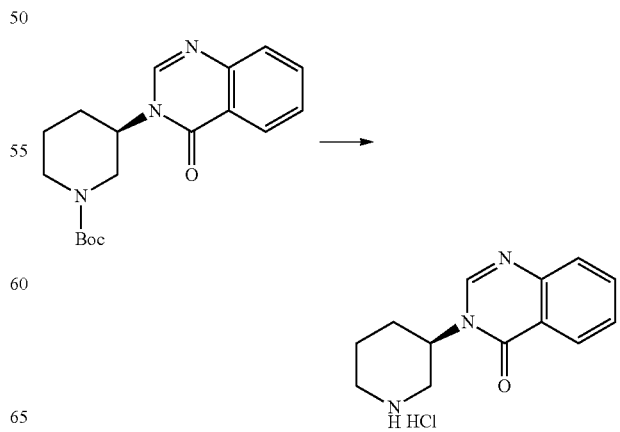

The reaction solution of (R)-tert-butyl 3-(4-oxoquinazolin-3(4H)-yl)piperidine-1-carboxylate (12.5 g, 36 mmol) in 1M HCl/MeOH (150 mL) was stirred at about rt for about 2.5 h. The mixture was filtered. The solid was washed with EtOAc and dried to give (R)-3-(piperidin-3-yl)quinazolin-4 (3H)-one (10 g, 98%) as a white solid. LCMS (ESI+): m/z 248 (M+H)$^+$, RT: 1.90 min $^1$H NMR (D$_2$O): δ 8.55-8.54 (d, J=2.8 Hz, 1H), 7.80-7.77 (dd, J=3.2 Hz, J=2.8 Hz, 1H), 7.68-7.60 (m, 2H), 4.95-4.89 (m, 1H), 3.61-3.57 (m, 1H), 3.46-3.43 (d, J=12.4 Hz, 1H), 3.37-3.31 (t, 1H), 3.04-2.97 (m, 1H), 2.24-2.14 (m, 3H), 1.94-1.87 (m, 1H).

Preparation #32: (R)-6-Fluoro-3-(piperidin-3-yl)quinazolin-4(3H)-one hydrochloride

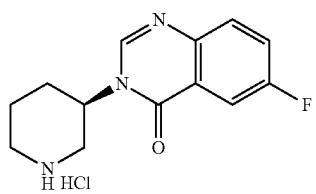 [SMILES: O=c1c2cc(F)ccc2ncn1[C@@H]1CCCNC1 ; Cl]

Step A: (R)-tert-Butyl 3-(6-fluoro-4-oxoquinazolin-3(4H)-yl)piperidine-1-carboxylate

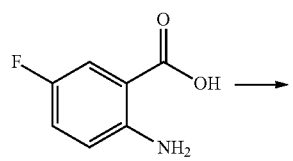

The reaction solution of 2-amino-5-fluorobenzoic acid (7.5 g, 48.4 mmol), 3-(R)-amino-piperidine-1-carboxylic acid tert-butyl ester (9.68 g, 48.4 mmol) and triethyl orthoformate (7.2 g, 48.4 mmol) in THF (20 mL) was heated to about 110° C. in a sealed tube overnight. After cooling to rt, the mixture was diluted with water. The aqueous layer was extracted with EtOAc. The combined organic phase was washed with brine, dried over anhydrous Na$_2$SO$_4$ and concentrated under reduced pressure to give a residue, which was purified by column chromatography on silica gel (eluting with 10:1 petroleum ether: EtOAc) to give (R)-tert-butyl 3-(6-fluoro-4-oxoquinazolin-3(4H)-yl)piperidine-1-carboxylate (6.25 g, 37%) as a solid. $^1$H NMR (CDCl$_3$): δ 8.08 (s, 1H), 7.97-7.95 (m, 1H), 7.76-7.72 (m, 1H), 7.53-7.48 (m, 1H), 4.74 (br, 1H), 4.24-4.12 (br, 2H), 3.24-3.19 (t, 1H), 2.89 (br, 1H), 2.14-2.10 (m, 2H), 2.04-2.01 (m, 1H), 1.91-1.71 (m, 1H), 1.49 (s, 9H).

Step B: (R)-6-Fluoro-3-(piperidin-3-yl)quinazolin-4(3H)-one hydrochloride

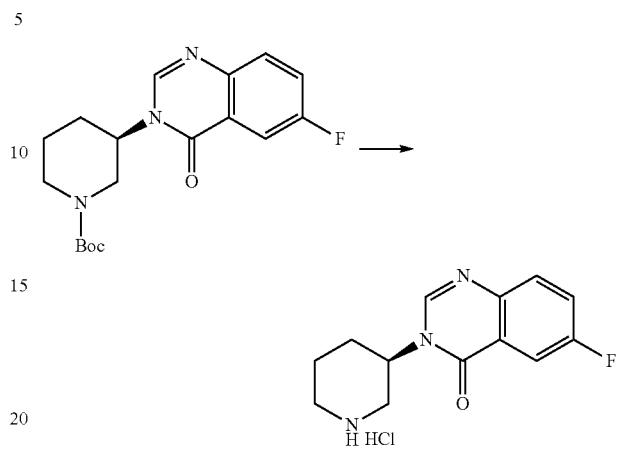

A solution of (R)-tert-butyl 3-(6-fluoro-4-oxoquinazolin-3(4H)-yl)piperidine-1-carboxylate (12.5 g, 36 mmol) in 1M HCl/MeOH (150 mL) was stirred at about rt about for about 2.5 h. The mixture was filtered and the solid was washed with EtOAc and dried to give (R)-6-fluoro-3-(piperidin-3-yl)quinazolin-4(3H)-one hydrochloride (10 g, 98%) as a solid. LC/MS (ESI+): m/z 248 (M+H)$^+$, RT: 1.90 min $^1$H NMR (D$_2$O): δ 8.55-8.54 (d, J=2.8 Hz, 1H), 7.80-7.77 (dd, J=3.2 Hz, J=2.8 Hz, 1H), 7.68-7.60 (m, 2H), 4.95-4.89 (m, 1H), 3.61-3.57 (m, 1H), 3.46-3.43 (d, J=12.4 Hz, 1H), 3.37-3.31 (t, 1H), 3.04-2.97 (m, 1H), 2.24-2.14 (m, 3H), 1.94-1.87 (m, 1H).

Preparation #33: 7-Cyclopropyl-5-fluoro-3-(piperidin-3-yl)quinazolin-4(3H)-one hydrochloride

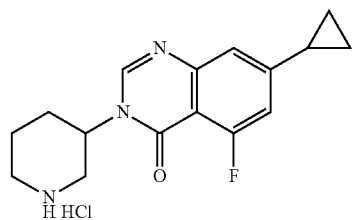 [SMILES: O=c1c2c(F)cc(C3CC3)cc2ncn1C1CCCNC1 ; Cl]

Step A: tert-Butyl 3-(7-bromo-5-fluoro-4-oxoquinazolin-3(4H)-yl)piperidine-1-carboxylate

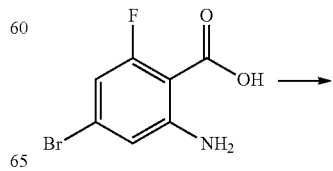

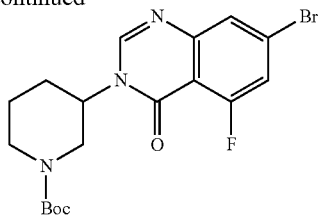

To a solution of 2-amino-4-bromo-6-fluorobenzoic acid (7 g, 0.03 mol, prepared according to WO 2011075699) and 3-amino-piperidine-1-carboxylic acid tert-butyl ester (6.6 g, 0.033 mol) in THF (50 mL) was added triethyl orthoformate (6.6 g, 0.044 mol). The reaction mixture was heated at about 110° C. in a sealed tube overnight. After cooling to about rt, the mixture was diluted with water. The aqueous was extracted with EtOAc. The combined organic phase was washed with brine, dried over anhydrous $Na_2SO_4$ and concentrated under reduced pressure to give a residue, which was purified by column chromatography on silica gel (eluting with 50:1 petroleum ether: EtOAc) to give tert-butyl 3-(7-bromo-5-fluoro-4-oxoquinazolin-3(4H)-yl)piperidine-1-carboxylate (6.4 g, 50%) as a solid. $^1$H NMR (CDCl$_3$): δ 8.1 (s, 1H), 7.54-7.52 (dd, J=2.4 Hz, 1H), 7.35-7.32 (dd, J=2.8 Hz, 1H), 4.7 (br, 1H), 4.2-4.16 (br, 1H), 4.07-4.03 (br, 1H), 3.24-3.18 (t, 1H), 2.92-2.89 (br, 1H), 2.11-2.09 (br, 1H), 1.98-1.96 (br, 1H), 1.89-1.85 (br, 1H), 1.74-1.64 (br, 1H), 1.45 (s, 9H).

Step B: tert-Butyl 3-(7-cyclopropyl-5-fluoro-4-oxo-quinazolin-3(4H)-yl)piperidine-1-carboxylate

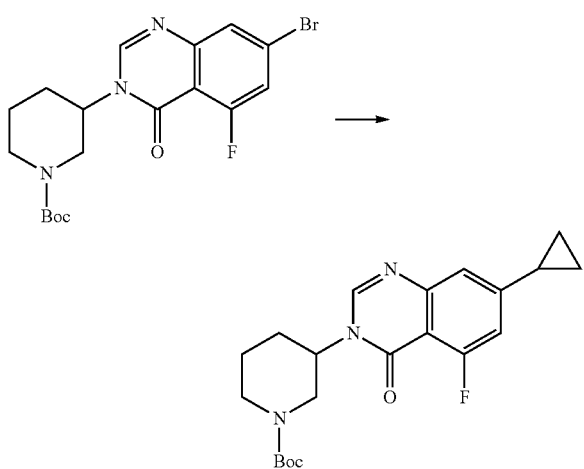

To a mixture of tert-butyl 3-(7-bromo-5-fluoro-4-oxoquinazolin-3(4H)-yl)piperidine-1-carboxylate (20 g, 0.047 mol), Pd(OAc)$_2$ (0.526 g, 0.002 mol), tricyclohexylphosphine (1.31 g, 0.005 mol), anhydrous K$_3$PO$_4$ (50 g, 0.236 mol) and water (40 mL) in toluene (200 mL) was added cyclopropylboronic acid (6.06 g, 0.07 mol). The reaction mixture was heated to reflux overnight under N$_2$. After cooling to rt, the mixture was diluted with water. The aqueous layer was extracted with EtOAc. The combined organic phase was washed with brine, dried over anhydrous Na$_2$SO$_4$ and concentrated under reduced pressure to give a residue, which was purified by column chromatography on silica gel (eluting with 50:1 petroleum ether: EtOAc) to give tert-butyl 3-(7-cyclopropyl-5-fluoro-4-oxoquinazolin-3 (4H)-yl)piperidine-1-carboxylate (15 g, 83%) as a solid. $^1$H NMR (CDCl$_3$): δ 7.96 (s, 1H), 7.07-7.04 (dd, J=2.4 Hz, 1H), 6.71-6.67 (dd, J=2.4 Hz, 1H), 4.68-4.65 (br, 1H), 4.16 (br, 1H), 4.06-4.02 (br, 1H), 3.37-3.33 (m, 1H), 3.08-3.02 (m, 1H), 2.82-2.76 (br, 1H), 2.06-2.01 (m, 1H), 1.90-1.69 (m, 2H), 1.64-1.60 (m, 1H), 1.40 (s, 9H), 1.20-1.06 (m, 2H), 0.712-0.608 (m, 2H).

Step C: 7-Cyclopropyl-5-fluoro-3-(piperidin-3-yl) quinazolin-4-(3H)-one hydrochloride

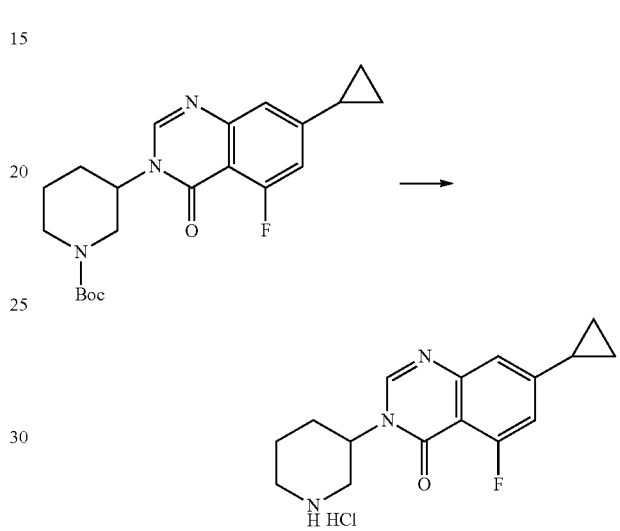

A solution of tert-butyl 3-(7-cyclopropyl-5-fluoro-4-oxo-quinazolin-3(4H)-yl)piperidine-1-carboxylate (15 g, 0.039 mmol) in 1M HCl/MeOH (150 mL) was stirred at about rt for about 2.5 h. The mixture was filtered, the solid was washed with EtOAc and dried to give 7-cyclopropyl-5-fluoro-3-(piperidin-3-yl)quinazolin-4(3H)-one hydrochloride (10 g, 91%) as a solid. LCMS (ESI+): m/z 288 (M+H)$^+$, 2.916 min $^1$H NMR (D$_2$O): δ 8.56 (s, 1H), 6.99-6.96 (m, 1H), 6.85-6.82 (dd, J=1.6 Hz, 1H), 4.87-4.83 (m, 1H), 3.54-3.51 (m, 1H), 3.41-3.38 (d, 1H), 3.24-3.18 (t, 1H), 2.96-2.89 (t, 1H), 2.84-2.81 (m, 1H), 2.13-2.09 (m, 3H), 1.89-1.82 (m, 1H), 0.96-094 (br, 2H), 0.61 (br, 2H).

Preparation #34: 2-(Benzyloxy)-5-(4,4,5,5-tetramethyl-1,3,2-dioxaborolan-2-yl)aniline

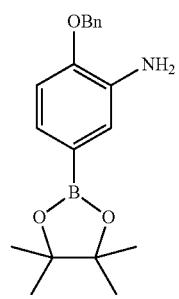 [SMILES: CC1(C)OB(c2ccc(OCc3ccccc3)c(N)c2)OC1(C)C]

Step A: 1-(Benzyloxy)-4-bromo-2-nitrobenzene

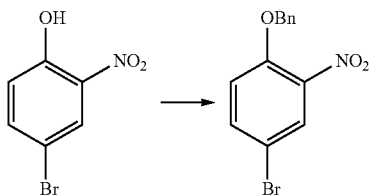 [SMILES: O=[N+]([O-])c1cc(Br)ccc1O ; O=[N+]([O-])c1cc(Br)ccc1OCc1ccccc1]

To a solution of 4-bromo-2-nitrophenol (5 g, 22.9 mmol) in acetone (100 mL) was added (bromomethyl)benzene (4.7 g, 27.5 mmol) and K$_2$CO$_3$ (6.3 g, 45.9 mmol). The mixture was refluxed overnight. After cooling to rt, the mixture was filtered. The filtrate was concentrated under reduced pressure to give a residue, which was washed with TBME to give 1-(benzyloxy)-4-bromo-2-nitrobenzene (6.3 g, 89%): $^1$H NMR (CDCl$_3$) δ 8.00 (d, J=2.2 Hz, 1H), 7.60 (dd, J=2.6, 8.8 Hz, 1H), 7.49-7.31 (m, 5H), 7.03 (d, J=8.8 Hz, 1H), 5.24 (s, 2H).

Step B: 2-(Benzyloxy)-5-bromoaniline

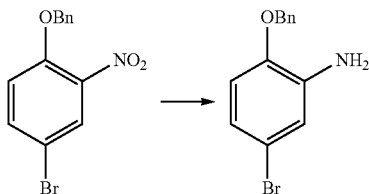 [SMILES: O=[N+]([O-])c1cc(Br)ccc1OCc1ccccc1 ; Nc1cc(Br)ccc1OCc1ccccc1]

To a solution of 1-(benzyloxy)-4-bromo-2-nitrobenzene (2 g, 6.5 mmol) in EtOH (80 mL) and water (20 mL) was added iron (1.8 g, 32.5 mmol) and NH$_4$Cl (1.7 g, 32.5 mmol). The resulting mixture was refluxed for 3 h. The mixture was filtered. The filtrate was diluted with water and extracted with EtOAc. The organic layer was concentrated to give 2-(benzyloxy)-5-bromoaniline (1.6 g, 89%): $^1$H NMR (CDCl$_3$) δ 7.51-7.30 (m, 5H), 6.86 (d, J=2.2 Hz, 1H), 6.83-6.76 (m, 1H), 6.74-6.66 (m, 1H), 5.07 (s, 2H), 3.91 (br, 2H)

Step C: 2-(Benzyloxy)-5-(4,4,5,5-tetramethyl-1,3,2-dioxaborolan-2-yl)aniline

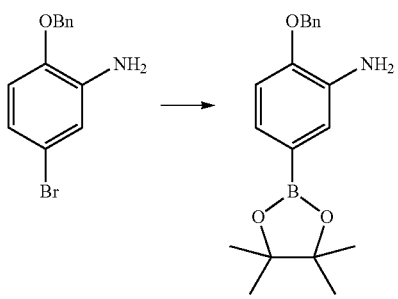 [SMILES: Nc1cc(Br)ccc1OCc1ccccc1 ; CC1(C)OB(c2ccc(OCc3ccccc3)c(N)c2)OC1(C)C]

To a solution of 2-(benzyloxy)-5-bromoaniline (2.0 g, 7.19 mmol) in DMSO (30 mL) was added 4,4,4',4',5,5,5',5'-octamethyl-2,2'-bi(1,3,2-dioxaborolane) (2.2 g, 8.6 mmol), Pd(dppf)Cl$_2$ (0.53 g, 0.72 mmol) and potassium acetate (2.1 g, 21.6 mmol). The mixture was stirred at 80° C. overnight under N$_2$. After cooling to rt, the mixture was diluted with water and extracted with EtOAc. The organic layer was concentrated and purified by column to give 2-(benzyloxy)-5-(4,4,5,5-tetramethyl-1,3,2-dioxaborolan-2-yl)aniline (1.5 g, 64%): $^1$H NMR (CDCl$_3$) δ 7.55-7.29 (m, 5H), 7.23-7.12 (m, 2H), 6.86 (d, J=7.9 Hz, 1H), 5.11 (s, 2H), 3.80 (br, 2H), 1.32 (s, 12H).

Preparation #35: 3-(Benzyloxy)-5-(4,4,5,5-tetramethyl-1,3,2-dioxaborolan-2-yl)aniline

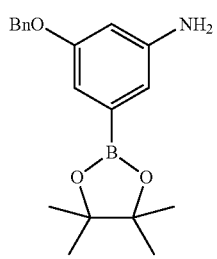 [SMILES: CC1(C)OB(c2cc(N)cc(OCc3ccccc3)c2)OC1(C)C]

Step A: 3-Bromo-5-nitrophenol

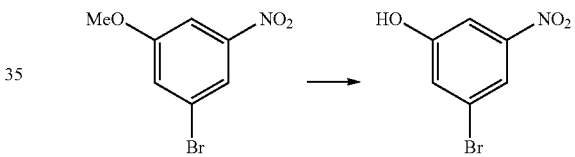

To a solution of 1-bromo-3-methoxy-5-nitrobenzene (19 g, 82 mmol) in DCM (800 mL) was added dropwise BBr$_3$ (27.9 mL, 295 mmol) in DCM (120 mL). The resulting mixture was heated to reflux overnight. After cooling in ice-water, the mixture was diluted by addition of water. Then the mixture was washed with brine. The organic phase was dried over Na$_2$SO$_4$, concentrated under reduced pressure to give a residue, which was purified by column chromatography on silica gel to give 3-bromo-5-nitrophenol (8 g, 44%) as a solid: $^1$H NMR (CDCl$_3$) δ 7.89 (s, 1H), 7.57 (s, 1H), 7.27 (s, 1H), 5.27 (s, 1H).

Step B: 1-(Benzyloxy)-3-bromo-5-nitrobenzene

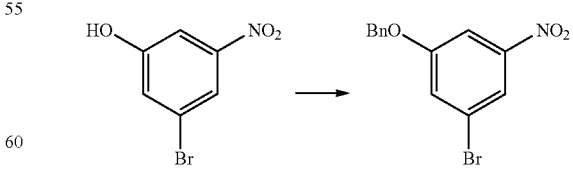

To a solution of 3-bromo-5-nitrophenol in acetone (50 mL) was added (bromomethyl)benzene (2.4 g, 13.8 mmol) and K$_2$CO$_3$ (3.2 g, 22.9 mmol). The resulting mixture was heated to reflux overnight. The mixture was filtered. The filtrate was concentrated under reduced pressure to give a residue, which was washed with TBME to give 1-(benzyloxy)-3-bromo-5-nitrobenzene (1.3 g, 37%) as a solid: $^1$H NMR (CDCl$_3$) δ 8.00 (s, 1H), 7.78-7.77 (m, 1H), 7.64-7.40 (m, 6H), 5.15 (s, 2H).

Step C: 3-(Benzyloxy)-5-bromoaniline

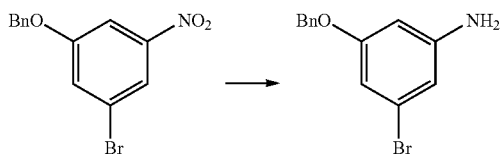 [SMILES: O=[N+]([O-])c1cc(Br)cc(OCc2ccccc2)c1 ; Nc1cc(Br)cc(OCc2ccccc2)c1]

To a solution of 1-(benzyloxy)-3-bromo-5-nitrobenzene (1.3 g, 4.2 mmol) in EtOH (30 mL) and water (7.5 mL) was added iron (1.2 g, 21.1 mmol) and NH$_4$Cl (1.1 g, 21.1 mmol). The mixture was heated to reflux overnight. The mixture was filtered. The filtrate was concentrated under reduced pressure to give a residue, which was diluted by addition of water and extracted by EtOAc. The organic layer was concentrated under reduced pressure to give 3-(benzyloxy)-5-bromoaniline (1 g, 85%): $^1$H NMR (CDCl$_3$) δ 7.33-7.31 (m, 5H), 6.48 (s, 1H), 6.39 (s, 1H), 6.14 (s, 1H), 4.92 (s, 2H), 3.63 (br, 2H).

Step D: 3-(Benzyloxy)-5-(4,4,5,5-tetramethyl-1,3,2-dioxaborolan-2-yl)aniline

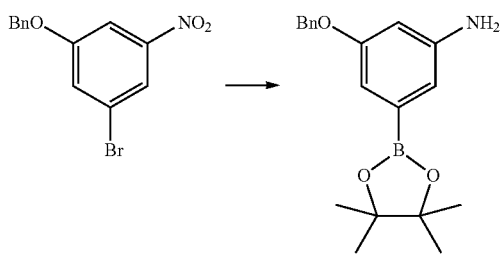 [SMILES: O=[N+]([O-])c1cc(Br)cc(OCc2ccccc2)c1 ; CC1(C)OB(c2cc(N)cc(OCc3ccccc3)c2)OC1(C)C]

To a solution of 3-(benzyloxy)-5-bromoaniline (1 g, 3.6 mmol) and 4,4,4',4',5,5,5',5'-octamethyl-2,2'-bi(1,3,2-dioxaborolane) (1.1 g, 4.3 mmol) in DMSO (1 mL) was added Pd(dppf)Cl$_2$ (0.26 g, 0.36 mmol) and potassium acetate (1.1 g, 10.8 mmol). The mixture was heated to about 80° C. overnight under N$_2$. After cooling to rt, the mixture was diluted by addition of water and extracted by EtOAc. The organic layer was concentrated under reduced pressure to give a residue, which was purified by column chromatography on silica gel to give 3-(benzyloxy)-5-(4,4,5,5-tetramethyl-1,3,2-dioxaborolan-2-yl)aniline (1 g, 86%) as a solid: $^1$H NMR (CDCl$_3$) δ 7.43-7.31 (m, 5H), 6.87 (s, 1H), 6.77 (s, 1H), 6.43-6.42 (m, 1H), 5.05 (s, 2H), 3.64 (br, 2H), 1.34 (s, 12H).

Preparation #36:
4-(Benzyloxy)-1-bromo-2-nitrobenzene

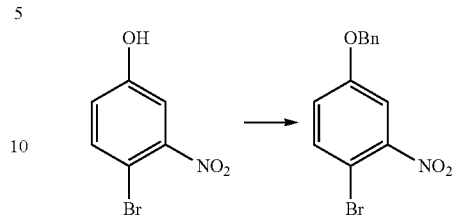

To a solution of 4-bromo-3-nitrophenol (2 g, 9.17 mmol, Preparation #S.1) in acetone (50 mL) was added BnBr (1.9 g, 11.0 mmol) and K$_2$CO$_3$ (2.5 g, 18.4 mmol). The mixture was filtered. The filtrate was concentrated under reduced pressure to give a residue, which was washed with TBME to give 4-(benzyloxy)-1-bromo-2-nitrobenzene (2.6 g, 92%): $^1$H NMR (CDCl$_3$) δ 7.62 (d, J=8.8 Hz, 1H), 7.48 (d, J=2.6 Hz, 1H), 7.45-7.35 (m, 5H), 7.07 (dd, J=2.9, 9.0 Hz, 1H), 5.12 (s, 2H).

Preparation #37:
4-(Benzyloxy)-1-bromo-2-nitrobenzene

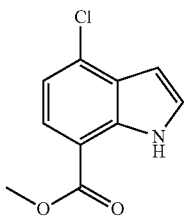

Step A: Methyl 2-(2-methoxy-2-oxoethyl)-1-(4-methoxybenzyl)-1H-pyrrole-3-carboxylate

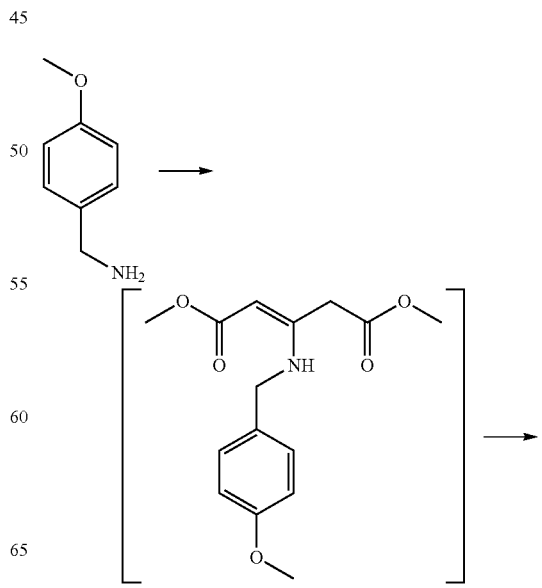

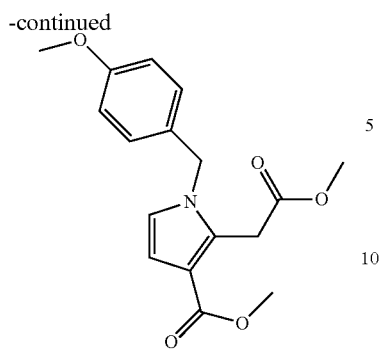

A flask was charged with dimethyl 3-oxopentanedioate (77.0 g, 442 mmol), (4-methoxyphenyl)methanamine (60.1 mL, 460 mmol) and anhydrous NaOAc (72.5 g, 884 mmol) in dioxane (100 mL). The reaction mixture was stirred at about rt for about 30 min, then heated to about 50° C. and stirred for about 16 h. The reaction mixture was cooled to rt and dioxane (250 mL) was added. 2-chloroacetaldehyde (51.9 mL, 442 mmol) was added via a dropping funnel. After about 7 h additional 2-chloroacetaldehyde (17.4 g, 221 mmol) was added and stirred for about 16 h. Additional 2-chloroacetaldehyde (17.4 g, 221 mmol) was added and stirred for about 5 h, more 2-chloroacetaldehyde was added (25.9 mL, 221 mmol), the final portion of 2-chloroacetaldehyde (25.9 mL, 221 mmol) was added after about 2 h and left to stir for about 72 h. NaOAc (36.3 g, 442 mmol) was added and the solution and stirred for about 16 h. The reaction mixture was cooled under an ice bath and ice-water added to it (about 500 mL). The mixture was extracted with DCM (850 mL). The organic layer was washed with water (4×700 mL). The organic layer was dried over MgSO$_4$, filtered and concentrated to give a viscous oil. The crude material was purified via flash chromatography (using heptane for 3 column volumes, 0-25% EtOAc/heptane over 4 column volumes, 20-35% over 4 column volumes). The pure fractions were combined and concentrated and minimal Et$_2$O added to precipitate out a first batch of product which was collected via filtration. The filtrate was combined with the impure fractions, concentrated under vacuum and recrystallized from isopropanol to give a solid which was collected via filtration and combined with the first batch of product. The material was dried in a vacuum oven at about 70° C. for about 16 h to give methyl 2-(2-methoxy-2-oxoethyl)-1-(4-methoxybenzyl)-1H-pyrrole-3-carboxylate (28.5 g, 20%): LC/MS (Table 1, Method as) R$_t$=2.20 min; MS m/z: 318 (M+H)$^+$.

Step B: Methyl 2-(1-amino-3-methoxy-3-oxoprop-1-en-2-yl)-1-(4-methoxybenzyl)-1H-pyrrole-3-carboxylate

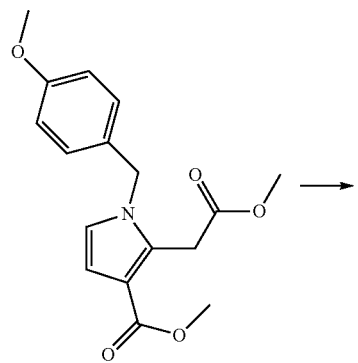

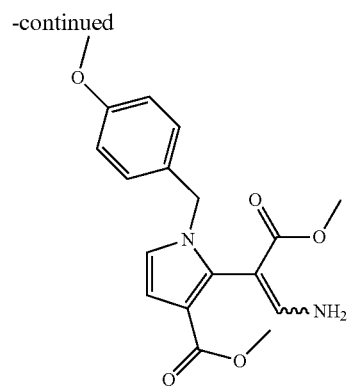

A flask was charged with NaH (23.3 g, 582 mmol) and THF (500 mL). The mixture was cooled to about 0° C. and methyl 2-(2-methoxy-2-oxoethyl)-1-(4-methoxybenzyl)-1H-pyrrole-3-carboxylate (28 g, 88 mmol) was added portion wise. The internal temperature measured below 10° C. during the addition. The suspension was stirred at about 0° C. for about 1 h. Methyl formate (7.62 mL, 124 mmol) was added. The reaction mixture was allowed to warm to rt and was stirred for about 16 h. Additional methyl formate (1.09 mL, 17.6 mmol) was added and the mixture stirred at rt for about 4 to 5 h, at which point all the starting material was consumed. The reaction was cooled on ice and quenched by the addition of MeOH (5 mL), and water was added carefully until effervescence stopped. The mixture was then acidified to pH of about 1 with aqueous 6N HCl, while keeping the flask on an ice bath. The reaction mixture was diluted with EtOAc (100 mL) and water (100 mL). The aqueous layer was separated and extracted with EtOAc (3×50 mL). The combined organic layers were then dried over MgSO$_4$ and filtered. The solvent was evaporated to yield an oil consisting of two layers. The thinner top layer was clear and was separated using a pipette and discarded. The remaining bottom layer was the crude intermediate, methyl 2-(1-hydroxy-3-methoxy-3-oxoprop-1-en-2-yl)-1-(4-methoxybenzyl)-1H-pyrrole-3-carboxylate. A flask was charged with this crude methyl 2-(1-hydroxy-3-methoxy-3-oxoprop-1-en-2-yl)-1-(4-methoxybenzyl)-1H-pyrrole-3-carboxylate (30 g, 87 mmol) and MeOH (300 mL). Ammonium acetate (33.5 g, 434 mmol) was added and the reaction mixture was refluxed for about 4 h and stirred at about 60° C. for about 72 h. The reaction mixture was concentrated under vacuum and diluted with water (200 mL) and EtOAc (200 mL). Part of the product precipitated out and was collected by filtration. The organic layer was separated. The aqueous layer was extracted again with EtOAc (2×80 mL). The combined organic layers were dried over MgSO$_4$, filtered, and concentrated. The residue was suspended in Et$_2$O (200 mL) and stirred for about 10 min and filtered to collect the product. This batch was combined with the previous precipitate and dried in a vacuum oven at about 70° C. for about 4 h to give methyl 2-(1-amino-3-methoxy-3-oxoprop-1-en-2-yl)-1-(4-methoxybenzyl)-1H-pyrrole-3-carboxylate (25.7 g, 82%): LC/MS (Table 1, Method as) R$_t$=1.88 min; MS m/z: 345 (M+H)$^+$.

Step C: Methyl 1-(4-methoxybenzyl)-4-oxo-4,5-dihydro-1H-pyrrolo[3,2-c]pyridine-7-carboxylate

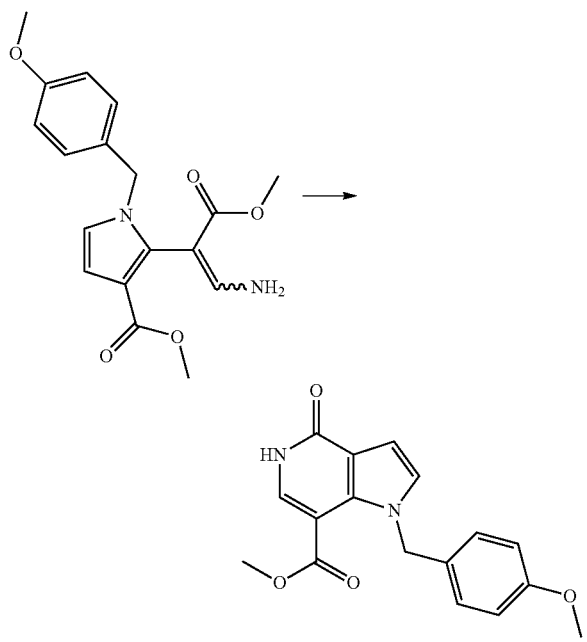

A flask was charged with methyl 2-(1-amino-3-methoxy-3-oxoprop-1-en-2-yl)-1-(4-methoxybenzyl)-1H-pyrrole-3-carboxylate (24.6 g, 71.4 mmol) and t-BuONa (6.87 g, 71.4 mmol) in DMA (100 mL). The solution was heated at about 150° C. for about 10 min, and cooled to rt. The solution was then poured onto ice-water (250 mL) and diluted with EtOAc (200 mL). The mixture was stirred at rt for about 45 min. The precipitate that formed was filtered and washed with water, then dried in a vacuum oven at about 70° C. for about 16 h to yield methyl 1-(4-methoxybenzyl)-4-oxo-4,5-dihydro-1H-pyrrolo[3,2-c]pyridine-7-carboxylate (18.9 g, 85%): LC/MS (Table 1, Method as) $R_f$=1.76 min; MS m/z: 313 (M+H)$^+$.

Step D: Methyl 4-chloro-1H-pyrrolo[3,2-c]pyridine-7-carboxylate

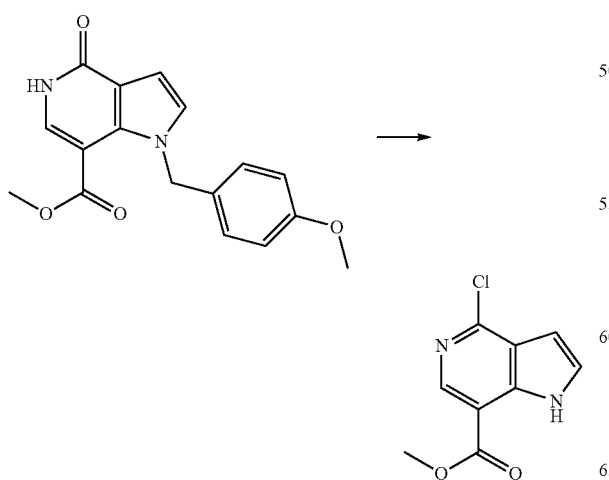

A mixture of methyl 1-(4-methoxybenzyl)-4-oxo-4,5-dihydro-1H-pyrrolo[3,2-c]pyridine-7-carboxylate (24 g, 76 mmol) in phenyl phosphorodichloridate (30.8 mL, 206 mmol) was heated at about 150° C. for about 30 min LCMS showed complete conversion to mixture of ester and acid. The reaction mixture was cooled to about 0° C. and 50% aqueous NaOH was added slowly until pH of about 7. The reaction mixture was extracted with DCM (3×100 mL). The organic layers were combined and concentrated under reduced pressure. The residue was suspended in Et$_2$O (100 mL), stirred at about 30° C. for about 1 h, cooled to rt and filtered. The filtrate was concentrated to give crude methyl 4-chloro-1-(4-methoxybenzyl)-1H-pyrrolo[3,2-c]pyridine-7-carboxylate (22.5 g, 75%) as a black oil. A mixture of this crude methyl 4-chloro-1-(4-methoxybenzyl)-1H-pyrrolo[3,2-c]pyridine-7-carboxylate (21.76 g, 65.8 mmol) and triflic anhydride (7.50 mL, 44.4 mmol) in TFA (50 mL) was stirred at about 50° C. for about 16 h. The reaction mixture was cooled to rt and added to ice cold NaHCO$_3$ solution. Aqueous NaOH was slowly added to adjust the pH to about 9. The solid was filtered and sonicated in Et$_2$O. The precipitate was filtered and the filtrate was concentrated to give methyl 4-chloro-1H-pyrrolo[3,2-c]pyridine-7-carboxylate (9.4 g, 68%): LCMS (Table 1, Method a)=1.83 min; MS m/z: 211 (M+H)$^+$.

Preparation #38: Methyl 4-(1-(tert-butoxycarbonyl)pyrrolidin-3-yl)-2-methyl-1H-indole-7-carboxylate

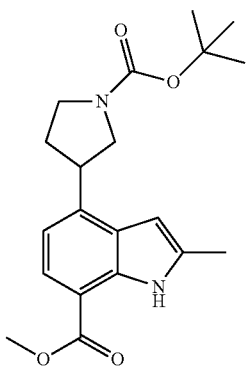 [SMILES: COC(=O)c1ccc(C2CCN(C(=O)OC(C)(C)C)C2)c2cc(C)[nH]c12]

Step A: 1-tert-Butyl 7-methyl 4-(1-(tert-butoxycarbonyl)pyrrolidin-3-yl)-2-methyl-1H-indole-1,7-dicarboxylate

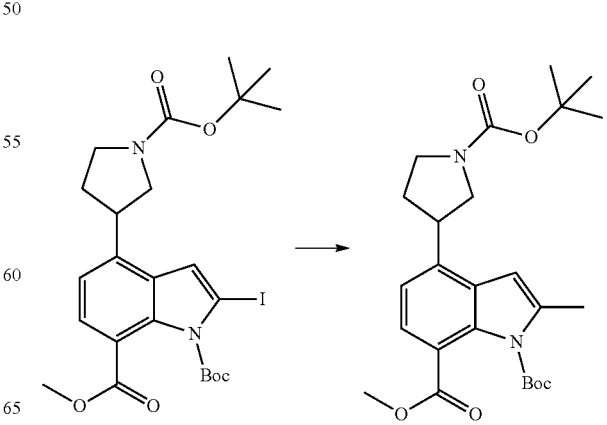

To a solution of 1-tert-butyl 7-methyl 4-(1-(tert-butoxycarbonyl)pyrrolidin-3-yl)-2-iodo-1H-indole-1,7-dicarboxylate (2.0 g, 3.5 mmol, Preparation #Y.1) in THF (35 mL) was added Zn(Me)$_2$ (1 M in hexane, 21.04 mL, 21.04 mmol). The mixture was degassed using nitrogen and Pd(dppf)Cl$_2$ (0.257 g, 0.351 mmol) was added in one portion and stirred at rt for about 19 h. The reaction was warmed to about 45° C. and stirred for about 22 h. The reaction mixture was carefully quenched by the addition of saturated aqueous NaHCO$_3$ (50 mL) and diluted with EtOAc (50 mL) and brine (20 mL). The layers were separated and the aqueous phase was extracted with EtOAc (2×50 mL). The combined organic extracts were washed with brine, dried over MgSO$_4$, filtered, concentrated under reduced pressure and purified by column chromatography on silica gel (0-50% EtOAc/heptane) to provide 1-tert-butyl 7-methyl 4-(1-(tert-butoxycarbonyl)pyrrolidin-3-yl)-2-methyl-1H-indole-1,7-dicarboxylate (1.45 g, 79%): LCMS (Table 1, Method ba) R$_t$=3.02 min; MS m/z: 476 (M+H)$^+$.

Step B: Methyl 4-(1-(tert-butoxycarbonyl)pyrrolidin-3-yl)-2-methyl-1H-indole-7-carboxylate

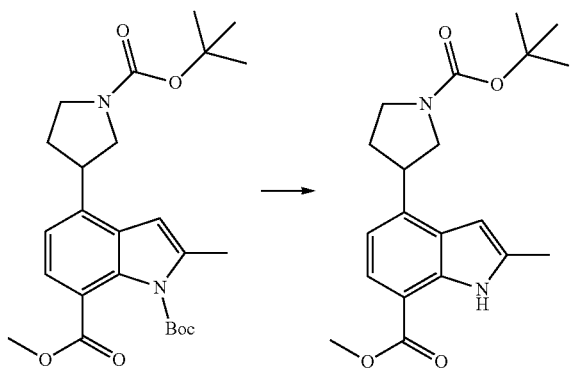 [SMILES: COC(=O)c1ccc(C2CCN(C(=O)OC(C)(C)C)C2)c2cc(C)n(C(=O)OC(C)(C)C)c12 ; COC(=O)c1ccc(C2CCN(C(=O)OC(C)(C)C)C2)c2cc(C)[nH]c12]

A solution of 1-tert-butyl 7-methyl 4-(1-(tert-butoxycarbonyl)pyrrolidin-3-yl)-2-methyl-1H-indole-1,7-dicarboxylate (1.40 g, 3.05 mmol) in MeOH (7 mL) was added to a microwave reaction vial and the solution was heated to about 120° C. for about 30 min. The reaction mixture was adsorbed onto silica gel and purified using silica gel chromatography (0-50% EtOAc/heptane) to give methyl 4-(1-(tert-butoxycarbonyl)pyrrolidin-3-yl)-2-methyl-1H-indole-7-carboxylate (1 g, 86%): LCMS (Table 1, Method as) R$_t$=2.58 min; MS m/z: 359 (M+NH$_4$)$^+$.

Preparation #39: Methyl 4-(1-(tert-butoxycarbonyl)-1,2,5,6-tetrahydropyridin-3-yl)-1-tosyl-1H-indole-7-carboxylate

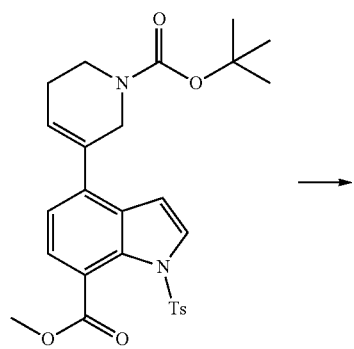

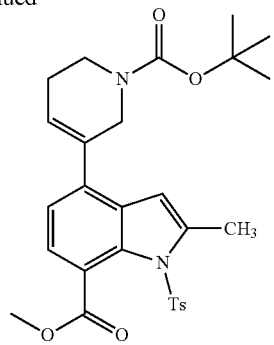

A flask was charged with methyl 4-(1-(tert-butoxycarbonyl)-1,2,5,6-tetrahydropyridin-3-yl)-1-tosyl-1H-indole-7-carboxylate (2.00 g, 3.92 mmol, prepared using A from Preparation #1, step B with tert-butyl 3-(4,4,5,5-tetramethyl-1,3,2-dioxaborolan-2-yl)-5,6-dihydropyridine-1(2H)-carboxylate) in THF (39.2 mL). The solution was cooled to about −71° C. LDA (1M solution in hexanes/THF, 5.88 mL, 5.88 mmol) was added drop wise over about 5 min while maintaining the temperature below −65° C. The solution was stirred at about −72° C. for about 45 min CH$_3$I (0.367 mL, 5.88 mmol) was added. The mixture was stirred at about −70° C. for a further 2.5 hours, and then quenched with a saturated aqueous Na$_2$CO$_3$ solution (150 mL). The mixture was extracted with EtOAc (2×200 mL) and DCM (1×100 mL). The combined organic layers were dried over Na$_2$SO$_4$, filtered, concentrated under reduced pressure and purified by column chromatography on silica gel (25-75% EtOAc/heptane) to provide methyl 4-(1-(tert-butoxycarbonyl)-1,2,5,6-tetrahydropyridin-3-yl)-1-tosyl-1H-indole-7-carboxylate (1.67 g, 57%, 70% purity): LCMS (Table 1, Method as) R$_t$=2.88 min; MS m/z: 542 (M+NH$_4$)$^+$.

Preparation #40: tert-butyl 3-((7-carbamoyl-2-iodo-1H-indol-4-yl)(methyl)amino) azetidine-1-carboxylate

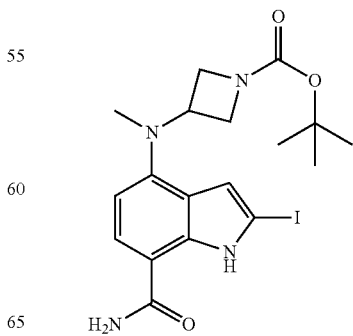

Step A: Methyl 4-((1-(tert-butoxycarbonyl)azetidin-3-yl)(methyl)amino)-2-iodo-1-tosyl-1H-indole-7-carboxylate

Step B: 4-((1-(tert-Butoxycarbonyl)azetidin-3-yl)(methyl)amino)-2-iodo-1H-indole-7-carboxylic acid

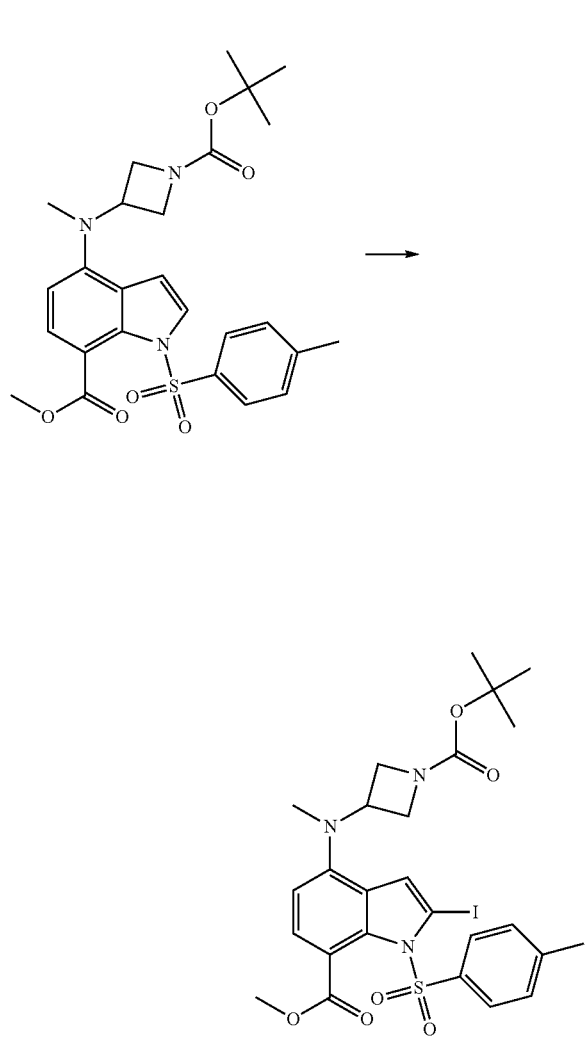

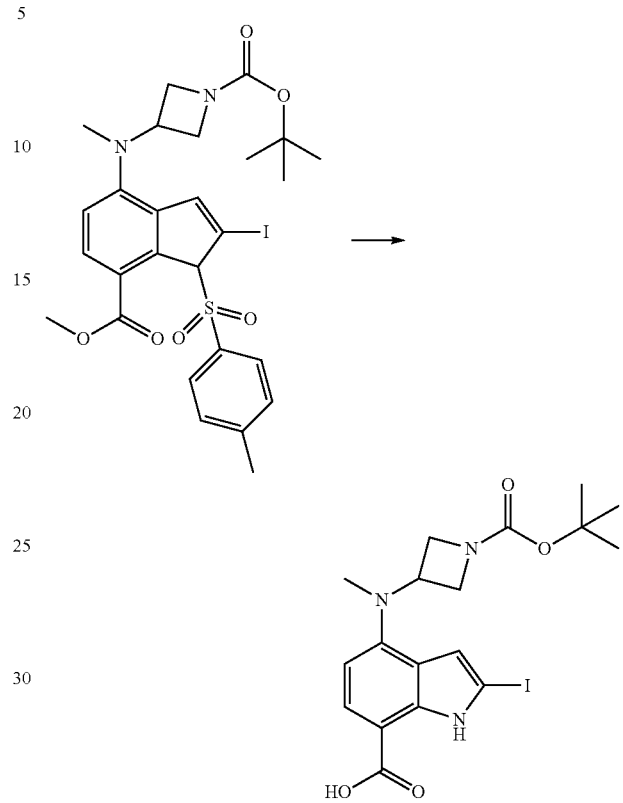

To a solution of methyl 4-((1-(tert-butoxycarbonyl)azetidin-3-yl)(methyl)amino)-1-tosyl-1H-indole-7-carboxylate (4.00 g, 7.79 mmol, prepared using T from Preparation #1, step C with tert-butyl-3-aminoazetidine-1-carboxylate and J with CH₃I) in THF (60 mL) at about −78° C. was added slowly LDA (2M solution in THF, 5.84 mL, 11.7 mmol). The reaction was stirred at about −78° C. for about 1 h and a solution of I₂ (2.97 g, 11.7 mmol) in THF (10 mL) was added slowly and the reaction stirred at about −78° C. for about 4 h. The cooling bath was removed to warm the reaction to rt and the reaction was quenched by the addition of saturated aqueous Na₂S₂O₃ (120 mL), extracted with additional EtOAc (2×150 mL) and washed with brine (2×150 mL). The combined organics were dried with anhydrous Na₂SO₄, filtered and concentrated under reduced pressure to give the crude product, methyl 4-((1-(tert-butoxycarbonyl)azetidin-3-yl)(methyl)amino)-2-iodo-1-tosyl-1,1-indole-7-carboxylate (4.1 g, 80%): LC/MS (Table 1, Method aa) R$_t$=1.87 min; MS m/z: 640 (M+H)⁺.

To a solution of methyl 4-((1-(tert-butoxycarbonyl)azetidin-3-yl)(methyl)amino)-2-iodo-1-tosyl-1H-indole-7-carboxylate (15.5 g, 24.2 mmol) in MeOH (75 mL):THF (75 mL):water (30 mL) was added KOH (9.52 g, 170 mmol). The mixture was stirred at about 60° C. for about 16 h, cooled, and acidified with aqueous 2N HCl. It was extracted with EtOAc (2×350 mL) and washed with brine (2×300 mL). The combined organics were dried with anhydrous Na₂SO₄, filtered and concentrated under reduced pressure to give the crude product 4-((1-(tert-butoxycarbonyl)azetidin-3-yl)(methyl)amino)-2-iodo-1H-indole-7-carboxylic acid (11.4 g, 99%): LC/MS (Table 1, Method aa) R$_t$=1.86 min; MS m/z: 416 (M+H-tBu)⁺.

Step C: tert-Butyl 34(7-carbamoyl-2-iodo-1H-indol-4-yl)(methyl)amino)azetidine-1-carboxylate

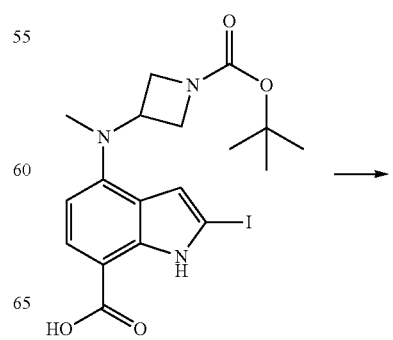

-continued

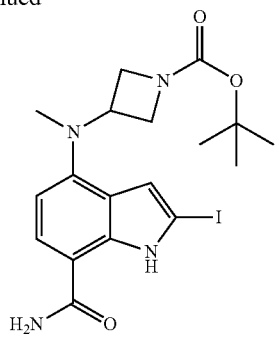

4-((1-(tert-Butoxycarbonyl)azetidin-3-yl)(methyl)amino)-2-iodo-1H-indole-7-carboxylic acid (13.7 g, 29.1 mmol), HOBt (8.90 g, 58.1 mmol) and EDC (11.2 g, 58.1 mmol) were dissolved in DMF (260 mL) and DIEA (25.4 mL, 145 mmol) was added. The mixture was stirred at rt for about 10 min and NH$_4$Cl (12.4 g, 233 mmol) was added. The mixture was stirred at rt for about 16 h and saturated aqueous NH$_4$Cl (1 L) was added. The solid was collected by filtration, washed with water, and dried to give the crude product tert-butyl 3-((7-carbamoyl-2-iodo-1H-indol-4-yl)(methyl)amino)azetidine-1-carboxylate (13.4 g, 97%): LC/MS (Table 1, Method aa) R$_t$=1.81 min; MS m/z: 471 (M+H)$^+$.

Preparation #41: 4-(Azetidin-3-yl(methyl)amino)-2-(tetrahydrofuran-3-yl)-1H-indole-7-carboxamide

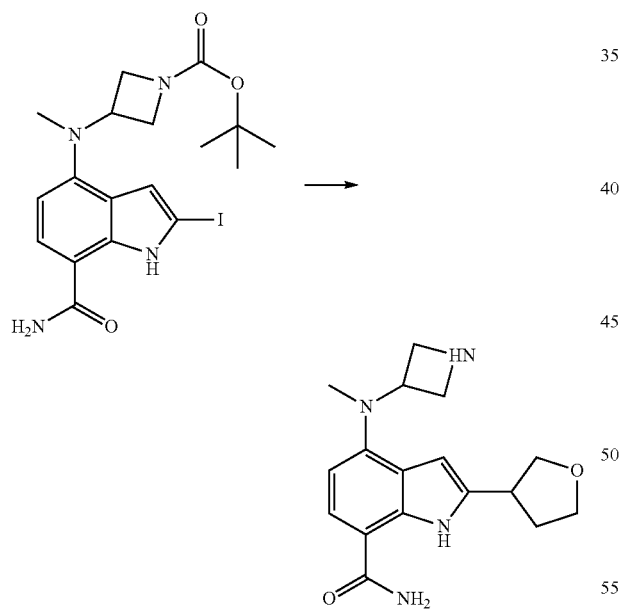

A reaction vial was charged with tert-butyl 3-((7-carbamoyl-2-iodo-1H-indol-4-yl)(methyl)amino)azetidine-1-carboxylate (0.050 g, 0.11 mmol, Preparation #40), (Z)-but-2-ene-1,4-diol (0.014 g, 0.16 mmol), NaHCO$_3$ (10.7 mg, 0.128 mmol) and PdCl$_2$ (1.885 mg, 10.63 µmol) in NMP (1.2 mL). The mixture was purged with nitrogen and heated at about 130° C. for about 1 h. It was extracted with EtOAc (2×20 mL) and washed with brine (2×20 mL). The combined organics were dried over anhydrous Na$_2$SO$_4$, filtered, concentrated under reduced pressure and purified by Prep TLC (EtOAc) to give crude tert-butyl 3-((7-carbamoyl-2-(2,3-dihydrofuran-3-yl)-1H-indol-4-yl)(methyl)amino)azetidine-1-carboxylate (0.028 g, 39%). A mixture of tert-butyl 3-((7-carbamoyl-2-(2,3-dihydrofuran-3-yl)-1H-indol-4-yl)(methyl)amino)azetidine-1-carboxylate (0.055 g, 0.081 mmol) in DCM (1.5 mL) was stirred at about 0° C. in an ice bath. Triethylsilane (0.014 g, 0.12 mmol) was added and then BF$_3$.OEt$_2$ (0.015 mL, 0.122 mmol) was added drop wise. The mixture was stirred at about 0° C. for about 1 h and quenched with a saturated aqueous solution of Na$_2$CO$_3$ to a pH of about 8 then filtered. The filtrate was purified by Prep HPLC (Table 1, method bc) to give 4-(azetidin-3-yl(methyl)amino)-2-(tetrahydrofuran-3-yl)-1H-indole-7-carboxamide (0.008 mg, 28%): LC/MS (Table 1, Method av) R$_t$=1.03 min; MS m/z: 315 (M+H)$^+$.

Preparation #42: Methyl 4-((1-(tert-butoxycarbonyl)azetidin-3-yl)methyl)amino)-2-(3-hydroxyoxetan-3-yl)-1-tosyl-1,1-indole-7-carboxylate

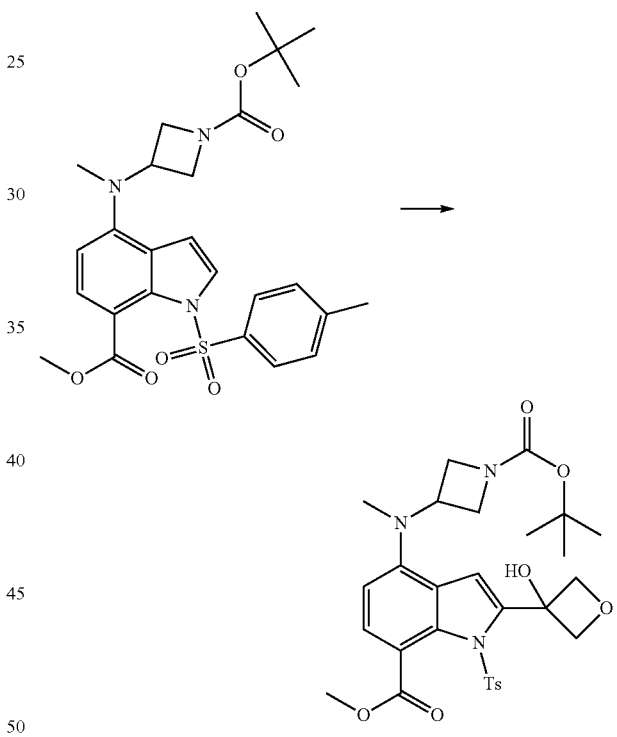

To a cold solution of methyl 4-((1-(tert-butoxycarbonyl)azetidin-3-yl)(methyl)amino)-1-tosyl-1H-indole-7-carboxylate (0.80 g, 1.56 mmol, prepared using T from Preparation #1, step C with tert-butyl-3-aminoazetidine-1-carboxylate and J with CH$_3$I) in THF (12 mL) at about −78° C. was added slowly LDA (2M solution in THF, 1.168 mL, 2.336 mmol). The reaction was stirred at about −78° C. for about 1 h, then a solution of oxetan-3-one (0.168 g, 2.34 mmol) in THF (1 mL) was added slowly and the reaction mixture was stirred at about −78° C. for about 4 h. The cooling bath was removed and the reaction was quenched with saturated aqueous NH$_4$Cl solution. The mixture was extracted with EtOAc (2×50 mL) and washed with brine (2×5 0 mL). The combined organics were dried over anhydrous Na$_2$SO$_4$, filtered, concentrated under reduced pressure and purified by Prep-TLC (1:1 EtOAc/pet. Et$_2$O) to give methyl 4-((1-(tert-butoxycarbonyl)azetidin-3-yl)(methyl)amino)-2-(3-hydroxyoxetan-3-yl)-1-tosyl-1H-indole-7-carboxylate (0.55 g, 59%): LC/MS (Table 1, Method av) R, =1.67 min; MS m/z: 586 (M+H)+.

Preparation #43: tert-Butyl 2-(7-cyano-1-tosyl-1H-indol-4-yl)morpholine-4-carboxylate

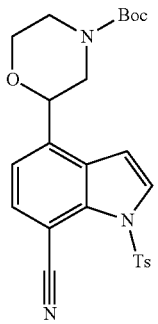 [SMILES: Cc1ccc(S(=O)(=O)n2ccc3c(C4CN(C(=O)OC(C)(C)C)CCO4)ccc(C#N)c32)cc1]

Step A: 4-Bromo-1-tosyl-1H-indole-7-carbonitrile

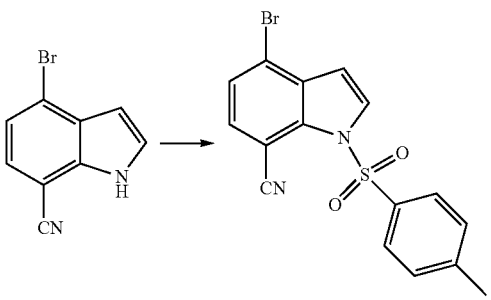 [SMILES: N#Cc1ccc(Br)c2cc[nH]c12 ; Cc1ccc(S(=O)(=O)n2ccc3c(Br)ccc(C#N)c32)cc1]

A round bottom flask was charged with 4-bromo-1H-indole-7-carbonitrile (4.50 g, 20.4 mmol) and THF (75 mL). The solution was cooled to about 0° C. followed by the addition of NaH (60% dispersion in mineral oil, 1.22 g, 30.5 mmol). The solution was stirred at about 0° C. for about 40 min followed by the addition of 4-methylbenzene-1-sulfonyl chloride (4.66 g, 24.4 mmol). The ice bath was removed and the mixture was stirred at rt for about 15 h. The mixture was poured onto ice water (~150 mL) and the product was extracted with EtOAc (4×75 mL). The combined extracts were washed with water (75 mL), dried over MgSO4, filtered and concentrated under reduced pressure to give 4-bromo-1-tosyl-1H-indole-7-carbonitrile (5.74 g, 75%): 1H NMR (400 MHz, DMSO-d6) δ 8.21 (d, J=3.9 Hz, 1H), 7.97-7.89 (m, 2H), 7.80-7.64 (m, 2H), 7.56-7.42 (m, 2H), 7.00 (d, J=3.8 Hz, 1H), 2.38 (s, 3H).

Step B: 1-Tosyl-4-vinyl-1H-indole-7-carbonitrile

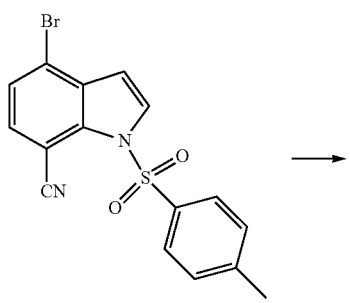

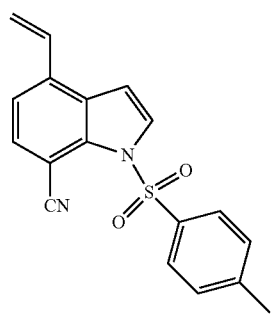

A round bottom flask was charged with 4-bromo-1-tosyl-1H-indole-7-carbonitrile (8.54 g, 22.8 mmol), Na2CO3 (7.24 g, 68.3 mmol) and PdCl2(dppf) (1.665 g, 2.276 mmol) followed by the addition of THF (70.2 mL): MeOH (10.03 mL): water (10.03 mL). The reaction mixture was purged with N2 for about 15 min, 4,4,5,5-tetramethyl-2-vinyl-1,3,2-dioxaborolane (4.63 mL, 27.3 mmol) was added and the mixture was heated to about 70° C. for about 5 h. The mixture was cooled to rt and DCM (75 mL) and water (50 mL) were added. The layers were separated and the aqueous layer was extracted with DCM (50 mL). The combined extracts were dried over MgSO4, filtered, concentrated under reduced pressure and passed through a plug of silica gel, eluting with DCM, and concentrated under vacuum. The residue was suspended in a mixture of Et2O/EtOAc, filtered and then washed the precipitate with a small amount of EtOAc/Et2O. The material thus obtained was dried in vacuum oven to give 1-tosyl-4-vinyl-1H-indole-7-carbonitrile (5.62 g, 77%): LC/MS (Table 1, Method as) R$_t$=2.57 min; MS m/z: 323 (M+H)+.

Step C: 4-(Oxiran-2-yl)-1-tosyl-1H-indole-7-carbonitrile

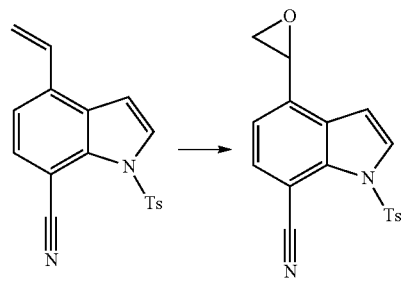 [SMILES: C=Cc1ccc(C#N)c2c1ccn2S(=O)(=O)c1ccc(C)cc1 ; Cc1ccc(S(=O)(=O)n2ccc3c(C4CO4)ccc(C#N)c32)cc1]

To a suspension of 1-tosyl-4-vinyl-1H-indole-7-carbonitrile (0.40 g, 1.241 mmol) in dioxane (16 mL) and water (8 mL) was added AcOH (0.0710 mL, 1.24 mmol). The mixture was cooled to about 0° C. NBS (0.243 g, 1.36 mmol) was added in one portion. The reaction was allowed to warm to rt and stirred for about 2 h. NaOH (2M aqueous solution, 8.0 mL, 16 mmol) was added in one portion. The solid formed was collected by filtration, washed with water and dried in a vacuum oven at about 60° C. for about 16 h to give 4-(oxiran-2-yl)-1-tosyl-1H-indole-7-carbonitrile (0.29 g, 68%): LC/MS (Table 1, Method as) R$_t$=2.36 min; MS m/z: 339 (M+H)+.

Step C: 4-(1-Hydroxy-2-((2-hydroxyethyl)amino)
ethyl)-1-tosyl-1H-indole-7-carbonitrile

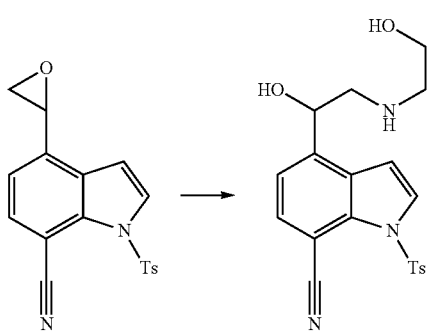 [SMILES: Cc1ccc(S(=O)(=O)n2ccc3c(C4CO4)ccc(C#N)c32)cc1 ; Cc1ccc(S(=O)(=O)n2ccc3c(C(O)CNCCO)ccc(C#N)c32)cc1]

To a suspension of 4-(oxiran-2-yl)-1-tosyl-1H-indole-7-carbonitrile (0.285 g, 0.841 mmol) in IPA (8 mL) was added TEA (0.586 mL, 4.21 mmol) followed by 2-aminoethanol (0.253 mL, 4.21 mmol). The mixture was heated at about 75° C. for about 3 h and concentrated under reduced pressure. The residue was partitioned between EtOAc and water. The mixture was extracted with EtOAc (2×10 mL). The combined organic layers were dried over $Na_2SO_4$, filtered, concentrated and dried under a vacuum pump to give 4-(1-hydroxy-2-((2-hydroxyethyl)amino)ethyl)-1-tosyl-1H-indole-7-carbonitrile (0.39 g, 94%): LC/MS (Table 1, Method as) $R_t$=1.53 min; MS m/z: 400 (M+H)$^+$.

Step D: tert-Butyl (2-(7-cyano-1-tosyl-1H-indol-4-yl)-2-hydroxyethyl)(2-hydroxyethyl)carbamate

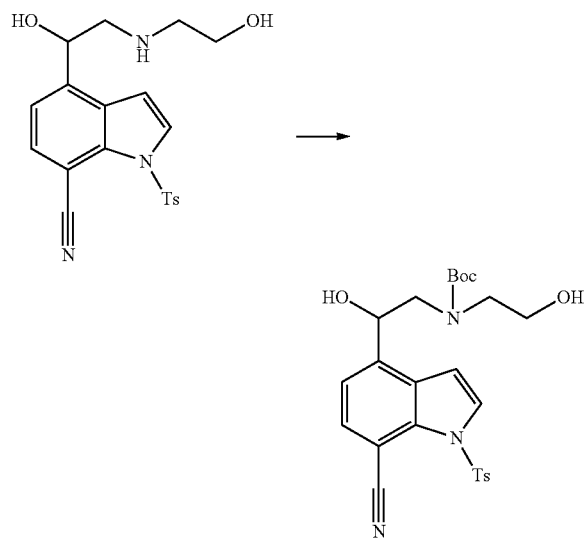

To a solution of 4-(1-hydroxy-2-((2-hydroxyethyl)amino) ethyl)-1-tosyl-1H-indole-7-carbonitrile (0.336 g, 0.673 mmol) in EtOAc (3 mL) was added DIEA (0.176 mL, 1.01 mmol) followed by drop wise addition of a solution of di-tert-butyl dicarbonate (0.220 g, 1.01 mmol) in EtOAc (1 mL) at rt. THF (1 mL) was added to help solubilize the mixture and stirred at rt for about 2 h. Additional DIEA (0.060 mL, 0.34 mmol) and di-tert-butyl dicarbonate (0.073 g, 0.34 mmol) were added. The mixture was stirred at rt for about another 2 h. The solvent was removed under reduced pressure and purified by flash chromatography (25-50% EtOAc/heptane) then by HPLC (Table 1, Method bd) to give tert-butyl (2-(7-cyano-1-tosyl-1H-indol-4-yl)-2-hydroxyethyl)(2-hydroxyethyl)carbamate (0.25 g, 74%): LC/MS (Table 1, Method as) $R_t$=2.22 min; MS m/z: 500 (M+H)$^+$.

Step E: tert-Butyl 2-(7-cyano-1-tosyl-1H-indol-4-yl)
morpholine-4-carboxylate

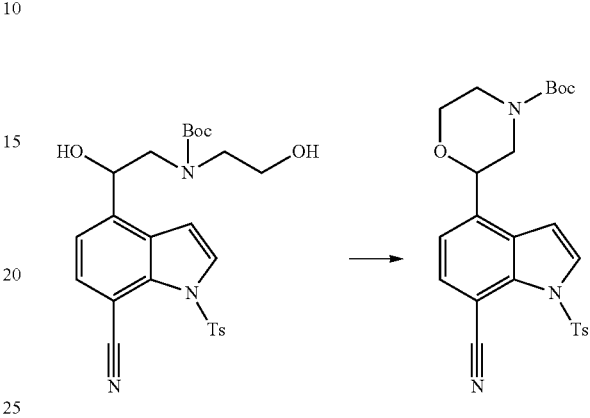

To a vial charged with tert-butyl-(2-(7-cyano-1-tosyl-1H-indol-4-yl)-2-hydroxyethyl) (2-hydroxyethyl)carbamate (0.50 g, 1.0 mmol) and $PPh_3$ (0.315 g, 1.20 mmol) in toluene (10 mL) at about 0° C. was added TEA (0.367 mL, 2.63 mmol) followed by addition of DCAD (0.441 g, 1.20 mmol). The solution was stirred at about 0° C. for about 5 min and then stirred at about rt for about 16 h. Additional $PPh_3$ (0.131 g, 0.500 mmol) and DCAD (0.184 g, 0.500 mmol) were added at rt and the mixture was stirred at about rt for about 6 h. The reaction mixture was filtered and the filtrate was concentrated and purified by flash chromatography (0-30% EtOAc/heptane) to give tert-butyl 2-(7-cyano-1-tosyl-1H-indol-4-yl)morpholine-4-carboxylate (0.41 g, 84%): LC/MS (Table 1, Method as) $R_t$=2.72 min; MS m/z: 499 (M+$H_2O$)$^+$.

Preparation #44:
2-Iodo-6,7-dihydro-4H-pyrazolo[5,1-c][1,4]oxazine

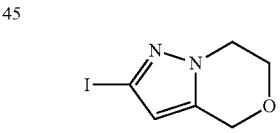

Step A:
2-Nitro-6,7-dihydro-4H-pyrazolo[5,1-c][1,4]oxazine

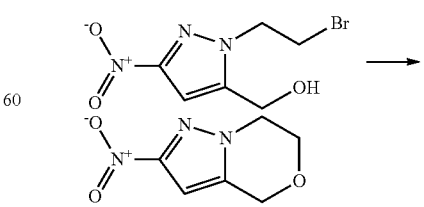

A mixture of (1-(2-bromoethyl)-3-nitro-1H-pyrazol-5-yl) methanol (4.0 g, 12 mmol) [Princeton] in NMP (7.7 mL) was heated at about 130° C. for about 16 h. The mixture was diluted with DCM and washed with water and brine. The organic layer was dried, concentrated and purified by chromatography on silica gel (0-5% MeOH/DCM) to give 2-nitro-6,7-dihydro-4H-pyrazolo[5,1-c][1,4]oxazine (1 g, 49%): $^1$H NMR (400 MHz, DMSO-$d_6$) δ 6.88 (s, 1H), 4.83 (s, 2H), 4.24 (t, J=5.2 Hz, 2H), 4.13 (dd, J=5.9, 4.6 Hz, 2H).

Step B:
6,7-dihydro-4H-pyrazolo[5,1-c][1,4]oxazin-2-amine

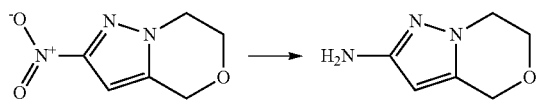

A flask was charged with Pd/C (10 wt %, 0.755 g, 0.709 mmol) under nitrogen before the addition of a solution of 2-nitro-6,7-dihydro-4H-pyrazolo[5,1-c][1,4]oxazine (4.0 g, 24 mmol) in EtOAc (59.1 mL) and MeOH (59.1 mL). The reaction stirred at rt for about 16 h. The reaction mixture was filtered through a plug of Celite® and the filtrate was concentrated under reduced pressure to afford 6,7-dihydro-4H-pyrazolo[5,1-c][1,4]oxazin-2-amine (3.2 g, 97%): LC/MS (Table 1, Method as) $R_f$=0.61 min; MS m/z: 140 (M+H)$^+$.

Step C:
2-Iodo-6,7-dihydro-4H-pyrazolo[5,1-c][1,4]oxazine

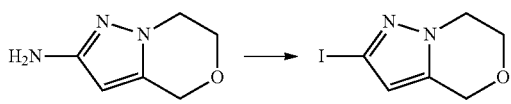 [SMILES: Nc1cc2n(n1)CCOC2 ; Ic1cc2n(n1)CCOC2]

A 50 mL round-bottom flask was charged with 6,7-dihydro-4H-pyrazolo[5,1-c][1,4]oxazin-2-amine (1.5 g, 11 mmol) and concentrated HCl (2.43 mL, 29.6 mmol). The mixture was cooled to about 0° C. A solution of NaNO$_2$ (0.707 g, 10.2 mmol) in water (10 mL) was added and the reaction stirred for about 15 min. A solution of KI (2.86 g, 17.3 mmol) in water (10 mL) was added carefully and the reaction was stirred at about 0° C. for about 1 h and stirred at rt for about 30 min. The reaction mixture was diluted with EtOAc (20 mL) and water (20 mL) and then separated from the aqueous layer. The solution was purified via chromatography on silica gel (0-50% EtOAc/heptane) to give 2-iodo-6,7-dihydro-4H-pyrazolo[5,1-c][1,4]oxazine (0.996 g, 37%): LC/MS (Table 1, Method as) $R_f$=1.58 min; MS m/z: 251 (M+H)$^+$.

Preparation #45: Methyl 4-chloro-1-tosyl-1H-pyrrolo[3,2-c]pyridine-7-carboxylate

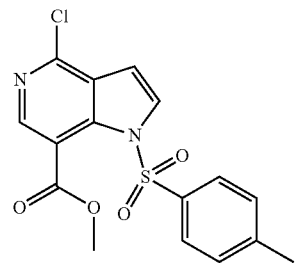 [SMILES: COC(=O)c1cnc(Cl)c2ccn(S(=O)(=O)c3ccc(C)cc3)c12]

Step A: Methyl 1-tosyl-1H-pyrrolo[3,2-c]pyridine-7-carboxylate

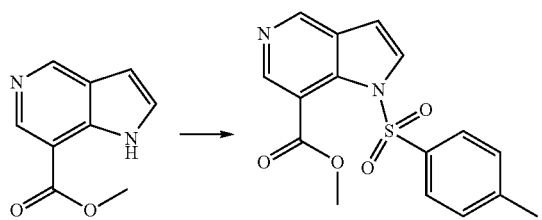 [SMILES: COC(=O)c1cncc2cc[nH]c12 ; COC(=O)c1cncc2ccn(S(=O)(=O)c3ccc(C)cc3)c12]

A round bottom flask was charged with methyl 1H-pyrrolo[3,2-c]pyridine-7-carboxylate (14 g, 79 mmol) and THF (225 mL) [Pharmablock] and the solution was cooled to about 5° C. followed by the addition of KHMDS (1M in THF, 79 mL, 79 mmol). The solution was then stirred for about 1 h followed by the addition of a solution of 4-methylbenzene-1-sulfonyl chloride (15.2 g, 79.0 mmol) in THF (25 mL). The mixture was stirred for about 2 h at about 0 to 5° C. followed by the addition of saturated aqueous NH$_4$Cl and DCM. The layers were separated and the organic solution was dried over MgSO$_4$, filtered, concentrated under reduced pressure and purified by silica gel chromatography (0-50% EtOAc/DCM) to give methyl 1-tosyl-1H-pyrrolo[3,2-c]pyridine-7-carboxylate (18.8 g, 72%): LC/MS (Table 1, Method as) $R_f$=2.10 min; MS m/z: 331 (M+H)$^+$.

Step B: 7-(Methoxycarbonyl)-1-tosyl-1H-pyrrolo[3,2-c]pyridine 5-oxide

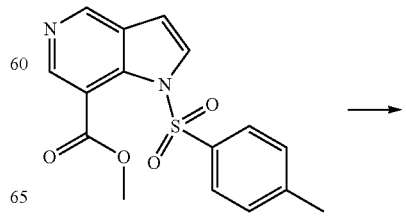

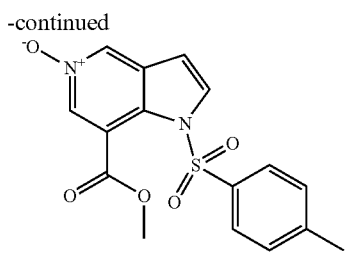

A round bottom flask was charged with methyl 1-tosyl-1H-pyrrolo[3,2-c]pyridine-7-carboxylate (16.0 g, 48.4 mmol) and EtOAc (150 mL). To the reaction solution was added a solution of 3-chlorobenzoperoxoic acid (14.2 g, 82 mmol) in EtOAc (80 mL) and stirred at rt for about 16 h. To the reaction mixture was added saturated aqueous $Na_2CO_3$ (50 mL) and the layers were separated. The aqueous layer was extracted with EtOAc (2×30 mL) and DCM (2×30 mL). The combined extracts were dried over $Na_2SO_4$, filtered and concentrated under reduced pressure to give a thick oil that was dried on a vacuum pump to give 7-(methoxycarbonyl)-1-tosyl-1H-pyrrolo[3,2-c]pyridine 5-oxide (11.6 g, 69%): LC/MS (Table 1, Method as) $R_t$=1.73 min; MS m/z: 347 (M+H)$^+$.

Step C: Methyl 4-chloro-1-tosyl-1H-pyrrolo[3,2-c]pyridine-7-carboxylate

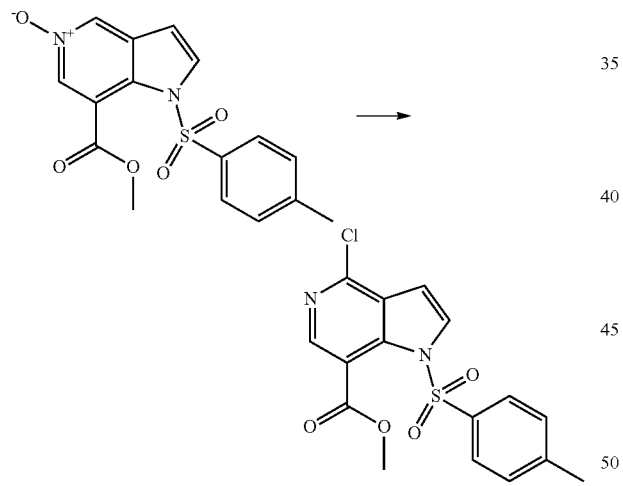

A round bottom flask was charged with 7-(methoxycarbonyl)-1-tosyl-1H-pyrrolo[3,2-c]pyridine 5-oxide (11.6 g, 33.5 mmol) and $PCl_3$ (26.5 mL, 285 mmol) and heated to about 60° C. for about 2 h. The solution was cooled to rt and slowly poured into ice water with stirring and the resulting mixture was neutralized with the addition of saturated aqueous $Na_2CO_3$. The aqueous mixture was extracted with EtOAc (3×40 mL) and the combined extracts were dried over $Na_2SO_4$, filtered and concentrated under reduced pressure to give methyl 4-chloro-1-tosyl-1H-pyrrolo[3,2-c]pyridine-7-carboxylate (8.47 g, 69%): LC/MS (Table 1, Method as) $R_t$=2.46 min; MS m/z: 365 (M+H)$^+$.

Preparation #46: 7-Chloro-2-(1-methyl-1H-pyrazol-4-yl)thiazolo[5,4-c]pyridine-4-carboxamide

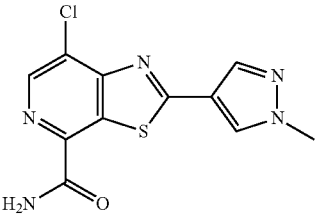 [SMILES: Cn1cc(-c2nc3c(Cl)cnc(C(N)=O)c3s2)cn1]

Step A: (E)-Ethyl 3-(2-bromothiazol-4-yl)acrylate

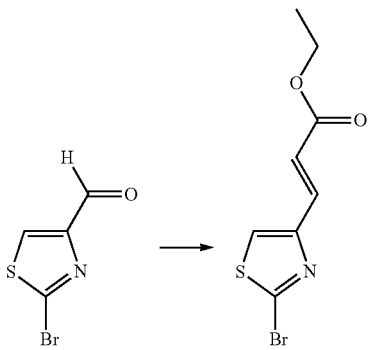

A 1 L round-bottom flask was charged with ethyl 2-(triphenylphosphoranylidene)acetate (37.2 g, 107 mmol) in DCM (130 mL) to give a colorless solution. The solution was cooled to about 0° C. and a solution of 2-bromothiazole-4-carbaldehyde (20.5 g, 107 mmol) [ArkPharm] in DCM (500 mL) was added drop wise via a dropping funnel. The reaction mixture was slowly warmed to rt and stirred for about 2 h then concentrated under reduced pressure. The mixture was taken up in $Et_2O$ (300 mL) and stirred at about 40° C. for about 30 min. It was then cooled, filtered and washed with $Et_2O$ (50 mL).

The precipitate was discarded and the filtrate was concentrated to half the volume. The precipitate formed was collected via filtration to give the first batch of product. The filtrate was concentrated and $Et_2O$ was added (60 mL), the mixture was stirred at rt for about 20 min and the newly formed precipitate was filtered again to collect a second batch of product. The filtrate from this batch was concentrated under reduced pressure and purified silica gel chromatography (0-10% EtOAc/heptane). The material thus obtained was recrystallized from $Et_2O$ to give a third and final batch of product. All the batches were combined to give white crystalline material, (E)-ethyl 3-(2-bromothiazol-4-yl)acrylate (20.1 g, 72%): LC/MS (Table 1, Method as) $R_t$=2.26 min; MS m/z: 262, 264 (M+H)$^+$.

Step B: (E)-Ethyl 3-(2-(1-methyl-1H-pyrazol-3-yl)thiazol-4-yl)acrylate

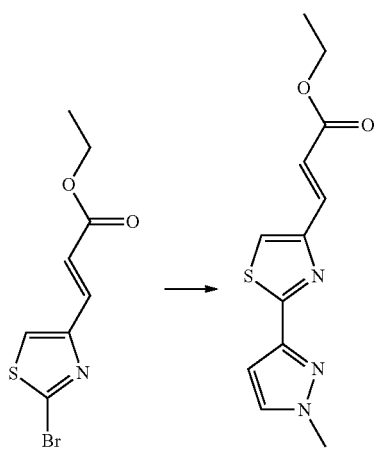 [SMILES: CCOC(=O)/C=C/c1csc(Br)n1 ; CCOC(=O)/C=C/c1csc(-c2ccn(C)n2)n1]

A 500 mL round bottom flask was charged with 1-methyl-4-(4,4,5,5-tetramethyl-1,3,2-dioxaborolan-2-yl)-1H-pyrazole (20.7 g, 100 mmol), (E)-ethyl 3-(2-bromothiazol-4-yl)acrylate (20.1 g, 77.0 mmol), Na$_2$CO$_3$ (24.4 g, 230 mmol), PdCl$_2$(dppf) (5.61 g, 7.67 mmol) and (E)-ethyl 3-(2-bromothiazol-4-yl)acrylate (20.1 g, 77.0 mmol). To the solid mixture was added THF (150 mL): MeOH (21.00 mL): water (21 mL) and the suspension was degassed and purged with N$_2$ for about 20 min. The reaction mixture was heated at about 75° C. for about 15 h. The reaction was filtered and washed with EtOAc (100 mL) and the filtrate was washed with water (70 mL). The aqueous layer was extracted with EtOAc (2×70 mL) and the combined organics were dried over MgSO$_4$, filtered and concentrated. To the residue was added DCM (50 mL) and heptane (150 mL). The entire suspension was filtered, washed with acetone and isopropanol and dried in a vacuum oven to give the first batch of product. The filtrate was concentrated, dissolved in DCM (40 mL) and passed through a silica gel plug (eluent: 50% EtOAc/heptane). The filtrate was concentrated and refluxed in acetone (35 mL) and cooled. The precipitate was filtered, washed with isopropanol, combined with the first batch and dried in a vacuum oven at about 70° C. for about 16 h to give (E)-ethyl 3-(2-(1-methyl-1H-pyrazol-3-yl)thiazol-4-yl)acrylate (15.2 g, 75%): LC/MS (Table 1, Method as) R$_t$=1.94 min; MS m/z: 264(M+H)$^+$.

Step C: (E)-3-(2-(1-Methyl-1H-pyrazol-4-yl)thiazol-4-yl)acrylic acid

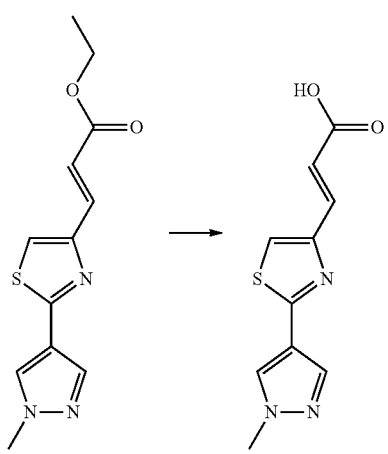 [SMILES: CCOC(=O)/C=C/c1csc(-c2cnn(C)c2)n1 ; Cn1cc(-c2nc(/C=C/C(=O)O)cs2)cn1]

In a 20 mL reaction vial, (E)-ethyl 3-(2-(1-methyl-1H-pyrazol-4-yl)thiazol-4-yl)acrylate (15.2 g, 57.7 mmol) and LiOH (4.15 g, 173 mmol) in MeOH (60 mL): water (12 mL) were added. The reaction mixture was stirred at about 40° C. for about 2 h. The reaction mixture was concentrated, diluted with water (50 mL) and washed with DCM (50×3 mL). The aqueous layer was acidified with 1N HCl until no more precipitate formed. The precipitate was collected via filtration and dried in a vacuum oven at about 60° C. for about 16 h to give (E)-3-(2-(1-methyl-1H-pyrazol-4-yl)thiazol-4-yl)acrylic acid (12.3 g, 91%): $^1$H NMR (400 MHz, DMSO-d$_6$) δ 12.42 (s, 1H), 8.38 (s, 1H), 7.94 (s, 2H), 7.56 (s, 1H), 6.56 (s, 1H), 3.90 (s, 3H).

Step D: (E)-3-(2-(1-Methyl-1H-pyrazol-4-yl)thiazol-4-yl)acryloyl azide

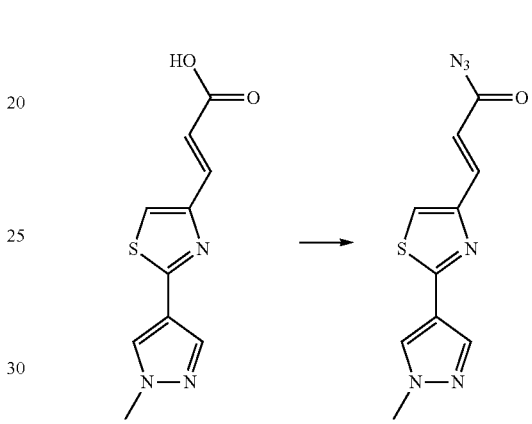

To a suspension of (E)-3-(2-(1-methyl-1H-pyrazol-4-yl)thiazol-4-yl)acrylic acid (11.2 g, 47.4 mmol) in acetone (170 mL) was added TEA (6.61 mL, 47.4 mmol) and the mixture was cooled in an ice bath. Isobutyl chloroformate (6.22 mL, 47.4 mmol) was added drop wise. After about 3.5 h a solution of NaN$_3$ (3.85 g, 59.2 mmol) in water (15 mL) was added carefully and the reaction was stirred for about 3 h at about 0° C. The reaction mixture was poured over ice and stirred for about 5 min, filtered and washed with water (50 mL). The precipitate was dried in a vacuum oven at about 60° C. for about 16 h to give (E)-3-(2-(1-methyl-1H-pyrazol-4-yl)thiazol-4-yl)acryloyl azide (9.6 g, 78%): LC/MS (Table 1, Method as) R$_t$=1.91 min; MS m/z: 261(M+H)$^+$.

Step E: 2-(1-methyl-1H-pyrazol-4-yl)thiazolo[5,4-c]pyridin-4(5H)-one

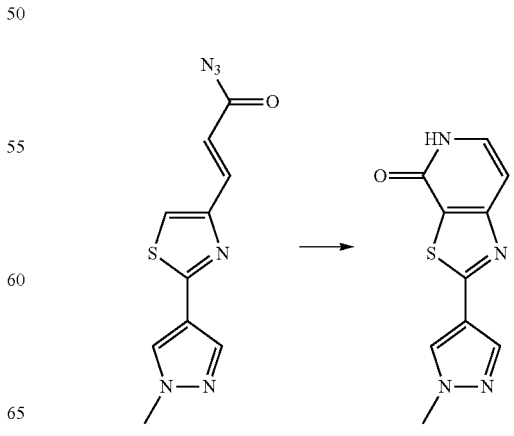

A 250 mL 3-neck round-bottomed flask was charged with tributylamine (6.10 mL, 25.6 mmol) in diphenylether (30 mL). The reaction mixture was heated to about 190° C. and a solution of (E)-3-(2-(1-methyl-1H-pyrazol-4-yl)thiazol-4-yl)acryloyl azide (5.60 g, 21.5 mmol) in diphenylether (80 mL) was added carefully and the reaction was stirred for about 5 h at about 190° C. The reaction mixture was cooled and poured onto petroleum ether (300 mL) and stirred for about 5 min and filtered. The precipitate was dried in a vacuum oven at about 70° C. for about 30 min. The material was suspended in Et$_2$O (100 mL) and heated at about 50° C. for about 20 min. It was then filtered and washed with cold Et$_2$O. The precipitate was dried in a vacuum oven at about 70° C. for about 10 h to give 2-(1-methyl-1H-pyrazol-4-yl)thiazolo[5,4-c]pyridin-4(5H)-one (3.8 g, 76%): LC/MS (Table 1, Method as) R$_t$=1.13 min; MS m/z: 233 (M+H)$^+$.

Step F: 7-Chloro-2-(1-methyl-1H-pyrazol-4-yl)thiazolo[5,4-c]pyridin-4(5H)-one

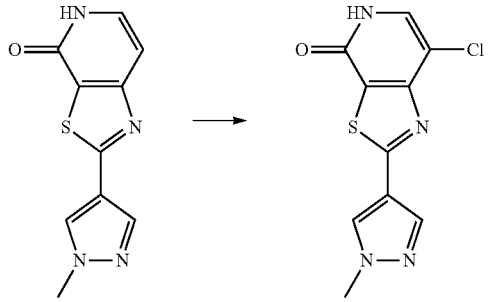 [SMILES: Cn1cc(-c2nc3cc[nH]c(=O)c3s2)cn1 ; Cn1cc(-c2nc3c(Cl)c[nH]c(=O)c3s2)cn1]

In a 250 mL round-bottom flask 2-(1-methyl-1H-pyrazol-4-yl)thiazolo[5,4-c]pyridin-4(5H)-one (3.7 g, 16 mmol) in MeCN (80 mL) was added to give a suspension. The reaction mixture was heated with stirring to about 80° C. A solution of NCS (3.19 g, 23.9 mmol)) in MeCN (25 mL) was added drop wise via a dropping funnel, and the reaction was stirred for about 5 h at about 80° C. The mixture was diluted with water (100 mL), filtered and washed with water (40 mL). The precipitate was dried in a vacuum oven at about 70° C. for about 16 h to give 7-chloro-2-(1-methyl-1H-pyrazol-4-yl)thiazolo[5,4-c]pyridin-4(5H)-one (3.55 g, 84%): LC/MS (Table 1, Method as) R$_t$=1.27 min; MS m/z: 267 (M+H)$^+$.

Step G: 4-Bromo-7-chloro-2-(1-methyl-1H-pyrazol-4-yl)thiazolo[5,4-c]pyridine

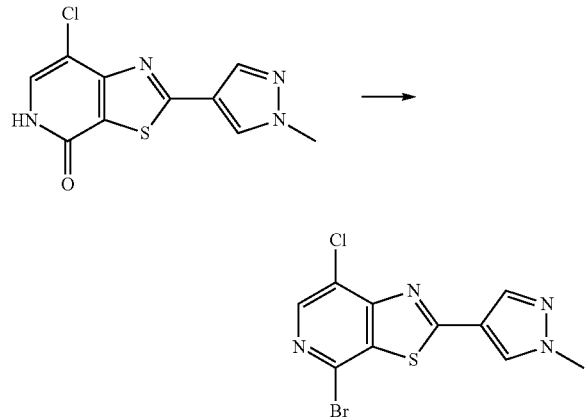

In a 100 mL 3-neck round-bottom flask a mixture of 7-chloro-2-(1-methyl-1H-pyrazol-4-yl)thiazolo[5,4-d]pyridin-4(5H)-one (1.30 g, 4.87 mmol) and POBr$_3$ (3.91 g, 13.6 mmol) was heated to about 70° C. for about 10 min then heated to about 120° C. for about 45 min. Additional POBr$_3$ (1.40 g, 4.87 mmol) was added and heated for about 50 min. The mixture was cooled on an ice bath and to it was added carefully a mixture of crushed ice and water (40 mL). The mixture was stirred at rt for about 16 h. To the suspension was added DCM (60 mL) and stirred for about 30 min, then filtered to remove some black solids. The DCM layer was separated and aqueous layer was extracted with DCM (2×20 mL). The combined organic layers were dried over MgSO$_4$, filtered and adsorbed on silica gel (4-6 g). The material was purified by silica gel chromatography (1-3% EtOAc/heptane) to give 4-bromo-7-chloro-2-(1-methyl-1H-pyrazol-4-yl)thiazolo[5,4-c]pyridine (0.85 g, 53%): LC/MS (Table 1, Method as) R$_t$=2.20 min; MS m/z: 331 (M+H)$^+$.

Step H: 7-Chloro-2-(1-methyl-1H-pyrazol-4-yl)thiazolo[5,4-c]pyridine-4-carbonitrile

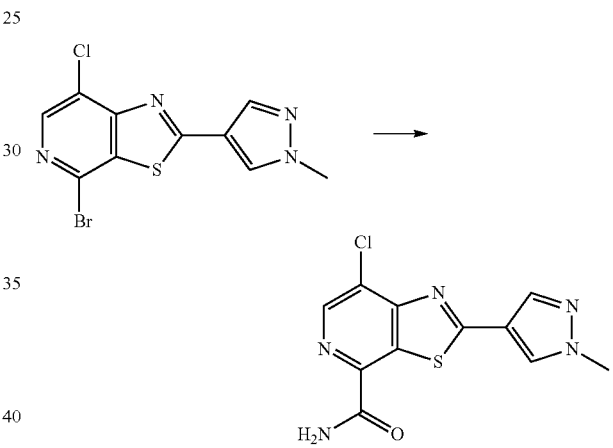

In a 50 mL round-bottom flask, 4-bromo-7-chloro-2-(1-methyl-1H-pyrazol-4-yl)thiazolo[5,4-c]pyridine (0.770 g, 2.13 mmol), Zn(CN)$_2$ (0.168 g, 1.44 mmol) and Pd(PPh$_3$)$_4$ (0.174 g, 0.151 mmol) in DMF (10 mL) were added. The flask was degassed and purged with nitrogen then heated thermally under nitrogen at about 110° C. to 120° C. for about 50 min. The reaction mixture was diluted with water (25 mL) and stirred for about 5 min, filtered and washed with water (6 mL). The precipitate was dried in a vacuum oven at about 70° C. for about 16 h to give crude 7-chloro-2-(1-methyl-1H-pyrazol-4-yl)thiazolo[5,4-c]pyridine-4-carbonitrile (0.67 g, 98%). To a flask charged with NaOH (1M aqueous solution, 7.29 mL, 7.29 mmol) in MeOH (12 mL) was added H$_2$O$_2$ (30% aqueous solution, 1.24 mL, 12.2 mmol). This solution was added to a flask containing 7-chloro-2-(1-methyl-1H-pyrazol-4-yl)thiazolo[5,4-c]pyridine-4-carbonitrile (0.670 g, 2.43 mmol) and stirred at about 30° C. for about 5 min. The reaction mixture was diluted with water (51 mL) and stirred at rt for about 5 min and filtered. The precipitate was triturated with Et$_2$O, filtered and dried in a vacuum oven for about 16 h to give 7-chloro-2-(1-methyl-1H-pyrazol-4-yl)thiazolo[5,4-c]pyridine-4-carboxamide (0.597 g, 84%): LC/MS (Table 1, Method as) R$_t$=1.58 min; MS m/z: 294(M+H)$^+$.

Preparation #47: Methyl 4-((1R,3R)-3-((tert-butoxy-carbonyl)amino)cyclopentyl)-1-tosyl-1H-indole-7-carboxylate

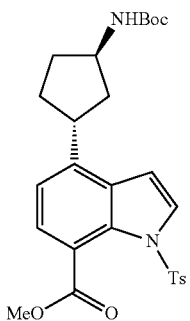

Step A: Methyl 4-(3-oxocyclopent-1-en-1-yl)-1-tosyl-1H-indole-7-carboxylate

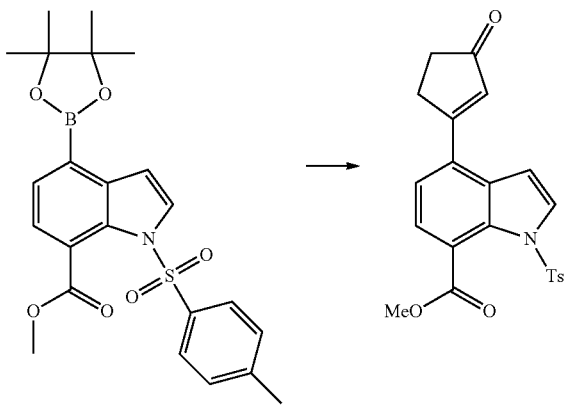

A flask was charged with methyl 4-(4,4,5,5-tetramethyl-1,3,2-dioxaborolan-2-yl)-1-tosyl-1H-indole-7-carboxylate (1.74 g, 3.82 mmol, prepared using A from Preparation #1, step C with bis(pinacolato)diboron) in 2-methyl-THF (18.64 mL) and water (12.43 mL). The mixture was cooled to about 10° C. in a cold water bath. NaIO$_4$ (1.23 g, 5.73 mmol) was added, the reaction was stirred for about 30 min and aqueous 1M HCl (8.41 mL, 8.41 mmol) was added drop wise. The mixture was stirred at rt for about 16 h. Additional 2-methyl-THF (50 mL) was added, the aqueous layer was separated and the organic layer was washed with 10% aqueous Na$_2$S$_2$O$_3$ (2×30 mL), saturated aqueous NaHCO$_3$ (30 mL) and brine (20 mL). The organic layer was then dried over Na$_2$SO$_4$, filtered and concentrated to afford crude (7-(methoxycarbonyl)-1-tosyl-1H-indol-4-yl)boronic acid. In a 100 mL round-bottom flask the crude (7-(methoxycarbonyl)-1-tosyl-1H-indol-4-yl)boronic acid (1.59 g, 4.26 mmol) in dioxane (17 mL) was added. A solution of Cs$_2$CO$_3$ (3.47 g, 10.7 mmol) in water (4.26 mL) was added, the mixture was degassed with nitrogen followed by the addition of PdCl$_2$(PPh$_3$)$_2$ (0.209 g, 0.298 mmol) and 3-bromocyclopent-2-enone (1.4 mL, 12.8 mmol) under inert atmosphere. The mixture was heated at about 80° C. for about 3 h then cooled to rt and added DCM (100 mL) and water (50 mL). The layers were separated and the aqueous layer was extracted with DCM (2×50 mL). The combined organics were dried over MgSO$_4$. The solvent was removed in vacuo and the residue was purified using silica gel chromatography (0-60% EtOAc/heptane) to afford methyl 4-(3-oxocyclopent-1-en-1-yl)-1-tosyl-1H-indole-7-carboxylate (1.2 g, 69%): $^1$H NMR (400 MHz, DMSO-d$_6$) δ 7.92 (d, J=3.9 Hz, 1H), 7.71 (d, J=7.9 Hz, 1H), 7.67-7.62 (m, 2H), 7.58 (d, J=7.9 Hz, 1H), 7.39-7.31 (m, 2H), 7.23 (d, J=3.9 Hz, 1H), 6.67 (t, J=1.8 Hz, 1H), 3.83 (s, 3H), 3.12 (dt, J=6.9, 1.9 Hz, 2H), 2.47 (dd, J=4.9, 2.5 Hz, 2H), 2.33 (s, 3H).

Step B: (R)-methyl 4-(3-oxocyclopentyl)-1-tosyl-1H-indole-7-carboxylate

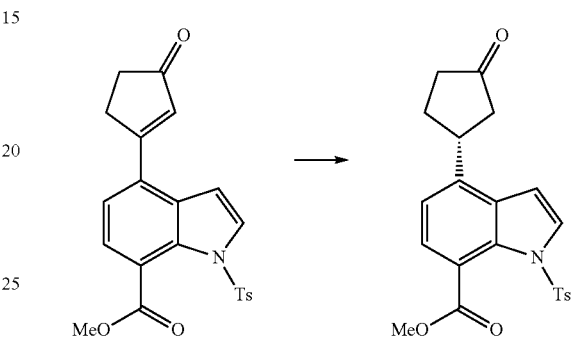

In a 40 mL reaction vial, (2S,5S)-5-benzyl-3-methyl-2-(5-methylfuran-2-yl)imidazolidin-4-one (0.190 g, 0.703 mmol) and methyl 4-(3-oxocyclopent-1-en-1-yl)-1-tosyl-1H-indole-7-carboxylate (3.05 g, 7.45 mmol) in THF (5.67 mL) were added. The mixture was cooled to about 0° C. and degassed with nitrogen. Di-tert-butyl 2,6-dimethyl-1,4-dihydropyridine-3,5-dicarboxylate (1.05 g, 3.40 mmol) and trichloroacetic acid (0.071 mL, 0.70 mmol) were added under inert atmosphere. The reaction mixture was stirred at about 4° C. for about 16 h. Additional di-tert-butyl 2,6-dimethyl-1,4-dihydropyridine-3,5-dicarboxylate (0.420 g, 1.36 mmol) was added, and reaction was stirred with cooling for about 72 h. The crude material was adsorbed onto silica gel and purified via silica gel chromatography (0-45% EtAOc/heptane) to afford (R)-methyl 4-(3-oxocyclopentyl)-1-tosyl-1H-indole-7-carboxylate (1 g, 79%). $^1$H NMR (400 MHz, CDCl$_3$-d) δ 7.67-7.58 (m, 2H), 7.58-7.45 (m, 2H), 7.23-7.10 (m, 3H), 6.75 (d, J=4.2 Hz, 1H), 3.91 (s, 3H), 3.73 (tdd, J=10.1, 7.6, 6.0 Hz, 1H), 2.73-2.61 (m, 1H), 2.51-2.24 (m, 7H), 2.16-1.98 (m, 1H).

Step C: Methyl 44(1R,3S)-3-hydroxycyclopentyl)-1-tosyl-1H-indole-7-carboxylate

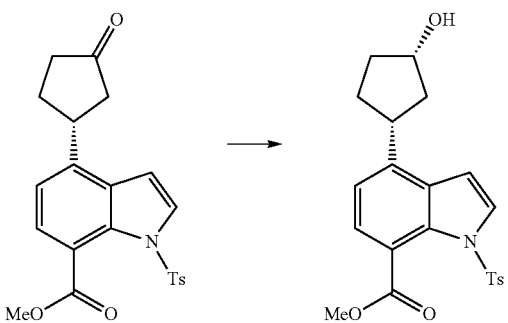 [SMILES: COC(=O)c1ccc([C@@H]2CCC(=O)C2)c2ccn(S(=O)(=O)c3ccc(C)cc3)c12 ; COC(=O)c1ccc([C@@H]2CC[C@H](O)C2)c2ccn(S(=O)(=O)c3ccc(C)cc3)c12]

In a 200 mL round-bottom flask, (R)-methyl 4-(3-oxocyclopentyl)-1-tosyl-1H-indole-7-carboxylate (1.60 g, 3.89 mmol) in THF (32.4 mL) was added. The solution was cooled to about −78° C. L-Selectride (7.78 mL, 7.78 mmol) was added drop wise over about 20 min and the mixture was stirred for about 16 h. The reaction mixture was cooled on an ice bath, saturated aqueous NH₄Cl (60 mL) was added drop wise then EtOAc (100 mL) and water (20 mL) were added. The organic layer was separated, washed with brine, dried over Na₂SO₄, filtered, concentrated and purified via silica gel chromatography (0-65% EtOAc/heptane). The residue obtained was purified using chiral chromatography (Table 2, Method 19) to give methyl 4-((1R,3S)-3-hydroxycyclopentyl)-1-tosyl-1H-indole-7-carboxylate (0.36 g, 22%): LC/MS (Table 1, Method a) $R_f$=2.21 min; MS m/z: 431 (M+H₂O)⁺.

Step D: Methyl 4-((1R,3R)-3-((tert-butoxycarbonyl)amino)cyclopentyl)-1-tosyl-1H-indole-7-carboxylate

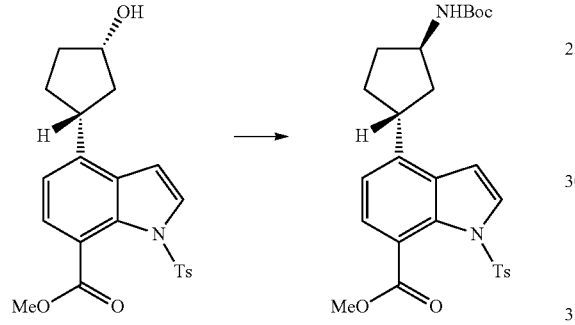

In a 40 mL reaction vial, methyl 44(1R,3S)-3-hydroxycyclopentyl)-1-tosyl-1H-indole-7-carboxylate (0.35 g, 0.85 mmol) and PPh₃ (0.266 g, 1.02 mmol) in THF (3.4 mL) were added. The solution was cooled to about 10° C., DIEA (0.148 mL, 0.846 mmol) was added followed by drop wise addition of DIAD (0.197 mL, 1.02 mmol) and the reaction mixture was stirred for about 30 min Diphenyl phosphorazidate (0.219 mL, 1.02 mmol) was added drop wise and stirred at rt for about 3 h. A solution of PPh₃ (0.289 g, 1.10 mmol) in THF (0.6 mL) was added drop wise and the mixture was stirred for about 18 h. Water (0.183 mL, 10.2 mmol) was added and the mixture was heated at about 45° C. for about 72 h. To the reaction mixture was added DCM (10.7 mL, 166 mmol) and a solution of potassium hydrogenphosphate (0.737 g, 4.23 mmol) in water (2.14 mL, 119 mmol). A solution of di-tert-butyl dicarbonate (0.393 mL, 1.69 mmol) in DCM (2.14 mL, 33.2 mmol) was added drop wise and stirred at rt for about 1 h. Brine (2 mL) was added, the organic layer was separated and washed with brine (3 mL), dried over Na₂SO₄, filtered, concentrated and purified via silica gel chromatography (0-40% EtOAc/heptane) to afford methyl 4-((1R,3R)-3-((tert-butoxycarbonyl)amino)cyclopentyl)-1-tosyl-1,1-indole-7-carboxylate (0.396 g, 59%): LC/MS (Table 1, Method a) $R_f$=2.72 min; MS m/z: 530 (M+H₂O)⁺.

Preparation #48: tert-Butyl 3-((7-carbamoyl-2-(5-(morpholinomethyl)pyridin-2-yl)-1H-indol-4-yl)(methyl)amino)azetidine-1-carboxylate

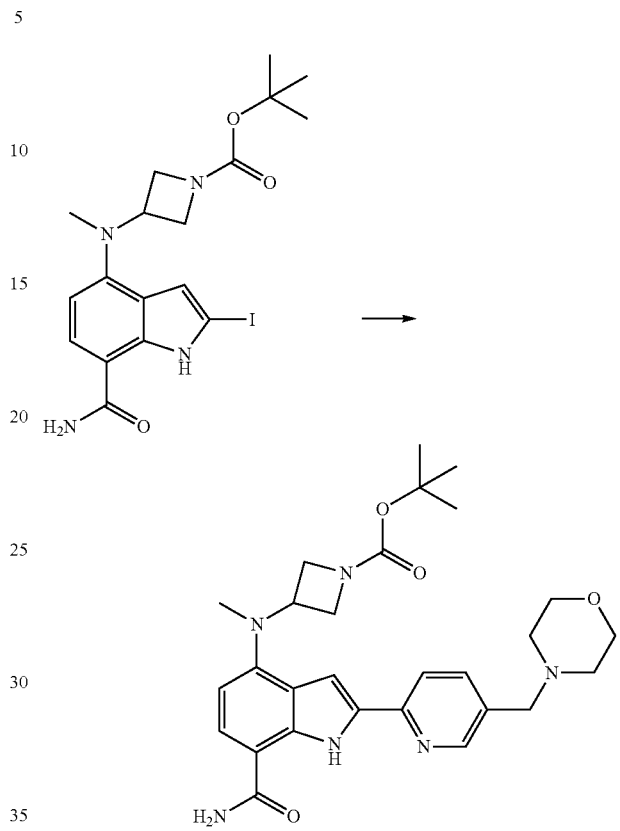

To a mixture of 4-((6-bromopyridin-3-yl)methyl)morpholine (0.300 g, 1.17 mmol) in THF (5 mL) was added n-BuLi (1.17 mL, 2.92 mmol). The mixture was stirred at about −78° C. for about 1 h, and then tributylchlorostannane (0.949 g, 2.92 mmol) was slowly added. The mixture was allowed to warm to rt over about 1 h, and a saturated solution of NH₄Cl was added. The mixture was extracted with EtOAc and the combined organic layers were dried over Na₂SO₄, filtered and concentrated in vacuo to yield crude 4-((6-(tributylstannyl)pyridin-3-yl)methyl)morpholine. A solution containing the tert-butyl 3-((7-carbamoyl-2-iodo-1H-indol-4-yl) (methyl)amino)azetidine-1-carboxylate (0.300 g, 0.638 mmol, preparation #40) in DMF (2 mL) was treated with LiCl (0.270 g, 6.38 mmol), PdCl₂(dppf)-CH₂Cl₂ adduct (0.156 g, 0.191 mmol) and 4-((6-(tributylstannyl)pyridin-3-yl)methyl)morpholine (0.894 g, 1.91 mmol). The mixture was heated at about 100° C. for about 16 h, cooled, filtered through Celite® and partitioned between EtOAc and water. The organic phase was washed with brine, dried over Na₂SO₄, filtered and concentrated. The residue was purified by silica gel chromatography (0-5% MeOH/DCM) to afford tert-butyl 3-((7-carbamoyl-2-(5-(morpholinomethyl)pyridin-2-yl)-1H-indol-4-yl)(methyl)amino)azetidine-1-carboxylate (0.172 g, 11%): LCMS (Table 1, Method av) $R_f$=1.24 min; MS m/z: 521 (M+H)⁺.

Preparation #49: tert-Butyl 6-(7-carbamoyl-1H-pyrrolo[2,3-c]pyridin-4-yl)-2,3-dihydro-1,4-oxazepine-4(7H)-carboxylate

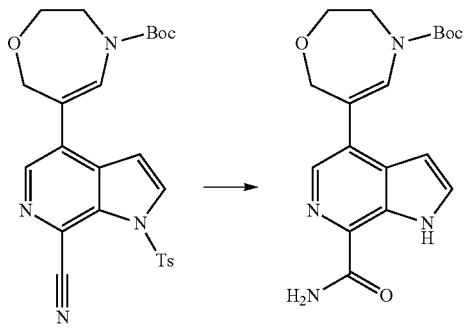 [SMILES: Cc1ccc(S(=O)(=O)n2ccc3c(C4=CN(C(=O)OC(C)(C)C)CCOC4)cnc(C#N)c32)cc1 ; CC(C)(C)OC(=O)N1C=C(c2cnc(C(N)=O)c3[nH]ccc23)COCC1]

To a solution of tert-butyl 6-(7-cyano-1-tosyl-1H-pyrrolo[2,3-c]pyridin-4-yl)-2,3-dihydro-1,4-oxazepine-4(7H)-carboxylate (0.973 g, 1.97 mmol, prepared using AG from tert-butyl 6-(((trifluoromethyl)sulfonyl)oxy)-2,3-dihydro-1,4-oxazepine-4(7H)-carboxylate (Preparation # W.1) with 4,4,4',4',5,5,5',5'-octamethyl-2,2'-bi(1,3,2-dioxaborolane) and Preparation #AH.1) in EtOH (3.93 mL) at about 0° C. was added NaOH (1N aqueous solution, 7.87 mL, 7.87 mmol) followed by $H_2O_2$ (30% aqueous solution, 1.12 mL, 9.84 mmol). After about 10 min the ice bath was removed. After about 1 h additional NaOH (1N aqueous solution, 7 mL, 7 mmol) and $H_2O_2$ (30% aqueous solution, 1.00 mL, 8.82 mmol) and DCM (3 mL) were added. The reaction mixture was allowed to stir for about 1 h and concentrated down to about 15 mL and diluted with water (10 mL) and DCM (20 mL). The suspension was filtered to remove any solids. The DCM layer was separated, dried over $MgSO_4$, filtered, concentrated and purified via silica gel chromatography to give tert-butyl 6-(7-carbamoyl-M-pyrrolo[2,3-c]pyridin-4-yl)-2,3-dihydro-1,4-oxazepine-4(7H)-carboxylate (0.138 g, 20%): LC/MS (Table 1, Method as) $R_t$=1.90 min; MS m/z: 359 (M+H)$^+$.

General Procedure A: Suzuki Reaction of an aryl or heteroaryl halide with an aryl or heteroaryl boronic acid or boronate To a mixture of an aryl halide (preferably 1 equiv), a boronic acid or boronate ester (1 to 2 equiv, preferably 1.1 equiv), and an inorganic base (such as, KF, $Na_2CO_3$, $K_2CO_3$ or $Cs_2CO_3$, preferably $Na_2CO_3$ or $Cs_2CO_3$) (1.1 to 16 equiv, preferably 2 equiv) in a solvent (such as THF, DME, DMF, 1,4-dioxane, 1,4-dioxane/water, DME/water, 1,4-dioxane/water, toluene/EtOH/water, 1,4-dioxane/EtOH/water or THF/MeOH/water preferably THF/MeOH/water, 1,4-dioxane/water, DME/water or 1,4-dioxane/EtOH/water) is added a palladium catalyst (for example $Pd(OAc)_2$, $Pd_2 dba_3$, $Pd(PPh_3)_4$, bis(acetato)triphenylphosphinepalladium(II), polymer-bound FibreCat™ 1032, SiliaCat DPP-Pd, $PdCl_2$(dppf), (1,1'-bis(diphenylphosphino)ferrocene)dichloropalladium(II), or $Pd(PPh_3)_2Cl_2$; preferably $PdCl_2$(dppf), (1,1'-bis(diphenylphosphino)ferrocene)dichloropalladium(II), or SiliaCat DPP-Pd 0.01 to 0.20 equiv, preferably 0.1 equiv) and a ligand (for example tricyclohexylphosphine, tri-tert-butyl-phosphine; preferably none or tricyclohexylphosphine; 0.01-1.0 equiv, preferably 0.16 equiv) is added optionally. The mixture is heated at about 40 to 120° C. (preferably about 70-85° C.) for about 1 to 48 h (preferably about 24 h) thermally, or at about 100 to 200° C. (preferably about 120 to 150° C.) for about 5 to 60 min (preferably about 20 to 45 min) in a microwave (preferably 5 min ramp time, 300 Watts max power, 250 psi max pressure). The mixture is allowed to cool to rt and is worked up using one of the following methods. Method 1. For reactions containing water, the mixture may be diluted with an organic solvent (such as DCM or EtOAc). The layers are separated, the organic solution is optionally washed with water and/or brine, dried over anhydrous $MgSO_4$ or $Na_2SO_4$, filtered, and the solvent is removed under reduced pressure to give the desired compound. Method 2. The mixture is concentrated under reduced pressure. Method 3. The catalyst is removed by filtration and the filtrate is concentrated under reduced pressure.

Illustration of General Procedure A

Preparation #A.1: 4-(3-Aminophenyl)-1H-indole-7-carboxamide

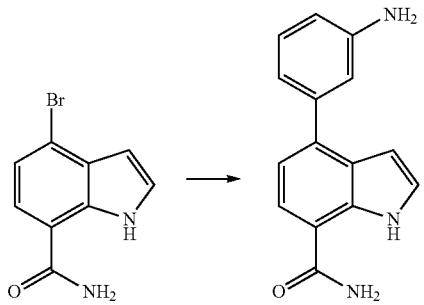 [SMILES: NC(=O)c1ccc(Br)c2cc[nH]c12 ; NC(=O)c1ccc(-c2cccc(N)c2)c2cc[nH]c12]

A vessel was charged with 4-bromo-1H-indole-7-carboxamide (2.08 g, 8.70 mmol, Preparation #2), 3-(4,4,5,5-tetramethyl-1,3,2-dioxaborolan-2-yl)aniline (2.10 g, 9.57 mmol), sodium carbonate (2.77 g, 26.1 mmol), [1,1'-bis(diphenylphosphino)ferrocene]dichloropalladium(II) (0.637 g, 0.870 mmol) and purged with nitrogen. A mixture of THF (71.4 mL), MeOH (10 mL), and water (10 mL) was added and the reaction was stirred at about 70° C. for about 24 h. The mixture was filtered through Celite®, the solvent was removed under reduced pressure and the residue was purified by column chromatograph on silica gel eluted with MeOH/DCM (0-10%) to provide a solid. The solid was triturated with ether to provide 4-(3-aminophenyl)-1H-indole-7-carboxamide (1.37 g, 63%): LC/MS (Table 1, Method f) 12, =0.76 min; MS m/z: 293(M+MeCN+H)$^+$.

TABLE A.1

Examples prepared from N-(2-methyl-3-(4,4,5,5-tetramethyl-1,3,2-dioxaborolan-2-yl)phenyl)acrylamide (prepared using E from 2-methyl-3-(4,4,5,5-tetramethyl-1,3,2-dioxaborolan-2-yl)aniline and acryloyl chloride) using General Procedure A

| Aryl Bromide | Product | Example # | $R_t$ min (Table 1, Method) | m/z ESI+ (M + H)+ | Btk IC$_{50}$ |
|---|---|---|---|---|---|
| 4-bromo-2-(3,5-dimethylisoxazol-4-yl)-1H-indole-7-carboxamide (prepared using A from Preparation #1 and 3,5-dimethylisoxazole-4-boronic acid pinacol ester) | | A.1.1 | 2.84 (d) | 415 | B |
| 4-bromo-2-(1-(tetrahydro-2H-pyran-2-yl)-1H-pyrazol-5-yl)-1H-indole-7-carboxamide (prepared using A from Preparation #1 and 1-(2-tetrahydropyranyl)-1H-pyrazole-5-boronic acid pinacol ester) | | A.1.2 | 2.87 (p) | 470 | A |
| 4-bromo-2-(3,5-dimethyl-1H-pyrazol-4-yl)-1H-indole-7-carboxamide (prepared using A from Preparation #1 and 3,5-dimethylpyrazole-4-boronic acid, pinacol ester) | | A.1.3 | 2.51 (d) | 414 | B |

TABLE A.1-continued

Examples prepared from N-(2-methyl-3-(4,4,5,5-tetramethyl-1,3,2-dioxaborolan-2-yl)phenyl)acrylamide (prepared using E from 2-methyl-3-(4,4,5,5-tetramethyl-1,3,2-dioxaborolan-2-yl)aniline and acryloyl chloride) using General Procedure A

| Aryl Bromide | Product | Example # | R$_t$ min (Table 1, Method) | m/z ESI+ (M + H)$^+$ | Btk IC$_{50}$ |
|---|---|---|---|---|---|
| 4-bromo-2-(1-isopropyl-1H-pyrazol-4-yl)-1H-indole-7-carboxamide (prepared using A from Preparation #1 and 1-isopropyl-1H-pyrazole-4-boronic acid pinacol ester) | | A.1.4 | 2.85 (d) | 428 | A |
| 4-bromo-2-(1,3-dimethyl-1H-pyrazol-4-yl)-1H-indole-7-carboxamide (prepared using A from Preparation #1 and 1,3-dimethyl-1H-pyrazole-4-boronic acid, pinacol ester) | | A.1.5 | 2.66 (d) | 414 | A |
| 4-bromo-2-(1-ethyl-1H-pyrazol-4-yl)-1H-indole-7-carboxamide (prepared using A from Preparation #1 and 1-ethyl-1H-pyrazole-4-boronic acid, pinacol ester) | | A.1.6 | 2.74 (d) | 414 | A |

TABLE A.1-continued

Examples prepared from N-(2-methyl-3-(4,4,5,5-tetramethyl-1,3,2-dioxaborolan-2-yl)phenyl)acrylamide (prepared using E from 2-methyl-3-(4,4,5,5-tetramethyl-1,3,2-dioxaborolan-2-yl)aniline and acryloyl chloride) using General Procedure A

| Aryl Bromide | Product | Example # | $R_t$ min (Table 1, Method) | m/z ESI+ (M + H)+ | Btk IC$_{50}$ |
|---|---|---|---|---|---|
| 4-bromo-2-(1-isobutyl-1H-pyrazol-4-yl)-1H-indole-7-carboxamide (prepared using A from Preparation #1 and 1-isobutyl-4-(4,4,5,5-tetramethyl-1,3,2-dioxaborolan-2-yl)-1H-pyrazole) | | A.1.7 | 2.98 (d) | 442 | A |
| 4-bromo-2-(1-(2-morpholinoethyl)-1H-pyrazol-4-yl)-1H-indole-7-carboxamide (prepared using A from Preparation #1 and 1-(2-morpholinoethyl)-1H-pyrazole-4-boronic acid, pinacol ester) | | A.1.8 | 2.28 (d) | 499 | A |
| 4-bromo-1H-indole-7-carboxamide (Preparation #2) | | A.1.9 | 1.31 (f) | 320 | B |

TABLE A.1-continued

Examples prepared from N-(2-methyl-3-(4,4,5,5-tetramethyl-1,3,2-dioxaborolan-2-yl)phenyl)acrylamide (prepared using E from 2-methyl-3-(4,4,5,5-tetramethyl-1,3,2-dioxaborolan-2-yl)aniline and acryloyl chloride) using General Procedure A

| Aryl Bromide | Product | Example # | $R_t$ min (Table 1, Method) | m/z ESI+ $(M + H)^+$ | Btk IC$_{50}$ |
|---|---|---|---|---|---|
| 4-bromo-2-(pyrimidin-5-yl)-1H-indole-7-carboxamide (prepared using A from Preparation #1 and Pyrimidine-5-boronic acid pinacol ester) | | A.1.10 | 2.56 (d) | 398 | A |
| 4-bromo-2-(1-methyl-1H-pyrazol-5-yl)-1H-indole-7-carboxamide (prepared using A from Preparation #1 and 1-methyl-1H-pyrazole-5-boronic acid pinacol ester) | | A.1.11 | 2.66 (d) | 400 | A |
| 4-bromo-2-(pyridin-4-yl)-1H-indole-7-carboxamide (prepared using A from Preparation #1 and 4-pyridineboronic acid pinacol ester) | | A.1.12 | 2.22 (d) | 397 | A |

TABLE A.1-continued

Examples prepared from N-(2-methyl-3-(4,4,5,5-tetramethyl-1,3,2-dioxaborolan-2-yl)phenyl)acrylamide (prepared using E from 2-methyl-3-(4,4,5,5-tetramethyl-1,3,2-dioxaborolan-2-yl)aniline and acryloyl chloride) using General Procedure A

| Aryl Bromide | Product | Example # | R$_t$ min (Table 1, Method) | m/z ESI+ (M + H)$^+$ | Btk IC$_{50}$ |
|---|---|---|---|---|---|
| 4-bromo-2-(2-methoxypyridin-4-yl)-1H-indole-7-carboxamide (prepared using A from Preparation #1 and 2-methoxy-pyridine-4-boronicacid) | | A.1.13 | 2.70 (d) | 427 | A |
| 4-bromo-2-(3-cyanophenyl)-1H-indole-7-carboxamide (prepared using A from Preparation #1 and 3-cyanophenyl-boronic acid) | | A.1.14 | 3.03 (d) | 421 | A |
| 2-(3-acetamidophenyl)-4-bromo-1H-indole-7-carboxamide (prepared using A from Preparation #1 and 3-acetamido-phenylboronic acid) | | A.1.15 | 2.79 (d) | 453 | A |

TABLE A.1-continued

Examples prepared from N-(2-methyl-3-(4,4,5,5-tetramethyl-1,3,2-dioxaborolan-2-yl)phenyl)acrylamide (prepared using E from 2-methyl-3-(4,4,5,5-tetramethyl-1,3,2-dioxaborolan-2-yl)aniline and acryloyl chloride) using General Procedure A

| Aryl Bromide | Product | Example # | R$_t$ min (Table 1, Method) | m/z ESI+ (M + H)$^+$ | Btk IC$_{50}$ |
|---|---|---|---|---|---|
| 4-bromo-2-(6-fluoropyridin-3-yl)-1H-indole-7-carboxamide (prepared using A from Preparation #1 and 2-fluoropyridine-5-boronic acid) | | A.1.16 | 2.87 (d) | 415 | A |
| 4-bromo-2-(2-fluoropyridin-3-yl)-1H-indole-7-carboxamide (prepared using A from Preparation #1 and 2-fluoropyridine-3-boronic acid) | | A.1.17 | 2.86 (d) | 415 | A |
| 4-bromo-2-(2-methoxypyridin-3-yl)-1H-indole-7-carboxamide (prepared using A from Preparation #1 and 2-methoxy-pyridine-3-boronic acid pinacol ester) | | A.1.18 | 2.97 (d) | 427 | A |

TABLE A.1-continued

Examples prepared from N-(2-methyl-3-(4,4,5,5-tetramethyl-1,3,2-dioxaborolan-2-yl)phenyl)acrylamide (prepared using E from 2-methyl-3-(4,4,5,5-tetramethyl-1,3,2-dioxaborolan-2-yl)aniline and acryloyl chloride) using General Procedure A

| Aryl Bromide | Product | Example # | $R_t$ min (Table 1, Method) | m/z ESI+ (M + H)$^+$ | Btk IC$_{50}$ |
|---|---|---|---|---|---|
| methyl 3-(4-bromo-7-carbamoyl-1H-indol-2-yl)benzoate (prepared using A from Preparation #1 and 3-methoxycarbonylphenylboronic acid) | 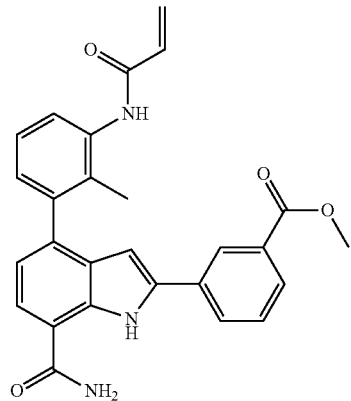 [SMILES: C=CC(=O)Nc1cccc(-c2ccc(C(N)=O)c3[nH]c(-c4cccc(C(=O)OC)c4)cc23)c1C] | A.1.19 | 2.77 (o) | 454 | A |
| methyl 4-(4-bromo-7-carbamoyl-1H-indol-2-yl)benzoate (prepared using A from Preparation #1 and 4-methoxycarbonylphenylboronic acid) | 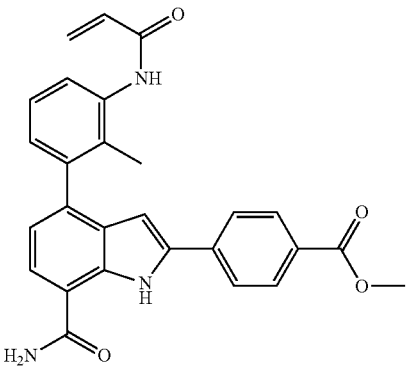 [SMILES: C=CC(=O)Nc1cccc(-c2ccc(C(N)=O)c3[nH]c(-c4ccc(C(=O)OC)cc4)cc23)c1C] | A.1.20 | 2.77 (o) | 454 | A |
| 4-bromo-2-(2,3-dihydrobenzofuran-5-yl)-1H-indole-7-carboxamide (prepared using A from Preparation #1 and 2,3-dihydrobenzofuran-5-boronic acid) | 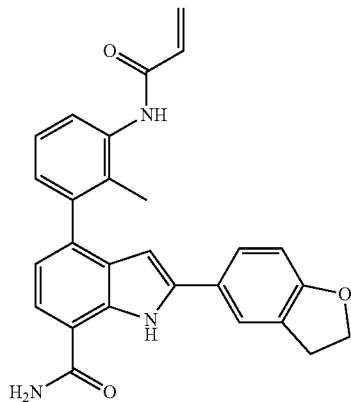 [SMILES: C=CC(=O)Nc1cccc(-c2ccc(C(N)=O)c3[nH]c(-c4ccc5c(c4)CCO5)cc23)c1C] | A.1.21 | 2.75 (o) | 438 | A |

TABLE A.1-continued

Examples prepared from N-(2-methyl-3-(4,4,5,5-tetramethyl-1,3,2-dioxaborolan-2-yl)phenyl)acrylamide (prepared using E from 2-methyl-3-(4,4,5,5-tetramethyl-1,3,2-dioxaborolan-2-yl)aniline and acryloyl chloride) using General Procedure A

| Aryl Bromide | Product | Example # | $R_t$ min (Table 1, Method) | m/z ESI+ $(M + H)^+$ | Btk IC$_{50}$ |
|---|---|---|---|---|---|
| 4-bromo-2-(3-methoxyphenyl)-1H-indole-7-carboxamide (prepared using A from Preparation #1 and 3-methoxy-phenylboronic acid) | | A.1.22 | 2.78 (o) | 426 | A |
| 4-bromo-2-(4-methoxyphenyl)-1H-indole-7-carboxamide (prepared using A from Preparation #1 and 4-methoxy-phenylboronic acid) | | A.1.23 | 2.76 (o) | 426 | A |
| 4-bromo-2-(6-methylpyridin-3-yl)-1H-indole-7-carboxamide (prepared using A from Preparation #1 and 6-methylpyridine-3-boronic acid) | | A.1.24 | 2.36 (d) | 411 | A |

TABLE A.1-continued

Examples prepared from N-(2-methyl-3-(4,4,5,5-tetramethyl-1,3,2-dioxaborolan-2-yl)phenyl)acrylamide (prepared using E from 2-methyl-3-(4,4,5,5-tetramethyl-1,3,2-dioxaborolan-2-yl)aniline and acryloyl chloride) using General Procedure A

| Aryl Bromide | Product | Example # | $R_t$ min (Table 1, Method) | m/z ESI+ (M + H)$^+$ | Btk IC$_{50}$ |
|---|---|---|---|---|---|
| 4-bromo-2-(3-carbamoylphenyl)-1H-indole-7-carboxamide (prepared using A from Preparation #1 and 3-aminocarbonylphenylboronic acid) | | A.1.25 | 2.68 (d) | 439 | A |
| 4-bromo-2-(3-fluorophenyl)-1H-indole-7-carboxamide (prepared using A from Preparation #1 and 3-fluorophenylboronic acid) | | A.1.26 | 2.82 (o) | 414 | A |
| 4-bromo-2-(3-(dimethylamino)phenyl)-1H-indole-7-carboxamide (prepared using A from Preparation #1 and 3-(N,N-dimethylamino)phenylboronic acid) | | A.1.27 | 2.24 (o) | 439 | A |

TABLE A.1-continued

Examples prepared from N-(2-methyl-3-(4,4,5,5-tetramethyl-1,3,2-dioxaborolan-2-yl)phenyl)acrylamide (prepared using E from 2-methyl-3-(4,4,5,5-tetramethyl-1,3,2-dioxaborolan-2-yl)aniline and acryloyl chloride) using General Procedure A

| Aryl Bromide | Product | Example # | R$_t$ min (Table 1, Method) | m/z ESI+ (M + H)$^+$ | Btk IC$_{50}$ |
|---|---|---|---|---|---|
| 4-bromo-2-(2-methyl-5-(pyrrolidin-1-ylsulfonyl)phenyl)-1H-indole-7-carboxamide (prepared using A from Preparation #1 and 2-methyl-5-(pyrrolidin-1-ylsulfonyl)phenylboronic acid) | | A.1.28 | 2.76 (o) | 543 | B |
| 4-bromo-2-(2-fluorophenyl)-1H-indole-7-carboxamide (prepared using A from Preparation #1 and 2-fluorophenylboronic acid) | | A.1.29 | 2.80 (o) | 414 | A |
| 4-bromo-2-(6-morpholinopyridin-3-yl)-1H-indole-7-carboxamide (prepared using A from Preparation #1 and 6-(morpholin-4-yl)pyridine-3-boronic acid pinacol ester) | | A.1.30 | 2.64 (d) | 482 | A |

TABLE A.1-continued

Examples prepared from N-(2-methyl-3-(4,4,5,5-tetramethyl-1,3,2-dioxaborolan-2-yl)phenyl)acrylamide (prepared using E from 2-methyl-3-(4,4,5,5-tetramethyl-1,3,2-dioxaborolan-2-yl)aniline and acryloyl chloride) using General Procedure A

| Aryl Bromide | Product | Example # | R$_t$ min (Table 1, Method) | m/z ESI+ (M + H)$^+$ | Btk IC$_{50}$ |
|---|---|---|---|---|---|
| 4-bromo-2-(4-(4-methylpiperazine-1-carbonyl)phenyl)-1H-indole-7-carboxamide (prepared using A from Preparation #1 and 3-(4-methyl-1-piperazinylcarbonyl)benzeneboronic acid pinacol ester) | 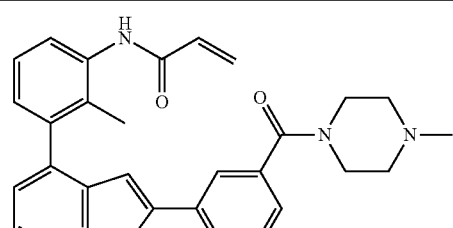 | A.1.31 | 2.34 (d) | 522 | A |
| 4-bromo-2-(4-fluorophenyl)-1H-indole-7-carboxamide (prepared using A from Preparation #1 and 4-fluorophenylboronic acid) | 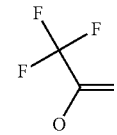 | A.1.32 | 2.80 (o) | 414 | A |
| 4-bromo-2-phenyl-1H-indole-7-carboxamide (prepared using A from Preparation #1 and phenylboronic acid pinacol ester) | 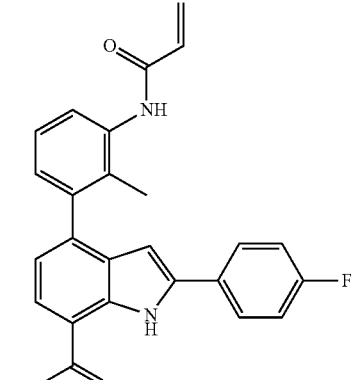 | A.1.33 | 2.77 (o) | 396 | A |

TABLE A.1-continued

Examples prepared from N-(2-methyl-3-(4,4,5,5-tetramethyl-1,3,2-dioxaborolan-2-yl)phenyl)acrylamide (prepared using E from 2-methyl-3-(4,4,5,5-tetramethyl-1,3,2-dioxaborolan-2-yl)aniline and acryloyl chloride) using General Procedure A

| Aryl Bromide | Product | Example # | $R_t$ min (Table 1, Method) | m/z ESI+ (M + H)+ | Btk IC$_{50}$ |
|---|---|---|---|---|---|
| 4-bromo-2-(2-(methylsulfonyl)phenyl)-1H-indole-7-carboxamide (prepared using A from Preparation #1 and 2-(methylsulfonyl)phenylboronic acid) | | A.1.34 | 2.85 (d) | 474 | B |
| 4-bromo-2-(4-(dimethylcarbamoyl)phenyl)-1H-indole-7-carboxamide (prepared using A from Preparation #1 and 4-(N,N-dimethylaminocarbonyl)phenylboronic acid) | | A.1.35 | 2.76 (d) | 467 | A |
| 4-bromo-2-(pyridin-3-yl)-1H-indole-7-carboxamide (prepared using A from Preparation #1 and 3-pyridineboronic acid pinacol ester) | | A.1.36 | 1.71 (a) | 397 | A |

TABLE A.1-continued

Examples prepared from N-(2-methyl-3-(4,4,5,5-tetramethyl-1,3,2-dioxaborolan-2-yl)phenyl)acrylamide (prepared using E from 2-methyl-3-(4,4,5,5-tetramethyl-1,3,2-dioxaborolan-2-yl)aniline and acryloyl chloride) using General Procedure A

| Aryl Bromide | Product | Example # | $R_t$ min (Table 1, Method) | m/z ESI+ $(M + H)^+$ | Btk IC$_{50}$ |
|---|---|---|---|---|---|
| 4-bromo-2-(4-(morpholine-4-carbonyl)phenyl)-1H-indole-7-carboxamide (prepared using A from Preparation #1 and 4-(morpholine-4-carbonyl)phenylboronic acid pinacol ester) | | A.1.37 | 2.74 (d) | 509 | A |
| 4-bromo-2-(4-(pyrrolidine-1-carbonyl)phenyl)-1H-indole-7-carboxamide (prepared using A from Preparation #1 and 4-(1-pyrrolidinylcarbonyl)benzeneboronic acid pinacol ester) | | A.1.38 | 2.87 (d) | 493 | A |
| 4-bromo-2-(4-(4-methylpiperazine-1-carbonyl)phenyl)-1H-indole-7-carboxamide (prepared using A from Preparation #1 and 4-(4-methyl-1-piperazinylcarbonyl)benzeneboronic acid pinacol ester) | | A.1.39 | 2.31 (d) | 522 | A |

TABLE A.1-continued

Examples prepared from N-(2-methyl-3-(4,4,5,5-tetramethyl-1,3,2-dioxaborolan-2-yl)phenyl)acrylamide (prepared using E from 2-methyl-3-(4,4,5,5-tetramethyl-1,3,2-dioxaborolan-2-yl)aniline and acryloyl chloride) using General Procedure A

| Aryl Bromide | Product | Example # | R$_t$ min (Table 1, Method) | m/z ESI+ (M + H)$^+$ | Btk IC$_{50}$ |
|---|---|---|---|---|---|
| 4-bromo-2-(4-(methylsulfonyl)phenyl)-1H-indole-7-carboxamide (prepared using A from Preparation #1 and 4-(methylsulfonyl)phenylboronic acid) | | A.1.40 | 2.49 (o) | 474 | A |
| 4-bromo-2-(6-methoxypyridin-3-yl)-1H-indole-7-carboxamide (prepared using A from Preparation #1 and 2-methoxy-5-pyridineboronic acid) | | A.1.41 | 2.89 (d) | 427 | A |
| 4-bromo-2-(4-cyanophenyl)-1H-indole-7-carboxamide (prepared using A from Preparation #1 and 4-cyanophenylboronic acid) | | A.1.42 | 3.01 (d) | 421 | A |

TABLE A.1-continued

Examples prepared from N-(2-methyl-3-(4,4,5,5-tetramethyl-1,3,2-dioxaborolan-2-yl)phenyl)acrylamide (prepared using E from 2-methyl-3-(4,4,5,5-tetramethyl-1,3,2-dioxaborolan-2-yl)aniline and acryloyl chloride) using General Procedure A

| Aryl Bromide | Product | Example # | R$_t$ min (Table 1, Method) | m/z ESI+ (M + H)+ | Btk IC$_{50}$ |
|---|---|---|---|---|---|
| 4-bromo-2-(2-methoxyphenyl)-1H-indole-7-carboxamide (prepared using A from Preparation #1 and 2-methoxy-phenylboronic acid) | | A.1.43 | 3.10 (d) | 426 | A |
| 4-bromo-2-(4-(morpholinomethyl)phenyl)-1H-indole-7-carboxamide (prepared using A from Preparation #1 and 4-(4-morpholinylmethyl)-benzeneboronic acid pinacol ester) | | A.1.44 | 2.37 (d) | 495 | A |
| 4-bromo-2-(4-carbamoylphenyl)-1H-indole-7-carboxamide (prepared using A from Preparation #1 and 4-aminocarbonylphenylboronic acid) | | A.1.45 | 2.61 (d) | 439 | A |

TABLE A.2

Examples prepared from N-(2-methyl-3-(4,4,5,5-tetramethyl-1,3,2-dioxaborolan-2-yl)phenyl)thiazole-2-carboxamide (Preparation #4) using General Procedure A

| Aryl Bromide | Product | Example # | R$_t$ min (Table 1, Method) | m/z ESI+ (M + H)$^+$ | Btk IC$_{50}$ |
|---|---|---|---|---|---|
| 4-bromo-2-(1-methyl-6-oxo-1,6-dihydropyridin-3-yl)-1H-indole-7-carboxamide (prepared using A from Preparation #1 and 1-methyl-5-(4,4,5,5-tetramethyl-1,3,2-dioxaborolan-2-yl)pyridin-2(1H)-one (Preparation #5) | 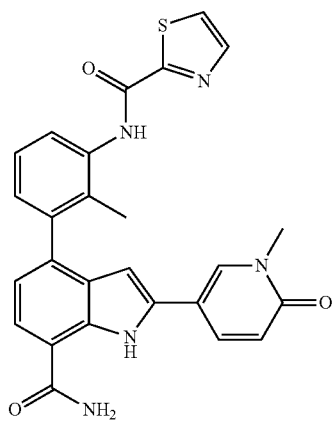 [SMILES: Cc1c(NC(=O)c2nccs2)cccc1-c1ccc(C(N)=O)c2[nH]c(-c3ccc(=O)n(C)c3)cc12] | A.2.1 | 2.90 (d) | 484 | A |
| 4-bromo-2-(1-methyl-1H-pyrazol-4-yl)-1H-indole-7-carboxamide (Preparation #10) | 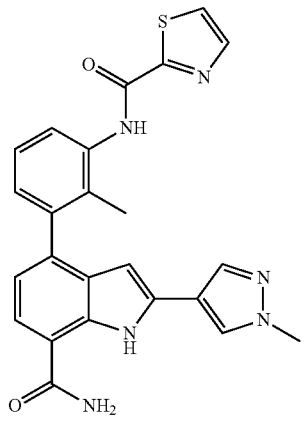 [SMILES: Cc1c(NC(=O)c2nccs2)cccc1-c1ccc(C(N)=O)c2[nH]c(-c3cnn(C)c3)cc12] | A.2.2 | 2.87 (d) | 457 | A |

TABLE A.3

Examples prepared from 2-(1-acetyl-1,2,3,6-tetrahydropyridin-4-yl)-4-bromo-1H-indole-7-carboxamide (prepared using A with 4-bromo-2-iodo-1H-indole-7-carboxamide (Preparation #1) and 1-(4-(4,4,5,5-tetramethyl-1,3,2-dioxaborolan-2-yl)-5,6-dihydropyridin-1(2H)-yl)ethanone [Combi-Blocks]) using General Procedure A

| Boronate | Product | Example # | $R_t$ min (Table 1, Method) | m/z ESI+ (M + H)$^+$ | Btk IC$_{50}$ |
|---|---|---|---|---|---|
| 3-(2-methyl-3-(4,4,5,5-tetramethyl-1,3,2-dioxaborolan-2-yl)phenyl)quinazolin-4(3H)-one [WO 2011159857] | 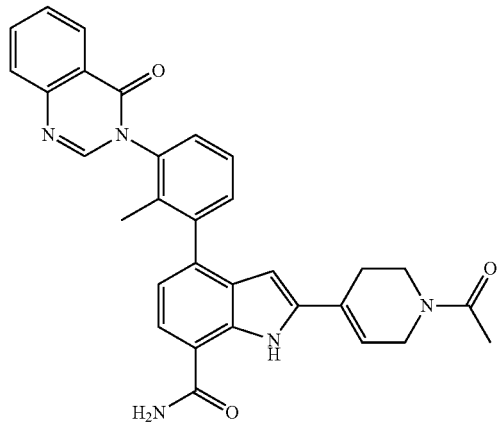 [SMILES: CC(=O)N1CC=C(c2cc3c(-c4cccc(-n5cnc6ccccc6c5=O)c4C)ccc(C(N)=O)c3[nH]2)CC1] | A.3.1 | 1.89 (g) | 518 | A |
| 6-fluoro-3-(2-methyl-3-(4,4,5,5-tetramethyl-1,3,2-dioxaborolan-2-yl)phenyl)quinazolin-4(3H)-one [WO 2011159857] | 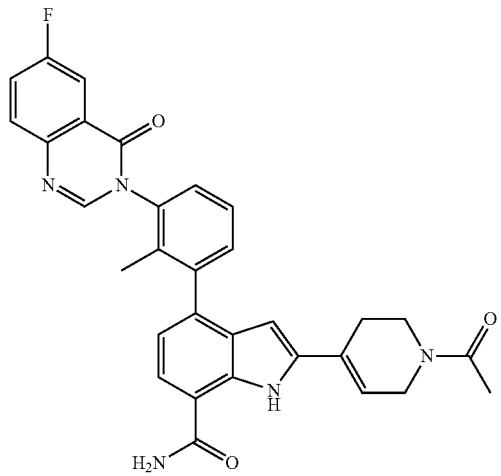 [SMILES: CC(=O)N1CC=C(c2cc3c(-c4cccc(-n5cnc6ccc(F)cc6c5=O)c4C)ccc(C(N)=O)c3[nH]2)CC1] | A.3.2 | 1.52 (g) | 536 | A |
| 4-tert-butyl-N-(2-methyl-3-(4,4,5,5-tetramethyl-1,3,2-dioxaborolan-2-yl)phenyl)benzamide [WO 2006/099075] | 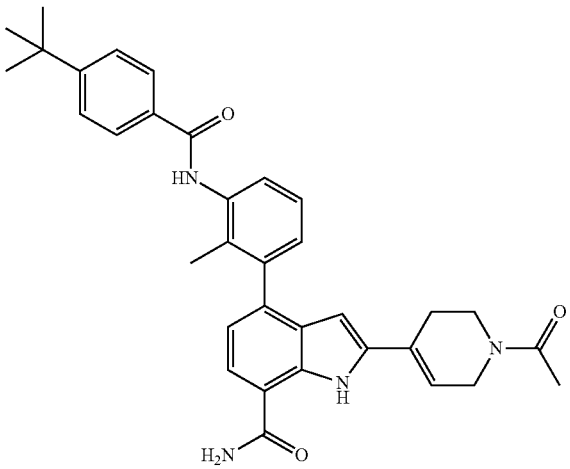 [SMILES: CC(=O)N1CC=C(c2cc3c(-c4cccc(NC(=O)c5ccc(C(C)(C)C)cc5)c4C)ccc(C(N)=O)c3[nH]2)CC1] | A.3.3 | 1.84 (g) | 549 | A |

TABLE A.3-continued

Examples prepared from 2-(1-acetyl-1,2,3,6-tetrahydropyridin-4-yl)-4-bromo-1H-indole-7-carboxamide (prepared using A with 4-bromo-2-iodo-1H-indole-7-carboxamide (Preparation #1) and 1-(4-(4,4,5,5-tetramethyl-1,3,2-dioxaborolan-2-yl)-5,6-dihydropyridin-1(2H)-yl)ethanone [Combi-Blocks]) using General Procedure A

| Boronate | Product | Example # | $R_t$ min (Table 1, Method) | m/z ESI+ (M + H)+ | Btk IC$_{50}$ |
|---|---|---|---|---|---|
| N-(2-methyl-3-(4,4,5,5-tetramethyl-1,3,2-dioxaborolan-2-yl)phenyl)thiazole-2-carboxamide (Preparation #4) | | A.3.4 | 1.51 (g) | 500 | A |
| N-(2-methyl-3-(4,4,5,5-tetramethyl-1,3,2-dioxaborolan-2-yl)phenyl)-4,5,6,7-tetrahydrobenzo[b]thiophene-2-carboxamide [WO 2006/099075] | | A.3.5 | 1.76 (g) | 553 | A |
| 4-cyclopropyl-N-(2-methyl-3-(4,4,5,5-tetramethyl-1,3,2-dioxaborolan-2-yl)phenyl)benzamide [US 20090105209] | | A.3.6 | 1.68 (g) | 533 | A |

TABLE A.3-continued

Examples prepared from 2-(1-acetyl-1,2,3,6-tetrahydropyridin-4-yl)-4-bromo-1H-
indole-7-carboxamide (prepared using A with 4-bromo-2-iodo-1H-indole-7-carboxamide
(Preparation #1) and 1-(4-(4,4,5,5-tetramethyl-1,3,2-dioxaborolan-2-yl)-5,6-dihydropyridin-
1(2H)-yl)ethanone [Combi-Blocks]) using General Procedure A

| Boronate | Product | Example # | $R_t$ min (Table 1, Method) | m/z ESI+ $(M + H)^+$ | Btk IC$_{50}$ |
|---|---|---|---|---|---|
| 4-(difluoromethyl)-N-(2-methyl-3-(4,4,5,5-tetramethyl-1,3,2-dioxaborolan-2-yl)phenyl)benzamide (Preparation #29) | 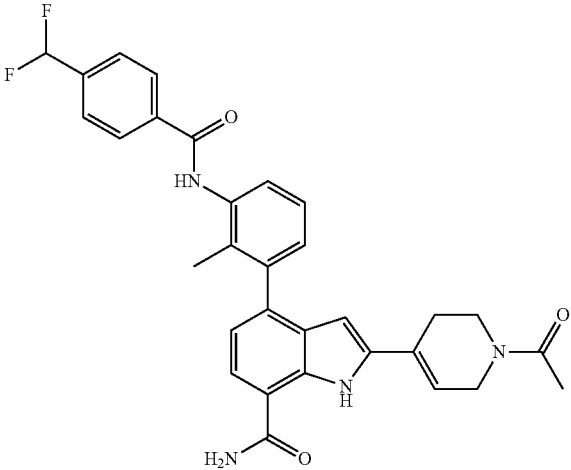 [SMILES: CC(=O)N1CC=C(c2cc3c(-c4cccc(NC(=O)c5ccc(C(F)F)cc5)c4C)ccc(C(N)=O)c3[nH]2)CC1] | A.3.7 | 1.59 (g) | 543 | A |
| 4-(2-cyanopropan-2-yl)-N-(2-methyl-3-(4,4,5,5-tetramethyl-1,3,2-dioxaborolan-2-yl)phenyl)benzamide (prepared using D from 2-methyl-3-(4,4,5,5-tetramethyl-1,3,2-dioxaborolan-2-yl)aniline [Combi-Block] and 4-(2-cyanopropan-2-yl)benzoic acid) | 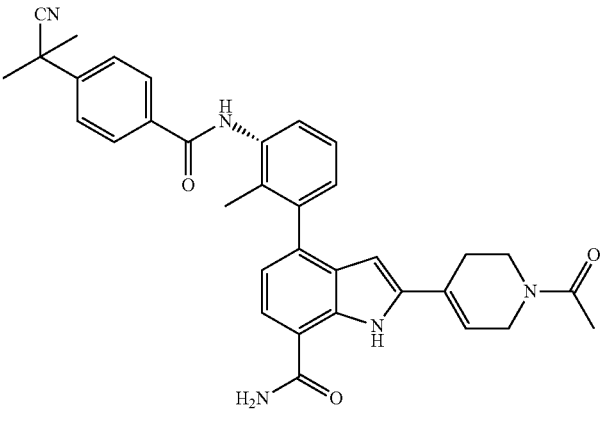 | A.3.8 | 1.69 (g) | 560 | A |

TABLE A.4

Examples prepared from 4-bromo-2-(1-(methylsulfonyl)-1,2,3,6-tetrahydropyridin-4-yl)-1H-indole-7-carboxamide (Preparation #18) using General Procedure A

| Boronate | Product | Example # | $R_t$ min (Table 1, Method) | m/z ESI+ (M + H)+ | Btk IC$_{50}$ |
|---|---|---|---|---|---|
| N-(3-(4,4,5,5-tetramethyl-1,3,2-dioxaborolan-2-yl)benzyl)acrylamide (prepared using E from (3-(4,4,5,5-tetramethyl-1,3,2-dioxaborolan-2-yl)phenyl)methanamine [ChemMaker] and acryloyl chloride) | 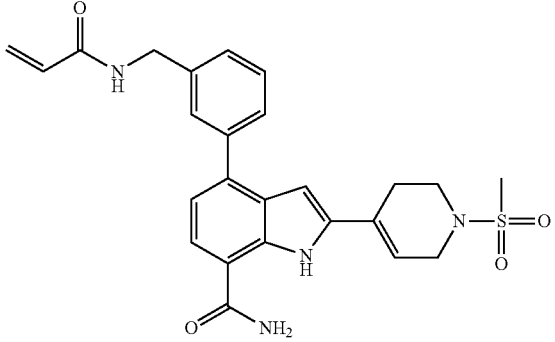 [SMILES: C=CC(=O)NCc1cccc(-c2ccc(C(N)=O)c3[nH]c(C4=CCN(S(C)(=O)=O)CC4)cc23)c1] | A.4.1 | 1.59 (g) | 479 | A |
| 2-(4,4,5,5-tetramethyl-1,3,2-dioxaborolan-2-yl)aniline | 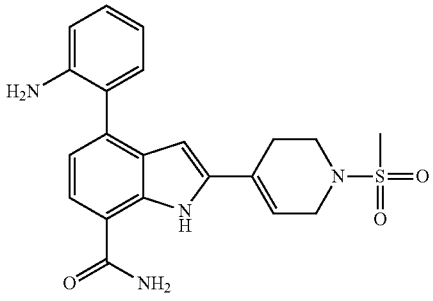 [SMILES: CS(=O)(=O)N1CC=C(c2cc3c(-c4ccccc4N)ccc(C(N)=O)c3[nH]2)CC1] | A.4.2 | 1.27 (f) | 411 | A |
| N-(2-(4,4,5,5-tetramethyl-1,3,2-dioxaborolan-2-yl)phenyl)acrylamide (prepared using E from 2-aminophenylboronic acid pinacol ester and acryloyl chloride) | 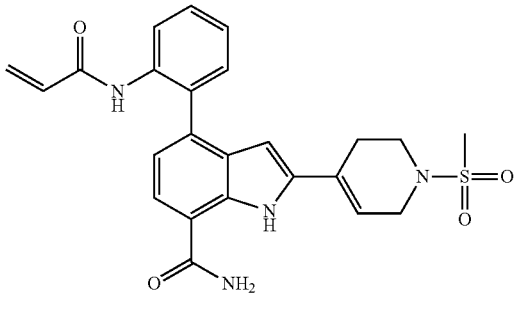 [SMILES: C=CC(=O)Nc1ccccc1-c1ccc(C(N)=O)c2[nH]c(C3=CCN(S(C)(=O)=O)CC3)cc12] | A.4.3 | 1.62 (g) | 465 | A |
| 2-((3-(4,4,5,5-tetramethyl-1,3,2-dioxaborolan-2-yl)phenoxy)methyl)thiazole (prepared using Q from 3-(4,4,5,5-tetramethyl-1,3,2-dioxaborolan-2-yl)phenol and thiazol-2-ylmethanol) | 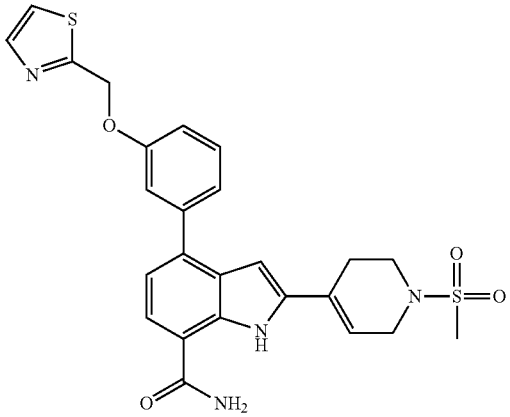 [SMILES: CS(=O)(=O)N1CC=C(c2cc3c(-c4cccc(OCc5nccs5)c4)ccc(C(N)=O)c3[nH]2)CC1] | A.4.4 | 1.83 (g) | 509 | A |

TABLE A.4-continued

Examples prepared from 4-bromo-2-(1-(methylsulfonyl)-1,2,3,6-tetrahydropyridin-4-yl)-1H-indole-7-carboxamide (Preparation #18) using General Procedure A

| Boronate | Product | Example # | $R_t$ min (Table 1, Method) | m/z ESI+ (M + H)+ | Btk IC$_{50}$ |
|---|---|---|---|---|---|
| 2-methyl-3-(4,4,5,5-tetramethyl-1,3,2-dioxaborolan-2-yl)aniline [CombiBlocks] | | A.4.5 | 1.15 (f) | 425 | A |
| 2-(2-methyl-3-(4,4,5,5-tetramethyl-1,3,2-dioxaborolan-2-yl)phenyl)-3,4-dihydroisoquinolin-1(2H)-one (Preparation #3) | | A.4.6 | 1.79 (f) | 555 | A |
| phenylboronic acid | | A.4.7 | 1.72 (f) | 396 | A |
| 4-(3-(4,4,5,5-tetramethyl-1,3,2-dioxaborolan-2-yl)phenylamino)pyrimidine-2-carbonitrile (Preparation #6) | | A.4.8 | 1.60 (f) | 514 | A |

TABLE A.4-continued

Examples prepared from 4-bromo-2-(1-(methylsulfonyl)-1,2,3,6-tetrahydropyridin-4-yl)-1H-indole-7-carboxamide (Preparation #18) using General Procedure A

| Boronate | Product | Example # | R$_t$ min (Table 1, Method) | m/z ESI+ (M + H)$^+$ | Btk IC$_{50}$ |
|---|---|---|---|---|---|
| (1s,4s)-4-hydroxy-N-(2-methyl-3-(4,4,5,5-tetramethyl-1,3,2-dioxaborolan-2-yl)phenyl)-4-(trifluoromethyl)cyclohexane-carboxamide (Preparation #8) | | A.4.9 | 1.56 (a) | 619 | A |
| 4-(difluoromethyl)-N-(2-methyl-3-(4,4,5,5-tetramethyl-1,3,2-dioxaborolan-2-yl)phenyl)benzamide (prepared using D from 4-(difluoromethyl)benzoic acid [Oakwood] and 2-methyl-3-(4,4,5,5-tetramethyl-1,3,2-dioxaborolan-2-yl)aniline [Combi-Blocks]) | | A.4.10 | 2.06 (a) | 579 | A |
| N-(2-methyl-3-(4,4,5,5-tetramethyl-1,3,2-dioxaborolan-2-yl)phenyl)oxetan-3-amine (prepared using H from 2-methyl-3-(4,4,5,5-tetramethyl-1,3,2-dioxaborolan-2-yl)aniline [Combi-Blocks] and 3-oxetanone [Molbridge]) | | A.4.11 | 1.84 (a) | 481 | A |

TABLE A.4-continued

Examples prepared from 4-bromo-2-(1-(methylsulfonyl)-1,2,3,6-tetrahydropyridin-4-yl)-1H-indole-7-carboxamide (Preparation #18) using General Procedure A

| Boronate | Product | Example # | R$_t$ min (Table 1, Method) | m/z ESI+ (M + H)$^+$ | Btk IC$_{50}$ |
|---|---|---|---|---|---|
| 4-(difluoromethyl)-N-(2-methyl-3-(4,4,5,5-tetramethyl-1,3,2-dioxaborolan-2-yl)phenyl)-N-(oxetan-3-yl)benzamide (Preparation #25) | | A.4.12 | 1.94 (a) | 635 | A |
| 2-(2-methyl-3-(4,4,5,5-tetramethyl-1,3,2-dioxaborolan-2-yl)phenylamino)ethanol (prepared using J from 2-methyl-3-(4,4,5,5-tetramethyl-1,3,2-dioxaborolan-2-yl)aniline [Combi-Blocks] and 2-iodo-ethanol) | | A.4.13 | 1.72 (a) | 469 | A |
| 4-(difluoromethyl)-N-(2-hydroxyethyl)-N-(2-methyl-3-(4,4,5,5-tetramethyl-1,3,2-dioxaborolan-2-yl)phenyl)benzamide (prepared using J from 2-methyl-3-(4,4,5,5-tetramethyl-1,3,2-dioxaborolan-2-yl)aniline [Combi-Blocks] and 2-iodo-ethanol, D from 4-(difluoromethyl)benzoic acid [Oakwood]) | | A.4.14 | 1.82 (a) | 623 | A |

TABLE A.4-continued

Examples prepared from 4-bromo-2-(1-(methylsulfonyl)-1,2,3,6-tetrahydropyridin-4-yl)-1H-indole-7-carboxamide (Preparation #18) using General Procedure A

| Boronate | Product | Example # | R$_t$ min (Table 1, Method) | m/z ESI+ (M + H)$^+$ | Btk IC$_{50}$ |
|---|---|---|---|---|---|
| N-(3-(4,4,5,5-tetramethyl-1,3,2-dioxaborolan-2-yl)phenyl)acrylamide (Preparation #22) | | A.4.15 | 1.63 (g) | 465 | A |
| 4-cyclopropyl-N-(2-methyl-3-(4,4,5,5-tetramethyl-1,3,2-dioxaborolan-2-yl)phenyl)benzamide [US 20090105209] | | A.4.16 | 1.85 (g) | 569 | A |
| N-(2-methyl-3-(4,4,5,5-tetramethyl-1,3,2-dioxaborolan-2-yl)phenyl)thiazole-2-carboxamide (Preparation #4) | | A.4.17 | 1.68 (g) | 536 | A |

TABLE A.4-continued

Examples prepared from 4-bromo-2-(1-(methylsulfonyl)-1,2,3,6-tetrahydropyridin-4-yl)-1H-indole-7-carboxamide (Preparation #18) using General Procedure A

| Boronate | Product | Example # | $R_t$ min (Table 1, Method) | m/z ESI+ (M + H)$^+$ | Btk IC$_{50}$ |
|---|---|---|---|---|---|
| 3-(2-methyl-3-(4,4,5,5-tetramethyl-1,3,2-dioxaborolan-2-yl)phenyl)quinazolin-4(3H)-one [WO 2011159857] | | A.4.18 | 1.66 (g) | 554 | A |
| 6-fluoro-3-(2-methyl-3-(4,4,5,5-tetramethyl-1,3,2-dioxaborolan-2-yl)phenyl)quinazolin-4(3H)-one [WO 2011159857] | | A.4.19 | 1.71 (g) | 572 | A |

TABLE A.5

Examples prepared from 4-bromo-1H-indole-7-carboxamide (Preparation #2) using General Procedure A

| Boronate | Product | Example # | $R_t$ min (Table 1, Method) | m/z ESI+ (M + H)$^+$ | Btk IC$_{50}$ |
|---|---|---|---|---|---|
| 2-(4,4,5,5-tetramethyl-1,3,2-dioxaborolan-2-yl)aniline | | A.5.1 | 1.04 (f) | 252 | C |

TABLE A.5-continued

Examples prepared from 4-bromo-1H-indole-7-carboxamide (Preparation #2) using General Procedure A

| Boronate | Product | Example # | R, min (Table 1, Method) | m/z ESI+ (M + H)+ | Btk IC$_{50}$ |
|---|---|---|---|---|---|
| N-(3-(4,4,5,5-tetramethyl-1,3,2-dioxaborolan-2-yl)phenyl)acrylamide (Preparation #22) | | A.5.2 | 1.36 (f) | 306 | B |
| 4-(4,4,5,5-tetramethyl-1,3,2-dioxaborolan-2-yl)pyridin-2-amine | | A.5.3 | 0.45 (f) | 253 | C |
| 5-(4,4,5,5-tetramethyl-1,3,2-dioxaborolan-2-yl)pyridin-3-amine [Maybridge] | | A.5.4 | 0.31 (f) | 253 | C |
| 3-(2-methyl-3-(4,4,5,5-tetramethyl-1,3,2-dioxaborolan-2-yl)phenyl)quinazolin-4(3H)-one [US 20100160303] | | A.5.5 | 1.82 (a) | 395 | B |

TABLE A.5-continued

Examples prepared from 4-bromo-1H-indole-7-carboxamide (Preparation #2) using General Procedure A

| Boronate | Product | Example # | R$_t$ min (Table 1, Method) | m/z ESI+ (M + H)$^+$ | Btk IC$_{50}$ |
|---|---|---|---|---|---|
| 4-(tert-butyl)-N-(2-methyl-3-(4,4,5,5-tetramethyl-1,3,2-dioxaborolan-2-yl)phenyl)benzamide [WO 2006/099075] | | A.5.6 | 2.28 (a) | 426 | C |

TABLE A.6

Examples prepared from 4-(4,4,5,5-tetramethyl-1,3,2-dioxaborolan-2-yl)-1H-indole-7-carboxamide (Preparation #P.1) using General Procedure A

| Arylbromide | Product | Example # | R$_t$ min (Table 1, Method) | m/z ESI+ (M + MeCN + H) | Btk IC$_{50}$ |
|---|---|---|---|---|---|
| 3-bromo-N-(cyanomethyl)benzenesulfonamide (Preparation #29) | | A.6.1 | 1.32 (f) | 396 | C |
| 3-bromo-N-methylaniline | | A.6.2 | 0.95 (f) | 307 | C |

TABLE A.7

Examples prepared from 4-iodo-2-(pyridin-3-yl)-1H-indole-7-carboxamide (Example #F.1) using General Procedure A

| Boronate | Product | Example # | $R_t$ min (Table 1, Method) | m/z APCI+ (M + H)$^+$ | Btk IC$_{50}$ |
|---|---|---|---|---|---|
| 4-(tert-butyl)-N-(2-methyl-3-(4,4,5,5-tetramethyl-1,3,2-dioxaborolan-2-yl)phenyl)benzamide [WO 2006/099075] | | A.7.1 | 1.93 (aa) | 503 | A |
| 3-(2-methyl-3-(4,4,5,5-tetramethyl-1,3,2-dioxaborolan-2-yl)phenyl)quinazolin-4(3H)-one [WO 2011159857] | | A.7.2 | 1.88 (ac) | 472 | A |
| N-(2-methyl-3-(4,4,5,5-tetramethyl-1,3,2-dioxaborolan-2-yl)phenyl)-4,5,6,7-tetrahydrobenzo[b]thiophene-2-carboxamide [WO 2006/099075] | | A.7.3 | 1.85 (ab) | 507 | A |

TABLE A.7-continued

Examples prepared from 4-iodo-2-(pyridin-3-yl)-1H-indole-7-carboxamide (Example #F.1) using General Procedure A

| Boronate | Product | Example # | R$_t$ min (Table 1, Method) | m/z APCI+ (M + H)$^+$ | Btk IC$_{50}$ |
|---|---|---|---|---|---|
| 2-(2-methyl-3-(4,4,5,5-tetramethyl-1,3,2-dioxaborolan-2-yl)phenyl)isoindolin-1-one [U.S. 20100160303] | 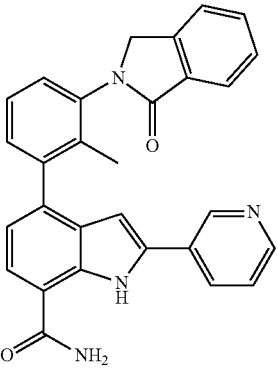 [SMILES: Cc1c(-c2ccc(C(N)=O)c3[nH]c(-c4cccnc4)cc23)cccc1N1Cc2ccccc2C1=O] | A.7.4 | 1.90 (ac) | 459 | A |
| 6-methyl-2-(2-methyl-3-(4,4,5,5-tetramethyl-1,3,2-dioxaborolan-2-yl)phenyl)isoindolin-1-one [U.S. 2010/0160303] | 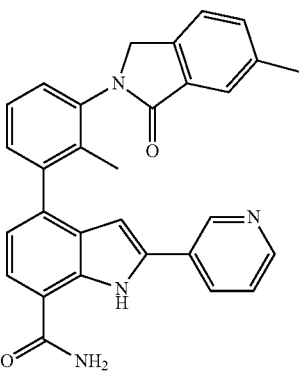 [SMILES: Cc1ccc2c(c1)C(=O)N(c1cccc(-c3ccc(C(N)=O)c4[nH]c(-c5cccnc5)cc34)c1C)C2] | A.7.5 | 1.99 (ac) | 473 | A |
| 6-fluoro-2-(2-methyl-3-(4,4,5,5-tetramethyl-1,3,2-dioxaborolan-2-yl)phenyl)isoindolin-1-one [WO 2011/159857 A1] | 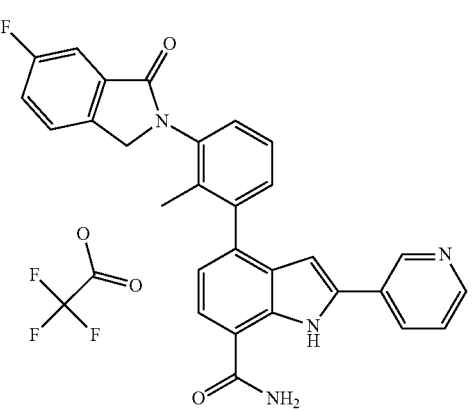 [SMILES: Cc1c(-c2ccc(C(N)=O)c3[nH]c(-c4cccnc4)cc23)cccc1N1Cc2ccc(F)cc2C1=O ; O=C(O)C(F)(F)F] | A.7.6 | 1.98 (a) | 477 | A |

TABLE A.7-continued

Examples prepared from 4-iodo-2-(pyridin-3-yl)-1H-indole-7-carboxamide (Example #F.1) using General Procedure A

| Boronate | Product | Example # | R$_t$ min (Table 1, Method) | m/z APCI+ (M + H)$^+$ | Btk IC$_{50}$ |
|---|---|---|---|---|---|
| N-(4-methyl-3-(4,4,5,5-tetramethyl-1,3,2-dioxaborolan-2-yl)phenyl)thiazole-2-carboxamide (prepared using E from 5-amino-2-methylphenylboronic acid, pinacol ester and 1,3-thiazole-2-carbonyl chloride [Maybridge-International]) | | A.7.7 | 1.65 (f) | 454 | C |
| N-(2-methyl-3-(4,4,5,5-tetramethyl-1,3,2-dioxaborolan-2-yl)phenyl)thiazole-2-carboxamide (Preparation #4) | | A.7.8 | 1.87 (a) | 454 | A |

TABLE A.8

Examples prepared from 4-iodo-2-(p-tolyl)-1H-indole-7-carboxamide (prepared using F from 1-(p-tolyl)ethanone) using General Procedure A

| Boronic Acid or Boronate | Product | Example # | R$_t$ min (Table 1, Method) | m/z APCI+ (M + H)$^+$ | Btk IC$_{50}$ |
|---|---|---|---|---|---|
| pyrazole-3-boronic acid | | A.8.1 | 1.93 (a) | 317 | B |

TABLE A.8-continued

Examples prepared from 4-iodo-2-(p-tolyl)-1H-indole-7-carboxamide (prepared using F from 1-(p-tolyl)ethanone) using General Procedure A

| Boronic Acid or Boronate | Product | Example # | $R_t$ min (Table 1, Method) | m/z APCI+ $(M + H)^+$ | Btk $IC_{50}$ |
|---|---|---|---|---|---|
| 3,5-dimethylisoxazole-4-boronic acid pinacol ester | | A.8.2 | 2.27 (a) | 346 | B |
| pyridine-3-boronic acid | | A.8.3 | 2.15 (a) | 328 | B |
| pyridine-4-boronic acid | | A.8.4 | 2.27 (a) | 328 | B |
| 5-acetylthiophen-2-ylboronic acid | | A.8.5 | 0.92 (e) | 375 | B |

TABLE A.8-continued

Examples prepared from 4-iodo-2-(p-tolyl)-1H-indole-7-carboxamide (prepared using F from 1-(p-tolyl)ethanone) using General Procedure A

| Boronic Acid or Boronate | Product | Example # | R$_t$ min (Table 1, Method) | m/z APCI+ (M + H)$^+$ | Btk IC$_{50}$ |
|---|---|---|---|---|---|
| 4,4,5,5-tetramethyl-2-(thiophen-3-yl)-1,3,2-dioxaborolane | 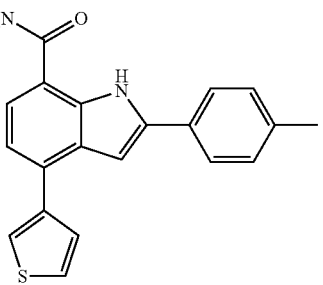 | A.8.6 | 0.97 (e) | 333 | B |
| 1-methyl-4-(4,4,5,5-tetramethyl-1,3,2-dioxaborolan-2-yl)-1H-pyrazole | 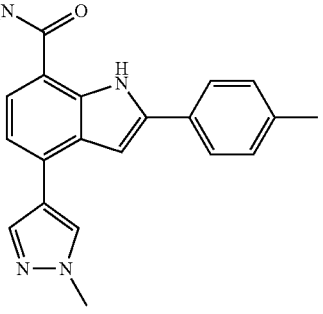 | A.8.7 | 0.83 (e) | 331 | B |
| 1H-pyrazol-3-ylboronic acid | 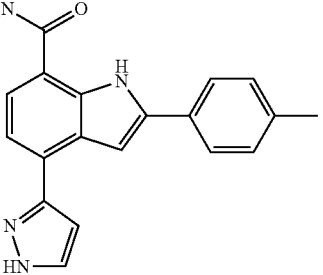 | A.8.8 | 0.81 (e) | 317 | B |
| thiophen-2-ylboronic acid | 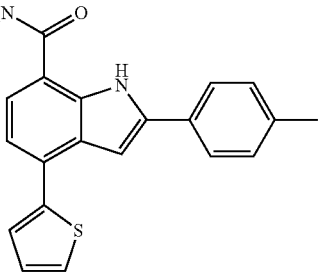 | A.8.9 | 0.97 (e) | 333 | B |
| thiophen-3-ylboronic acid | 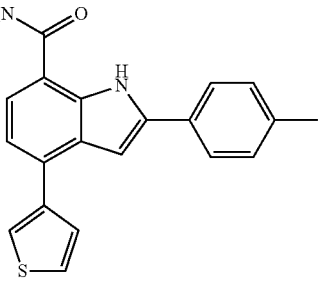 | A.8.10 | 0.97 (e) | 333 | B |

TABLE A.9

Examples prepared from 4-iodo-2-(p-tolyl)-1H-indole-7-carboxamide (prepared with F using 1-(4-fluorophenyl)ethanone) using General Procedure A

| Boronic Acid or Boronate | Product | Example # | R$_t$ min (Table 1, Method) | m/z APCI+ (M + H)$^+$ | Btk IC$_{50}$ |
|---|---|---|---|---|---|
| pyrimidine-5-boronic acid | 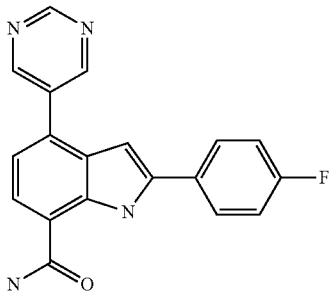 [SMILES: NC(=O)c1ccc(-c2cncnc2)c2cc(-c3ccc(F)cc3)[nH]c12] | A.9.1 | 1.82 (a) | 333 | B |
| pyridine-3-boronic acid | 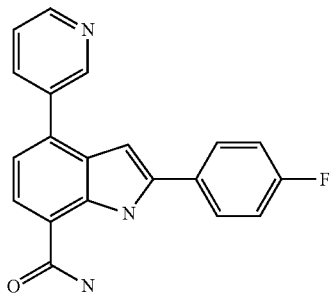 [SMILES: NC(=O)c1ccc(-c2cccnc2)c2cc(-c3ccc(F)cc3)[nH]c12] | A.9.2 | 2.05 (a) | 332 | A |
| 3,5-dimethylisoxazole-4-boronic acid pinacol ester | 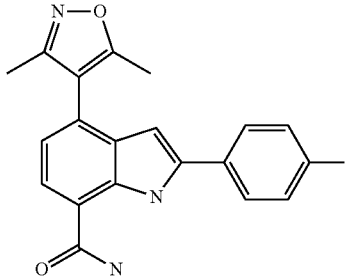 | A.9.3 | 2.18 (a) | 350 | B |
| pyridine-4-boronic acid | 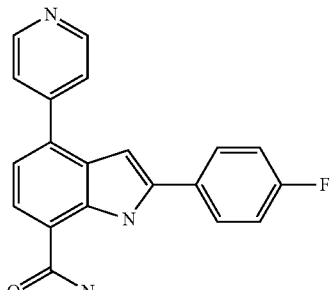 | A.9.4 | 2.15 (a) | 332 | B |
| pyrazole-3-boronic acid | 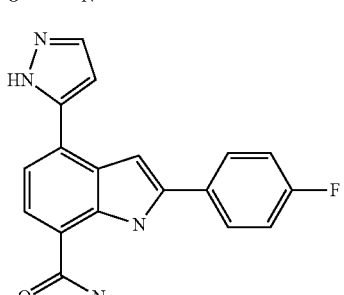 | A.9.5 | 1.87 (a) | 321 | B |

TABLE A.9-continued

Examples prepared from 4-iodo-2-(p-tolyl)-1H-indole-7-carboxamide (prepared with F using 1-(4-fluorophenyl)ethanone) using General Procedure A

| Boronic Acid or Boronate | Product | Example # | $R_t$ min (Table 1, Method) | m/z APCI+ $(M + H)^+$ | Btk $IC_{50}$ |
|---|---|---|---|---|---|
| 6-fluoro-2-(2-methyl-3-(4,4,5,5-tetramethyl-1,3,2-dioxaborolan-2-yl)phenyl)isoindolin-1-one [WO 2011/159857] | | A.9.6 | 2.37 (a) | 494 | A |
| N-(2-methyl-3-(4,4,5,5-tetramethyl-1,3,2-dioxaborolan-2-yl)phenyl)-4,5,6,7-tetrahydrobenzo[b]thiophene-2-carboxamide [WO 2006/099075] | | A.9.7 | 2.66 (a) | 524 | C |

TABLE A.10

Examples prepared from 4-bromo-2-(1-methyl-1H-pyrazol-4-yl)-1H-indole-7-carboxamide (prepared using A from 4-bromo-2-iodo-1H-indole-7-carboxamide (Preparation #1) with 1-methyl-4-(4,4,5,5-tetramethyl-1,3,2-dioxaborolan-2-yl)-1H-pyrazole) using General Procedure A

| Boronate | Product | Example # | $R_t$ min (Table 1, Method) | m/z APCI+ $(M + H)^+$ | Btk $IC_{50}$ |
|---|---|---|---|---|---|
| 3-(2-methyl-3-(4,4,5,5-tetramethyl-1,3,2-dioxaborolan-2-yl)phenyl)quinazolin-4(3H)-one [WO 2011159857] | | A.10.1 | 2.11 (c) | 475 | A |

TABLE A.10-continued

Examples prepared from 4-bromo-2-(1-methyl-1H-pyrazol-4-yl)-1H-indole-7-carboxamide (prepared using A from 4-bromo-2-iodo-1H-indole-7-carboxamide (Preparation #1) with 1-methyl-4-(4,4,5,5-tetramethyl-1,3,2-dioxaborolan-2-yl)-1H-pyrazole) using General Procedure A

| Boronate | Product | Example # | $R_t$ min (Table 1, Method) | m/z APCI+ $(M + H)^+$ | Btk $IC_{50}$ |
|---|---|---|---|---|---|
| 6-fluoro-3-(2-methyl-3-(4,4,5,5-tetramethyl-1,3,2-dioxaborolan-2-yl)phenyl)quinazolin-4(3H)-one [US 2010/0160303] | | A.10.2 | 1.90 (a) | 493 | A |
| N-(3-(7-carbamoyl-2-(1-methyl-1H-pyrazol-4-yl)-1H-indol-4-yl)-2-methylphenyl)-N-(oxetan-3-yl)thiazole-2-carboxamide (prepared using H from 2-methyl-3-(4,4,5,5-tetramethyl-1,3,2-dioxaborolan-2-yl)aniline [Combi-Blocks] and 3-oxetanone [Molbridge]), E with thiazole-2-carbonyl chloride [Maybridge]) | | A.10.3 | 1.48 (g) | 513 | A |
| N-methyl-N-(2-methyl-3-(4,4,5,5-tetramethyl-1,3,2-dioxaborolan-2-yl)phenyl)thiazole-2-carboxamide (Preparation #19) | | A.10.4 | 1.52 (f) | 471 | B |

TABLE A.10-continued

Examples prepared from 4-bromo-2-(1-methyl-1H-pyrazol-4-yl)-1H-indole-7-carboxamide (prepared using A from 4-bromo-2-iodo-1H-indole-7-carboxamide (Preparation #1) with 1-methyl-4-(4,4,5,5-tetramethyl-1,3,2-dioxaborolan-2-yl)-1H-pyrazole) using General Procedure A

| Boronate | Product | Example # | $R_t$ min (Table 1, Method) | m/z APCI+ (M + H)+ | Btk IC$_{50}$ |
|---|---|---|---|---|---|
| N-(2-methyl-3-(4,4,5,5-tetramethyl-1,3,2-dioxaborolan-2-yl)phenyl)-4,5,6,7-tetrahydrobenzo[b]thiophene-2-carboxamide [WO 2006/099075] | | A.10.5 | 1.84 (g) | 510 | A |

TABLE A.11

Examples prepared from 4-bromo-2-(3,6-dihydro-2H-pyran-4-yl)-1H-indole-7-carboxamide (prepared using A from 4-bromo-2-iodo-1H-indole-7-carboxamide (Preparation #1) and 2-(3,6-dihydro-2H-pyran-4-yl)-4,4,5,5-tetramethyl-1,3,2-dioxaborolane) using General Procedure A

| Boronate | Product | Example # | $R_t$ min (Table 1, Method) | m/z ESI+ (M + H)+ | Btk IC$_{50}$ |
|---|---|---|---|---|---|
| 3-(2-methyl-3-(4,4,5,5-tetramethyl-1,3,2-dioxaborolan-2-yl)phenyl)quinazolin-4(3H)-one [WO 2011159857] | | A.11.1 | 1.51 (g) | 477 | A |

TABLE A.11-continued

Examples prepared from 4-bromo-2-(3,6-dihydro-2H-pyran-4-yl)-1H-indole-7-carboxamide (prepared using A from 4-bromo-2-iodo-1H-indole-7-carboxamide (Preparation #1) and 2-(3,6-dihydro-2H-pyran-4-yl)-4,4,5,5-tetramethyl-1,3,2-dioxaborolane) using General Procedure A

| Boronate | Product | Example # | $R_t$ min (Table 1, Method) | m/z ESI+ $(M + H)^+$ | Btk $IC_{50}$ |
|---|---|---|---|---|---|
| 6-fluoro-3-(2-methyl-3-(4,4,5,5-tetramethyl-1,3,2-dioxaborolan-2-yl)phenyl)quinazolin-4(3H)-one [WO 2011159857] | 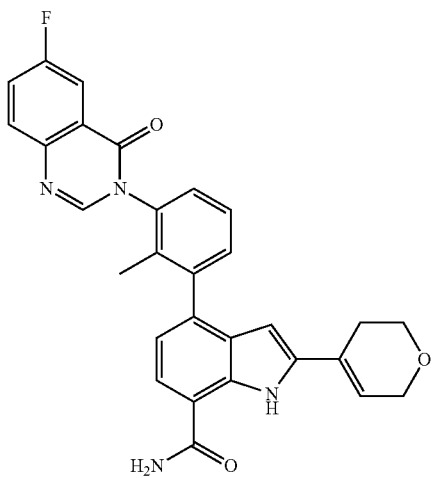 [SMILES: Cc1c(-c2ccc(C(N)=O)c3[nH]c(C4=CCOCC4)cc23)cccc1-n1cnc2ccc(F)cc2c1=O] | A.11.2 | 1.55 (g) | 495 | A |

TABLE A.12

Examples prepared from 4-bromo-2-(4-fluorophenyl)-1H-indole-7-carboxamide (prepared using A from 4-bromo-2-iodo-1H-indole-7-carboxamide (Preparation #1) and 2-(4-fluorophenyl)-4,4,5,5-tetramethyl-1,3,2-dioxaborolane) using General Procedure A

| Boronate | Product | Example # | $R_t$ min (Table 1, Method) | m/z ESI+ $(M + H)^+$ | Btk $IC_{50}$ |
|---|---|---|---|---|---|
| 3-(2-methyl-3-(4,4,5,5-tetramethyl-1,3,2-dioxaborolan-2-yl)phenyl)quinazolin-4(3H)-one [WO 2011159857] | 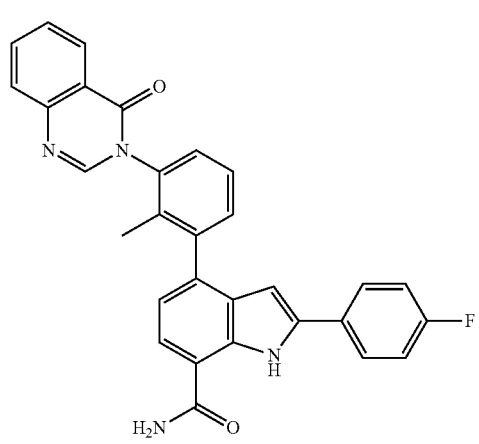 [SMILES: Cc1c(-c2ccc(C(N)=O)c3[nH]c(-c4ccc(F)cc4)cc23)cccc1-n1cnc2ccccc2c1=O] | A.12.1 | 1.78 (g) | 489 | A |

TABLE A.13

Examples prepared from 4-bromo-2-(pyrimidin-5-yl)-1H-indole-7-carboxamide (prepared using A from 4-bromo-2-iodo-1H-indole-7-carboxamide (Preparation #1) and 5-(4,4,5,5-tetramethyl-1,3,2-dioxaborolan-2-yl)pyrimidine) using General Procedure A

| Boronate | Product | Example # | $R_t$ min (Table 1, Method) | m/z ESI+ $(M + H)^+$ | Btk $IC_{50}$ |
|---|---|---|---|---|---|
| 3-(2-methyl-3-(4,4,5,5-tetramethyl-1,3,2-dioxaborolan-2-yl)phenyl)quinazolin-4(3H)-one [WO 2011159857] | 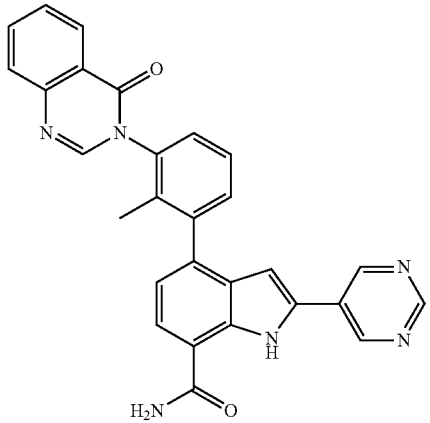 [SMILES: Cc1c(-c2ccc(C(N)=O)c3[nH]c(-c4cncnc4)cc23)cccc1-n1cnc2ccccc2c1=O] | A.13.1 | 1.52 (g) | 473 | B |
| 6-fluoro-3-(2-methyl-3-(4,4,5,5-tetramethyl-1,3,2-dioxaborolan-2-yl)phenyl)quinazolin-4(3H)-one [WO 2011159857] | 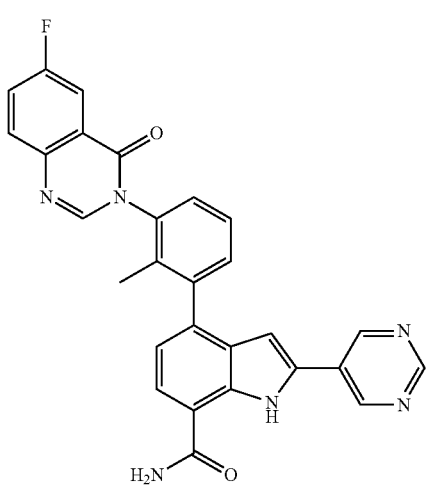 [SMILES: Cc1c(-c2ccc(C(N)=O)c3[nH]c(-c4cncnc4)cc23)cccc1-n1cnc2ccc(F)cc2c1=O] | A.13.2 | 1.59 (g) | 491 | B |
| 4-(difluoromethyl)-N-(2-methyl-3-(4,4,5,5-tetramethyl-1,3,2-dioxaborolan-2-yl)phenyl)benzamide (Preparation #29) | 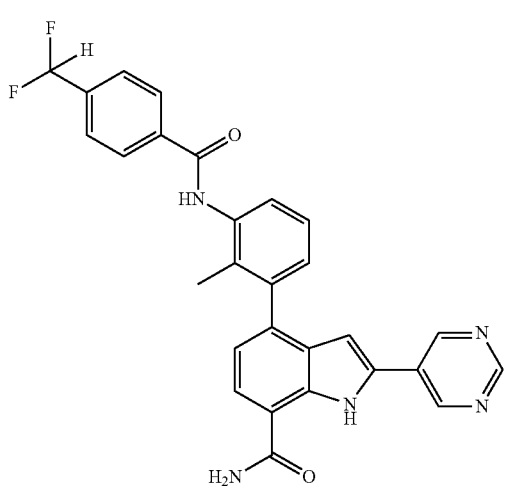 [SMILES: Cc1c(NC(=O)c2ccc(C(F)F)cc2)cccc1-c1ccc(C(N)=O)c2[nH]c(-c3cncnc3)cc12] | A.13.3 | 1.64 (g) | 498 | B |

TABLE A.13-continued

*Examples prepared from 4-bromo-2-(pyrimidin-5-yl)-1H-indole-7-carboxamide (prepared using A from 4-bromo-2-iodo-1H-indole-7-carboxamide (Preparation #1) and 5-(4,4,5,5-tetramethyl-1,3,2-dioxaborolan-2-yl)pyrimidine) using General Procedure A*

| Boronate | Product | Example # | R$_t$ min (Table 1, Method) | m/z ESI+ (M + H)+ | Btk IC$_{50}$ |
|---|---|---|---|---|---|
| 4-cyclopropyl-N-(2-methyl-3-(4,4,5,5-tetramethyl-1,3,2-dioxaborolan-2-yl)phenyl)benzamide (prepared using B with 2-methyl-3-(4,4,5,5-tetramethyl-1,3,2-dioxaborolan-2-yl)aniline and 4-(2-cyanopropan-2-yl)benzoic acid) | | A.13.4 | 1.73 (g) | 488 | B |

TABLE A.14

*Examples prepared from 4-bromo-2-(1-(2-hydroxy-2-methylpropyl)-1H-pyrazol-4-yl)-1H-indole-7-carboxamide (prepared using A from 4-bromo-2-iodo-1H-indole-7-carboxamide (Preparation #1) and 2-methyl-1-(4-(4,4,5,5-tetramethyl-1,3,2-dioxaborolan-2-yl)-1H-pyrazol-1-yl)propan-2-ol (Preparation #26) using General Procedure A*

| Boronate | Product | Example # | R$_t$ min (Table 1, Method) | m/z ESI+ (M + H)+ | Btk IC$_{50}$ |
|---|---|---|---|---|---|
| 6-fluoro-3-(2-methyl-3-(4,4,5,5-tetramethyl-1,3,2-dioxaborolan-2-yl)phenyl)quinazolin-4(3H)-one [WO 2011159857] | | A.14.1 | 1.65 (g) | 551 | A |

TABLE A.15

Examples prepared from 2-(3-chloro-2-(hydroxymethyl)phenyl)-6-cyclopropyl-8-fluoroisoquinolin-1(2H)-one [U.S. 20100222325] using General Procedure A

| Boronate | Product | Example # | $R_t$ min (Table 1, Method) | m/z ESI+ $(M + H)^+$ | Btk $IC_{50}$ |
|---|---|---|---|---|---|
| 2-(1-methyl-1H-pyrazol-4-yl)-4-(4,4,5,5-tetramethyl-1,3,2-dioxaborolan-2-yl)-1H-indole-7-carboxamide (prepared using A from Preparation #1 with 1-methyl-4-(4,4,5,5-tetramethyl-1,3,2-dioxaborolan-2-yl)-1H-pyrazole, and P with 4,4,4',4',5,5,5',5'-octamethyl-2,2'-bi(1,3,2-dioxaborolane)) | | A.15.1 | 2.77 (o) | 548 | A |

General Procedure B: Nucleophilic displacement of an aryl halide with an amine

To a solution of an aryl halide or heteroaryl halide and an appropriate organic solvent (such as DMSO, 1,4-dioxane, n-butanol, THF, pyridine, preferably DMSO or pyridine) was added an amine (1 to 10 equiv, preferably 1 equiv) and a base (such as TEA, pyridine, DIEA, $K_2CO_3$, preferably TEA; 1 to 5 equiv, preferably 1 equiv.). The resulting solution is stirred at about 20 to 150° C. (preferably about 130-150° C.) thermally for a period of about 1 h to 72 h (preferably about 24 h) or in a microwave for about 5 min to 2 h (preferably about 30 min). The mixture is optionally concentrated in vacuo or under a warm nitrogen stream to give the intermediates or targeted compound or optionally filtered through a media (such as $SiCO_3$ or Celite®) which is rinsed with an appropriate solvent (such as EtOAc, 1,4-dioxane, THF, MeCN, DCM, $Et_2O$, MeOH, EtOH, DMSO, 1:1 MeOH/DMSO, 2:1 MeOH/DMSO) and then optionally concentrated in vacuo or under a warm nitrogen stream to give the targeted compound.

Illustration of General Procedure B

Preparation #B.1: (R)-tert-Butyl 1-(7-cyano-1H-indol-4-yl)piperidin-3-ylcarbamate

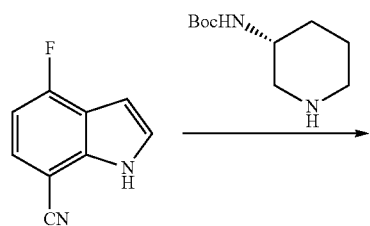

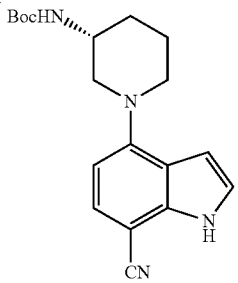

A mixture of (R)-tert-butyl piperidin-3-ylcarbamate (1.501 g, 7.49 mmol) and 4-fluoro-1H-indole-7-carbonitrile (0.6 g, 3.75 mmol) in pyridine (3.02 mL, 37.5 mmol) were heated at about 150° C. for about 30 min in a microwave oven. The mixture was evaporated to dryness and the resulting residue was purified by silica gel chromatography eluting with a gradient 30 to 100% of EtOAc in hexanes to give (R)-tert-butyl 1-(7-cyano-1H-indol-4-yl)piperidin-3-ylcarbamate (0.4 g, 31%); LC/MS (Table 1, Method g) $R_t$=1.69 min; MS m/z: 341 $(M+H)^+$ General Procedure C: Hydrolysis of an ester to a carboxylic acid To a flask containing an ester (preferably 1 equiv) either neat or in an organic solvent (such as 1,4-dioxane, MeOH, or THF/MeOH, preferably 1,4-dioxane) is added an aqueous base (such as aqueous NaOH or LiOH; 1-10 equiv, preferably 2-6 equiv). The mixture is stirred at about 0 to 100° C. (preferably about 25 to 60° C.) for about 1 to 48 h (preferably about 4 to 24 h). The organic solvent is optionally be concentrated in vacuo. The mixture is then acidified by the addition of a suitable aqueous acid (such as aqueous HCl). If a precipitate forms, it may be collected via filtration to give product. The mixture or the filtrate if the solid is not product may optionally be concentrated in vacuo to give the target compound as a carboxylate salt. Alternatively, the mixture is optionally filtered through a media (such as silica gel or Celite®) which is rinsed with an appropriate solvent (such as EtOAc, 1,4-dioxane, THF, MeCN, DCM, Et₂O, MeOH, EtOH) and then optionally concentrated in vacuo to give a residue as the target compound. Either the residue or the solution may be optionally partitioned between water and an organic solvent (such as EtOAc, Et₂O or DCM). The organic layer is isolated and may optionally be washed in no particular order with water and/or aqueous solutions containing an acid (such as HCl, AcOH or NH₄Cl) and/or aqueous solutions containing a base (such as NaHCO₃, Na₂CO₃, NaOH, KOH or NH₄OH) and/or aqueous solutions containing an inorganic salt (such as NaCl, Na₂SO₃ or Na₂S₂O₃). The organic solution may then be optionally dried with a drying agent (such as anhydrous MgSO₄ or Na₂SO₄), filtered and concentrated in vacuo to give the target compound.

Illustration of General Procedure C

Example #C.1

(E)-4-((3-(7-Carbamoyl-1H-indol-4-yl)phenyl)amino)-4-oxobut-2-enoic acid

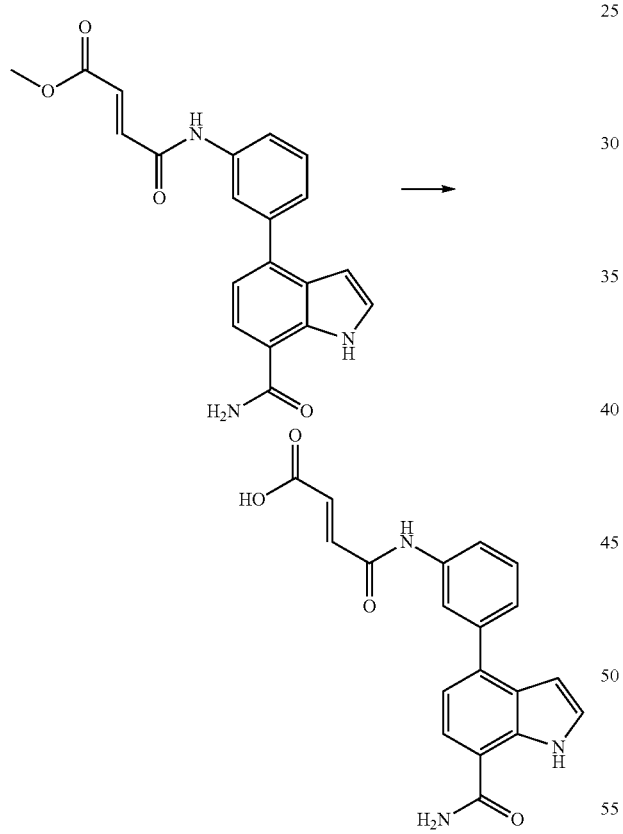

(E)-Methyl 4-((3-(7-carbamoyl-1H-indol-4-yl)phenyl)amino)-4-oxobut-2-enoate (0.610 g, 1.68 mmol, Example #D.1) was suspended in 1,4-dioxane (8.39 mL). Lithium hydroxide (1M in water, 8.39 mL, 8.39 mmol) was added and the mixture was stirred at about 60° C. for about 1 h. The reaction was concentrated to about 8 mL and diluted with water (10 mL). The pH was adjusted to about 4 using 1N HCl. The solids were collected, washed with water, and dried under vacuum to provide (E)-4-((3-(7-carbamoyl-1H-indol-4-yl)phenyl)amino)-4-oxobut-2-enoic acid (0.45 g, 77%) as a solid. 50 mg of the crude product was further purified by preparative-HPLC (Table 1, Method af) to afford 30.9 mg to provide analytically pure (E)-4-((3-(7-carbamoyl-1H-indol-4-yl)phenyl)amino)-4-oxobut-2-enoic acid: LC/MS (Table 1, Method f) R$_t$=1.64 min; MS m/z: 350 (M+H)⁺ (Btk IC$_{50}$=C)

General Procedure D: Formation of an amide from an amine and a carboxylic acid

To a flask is added in no particular order, a carboxylic acid or carboxylate salt (1 to 5 equiv, preferably 1.1 to 1.5 equiv), an amine (1 to 5 equiv, preferably 1 to 1.5 equiv), an organic solvent (such as DCM, DCE, THF, or 1,4-dioxane, DMF, DMF/pyridine preferably DCM or DMF/pyridine), a peptide coupling reagent (such as BOP-Cl, HATU, EDC, DCI, PyBOP, or EDC.HCl, preferably HATU or EDC; 1 to 10 equiv, preferably 1 to 2.5 equiv), a base (such as TEA, DIEA, pyridine or DIEA, preferably DIEA; 1 to 20 equiv, preferably 1 to 5 equiv) and optionally HOBt (0 to 5 equiv, preferably 0 to 1 equiv). The mixture is then stirred at about 10 to 60° C. (preferably about 25 to 50° C.) for about 5 min to 48 h (preferably about 5 min to 24 h). Optionally, additional amounts of the reagents above can be added to drive the reaction to completion. The mixture is optionally concentrated in vacuo to give the targeted compound. The mixture is optionally filtered through a media (such as silica gel or Celite®) which is rinsed with an appropriate solvent (such as EtOAc, 1,4-dioxane, THF, MeCN, DCM, Et₂O, MeOH, EtOH) and then optionally concentrated in vacuo to give a residue. Either the residue or the solution may be optionally partitioned between water and an organic solvent (such as EtOAc, Et₂O or DCM). If the product does not partition, the mixture may be stirred for 5 min to 1 h (preferably 30 min) and the solid may be collected via vacuum filtration.

Alternatively, the organic layer is isolated and may be optionally washed in no particular order with water and/or aqueous solutions containing an acid (such as HCl, AcOH or NH₄Cl) and/or aqueous solutions containing a base (such as NaHCO₃, Na₂CO₃, NaOH, KOH or NH₄OH) and/or aqueous solutions containing an inorganic salt (such as NaCl, Na₂SO₃ or Na₂S₂O₃). The organic solution may then be optionally dried with a drying agent (such as anhydrous MgSO₄ or Na₂SO₄), filtered and concentrated in vacuo to give the targeted compound.

Illustration of General Procedure D:

Example #D.1

(E)-Methyl 4-((3-(7-carbamoyl-1H-indol-4-yl)phenyl)amino)-4-oxobut-2-enoate

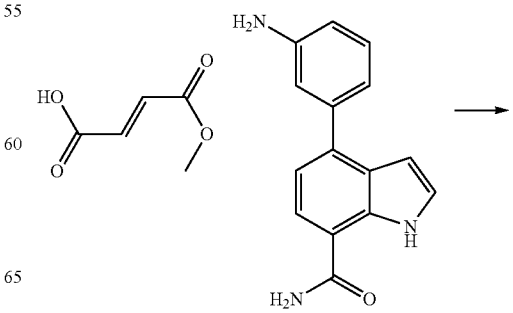

-continued

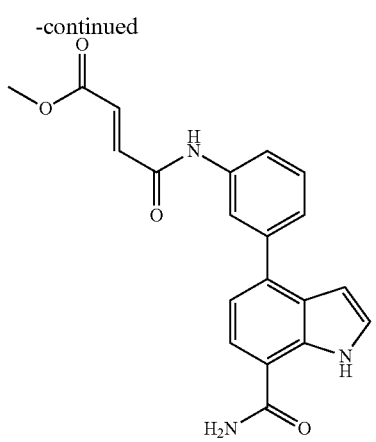

To a solution of (E)-4-methoxy-4-oxobut-2-enoic acid (0.43 g, 3.28 mmol) in DCM (40 mL) and DIEA (0.59 mL, 3.58 mmol) was added HATU (1.362 g, 3.58 mmol). The mixture was stirred at rt for 5 min then 4-(3-aminophenyl)-1H-indole-7-carboxamide (0.75 g, 2.98 mmol, Preparation #A.1) was added. The mixture was stirred at rt for about 3 h. The mixture was concentrated and the residue was suspended between water and EtOAc. The mixture was stirred at rt for about 30 min, filtered to collect the solid, which was washed with water and EtOAc, and dried under vacuum to provided (E)-methyl 4-(3-(7-carbamoyl-1H-indol-4-yl)phenyl)amino)-4-oxobut-2-enoate (0.64 g, 59%): LC/MS (Table 1, Method f) $R_t$=1.45 min; MS m/z: 364 (M+H)$^+$ (Btk IC$_{50}$=A)

TABLE D.1

Examples prepared from N-(3-(2-(2-(aminomethyl)phenyl)-7-carbamoyl-1H-indol-4-yl)-2-methylphenyl)thiazole-2-carboxamide (Example #1) using General Procedure D

| Acid | Product | Example # | $R_t$ min (Table 1, Method) | m/z ESI+ (M + H)$^+$ | Btk IC$_{50}$ |
|---|---|---|---|---|---|
| but-2-ynoic acid | | D.1.1 | 3.13 (d) | 548 | C |
| acrylic acid | | D.1.2 | 3.10 (d) | 536 | C |

TABLE D.1-continued

Examples prepared from N-(3-(2-(2-(aminomethyl)phenyl)-7-carbamoyl-1H-indol-4-yl)-2-methylphenyl)thiazole-2-carboxamide (Example #1) using General Procedure D

| Acid | Product | Example # | R$_t$ min (Table 1, Method) | m/z ESI+ (M + H)$^+$ | Btk IC$_{50}$ |
|---|---|---|---|---|---|
| 2-cyanoacetic acid | | D.1.3 | 3.05 (d) | 549 | B |
| 3-(dimethylamino) propanoic acid HCl | | D.1.4 | 2.64 (d) | 581 | B |
| 3-(piperidin-1-yl)propanoic acid | | D.1.5 | 2.38 (o) | 621 | C |

TABLE D.1-continued

Examples prepared from N-(3-(2-(2-(aminomethyl)phenyl)-7-carbamoyl-1H-indol-4-yl)-2-methylphenyl)thiazole-2-carboxamide (Example #1) using General Procedure D

| Acid | Product | Example # | $R_t$ min (Table 1, Method) | m/z ESI+ (M + H)$^+$ | Btk IC$_{50}$ |
|---|---|---|---|---|---|
| 2-phenoxyacetic acid | | D.1.6 | 3.06 (o) | 616 | C |
| 2-(4-fluorophenoxy) acetic acid | | D.1.7 | 3.08 (o) | 634 | C |
| butyric acid | | D.1.8 | 2.87 (o) | 552 | C |

TABLE D.1-continued

Examples prepared from N-(3-(2-(2-(aminomethyl)phenyl)-7-carbamoyl-1H-indol-4-yl)-2-methylphenyl)thiazole-2-carboxamide (Example #1) using General Procedure D

| Acid | Product | Example # | $R_t$ min (Table 1, Method) | m/z ESI+ $(M + H)^+$ | Btk IC$_{50}$ |
|---|---|---|---|---|---|
| (E)-but-2-enoic acid | | D.1.9 | 2.84 (o) | 550 | C |
| methacrylic acid | | D.1.10 | 3.20 (d) | 550 | C |
| propiolic acid | | D.1.11 | 3.10 (d) | 534 | B |

TABLE D.2

Examples prepared from an amine and 2-(3-oxobenzo[d]isothiazol-2(3H)-yl)acetic acid [Matrix] using General Procedure D

| Amine | Product | Example # | $R_t$ min (Table 1, Method) | m/z ESI+ (M + H)$^+$ | Btk IC$_{50}$ |
|---|---|---|---|---|---|
| 4-(2-aminophenyl)-1H-indole-7-carboxamide (prepared using A from 4-bromo-1H-indole-7-carboxamide (Preparation #2) and 2-(4,4,5,5-tetramethyl-1,3,2-dioxaborolan-2-yl)aniline) | | D.2.1 | 1.42 (f) | 443 | C |

TABLE D.3

Examples prepared from N-(3-(3-amino-7-carbamoyl-1H-indol-4-yl)-2-methylphenyl)thiazole-2-carboxamide (Preparation #7) using General Procedure D

| Acid | Product | Example # | $R_t$ min (Table 1, Method) | m/z ESI+ (M + H)$^+$ | Btk IC$_{50}$ |
|---|---|---|---|---|---|
| 2-cyanoacetic acid | | D.3.1 | 2.58 (d) | 459 | C |
| acrylic acid | | D.3.2 | 2.69 (d) | 446 | C |

TABLE D.3-continued
Examples prepared from N-(3-(3-amino-7-carbamoyl-1H-indol-4-yl)-2-methylphenyl)thiazole-2-carboxamide
(Preparation #7) using General Procedure D
| Acid | Product | Example # | $R_t$ min (Table 1, Method) | m/z ESI+ (M + H)+ | Btk $IC_{50}$ |
|---|---|---|---|---|---|
| (E)-but-2-enoic acid | 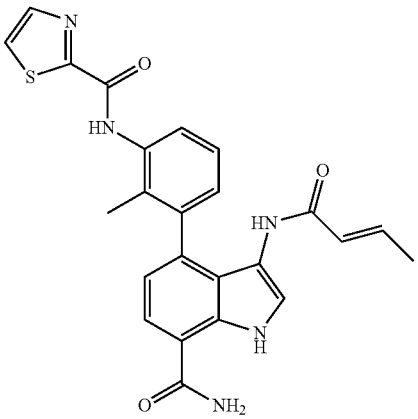 [SMILES: C/C=C/C(=O)Nc1c[nH]c2c(C(N)=O)ccc(-c3cccc(NC(=O)c4nccs4)c3C)c12] | D.3.3 | 2.82 (d) | 460 | C |
| methacrylic acid | 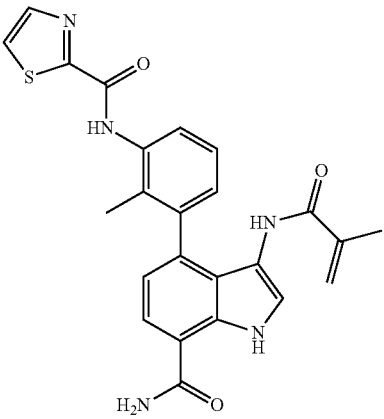 [SMILES: C=C(C)C(=O)Nc1c[nH]c2c(C(N)=O)ccc(-c3cccc(NC(=O)c4nccs4)c3C)c12] | D.3.4 | 2.89 (d) | 460 | C |
| but-2-ynoic acid | 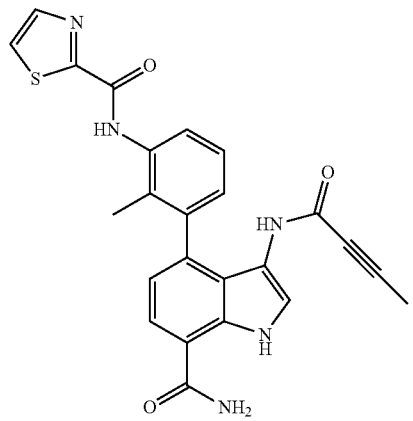 [SMILES: CC#CC(=O)Nc1c[nH]c2c(C(N)=O)ccc(-c3cccc(NC(=O)c4nccs4)c3C)c12] | D.3.5 | 2.52 (d) | 458 | C |

TABLE D.3-continued

Examples prepared from N-(3-(3-amino-7-carbamoyl-1H-indol-4-yl)-2-methylphenyl)thiazole-2-carboxamide (Preparation #7) using General Procedure D

| Acid | Product | Example # | $R_t$ min (Table 1, Method) | m/z ESI+ (M + H)+ | Btk IC$_{50}$ |
|---|---|---|---|---|---|
| 2-(4-fluorophenoxy) acetic acid | 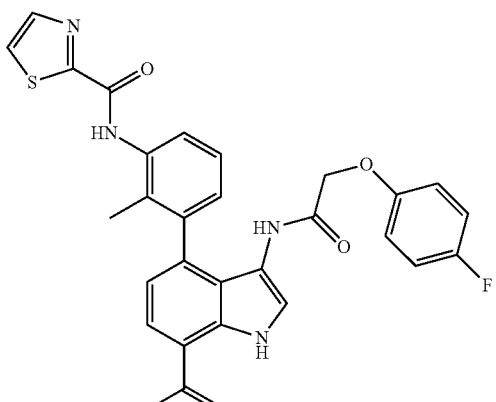 | D.3.6 | 3.09 (d) | 544 | C |

TABLE D.4

Examples prepared from an (E)-4-((3-(7-carbamoyl-1H-indol-4-yl)phenyl)amino)-4-oxobut-2-enoic acid (Example #C.1) using General Procedure D

| Amine | Product | Example # | $R_t$ min (Table 1, Method) | m/z ESI+ (M + H)+ | Btk IC$_{50}$ |
|---|---|---|---|---|---|
| Methylamine | 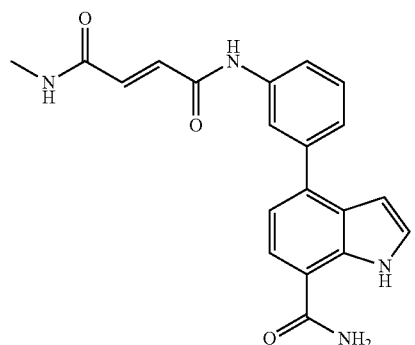 | D.4.1 | 1.60 (f) | 363 | C |
| Dimethylamine | 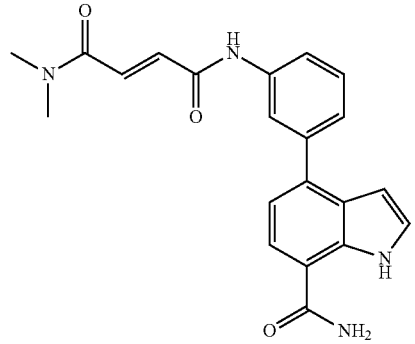 [SMILES: CN(C)C(=O)/C=C/C(=O)Nc1cccc(-c2ccc(C(N)=O)c3[nH]ccc23)c1] | D.4.2 | 1.66 (f) | 377 | C |

TABLE D.4-continued

Examples prepared from an (E)-4-((3-(7-carbamoyl-1H-indol-4-yl)phenyl)amino)-4-oxobut-2-enoic acid (Example #C.1) using General Procedure D

| Amine | Product | Example # | $R_t$ min (Table 1, Method) | m/z ESI+ (M + H)+ | Btk IC$_{50}$ |
|---|---|---|---|---|---|
| ethanamine | (structure) | D.4.3 | 1.68 (f) | 377 | C |
| cyclopropanamine | (structure) | D.4.4 | 1.70 (f) | 389 | C |

TABLE D.5

Examples prepared from an acid and 2-(1-acetylpiperidin-4-yl)-4-(3-amino-2-methylphenyl)-1H-indole-7-carboxamide (Example #L.1) using General Procedure D

| Acid | Product | Example # | $R_t$ min (Table 1, Method) | m/z ESI+ (M + H)+ | Btk IC$_{50}$ |
|---|---|---|---|---|---|
| 4-cyclopropylbenzoic acid [Astra tech] | (structure) | D.5.1 | 1.77 (f) | 535 | B |

TABLE D.6

Examples prepared from 4-(3-aminophenyl)-1H-indole-7-carboxamide (Preparation #A.1) using General Procedure B

| Acid | Product | Example # | R$_t$ min (Table 1, Method) | m/z ESI+ (M + H)$^+$ | Btk IC$_{50}$ |
|---|---|---|---|---|---|
| 2-((dimethylamino)methyl) acrylic acid (prepared using J from 2-(bromomethyl) acrylic acid and dimethylamine hydrochloride) | | D.6.1 | 2.24 (d) | 363 | A |
| 2-((dimethylamino)methyl) acrylic acid (prepared using J from 2-(bromomethyl) acrylic acid and morpholine) | | D.6.2 | 2.27 (d) | 405 | A |

TABLE D.7

Examples prepared from 4-(3-amino-2-methylphenyl)-2-(1-(methylsulfonyl)-1,2,3,6-tetrahydropyridin-4-yl)-1H-indole-7-carboxamide (Example #A.4.5) using General Procedure D.

| Acid | Product | Example # | R$_t$ min | m/z ESI+ (M + H)$^+$ | Btk IC$_{50}$ |
|---|---|---|---|---|---|
| (Z)-2-methylbut-2-enoic acid | | D.7.1 | 0.73 (e) | 507 | A |

TABLE D.7-continued

Examples prepared from 4-(3-amino-2-methylphenyl)-2-(1-(methylsulfonyl)-1,2,3,6-tetrahydropyridin-4-yl)-1H-indole-7-carboxamide (Example #A.4.5) using General Procedure D.

| Acid | Product | Example # | $R_t$ min | m/z ESI+ $(M + H)^+$ | Btk $IC_{50}$ |
|---|---|---|---|---|---|
| (E)-4-(dimethylamino)but-2-enoic acid hydrochloride | | D.7.2 | 0.57 (e) | 536 | A |
| 3-(piperidin-1-yl)propanoic acid | | D.7.3 | 0.59 (e) | 564 | B |
| 2-cyanoacetic acid | | D.7.4 | 0.66 (e) | 492 | A |
| methacrylic acid | | D.7.5 | 0.71 (e) | 493 | A |

TABLE D.7-continued

Examples prepared from 4-(3-amino-2-methylphenyl)-2-(1-(methylsulfonyl)-1,2,3,6-tetrahydropyridin-4-yl)-1H-indole-7-carboxamide (Example #A.4.5) using General Procedure D.

| Acid | Product | Example # | $R_t$ min | m/z ESI+ $(M + H)^+$ | Btk $IC_{50}$ |
|---|---|---|---|---|---|
| acrylic acid | | D.7.6 | 0.68 (e) | 479 | A |
| 2-chloro-2,2-difluoroacetic acid | | D.7.7 | 0.77 (e) | 537 | A |
| 2-chloropropanoic acid | | D.7.8 | 0.72 (e) | 515 | A |
| (E)-but-2-enoic acid | | D.7.9 | 0.71 (e) | 493 | A |

TABLE D.7-continued
Examples prepared from 4-(3-amino-2-methylphenyl)-2-(1-(methylsulfonyl)-1,2,3,6-tetrahydropyridin-4-yl)-1H-indole-7-carboxamide (Example #A.4.5) using General Procedure D.
| Acid | Product | Example # | $R_t$ min | m/z ESI+ $(M + H)^+$ | Btk $IC_{50}$ |
|---|---|---|---|---|---|
| (Z)-4-amino-4-oxobut-2-enoic acid | 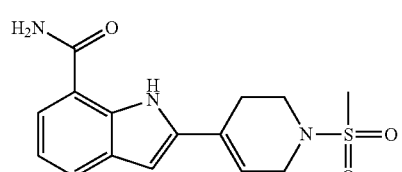 | D.7.10 | 0.62 (e) | 522 | A |
| 2-(4-fluorophenoxy)acetic acid | 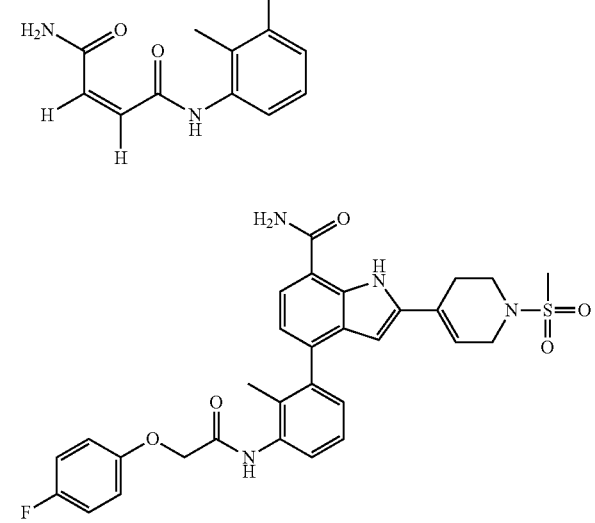 | D.7.11 | 0.78 (e) | 577 | A |
| 3-(pyrrolidin-1-yl)propanoic acid | 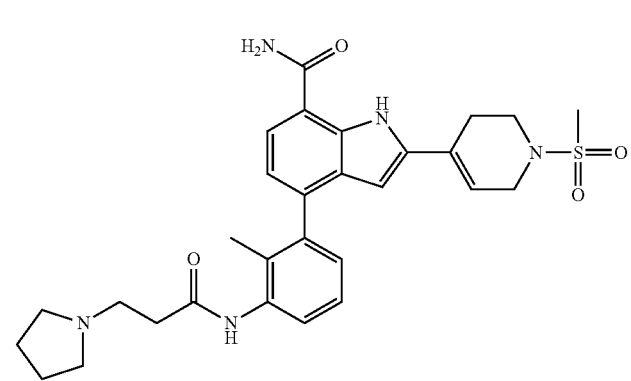 [SMILES: Cc1c(NC(=O)CCN2CCCC2)cccc1-c1ccc(C(N)=O)c2[nH]c(C3=CCN(S(C)(=O)=O)CC3)cc12] | D.7.12 | 0.58 (e) | 550 | A |
| 2-(4-cyanophenoxy)acetic acid | 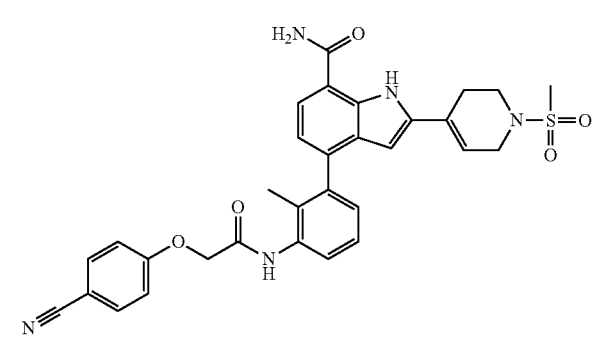 [SMILES: Cc1c(NC(=O)COc2ccc(C#N)cc2)cccc1-c1ccc(C(N)=O)c2[nH]c(C3=CCN(S(C)(=O)=O)CC3)cc12] | D.7.13 | 0.75 (e) | 584 | A |

TABLE D.7-continued

Examples prepared from 4-(3-amino-2-methylphenyl)-2-(1-(methylsulfonyl)-1,2,3,6-tetrahydropyridin-4-yl)-1H-indole-7-carboxamide (Example #A.4.5) using General Procedure D.

| Acid | Product | Example # | $R_t$ min | m/z ESI+ (M + H)+ | Btk IC$_{50}$ |
|---|---|---|---|---|---|
| 2-(pyridin-3-yloxy)acetic acid | | D.7.14 | 0.58 (e) | 560 | A |
| cyclopent-1-enecarboxylic acid | | D.7.15 | 0.75 (e) | 519 | A |
| (E)-2-methylpent-2-enoic acid | | D.7.16 | 0.78 (e) | 521 | A |
| (Z)-3-chloroacrylic acid | | D.7.17 | 0.70 (e) | 513 | A |

TABLE D.7-continued

Examples prepared from 4-(3-amino-2-methylphenyl)-2-(1-(methylsulfonyl)-1,2,3,6-tetrahydropyridin-4-yl)-1H-indole-7-carboxamide (Example #A.4.5) using General Procedure D.

| Acid | Product | Example # | $R_t$ min | m/z ESI+ $(M + H)^+$ | Btk $IC_{50}$ |
|---|---|---|---|---|---|
| (E)-4-methoxy-4-oxobut-2-enoic acid | | D.7.18 | 0.72 (e) | 537 | A |
| cyclohex-1-enecarboxylic acid | | D.7.19 | 0.78 (e) | 533 | A |
| (E)-4-ethoxy-4-oxobut-2-enoic acid | | D.7.20 | 0.75 (e) | 551 | A |
| 2-phenoxyacetic acid | | D.7.21 | 0.79 (e) | 559 | A |

TABLE D.7-continued

Examples prepared from 4-(3-amino-2-methylphenyl)-2-(1-(methylsulfonyl)-1,2,3,6-tetrahydropyridin-4-yl)-1H-indole-7-carboxamide (Example #A.4.5) using General Procedure D.

| Acid | Product | Example # | $R_t$ min | m/z ESI+ (M + H)+ | Btk IC$_{50}$ |
|---|---|---|---|---|---|
| 2-fluoroacetic acid | | D.7.22 | 0.66 (e) | 485 | A |
| 3-(dimethylamino)propanoic acid | | D.7.23 | 0.58 (h) | 524 | A |
| 2-(pyridin-2-yloxy)acetic acid | | D.7.24 | 0.69 (e) | 560 | A |
| (E)-4-amino-4-oxobut-2-enoic acid | | D.7.25 | 0.59 (e) | 522 | A |

TABLE D.7-continued

Examples prepared from 4-(3-amino-2-methylphenyl)-2-(1-(methylsulfonyl)-1,2,3,6-tetrahydropyridin-4-yl)-1H-indole-7-carboxamide (Example #A.4.5) using General Procedure D.

| Acid | Product | Example # | R$_t$ min | m/z ESI+ (M + H)$^+$ | Btk IC$_{50}$ |
|---|---|---|---|---|---|
| 2-chlorobutanoic acid | | D.7.26 | 0.74 (e) | 529 | A |
| 3-(4-methylpiperazin-1-yl)propanoic acid | | D.7.27 | 0.52 (e) | 579 | A |
| 2-(pyridazin-3-yloxy)acetic acid | | D.7.28 | 0.61 (e) | 561 | A |
| cyclohexanecarboxylic acid | | D.7.29 | 1.75 (e) | 535 | A |

TABLE D.7-continued

Examples prepared from 4-(3-amino-2-methylphenyl)-2-(1-(methylsulfonyl)-1,2,3,6-tetrahydropyridin-4-yl)-1H-indole-7-carboxamide (Example #A.4.5) using General Procedure D.

| Acid | Product | Example # | $R_t$ min | m/z ESI+ (M + H)+ | Btk IC$_{50}$ |
|---|---|---|---|---|---|
| 2-methylthiazole-4-carboxylic acid | | D.7.30 | 0.75 (ae) | 550 | A |
| cyclopentanecarboxylic acid | | D.7.31 | 0.75 (ae) | 521 | A |
| 5-methylthiazole-2-carboxylic acid | | D.7.32 | 0.77 (ae) | 550 | A |
| tetrahydro-2H-pyran-4-carboxylic acid | | D.7.33 | 0.65 (ae) | 537 | A |

TABLE D.7-continued

Examples prepared from 4-(3-amino-2-methylphenyl)-2-(1-(methylsulfonyl)-1,2,3,6-tetrahydropyridin-4-yl)-1H-indole-7-carboxamide (Example #A.4.5) using General Procedure D.

| Acid | Product | Example # | $R_t$ min | m/z ESI+ (M + H)+ | Btk IC$_{50}$ |
|---|---|---|---|---|---|
| 3-methoxycyclohexane-carboxylic acid | | D.7.34 | 0.71 (ae) | 565 | A |
| 3-methylbutanoic acid | | D.7.35 | 0.73 (ae) | 509 | A |
| 1-methylpiperidine-4-carboxylic acid | | D.7.36 | 0.56 (ae) | 550 | A |
| 1-methylpiperidine-3-carboxylic acid | | D.7.37 | 0.57 (ae) | 550 | B |

TABLE D.7-continued
Examples prepared from 4-(3-amino-2-methylphenyl)-2-(1-(methylsulfonyl)-1,2,3,6-tetrahydropyridin-4-yl)-1H-indole-7-carboxamide (Example #A.4.5) using General Procedure D.
| Acid | Product | Example # | $R_t$ min | m/z ESI+ $(M + H)^+$ | Btk $IC_{50}$ |
|---|---|---|---|---|---|
| isothiazole-4-carboxylic acid | 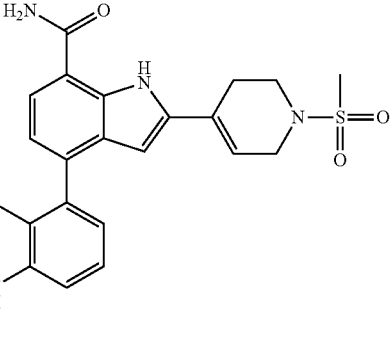 | D.7.38 | 0.67 (ae) | 536 | A |
| nicotinic acid | 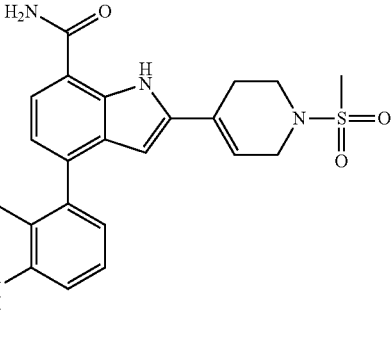 | D.7.39 | 0.59 (ae) | 530 | A |
| isobutyric acid | 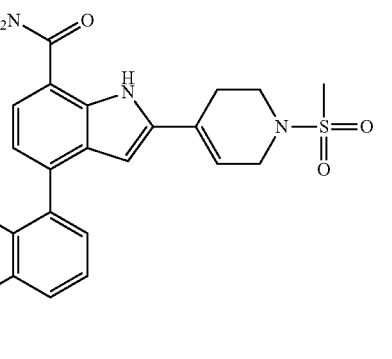 | D.7.40 | 0.69 (ae) | 495 | A |
| propionic acid | 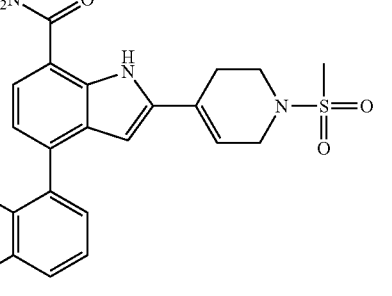 | D.7.41 | 0.67 (e) | 481 | A |

TABLE D.8

Compounds made from 4-(3-amino-2-methylphenyl)-1H-indole-7-carboxamide (Example #16) using General Procedure D.

| Acid | Product | Example # | R$_t$ min | m/z ESI+ (M + H)$^+$ | Btk IC$_{50}$ |
|---|---|---|---|---|---|
| (E)-4-ethoxy-4-oxobut-2-enoic acid | | D.8.1 | 0.69 (ae) | 392 | A |
| (E)-3-(1-methyl-1H-pyrazol-4-yl)acrylic acid | | D.8.2 | 0.62 (ae) | 400 | B |
| (E)-3-(pyridin-2-yl)acrylic acid | | D.8.3 | 0.55 (ae) | 397 | B |
| (E)-3-(pyridin-3-yl)acrylic acid | | D.8.4 | 0.53 (ae) | 397 | B |

TABLE D.8-continued

Compounds made from 4-(3-amino-2-methylphenyl)-1H-indole-7-carboxamide
(Example #16) using General Procedure D.

| Acid | Product | Example # | R$_t$ min | m/z ESI+ (M + H)+ | Btk IC$_{50}$ |
|---|---|---|---|---|---|
| (E)-3-(thiazol-2-yl)acrylic acid | | D.8.5 | 0.65 (ae) | 403 | B |
| (E)-3-cyclopropylacrylic acid | | D.8.6 | 0.69 (ae) | 360 | B |
| 2-phenylacrylic acid | | D.8.7 | 0.75 (ae) | 396 | B |

TABLE D.8-continued
Compounds made from 4-(3-amino-2-methylphenyl)-1H-indole-7-carboxamide (Example #16) using General Procedure D.
| Acid | Product | Example # | R$_t$ min | m/z ESI+ (M + H)$^+$ | Btk IC$_{50}$ |
|---|---|---|---|---|---|
| (E)-4-methylpent-2-enoic acid | 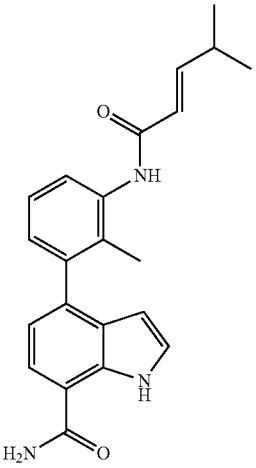 [SMILES: Cc1c(NC(=O)/C=C/C(C)C)cccc1-c1ccc(C(N)=O)c2[nH]ccc12] | D.8.8 | 0.74 (ae) | 362 | B |
| (E)-but-2-enoic acid | 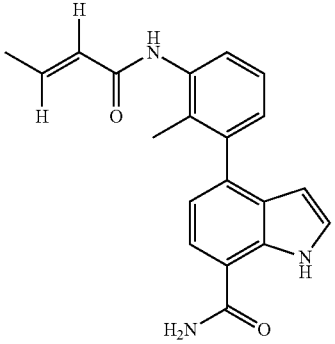 [SMILES: C/C=C/C(=O)Nc1cccc(-c2ccc(C(N)=O)c3[nH]ccc23)c1C] | D.8.9 | 0.64 (ae) | 334 | B |
| methacrylic acid | 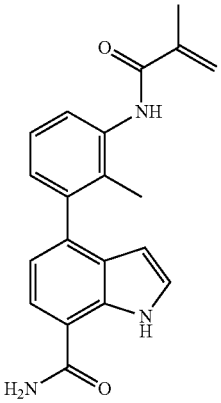 [SMILES: C=C(C)C(=O)Nc1cccc(-c2ccc(C(N)=O)c3[nH]ccc23)c1C] | D.8.10 | 0.65 (ae) | 334 | C |

TABLE D.8-continued

Compounds made from 4-(3-amino-2-methylphenyl)-1H-indole-7-carboxamide (Example #16) using General Procedure D.

| Acid | Product | Example # | $R_t$ min | m/z ESI+ $(M + H)^+$ | Btk $IC_{50}$ |
|---|---|---|---|---|---|
| 2-methylenebutanoic acid | | D.8.11 | 0.65 (ae) | 348 | C |
| acetic acid | | D.8.12 | 0.56 (ae) | 308 | C |
| 3-morpholinopropanoic acid | | D.8.13 | 0.65 (ae) | 407 | C |
| 3-(pyrrolidin-1-yl)propanoic acid | | D.8.14 | 0.51 (ae) | 391 | C |

TABLE D.8-continued

Compounds made from 4-(3-amino-2-methylphenyl)-1H-indole-7-carboxamide (Example #16) using General Procedure D.

| Acid | Product | Example # | R$_t$ min | m/z ESI+ (M + H)$^+$ | Btk IC$_{50}$ |
|---|---|---|---|---|---|
| (Z)-4-(ethylamino)-4-oxobut-2-enoic acid | *structure* | D.8.15 | 0.62 (ae) | 391 | A |

TABLE D.9

Examples prepared from (Z)-4-((3-(7-carbamoyl-1H-indol-4-yl)phenyl)amino)-4-oxobut-2-enoic acid (Preparation #14) using General Procedure D

| Amine | Product | Example # | R$_t$ min (Table 1, Method) | m/z ESI+ (M + H)$^+$ | Btk IC$_{50}$ |
|---|---|---|---|---|---|
| 2-methoxyethylamine | *structure* | D.9.1 | 1.42 (g) | 407 | B |
| Ethanamine | *structure* | D.9.2 | 1.41 (g) | 377 | A |

TABLE D.10

Examples prepared from propiolic acid with an amine using General Procedure D

| Amine | Product | Example # | R$_t$ min (Table 1, Method) | m/z ESI+ (M + H)$^+$ | Btk IC$_{50}$ |
|---|---|---|---|---|---|
| 4-(Azetidin-3-yl(methyl)amino)-2-methyl-1H-indole-7-carboxamide hydrochloride (Prepared using A from Preparation #40 with methylboronic acid and G with HCl) | (structure) | D.10.1 | 1.35 (at) | 311 | A |

General Procedure E: Formation of an Amide from an Amine and an Acid Halide or Anhydride To a solution of an amine (1 to 3 equiv, preferably 1 to 3 equiv), optionally as a hydrochloride salt, in an organic solvent (such as DCM, DCE, DMF, DMA, NMP, THF, Et$_2$O or 1,4-dioxane, preferably DMF, DMA, or DCM) is added a base (such as TEA, DIEA or pyridine; 1 to 4 equiv, preferably TEA or DIEA 1 to 3 equiv) and an acid halide or anhydride (1 to 4 equiv, preferably 1 to 4 equiv). The mixture is optionally cooled to about 0° C. prior to addition of an acid halide or anhydride. The mixture is allowed to stir at about 0 to 60° C. (preferably about 0 to 50° C.) for about 5 min to 20 h (preferably about 20 min to 2 h). The mixture is optionally neutralized with AcOH. The mixture is optionally concentrated in vacuo to give the final compound. The mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound. Alternatively, the residue from concentration of the reaction is suspended in water, sonicated, and collected via vacuum filtration.

Illustration of General Procedure E:

Example #E.1

4-(3-Acrylamido-2-methylphenyl)-2-(4,4-difluorocyclohex-1-en-1-yl)-1H-indole-7-carboxamide

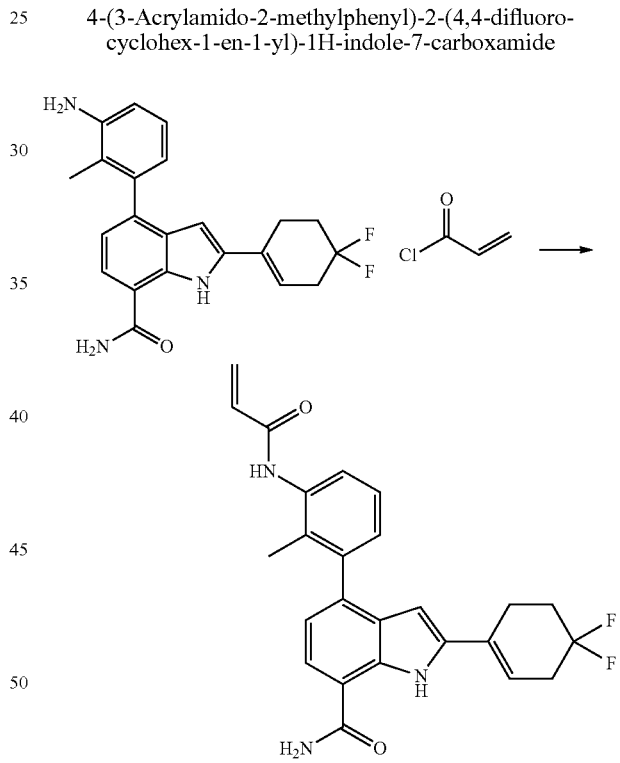

To a vial was added 4-(3-amino-2-methylphenyl)-2-(4,4-difluorocyclohex-1-en-1-yl)-1H-indole-7-carboxamide (0.189 g, 0.496 mmol, Example #21) in DCM (5 mL), and DIEA (0.129 mL, 0.743 mmol). The mixture was cooled to about 0° C. and acryloyl chloride (0.044 mL, 0.545 mmol) was added while stirring. The mixture was warmed to rt over about 20 min, then concentrated and the residue was suspended in water (30 mL). The suspension was sonicated for about 5 min, filtered, washed with water, ether, and dried under vacuum. The crude product was added to a silica gel column and eluted with heptane/EtOAc (0-100%) to provide 4-(3-acrylamido -2-methylphenyl)-2-(4,4-difluorocyclohex-1-en-1-yl)-1H-indole-7-carboxamide (0.16 g, 74%): LC/MS (Table 1, Method g) R$_t$=3.02 min; MS m/z: 436 (M+H)$^+$. (BTK IC$_{50}$=A)

TABLE E.1

Examples prepared from acryloyl chloride using General Procedure E

| Amine | Product | Example # | $R_t$ min (Table 1, Method) | m/z ESI+ $(M + H)^+$ | Btk $IC_{50}$ |
|---|---|---|---|---|---|
| 4-(2-(aminomethyl)phenyl)-2-(1-(methylsulfonyl)-1,2,3,6-tetrahydropyridin-4-yl)-1H-indole-7-carboxamide hydrochloride (prepared using A from Preparation #18 and tert-butyl 2-(4,4,5,5-tetramethyl-1,3,2-dioxaborolan-2-yl)benzylcarbamate [JW] and G with HCl) | | E.1.1 | 1.47 (f) | 479 | A |
| 4-(2-aminophenyl)-1H-indole-7-carboxamide (Example #A.5.1) | | E.1.2 | 1.32 (f) | 306 | C |
| 4-(2-aminopyridin-4-yl)-1H-indole-7-carboxamide (Example #A.5.3) | | E.1.3 | 0.96 (f) | 307 | A |
| 4-(5-aminopyridin-3-yl)-1H-indole-7-carboxamide (Example #A.5.4) | | E.1.4 | 0.90 (f) | 307 | A |

TABLE E.1-continued

Examples prepared from acryloyl chloride using General Procedure E

| Amine | Product | Example # | $R_t$ min (Table 1, Method) | m/z ESI+ (M + H)+ | Btk IC$_{50}$ |
|---|---|---|---|---|---|
| 4-(3-(methylamino)phenyl)-1H-indole-7-carboxamide (prepared using A from Preparation #P.1 and 3-bromo-N-methylaniline) | | E.1.5 | 1.41 (f) | 320 | A |
| 4-(2-methyl-3-(methylamino)phenyl)-1H-indole-7-carboxamide (prepared using A from Preparation #P.1 and 3-bromo-N,2-dimethylaniline [Beta Pharm]) | | E.1.6 | 1.45 (f) | 334 | B |
| 4-(2-methyl-3-(thiazol-2-ylmethylamino)phenyl)-2-(1-(methylsulfonyl)-1,2,3,6-tetrahydropyridin-4-yl)-1H-indole-7-carboxamide (Example #H.2.1) | | E.1.7 | 1.75 (g) | 576 | A |

TABLE E.1-continued

Examples prepared from acryloyl chloride using General Procedure E

| Amine | Product | Example # | $R_t$ min (Table 1, Method) | m/z ESI+ $(M + H)^+$ | Btk $IC_{50}$ |
|---|---|---|---|---|---|
| 4-(3-amino-4-methoxyphenyl)-1H-indole-7-carboxamide (prepared using A from Preparation #P.1 and 5-bromo-2-methoxyaniline) | | E.1.8 | 0.63 (ae) | 336 | B |
| 4-(3-amino-2-methylphenyl)-1H-pyrrolo[3,2-c]pyridine-7-carboxamide (prepared using A from Preparation #9 and 2-methyl-3-(4,4,5,5-tetramethyl-1,3,2-dioxaborolan-2-yl)aniline [CombiBlocks]) | | E.1.9 | 1.94 (d) | 321 | A |
| 4-(3-amino-2-methylphenyl)-1H-pyrrolo[3,2-c]pyridine-7-carboxamide (prepared using A from Preparation #9 and 3-(4,4,5,5-tetramethyl-1,3,2-dioxaborolan-2-yl)aniline) | | E.1.10 | 2.04 (d) | 307 | A |

TABLE E.1-continued

Examples prepared from acryloyl chloride using General Procedure E

| Amine | Product | Example # | R$_t$ min (Table 1, Method) | m/z ESI+ (M + H)$^+$ | Btk IC$_{50}$ |
|---|---|---|---|---|---|
| (R)-4-(3-aminopiperidin-1-yl)-2-(1-(methylsulfonyl)-1,2,3,6-tetrahydropyridin-4-yl)-1H-indole-7-carboxamide (prepared using B from Preparation #27 and (R)-tert-butyl piperidin-3-ylcarbamate, N with Cs$_2$CO$_3$, G with HCl, and O) | | E.1.11* | 1.27 (f) | 472 | A |
| 4-(3-amino-4-(benzyloxy)phenyl)-1H-indole-7-carboxamide (prepared using A Preparation #2 and Preparation #34) | | E.1.12 | 3.18 (d) | 412 | C |
| 4-(3-amino-4-(thiazol-2-ylmethoxy)phenyl)-1H-indole-7-carboxamide (prepared using R from Preparation #Q.1, A from Preparation #P.1) | | E.1.13 | 2.79 (d) | 419 | B |

TABLE E.1-continued

Examples prepared from acryloyl chloride using General Procedure E

| Amine | Product | Example # | $R_t$ min (Table 1, Method) | m/z ESI+ (M + H)+ | Btk IC$_{50}$ |
|---|---|---|---|---|---|
| 4-(3-amino-5-(thiazol-2-ylmethoxy)phenyl)-1H-indole-7-carboxamide (prepared using A Preparation #2 and Preparation #35) | | E.1.14 | 2.80 (o) | 412 | C |
| 4-(3-amino-5-(thiazol-2-ylmethoxy)phenyl)-1H-indole-7-carboxamide (prepared using S from 1-bromo-3-methoxy-5-nitrobenzene with BBr$_3$, Q from thiazol-2-ylmethanol, R with Fe, P with 4,4,4',4',5,5,5',5'-octamethyl-2,2'-bi(1,3,2-dioxaborolane), and A from Preparation #2 | | E.1.15 | 2.77 (d) | 419 | B |
| 4-(2-amino-4-(thiazol-2-ylmethoxy)phenyl)-1H-indole-7-carboxamide (prepared using A from Preparation #P.1 and Preparation #R.1) | | E.1.16 | 2.77 (d) | 419 | C |

TABLE E.1-continued

Examples prepared from acryloyl chloride using General Procedure E

| Amine | Product | Example # | $R_t$ min (Table 1, Method) | m/z ESI+ $(M + H)^+$ | Btk $IC_{50}$ |
|---|---|---|---|---|---|
| 4-(2-amino-4-(benzyloxy)phenyl)-1H-indole-7-carboxamide (prepared using R from Preparation #36 with Fe, and A from Preparation #P.1) | | E.1.17 | 3.29 (d) | 412 | C |
| 4-(3-aminophenyl)-2-ethyl-1H-indole-7-carboxamide (Example #20, Step C) | | E.1.18 | 2.93 (d) | 332 | A |
| 4-(3-amino-4-chlorophenyl)-1H-indole-7-carboxamide (prepared using A from Preparation #P.1 and 5-bromo-2-chloroaniline) | | E.1.19 | 0.67 (ae) | 340 | A |
| 4-(3-amino-2,6-difluorophenyl)-1H-indole-7-carboxamide (prepared using A from Preparation #P.1 and 3-bromo-2,4-difluoroaniline) | | E.1.20 | 0.62 (ae) | 342 | A |

TABLE E.1-continued

Examples prepared from acryloyl chloride using General Procedure E

| Amine | Product | Example # | R$_t$ min (Table 1, Method) | m/z ESI+ (M + H)$^+$ | Btk IC$_{50}$ |
|---|---|---|---|---|---|
| 4-(5-amino-2,3-difluorophenyl)-1H-indole-7-carboxamide(prepared using A from Preparation #P.1 and 3-bromo-4,5-difluoroaniline) | | E.1.21 | 0.66 (ae) | 342 | A |
| 4-(5-amino-2,4-difluorophenyl)-1H-indole-7-carboxamide(prepared using A from Preparation #P.1 and 5-bromo-2,4-difluoroaniline) | | E.1.22 | 0.62 (ae) | 342 | A |
| 4-(3-amino-4-fluorophenyl)-1H-indole-7-carboxamide(prepared using A from Preparation #P.1 and 5-bromo-2-fluoroaniline) | | E.1.23 | 0.62 (ae) | 324 | A |
| 4-(5-amino-2-chlorophenyl)-1H-indole-7-carboxamide(prepared using A from Preparation #P.1 and 3-bromo-4-chloroaniline) | | E.1.24 | 0.65 (ae) | 340 | A |

TABLE E.1-continued

Examples prepared from acryloyl chloride using General Procedure E

| Amine | Product | Example # | $R_t$ min (Table 1, Method) | m/z ESI+ $(M + H)^+$ | Btk $IC_{50}$ |
|---|---|---|---|---|---|
| 4-(3-amino-4-methylphenyl)-1H-indole-7-carboxamide(prepared using A from Preparation #P.1 and 5-bromo-2-methylaniline) | | E.1.25 | 0.63 (ae) | 320 | A |
| 4-(3-amino-5-cyanophenyl)-1H-indole-7-carboxamide (prepared using A from Preparation #P.1 and 3-bromo-3-cyano aniline) | | E.1.26 | 0.63 (ae) | 331 | B |
| 4-(3-amino-2-cyanophenyl)-1H-indole-7-carboxamide (prepared using A from Preparation #P.1 and 3-bromo-2cyano aniline) | | E.1.27 | 0.58 (ae) | 331 | B |
| 4-(3-amino-5-methoxyphenyl)-1H-indole-7-carboxamide(prepared using A from Preparation #P.1 and 3-bromo-5-methoxyaniline) | | E.1.28 | 0.63 (ae) | 336 | B |

TABLE E.1-continued

Examples prepared from acryloyl chloride using General Procedure E

| Amine | Product | Example # | R$_t$ min (Table 1, Method) | m/z ESI+ (M + H)$^+$ | Btk IC$_{50}$ |
|---|---|---|---|---|---|
| 4-(3-amino-5-methylphenyl)-1H-indole-7-carboxamide(prepared using A from Preparation #P.1 and 3-bromo-5-methylaniline) | | E.1.29 | 0.65 (ae) | 320 | B |
| 4-(3-amino-2-methoxyphenyl)-1H-indole-7-carboxamide 2 (prepared using A from Preparation #P.1 and 3-bromo-2-methoxyaniline) | | E.1.30 | 0.63 (ae) | 336 | B |
| 4-(3-amino-4-cyanophenyl)-1H-indole-7-carboxamide (prepared using A from Preparation #P.1 and 2-amino-4-bromobenzonitrile) | | E.1.31 | 0.59 (ae) | 331 | A |
| 4-(5-amino-2-fluorophenyl)-1H-indole-7-carboxamide (prepared using A from Preparation #P.1 and 3-bromo-4-fluoroaniline) | | E.1.32 | 0.63 (ae) | 324 | B |

TABLE E.1-continued

Examples prepared from acryloyl chloride using General Procedure E

| Amine | Product | Example # | $R_t$ min (Table 1, Method) | m/z ESI+ (M + H)$^+$ | Btk IC$_{50}$ |
|---|---|---|---|---|---|
| 4-(3-amino-2-fluorophenyl)-1H-indole-7-carboxamide (prepared using A from Preparation #P.1 and 3-bromo-2-fluoroaniline) | | E.1.33 | 0.62 (ae) | 324 | A |
| 4-(3-(N-(cyclopentylmethyl)acrylamido)phenyl)-1H-indole-7-carboxamide (prepared using H from Preparation #A.1 and cyclopentanecarbaldehyde) | | E.1.34 | 0.79 (ae) | 388 | C |
| 4-(3-(N-isobutylacrylamido)phenyl)-1H-indole-7-carboxamide (prepared using H from Preparation #A.1 and isobutyraldehyde) | | E.1.35 | 0.75 (ae) | 362 | B |

TABLE E.2

Examples prepared from 4-(3-aminophenyl)-1H-indole-7-carboxamide (Preparation #A.1) using General Procedure E

| Acid Chloride | Product | Example # | $R_t$ min (Table 1, Method) | m/z ESI+ (M + H)+ | Btk IC$_{50}$ |
|---|---|---|---|---|---|
| 5-methylisoxazole-4-carbonyl chloride | | E.2.1 | 2.61 (c) | 361 | C |
| 1-methyl-1,2,5,6-tetrahydropyridine-3-carbonyl chloride hydrochloride [J. Med. Chem., 1980, 23 (8) 865] | | E.2.2 | 1.36 (f) | 375 | C |

TABLE E.3

Examples prepared from 4-(2-aminophenyl)-2-(1-(methylsulfonyl)-1,2,3,6-tetrahydropyridin-4-yl)-1H-indole-7-carboxamide (Example #A.4.2) using General Procedure E

| Acid Chloride | Product | Example # | $R_t$ min (Table 1, Method) | m/z ESI+ (M + H)+ | Btk IC$_{50}$ |
|---|---|---|---|---|---|
| acetyl chloride | | E.3.1 | 1.41 (f) | 453 | B |

TABLE E.4

Examples prepared from N-(3-(2-(2-(aminomethyl)phenyl)-7-carbamoyl-1H-indol-4-yl)-2-methylphenyl)thiazole-2-carboxamide (Example #1) using General Procedure E

| Acid Chloride or Anhydride | Product | Example # | $R_t$ min (Table 1, Method) | m/z ESI+ (M + H)+ | Btk IC$_{50}$ |
|---|---|---|---|---|---|
| 2-chloroacetyl chloride | | E.4.1 | 3.17 (d) | 558 | B |
| propionyl chloride | | E.4.2 | 3.10 (d) | 538 | C |
| acetic anhydride | | E.4.3 | 3.01 (d) | 524 | B |

TABLE E.5

Examples prepared from N-(3-(3-amino-7-carbamoyl-1H-indol-4-yl)-2-methylphenyl)thiazole-2-carboxamide (Preparation #7) using General Procedure E

| Acid Chloride or Anhydride | Product | Example # | R$_t$ min (Table 1, Method) | m/z ESI+ (M + H)+ | Btk IC$_{50}$ |
|---|---|---|---|---|---|
| 2-chloroacetyl chloride | 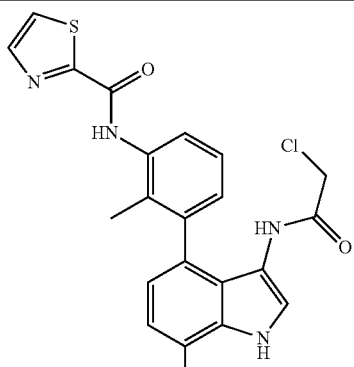 | E.5.1 | 2.79(d) | 468 | C |

TABLE E.6

Examples prepared from ethyl carbono-chloridate using General Procedure E

| Amine | Product | Example # | R$_t$ min (Table 1, Method) | m/z ESI+ (M + H)+ | Btk IC$_{50}$ |
|---|---|---|---|---|---|
| 2-(2,5-dihydro-1H-pyrrol-3-yl)-4-(2-methyl-3-(4-oxoquinazolin-3(4H)-yl)phenyl)-1H-indole-7-carboxamide (Example #G.1) | | E.6.1 | 2.74 (o) | 534 | A |
| 4-(2-methyl-3-(4-oxoquinazolin-3(4H)-yl)phenyl)-2-(1,2,3,6-tetrahydropyridin-4-yl)-1H-indole-7-carboxamide (Example #G.1.1) | | E.6.2 | 2.82 (o) | 548 | A |

TABLE E.7

Examples prepared from 2-oxopropanoyl chloride (prepared from pyruvic acid and 1,1-dichlorodimethyl ether [Synthesis, 1975, 3 163-164]) using General Procedure E

| Amine | Product | Example # | $R_t$ min (Table 1, Method) | m/z ESI+ (M + H)+ | Btk IC$_{50}$ |
|---|---|---|---|---|---|
| 4-(3-aminophenyl)-1H-indole-7-carboxamide (Preparation #A.1) | | E.7.1 | 1.47 (g) | 322 | B |
| 4-(3-(aminomethyl)phenyl)-1H-indole-7-carboxamide (prepared using A from (3-(4,4,5,5-tetramethyl-1,3,2-dioxaborolan-2-yl)phenyl)methanamine hydrochloride with 4-bromo-1H-indole-7-carboxamide [Preparation #2]) | | E.7.2 | 1.41 (g) | 336 | B |

TABLE E.8

Examples prepared from acetyl chloride using General Procedure E

| Acid Chloride | Product | Example # | $R_t$ min (Table 1, Method) | m/z ESI+ (M + H)+ | Btk IC$_{50}$ |
|---|---|---|---|---|---|
| 2-(2,5-dihydro-1H-pyrrol-3-yl)-4-(2-methyl-3-(4-oxoquinazolin-3(4H)-yl)phenyl)-1H-indole-7-carboxamide (Example #G.1) | | E.8.1 | 2.72 (d) | 504 | A |

TABLE E.8-continued

Examples prepared from acetyl chloride using General Procedure E

| Acid Chloride | Product | Example # | R$_t$ min (Table 1, Method) | m/z ESI+ (M + H)$^+$ | Btk IC$_{50}$ |
|---|---|---|---|---|---|
| 4-(2-methyl-3-(4-oxoquinazolin-3(4H)-yl)phenyl)-2-(1,2,3,6-tetrahydropyridin-4-yl)-1H-indole-7-carboxamide (Example #G.1.1) | | E.8.2 | 1.78 (a) | 518 | A |

TABLE E.9

Examples prepared from acryloyl chloride with an amine using General Procedure E

| Amine | Product | Example # | R$_t$ min (Table 1, Method) | m/z ESI+ (M + H)$^+$ | Btk IC$_{50}$ |
|---|---|---|---|---|---|
| 4-(2-(Aminomethyl)phenyl)-2-(1-(methylsulfonyl)-1,2,3,6-tetrahydropyridin-4-yl)-1H-indole-7-carboxamide hydrochloride (prepared using A from Preparation #18 with tert-butyl 2-(4,4,5,5-tetramethyl-1,3,2-dioxaborolan-2-yl)benzylcarbamate [JW] and G with HCl) | | E.9.1 | 1.47 (f) | 479 | A |
| 4-(Azetidin-3-yl(methyl)amino)-2-cyclopropyl-1H-indole-7-carboxamide (prepared using A from Preparation #40 with Cyclopropylboronic acid [SCRC] and G with HCl) | | E.9.2 | 1.38 (aa) | 339 | A |

TABLE E.9-continued

Examples prepared from acryloyl chloride with an amine using General Procedure E

| Amine | Product | Example # | R, min (Table 1, Method) | m/z ESI+ (M + H)+ | Btk IC$_{50}$ |
|---|---|---|---|---|---|
| 4-(Azetidin-3-yl(methyl)amino)-2-(isochroman-7-yl)-1H-indole-7-carboxamide (prepared using A from Preparation #40 with 2-(isochroman-7-yl)-4,4,5,5-tetramethyl-1,3,2-dioxaborolane [prepared using P and 7-bromoisochroman] and G with HCl) | 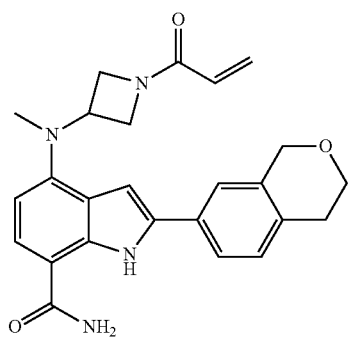 [SMILES: C=CC(=O)N1CC(N(C)c2ccc(C(N)=O)c3[nH]c(-c4ccc5c(c4)COCC5)cc23)C1] | E.9.3 | 1.44 (aa) | 431 | A |
| 4-(Azetidin-3-yl(methyl)amino)-2-(6,7-dihydro-4H-pyrazolo[5,1-c][1,4]oxazin-2-yl)-1H-indole-7-carboxamide (Prepared using P from preparation #40, Step A with 4,4,5,5-tetramethyl-1,3,2-dioxaborolane, A with Preparation #44, C with LiOH, D with NH$_4$Cl and G with HCl) | 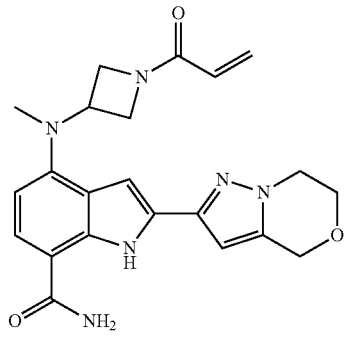 [SMILES: C=CC(=O)N1CC(N(C)c2ccc(C(N)=O)c3[nH]c(-c4cc5n(n4)CCOC5)cc23)C1] | E.9.4 | 1.46 (a) | 421 | A |
| 4-(Azetidin-3-yl(methyl)amino)-2-(4,4-difluorocyclohex-1-en-1-yl)-1H-indole-7-carboxamide (prepared using A from Preparation #40 with 2-(4,4-difluorocyclohex-1-en-1-yl)-4,4,5,5-tetramethyl-1,3,2-dioxaborolane [Syngene] and G with HCl) | 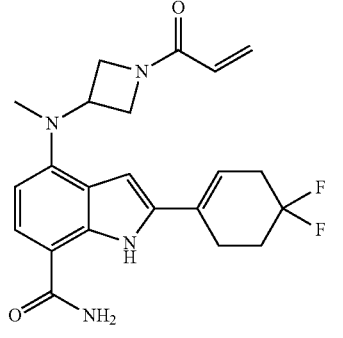 [SMILES: C=CC(=O)N1CC(N(C)c2ccc(C(N)=O)c3[nH]c(C4=CCC(F)(F)CC4)cc23)C1] | E.9.5 | 1.53 (aa) | 415 | A |
| 4-(Azetidin-3-yl(methyl)amino)-2-(4-(methylsulfonyl)cyclohex-1-en-1-yl)-1H-indole-7-carboxamide hydrochloride (prepared using A from Preparation #40 with 4,4,5,5-tetramethyl-2-(4-(methylsulfonyl)cyclohex-1-en-1-yl)-1,3,2-dioxaborolane (WO2005/73206 A1) and G with HCl | 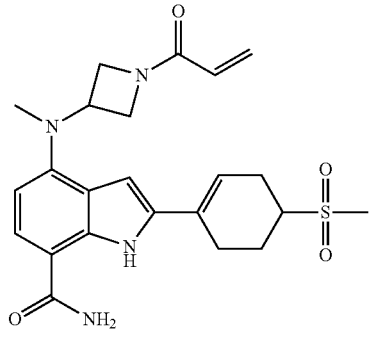 [SMILES: C=CC(=O)N1CC(N(C)c2ccc(C(N)=O)c3[nH]c(C4=CCC(S(C)(=O)=O)CC4)cc23)C1] | E.9.6 | 1.44 (ab) | 457 | A |

TABLE E.9-continued

Examples prepared from acryloyl chloride with an amine using General Procedure E

| Amine | Product | Example # | $R_t$ min (Table 1, Method) | m/z ESI+ $(M + H)^+$ | Btk IC$_{50}$ |
|---|---|---|---|---|---|
| (S)-2-Methyl-4-(piperidin-3-yl)-1H-indole-7-carboxamide hydrochloride (prepared using X from Preparation #39 with LiOH, D with NH$_4$Cl, L with Pd/C, chiral separation (Table 2, Method 5) and G with HCl) | | E.9.7 | 1.58 (a) | 312 | A |
| (R)-2-Methyl-4-(piperidin-3-yl)-1H-indole-7-carboxamide hydrochloride (prepared using X from Preparation #39 with LiOH, D with NH$_4$Cl, L with Pd/C, chiral separation (Table 2, Method 5) and G with HCl) | | E.9.8 | 1.64 (a) | 312 | A |
| 4-(Azetidin-3-yl)(methyl)amino)-2-(6-morpholinopyridin-3-yl)-1H-indole-7-carboxamide (Prepared using A from Preparation #40 with 4-(5-(4,4,5,5-tetramethyl-1,3,2-dioxaborolan-2-yl)pyridin-2-yl)morpholine and G with HCl) | | E.9.10 | 1.22 (at) | 461 | A |
| 4-(Azetidin-3-yl(methyl)amino)-2-(7,8-dihydro-5H-pyrano[4,3-b]pyridin-3-yl)-1H-indole-7-carboxamide hydrochloride (Prepared using A from Preparation #40 with (7,8-dihydro-5H-pyrano[4,3-b]pyridin-3-yl)boronic acid [Anichem]) and G with HCl) | | E.9.11 | 1.48 (au) | 432 | A |

TABLE E.9-continued

Examples prepared from acryloyl chloride with an amine using General Procedure E

| Amine | Product | Example # | $R_t$ min (Table 1, Method) | m/z ESI+ (M + H)+ | Btk IC$_{50}$ |
|---|---|---|---|---|---|
| 4-(Azetidin-3-yl(methyl)amino)-2-(chroman-7-yl)-1H-indole-7-carboxamide hydrochloride (Prepared using P from 7-bromochroman [Arkpharm] with bis(pinacolato)diboron, A with Preparation #40 and G with HCl) | | E.9.12 | 1.51 (av) | 431 | A |
| 4-(Azetidin-3-yl)(methyl)amino)-2-(5-(morpholinomethyl)pyridin-2-yl)-1H-indole-7-carboxamide (Prepared using G from Preparation #48 with HCl) | | E.9.13 | 1.60 (aw) | 475 | A |
| 4-(Azetidin-3-yl(methyl)amino)-2-(1-methyl-1H-pyrazol-4-yl)-1H-indole-7-carboxamide hydrochloride (Prepared using A from Preparation #40 with 1-methyl-4-(4,4,5,5-tetramethyl-1,3,2-dioxaborolan-2-yl)-1H-pyrazole and G with HCl) | | E.9.14 | 1.51 (aw) | 379 | A |
| 4-(Azetidin-3-yl(methyl)amino)-2-(3,4-dihydro-2H-benzo[b][1,4]oxazin-6-yl)-1H-indole-7-carboxamide dihydrochloride (Prepared using A from Preparation #40 with tert-butyl 3-((7-carbamoyl-2-iodo-1H-indol-4-yl)(methyl)amino)azetidine-1-carboxylate[Arkpharminc] and G with HCl) | | E.9.15 | 1.37 (av) | 432 | A |

TABLE E.9-continued

Examples prepared from acryloyl chloride with an amine using General Procedure E

| Amine | Product | Example # | $R_t$ min (Table 1, Method) | m/z ESI+ $(M + H)^+$ | Btk IC$_{50}$ |
|---|---|---|---|---|---|
| 4-(Azetidin-3-yl(methyl)amino)-2-(1-methyl-1H-pyrazol-5-yl)-1H-indole-7-carboxamide hydrochloride (Prepared using A from Preparation #40 with 1-methyl-5-(4,4,5,5-tetramethyl-1,3,2-dioxaborolan-2-yl)-1H-pyrazole and G with HCl) | | E.9.16 | 1.28 (be) | 379 | A |
| 4-(Azetidin-3-yl(methyl)amino)-2-(2-ethyl-1,2,3,4-tetrahydroisoquinolin-6-yl)-1H-indole-7-carboxamide hydrochloride (Prepared using A from Preparation #40 with 1-methyl-5-(4,4,5,5-tetramethyl-1,3,2-dioxaborolan-2-yl)-1H-pyrazole and G with HCl) | | E.9.17 | 1.12 (av) | 458 | A |
| 4-(Azetidin-3-yl(methyl)amino)-2-(1,3-dimethyl-1H-pyrazol-4-yl)-1H-indole-7-carboxamide hydrochloride (Prepared using A from Preparation #40 with 1,3-dimethyl-4-(4,4,5,5-tetramethyl-1,3,2-dioxaborolan-2-yl)-1H-pyrazole and G with HCl) | | E.9.18 | 1.29 (av) | 393 | A |
| 4-(Azetidin-3-yl(methyl)amino)-2-(1,1-dioxidotetrahydro-2H-thiopyran-4-yl)-1H-indole-7-carboxamide hydrochloride (Prepared using A from Preparation #40 with 4-(4,4,5,5-tetramethyl-1,3,2-dioxaborolan-2-yl)-3,6-dihydro-2H-thiopyran 1,1-dioxide [JWpharmlab], L with Pd/C and G with HCl) | | E.9.19 | 1.41 (aw) | 431 | A |

TABLE E.9-continued

Examples prepared from acryloyl chloride with an amine using General Procedure E

| Amine | Product | Example # | R$_t$ min (Table 1, Method) | m/z ESI+ (M + H)$^+$ | Btk IC$_{50}$ |
|---|---|---|---|---|---|
| 4-(Azetidin-3-yl)(methyl)amino)-2-(1-propylpiperidin-4-yl)-1H-indole-7-carboxamide (Prepared using J from 1-iodopropane with 4-(4,4,5,5-tetramethyl-1,3,2-dioxaborolan-2-yl)-1,2,3,6-tetrahydropyridine [Arkpharminc], A with Preparation #40, L with Pd/C and G with HCl) | 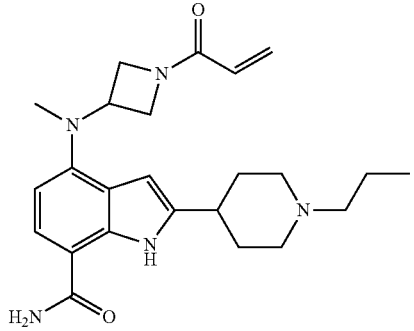 [SMILES: C=CC(=O)N1CC(N(C)c2ccc(C(N)=O)c3[nH]c(C4CCN(CCC)CC4)cc23)C1] | E.9.20 | 1.10(av) | 424 | A |
| 4-(Azetidin-3-yl)(methyl)amino)-2-(tetrahydrofuran-3-yl)-1H-indole-7-carboxamide (Preparation #41) | 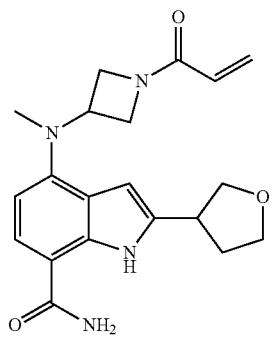 [SMILES: C=CC(=O)N1CC(N(C)c2ccc(C(N)=O)c3[nH]c(C4CCOC4)cc23)C1] | E.9.21 | 1.28 (av) | 369 | A |
| 4-(Azetidin-3-yl(methyl)amino)-2-(3-hydroxyoxetan-3-yl)-1H-indole-7-carboxamide 2,2,2-trifluoroacetate (Prepared using X from Preparation #42 with KOH, D with NH$_4$Cl and G with TFA) | 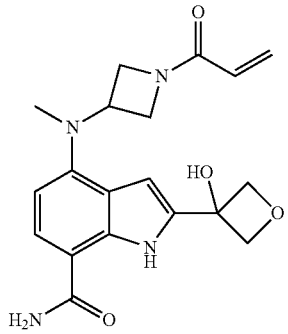 [SMILES: C=CC(=O)N1CC(N(C)c2ccc(C(N)=O)c3[nH]c(C4(O)COC4)cc23)C1] | E.9.22 | 1.18 (ay) | 372 | B |
| (R)-2-(1-Methyl-1H-pyrazol-4-yl)-4-(morpholin-2-yl)-1H-indole-7-carboxamide hydrochloride (Prepared using Y from Preparation #43, A with 1-methyl-4-(4,4,5,5-tetramethyl-1,3,2-dioxaborolan-2-yl)-1H-pyrazole [Arkpharm], O chiral separation (Table 2, Method 4) and G with HCl) | 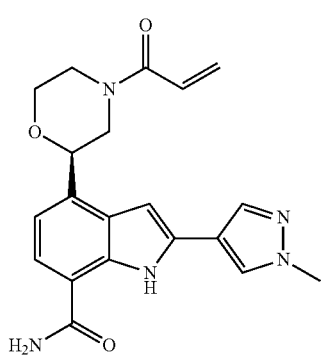 [SMILES: C=CC(=O)N1CCC[C@H](c2cnc(C(N)=O)c3sc(-c4cnn(C)c4)nc23)C1] | E.9.23 | 1.40(a) | 380 | A |

TABLE E.9-continued

Examples prepared from acryloyl chloride with an amine using General Procedure E

| Amine | Product | Example # | R$_t$ min (Table 1, Method) | m/z ESI+ (M + H)$^+$ | Btk IC$_{50}$ |
|---|---|---|---|---|---|
| (S)-2-(1-Methyl-1H-pyrazol-4-yl)-4-(morpholin-2-yl)-1H-indole-7-carboxamide hydrochloride (Prepared using Y from Preparation #43, A with 1-methyl-4-(4,4,5,5-tetramethyl-1,3,2-dioxaborolan-2-yl)-1H-pyrazole [Arkpharm], O, chiral separation (Table 2, Method 4) and G with HCl)) | | E.9.24 | 1.36(a) | 380 | A |
| 4-(Azetidin-3-yl(methyl)amino)-2-methyl-1H-indole-7-carboxamide hydrochloride (Prepared using A from Preparation #40 with methylboronic acid and G with HCl) | | E.9.25 | 1.30 (az) | 313 | A |
| (R)-2-(6,7-Dihydro-4H-pyrazolo[5,1-c][1,4]oxazin-2-yl)-4-(pyrrolidin-3-yl)-1H-indole-7-carboxamide (Prepared using P from Preparation #Y.1 with 4,4,5,5-tetramethyl-1,3,2-dioxaborolane, A with Preparation #44, chiral separation (Table 2, Method 6), C with LiOH, D with NH$_3$ and G with HCl) | | E.9.26 | 1.58 (ba) | 406 | A |
| (S)-2-(6,7-Dihydro-4H-pyrazolo[5,1-c][1,4]oxazin-2-yl)-4-(pyrrolidin-3-yl)-1H-indole-7-carboxamide (Prepared using P from Preparation #Y.1 with 4,4,5,5-tetramethyl-1,3,2-dioxaborolane, A with Preparation #44, chiral separation (Table 2, Method 6), C with LiOH, D with NH$_3$ and G with HCl) | | E.9.27 | 1.58 (ba) | 406 | A |

TABLE E.9-continued

Examples prepared from acryloyl chloride with an amine using General Procedure E

| Amine | Product | Example # | $R_t$ min (Table 1, Method) | m/z ESI+ (M + H)+ | Btk IC$_{50}$ |
|---|---|---|---|---|---|
| (R)-4-(1-(Azetidin-3-yl)ethyl)-1H-pyrrolo[3,2-c]pyridine-7-carboxamide (prepared using AA from tert-butyl 3-acetylazetidine-1-carboxylate [JWpharm] with N-(5-chloropyridin-2-yl)-1,1,1-trifluoro-N-((trifluoromethyl)sulfonyl) methane sulfonamide, W with 4,4,4',4',5,5,5',5'-octamethyl-2,2'-bi(1,3,2-dioxaborolane)], A with Preparation #37, L with Pd/C, C with LiOH, D with NH$_4$Cl, chiral separation (Table 2, Method 7) and G with HCl) | | E.9.28 | 1.03 (a) | 299 | A |
| (S)-4-(1-(Azetidin-3-yl)ethyl)-1H-pyrrolo[3,2-c]pyridine-7-carboxamide (prepared using AA from tert-butyl 3-acetylazetidine-1-carboxylate [JWpharm] with N-(5-chloropyridin-2-yl)-1,1,1-trifluoro-N-((trifluoromethyl)sulfonyl) methane sulfonamide, W with 4,4,4',4',5,5,5',5'-octamethyl-2,2'-bi(1,3,2-dioxaborolane)], A with Preparation #37, L with Pd/C, C with LiOH, D with NH$_4$Cl, chiral separation (Table 2, Method 7) and G with HCl) | | E.9.29 | 0.99 (a) | 299 | B |
| 4-((R)-1,4-Oxazepan-6-yl)-7,7a-dihydro-1H-pyrrolo[3,2-c]pyridine-7-carboxamide (prepared using C from Preparation #AH.1 with LiOH, D with NH$_4$Cl, L with Pd(OH)$_2$, chiral separation (Table 2, Method 8) and G with HCl) | | E.9.30 | 0.97 | 315 (a) | A |

TABLE E.9-continued

Examples prepared from acryloyl chloride with an amine using General Procedure E

| Amine | Product | Example # | R$_t$ min (Table 1, Method) | m/z ESI+ (M + H)+ | Btk IC$_{50}$ |
|---|---|---|---|---|---|
| 4-((S)-1,4-Oxazepan-6-yl)-7,7a-dihydro-1H-pyrrolo[3,2-c]pyridine-7-carboxamide (prepared using C from Preparation #AH.1 with LiOH, D with NH$_4$Cl, L with Pd(OH)$_2$, chiral separation (Table 2, Method 8) and G with HCl) | | E.9.31 | 0.97 (as) | 315 | C |
| (R)-4-(Piperidin-3-yl)-1H-pyrrolo[3,2-c]pyridine-7-carboxamide hydrochloride (prepared using Z from Preparation #AB.1, chiral separation (Table 2, Method 9) and G with HCl) | | E.9.32 | 1.04 (as) | 299 | A |
| (S)-4-(Piperidin-3-yl)-1H-pyrrolo[3,2-c]pyridine-7-carboxamide hydrochloride (prepared using Z from Preparation #AB.1, chiral separation (Table 2, Method 9) and G with HCl) | | E.9.33 | 1.04 (a) | 299 | B |
| 4-(Azetidin-3-ylamino)-1H-pyrrolo[2,3-c]pyridine-7-carboxamide (prepared using O from Preparation #AD.1, T with tert-butyl 3-aminoazetidine-1-carboxylate[arkpharm] and G with HCl) | | E.9.34 | 1.10 (ba) | 286 | A |

TABLE E.9-continued

Examples prepared from acryloyl chloride with an amine using General Procedure E

| Amine | Product | Example # | $R_t$ min (Table 1, Method) | m/z ESI+ $(M + H)^+$ | Btk IC$_{50}$ |
|---|---|---|---|---|---|
| tert-Butyl 3-((7-carbamoyl-1H-indol-4-yl)(methyl)amino)-3-methylazetidine-1-carboxylate (Prepared using T from Preparation #1, Step C and tert-butyl 3-amino-3-methylazetidine-1-carboxylate [AKSCI], J with CH$_3$I, X with LiOH, D with NH$_4$Cl and G with HCl) | | E.9.35 | 1.47 (a) | 313 | A |
| (R)-2-(1-Methyl-1H-pyrazol-4-yl)-7-(piperidin-3-yl)thiazolo[5,4-c]pyridine-4-carboxamide (Prepared using A from Preparation #46 with tert-butyl 3-(4,4,5,5-tetramethyl-1,3,2-dioxaborolan-2-yl)-5,6-dihydropyridine-1(2H)-carboxylate, L with Pd/C, chiral separation (Table 2, Method 10) and G with HCl) | | E.9.36 | 1.62 (as) | 397 | A |
| (S)-2-(1-Methyl-1H-pyrazol-4-yl)-7-(piperidin-3-yl)thiazolo[5,4-c]pyridine-4-carboxamide (Prepared using A from Preparation #46 with tert-butyl 3-(4,4,5,5-tetramethyl-1,3,2-dioxaborolan-2-yl)-5,6-dihydropyridine-1(2H)-carboxylate, L with Pd/C, chiral separation (Table 2, Method 10) and G with HCl) | | E.9.37 | 1.60 (as) | 397 | A |
| (S)-4-(1,4-Oxazepan-6-yl)-1H-indole-7-carboxamide (prepared using AA with tert-butyl 6-oxo-1,4-oxazepane-4-carboxylate[Arkpharm] and 1,1,1-trifluoro-N-phenyl-N-((trifluoromethyl)sulfonyl) methane sulfonamide, A with Preparation #P.1, L with Pd/C, chiral separation (Table 2, Method 11) and G with HCl) | | E.9.38 | 1.34 (a) | 314 | A |

TABLE E.9-continued

Examples prepared from acryloyl chloride with an amine using General Procedure E

| Amine | Product | Example # | R$_t$ min (Table 1, Method) | m/z ESI+ (M + H)$^+$ | Btk IC$_{50}$ |
|---|---|---|---|---|---|
| (R)-4-(1,4-Oxazepan-6-yl)-1H-indole-7-carboxamide (prepared using AA with tert-butyl 6-oxo-1,4-oxazepane-4-carboxylate [Arkpharm] and 1,1,1-trifluoro-N-phenyl-N-((trifluoromethyl)sulfonyl)methane sulfonamide, A with Preparation #P.1, L with Pd/C, chiral separation (Table 2, Method 11) and G with HCl) | | E.9.39 | 1.33 (a) | 314 | C |
| (S)-2-Methyl-4-(pyrrolidin-3-yl)-1H-indole-7-carboxamide (Prepared using chiral separation (Table 2, Method 3) from Preparation #38, C with LiOH, D with NH$_3$ and G with HCl) | | E.9.40* | 1.52 (ba) | 298 | B |
| (R)-2-Methyl-4-(pyrrolidin-3-yl)-1H-indole-7-carboxamide (Prepared using chiral separation (Table 2, Method 3) from Preparation #38, C with LiOH, D with NH$_3$ and G with HCl) | | E.9.41* | 1.60 (ba) | 298 | B |
| 4-((1S,5S)-3,6-Diazabicyclo[3.2.0]heptan-3-yl)-1H-indole-7-carboxamide (Prepared using A from 4-bromo-1H-indole-7-carboxamide[Anthem] with tert-butyl 3,6-diazabicyclo[3.2.0]heptane-6-carboxylate [Arkpharm], chiral separation (Table 2, Method 13) and G with HCl) | | E.9.42 | 1.39 (ba) | 311 | B |

TABLE E.9-continued

Examples prepared from acryloyl chloride with an amine using General Procedure E

| Amine | Product | Example # | $R_t$ min (Table 1, Method) | m/z ESI+ (M + H)+ | Btk IC$_{50}$ |
|---|---|---|---|---|---|
| 4-((1R,5R)-3,6-Diazabicyclo[3.2.0]heptan-3-yl)-1H-indole-7-carboxamide (Prepared using A from 4-bromo-1H-indole-7-carboxamide[Anthem] with tert-butyl 3,6-diazabicyclo[3.2.0]heptane-6-carboxylate [Arkpharm], chiral separation (Table 2, Method 13) and G with HCl) | | E.9.43 | 1.40 (ba) | 311 | B |
| 4-((3S,5R)-5-(Hydroxymethyl)piperidin-3-yl)-1H-indole-7-carboxamide (Prepared using chiral separation (Table 2, Method 14) from Preparation #AE.1 and G with HCl) | | E.9.44 | 1.31 (ba) | 328 | B |
| 4-((3S,5S)-5-(Hydroxymethyl)piperidin-3-yl)-1H-indole-7-carboxamide (Prepared using chiral separation (Table 2, Method 14) from Preparation #AE.1 and G with HCl) | | E.9.45 | 1.29 (ba) | 328 | C |
| 4-(5-(Hydroxymethyl)piperidin-3-yl)-1H-indole-7-carboxamide (Prepared using chiral separation (Table 2, Method 14) from Preparation #AE.1 and G with HCl) | | E.9.46 | 1.34 (ba) | 328 | C |

TABLE E.9-continued

Examples prepared from acryloyl chloride with an amine using General Procedure E

| Amine | Product | Example # | $R_t$ min (Table 1, Method) | m/z ESI+ (M + H)+ | Btk IC$_{50}$ |
|---|---|---|---|---|---|
| 4-(5-(Hydroxymethyl)piperidin-3-yl)-1H-indole-7-carboxamide (Prepared using chiral separation (Table 2, Method 14) from Preparation #AE.1 and G with HCl) | | E.9.47 | 1.30 (ba) | 328 | B |
| (R)-2-(1-Methyl-1H-pyrazol-4-yl)-4-(pyrrolidin-3-yl)-1H-indole-7-carboxamide hydrochloride (Prepared using A from Preparation #Y.1 with 1-methyl-4-(4,4,5,5-tetramethyl-1,3,2-dioxaborolan-2-yl)-1H-pyrazole[arkpharm], chiral separation (Table 2, Method 17), C with LiOH, D with NH$_3$ and G with HCl) | | E.9.48 | 1.39 (a) | 364 | A |
| (S)-2-(1-Methyl-1H-pyrazol-4-yl)-4-(pyrrolidin-3-yl)-1H-indole-7-carboxamide (Prepared using A from Preparation #Y.1 with 1-methyl-4-(4,4,5,5-tetramethyl-1,3,2-dioxaborolan-2-yl)-1H-pyrazole[arkpharm], chiral separation (Table 2, Method 17), C with LiOH, D with NH$_3$ and G with HCl) | | E.9.49 | 1.50 (ba) | 364 | B |
| 4-((1R,3R)-3-Aminocyclopentyl)-1H-indole-7-carboxamide hydrochloride (Prepared using C from Preparation #47 with LiOH, D with NH$_4$Cl and G with HCl) | | E.9.50 | 1.43(a) | 298 | A |

TABLE E.9-continued

Examples prepared from acryloyl chloride with an amine using General Procedure E

| Amine | Product | Example # | $R_t$ min (Table 1, Method) | m/z ESI+ (M + H)+ | Btk IC$_{50}$ |
|---|---|---|---|---|---|
| (S)-4-(Piperidin-3-yl)-1H-pyrrolo[2,3-c]pyridine-7-carboxamide (Prepared using A from Example #29, Step A with tert-butyl 3-(4,4,5,5-tetramethyl-1,3,2-dioxaborolan-2-yl)-5,6-dihydropyridine-1(2H)-carboxylate, O, L with Pd/C, chiral separation (Table 2, Method 18) and G with acetyl chloride) | | E.9.51 | 1.42 (ba) | 299 | B |
| (R)-4-(Piperidin-3-yl)-1H-pyrrolo[2,3-c]pyridine-7-carboxamide (Prepared using A from Example #29, Step A with tert-butyl 3-(4,4,5,5-tetramethyl-1,3,2-dioxaborolan-2-yl)-5,6-dihydropyridine-1(2H)-carboxylate, O, L with Pd/C, chiral separation (Table 2, Method 18) and G with acetyl chloride) | | E.9.52 | 1.43 (ba) | 299 | B |

TABLE E.9.1

Examples prepared from acryloyl chloride with an amine using General Procedure E

| Amine | Product | Example # | $R_t$ min (Table 1, Method) | m/z ESI+ (M + H$_2$O + H)+ | Btk IC$_{50}$ |
|---|---|---|---|---|---|
| 4-(Azetidin-3-yl(methyl)amino)-2-(3-hydroxyoxetan-3-yl)-1H-indole-7-carboxamide 2,2,2-trifluoroacetate (Prepared using X from Preparation #42 with KOH, D with NH$_4$Cl and G with TFA) | | E.9.1.1 | 1.18 (ay) | 353 | B |

TABLE E.10

Examples prepared from propionyl chloride with an amine using General Procedure E

| Amine | Product | Example # | $R_t$ min (Table 1, Method) | m/z ESI+ (M + H)+ | Btk IC$_{50}$ |
|---|---|---|---|---|---|
| (R)-2-Methyl-4-(pyrrolidin-3-yl)-1H-indole-7-carboxamide (Prepared using chiral separation (Table 2, Method 12) from Preparation #38, C with LiOH, D with NH$_3$ and G with HCl) | | E.10.1 | 1.64 (ba) | 300 | B |
| (S)-2-Methyl-4-(pyrrolidin-3-yl)-1H-indole-7-carboxamide (Prepared using chiral separation (Table 2, Method 12) from Preparation #38, C with LiOH, D with NH$_3$ and G with HCl) | | E.10.2 | 1.63 (ba) | 300 | B |

General Procedure F: Formation of a 4-iodoindole-7-carboxamide

To a solution of 2-amino-4-nitrobenzoic acid (preferably 1 equiv) in MeOH is added slowly concentrated sulfuric acid (preferably 1 equiv). The resulting solution is heated at about 75° C. for about 3 days. After cooling, the reaction is neutralized by addition of aqueous NaOH solution until pH~10. The reaction is extracted with EtOAc, dried over anhydrous sodium sulfate, filtered and concentrated. To this intermediate (preferably 1 equiv) is added a methyl ketone (1-2 equiv, preferably 2 equiv) and an organic solvent (preferably dimethyl sulfoxide). The reaction is cooled to about −15° C. A base (preferably potassium tert-butoxide 2 equiv) is added. After stirring for about 2.5 h at rt, the reaction is quenched with saturated aqueous ammonium chloride solution and then stirred for about 1 h at rt. The resulting suspension was filtered, washed with water and the solid is dried under high vacuum. To this intermediate (preferably 1 equiv) is added ((1H -benzo[d][1,2,3]triazol-1-yl) oxy)tri(pyrrolidin-1-yl)phosphonium hexafluorophosphate(V) (preferably 2 equiv), hydroxybenzotriazole hydrate (preferably 2 equiv) and ammonium chloride (preferably 1.5 equiv) and an organic solvent (preferably DMF). An organic base (preferably diisopropylethylamine, 4 equiv) is added. The reaction mixture is stirred at rt overnight. The mixture is poured into water and the resulting precipitate is filtered, washed with water and EtOAc, and collected. To this intermediate (preferably 1 equiv) is added an organic solvent (preferably MeOH), and the solution is purged with nitrogen. To this solution is added 10% palladium on carbon (preferably 0.1 equiv). The resulting suspension is treated with hydrogen (30 psi). After stirring overnight at rt, the reaction is filtered, and the solids are rinsed with MeOH. The filtrate is concentrated. A solution of sodium nitrite (preferably 2.2 equiv) in water is added to an ice cold suspension of this intermediate (preferably 1 equiv) in an organic solvent (preferably MeCN) and 2N HCl (preferably 5.4 equiv) with stirring, maintaining the temperature below about −5° C. After stirring for about 30 min, a cold solution of aqueous potassium iodide (preferably 2.5 equiv) is added to the reaction and the resulting mixture was stirred at rt for about 30 min. The reaction is heated to about 85° C. for about 5 min. The reaction is cooled to rt and neutralized with saturated aqueous sodium bicarbonate to pH 8. The mixture is extracted with DCM. The organic layer is washed with brine, dried over sodium sulfate, filtered and concentrated. The residue is purified by flash chromatography (preferably silica gel, petroleum ether) to give the target compound.

Illustration of General Procedure F

Example #F.1

4-Iodo-2-(pyridin-3-yl)-1H-indole-7-carboxamide

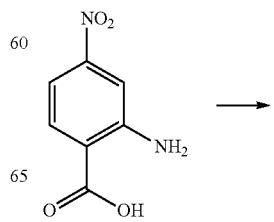

-continued

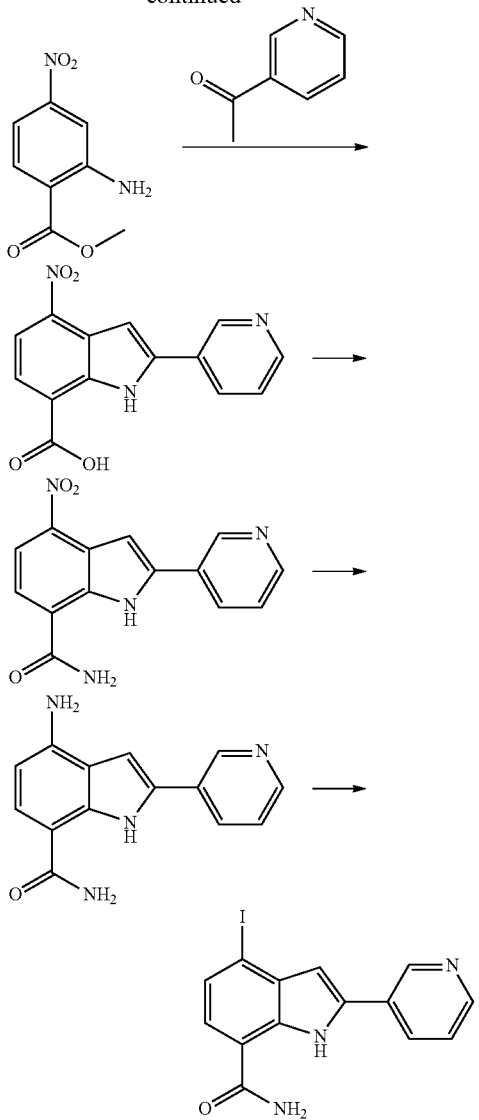

To a solution of 2-amino-4-nitrobenzoic acid (102 g, 560 mmol) in MeOH (1.5 L) was added slowly concentrated sulfuric acid (0.030 L, 560 mmol). The resulting solution was heated at about 75° C. for about 3 days. After cooling, the product was neutralized by addition of aqueous NaOH solution until pH~10. The crude product was extracted with EtOAc, dried over anhydrous sodium sulfate, filtered and concentrated to provide methyl 2-amino-4-nitrobenzoate (100 g, 91%). LC/MS (Table 1, Method ar) $R_t$=1.85 min; MS m/z 197.1 (M+H)$^+$. To a portion of this material (25 g, 127 mmol) and 1-(pyridin-3-yl)ethanone (30.9 g, 255 mmol) in dimethyl sulfoxide (150 mL) at about −15° C. was added potassium tert-butoxide (28.6 g, 255 mmol). After stirring for about 2.5 h at rt, the reaction was quenched with saturated aqueous ammonium chloride solution (100 mL) and then stirred for about 1 hr at rt. The resulting suspension was filtered, washed with water and dried under high vacuum to provide 4-nitro-2-(pyridin-3-yl)-1H-indole-7-carboxylic acid (22.4 g, 34%). LC/MS (Table 1, Method ab) $R_t$=1.50 min; MS m/z 284.1 (M+H)$^+$. To a mixture of this material (26.9 g, 95 mmol), ((1H-benzo[d][1,2,3]triazol-1-yl) oxy)tri(pyrrolidin-1-yl)phosphonium hexafluorophosphate(V) (99 g, 190 mmol), hydroxybenzotriazole hydrate (29.1 g, 190 mmol) and ammonium chloride (7.62 g, 142 mmol) in DMF (150 mL) was added diisopropylethylamine (66.3 mL, 380 mmol). The reaction mixture was stirred at rt overnight. The mixture was poured into 1000 mL water and the precipitate was filtered, washed with water and EtOAc, and collected to provide 4-nitro-2-(pyridin-3-yl)-1H-indole-7-carboxamide (17.48 g, 56%). LC/MS (Table 1, Method ar) $R_t$=1.44 min; MS m/z 283.1 (M+H)$^+$. To a nitrogen-purged stirred solution of this material (17.5 g, 52.6 mmol) in MeOH (1.5 L) was added 10% palladium on carbon (5.60 g, 5.26 mmol). The resulting suspension was treated with hydrogen (30 psi). After stirring overnight at rt, the reaction was filtered, and the solids were rinsed with MeOH. The filtrate was concentrated to provide 4-amino-2-(pyridin-3-yl)-1H-indole-7-carboxamide (10 g, 75%). LC/MS (Table 1, Method ar) $R_t$=1.10 min; MS m/z 253.1 (M+H)$^+$. A solution of sodium nitrite (7.82 g, 113 mmol) in water (20 mL) was added to an ice cold suspension of this material (13 g, 51.5 mmol) in MeCN (150 mL) and 2N hydrogen chloride (188 mL, 376 mmol) with stirring, maintaining the temperature below about −5° C. After stirring for about 30 min, a cold solution of aqueous potassium iodide (21.4 g, 129 mmol) was added to the reaction and the resulting mixture was stirred at rt for about 30 min. The reaction was heated on a water bath (85° C.) for 5 min. The reaction was cooled to rt and neutralized with saturated aqueous sodium bicarbonate to pH 8. The mixture was extracted with DCM. The organic layer was washed with brine, dried over sodium sulfate, filtered and concentrated. The residue was purified by flash chromatography (silica gel, petroleum ether) to provide 4-iodo-2-(pyridin-3-yl)-1H-indole-7-carboxamide (2.0 g, 9%). LC/MS (Table 1, Method ab) $R_t$=1.88 min; MS m/z 364.0 (M+H)$^+$. (Btk IC$_{50}$=B)

General Procedure G: Acidic Cleavage of a Boc-Protected Amine

To a solution of an N-Boc amine (1 equiv) in an organic solvent (such as DCM, DCE, 1,4-dioxane, EtOAc, or MeOH, preferably DCM, EtOAc, or 1,4-dioxane) is added an acid (such as TFA or HCl, preferably TFA; 2 to 35 equiv, preferably 15 to 25 equiv). The mixture is stirred at about 0 to 100° C. (preferably about 20 to 60° C.) for about 1 to 24 h (preferably about 1 to 6 h). Optionally, additional acid (2 to 35 equiv, preferably 20 to 25 equiv) may be added and the mixture stirred at about 0 to 100° C. (preferably about 15 to 60° C.) for about 1 to 24 h (preferably about 1 to 6 h). If a solid is present in the mixture, the mixture may be optionally filtered and the solid washed with an organic solvent such as 1,4-dioxane or Et$_2$O. The resulting solid is then optionally dried under reduced pressure to give the targeted compound. Alternatively, the mixture may be optionally concentrated in vacuo to give final compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as

Example #G.1

2-(2,5-Dihydro-1H-pyrrol-3-yl)-4-(2-methyl-3-(4-oxoquinazolin-3(4H)-yl)phenyl)-1H-indole-7-carboxamide

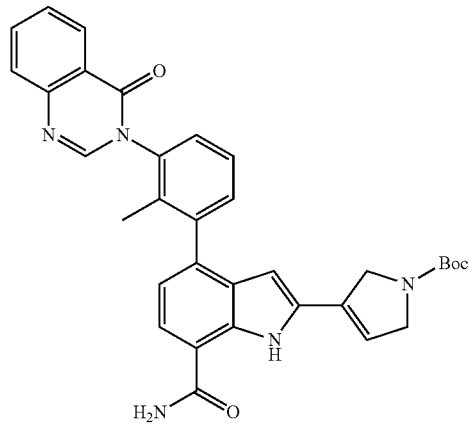

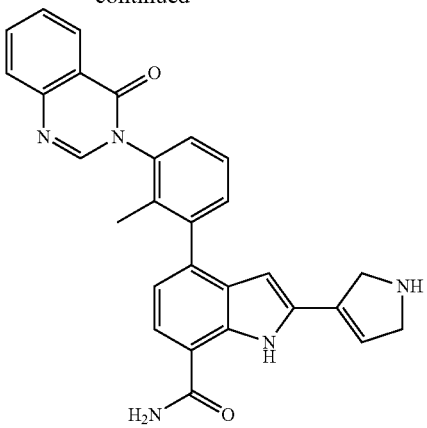

To a solution of tert-butyl 3-(7-carbamoyl-4-(2-methyl-3-(4-oxoquinazolin-3(4H)-yl)-phenyl)-1H-indol-2-yl)-2,5-dihydro-1H-pyrrole-1-carboxylate (0.6 g, 1 mmol, Preparation #15) in EtOAc (20 mL) was added HCl/EtOAc at rt. The reaction mixture was stirred at rt for 1 h. The solid was collected as a salt via filtration and dried to give 2-(2,5-dihydro-1H-pyrrol-3-yl)-4-(2-methyl-3-(4-oxoquinazolin-3(4H)-yl)phenyl)-1H-indole-7-carboxamide hydrochloride (0.5 g, 94%): LC/MS (Table 1, Method d) $R_t$=2.39 min; MS m/z: 462 (M+H)$^+$ (Btk IC$_{50}$=A).

TABLE G.1

Examples prepared using General Procedure G

| N-Boc Amine | Product | Example # | $R_t$ min (Table 1, Method) | m/z ESI+ (M + H)$^+$ | Btk IC$_{50}$ |
|---|---|---|---|---|---|
| tert-butyl 4-(7-carbamoyl-4-(2-methyl-3-(4-oxoquinazolin-3(4H)-yl)phenyl)-1H-indol-2-yl)-5,6-dihydropyridine-1(2H)-carboxylate (Preparation #2) |  | G.1.1 | 2.13 (o) | 476 | A |

TABLE G.1-continued

Examples prepared using General Procedure G

| N-Boc Amine | Product | Example # | R, min (Table 1, Method) | m/z ESI+ (M + H)+ | Btk IC$_{50}$ |
|---|---|---|---|---|---|
| di-tert-butyl (2-((3-(7-carbamoyl-1H-indol-4-yl)phenyl)carbamoyl)allyl)carbamate (prepared using J from 2-(bromomethyl)acrylic acid and di-tert-butyl iminodicarboxylate, D from Preparation #A.1) | 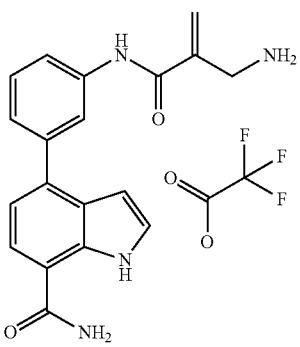 | G.1.2 | 2.17 (d) | 335 | A |
| tert-butyl (2-((3-(7-carbamoyl-1H-indol-4-yl)phenyl)carbamoyl)allyl)-(methyl)carbamate (prepared using J from 2-(bromomethyl)acrylic acid and tert-butyl methylcarbamate, D from Preparation #A.1) | 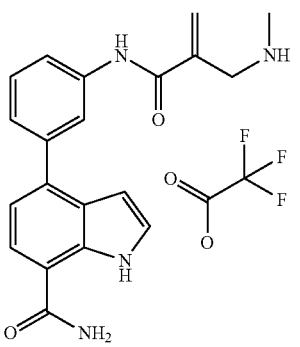 | G.1.3 | 2.20 (d) | 349 | A |

General Procedure H: Reductive Amination of an Aldehyde or Ketone with a Primary or Secondary Amine An aldehyde or ketone (preferably 1.0 equiv to 1.3 equiv) and an amine or amine salt (preferably 1.0 to 2.2 equiv) are added in an organic solvent or mixture of organic solvents (such as DCM, DCE or MeOH, or a mixture of DCE and MeOH, preferably DCE, MeOH, or 1:1 MeOH/DCM) at about rt to about 80° C. (preferably about rt). If an amine salt is used, then an amine base (such as TEA or DIEA, 1.0 to 2.2 equiv) is optionally added. AcOH (0.1 equiv to 5.0 equiv) is optionally added. The mixture is stirred at rt for about 1 to 90 min (preferably 5 to 30 min). A reducing agent (such as NaBH(OAc)$_3$, Na(CN)BH$_3$, NaBH$_4$, MP-Cyanoborohydride from Biotage™, 0.5 to 5.0 equiv, preferably 2.5-3.0 equiv of NaBH(OAc)$_3$, is added as a solid or as a solution in an organic solvent (as DCM, DCE or MeOH, or a mixture of DCE and MeOH). The mixture is stirred at rt for about 30 min to 72 h (preferably 1 to 24 h). The crude mixture may be concentrated under reduced pressure or optionally partitioned between water and an organic solvent (such as EtOAc, Et$_2$O or DCM). The organic layer is isolated and may be optionally washed with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl or Na$_2$SO$_3$). The organic solution may then be optionally dried with a drying agent (such as MgSO$_4$ or Na$_2$SO$_4$), filtered and concentrated in vacuo to give the target compound.

Illustration of General Procedure H

Example #H.1

2-(1-Methyl-2,5-dihydro-1H-pyrrol-3-yl)-4-(2-methyl-3-(4-oxoquinazolin-3(4H)-yl)phenyl)-1H-indole-7-carboxamide

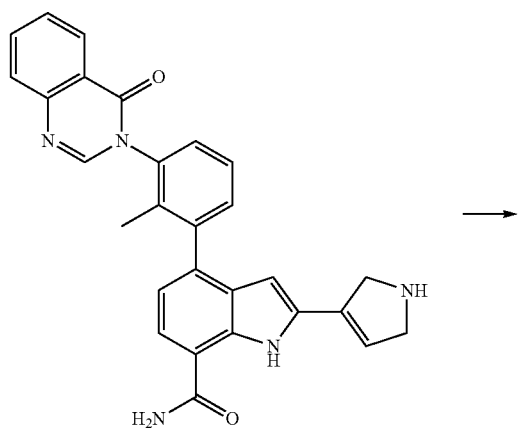

-continued

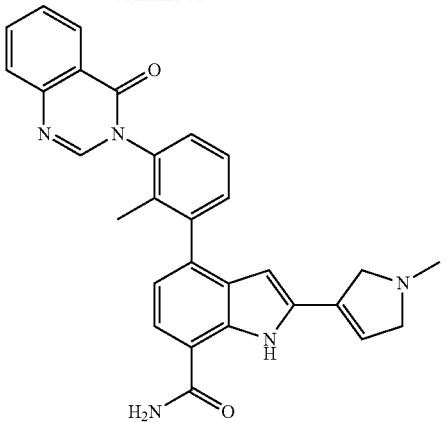

To a solution of 2-(2,5-dihydro-1H-pyrrol-3-yl)-4-(2-methyl-3-(4-oxoquinazolin-3(4H)-yl)phenyl)-1H-indole-7-carboxamide (50 mg, 0.1 mmol, Example #G.1) in MeOH (1 mL) was added (CH$_2$O). (1.6 mg, 0.054 mmol) at rt. After stirring at rt for 1 h under N$_2$ atmosphere, NaBH(OAc)$_3$ (60 mg, 0.27 mmol) was added. The resulting mixture was stirred at rt for 2 h. The solvent was removed under reduced pressure to give a residue, which was purified by prep-HPLC to give 2-(1-methyl-2,5-dihydro-1H-pyrrol-3-yl)-4-(2-methyl-3-(4-oxoquinazolin-3(4H)-yl)phenyl)-1H-indole-7-carboxamide (15 mg, 32%): LC/MS (Table 1, Method o) R$_t$=2.05 min; MS m/z: 476 (M+H)$^+$ (Btk IC$_{50}$ =A).

TABLE H.1

Examples prepared from 4-(2-methyl-3-(4-oxoquinazolin-3(4H)-yl)phenyl)-2-(1,2,3,6-tetrahydropyridin-4-yl)-1H-indole-7-carboxamide (Example #G.1.1) using General Procedure H

| Aldehyde | Product | Example # | R$_t$ min (Table 1, Method) | m/z ESI+ (M + H)$^+$ | Btk IC$_{50}$ |
|---|---|---|---|---|---|
| paraformaldehyde | | H.1.1 | 2.08 (o) | 490 | A |

TABLE H.2

Examples prepared from 4-(3-amino-2-methylphenyl)-2-(1-(methylsulfonyl)-1,2,3,6-tetrahydropyridin-4-yl)-1H-indole-7-carboxamide (Example #A.4.5) using General Procedure H

| Aldehyde | Product | Example # | R$_t$ min (Table 1, Method) | m/z ESI+ (M + H)$^+$ | Btk IC$_{50}$ |
|---|---|---|---|---|---|
| thiazole-2-carbaldehyde | | H.2.1 | 1.74 (g) | 522 | A |

General Procedure I: Formation of a Sulfonamide from an Amine and a Sulfonyl Chloride To a flask is added an amine (1.0 equiv), optionally as a hydrochloride salt, a solvent or mixture of solvents (such as DCM, DCE, EtOAc, THF, 1,4-dioxane, pyridine, DME, or pyridine/DCM, preferably THF, optionally with a base (such as TEA, DIEA, preferably DIEA; 1 to 5 equiv, preferably 1-2 equiv) and a sulfonyl chloride (0.9 to 2.0 equiv, preferably 1.0 to 1.25 equiv). The mixture is stirred at about 0 to 80° C. (preferably about 0 to 35° C.) for about 1 h to 24 h (preferably 5 to 16 h). The mixture may optionally be concentrated in vacuo to give a residue as the target compound. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure I

Example #I.1

4-(3-(Vinylsulfonamido)phenyl)-1H-indole-7-carboxamide

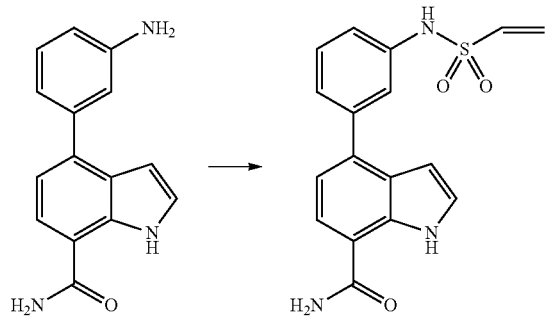 [SMILES: NC(=O)c1ccc(-c2cccc(N)c2)c2cc[nH]c12 ; C=CS(=O)(=O)Nc1cccc(-c2ccc(C(N)=O)c3[nH]ccc23)c1]

To a mixture of 4-(3-aminophenyl)-1H-indole-7-carboxamide (0.11 g, 0.438 mmol, Preparation #A.1), THF (4 mL) and DIEA (0.152 mL, 0.876 mmol) at about 0° C. (ice bath) was added ethenesulfonyl chloride (0.058 g, 0.460 mmol, FCH Group). The ice bath was removed and mixture was stirred for about 6 h at rt. The reaction mixture was concentrated under reduced pressure and the residue was dissolved in DCM and washed water (2×), brine, and passed through a Biotage Phase separator. The mixture was concentrated under reduced pressure and the residue was purified on silica gel using a gradient of 0-10% MeOH in DCM to provide a solid. The solid was triturated with ether (3×, sonicating after each addition of ether). The solid was dried over night under reduced pressure at 75° C. to provide 4-(3-(vinylsulfonamido)phenyl)-1H-indole-7-carboxamide (29 mg, 19%): LC/MS (Table 1, Method c) R$_t$=2.34 min; MS m/z 342 (M+H)$^+$. (Btk IC$_{50}$=A)

General Procedure J: Substitution of an Alkyl Halide with an Amine Nucleophile

A flask is charged with an alkyl halide (preferably 1 equiv) and an organic solvent (such as THF, MeCN, DMF, DMA, NMP or DMSO; preferably THF or MeCN). To the flask are added in no particular order the amine nucleophile (1 to 25 equiv, preferably 1.2-20 equiv) and an optionally a base (such as LiHMDS, NaH, K$_2$CO$_3$, NaHMDS, NaOt-Bu, KHMDS or KOt-Bu, preferably none, NaH or K$_2$CO$_3$; 1 to 5 equiv, preferably 1-3 equiv). The mixture is stirred at about 0 to 100° C. (preferably about 0-40° C.) for about 1 to 24 h (preferably about 3 to 20 h). The mixture may optionally be concentrated in vacuo to give a residue as the target compound. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound. Alternatively, the residue from concentrating the reaction mixture may be suspended in water, sonicated and collected via vacuum filtration.

Illustration of General Procedure J

Example #J.1

(E)-4-(3-(4-(Dimethylamino)but-2-enamido)-2-methylphenyl)-1H-indole-7-carboxamide

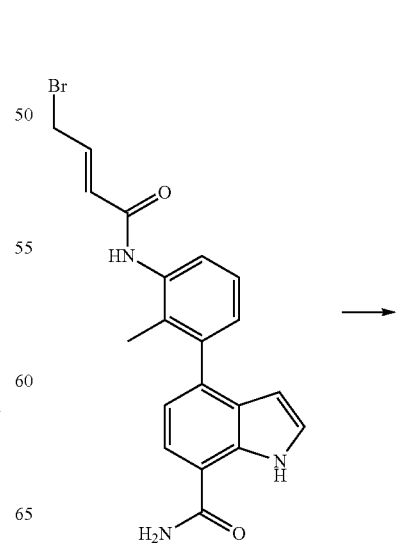

-continued

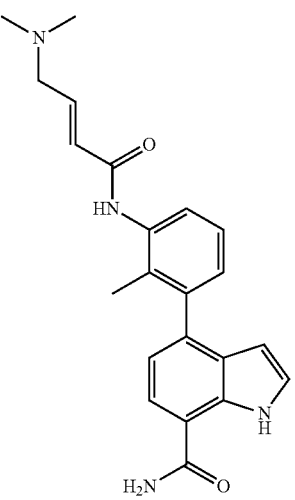

To a solution of (E)-4-(3-(4-bromobut-2-enamido)-2-methylphenyl)-1H-indole-7-carboxamide (1.4 g, 3.40 mmol, prepared using E from 4-(3-amino-2-methylphenyl)-1H-indole-7-carboxamide (Example #16) and (E)-4-bromobut-2-enoyl chloride [*J. Org. Chem.* 2011, 76, 4467]) in THF (24 mL) at 0° C. was added 2 M dimethylamine in THF (34.0 mL, 67.9 mmol). The mixture was stirred for 3 h while warming to rt. The mixture was concentrated under reduced pressure and water (15 mL) was added to the residue. The mixture was sonicated for about 20 min at rt, filtered, washed with water and dried under reduced pressure. The residue was added to a silica gel column and was eluted with MeOH/DCM (0-15%,) to provide the crude product (0.650 g). The crude product was dissolved in DMA (5 mL) and water (100 mL) added while stirring for 20 min at rt. The mixture was filtered, washed with water (50 mL×3), and dried under reduced pressure to provide (E)-4-(3-(4-(dimethylamino)but-2-enamido)-2-methylphenyl)-1H-indole-7-carboxamide (0.40 g, 31%): LC/MS (Table 1, Method f) $R_t$=1.05 min; MS m/z 377 (M+H)$^+$. (Btk IC$_{50}$ B)

TABLE J.1

Examples prepared from an (E)-4-(3-(4-bromobut-2-enamido)-2-methylphenyl)-1H-indole-7-carboxamide (prepared using E from 4-(3-amino-2-methylphenyl)-1H-indole-7-carboxamide (Example #16) and (E)-4-bromobut-2-enoyl chloride [*J. Org. Chem.* 2011, 76, 4467]) using General Procedure J

| Amine | Product | Example # | $R_t$ min (Table 1, Method) | m/z ESI+ (M + H)$^+$ | Btk IC$_{50}$ |
|---|---|---|---|---|---|
| piperidine | | J.1.1 | 1.13 (f) | 417 | B |
| (tetrahydrofuran-2-yl)methanamine | | J.1.2 | 1.13 (f) | 433 | B |

TABLE J.1-continued

Examples prepared from an (E)-4-(3-(4-bromobut-2-enamido)-2-methylphenyl)-1H-indole-7-carboxamide (prepared using E from 4-(3-amino-2-methylphenyl)-1H-indole-7-carboxamide (Example #16) and (E)-4-bromobut-2-enoyl chloride [*J. Org. Chem.* 2011, 76, 4467]) using General Procedure J

| Amine | Product | Example # | $R_t$ min (Table 1, Method) | m/z ESI+ (M + H)+ | Btk IC$_{50}$ |
|---|---|---|---|---|---|
| 2-methoxyethanamine | | J.1.3 | 1.09 (f) | 407 | C |
| cyclopropanamine | | J.1.4 | 1.09 (f) | 389 | B |
| morpholine | | J.1.5 | 1.06 (f) | 419 | C |

TABLE J.1-continued

Examples prepared from an (E)-4-(3-(4-bromobut-2-enamido)-2-methylphenyl)-1H-
indole-7-carboxamide (prepared using E from 4-(3-amino-2-methylphenyl)-1H-indole-7-
carboxamide (Example #16) and (E)-4-bromobut-2-enoyl chloride [*J. Org. Chem.* 2011, 76, 4467])
using General Procedure J

| Amine | Product | Example # | $R_t$ min (Table 1, Method) | m/z ESI+ (M + H)+ | Btk IC$_{50}$ |
|---|---|---|---|---|---|
| 1-methylpiperazine | | J.1.6 | 1.14 (f) | 432 | C |

TABLE J.2

Example prepared from (E)-4-(3-(4-bromobut-2-enamido)-2-methylphenyl)-1H-
pyrrolo[2,3-c]pyridine-7-carboxamide (prepared using E from 4-(3-amino-2-methylphenyl)-1H-
pyrrolo[2,3-c]pyridine-7-carboxamide (Example #2) and (E)-4-bromobut-2-enoyl chloride
[*J. Org. Chem.* 2011, 76, 4467]) using General Procedure J

| Amine | Product | Example # | $R_t$ min (Table 1, Method) | m/z ESI+ (M + H)+ | Btk IC$_{50}$ |
|---|---|---|---|---|---|
| Dimethyl-amine | | J.2.1 | 0.70 (g) | 378 | B |

TABLE J.3

Example prepared from cyanic bromide with an amine using General Procedure J

| Amine | Product | Example # | $R_t$ min (Table 1, Method) | m/z ESI+ (M + H)+ | Btk IC$_{50}$ |
|---|---|---|---|---|---|
| 4-(Azetidin-3-yl(methyl)amino)-2-methyl-1H-indole-7-carboxamide hydrochloride (Prepared using A from Preparation #40 with methylboronic acid and G with HCl) | | J.3.1 | 1.39 (at) | 284 | B |

General Procedure K: Hydrolysis of an Acetonide

To a solution of an acetonide (preferably 1 equiv) in an organic solvent (such as 1,4-dioxane and THF, preferably THF) is added an acid, such as 4 M HCl in-1,4-dioxane (3-100 equiv, preferably 30-40 equiv). The reaction mixture is heated at about 20-120° C. (preferably about rt using conventional heating; about 120° C. using microwave irradiation) for about 0.25-24 h (preferably about 4 h using conventional heating; about 20 min using microwave irradiation). The reaction mixture is allowed to cool to ambient temperature before it is optionally partitioned between an organic solvent (such as EtOAc or DCM) and aqueous base (such as NaHCO$_3$, Na$_2$CO$_3$ or NaOH, preferably NaHCO$_3$) and the aqueous layer is optionally extracted with additional organic solvent (such as EtOAc or DCM). The organic layer is dried over anhydrous MgSO$_4$ or Na$_2$SO$_4$, filtered, and concd under reduced pressure. Alternatively the solvent is removed under reduced pressure to give the desired compound.

Illustration of General Procedure K:

Example #K.1*

2-(14(R)-2,3-Dihydroxypropyl)-1H-pyrazol-4-yl)-4-(2-methyl-3-(4-oxoquinazolin-3(4H)-yl)phenyl)-1H-indole-7-carboxamide

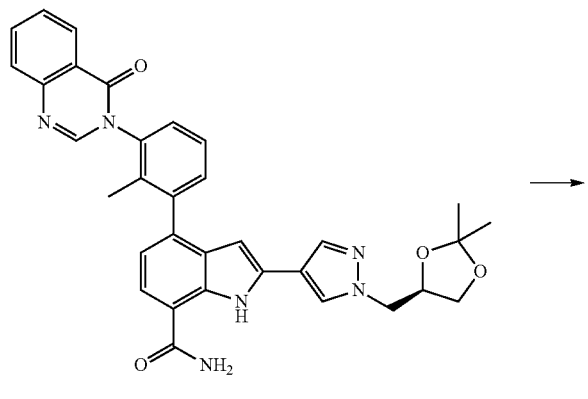

→

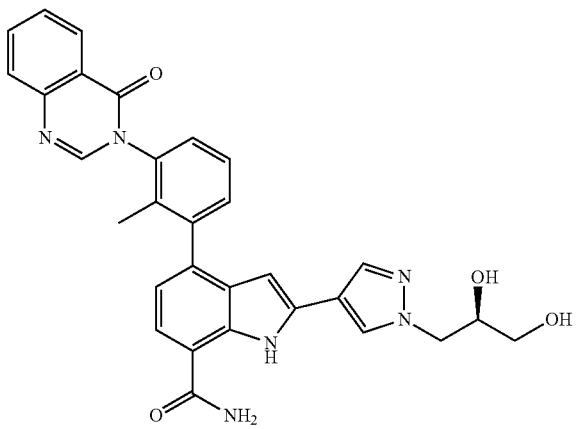

To a solution of 2-(1-(((R)-2,2-dimethyl-1,3-dioxolan-4-yl)methyl)-1H-pyrazol-4-yl)-4-(2-methyl-3-(4-oxoquinazolin-3(4H)-yl)phenyl)-1H-indole-7-carboxamide (0.047 g, 0.082 mmol, prepared using A from 4-bromo-2-iodo-1H-indole-7-carboxamide and (R)-1-((2,2-dimethyl-1,3-dioxolan-4-yl)methyl)-4-(4,4,5,5-tetramethyl-1,3,2-dioxaborolan-2-yl)-1H -pyrazole (Preparation #20), A from 3-(2-methyl-3-(4,4,5,5-tetramethyl-1,3,2-dioxaborolan-2-yl) phenyl)quinazolin-4(3H)-one [PCT Int. Appl., WO 2011159857]) in THF (5 mL) was added 4 M HCl in 1,4-dioxane (0.5 mL). The mixture was stirred at rt for about 4 h. The reaction mixture was concentrated under reduced pressure and the residue was purified by prep-HPLC (Table 1, Method at) to provide 2-(1-((R)-2,3-dihydroxypropyl)-1H-pyrazol-4-yl)-4-(2-methyl-3-(4-oxoquinazolin-3(4H)-yl)phenyl)-1H-indole-7-carboxamide (0.035 g, 80%): LC/MS (Table 1, Method a) R$_t$=1.65 min; MS m/z 535. (Btk IC$_{50}$=A)

TABLE K.1

Examples prepared from an acetonide using General Procedure K

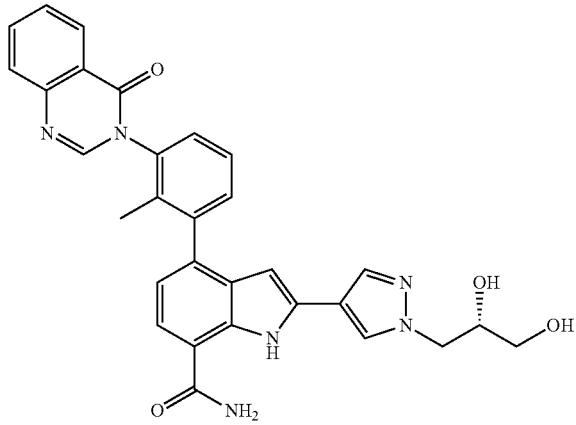 [SMILES: Cc1c(-c2ccc(C(N)=O)c3[nH]c(-c4cnn(C[C@H](O)CO)c4)cc23)cccc1-n1cnc2ccccc2c1=O]

| Acetonide | Product | Example # | R$_t$ min (Table 1, Method) | m/z ESI+ (M + H)$^+$ | Btk IC$_{50}$ |
|---|---|---|---|---|---|
| 2-(1-(((S)-2,2-dimethyl-1,3-dioxolan-4-yl)methyl)-1H-pyrazol-4-yl)-4-(2-methyl-3-(4-oxoquinazolin-3(4H)-yl)phenyl)-1H-indole-7-carboxamide (prepared using A from 4-bromo-2-iodo-1H-indole-7-carboxamide and Preparation #21, A from 3-(2-methyl-3-(4,4,5,5-tetramethyl-1,3,2-dioxaborolan-2-yl)phenyl)quinazolin-4(3H)-one [WO 2011159857]) | | K.1.1 | 1.64 (a) | 535 | A |

General Procedure L: Hydrogenation of an Alkene

A round bottom flask is charged with a palladium catalyst, such as Pd/C or Pd(OH)$_2$ (10 or 20 wt %, about 0.005 to 1.0 equiv, preferably 0.5 to 1.0 equiv). The flask is evacuated then flushed with nitrogen 2 to 5 times (preferably 3 times) prior to addition of an organic solvent or mixture of solvents (such as EtOAc, MeOH, EtOH or MeOH/AcOH, preferably MeOH/AcOH) under a nitrogen atmosphere. To the mixture is added an alkene (preferably 1 equiv), neat or optionally as a solution in an organic solvent or mixture of solvents (such as EtOAc, MeOH, EtOH or MeOH/AcOH, preferably MeOH). The mixture is stirred under a hydrogen atmosphere (about 30 to 50 psi) for about 1 to 60 h (preferably about 4 to 5 h). Optionally the reaction may be performed using an H-cube instrument with either Pd/C or Pd(OH)$_2$ cartridges (10 or 20 wt %) and the starting material is passed through the system as a solution in the preferred solvent/s. In cases where the reaction does not proceed to completion as monitored by TLC, LC/MS, or HPLC, the mixture can be optionally heated to about 30 to 80° C. (preferably about 50° C.) for about 1 to 24 h (preferably about 16 h) and in cases where the H-cube is used to perform the reaction, the pressure may be increased (25 to 50 bar, preferably 40 to 50 bar). The mixture is then filtered and the filter cake is rinsed with an organic solvent (such as EtOAc, MeOH or EtOH, preferably the reaction solvent) and the filtrate is concentrated under reduced pressure to give the crude product.

Illustration of General Procedure L

Example #L.1

2-(1-Acetylpiperidin-4-yl)-4-(3-amino-2-methylphenyl)-1H-indole-7-carboxamide

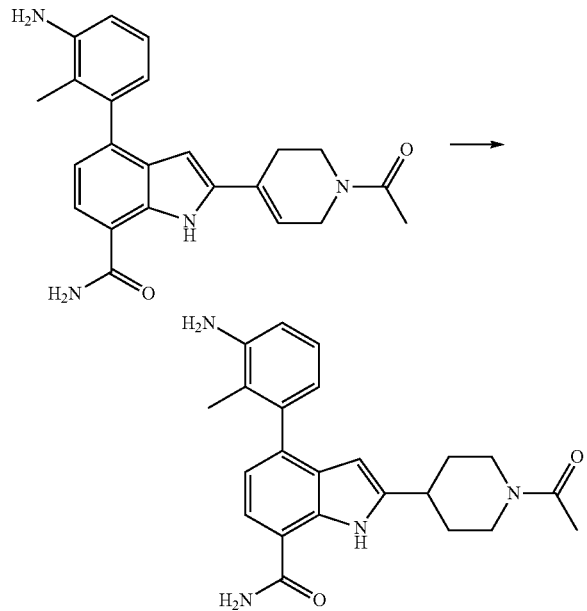

2-(1-Acetyl-1,2,3,6-tetrahydropyridin-4-yl)-4-(3-amino-2-methylphenyl)-1H-indole-7-carboxamide (300 mg, 0.772 mmol, prepared using A with 4-bromo-2-iodo-1H-indole-7-carboxamide (Preparation #1) and 1-(4-(4,4,5,5-tetramethyl-1,3,2-dioxaborolan-2-yl)-5,6-dihydropyridin-1(2H)-yl) ethanone [Combi-Blocks], A with 3-amino-2-methylphenylboronic acid, pinacol ester [Combi-Blocks]) and solvent MeOH (72 mL) were added to 20 wt % Pd/C (60.0 mg, 0.564 mmol) in a 250 mL stainless steel pressure bottle and stirred for about 4.5 h at 30 psi then at about 50° C. for about 16 h. The reaction was filtered, concentrated in vacuo and the residue was purified on silica gel using a gradient of 0-10% MeOH in DCM to provide 2-(1-acetylpiperidin-4-yl)-4-(3-amino-2-methylphenyl)-1H-indole-7-carboxamide (77.1 mg, 0.197 mmol): LC/MS (Table 1, Method f) R$_t$=1.06 min; MS m/z 391. (Btk IC$_{50}$=B)

General Procedure M: Removal of a Silyl Group from an O-Silyl Ether

Method 1:

To a solution of an O-silyl-ether (1 equiv) in an organic solvent (such as DMF, 1,4-dioxane, or DCM, preferably DCM) is added an acid (such as TFA or HCl, 5 to 50 equiv, preferably 30 equiv) and the mixture is stirred at about 0 to 50° C. (preferably about 15 to 25° C.) for about 1 to 48 h (preferably about 4 to 16 h). Alternatively, additional acid (5 to 20 equiv, preferably 10 equiv) may be added and the mixture is heated to about 30 to 100° C. (preferably about 50 to 80° C.) for about 0.5 to 10 h (preferably about 1 to 5 h).

Method 2:

To a solution of an O-silyl ether (1 equiv) in an organic solvent (such as DMF, 1,4-dioxane, or DCM, preferably DMF) is added a fluoride source such as HF, TBAF (1 to 10 equiv, preferably 4 equiv), and the mixture is stirred at about 20 to 110° C. (preferably about 25 to 60° C.) for about 1 to 20 h (preferably about 2 to 8 h).

For either method, the targeted compound may optionally be isolated by cooling the mixture and filtering the precipitate. Alternatively, the mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure M:

Example #M.1

N-(3-(7-carbamoyl-2-(1-methyl-1H-pyrazol-4-yl)-1H-indol-4-yl)-2-(hydroxymethyl)phenyl)thiazole-2-carboxamide

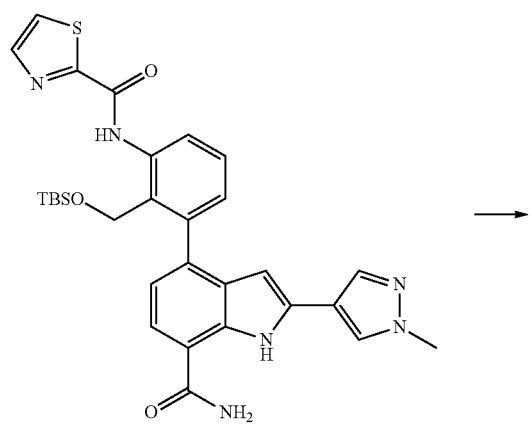

→

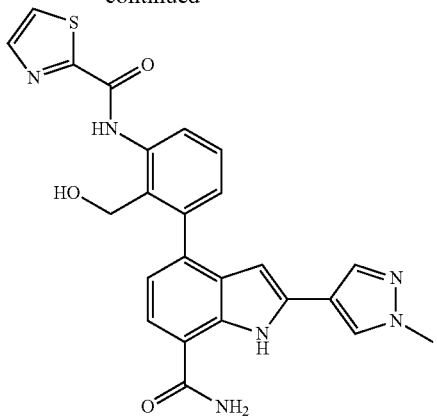

To a solution of N-(2-(((tert-butyldimethylsilyl)oxy)methyl)-3-(7-carbamoyl-2-(1-methyl-1H-pyrazol-4-yl)-1H-indol-4-yl)phenyl)thiazole-2-carboxamide (100 mg, 0.170 mmol, prepared using D from thiazole-2-carboxylic acid and 2-((tert-butyldimethylsilyloxy)methyl)-3-(4,4,5,5-tetramethyl-1,3,2-dioxaborolan-2-yl)aniline [Matrix], A and Preparation #10) in 1,4-dioxane (2 mL) was added 3 N aqueous HCl (2 mL, 6.00 mmol) and the mixture was stirred at about 25° C. for about 3 h. The resulting solution was diluted with EtOAc (5 mL) and washed with water (3 mL). The organic phase was dried over $Na_2SO_4$ and concentrated to give a crude product, which was purified by Prep-TLC (DCM:MeOH=20:1) to provide N-(3-(7-carbamoyl-2-(1-methyl-1H-pyrazol-4-yl)-1H-indol-4-yl)-2-(hydroxymethyl)phenyl)thiazole-2-carboxamide (36 mg, 45%): $^1$H NMR (DMSO-d6) δ 11.16 (s, 1H), 10.92 (s, 1H), 8.32 (s, 1H), 8.27-8.25 (d, J=8.4 Hz, 1H), 8.14-8.07 (m, 3H), 7.94 (s, 1H), 7.67-7.65 (d, J=6.4 Hz, 1H), 7.46-7.43 (m, 2H), 7.14-7.12 (d, J=7.6 Hz, 1H), 6.96-6.94 (d, J=7.6 Hz, 1H), 6.31 (s, 1H), 5.78 (s, 1H), 4.54-4.47 (m, 2H), 3.82 (s, 3H). LC/MS (Table 1, Method o) $R_t$=2.73 min; MS m/z: 473 (M−H)$^+$. (Btk IC$_{50}$=A)

TABLE M.1

Examples prepared from an O-silyl ether using General Procedure M

| O-silyl ether | Product | Example # | $R_t$ min (Table 1, Method) | m/z ESI+ (M + H)$^+$ | Btk IC$_{50}$ |
|---|---|---|---|---|---|
| 4-(2-(((tert-butyldimethylsilyl)oxy)methyl)-3-(6-fluoro-4-oxoquinazolin-3(4H)-yl)phenyl)-2-(1-methyl-1H-pyrazol-4-yl)-1H-indole-7-carboxamide (prepared using A from Preparation #10 and Preparation #11) | | M.1.1 | 3.22 (v) | 509 | A |

TABLE M.1-continued

Examples prepared from an O-silyl ether using General Procedure M

| O-silyl ether | Product | Example # | R, min (Table 1, Method) | m/z ESI+ (M + H)+ | Btk IC50 |
|---|---|---|---|---|---|
| 4-bromo-2-(1-(2-(tert-butyldimethylsilyloxy)ethyl)-1H-pyrazol-4-yl)-1H-indole-7-carboxamide (prepared using J from 4-(4,4,5,5-tetramethyl-1,3,2-dioxaborolan-2-yl)-1H-pyrazole with A with (2-bromoethoxy)-tert-butyldimethylsilane, 4-bromo-2-iodo-1H-indole-7-carboxamide, A with 3-(2-methyl-3-(4,4,5,5-tetramethyl-1,3,2-dioxaborolan-2-yl)phenyl)quinazolin-4(3H)-one [WO 2011159857]) | | M.1.2 | 1.70 (a) | 505 | A |

General Procedure N: Hydrolysis of a Sulfonamide

To a flask containing a sulfonamide, for example, a sulfonyl-protected indole, (preferably 1 equiv) in an organic solvent (such as 1,4-dioxane, MeOH, or THF/MeOH, preferably 1,4-dioxane) is added an base (such as $K_2CO_3$, $Cs_2CO_3$, aqueous $Na_2CO_3$ or aqueous NaOH, 1-30 equiv; preferably 1-5 equiv for $Cs_2CO_3$,). The mixture is stirred at about 25-100° C. (preferably about 60° C.) for about 1-72 h (preferably about 1-18 h). In cases where the reaction does not proceed to completion as monitored by TLC, LC/MS, or HPLC, additional base (such as $K_2CO_3$, $Cs_2CO_3$, aqueous $Na_2CO_3$ or aqueous NaOH, preferably 1-5 equiv for $Cs_2CO_3$,) and/or a cosolvent (such as EtOH) is added. The reaction is continued at about 25-100° C. (preferably about 60° C.) for about 0.25-3 h (preferably about 1-2 h). In any case where an additional base labile group is present (for example, an ester or a cyano group), this group may also be hydrolyzed. The reaction is worked up using one of the following methods. Method 1. The organic solvent is optionally removed under reduced pressure and the aqueous solution is neutralized with the addition of a suitable aqueous acid (such as aqueous HCl). A suitable organic solvent (such as EtOAc or DCM) and water are added, the layers are separated, and the organic solution is dried over anhydrous $Na_2SO_4$ or $MgSO_4$, filtered, and concentrated to dryness under reduced pressure to give the target compound. Method 2. The organic solvent is optionally removed under reduced pressure a suitable organic solvent (such as EtOAc or DCM) and water are added, the layers are separated, and the organic solution is dried over anhydrous $Na_2SO_4$ or $MgSO_4$, filtered, and concentrated to dryness under reduced pressure to give the target compound. Method 3. The reaction mixtureis concentrated under reduced pressure and directly purified by one of the subsequent methods.

Illustration of General Procedure N:

Preparation #N.1: (R)-4-(3-(4-oxoquinazolin-3(4H)-yl)piperidin-1-yl)-1H-indole-7-carbonitrile

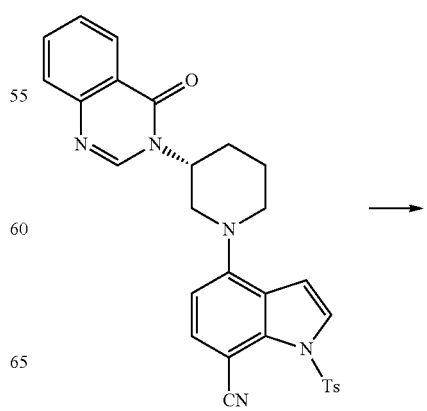

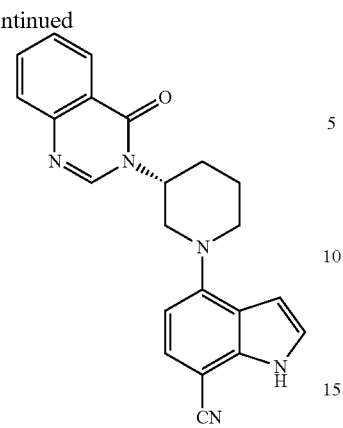

To a mixture of (R)-4-(3-(4-oxoquinazolin-3(4H)-yl)piperidin-1-yl)-1-tosyl-1H-indole-7-carbonitrile (0.12 g, 0.229 mmol, prepared using B from 4-fluoro-1-tosyl-1H-indole-7-carbonitrile (Preparation #27, step A) and (R)-3-(piperidin-3-yl)quinazolin-4(3H)-one (Preparation #31) in THF (2 mL) and MeOH (1 mL) was added cesium carbonate (0.128 mL, 1.60 mmol) and stirred at rt for about 18 h. The reaction was diluted with water (60 mL) and stirred for another 20 min. The mixture was extracted into DCM, dried by passing through a Biotage phase separator to remove residual water and evaporated to dryness to give (R)-4-(3-(4-oxoquinazolin-3(4H)-yl)piperidin-1-yl)-1H-indole-7-carbonitrile (0.044 g, 52%); LC/MS (Table 1, Method g) $R_t$=1.50 min; MS m/z: 370 (M+H)$^+$ General Procedure O: Hydrolysis of a Nitrile to a Primary Amide To a flask containing a nitrile, (preferably 1 equiv) in an organic solvent (such as MeOH, EtOH, DMSO, DMSO/MeOH, or DMSO/EtOH, preferably DMSO/EtOH) is added a base (such as KOH, aqueous KOH or aqueous NaOH, 1-30 equiv, preferably 3-5 equiv for KOH, preferably 10-15 equiv for aqueous NaOH). The mixture is stirred at about rt for about 1-30 min (preferably about 1-10 min) then 30% $H_2O_2$ (5-30 equiv preferably 9-27 equiv) was added to the mixture slowly and the reaction mixture was stirred at rt for about 10-30 min. In cases where the reaction does not proceed to completion as monitored by TLC, LC/MS, or HPLC, the reaction is continued at rt for about 0.25-1 h (preferably about 0.25-0.5 h). The reaction is worked up using one of the following methods. Method 1. The mixture is diluted with saturated NH$_4$Cl and water, stirred at about rt for about 1-30 min. The resulting suspension is collected by filtration, washed with a suitable solvent (such as MeOH, EtOH, or water), and the filtercake is dried under vacuum to give the target compound. Method 2. The organic solvent is optionally removed under reduced pressure a suitable organic solvent (such as EtOAc or DCM) and water are added, the layers are separated, and the organic solution is dried over anhydrous Na$_2$SO$_4$ or MgSO$_4$, filtered, and concentrated to dryness under reduced pressure to give the target compound. Method 3. The reaction mixture is concentrated under reduced pressure and directly purified by one of the subsequent methods Illustration of General Procedure O:

Example #O.1

N-(trans-1-(7-carbamoyl-2-(1-(methylsulfonyl)-1,2,3,6-tetrahydropyridin-4-yl)-1H-indol-4-yl)-4-hydroxypiperidin-3-yl)thiazole-2-carboxamide

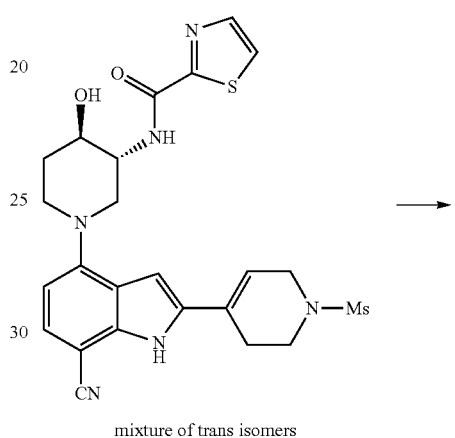

mixture of trans isomers

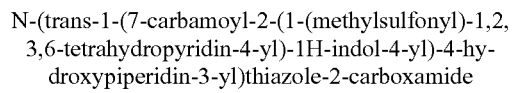

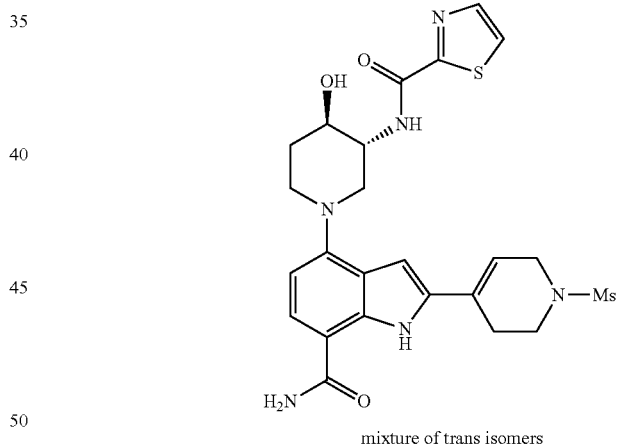

mixture of trans isomers

To a stirred solution of N-(trans-1-(7-cyano-2-(1-(methylsulfonyl)-1,2,3,6-tetrahydropyridin-4-yl)-1H-indol-4-yl)-4-hydroxypiperidin-3-yl)thiazole-2-carboxamide (36 mg, 0.068 mmol, prepared using B Preparation #27 and Preparation #23, N with Cs$_2$CO$_3$) in DMSO (0.8 mL) was added EtOH (4.8 mL) and KOH (12.81 mg, 0.228 mmol). The mixture was stirred at rt for about 10 min, then 30% H$_2$O$_2$ (0.070 mg, 0.615 umol) was added to the mixture slowly and the reaction mixture was stirred at rt for about 15 min. Then water (6 mL) was added to the mixture and the solution was extracted with EtOAc (3×20 mL). The organic layer was washed with brine, dried over Na$_2$SO$_4$, filtered and concentrated to give the crude product which was purified by flash chromatography to provide N-(trans-1-(7-carbamoyl-2-(1-(methylsulfonyl)-1,2,3,6-tetrahydropyridin-4-yl)-1H-indol-4-yl)-4-hydroxypiperidin-3-yl)thiazole-2-carboxamide (15 mg, 40%): LC/MS (Table 1, Method d) $R_t$=2.52 min; MS m/z: 545 (M+H)$^+$. (Btk IC$_{50}$=A)

TABLE O.1

Examples prepared using General Procedure O

| Nitrile | Product | Example # | $R_t$ min (Table 1, Method) | m/z ESI+ (M + H)$^+$ | Btk IC$_{50}$ |
|---|---|---|---|---|---|
| N-(3-(7-cyano-1H-indol-4-yl)-2-methylphenyl)-4-(difluoromethyl)benzamide (prepared using A from 4-bromo-1H-indole-7-carbonitrile and 2-methyl-3-(4,4,5,5-tetramethyl-1,3,2-dioxaborolan-2-yl)aniline [Combi-Blocks]), N with Cs$_2$CO$_3$ | | O.1.1 | 1.69 (f) | 420 | B |
| 4-(2-methyl-3-(oxetan-3-ylamino)phenyl)-1H-indole-7-carbonitrile (prepared using A from 4-bromo-1H-indole-7-carbonitrile and 2-methyl-3-(4,4,5,5-tetramethyl-1,3,2-dioxaborolan-2-yl)aniline [CombiBlocks]), H from oxetan-3-one, N with Cs$_2$CO$_3$ | | O.1.2 | 1.72 (f) | 322 | C |
| (R)-2-(1-(methylsulfonyl)-1,2,3,6-tetrahydropyridin-4-yl)-4-(3-(8-oxo-5,6-dihydroimidazo[1,2-a]pyrazin-7(8H)-yl)piperidin-1-yl)-1H-indole-7-carbonitrile (prepared using B from Preparation #27 and Preparation #13, N with Cs$_2$CO$_3$ | | O.1.3* | 0.99 (f) | 538 | A |

TABLE O.1-continued

Examples prepared using General Procedure O

| Nitrile | Product | Example # | R, min (Table 1, Method) | m/z ESI+ (M + H)+ | Btk IC50 |
|---|---|---|---|---|---|
| (R)-2-(1-(methylsulfonyl)-1,2,3,6-tetrahydropyridin-4-yl)-4-(3-(8-oxoimidazo[1,2-a]pyrazin-7(8H)-yl)piperidin-1-yl)-1H-indole-7-carbonitrile (prepared using B from Preparation #27 and Preparation #12, N with Cs₂CO₃ | | O.1.4* | 1.18 (f) | 536 | A |
| (R)-N-(1-(7-cyano-2-(1-(methylsulfonyl)-1,2,3,6-tetrahydropyridin-4-yl)-1H-indol-4-yl)piperidin-3-yl)-2-methyloxazole-4-carboxamide (prepared using B from Preparation #27 and (R)-tert-butyl piperidin-3-ylcarbamate, G with HCl, and D with 2-methyloxazole-4-carboxylic acid, N with Cs₂CO₃ | | O.1.5* | 1.43 (f) | 527 | A |
| (R)-N-(1-(7-cyano-1H-indol-4-yl)piperidin-3-yl)-2-methyloxazole-4-carboxamide (Preparation #V.1) , N with Cs₂CO₃ | | O.1.6* | 1.08 (g) | 368 | |

TABLE O.1-continued

Examples prepared using General Procedure O

| Nitrile | Product | Example # | R, min (Table 1, Method) | m/z ESI+ (M + H)+ | Btk IC50 |
|---|---|---|---|---|---|
| (R)-1-(1-(7-cyano-1H-indol-4-yl)piperidin-3-yl)-3-(thiazol-2-yl)urea (prepared using V with thiazol-2-ylcarbamic acid and Preparation #B.1, N with Cs2CO3) | | O.1.7* | 0.72 (g) | 385 | C |
| (R)-N-(1-(7-cyano-1H-indol-4-yl)piperidin-3-yl)-4-(trifluoromethyl)benzamide (prepared using V with 4-(trifluoromethyl)benzoic acid and Preparation #B.1, N with Cs2CO3) | | O.1.8* | 1.62 (g) | 431 | C |
| (R)-N-(1-(7-cyano-1H-indol-4-yl)piperidin-3-yl)-4-methoxybenzamide (prepared using V with 4-methoxybenzoic acid and Preparation #B.1, N with Cs2CO3) | | O.1.9* | 1.30 (g) | 393 | C |

TABLE O.1-continued

Examples prepared using General Procedure O

| Nitrile | Product | Example # | R$_t$ min (Table 1, Method) | m/z ESI+ (M + H)+ | Btk IC$_{50}$ |
|---|---|---|---|---|---|
| (R)-5-tert-butyl-N-(1-(7-cyano-1H-indol-4-yl)piperidin-3-yl)isoxazole-3-carboxamide (prepared using V with 5-tert-butylisoxazole-3-carboxylic acid and Preparation #B.1, N with Cs$_2$CO$_3$ | | O.1.10* | 1.70 (g) | 410 | C |
| (R)-4-(3-aminopiperidin-1-yl)-1H-indole-7-carboxamide (prepared using V with 4-tert-butylbenzoic acid and Preparation #B.1, N with Cs$_2$CO$_3$ | | O.1.11* | 1.55 (g) | 419 | C |
| (R)-4-(3-(4-oxoquinazolin-3(4H)-yl)piperidin-1-yl)-1H-indole-7-carbonitrile (Preparation #N.1) | | O.1.12* | 1.28 (g) | 388 | C |

TABLE O.1-continued

Examples prepared using General Procedure O

| Nitrile | Product | Example # | R$_t$ min (Table 1, Method) | m/z ESI+ (M + H)$^+$ | Btk IC$_{50}$ |
|---|---|---|---|---|---|
| 4-(3-(7-cyclopropyl-5-fluoro-4-oxoquinazolin-3(4H)-yl)piperidin-1-yl)-1H-indole-7-carbonitrile (prepared using B from Preparation #27, step A and Preparation #33, N with Cs$_2$CO$_3$ | | O.1.13 | 1.63 (g) | 446 | C |
| (R)-2-(4-fluorophenyl)-4-(3-(4-oxoquinazolin-3(4H)-yl)piperidin-1-yl)-1H-indole-7-carbonitrile (prepared using A from Preparation #27, step B and 2-(4-fluorophenyl)-4,4,5,5-tetramethyl-1,3,2-dioxaborolane, B from Preparation #31, N with Cs$_2$CO$_3$ | | O.1.14* | 1.69 (g) | 482 | B |
| (R)-4-(3-(6-fluoro-4-oxoquinazolin-3(4H)-yl)piperidin-1-yl)-2-(4-fluorophenyl)-1H-indole-7-carbonitrile (prepared using A from Preparation #27, step B and 2-(4-fluorophenyl)-4,4,5,5-tetramethyl-1,3,2-dioxaborolane, B from Preparation #32, N with Cs$_2$CO$_3$ | | O.1.15* | 1.75 (g) | 500 | C |

TABLE O.1-continued

Examples prepared using General Procedure O

| Nitrile | Product | Example # | R, min (Table 1, Method) | m/z ESI+ (M + H)+ | Btk IC50 |
|---|---|---|---|---|---|
| (R)-2-(1-methyl-1H-pyrazol-4-yl)-4-(3-(4-oxoquinazolin-3(4H)-yl)piperidin-1-yl)-1H-indole-7-carbonitrile (prepared using A from Preparation #27, step B and 1-methyl-4-(4,4,5,5-tetramethyl-1,3,2-dioxaborolan-2-yl)-1H-pyrazole, B from Preparation #31, N with Cs₂CO₃ | | O.1.16* | 1.39 (g) | 468 | B |
| (R)-4-(3-(6-fluoro-1-oxoisoindolin-2-yl)piperidin-1-yl)-2-(1-methyl-1H-pyrazol-4-yl)-1H-indole-7-carbonitrile (prepared using A from Preparation #27, step B and 1-methyl-4-(4,4,5,5-tetramethyl-1,3,2-dioxaborolan-2-yl)-1H-pyrazole, B from Preparation #30, N with Cs₂CO₃ | | O.1.18* | 1.48 (g) | 473 | C |
| (R)-4-tert-butyl-N-(1-(7-cyano-2-(1-methyl-1H-pyrazol-4-yl)-1H-indol-4-yl)piperidin-3-yl)benzamide (prepared using A from Preparation #27, step B and 1-methyl-4-(4,4,5,5-tetramethyl-1,3,2-dioxaborolan-2-yl)-1H-pyrazole, B from (R)-tert-butyl piperidin-3-ylcarbamate, V with 4-tert-butylbenzoic acid, N with Cs₂CO₃ | | O.1.19* | 1.73 (g) | 499 | A |

TABLE O.1-continued

Examples prepared using General Procedure O

| Nitrile | Product | Example # | R$_t$ min (Table 1, Method) | m/z ESI+ (M + H)$^+$ | Btk IC$_{50}$ |
|---|---|---|---|---|---|
| (R)-N-(1-(7-cyano-2-(1-methyl-1H-pyrazol-4-yl)-1H-indol-4-yl)piperidin-3-yl)-4-methoxybenzamide (prepared using A from Preparation #27, step B and 1-methyl-4-(4,4,5,5-tetramethyl-1,3,2-dioxaborolan-2-yl)-1H-pyrazole, B with (R)-tert-butyl piperidin-3-ylcarbamate, V with 4-methoxybenzoic acid, N with Cs$_2$CO$_3$ | | O.1.20* | 1.32 (g) | 473 | B |
| (R)-N-(1-(7-cyano-2-(1-methyl-1H-pyrazol-4-yl)-1H-indol-4-yl)piperidin-3-yl)-4-(trifluoromethyl)benzamide methoxybenzamide (prepared using A from Preparation #27, step B and 1-methyl-4-(4,4,5,5-tetramethyl-1,3,2-dioxaborolan-2-yl)-1H-pyrazole, B with (R)-tert-butyl piperidin-3-ylcarbamate, V with 4-(trifluoromethyl)benzoic acid, N with Cs$_2$CO$_3$ | | O.1.21* | 1.65 (g) | 511 | B |
| (R)-N-(1-(7-cyano-2-(1-methyl-1H-pyrazol-4-yl)-1H-indol-4-yl)piperidin-3-yl)-4-(difluoromethyl)benzamide (prepared using A from Preparation #27, step B and 1-methyl-4-(4,4,5,5-tetramethyl-1,3,2-dioxaborolan-2-yl)-1H-pyrazole, B with (R)-tert-butyl piperidin-3-ylcarbamate, V with 4-(difluoromethyl)benzoic acid, N with Cs$_2$CO$_3$ | | O.1.22* | 1.51 (g) | 493 | B |

TABLE O.1-continued

Examples prepared using General Procedure O

| Nitrile | Product | Example # | R, min (Table 1, Method) | m/z ESI+ (M + H)+ | Btk IC$_{50}$ |
|---|---|---|---|---|---|
| (R)-N-(1-(7-cyano-2-(1-methyl-1H-pyrazol-4-yl)-1H-indol-4-yl)piperidin-3-yl)-4-(2-cyanopropan-2-yl)benzamide (prepared using A from Preparation #27, step B and 1-methyl-4-(4,4,5,5-tetramethyl-1,3,2-dioxaborolan-2-yl)-1H-pyrazole, B with (R)-tert-butyl piperidin-3-ylcarbamate, V with 4-(1-amino-2-methyl-1-oxopropan-2-yl)benzoic acid, N with Cs$_2$CO$_3$ | | O.1.23* | 1.28 (g) | 528 | B |
| (R)-N-(1-(7-cyano-2-(1-methyl-1H-pyrazol-4-yl)-1H-indol-4-yl)piperidin-3-yl)-4-(trifluoromethoxy)benzamide (prepared using A from Preparation #27, step B and 1-methyl-4-(4,4,5,5-tetramethyl-1,3,2-dioxaborolan-2-yl)-1H-pyrazole, B with (R)-tert-butyl piperidin-3-ylcarbamate, V with 4-(trifluoromethoxy)benzoic acid, N with Cs$_2$CO$_3$ | | O.1.24* | 1.68 (g) | 527 | B |
| (R)-N-(1-(7-cyano-2-(1-methyl-1H-pyrazol-4-yl)-1H-indol-4-yl)piperidin-3-yl)-4-cyclopropylbenzamide (prepared using A from Preparation #27, step B and 1-methyl-4-(4,4,5,5-tetramethyl-1,3,2-dioxaborolan-2-yl)-1H-pyrazole, B with (R)-tert-butyl piperidin-3-ylcarbamate, V with 4-cyclopropylbenzoic acid, N with Cs$_2$CO$_3$ | | O.1.25* | 1.40 (g) | 483 | A |

TABLE O.1-continued

Examples prepared using General Procedure O

| Nitrile | Product | Example # | R$_t$ min (Table 1, Method) | m/z ESI+ (M + H)+ | Btk IC$_{50}$ |
|---|---|---|---|---|---|
| (R)-4-tert-butyl-N-(1-(7-cyano-2-(pyridin-3-yl)-1H-indol-4-yl)piperidin-3-yl)benzamide (prepared using A from Preparation #27, step B and pyridin-3-ylboronic acid, B with (R)-tert-butyl piperidin-3-ylcarbamate, V with 4-tert-butylbenzoic acid, N with Cs$_2$CO$_3$) | 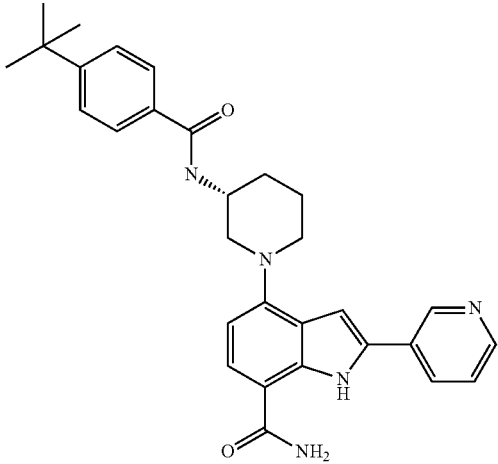 [SMILES: CC(C)(C)c1ccc(C(=O)N[C@@H]2CCCN(c3ccc(C(N)=O)c4[nH]c(-c5cccnc5)cc34)C2)cc1] | O.1.26 | 1.56 (g) | 496 | A |
| (R)-4-(3-(4-oxoquinazolin-3(4H)-yl)piperidin-1-yl)-2-(pyridin-3-yl)-1H-indole-7-carbonitrile (prepared using A from Preparation #27, step B and pyridin-3-ylboronic acid with Cs$_2$CO$_3$, B from Preparation #31, N with Cs$_2$CO$_3$) | 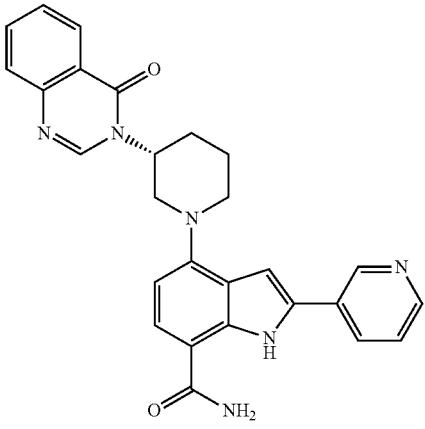 [SMILES: NC(=O)c1ccc(N2CCC[C@@H](n3cnc4ccccc4c3=O)C2)c2cc(-c3cccnc3)[nH]c12] | O.1.27* | 1.22 | 465 | B |

General Procedure P: Formation of a Boronate from an Aryl Halide or Heteroaryl Halide To a mixture of an halide, for example, a bromo indole (preferably 1 equiv), 4,4,4',4',5,5,5',5'-octamethyl-2,2'-bi(1,3,2-dioxaborolane) (1 to 3 equiv, preferably 1.2 equiv), potassium acetate (2 to 5 equiv, preferably 3 equiv), and in a solvent (such as THF or 1,4-dioxane; preferably 1,4-dioxane) is added a palladium catalyst (for example Pd$_2$ dba$_3$ or (1,1'-bis(diphenylphosphino)ferrocene)dichloropalladium(II) complex with DCM; preferably 1,1'-bis(diphenylphosphino)ferrocene)dichloropalladium(II) complex with DCM, 0.01 to 0.20 equiv, preferably 0.1 equiv). The mixture is heated at about 40 to 120° C. (preferably about 80° C.) for about 1 to 24 h (preferably about 16 h). The mixture is allowed to cool to rt and is worked up using one of the following methods. Method 1. The mixture may be diluted with an organic solvent (such as DCM or EtOAc) and the organic solution is optionally washed with water and/or brine, dried over anhydrous MgSO$_4$ or Na$_2$SO$_4$, filtered, and the solvent is removed under reduced pressure to give the desired compound. Method 2. The mixture is concentrated under reduced pressure and optionally purified using one or more of the Purification Methods described above to give the desired compound. Method 3. The catalyst is removed by filtration and the filtrate is concentrated under reduced pressure.

Illustration of General Procedure P

Preparation #P.1: 4-(4,4,5,5-Tetramethyl-1,3,2-dioxaborolan-2-yl)-1H-indole-7-carboxamide

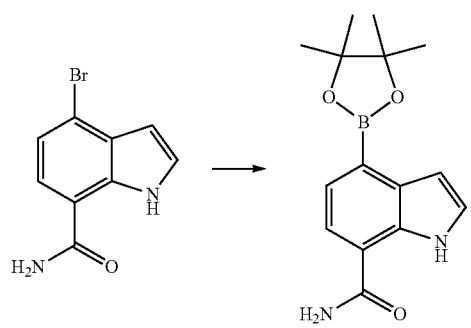 [SMILES: NC(=O)c1ccc(Br)c2cc[nH]c12 ; CC1(C)OB(c2ccc(C(N)=O)c3[nH]ccc23)OC1(C)C]

A mixture of 4-bromo-1H-indole-7-carboxamide (5 g, 20.9 mmol, Preparation #2), 4,4,4',4',5,5,5',5'-octamethyl-2,2'-bi(1,3,2-dioxaborolane) (6.37 g, 25.1 mmol), potassium acetate (6.16 g, 62.7 mmol) and Pd(dppf)C$_{12}$-DCM (0.85 g, 1.05 mmol) in 1,4-dioxane (2 mL) was heated at about 80° C. under N$_2$ overnight. The solvent was removed under reduced pressure to get a residue, which was purified by column chromatography on silica gel to afford 4-(4,4,5,5-tetramethyl-1,3,2-dioxaborolan-2-yl)-1H-indole-7-carboxamide (3 g, 50%): $^1$H NMR (CDCl$_3$) δ 10.30 (br, 1H), 7.64-7.62 (d, J=8 Hz, 1H), 7.40-7.38 (m, 2H), 7.08-7.07 (m, 1H), 1.42 (s, 12H).

General Procedure Q: Mitsunobu Reaction of an Alcohol

To an alcohol (preferably 1 equiv) in an organic solvent (such as THF, benzene, toluene, or 1,4-dioxane, preferably toluene or 1,4-dioxane) is added a suitably acidic reactant (such as a carboxylic acid, a phenol or a heteroaryl alcohol, 1-3 equiv, preferably 1 equiv), followed by tri-n-butylphosphine, triphenylphosphine or polymer bound triphenylphosphine (preferably triphenylphosphine, 1-3 equiv, preferably 1.2 equiv), and TMAD, 1,1'-(azodicarbonyl)dipiperidine, DIAD or DEAD (preferably DEAD, 1-3 equiv, preferably 1.2 equiv) is added dropwise at about 0-120° C. (preferably 0-25° C.). The reaction mixture is stirred at about 25-120° C. for about 5-48 h (preferably about 16 h). Alternatively, after about 0.1-24 h additional phosphine reagent (0.2-2 equiv) and TMAD, 1,1'-(azodicarbonyl)dipiperidine, DIAD or DEAD (0.2-1 equiv) are added to drive the reaction to completion. Method 1. When polymer bound reagent is used, the reaction mixture is filtered and washed with a mixture of solvents such as DCM, EtOAc and MeOH (preferably DCM then MeOH). The filtrate is concentrated under reduced pressure. Method 2. When no polymer bound reagent is used, the reaction mixture is optionally diluted with an organic solvent such as DCM or EtOAc and then washed with water, saturated aqueous NaHCO$_3$, brine and dried over anhydrous Na$_2$SO$_4$ or MgSO$_4$, filtered, and concentrated under reduced pressure. Alternatively, the reaction mixture is directly concentrated under reduced pressure.

Illustration of General Procedure Q

Preparation #Q.1:
2-((4-Bromo-3-nitrophenoxy)methyl)thiazole

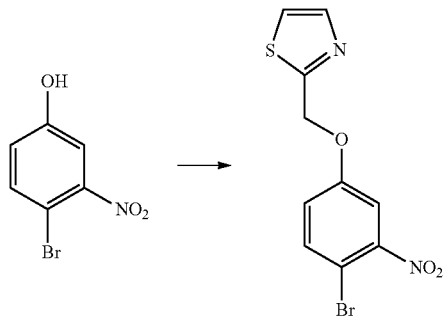 [SMILES: O=[N+]([O-])c1cc(O)ccc1Br ; O=[N+]([O-])c1cc(OCc2nccs2)ccc1Br]

To a solution of 4-bromo-3-nitrophenol (2 g, 9.17 mmol, Preparation #S.1), thiazol-2-ylmethanol (1.01 g, 9.17 mmol) and triphenylphosphine (2.9 g, 11.01 mmol) in anhydrous toluene (50 mL) was added DEAD (1.7 mL, 11.01 mmol) at about 0° C. under N$_2$. Then the mixture was heated to reflux overnight. After cooling to rt, the mixture was concentrated under reduced pressure to give a residue, which was purified by column chromatography on silica gel to give 2-((4-bromo-3-nitrophenoxy)methyl)thiazole (2 g, 69%): $^1$H NMR (CDCl$_3$) δ 7.83 (d, J=3.1 Hz, 1H), 7.63 (d, J=8.8 Hz, 1H), 7.53 (d, J=3.1 Hz, 1H), 7.42 (d, J=3.1 Hz, 1H), 7.12 (dd, J=3.1, 8.8 Hz, 1H), 5.43 (s, 2H).

General Procedure R: Reduction of a Nitro Group to an Amine Using Fe

To a mixture of a nitro-containing compound in a solvent (such as MeOH, EtOH, MeOH/water or EtOH/water, preferably EtOH/water) is added Fe (3 to 5 equiv, preferably 5 equiv) and NH$_4$Cl (3 to 5 equiv, preferably 5 equiv). The mixture is heated at about 40 to 100° C. (preferably about 80° C.) for about 2 to 24 h (preferably about 16 h). The mixture is allowed to cool to rt and is worked up using one of the following methods. Method 1. The mixture may be diluted with an organic solvent (such as DCM or EtOAc) and the organic solution is optionally washed with water and/or brine, dried over anhydrous MgSO$_4$ or Na$_2$SO$_4$, filtered, and the solvent is removed under reduced pressure to give the desired compound. Method 2. The mixture is concentrated under reduced pressure and optionally purified using one or more of the Purification Methods described above to give the desired compound. Method 3. The catalyst is removed by filtration and the filtrate is concentrated under reduced pressure. Intermediates and final compounds prepared via this General Procedure can be optionally purified using one or more of the Purification Methods described above.

Illustration of General Procedure R

Preparation #R.1:
2-Bromo-5-(thiazol-2-ylmethoxy)aniline

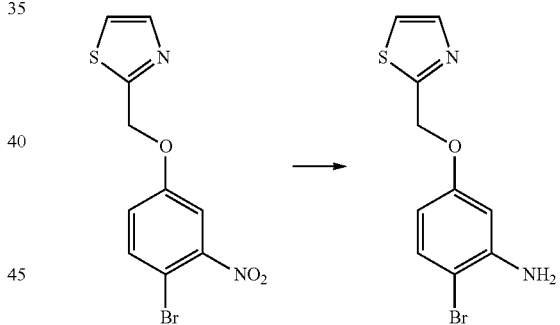

To a solution of 2-((4-bromo-3-nitrophenoxy)methyl)thiazole (1 g, 3.2 mmol) in EtOH (40 mL) and water (20 mL) was added iron (0.88 g, 15.8 mmol) and NH$_4$Cl (0.85 g, 15.8 mmol). The mixture was heated to reflux overnight. The mixture was filtered and the filtrate was concentrated under reduced pressure to get a residue, which was diluted by addition of water and extracted by EtOAc. The organic layer was concentrated under reduced pressure to provide 2-bromo-5-(thiazol-2-ylmethoxy)aniline (0.7 g, 77%): LC/MS (Table 1, Method I) R$_t$=1.46 min; MS m/z 285 (M+H)$^+$.

General Procedure S: Demethylation of Aryl Methyl Ether

To a mixture of a methoxy compound in a solvent (such as DCM, DCE, THF, benzene, toluene, or 1,4-dioxane, preferably DCM) is slowly added BBr$_3$ (2 to 24 equiv, preferably 2.5 equiv). The mixture is heated at about 30 to 110° C. (preferably about 45° C.) for about 2 to 24 h (preferably about 4-24 h). The mixture is allowed to cool to 0-10° C. (preferably about 0° C.) and is diluted with water.

The mixture may be diluted with an organic solvent (such as DCM or EtOAc) and the organic solution is optionally washed with water and/or saturated NaHCO$_3$ and/or brine, dried over anhydrous MgSO$_4$ or Na$_2$SO$_4$, filtered, and the solvent is removed under reduced pressure to give the desired compound.

Illustration of General Procedure S

Preparation #S.1: 4-Bromo-3-nitrophenol

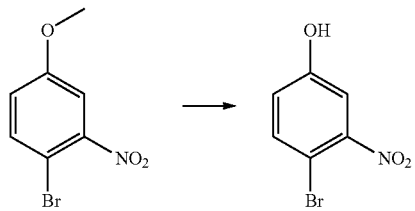

To a solution of 1-bromo-4-methoxy-2-nitrobenzene (20 g, 82 mmol) in DCM (800 mL) was added dropwise BBr$_3$ (19 mL, 207 mmol) in DCM (120 mL). The resulting mixture was heated to reflux overnight. The mixture was cooled in ice-water and was diluted by addition of water. Then the mixture was washed with saturated NaHCO$_3$ and brine. The organic phase was dried over Na$_2$SO$_4$, concentrated under reduced pressure to give a residue, which was purified by column chromatography on silica gel to provide 4-bromo-3-nitrophenol (6 g, 31%) as a solid: $^1$H NMR (CDCl$_3$): δ 7.57 (d, J=8.8 Hz, 1H), 7.35 (d, J=2.6 Hz, 1H), 6.94 (dd, J=2.9, 8.6 Hz, 1H), 5.90 (br., 1H).

General Procedure T: Buchwald Reaction of an Aryl Halide or a Heteroaryl Halide with an Amine A mixture of an aryl halide or heteroaryl halide (1.0 equiv), an amine (1 to 2.2 equiv, preferably 1 to 1.2 equiv), a palladium catalyst (such as Pd$_2$ dba$_3$ or Pd(OAc)$_2$, preferably Pd$_2$ dba$_3$; 0.01 to 1.0 equiv, preferably 0.04 to 0.1 equiv), a ligand (such as X-phos, Xanthphos or tert-butyl-X-phos, preferably tert-butyl-X-phos or X-Phos, 0.01 to 2.0 equiv, preferably 0.04 to 0.1 equiv) and a base (such as K$_2$CO$_3$, Na$_2$CO$_3$, Cs$_2$CO$_3$, K$_3$PO$_4$, NaOt-Bu, KOt-Bu, KOAc, KOH, preferably K$_2$CO$_3$; 1 to 5 equiv, preferably 1 to 3 equiv) are added to a solvent (such as 1,4-dioxane, t-BuOH, preferably t-BuOH). The mixture is degassed under an inert atmosphere (such as nitrogen or argon, preferably nitrogen) and heated with conventional heating at about 80 to 100° C. (preferably about 85 to 95° C.) for about 2 to 24 h (preferably about 18 h) or with microwave heating at about 100-150° C. for about 30 min to 2 h. The mixture is cooled to rt. The mixture is optionally filtered through a media (such as silica gel or Celite®) which is rinsed with an appropriate solvent (such as EtOAc, 1,4-dioxane, THF, MeCN, DCM, Et$_2$O, MeOH, EtOH, DMSO, 1:1 MeOH/DMSO or 2:1 MeOH/DMSO, preferably MeOH/DMSO) and then the filtrate is optionally concentrated in vacuo or under a warm nitrogen stream to give a residue.

Illustration of General Procedure T

Preparation #T.1: 4-(1-Methyl-1H-pyrazol-5-ylamino)-2-p-tolyl-1H-indole-7-carboxamide

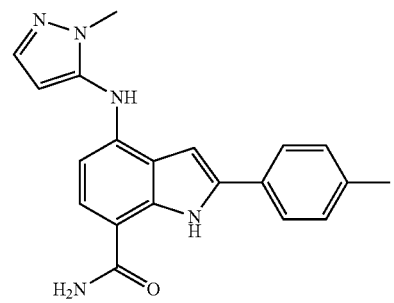 [SMILES: Cc1ccc(-c2cc3c(Nc4ccnn4C)ccc(C(N)=O)c3[nH]2)cc1]

4-Iodo-2-(p-tolyl)-1H-indole-7-carboxamide (99 mg, 0.26 mmol, prepared using F with 1-(p-tolyl)ethanone), 1-methyl-1H-pyrazol-5-ylamine (27 mg, 0.26 mmol, Maybridge-Int), X -Phos (7.53 mg, 0.016 mmol), K$_2$CO$_3$ (44 mg, 0.316 mmol), and Pd$_2$ dba$_3$ (14 mg, 0.016 mmol) were combined in t-BuOH (1.32 mL) in a sealed microwaved tube. The tube was degassed and purged with N$_2$ and heated at about 85° C. for 18 h. The reaction was cooled to rt and filtered through Celite®. The filtrate was extracted twice with DCM. The combined organic layers were concentrated. The residue product was purified on a normal phase column (18 mg, 20%): LC/MS (Table 1, Method f) R$_t$=1.48 min; MS m/z 346 (M+H)$^+$. (Btk IC$_{50}$=B)

TABLE T.1

Examples prepared from 4-iodo-2-(p-tolyl)-1H-indole-7-carboxamide (prepared using F with 1-(p-tolyl)ethanone) using General Procedure T

| Amine | Product | Example # | R$_t$ min (Table 1, Method) | m/z ESI+ (M + H)$^+$ | Btk IC$_{50}$ |
|---|---|---|---|---|---|
| 1-(4-methoxybenzyl)-1H-pyrazol-5-amine | | T.1.1 | 1.77 (f) | 452 | B |

General Procedure U: Negishi Cross-Coupling Reaction of an Aryl Halide or a Heteroaryl Halide with an Organozinc A mixture of an aryl halide or heteroaryl halide (preferably 1.0 equiv) an organic solvent or mixture of solvents (such as THF, Et$_2$O or 1,4-dioxane, preferably THF), an organozinc compound (0.67 to 1.5 equiv, preferably 0.9 to 1.2 equiv), a palladium catalyst (such as Pd(PPh$_3$)$_4$, 0.01 to 1.0 equiv, preferably 0.025 to 0.10 equiv) is stirred at about rt to 90° C. (preferably about 85° C.) for about 1 to 24 h (preferably about 18 h). The mixture is cooled to rt. The mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure U

Preparation #U.1: 4-(2-Chloro-6-fluorobenzyl)-2-p-tolyl-1H-indole-7-carboxamide

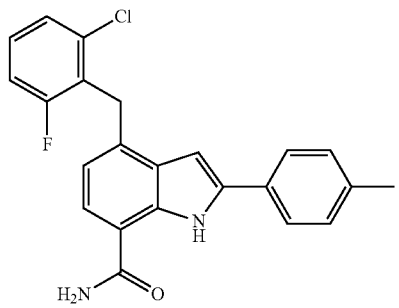 [SMILES: Cc1ccc(-c2cc3c(Cc4c(F)cccc4Cl)ccc(C(N)=O)c3[nH]2)cc1]

4-Iodo-2-(p-tolyl)-1H-indole-7-carboxamide (97 mg, 0.258 mmol, prepared using F from 1-(p-tolyl)ethanone), (2-chloro-6-fluorobenzyl)zinc(II) bromide (0.77 mL, 0.387 mmol) and tetrakis(triphenylphosphine)palladium(0) (15 mg, 0.013 mmol) were dissolved in THF (0.82 mL) in a sealed microwave tube and heated thermally at 85° C. for about 18 h. The reaction was cooled to rt and filtered through Celite®. The filtrate was concentrated to give a residue. The residue was purified on a normal phase column eluting with EtOAc in hexane to give 4-(2-chloro-6-fluorobenzyl)-2-p-tolyl-1H-indole-7-carboxamide (30 mg, 30%): LC/MS (Table 1, Method f) 12, =2.09 min; MS m/z 393 (M+H)$^+$.

TABLE U.1

Examples prepared from 4-iodo-2-(p-tolyl)-1H-indole-7-carboxamide (prepared using F with 1-(p-tolyl)ethanone) using General Procedure U

| Organozinc | Product | Example # | R$_t$ min (Table 1, Method) | m/z ESI+ (M + H)$^+$ | Btk IC$_{50}$ |
|---|---|---|---|---|---|
| (2,6-dichlorobenzyl)zinc(II) bromide | | U.1.1 | 2.13 (f) | 409 | C |
| 2-Thiazolylzinc bromide | | U.1.2 | 1.76 (f) | 334 | A |

TABLE U.1-continued

Examples prepared from 4-iodo-2-(p-tolyl)-1H-indole-7-carboxamide (prepared using F with 1-(p-tolyl)ethanone) using General Procedure U

| Organozinc | Product | R, min Example # (Table 1, Method) | m/z ESI+ (M + H)+ | Btk IC50 |
|---|---|---|---|---|
| 2-Pyridylzinc bromide | 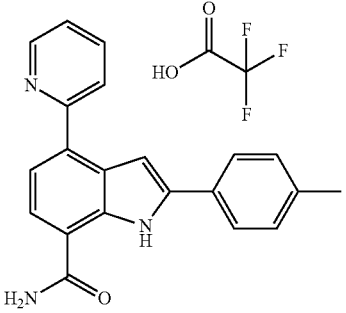 | U.1.3  1.34 (g) | 328 | B |

General Procedure V: Formation of an Amide from a Boc-Protected Amine and a Carboxylic Acid To a solution of an N-Boc amine (1 equiv) in an organic solvent (such as DCM, DCE, 1,4-dioxane or MeOH, preferably DCM or 1,4-dioxane) is added an acid (such as TFA or HCl, preferably TFA; 2 to 100 equiv, preferably 25 to 50 equiv). The mixture is stirred at about 0 to 100° C. (preferably about 20 to 60° C.) for about 0.5 to 24 h (preferably about 0.5 to 6 h). Optionally, additional acid (2 to 35 equiv, preferably 20 to 25 equiv) may be added and the mixture stirred at about 0 to 100° C. (preferably about 20 to 60° C.) for about 1 to 24 h (preferably about 1 to 6 h). If a solid is present in the mixture, the mixture may be optionally filtered and the solid washed with an organic solvent such as 1,4-dioxane or Et$_2$O. The resulting solid is then optionally dried under reduced pressure. Alternatively, the reaction mixture is concentrated under reduced pressure. To the residue in a flask is added in no particular order, a carboxylic acid or carboxylate salt (1 to 5 equiv, preferably 1.1 to 1.5 equiv) an organic solvent (such as DCM, DCE, DMF, THF, or 1,4-dioxane, preferably DCM or DMF), a peptide coupling reagent (such as BOP-Cl, IBCF, HATU, DCI, PyBOP, or EDC.HCl, preferably HATU; 1 to 10 equiv, preferably 1 to 2 equiv), a base (such as TEA, DIEA, pyridine or DIEA, preferably DIEA; 1 to 20 equiv, preferably 1 to 5 equiv) and optionally HOBt (0 to 5 equiv, preferably 0 to 1 equiv). The mixture is then stirred at about 10 to 60° C. (preferably about 25 to 50° C.) for about 15 min to 48 h (preferably about 15 min to 24 h). Optionally, additional amounts of the reagents above can be added to drive the reaction to completion. The mixture is optionally concentrated in vacuo to give the targeted compound. The mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure V

Preparation #V.1: (R)—N-(1-(7-cyano-1H-indol-4-yl)piperidin-3-yl)-2-methyloxazole-4-carboxamide

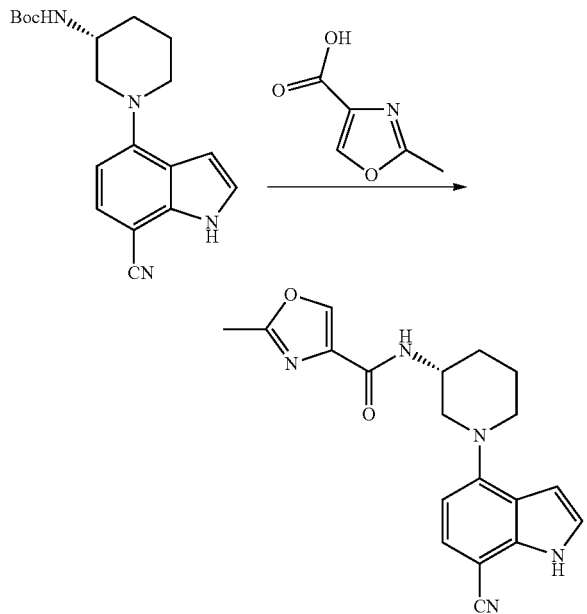

To a solution of (R)-tert-butyl 1-(7-cyano-1H-indol-4-yl)piperidin-3-ylcarbamate (0.11 g, 0.333 mmol, Preparation #B.1) in DCM (1 mL) was added TFA (1 mL) and the solution stirred at about 25° C. for about 30 min. The mixture was evaporated to dryness followed by the addition of DMF (2 mL), TEA (0.139 mL, 0.999 mmol), HATU (190 mg, 0.499 mmol) and 2-methyloxazole-4-carboxylic acid (0.055 g, 0.433 mmol). The mixture was stirred at about rt for about 18 h. The reaction was evaporated and the resulting residue was purified by silica gel chromatography eluting with a gradient of 30-100% EtOAc in hexane to (R)—N-

(1-(7-cyano-1H-indol-4-yl)piperidin-3-yl)-2-methyloxazole-4-carboxamide (0.092 g, 79%); LC/MS (Table 1, Method g) $R_t$=1.35 min; MS m/z: 350 (M+H)$^+$ General Procedure W: Conversion of a Vinyl Triflate to a Vinyl Boronate or Boronic Acid To a mixture of a boronic acid or boronate (1 to 2 equiv, preferably 1.1 equiv) a palladium catalyst (for example Pd(OAc)$_2$, Pd$_2$dba$_3$, Pd(PPh$_3$)$_4$, bis(acetato)triphenylphosphinepalladium(II), PdCl2(dppf), (1,1'-bis(diphenylphosphino)ferrocene)dichloropalladium(II), or Pd(PPh$_3$)$_2$Cl$_2$; preferably PdCl$_2$(dppf) or Pd(PPh$_3$)$_2$Cl$_2$; 0.01 to 0.20 equiv, preferably 0.05 to 0.1 equiv), a base (such as KF, KOAc, Na$_2$CO$_3$, K$_2$CO$_3$ or Cs$_2$CO$_3$, preferably K$_2$CO$_3$ or KOAc) (1.1 to 16 equiv, preferably 1.5 to 2 equiv) and optionally a phosphine additive (preferably PPh$_3$; 0.01 to 0.1 equiv, preferable 0.06 equiv) in an organic solvent (such as dioxane, DME or DCE, preferably dioxane) is added a vinyl triflate (1 equiv). The mixture is heated under inert atmosphere at about 60 to 90° C. (preferably 70 to 80° C.) for about 1 to 20 h (preferably 8 to 16 h). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, ACN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure W

Preparation #W.1: tert-Butyl 6-(4,4,5,5-tetramethyl-1,3,2-dioxaborolan-2-yl)-2,3-dihydro-1,4-oxazepine-4(7H)-carboxylate

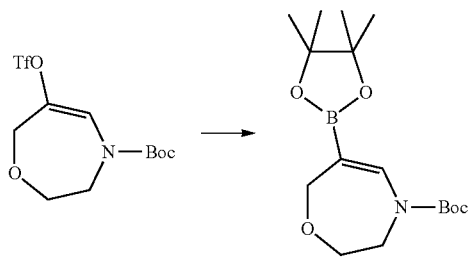 [SMILES: CC(C)(C)OC(=O)N1C=C(OS(=O)(=O)C(F)(F)F)COCC1 ; CC(C)(C)OC(=O)N1C=C(B2OC(C)(C)C(C)(C)O2)COCC1]

A 100 mL 3 neck round-bottomed flask was charged with 4,4,4',4',5,5,5',5'-octamethyl-2,2'-bi(1,3,2-dioxaborolane) (1.10 g, 4.34 mmol, Preparation #AA.1), PPh$_3$ (0.062 g, 0.24 mmol), Pd(PPh$_3$)$_2$Cl$_2$ (0.138 g, 0.197 mmol) and K$_2$CO$_3$ (0.818 g, 5.92 mmol). To this mixture was added a solution of tert-butyl 6-(((trifluoromethyl)sulfonyl)oxy)-2,3-dihydro-1,4-oxazepine-4(7H)-carboxylate (1.37 g, 3.94 mmol) in dioxane (30 mL). The entire mixture was degassed for about 5 min and purged with nitrogen. The mixture was heated at about 75° C. for about 15 h. The mixture was diluted with EtOAc (30 mL) and water (30 mL). The organic layer was separated, dried over MgSO$_4$, filtered and concentrated. The resulting mixture was purified silica gel chromatography (10-40% EtOAc/heptane) to give tert-butyl 6-(4,4,5,5-tetramethyl-1,3,2-dioxaborolan-2-yl)-2,3-dihydro-1,4-oxazepine-4(7H)-carboxylate (0.57 g, 44%): LC/MS (Table 1, Method as) $R_t$=2.65 min; MS m/z: 226 (M+H-Boc)$^+$ General Procedure X: Hydrolysis of an Ester to a Carboxylic Acid Under Basic Conditions and Removal of a Tosyl Group from an N-Tosyl Protected Heteroaryl Ring To a flask containing a compound with and ester functionality and a tosyl-protected heteroaromatic ring (1 equiv) either neat or in an organic solvent (such as 1,4-dioxane, MeOH, or THF/MeOH, THF/water/MeOH preferably THF/water/MeOH) is added a base or combination of bases (such as aqueous or solid Na$_2$CO$_3$, KOH, Cs$_2$CO$_3$, K$_2$CO$_3$, NaOH or LiOH, preferably LiOH, or KOH; 1 to 10 equiv, preferably 5 to 10 equiv). The mixture is stirred at about 0 to 100° C. (preferably about 40 to 85° C.) for about 1 to 48 h (preferably about 1 to 24 h). Optionally, more base is added (such as aqueous or solid Na$_2$CO$_3$, KOH, Cs$_2$CO$_3$, K$_2$CO$_3$, NaOH or LiOH, preferably LiOH or NaOH, 1 to 10 equiv, preferably 2 to 6 equiv) and the mixture is stirred at about 0 to 100° C. (preferably about 10 to 100° C.) for about 1 to 48 h (preferably about 4 to 24 h). The mixture is then acidified with the addition of a suitable aqueous acid (such as aqueous HCl, AcOH or citric acid, preferably citric acid). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, ACN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure X

Preparation #X.1: 4-(1-(tert-Butoxycarbonyl)-1,2,5,6-tetrahydropyridin-3-yl)-2-methyl-1H-indole-7-carboxylic acid

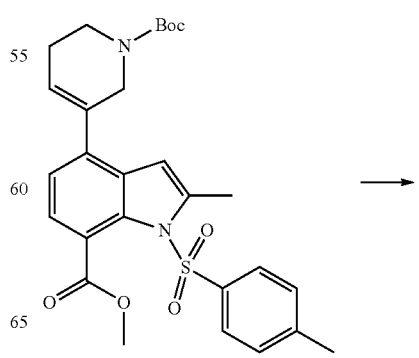

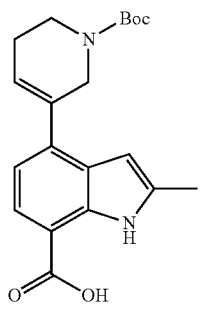

A round bottom flask was charged with methyl 4-(1-(tert-butoxycarbonyl)-1,2,5,6-tetrahydropyridin-3-yl)-2-methyl-1-tosyl-1H-indole-7-carboxylate (1.67 g, 2.30 mmol, Preparation #39) in THF (12 mL), water (4 mL) and MeOH (4 mL). LiOH (monohydrate, 0.468 g, 11.1 mmol) was added. The mixture was stirred at about 60° C. After about 7 h additional LiOH (monohydrate, 0.234 g, 5.57 mmol) was added and the mixture was allowed to stir for about 24 h at about 60° C. The mixture was diluted with 5% citric acid (200 mL) and extracted with DCM (2×100 mL) and 3:1, CHCl$_3$: isopropanol (100 mL). The combined organic layers were washed with water (50 mL) and dried over Na$_2$SO$_4$, filtered and concentrated under reduced pressure to give 4-(1-(tert-butoxycarbonyl)-1,2,5,6-tetrahydropyridin-3-yl)-2-methyl-1H-indole-7-carboxylic acid (1.16 g, 93%): LC/MS (Table 1, Method as) R$_f$=2.33 min; MS m/z: 355 (M−H)$^-$.

General Procedure Y: Iodination of a 1H-Indole or a 1H-Aza Indole Ring to Give a 2-Iodo-1H-Indole or a 2-Iodo-1H-Azaindole Ring To a solution of an indole or azaindole (1 equiv) in an organic solvent (such as THF or Et$_2$O, preferably THF) at about −60 to −78° C. (preferably about −70 to −78° C.) is added a base (such as BuLi or LDA, preferably LDA; 1 to 2 equiv, preferably 1.1 to 1.5 equiv). The reaction mixture is then stirred for about 30 to 45 min and iodine (1 to 2 equiv, preferably 1.4 to 1.6 equiv) is then added. The reaction mixture is stirred for about 10 to 60 min (preferably about 10 to 30 min). The mixture is optionally quenched with Na$_2$S$_2$O$_3$. The mixture is optionally concentrated in vacuo to give the targeted compound. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure Y

Preparation #Y.1: 1-tert-Butyl 7-methyl 4-(1-(tert-butoxycarbonyl)pyrrolidin-3-yl)-2-iodo-1H-indole-1,7-dicarboxylate

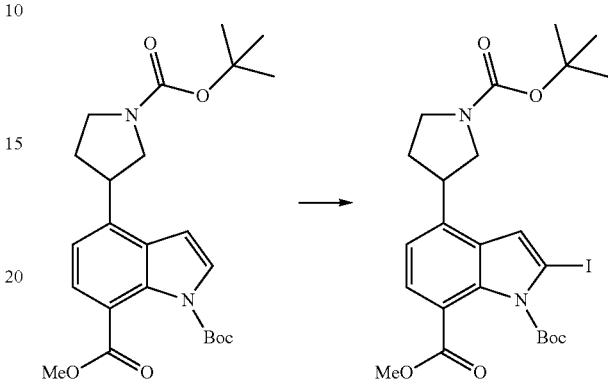

A solution of anhydrous 1-tert-butyl 7-methyl 4-(1-(tert-butoxycarbonyl)pyrrolidin-3-yl)-1H-indole-1,7-dicarboxylate (10.0 g, 22.5 mmol, (Preparation #Z.1) in THF (136 mL) was cooled to about −78° C. and LDA (1M in THF, 33.7 mL, 33.7 mmol) was added drop wise. After about 45 min, a solution of iodine (7.99 g, 31.5 mmol) in THF (15 mL) was added drop wise while maintaining the temperature at about −71° C. The reaction mixture was then quenched by pouring into an aqueous solution of Na$_2$S$_2$O$_3$ and NaHCO$_3$ (10:1, 150 mL). The mixture was diluted with EtOAc and the layers were separated. The aqueous phase was extracted with EtOAc (3×50 mL). The combined organic layers were washed with brine, dried over MgSO$_4$ and filtered. The solvent was removed under reduced pressure to give methyl 4-(1-(tert-butoxycarbonyl)-2,5-dihydro-1H-pyrrol-3-yl)-1H-indole-7-carboxylate (10.4 g, 97%): LC/MS (Table 1, Method as) R$_f$=2.90 min; MS m/z: 588 (M+NH$_4$)$^+$.

General Procedure Z: Formation of an N-Boc Protected Amine

To a solution of an amine or amine salt (preferably 1 equiv) in an organic solvent (such as ACN, 1,4-dioxane, DCM, DMF or THF, preferably DCM) is added an aqueous base such as Na$_2$CO$_3$, NaOH, K$_2$CO$_3$ or NaHCO$_3$, preferably Na$_2$CO$_3$ (2 to 20 equiv, preferably 2 to 10 equiv) or an organic base such as TEA or DIEA, preferably TEA (1 to 5 equiv, preferably 1 to 2 equiv) followed by addition of a Boc transfer reagent such as BoC$_2$O, Boc ON, Boc-azide or Boc-OSu preferably Boc$_2$O (1 to 4 equiv, preferably 1 to 2 equiv). Optionally, an additive, such as DMAP (0.01 to 0.1 equiv, preferable 0.05 equiv) may be added. The addition of base is optional if an amine salt is not used. The mixture is stirred at about 0 to 40° C. (preferably about 0 to 25° C.) for about 2 to 24 h (preferably about 2 to 16 h). The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, ACN, DCM, Et$_2$O, MeOH, EtOH) and then optionally concentrated in vacuo to give a residue as the target compound. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH₄Cl) and/or aqueous solutions containing a base (such as NaHCO₃, Na₂CO₃, NaOH, KOH or NH₄OH) and/or aqueous solutions containing an inorganic salt (such as NaCl Na₂SO₃ or Na₂S₂O₃). The organic solution may then be optionally dried with a drying agent (such as anhydrous MgSO₄ or Na₂SO₄), filtered and concentrated in vacuo to give the target compound.

Illustration of General Procedure Z

Preparation #Z.1: 1-tert-Butyl 7-methyl 4-(1-(tert-butoxycarbonyl)pyrrolidin-3-yl)-1H-indole-1,7-dicarboxylate

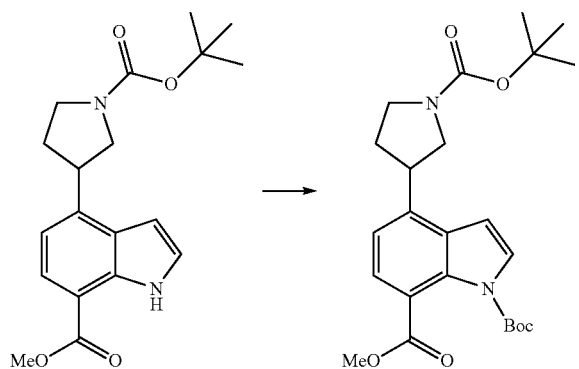 [SMILES: COC(=O)c1ccc(C2CCN(C(=O)OC(C)(C)C)C2)c2cc[nH]c12 ; COC(=O)c1ccc(C2CCN(C(=O)OC(C)(C)C)C2)c2ccn(C(=O)OC(C)(C)C)c12]

In a 200 mL round-bottomed flask, methyl 4-(1-(tert-butoxycarbonyl)pyrrolidin-3-yl)-1H-indole-7-carboxylate (12.4 g, 36.0 mmol, prepared using A from methyl 4-bromo-1H-indole-7-carboxylate [Anthem] with tert-butyl 3-(4,4,5,5-tetramethyl-1,3,2-dioxaborolan-2-yl)-2,5-dihydro-1H-pyrrole-1-carboxylate [AKSCI] and L with Pd/C) and di-tert-butyl dicarbonate (9.43 g, 43.2 mmol)) in ACN (100 mL) were added. DMAP (0.22 g, 1.8 mmol) was added, the reaction mixture was stirred at rt for about 18 h, TEA (10 mL, 72 mmol) and di-tert-butyl dicarbonate (1.60 mL, 6.87 mmol) were added. The reaction mixture was stirred at rt for about 16 h. The mixture was extracted with dilute acetic acid and EtOAc. The combined organic layers were dried over MgSO4, concentrated under reduced pressure and purified using silica gel chromatography (0-25% EtOAC/heptane) to give 1-tert-butyl 7-methyl 4-(1-(tert-butoxycarbonyl)pyrrolidin-3-yl)-1H-indole-1,7-dicarboxylate (12.5 g, 70%, 89% purity): LC/MS (Table 1, Method as) R$_f$=2.79 min; MS m/z: 462 (M+NHX.

General Procedure AA: Conversion of a Cyclic Ketone to a Cyclic Vinyl Triflate

A solution of a ketone (1 equiv) in an organic solvent (such as THF, dioxane or ether preferably THF) is cooled to about −60 to −78° C. (preferably about −65 to −75° C.). A base is then added slowly (such as LiHMDS, KHMDS or NaHMDS preferably KHMDS). After about 20 to 60 min (preferably 60 min) a solution of a triflating reagent is added, such as, N-(5-Chloro-2-pyridyl)bis(trifluoromethane sulfonimide)) or 1,1,1-trifluoro-N-phenyl-N-((trifluoromethyl)sulfonyl)methanesulfonamide in THF. The reaction mixture is then allowed to warm to rt over about 1 to 1.5 h. The reaction mixture may then be quenched with a saturated solution of NH₄Cl or water and diluted with an organic solvent (such as DCM or EtOAc). The layers are separated, the organic solution is optionally washed with water and/or brine, dried over anhydrous MgSO₄ or Na₂SO₄, filtered, and the solvent is removed under reduced pressure to give the desired compound.

Illustration of General Procedure AA

Preparation #AA.1: tert-Butyl 6-(((trifluoromethyl)sulfonyl)oxy)-2,3-dihydro-1,4-oxazepine-4(7H)-carboxylate

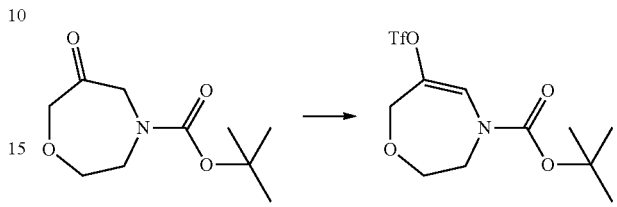

To a solution of tert-butyl 6-oxo-1,4-oxazepane-4-carboxylate (5.00 g, 23.2 mmol) [Arkpharm] in THF (51.6 mL) at about −78° C. was added KHMDS (1M in THF, 30.2 mL, 30.2 mmol) drop wise maintaining internal temperature of about −72 to −74° C. The mixture was then stirred at about −77° C. for about 1 h. A solution of 1,1,1-trifluoro-N-phenyl-N-((trifluoromethyl)sulfonyl)methanesulfonamide (7.88 g, 22.1 mmol) in THF (25.8 mL) was added drop wise. The mixture was gradually warmed to about 0° C. over about 1 to 2 h. The reaction mixture was quenched with a saturated aqueous solution of NH₄Cl and extracted with EtOAc (2×75 mL). The combined organic layers were washed with brine, dried over MgSO₄, filtered, concentrated under reduced pressure and passed through a plug of neutral alumina (EtOAc/heptane as eluent) to yield (((trifluoromethyl)sulfonyl)oxy)-2,3-dihydro-1,4-oxazepine-4(7H) -carboxylate (5.1 g, 63.2%); ¹H NMR (400 MHz, DMSO-d₆) δ 7.17 (s, 1H), 4.41 (s, 2H), 3.77 (q, J=2.3 Hz, 4H), 1.45 (s, 9H).

General Procedure AB: Reduction of a Double Bond and Removal of a CBZ Group from a CBZ Protected Amine A round bottom flask is charged with a palladium catalyst, such as Pd/C or Pd(OH)₂ (10 or 20 wt %, about 0.005 to 1.0 equiv, preferably 0.5 to 1.0 equiv). The flask is evacuated then flushed with nitrogen 2 to 5 times (preferably 3 times) prior to addition of an organic solvent or mixture of solvents (such as EtOAc, MeOH, EtOH or MeOH/AcOH, preferably MeOH/AcOH) under a nitrogen atmosphere. To the mixture is added a compound with an alkene functionality and an N-CBZ protected amine (preferably 1 equiv), neat or optionally as a solution in an organic solvent or mixture of solvents (such as EtOAc, MeOH, EtOH or MeOH/AcOH, preferably MeOH). The mixture is stirred under a hydrogen atmosphere (about 30 to 50 psi) for about 1 to 60 h (preferably about 4 to 5 h). Optionally the reaction may be performed using an H-cube instrument with either Pd/C or Pd(OH)₂ cartridges (10 or 20 wt %) and the starting material is passed through the system as a solution in the preferred solvent/s. In cases where the reaction does not proceed to completion as monitored by TLC, LC/MS, or HPLC, the mixture can be optionally heated to about 30 to 80° C. (preferably about 50° C.) for about 1 to 24 h (preferably about 16 h) and in cases where the H-cube is used to perform the reaction, the pressure may be increased (25 to 50 bar, preferably 40 to 50 bar). The mixture is then filtered and the filter cake is rinsed with an organic solvent (such as EtOAc, MeOH or EtOH, preferably the reaction solvent) and the filtrate is concentrated under reduced pressure to give the crude product.

Illustration of General Procedure AB Preparation #AB.1: 4-(Piperidin-3-yl)-1H-pyrrolo[3,2-c]pyridine-7-carboxamide

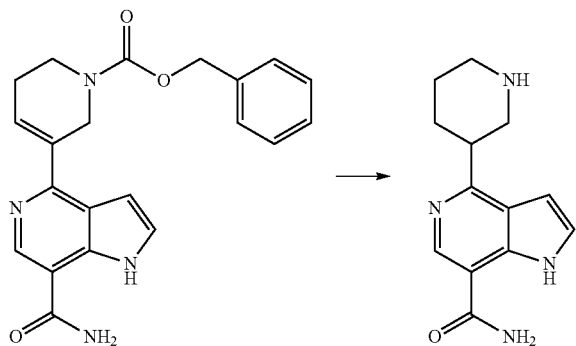 [SMILES: NC(=O)c1cnc(C2=CCCN(C(=O)OCc3ccccc3)C2)c2cc[nH]c12 ; NC(=O)c1cnc(C2CCCNC2)c2cc[nH]c12]

A round bottom flask was charged with Pd(OH)$_2$ (20 wt %, 0.336 g, 0.478 mmol) followed by the slow addition of a solution of benzyl 3-(7-carbamoyl-1H-pyrrolo[3,2-c]pyridin-4-yl)-5,6-dihydropyridine-1(2H)-carboxylate (1.8 g, 4.8 mmol, prepared using A from Preparation #45 and benzyl 3-(4,4,5,5-tetramethyl-1,3,2-dioxaborolan-2-yl)-5,6-dihydropyridine-1(2H)-carboxylate [Arkpharm], Y with LiOH and D with NH$_4$Cl) in MeOH (30 mL) and AcOH (10 mL). The flask was purged with N$_2$, then filled with H$_2$ using a balloon. The reaction mixture was then heated at about 45° C. for about 3 h. The reaction mixture was cooled to rt and filtered through a pad of Celite®, washing with MeOH. The filtrate was concentrated under reduced pressure, dissolved in MeOH and then treated with MP-carbonate beads by stirring at rt for about 2 h. The beads were filtered off and the filtrate was concentrated under reduced pressure to give 4-(piperidin-3-yl)-1H-pyrrolo[3,2-c]pyridine-7-carboxamide (0.84 g, 72%): LC/MS (Table 1, Method as) R$_t$=0.58 min; MS m/z: 245 (M+H)$^+$.

General Procedure AC: N-Oxidation of an N Containing Hetero Aromatic Ring

A solution of an N-containing hetero aromatic compound (1 equiv) in an organic solvent (such as DCE, DME, DCM or EtOAc, preferably DCM) is cooled to about 0° C. and an oxidizing reagent such as 3-chlorobenzoperoxoic acid or magnesium monoperoxyphthalate hexahydrate (1 to 3 equiv, preferably 2 equiv). The solution is stirred at rt for about 2 to 24 h (preferably about 10 to 16 h). The mixture is optionally filtered to give the desired product or optionally concentrated in vacuo to give a residue, either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure AC

Preparation #AC.1: 4-Bromo-1H-pyrrolo[2,3-c]pyridine 6-oxide

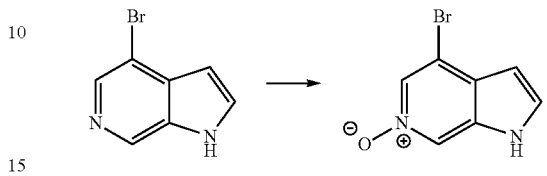

A flask was charged with 4-bromo-1H-pyrrolo[2,3-c]pyridine (10.0 g, 50.8 mmol) [Combiblocks] and dissolved in EtOAc (254 mL). The flask was cooled to about 0° C. and a solution of 3-chlorobenzoperoxoic acid (10.5 g, 60.9 mmol) in EtOAc (254 mL) was slowly added. The reaction was stirred warming to rt for about 16 h. The precipitate that had formed was collected via filtration and dried in vacuum oven to afford 4-bromo-1H-pyrrolo[2,3-c]pyridine 6-oxide (0.85 g, 79%): LC/MS (Table 1, Method as) R$_t$=1.18 min; MS m/z: 213, 215(M+H)$^+$.

General Procedure AD: Cyanation of an N-Oxide Containing Heteroaryl Ring

A flask is charged with an N-oxide heteroaromatic compound (1 equiv) in an appropriate organic solvent, such as ACN. TEA is added (1 to 2 equiv, preferably 1.5 equiv). TMSCN (2 to 5 equiv, preferable 3 to 4 equiv) is then added using a syringe. The reaction mixture is refluxed until complete consumption of starting material is observed either via TLC or LC/MS. The reaction mixture is cooled to rt and quenched appropriately, preferable with an aqueous solution of NaOH and extracted with an organic solvent, such as DCM or EtOAC. The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure AD

Preparation #AD.1: 4-Bromo-1H-pyrrolo[2,3-c]pyridine-7-carbonitrile

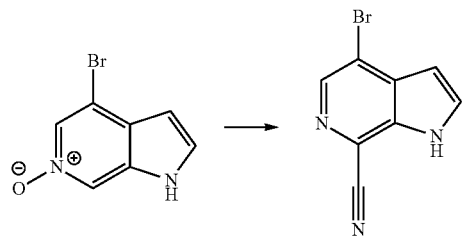

A flask was charged with 4-bromo-1H-pyrrolo[2,3-c]pyridine-6-oxide 3-chlorobenzoate (6.25 g, 16.91 mmol, Preparation #AC.1) in ACN (97 mL) and TEA (3.56 mL, 25.4 mmol). TMSCN (9.02 mL, 67.6 mmol) was added in one portion via syringe the mixture was refluxed for about 45 min. The reaction was quenched by careful addition of 50 mL of aqueous 1 M NaOH solution, transferred to a separatory funnel and diluted with aqueous 1M NaOH solution (200 mL) and EtOAc (200 mL). The layers were separated and the organic phase was washed again with 50 mL of aqueous 1 M NaOH solution. The combined aqueous extracts were washed with EtOAc (4×75 mL) and then with 1 M NaOH (2×20 mL) and brine (1×50 mL), dried over $Na_2SO_4$, filtered and the solvent was removed to afford 4-bromo-1H-pyrrolo[2,3-c]pyridine-7-carbonitrile (3.84 g, 93%): $^1$H NMR (400 MHz, DMSO-$d_6$) δ 8.27 (s, 1H), 7.90 (d, J=2.8 Hz, 1H), 6.60 (d, J=2.8 Hz, 1H).

General Procedure AE: Reduction of an Ester to Form an Alcohol

To a solution of an ester in an appropriate organic solvent (such as THF, dioxane, DCM or EtOAc, preferably THF) is optionally added water (1 to 4 equiv, preferably 2 equiv). The mixture is then cooled to about 0° C. and a reducing agent is added (such as $LiBH_4$ or LAH, preferably $LiBH_4$; 2 to 12 equiv, preferably 6 equiv). The reaction mixture is stirred for about 5 to 24 h until complete consumption of the ester. Additional reducing agent may be optionally added as required. The reaction mixture is then quenched with an aqueous solution of $NH_4Cl$. The organic layer is isolated and may optionally be washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl $Na_2SO_3$ or $Na_2S_2O_3$). The organic solution may then be optionally dried with a drying agent (such as anhydrous $MgSO_4$ or $Na_2SO_4$), filtered and concentrated in vacuo to give the target compound.

Illustration of General Procedure AE

Preparation #AE.1: tert-Butyl 3-(7-carbamoyl-1H-indol-4-yl)-5-(hydroxymethyl)piperidine-1-carboxylate In a 500 mL round-bottomed flask, 1-tert-butyl 3-methyl 5-(7-carbamoyl-1H-indol-4-yl)piperidine-1,3-dicarboxylate (6.75 g, 16.8 mmol, prepared using Z from Preparation #AF.1) in THF (150 mL) was added. The reaction mixture was cooled to about 0° C. and water (0.606 mL, 33.6 mmol) was added. $LiBH_4$ (2.93 g, 135 mmol) was added and reaction mixture stirred at rt for about 12 h. Additional $LiBH_4$ (2.93 g, 135 mmol) was added and reaction mixture was stirred for about 3 h. The reaction mixture was carefully added to a saturated aqueous solution of $NH_4Cl$ (800 mL) at about −10° C. The mixture was extracted with DCM (500 mL). The DCM layer was dried over $MgSO_4$, filtered and concentrated to give crude tert-butyl 3-(7-carbamoyl-1H-indol-4-yl)-5-(hydroxymethyl)piperidine-1-carboxylate (6.35 g, 101%): LC/MS (Table 1, Method as) $R_t$=1.74 min; MS m/z: 374 (M+H)$^+$.

General Procedure AF: Reduction of a Pyridine Ring to a Piperiding Ring

To a solution of the pyridine (1 equiv) in acetic acid is added a reducing reagent (such as $PtO_2$, $Pd(OH)_2$ or Pd/C, preferably $PtO_2$; 0.05 to 0.5 equiv, preferable 0.1 to 0.2 equiv). The reaction mixture is heated at about 50° C. at about 20 to 50 psi (preferably about 30 psi) for about 6 to 12 h (preferably about 10 h). The reaction mixture is concentrated under reduced pressure to give the desired compound.

Illustration of General Procedure AF

Preparation #AF.1: Methyl 5-(7-carbamoyl-1H-indol-4-yl)piperidine-3-carboxylate

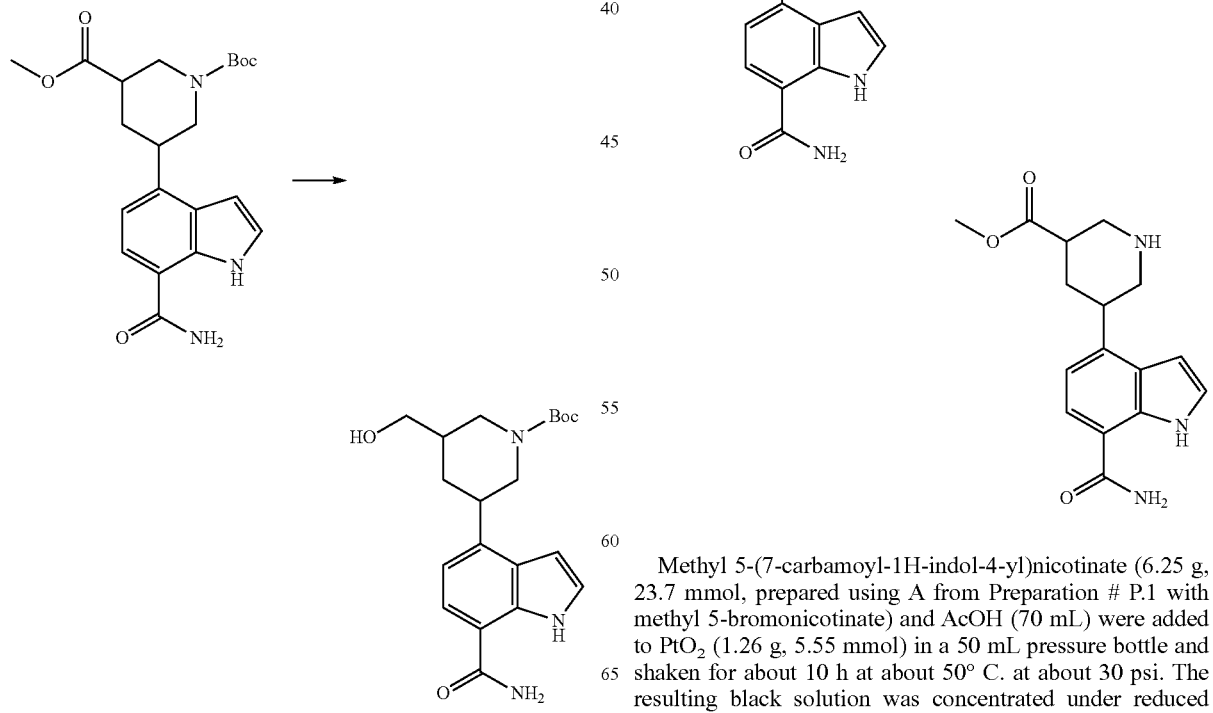

Methyl 5-(7-carbamoyl-1H-indol-4-yl)nicotinate (6.25 g, 23.7 mmol, prepared using A from Preparation # P.1 with methyl 5-bromonicotinate) and AcOH (70 mL) were added to $PtO_2$ (1.26 g, 5.55 mmol) in a 50 mL pressure bottle and shaken for about 10 h at about 50° C. at about 30 psi. The resulting black solution was concentrated under reduced pressure and filtered through a plug of Celite® and washed with DCM. The filtrate was then concentrated to a thick viscous black oily residue. This material was dissolved in 15% MeOH/EtOAc and passed through a large silica gel plug. The plug was flushed with 10% MeOH/EtOAc (250 mL), then 35-40% MeOH/EtOAc (1.5 L) to afford methyl 5-(7-carbamoyl-1H-indol-4-yl)piperidine-3-carboxylate (6.3 g, 79%): LC/MS (Table 1, Method a) $R_t$=0.96 min; MS m/z: 302 (M+H)$^+$.

General Procedure AG: One Pot Borylation of a Triflate and Suzuki Reaction of the In Situ Formed Boronate with an Aryl Halide To a mixture of a vinyl triflate (preferably 1 equiv), a boronic acid or boronate ester (1 to 2 equiv, preferably 1.1 equiv), and an inorganic base (such as KF, Na$_2$CO$_3$, K$_2$CO$_3$ or Cs$_2$CO$_3$, preferably Na$_2$CO$_3$ or Cs$_2$CO$_3$; 1.1 to 16 equiv, preferably 2 equiv) in a solvent (such as THF, DME, DMF, 1,4-dioxane, 1,4-dioxane, preferably dioxane) is added a palladium catalyst (for example Pd(OAc)$_2$, Pd$_2$ dba$_3$, Pd(PPh$_3$)$_4$, bis(acetato)triphenylphosphinepalladium(II), polymer-bound FibreCat™ 1032, SiliaCat DPP-Pd, PdCl$_2$(dppf) or Pd(PPh$_3$)$_2$Cl$_2$; preferably PdCl$_2$(dppf) or Pd(PPh$_3$)$_2$ Cl$_2$; 0.01 to 0.20 equiv, preferably 0.05 to 0.1 equiv) and a ligand (for example tricyclohexylphosphine, tri-tert-butyl-phosphine; preferably none or PPh$_3$; 0.01 to 1.0 equiv, preferably 0.01 to 0.03 equiv) is added optionally. The mixture is heated at about 40 to 120° C. (preferably about 70 to 85° C.) for about 1 to 48 h (preferably about 2 to 4 h) thermally, or at about 100 to 200° C. (preferably about 120 to 150° C.) for about 5 to 60 min (preferably about 20 to 45 min) in a microwave (preferably 5 min ramp time, 300 Watts max power, 250 psi max pressure). The mixture is optionally allowed to cool to rt and filtered. To the reaction mixture is added the aryl halide (1 to 2 equiv), water (about ⅓ to ¼ the volume of the original organic solvent used) and optionally additional catalyst, base and ligand is added (preferably the same ones used in the first reaction) and heated at the same temperature for about 3 to 24 h (preferably about 8 to 10 h) and is worked up using one of the following methods. Method 1. For reactions containing water, the mixture may be diluted with an organic solvent (such as DCM or EtOAc). The layers are separated, the organic solution is optionally washed with water and/or brine, dried over anhydrous MgSO$_4$ or Na$_2$SO$_4$, filtered, and the solvent is removed under reduced pressure to give the desired compound. Method 2. The mixture is concentrated under reduced pressure. Method 3. The catalyst is removed by filtration and the filtrate is concentrated under reduced pressure Illustration of General Procedure AG Preparation #AG.1: tert-Butyl 6-(7-(methoxycarbonyl)-1H-pyrrolo[3,2-c]pyridin-4-yl)-2,3-dihydro-1,4-oxazepine-4(7H)-carboxylate

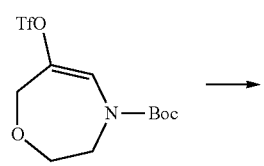

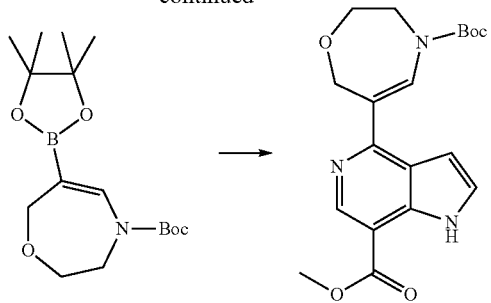

A 40 mL microwave reaction vial was charged with 4,4,4',4',5,5,5',5'-octamethyl-2,2'-bi(1,3,2-dioxaborolane) (0.995 g, 3.92 mmol), PPh$_3$(0.056 g, 0.214 mmol), Pd(PPh$_3$)$_2$Cl$_2$ (0.125 g, 0.178 mmol) and K$_2$CO$_3$ (0.738 g, 5.34 mmol). To this mixture was added a solution of tert-butyl 6-(((trifluoromethyl) sulfonyl)oxy)-2,3-dihydro-1,4-oxazepine-4(7H)-carboxylate (1.24 g, 3.56 mmol, Preparation #AA.1) in dioxane (13 mL). The entire mixture was degassed for about 5 min and purged with nitrogen. The mixture was heated at about 75° C. for about 2 h. To the reaction mixture was added methyl 4-chloro-1H-pyrrolo[3,2-c]pyridine-7-carboxylate (0.600 g, 2.85 mmol), Pd(PPh$_3$)$_2$Cl$_2$ (125 mg, 0.178 mmol), K$_2$CO$_3$ (0.492 g, 3.56 mmol) and water (3.25 mL). The entire suspension was degassed with nitrogen for about 10 min and heated at about 75° C. for about 8 h. The reaction mixture was cooled, filtered over a plug of Celite® and MgSO$_4$, concentrated and purified via silica gel chromatography (0-40% EtOAc/heptane) to give tert-butyl 6-(7-(methoxycarbonyl)-1H-pyrrolo[3,2-c]pyridin-4-yl)-2,3-dihydro-1,4-oxazepine-4(7H) -carboxylate (0.3 g, 23%): LC/MS (Table 1, Method as) $R_t$=2.04 min; MS m/z: 374(M+H)$^+$.

General Procedure AH: Formation of an N-Tosyl Protected Heteroaromatic Ring

A solution of a compound with an N-heteroaromatic ring, such as an indole or azaindole (1 equiv) in an appropriate organic solvent (such as THF, DMF, DCE, toluene or dioxane, preferably THF) is optionally cooled to about 0° C. and a base (such as NaH, KOH or NaOH, preferable NaH; 1 to 2 equiv, preferable 1.1 to 1.3 equiv) is added. The reaction mixture is stirred for about 10 to 30 min and 4-methyl-benzenesulfonyl chloride (1 to 3 equiv, preferable 1 to 1.5 equiv) is added. The reaction mixture is optionally allowed to warm to rt if cooled or optionally heated at about 30 to 90° C. until complete consumption of the starting N-heteroaromatic compound. Additional base and tosylating reagent may be optionally added as required. The reaction mixture is quenched by the addition of water and extracted with an organic solvent (such as EtOAc or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Illustration of General Procedure AH Preparation #AH.1:
4-Bromo-1-tosyl-1H-pyrrolo[2,3-c]pyridine-7-carbonitrile

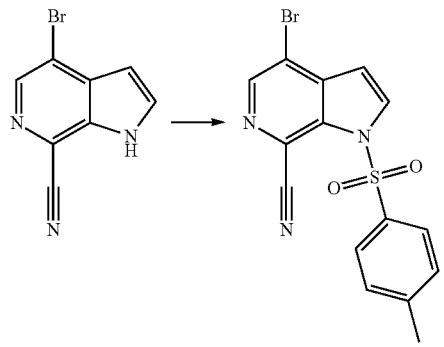 [SMILES: N#Cc1ncc(Br)c2cc[nH]c12 ; Cc1ccc(S(=O)(=O)n2ccc3c(Br)cnc(C#N)c32)cc1]

A flask is charged with 4-bromo-1H-pyrrolo[2,3-c]pyridine-7-carbonitrile (0.985 g, 4.44 mmol, Preparation # AD.1) in THF (30 mL). NaH (60% dispersion in mineral oil, 0.213 g, 5.32 mmol) was added portion wise at about 0° C. The mixture was allowed to stir for about 15 min, then 4-methyl-benzenesulfonyl chloride (0.930 g, 4.88 mmol) was added in one portion and the reaction was allowed to warm to room temperature and stirred or about 16 h. Additional NaH (60% dispersion in mineral oil, 0.355 g, 0.89 mmol) and 4-methylbenzene-1-sulfonyl chloride (0.254 g, 1.33 mmol) were added in sequence and stirred at rt for about 1 h. The reaction mixture was diluted with water (30 mL) and extracted with EtOAc (60 mL). The organic layer was dried over MgSO$_4$, filtered, concentrated and purified using silica gel chromatography (0-35% EtOAc/heptane) to give 4-bromo -1-tosyl-1H-pyrrolo[2,3-c]pyridine-7-carbonitrile (1.35 g, 81%): LC/MS (Table 1, Method as) R$_t$=2.51 min; MS m/z: 376, 378(M+H)$^+$.

Example #1 tert-Butyl 2-(4-bromo-7-carbamoyl-1H-indol-2-yl)benzylcarbamate methylphenyl)thiazole-2-carboxamide

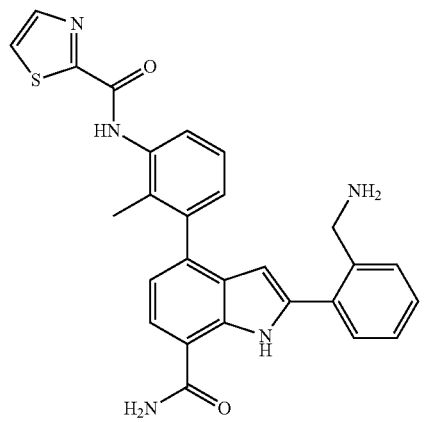 [SMILES: Cc1c(NC(=O)c2nccs2)cccc1-c1ccc(C(N)=O)c2[nH]c(-c3ccccc3CN)cc12]

Step A: tert-Butyl 2-(4-bromo-7-carbamoyl-1H-indol-2-yl)benzylcarbamate

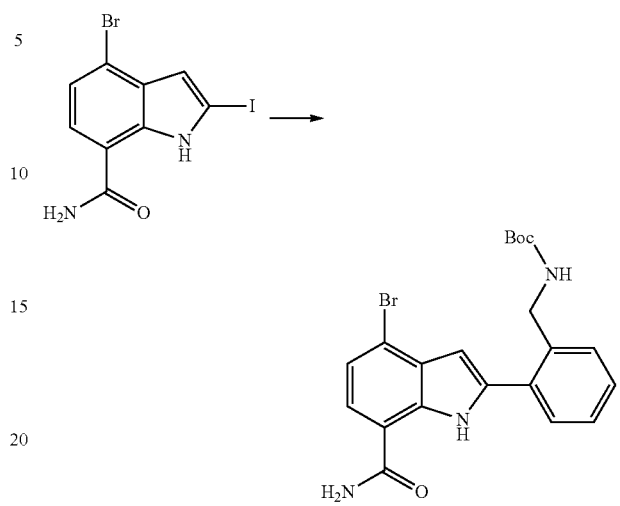

To a solution of 4-bromo-2-iodo-1H-indole-7-carboxamide (2.5 g, 6.8 mmol, Preparation #1) in THF (185 mL), MeOH (25 mL) and water (25 mL) was added tert-butyl 2-(4,4,5,5-tetramethyl-1,3,2-dioxaborolan-2-yl)benzylcarbamate (2.7 g, 8.2 mmol, JW), Pd(dppf)Cl$_2$ (0.5 g, 0.7 mmol) and Na$_2$CO$_3$ (2.2 g, 20.6 mmol). The mixture was stirred at about 80° C. overnight under nitrogen. The solvent was removed under reduced pressure to give a residue, which was purified by column chromatography on silica gel to provide crude tert-butyl 2-(4-bromo-7carbamoyl -1H-indol-2-yl)benzylcarbamate (2.5 g, 5.6 mmol).

Step B: tert-Butyl 2-(7-carbamoyl-4-(2-methyl-3-(thiazole-2-carboxamido)phenyl)-1H-indol-2-yl)benzylcarbamate

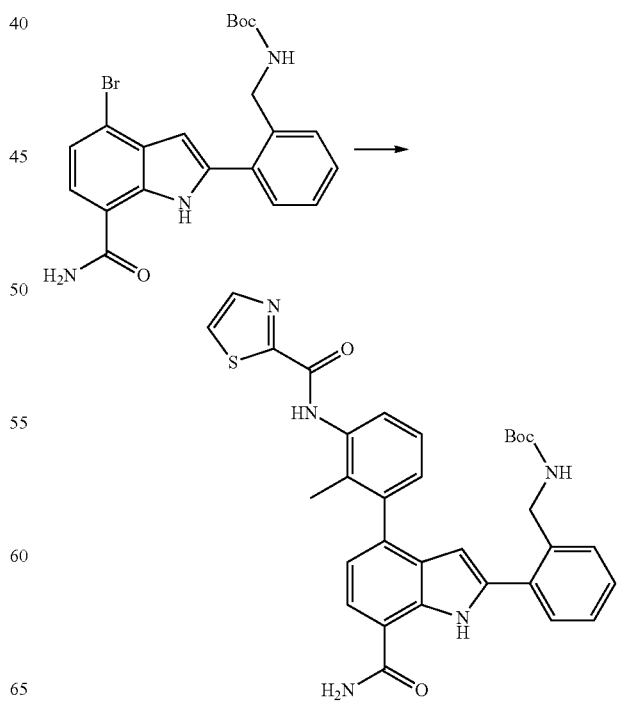

To a solution of 2-(4-bromo-7-carbamoyl-1H-indol-2-yl) benzylcarbamate (2.5 g, 5.6 mmol) in THF (185 mL), MeOH (25 mL) and water (25 mL) was added N-(2-methyl-3-(4,4,5,5-tetramethyl-1,3,2-dioxaborolan-2-yl)phenyl)thiazole-2-carboxamide (2.3 g, 6.8 mmol, Preparation #4), Pd(dppf)Cl$_2$ (0.4 g, 0.6 mmol) and Na$_2$CO$_3$ (1.8 g, 16.9 mmol). The mixture was stirred at about 80° C. overnight under nitrogen. The solvent was removed under reduced pressure to give a residue, which was purified by column chromatograph on silica gel to provide tert-butyl 2-(7-carbamoyl-4-(2-methyl-3-(2-oxo-2-(thiazol-2-yl)ethyl)phenyl)-1H-indol-2-yl)benzylcarbamate (3 g, 92%): $^1$H NMR (CDCl$_3$) δ 10.57 (s, 1H), 9.25 (s, 1H), 8.22-8.20 (d, J=7.6 Hz, 1H), 7.92-7.91 (d, J=3.2 Hz, 1H), 7.64-7.63 (d, J=3.2 Hz, 1H), 7.50-7.45 (m, 3H), 7.37-7.35 (m, 3H), 7.26-7.24 (m, 2H), 7.04-7.02 (d, J=3.6 Hz, 1H), 6.32 (s, 1H), 4.43 (s, 2H), 2.25 (s, 3H), 1.38 (s, 9H).

Step C: N-(3-(2-(2-(aminomethyl)phenyl)-7-carbamoyl-1H-indol-4-yl)-2-methylphenyl)thiazole-2-carboxamide

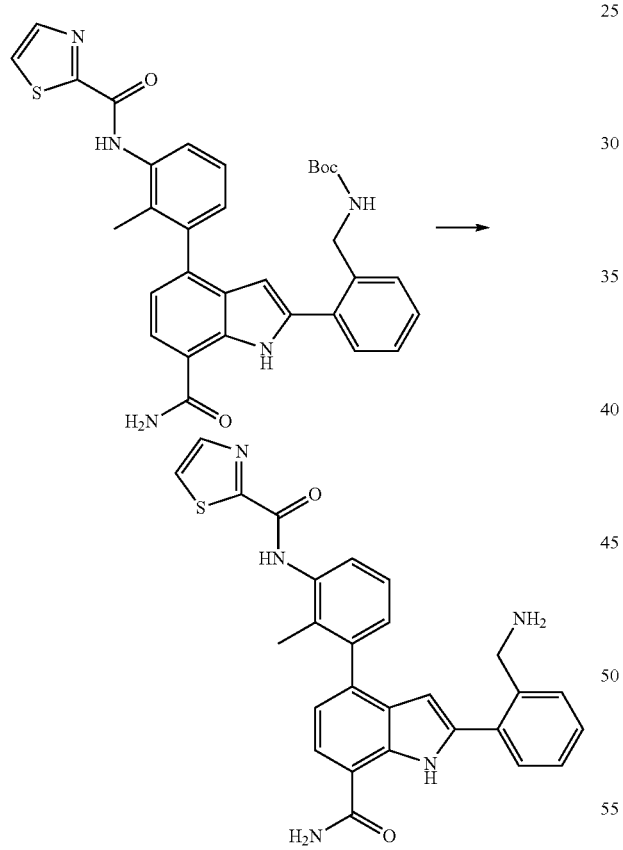

A solution of tert-butyl 2-(7-carbamoyl-4-(2-methyl-3-(2-exo-2-(thiazol-2-yl)ethyl)phenyl)-1H-indol-2-yl)benzylcarbamate (3 g, 5.2 mmol) in DCM (50 mL) and TFA (10 mL) was stirred at about 25° C. for about 6 h. The solvent was removed by reduced pressure. Water was added and the solution was basified by addition of saturated aqueous NaHCO$_3$ to pH 9. The mixture was extracted with EtOAc. The organic phase was concentrated to provide N-(3-(2-(2-(aminomethyl)phenyl) -7-carbamoyl-1H-indol-4-yl)-2-methylphenyl)thiazole-2-carboxamide (2.2 g, 89%): LC/MS (Table 1, Method b) R$_f$=2.53 min; MS m/z: 482(M+H)$^+$. (Btk IC$_{50}$=B)

Example #2

4-(3-Amino-2-methylphenyl)-1H-pyrrolo[2,3-c]pyridine-7-carboxamide

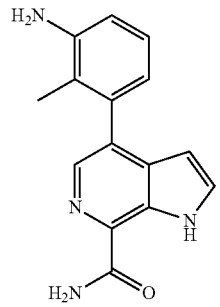 [SMILES: Cc1c(N)cccc1-c1cnc(C(N)=O)c2[nH]ccc12]

Step A:
4-Bromo-7-chloro-1H-pyrrolo[2,3-c]pyridine

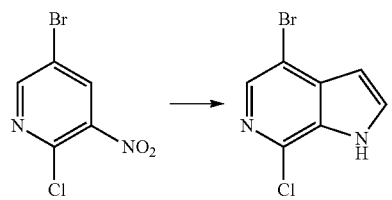 [SMILES: O=[N+]([O-])c1cc(Br)cnc1Cl ; Clc1ncc(Br)c2cc[nH]c12]

To a solution of 5-bromo-2-chloro-3-nitropyridine (10 g, 0.042 mol) in anhydrous THF (150 mL), a solution of vinylmagnesium bromide (17 g, 0.127 mol) in THF was added dropwise at −30 to −50° C. The reaction mixture was stirred at −30 to −40° C. for 2 h. Then the reaction mixture was poured into saturated aqueous NH$_4$Cl solution and the mixture was extracted with EtOAc (50 mL×3). The combined organic layers were washed with brine, dried over anhydrous Na$_2$SO$_4$, filtered and concentrated under reduced pressure and the residue was purified by column chromatography to provide 4-bromo-7-chloro-1H-pyrrolo[2,3-c] pyridine (3 g, 31%): $^1$H NMR: (DMSO-d6) δ 12.45 (s, 1H), 8.04 (s, 1H), 7.79-7.78 (m, 1H), 6.59-6.58 (d, J=2.0, 1H).

Step B: 3-(7-Chloro-1H-pyrrolo[2,3-c]pyridin-4-yl)-2-methylaniline

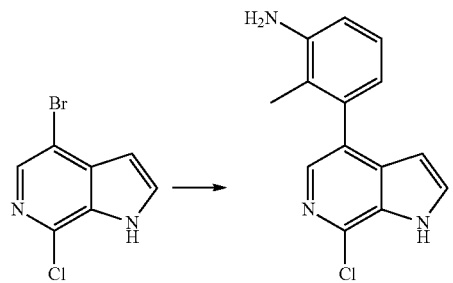 [SMILES: Clc1ncc(Br)c2cc[nH]c12 ; Cc1c(N)cccc1-c1cnc(Cl)c2[nH]ccc12]

To a mixture of 4-bromo-7-chloro-1H-pyrrolo[2,3-c]pyridine [Matrix] (5 g, 21.6 mmol), 2-methyl-3-(4,4,5,5-tetramethyl-1,3,2-dioxaborolan-2-yl)aniline (7.55 g, 32.4 mmol, CombiBlocks) and sodium carbonate (1.6 g, 64.8 mmol) in THF (80 mL), MeOH (80 mL) and water (20 mL), Pd(dppf)Cl₂ (1.6 g, 2.16 mmol) was added and the mixture was degassed several times and heated to about 70° C. overnight under N₂. The reaction mixture was filtered through Celite® and concentrated under reduced pressure and the residue was purified by column chromatography to provide 3-(7-chloro-1H-pyrrolo[2,3-c]pyridin-4-yl)-2-methylaniline (2.2 g, 40%): $^1$H NMR (DMSO-d6) δ 12.05 (s, 1H), 7.71 (s, 1H), 7.64 (d, J=2.4, 1H), 6.99-6.96 (m, 1H), 6.72-6.70 (d, J=8.0, 1H), 6.48 (d, J=6.8, 1H), 6.2 (d, J=2.8, 1H), 4.95 (s, 2H), 1.82 (s, 3H).

Step C: Methyl 4-(3-amino-2-methylphenyl)-1H-pyrrolo[2,3-c]pyridine-7-carboxylate

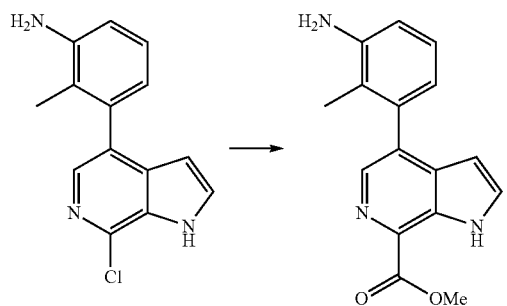 [SMILES: Cc1c(N)cccc1-c1cnc(Cl)c2[nH]ccc12 ; COC(=O)c1ncc(-c2cccc(N)c2C)c2cc[nH]c12]

To a solution of 3-(7-chloro-1H-pyrrolo[2,3-c]pyridin-4-yl)-2-methylaniline (800 mg, 3.1 mmol) in anhydrous MeOH (80 mL), Et₃N (3.1 g, 31 mmol) and Pd(dppf)Cl₂ (0.45 g, 0.62 mmol) were added and the reaction mixture was heated to about 130° C. for about 24 h under CO. The reaction mixture was concentrated under reduced pressure and the residue was purified by silica gel column to provide methyl 4-(3-amino-2-methylphenyl)-1H-pyrrolo[2,3-c]pyridine-7-carboxylate (0.60 g, 69%): $^1$H NMR (DMSO-d6): δ11.65 (br. s., 1H), 8.09 (s, 1 H) 7.65 (s, 1 H) 7.02 (t, J=7.72 Hz, 1 H), 6.74 (d, J=7.94 Hz, 1 H), 6.52 (d, J=7.50 Hz, 1 H) 6.26 (d, J=2.65 Hz, 1 H), 5.02 (s, 2 H), 4.0 (s, 3 H), 1.83 (s, 3 H)

Step D: 4-(3-Amino-2-methylphenyl)-1H-pyrrolo[2,3-c]pyridine-7-carboxamide

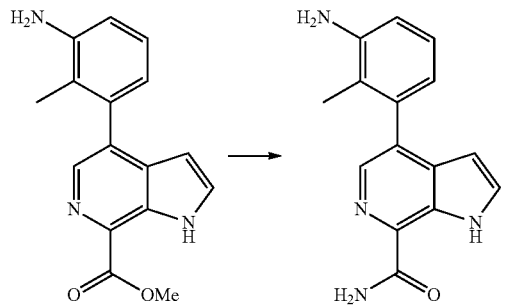 [SMILES: COC(=O)c1ncc(-c2cccc(N)c2C)c2cc[nH]c12 ; Cc1c(N)cccc1-c1cnc(C(N)=O)c2[nH]ccc12]

To a solution of methyl 4-(3-amino-2-methylphenyl)-1H-pyrrolo[2,3-c]pyridine-7-carboxylate (600 mg, 2.13 mmol) in MeOH (10 mL), ammonia (2 mL) was added and the reaction mixture was stirred overnight at rt. The mixture was concentrated and the residue was purified by prep-TLC (30:1 DCM/MeOH) to provide 4-(3-amino-2-methylphenyl)-1H-pyrrolo[2,3-c]pyridine-7-carboxamide (320 mg, 56%): $^1$H NMR (DMSO-d6): δ 11.56 (s, 1H), 8.2 (s, 1H), 7.97 (s, 1H), 7.64 (s, 1H), 7.55 (s, 1H), 7.0-6.97 (m, 1H), 6.71 (d, J=7.6, 1H), 6.50 (d, J=4.4, 1H), 6.17 (s, 1H), 4.97 (s, 2H), 1.82 (s, 3H); (Table 1, Method d) R$_f$=1.95 min; MS m/z: 267 (M+H)⁺. (BtkIC₅₀=C)

Example #3

N-(3-(7-carbamoyl-3-methyl-1H-indol-4-yl)-2-methylphenyl)thiazole-2-carboxamide

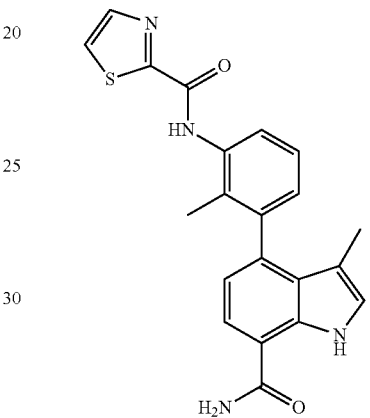

Step A: Methyl 4-bromo-3-formyl-1H-indole-7-carboxylate

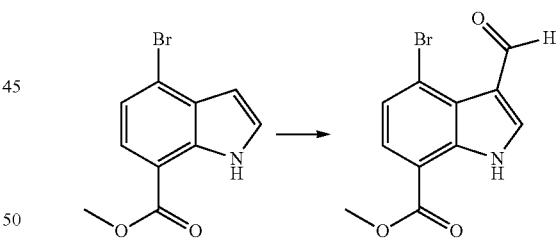

POCl₃ (2.4 mL, 26 mmol) was added into DMF (60 mL) solution dropwise at 0° C. and stirred for about 30 min. Then a solution of methyl 4-bromo-1H-indole-7-carboxylate (5 g, 13 mmol, Preparation #1, step B) in DMF (60 mL) was added dropwise into the above reaction mixture at about 0° C. and stirred for about 20 min. The resulting reaction mixture was heated to about 90° C. for about 3 h. After cooling to rt, the mixture was poured into ice water and basified by addition of aqueous NaOH solution to pH=8 to 9. The aqueous mixture was extracted with EtOAc. The combined organic phase was washed with brine, dried over Na₂SO₄, filtered and concentrated under reduced pressure to get a residue, which was purified by column chromatography on silica gel to provide methyl 4-bromo-3-formyl-1H-indole-7-carboxylate (3.5 g, 95%): $^1$H NMR (DMSO-d6): δ

12.33 (br, 1H), 10.69 (s, 1H), 8.20 (d, J=2.0 Hz, 1H), 7.76-7.74 (d, J=8.0 Hz, 1H), 7.61-7.59 (d, J=8.4 Hz, 1H), 3.94 (s, 3H).

Step B: Methyl 4-bromo-3-4(4-methoxybenzyl) amino)methyl)-1H -indole-7-carboxylate

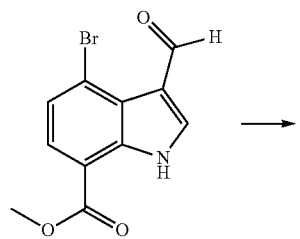

To a solution of methyl 4-bromo-3-formyl-1H-indole-7-carboxylate (3.5 g, 12.4 mmol) in anhydrous DCE (50 mL) was added (4-methoxyphenyl)methanamine (2.6 g, 18.6 mmol) and a catalyst amount of AcOH. The reaction mixture was stirred at rt for about 1 h. Then NaBH(OAc)$_3$ (13.2 g, 62 mmol) was added in portions and stirred at rt overnight. When the reaction was completed, water was added to quench the reaction. The aqueous phase was extracted with DCM. The combined organic phase was concentrated under reduced pressure to get a residue, which was purified by column chromatography on silica gel to provide methyl 4-bromo-3-(((4-methoxybenzyl)amino)methyl)-1H-indole-7-carboxylate (4 g, 80%): $^1$H NMR (DMSO-d6): δ 11.25 (br, 1H), 7.61-7.59 (d, J=8.4 Hz, 1H), 7.41 (s, 1H), 7.30-7.23 (m, 3H), 6.85-6.83 (d, J=8.4 Hz, 2H), 4.02 (s, 2H), 3.90 (s, 3H), 3.70-3.69 (m, 5H), 1.88 (s, 1H).

Step C: 4-Bromo-3-(((4-methoxybenzyl)amino) methyl)-1H-indole-7-carboxylic acid

To a solution of methyl 4-bromo-3-(((4-methoxybenzyl)amino)methyl)-1H -indole-7-carboxylate (5.4 g, 13.4 mmol) in THF (250 mL), MeOH (50 mL) and water (50 mL) was added LiOH (1.6 g, 67.0 mmol) and heated to reflux for about 6 h. After cooling to rt, the organic solvent was removed under reduced pressure. The aqueous phase was acidified with 1 N HCl to pH=5 to 6. Then the suspension was filtered and the filter cake was washed with water and dried to afford 4-bromo-3-(((4-methoxybenzyl)amino) methyl)-1H-indole-7-carboxylic acid (4 g, 77%): $^1$H NMR (DMSO-d6) δ 11.40 (br, 1H), 7.58-7.56 (d, J=8.0 Hz, 1H), 7.53 (s, 1H), 7.40-7.38 (d, J=8.4 Hz, 2H), 7.27-7.25 (d, J=8.0 Hz, 1H), 6.94-6.92 (d, J=8.4 Hz, 2H), 4.31 (s, 2H), 3.98 (s, 2H), 3.74 (s, 3H).

Step D: 4-Bromo-3-(((4-methoxybenzyl)amino) methyl)-1H-indole-7-carboxamide

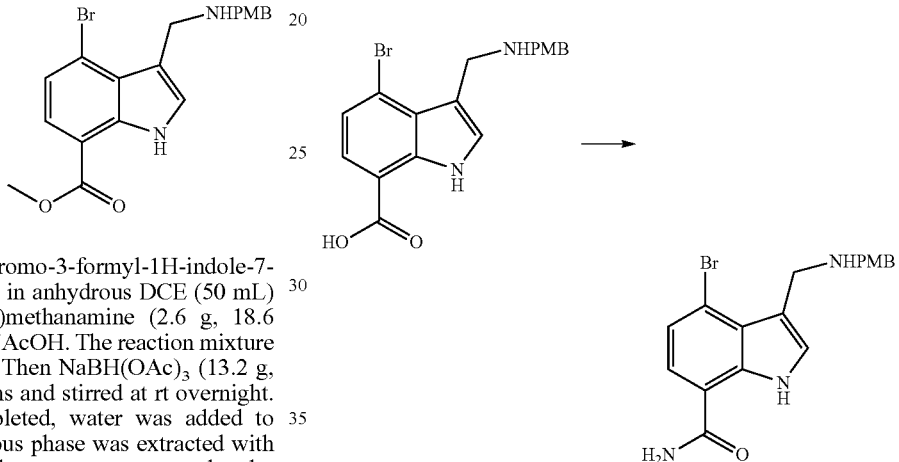

A mixture of 4-bromo-3-(((4-methoxybenzyl)amino) methyl)-1H-indole-7-carboxylic acid (9.3 g, 23.9 mmol), EDCI (5.5 g, 28.7 mmol) and HOBt (4.4 g, 28.7 mmol) in THF (350 mL) and DCM (420 mL) was stirred at rt for about 1 h. Then the reaction mixture was bubbled with ammonia gas for about 15 min at about −60° C., then warmed to rt and stirred overnight. The solvent was removed under reduced pressure and MeOH was added. The suspension was filtered and the filtrated was concentrated under reduced pressure to get a residue, which was purified by Prep-HPLC (Table 1, Method s) to provide 4-bromo-34(4-methoxybenzyl)amino) methyl)-1H-indole-7-carboxamide (2.1 g, 23%): LC/MS (Table 1, Method d) R$_t$=2.31 min; MS m/z: 388 (M+H)$^+$ Step E: N-(3-(7-carbamoyl-3-4(4-methoxybenzyl) amino)methyl)-1H-indol-4-yl)-2-methylphenyl)thi-azole-2-carboxamide

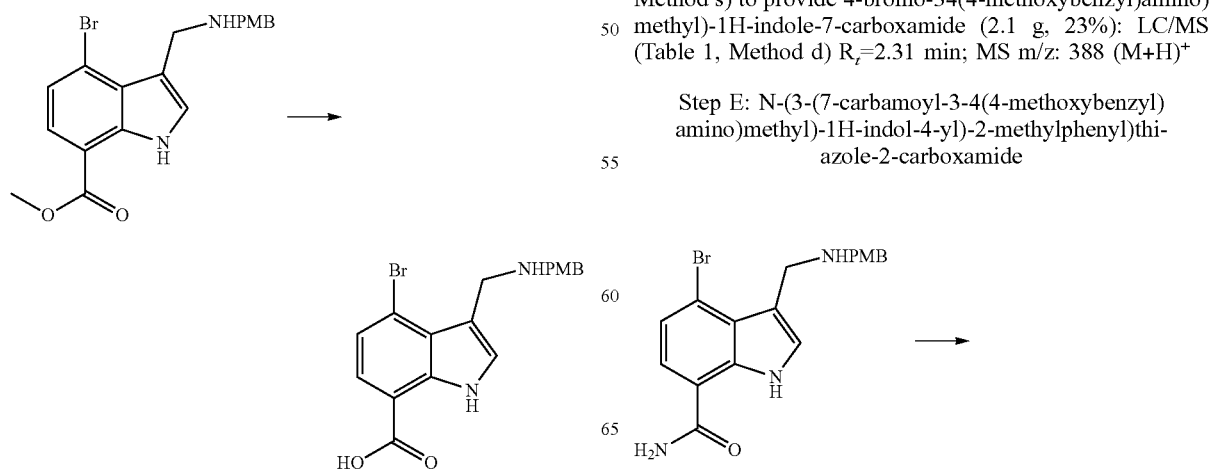

439

-continued

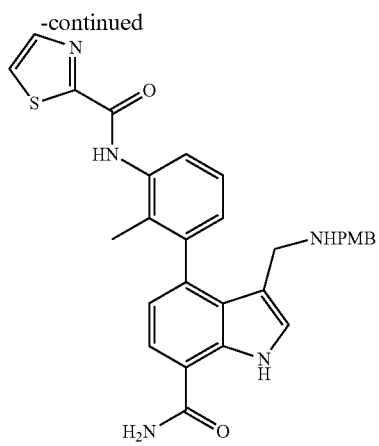

440

-continued

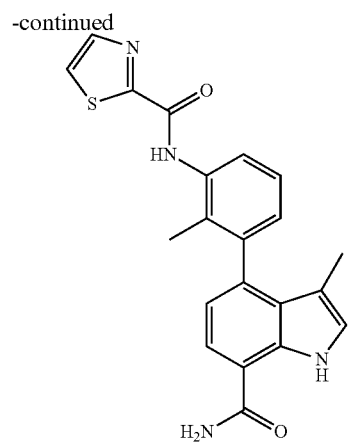

To a solution of 4-bromo-3-(((4-methoxybenzyl)amino) methyl)-1H-indole -7-carboxamide (100 mg, 0.26 mmol), N-(2-methyl-3-(4,4,5,5-tetramethyl-1,3,2-dioxaborolan -2-yl)phenyl)thiazole-2-carboxamide (116 mg, 0.39 mmol, Preparation #4) and CsF (39 mg, 0.26 mmol) in 1,4-dioxane (2 mL) and water (0.4 mL) was added Pd(PPh$_3$)$_4$ (29.8 mg, 0.03 mmol). Then the reaction mixture was heated to about 100° C. under nitrogen for about 12 h. After cooling to rt, water was added and extracted with EtOAc. The combined organic phase was washed with brine, dried over Na$_2$SO$_4$, filtered and concentrated under reduced pressure to get a crude product, which was purified by Prep-HPLC (Table 1, Method r) to provide N-(3-(7-carbamoyl-34(4-methoxyben-zyl)amino)methyl)-1H-indol-4-yl)-2-methylphenyl)thiaz-ole-2-carboxamide (10 mg, 8%): $^1$H NMR (DMSO-d6): δ 11.05 (br, 1H), 10.23 (br, 1H), 8.14-8.10 (m, 3H), 7.72-7.65 (m, 2H), 7.27 (br, 1H), 7.26-7.24 (m, 2H), 7.11-7.09 (m, 1H), 7.02-7.00 (d, J=8.8 Hz, 2H), 6.77-6.71 (m, 3H), 3.63 (s, 3H), 3.24-3.21 (m, 4H), 1.88 (s, 3H), 1.83 (s, 1H)

Step F: N-(3-(7-carbamoyl-3-methyl-1H-indol-4-yl)-2-methylphenyl)thiazole-2-carboxamide

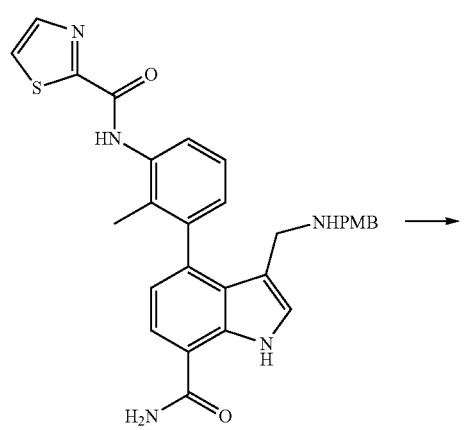

To a solution of N-(3-((7-carbamoyl-3-(((4-methoxyben-zyl)amino)methyl)-1H-indol-4-yl)-2-methylphenyl)thiaz-ole-2-carboxamide (10 mg, 0.02 mmol) in anhydrous MeOH (5 mL) was added dry Pd/C (5 mg) and stirred at rt under hydrogen (50 Psi) overnight. Then the reaction mixture was filtered and the filtrated was concentrated under reduced pressure to get a residue, which was purified by Prep-HPLC (Table 1, Method q) to provide N-(3-(7-carbamoyl-3-methyl-1H-indol-4-yl)-2-methylphenyl)thiazole-2-carbox-amide (1.1 mg, 15%): LC/MS (Table 1, Method j) R$_t$=3.05 min; MS m/z: 391 (M+H)$^+$. (Btk IC$_{50}$=B)

Example #4

N-(3-(7-carbamoyl-3-methyl-1H-indol-4-yl)-2-meth-ylphenyl)thiazole-2-carboxamide

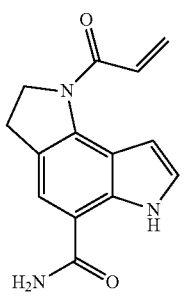 [SMILES: C=CC(=O)N1CCc2cc(C(N)=O)c3[nH]ccc3c21]

Step A: 5-Bromo-6-nitroindoline

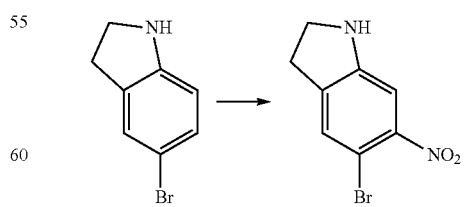

To a solution of 5-bromoindoline (12.33 g, 83 mmol) in H$_2$SO$_4$ (60 mL) was added KNO$_3$ (7.55 mL, 74.7 mmol) at about 0° C. The solution was stirred at 0-10° C. for about 1 h, and then the mixture was stirred overnight at rt. The mixture was poured into ice water, basified with NaCO₃ to about pH 8. The mixture was extracted with EtOAc (300 mL×3), the organic phase was dried with NaSO₄, concentrated under reduced pressure and the residue was purified by column chromatography on silica gel (Pet ether: EtOAc=20:1) to provide 5-bromo-6-nitroindoline (12.3 g, 81%): ¹H NMR (CDCl₃) δ 7.25 (s, 1H), 6.91 (s, 1H), 3.98 (s, 1H), 3.66-3.56 (m, 2H), 3.08-2.96 (m, 2H).

Step B: tert-Butyl 5-bromo-6-nitroindoline-1-carboxylate

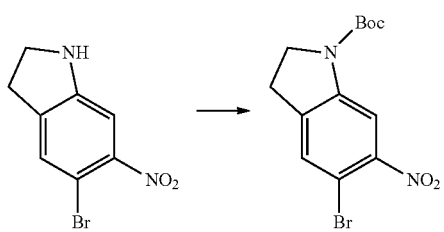 [SMILES: O=[N+]([O-])c1cc2c(cc1Br)CCN2 ; CC(C)(C)OC(=O)N1CCc2cc(Br)c([N+](=O)[O-])cc21]

To a solution of 5-bromo-6-nitroindoline (7.5 g, 30.9 mmol) in DCM (750 mL) was added (Boc)₂O (13.47 g, 61.7 mmol) at 0° C. Then Et₃N (9.37 g, 93 mmol) and DMAP (0.337 g, 3.09 mmol) were added to the mixture. The mixture was stirred overnight at rt. The reaction mixture was poured into water, extracted with DCM (300 mL×3) and the organic phase was dried with NaSO₄, concentrated under reduced pressure and the residue was purified by silica gel column (Pet ether:EtOAc=30:1) to provide tert-butyl 5-bromo-6-nitroindoline-1-carboxylate (6.7 g, 63%): ¹H NMR (CDCl₃) δ 8.29 (s, 1H), 7.42 (s, 1H), 4.06 (s, 2H), 3.18-3.13 (m, 2H) 1.57 (s, 9H).

Step C: tert-Butyl 5-bromo-2,3-dihydropyrrolo[2,3-e]indole-1(6H)-carboxylate

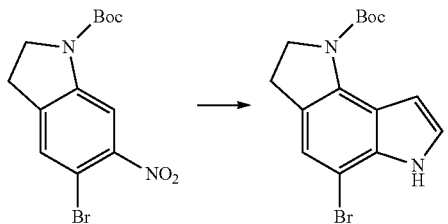 [SMILES: CC(C)(C)OC(=O)N1CCc2cc(Br)c([N+](=O)[O-])cc21 ; CC(C)(C)OC(=O)N1CCc2cc(Br)c3[nH]ccc3c21]

To a mixture of tert-butyl 5-bromo-6-nitroindoline-1-carboxylate (4 g, 11.66 mmol) in THF (60 mL) was added vinylmagnesium bromide (6.43 g, 49.0 mmol) at −40 to 50° C., then the resulting mixture was stirred at −20 to −30° C. for about 2 h, and then overnight at rt. The mixture was poured into saturated NH₄Cl solution and extracted with EtOAc (100 mL×3). The organic phase was dried with NaSO₄, concentrated under reduced pressure and the residue was purified by gel chromatography silica (Pet ether:EtOAc=50:1) to provide tert-butyl 5-bromo-2,3-dihydropyrrolo[2,3-e]indole-1(6H)-carboxylate (0.7 g, 18%): ¹H NMR (CDCl₃) δ 8.17 (s, 1H), 7.13-7.10 (m, 2H), 7.07 (m, 1H), 4.05-4.00 (t, J=8.4 Hz, 2H), 3.07-3.03 (t, J=8.4 Hz, 2H), 1.5 (s, 9H).

Step D: 1,2,3,6-Tetrahydropyrrolo[2,3-e]indole-5-carbonitrile

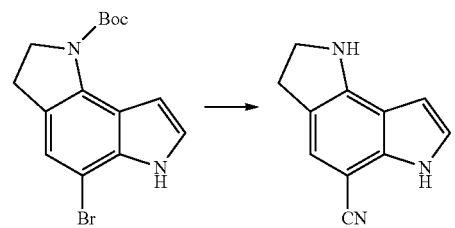 [SMILES: CC(C)(C)OC(=O)N1CCc2cc(Br)c3[nH]ccc3c21 ; N#Cc1cc2c(c3cc[nH]c13)NCC2]

To the solution of tert-butyl 5-bromo-2,3-dihydropyrrolo[2,3-e]indole-1(6H)-carboxylate (60 mg, 0.178 mmol) in DMF (2 mL) was added Zn(CN)₂ (12.53 mg, 0.107 mmol) and Pd(PPh₃)₄ (20.56 mg, 0.018 mmol). The solution was heated at about 145° C. for about 50 min by microwave under N₂. The mixture was concentrated under reduced pressure and the residue was purified by prep-HPLC (Table 1, Method aj) to provide 1,2,3,6-tetrahydropyrrolo[2,3-e]indole-5-carbonitrile (20 mg, 61%): ¹H NMR (MeOD): δ 7.34 (s, 1H), 7.30 (d, J=3.2, 1H), 6.51 (d, J=3.2, 1H), 3.82-3.78 (t, J=8 Hz, 2H), 3.23-3.18 (t, J=8.4 Hz, 2H).

Step E: 1,2,3,6-Tetrahydropyrrolo[2,3-e]indole-5-carboxamide

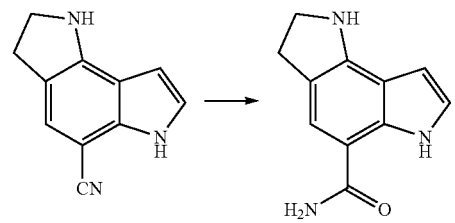 [SMILES: N#Cc1cc2c(c3cc[nH]c13)NCC2 ; NC(=O)c1cc2c(c3cc[nH]c13)NCC2]

To a solution of 1,2,3,6-tetrahydropyrrolo[2,3-e]indole-5-carbonitrile (160 mg, 0.873 mmol) in DMSO (4 mL), K₂CO₃ (300 mg, 2.171 mmol) was added, then H₂O₂ (4 mL, 39.2 mmol) was added dropwise at rt. And the reaction mixture was stirred overnight at rt. The mixture was poured into water, extracted with EtOAc (20 mL×3) and the organic phase was washed by saturated aqueous Na₂S₂O₃, dried and concentrated and the residue was purified by prep-HPLC (Table 1, Method ak) to provide 1,2,3,6-tetrahydropyrrolo[2,3-e]indole-5-carboxamide (70 mg, 40%): LC/MS (Table 1, Method d) R$_t$=1.43 min; MS m/z: 202 (M+H)⁺.

Step F: 1-Acryloyl-1,2,3,6-tetrahydropyrrolo[2,3-e]indole-5-carboxamide

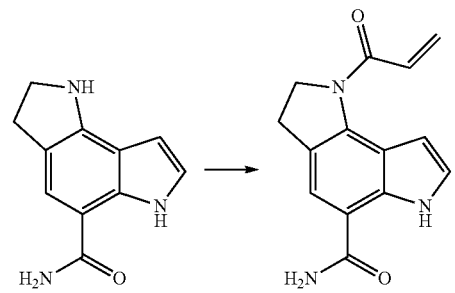 [SMILES: NC(=O)c1cc2c(c3cc[nH]c13)NCC2 ; C=CC(=O)N1CCc2cc(C(N)=O)c3[nH]ccc3c21]

To a solution of 1,2,3,6-tetrahydropyrrolo[2,3-e]indole-5-carboxamide (15 mg, 0.075 mmol) in DCM (10 mL), Et₃N (1 mL, 7.17 mmol) was added, and then a solution of acryloyl chloride (10 mg, 0.11 mmol) in DCM (0.5 mL) was added dropwise at 0° C. The reaction mixture was stirred overnight ar rt. The reaction solution was concentrated under reduced pressure and the residue was purified by prep-HPLC (Table 1, Method t) to provide 1-acryloyl-1,2,3,6-tetrahydropyrrolo[2,3-e]indole-5-carboxamide (12 mg, 63%): ¹H NMR: (DMSO-d6) δ11.13 (s, 1H), 7.93 (s, 1H), 7.61 (s, 1H), 7.21 (s, 2H), 6.8-6.73 (m, 2H), 6.34-6.30 (m, 1H), 5.84-5.82 (d, J=10.4, 1H), 4.25-4.21 (t, J=8.0, 2H), 3.21-3.13 (m, 2H); LC/MS (Table 1, Method d) R$_t$=2.39 min; MS m/z: 256 (M+H)⁺. (Btk IC$_{50}$=B)

Example #5

4-Acrylamido-1H-indole-7-carboxamide

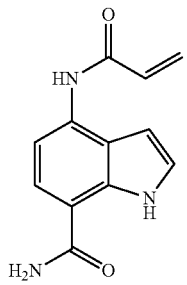 [SMILES: C=CC(=O)Nc1ccc(C(N)=O)c2[nH]ccc12]

Step A: 4-Amino-1-tosyl-1H-indole-7-carbonitrile

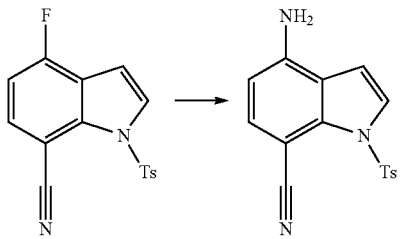 [SMILES: Cc1ccc(S(=O)(=O)n2ccc3c(F)ccc(C#N)c32)cc1 ; Cc1ccc(S(=O)(=O)n2ccc3c(N)ccc(C#N)c32)cc1]

To a solution of 4-fluoro-1-tosyl-1H-indole-7-carbonitrile (500 mg, 1.59 mmol, Preparation #27, step A) in 1,4-dioxane (5 mL), ammonia (2.5 mL, 116 mmol) was added. The mixture was stirred at about 120° C. overnight. The reaction mixture was concentrated under reduced pressure and the residue was purified by silica gel column to provide 4-amino-1-tosyl-1H-indole-7-carbonitrile (100 mg, 20%): ¹H NMR (DMSO-d6): δ 7.86-7.84 (m, 2H), 7.77-7.76 (d, J=4, 1H), 7.46-7.44 (d, J=8, 2H), 7.37-7.35 (d, J=8, 1H), 7.12 (s, 1H), 6.70 (s, 2H), 6.46-6.44 (d, J=8, 1H), 2.37 (s, 3H).

Step B: 4-Amino-1H-indole-7-carbonitrile

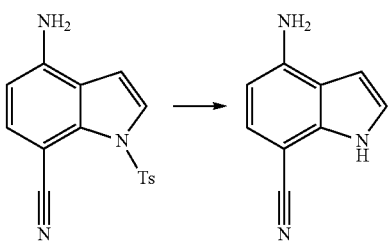 [SMILES: Cc1ccc(S(=O)(=O)n2ccc3c(N)ccc(C#N)c32)cc1 ; N#Cc1ccc(N)c2cc[nH]c12]

To a solution of 4-amino-1-tosyl-1H-indole-7-carbonitrile (90 mg, 0.289 mmol) in THF (2 mL), MeOH (1 mL) and water (1 mL) was added LiOH (69 mg, 2.89 mmol). The mixture was stirred at about 40° C. overnight. The reaction mixture was concentrated under reduced pressure, water was added, and extracted with EtOAc (20 mL×3). The combined organics were dried over Na₂SO₄, filtered, and concentrated under reduced pressure to provide 4-amino-1H-indole-7-carbonitrile (40 mg, 88%): ¹H NMR (DMSO-d6): δ 11.43 (s, 1H), 7.21-7.19 (d, J=8, 1H), 7.13-7.12 (m, 1H), 6.67-6.62 (m, 1H), 6.20-6.18 (d, J=8, 1H).

Step C: 4-Amino-1H-indole-7-carboxamide

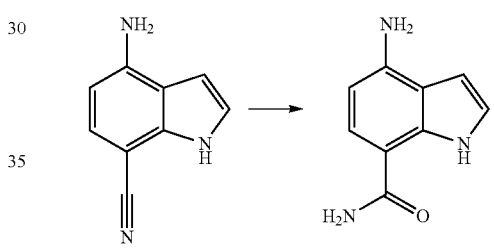

To a solution of 4-amino-1H-indole-7-carbonitrile (40 mg, 0.254 mmol) in DMSO (2 mL), K₂CO₃ (52.8 mg, 0.382 mmol) and 30% H₂O₂ (2 mL) were added at rt. The reaction mixture was stirred at rt for 5 h. Water was added to the reaction mixture and the mixture was extracted with EtOAc (20 mL×3) and the organic phase was dried over Na₂SO₄, concentrated under reduced pressure and the residue was purified by prep-TLC (DCM:MeOH=15:1) to provide 4-amino-1H-indole-7-carboxamide (30 mg, 67%): ¹H NMR (DMSO-d6) δ 10.79 (s, 1H), 7.43-7.41 (d, J=8, 1H), 7.04 (s, 1H), 6.52 (s, 1H), 6.10-6.08 (d, J=8, 1H), 5.83 (s, 2H).

Step D: 4-Acrylamido-1H-indole-7-carboxamide

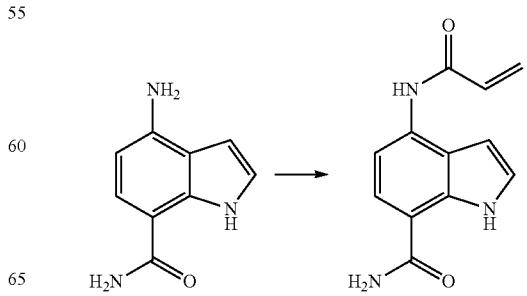

445

To a solution of 4-amino-1H-indole-7-carboxamide (30 mg, 0.171 mmol) in DCM (3 mL), DIEA (0.060 mL, 0.342 mmol) and acroyloyl chloride (18.60 mg, 0.205 mmol) were added and the reaction mixture was stirred overnight at rt. Then the reaction mixture was concentrated under reduced pressure and the residue was purified by prep-HPLC (Table 1, Method u) to provide 4-acrylamido-1H-indole-7-carboxamide (17 mg, 43%): LC/MS (Table 1, Method d) $R_t$=2.10 min; MS m/z: 230 (M+H)$^+$. (Btk IC$_{50}$=C)

Example #6

4-Acrylamido-1H-indole-7-carboxamide

Step A: 4-(3-Acrylamido-5-aminophenyl)-2-(1-(methylsulfonyl)-1,2,3,6-tetrahydropyridin-4-yl)-1H-indole-7-carboxamide

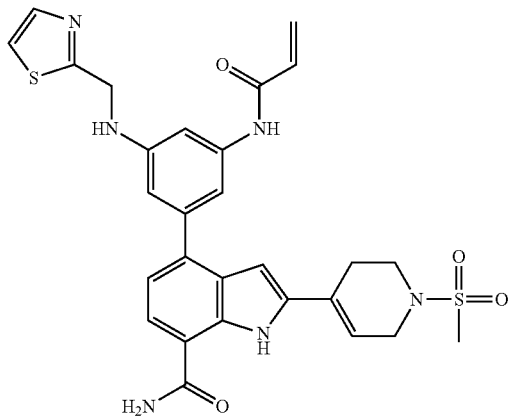 [SMILES: C=CC(=O)Nc1cc(NCc2nccs2)cc(-c2ccc(C(N)=O)c3[nH]c(C4=CCN(S(C)(=O)=O)CC4)cc23)c1]

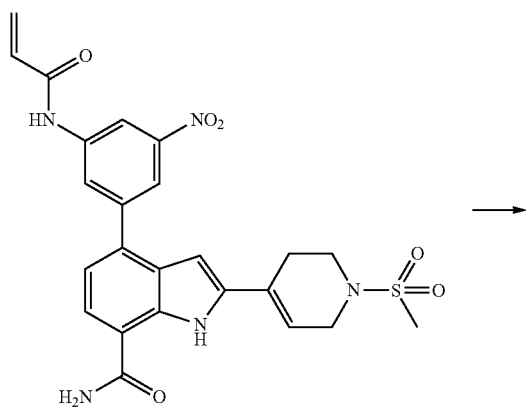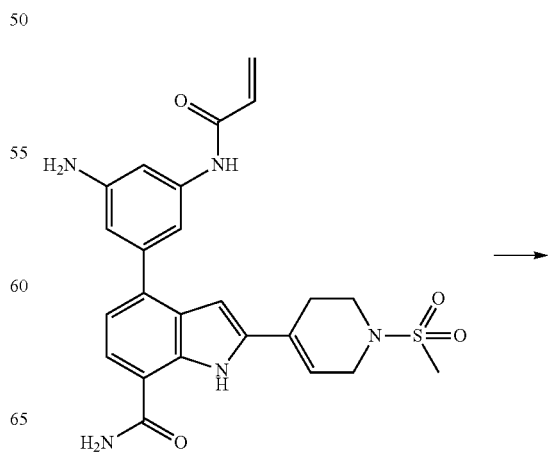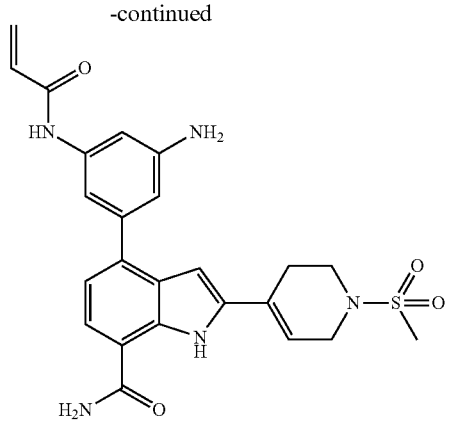

To a round bottom flask was added 4-(3-acrylamido-5-nitrophenyl)-2-(1-(methylsulfonyl)-1,2,3,6-tetrahydropyridin-4-yl)-1H-indole-7-carboxamide (0.175 g, 0.343 mmol, prepared using A from 4-bromo-2-(1-(methylsulfonyl)-1,2,3,6-tetrahydropyridin-4-yl)-1H-indole-7-carboxamide (Preparation #18) and 3-amino-5-nitrophenylboronic acid hydrochloride [CombiBlocks], E and acryloyl chloride) in NMP (2 mL) and HCl, 37% (0.222 mL) to give a red suspension. The reaction was heated to about 85° C. and tin (II) chloride (0.600 g, 0.316 mmol) was added. The reaction was stirred at about 85° C. for about 1.5 h. Additional tin (II) chloride (2.39 g, 1.26 mmol) was added and the reaction was further stirred at about 85° C. for about 2 h. The reaction was cooled to rt and DCM (30 mL), MeOH (10 mL), and 1N NaOH (15 mL) were added. The mixture was stirred vigorously for about 2 h, filtered, and the filtrate extracted with DCM (3×). The organic layers were combined and the solvent removed under vacuum. Water and EtOAc was added to the residue and extracted with EtOAc (4×). The organic layers were combined and washed with water and brine. The organic layers were combined and solvent removed under vacuum. The crude product was added to a silica gel column and was eluted with 0-10% MeOH in DCM. The material was further purified by prep-HPLC (Table 1, Method ag) to provide 4-(3-acrylamido-5-aminophenyl)-2-(1-(methylsulfonyl)-1,2,3,6-tetrahydropyridin-4-yl)-1H-indole-7-carboxamide (20 mg, 12%): LC/MS (Table 1, Method g)=1.12 min; MS m/z: 480 (M+H)$^+$.

Step B: 4-(3-Acrylamido-5-(thiazol-2-ylmethylamino)phenyl)-2-(1-(methylsulfonyl)-1,2,3,6-tetrahydropyridin-4-yl)-1H-indole-7-carboxamide

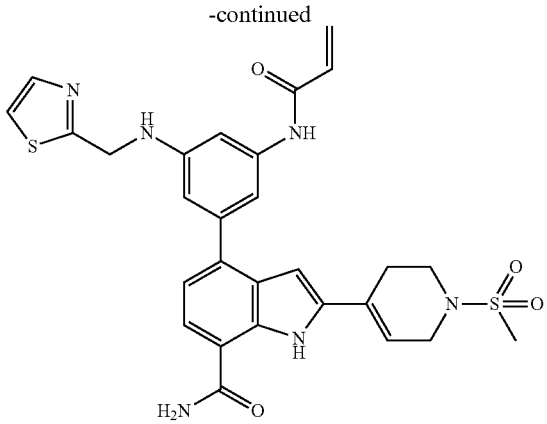

To a stirring solution of 4-(3-acrylamido-5-aminophenyl)-2-(1-(methylsulfonyl)-1,2,3,6-tetrahydropyridin-4-yl)-1H-indole-7-carboxamide (20 mg, 0.042 mmol) and thiazole-2-carbaldehyde (4.03 µL, 0.046 mmol) in MeOH (1 mL) was added MP-Cyanoborohydride (88 mg, 0.167 mmol) and acetic acid (9.55 µL, 0.167 mmol). The slurry was stirred at about 40° C. for about 40 h. The suspension was filtered and the resin washed with DCM and MeOH. The filtrate was passed through a plug of Si-carbonate. The filtrate was concentrated under reduced pressure and the residue was purified by Prep-TLC (10% MeOH/DCM) follow by a second purification by Prep-TLC (5% MeOH/DCM) to provide 4-(3-acrylamido-5-(thiazol-2-ylmethylamino)phenyl)-2-(1-(methylsulfonyl)-1,2,3,6-tetrahydropyridin-4-yl)-1H-indole-7-carboxamide (7.2 mg, 25%): LC/MS (Table 1, Method g) $R_f$=1.56 min; MS m/z: 577 (M+H)$^+$. (Btk IC$_{50}$=A)

Example #7

(E)-4-(3-(2-Cyano-3-hydroxybut-2-enamido)phenyl)-1H-indole-7-carboxamide

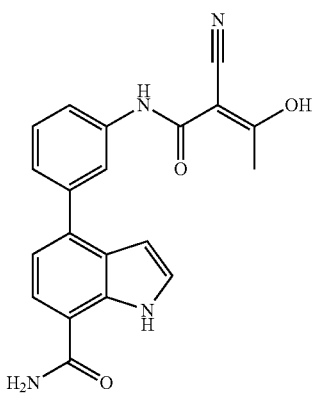 [SMILES: C/C(O)=C(/C#N)C(=O)Nc1cccc(-c2ccc(C(N)=O)c3[nH]ccc23)c1]

A mixture of N-(3-(7-carbamoyl-1H-indol-4-yl)phenyl)-5-methylisoxazole-4-carboxamide (0.060 g, 0.166 mmol, Example #E.2.1) and NaOH (0.008 g, 0.200 mmol) in MeOH (1.9 mL) was heated in a vial at about 60° C. After about 2 h, the reaction was cooled to rt and 1N aqueous HCl was added to acidify. The resulting precipitate was collected via vacuum filtration to provide (E)-4-(3-(2-cyano-3-hydroxybut-2-enamido)phenyl)-1H-indole-7-carboxamide (0.047 g, 78%) as a solid after drying under vacuum at about 55° C.: LC/MS (Table 1, Method c) $R_f$=2.79 min; MS m/z: 361 (M+H)$^+$. (Btk IC$_{50}$=C)

Example #8

4-(cis-3-Acrylamidocyclohexyl)-1H-indole-7-carboxamide and Example #9. 4-(trans-3-Acrylamidocyclohexyl)-1H-indole-7-carboxamide

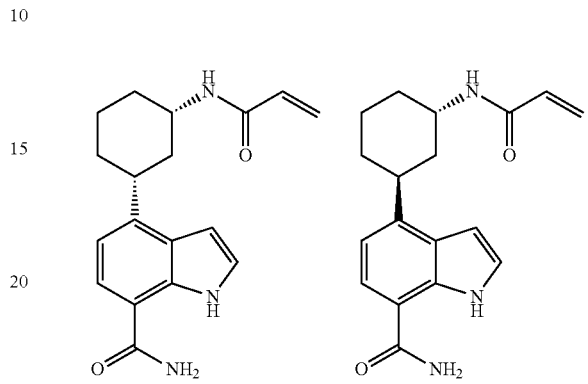

Step A: tert-Butyl (3-(7-carbamoyl-1H-indol-4-yl)cyclohex-2-en-1-yl)carbamate and tert-Butyl (3-(7-carbamoyl-1H-indol-4-yl)cyclohex-3-en-1-yl)carbamate

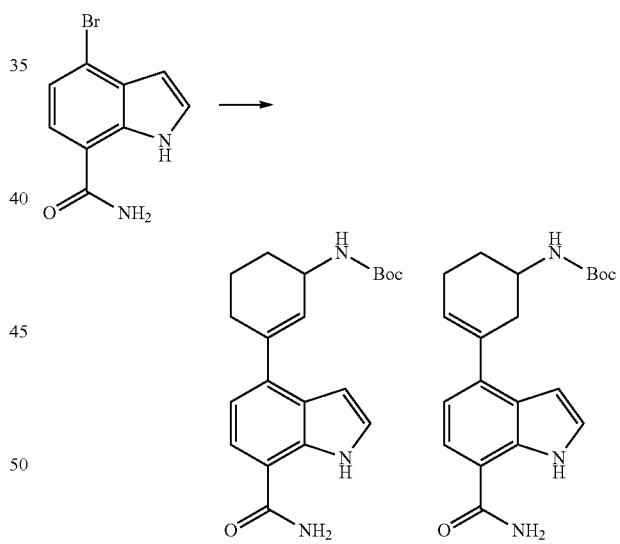

To a solution of 4-bromo-1H-indole-7-carboxamide (296 mg, 1.237 mmol, Preparation #2), a mixture of [3-(4,4,5,5-tetramethyl[1,3,2]dioxaborolan-2-yl)-cyclohex-3-enyl]-carbamic acid tert-butyl ester and [3-(4,4,5,5-tetramethyl-[1,3,2]dioxaborolan-2-yl)-cyclohex-2-enyl]-carbamic acid tert-butyl ester (400 mg, 1.237 mmol, U.S. 2009/0197864), Na$_2$CO$_3$ (328 mg, 3.09 mmol), PdCl$_2$(dppf)-DCM Adduct (101 mg, 0.124 mmol) in THF:MeOH:H$_2$O (Ratio: 4:2:2, 20 mL) under N$_2$ atmosphere, the mixture was heated at about 100° C. overnight. The reaction mixture was filtered through a pad of Celite®.

The resulting mixture was diluted with EtOAc (30 mL), washed with H$_2$O (20 mL×2), dried with Na$_2$SO$_4$, concentrated under reduced pressure and the residue was purified by prep-HPLC (Table 1, Method x) to provide a mixture of tert-butyl (3-(7-carbamoyl-1H-indol-4-yl)cyclohex-2-en-1-yl)carbamate and tert-butyl (3-(7-carbamoyl-1H-indol-4-yl)cyclohex-3-en-1-yl)carbamate (300 mg, 68%): LC/MS (Table 1, Method I) $R_t$=1.67 min; MS m/z: 356 (M+H)$^+$.

Step B: tert-Butyl (3-(7-carbamoyl-1H-indol-4-yl)cyclohexyl)carbamate

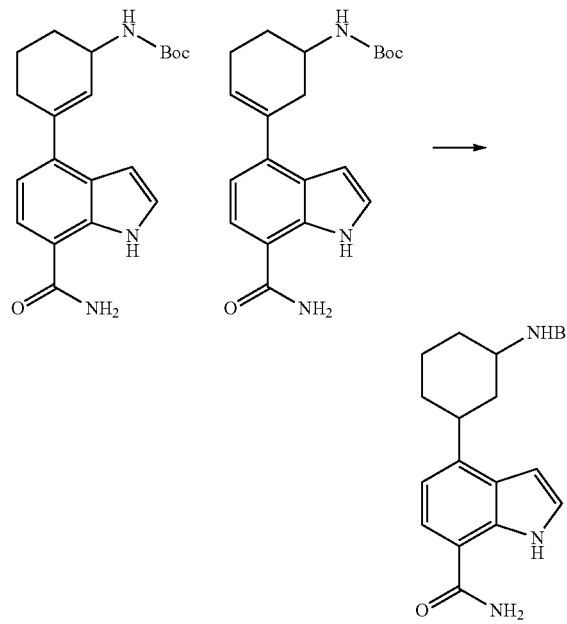

To a solution of tert-butyl (3-(7-carbamoyl-1H-indol-4-yl)cyclohex-2-en-1-yl)carbamate and tert-butyl (3-(7-carbamoyl-1H-indol-4-yl)cyclohex-3-en-1-yl)carbamate (300 mg, 0.844 mmol) in THF (20 mL), Pd/C (44.9 mg, 0.422 mmol) was added and the reaction mixture was stirred at rt for about 3 h under H$_2$ atmosphere. The mixture was filtered and concentrated under reduced pressure to give crude product tert-butyl (3-(7-carbamoyl-1H-indol-4-yl)cyclohexyl)carbamate (290 mg, 96%), which was used to next step directly. LC/MS (Table 1, Method I) $R_t$=1.53 min; MS m/z: 358 (M+H)$^+$.

Step C: 4-(3-Aminocyclohexyl)-1H-indole-7-carboxamide

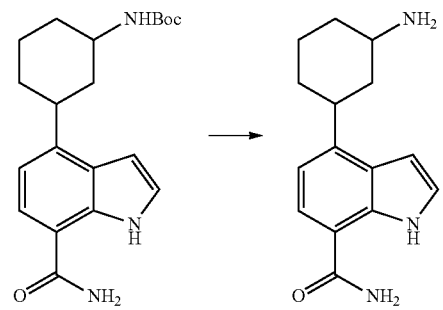 [SMILES: CC(C)(C)OC(=O)NC1CCCC(c2ccc(C(N)=O)c3[nH]ccc23)C1 ; NC(=O)c1ccc(C2CCCC(N)C2)c2cc[nH]c12]

To a solution of tert-butyl (3-(7-carbamoyl-1H-indol-4-yl)cyclohexyl)carbamate (220 mg, 0.615 mmol) in MeOH (10 mL), MeOH/HCl (10 mL) was added at about 0° C., then the reaction mixture was stirred at rt for about 3 h. The reaction mixture was concentrated under reduced pressure to give crude product 4-(3-aminocyclohexyl)-1H-indole-7-carboxamide (100 mg, 63%), which was used to next step directly. LC/MS (Table 1, Method I) $R_t$=0.54 min; MS m/z: 258 (M+H)$^+$.

Step D: 4-(cis-3-Acrylamidocyclohexyl)-1H-indole-7-carboxamide and 4-(trans-3-Acrylamidocyclohexyl)-1H-indole-7-carboxamide

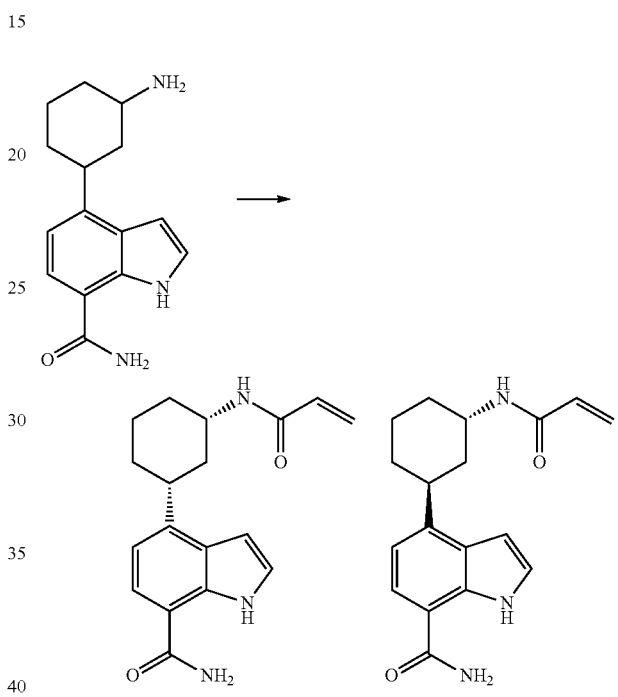

To a solution of 4-(3-aminocyclohexyl)-1H-indole-7-carboxamide (120 mg, 0.466 mmol) in DCM (3 mL), DIEA (120 mg, 0.933 mmol) was added, acryloyl chloride (42.2 mg, 0.466 mmol) was added at about 0° C. dropwise and the mixture was stirred at about 0° C. for about 10 min, then concentrated under reduced pressure and the residue was purified by prep-HPLC (Table 1, Method y) to provide 4-(cis-3-acrylamidocyclohexyl)-1H-indole-7-carboxamide (27 mg, 19%) $^1$H NMR: (MeOD) δ 7.59 (d, J=8, 1H), 7.33 (d, J=3.2, 1H), 6.95 (d, J=8, 1H), 6.64 (d, J=4, 1H), 6.26-6.17 (m, 2H), 5.67-5.58 (m, 1H), 4.01-3.96 (m, 1H), 3.22-3.13 (m, 1H), 2.19-1.97 (m, 4H), 1.65-1.59 (m, 3H), 1.37-1.34 (m, 1H); LC/MS (Table 1, Method d) $R_t$=2.56 min; MS m/z: 312 (M+H)$^+$. (Btk IC$_{50}$=A) and 4-(trans-3-acrylamidocyclohexyl)-1H-indole-7-carboxamide (33 mg, 23%): $^1$H NMR: (MeOD) δ 7.58 (d, J=8, 1H), 7.31 (d, J=3.2, 1H), 6.98 (d, J=8, 1H), 6.59 (d, J=2.8, 1H), 6.52-6.46 (m, 1H), 6.28-6.24 (m, 1H), 5.69-5.64 (m, 1H), 4.35 (s, 1H), 3.42-3.36 (m, 1H), 2.13-1.72 (m, 8H); LC/MS (Table 1, Method d) $R_t$=2.56 min; MS m/z: 312 (M+H)$^+$. (Btk IC$_{50}$=B)

Examples #10 and #11

4-(cis-3-Acrylamidocyclopentyl)-1H-indole-7-carboxamide and 4-(trans-3-Acrylamidocyclopentyl)-1H-indole-7-carboxamide Example #10

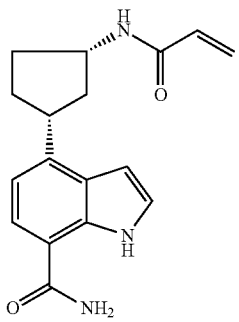

Example #11

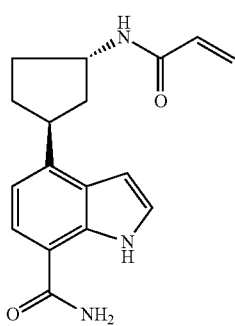

Step A: 3-((tert-Butoxycarbonyl)amino)cyclopent-1-en-1-yl trifluoromethanesulfonate and 4-((tert-butoxycarbonyl)amino)cyclopent-1-en-1-yl trifluoromethanesulfonate

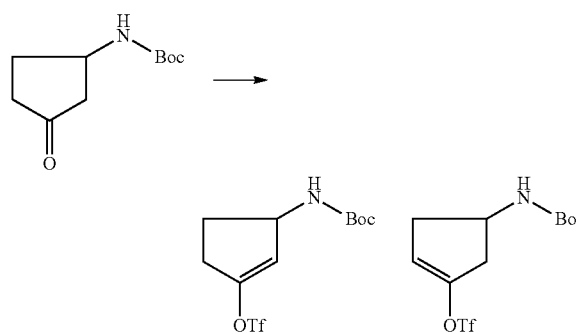

To a freshly prepared LDA solution (2M in THF, 9.38 mL) was added tert-butyl (3-oxocyclopentyl)carbamate (2.00 g, 10.0 mmol) in THF (4 mL) at about −78° C. dropwise. The mixture was warmed to rt for about 30 min and then cooled to about −78° C. again. A solution of 1,1,1-trifluoro-N-phenyl-N-fitrifluoromethylisulfonyfimethanesulfonamide (5.38 g, 15.1 mmol) in THF (10 mL) was added dropwise to the reaction mixture at about −78° C. The resulting mixture was warmed to rt and stirred for another 3 h. Treated with EtOAc (30 mL), the mixture was washed with H$_2$O (20 mL×3) and brine (10 mL), dried with Na$_2$SO$_4$, concentrated under reduced pressure and the residue was purified by chromatography on silica gel to provide a mixture of 3-((tert-butoxycarbonyl)amino)cyclopent-1-en-1-yl trifluoromethanesulfonate and 4-((tert-butoxycarbonyl)amino)cyclopent-1-en-1-yl trifluoromethanesulfonate (0.82 g, 25%), which was used in next step without further purificaiton.

Step B: tert-Butyl (3-(4,4,5,5-tetramethyl-1,3,2-dioxaborolan-2-yl)cyclopent-2-en-1-yl)carbamate and tert-butyl (3-(4,4,5,5-tetramethyl-1,3,2-dioxaborolan-2-yl)cyclopent-3-en-1-yl)carbamate

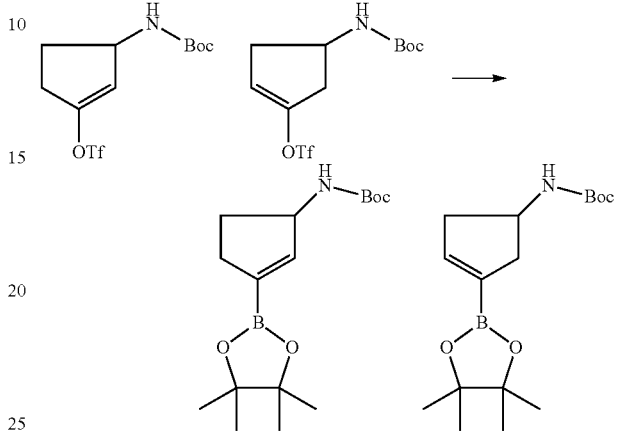

A mixture of 3-((tert-butoxycarbonyl)amino)cyclopent-1-en-1-yl trifluoromethanesulfonate and 4-((tert-butoxycarbonyl)amino)cyclopent-1-en-1-yl trifluoromethanesulfonate (720 mg, 2.173 mmol), 4,4,4',4',5,5,5',5'-octamethyl-2,2'-bi(1,3,2-dioxaborolane) (662 mg, 2.61 mmol), PdCl$_2$(dppf)-DCM adduct (177 mg, 0.217 mmol) and KOAc (427 mg, 4.35 mmol) in 1,4-dioxane (20 mL) under N$_2$ atmosphere was heated at about 100° C. overnight. The resulting mixture was diluted with DCM (30 mL), washed with H$_2$O (20 mL×2), concentrated under reduced pressure and the residue was purified by silica gel to give crude mixture of tert-butyl (3-(4,4,5,5-tetramethyl-1,3,2-dioxaborolan-2-yl)cyclopent-2-en-1-yl)carbamate and tert-butyl (3-(4,4,5,5-tetramethyl-1,3,2-dioxaborolan-2-yl)cyclopent-3-en-1-yl)carbamate (0.42 g, 63%), which was used directly in the next step without further purification.

Step C: tert-Butyl (3-(7-carbamoyl-1H-indol-4-yl)cyclopent-2-en-1-yl)carbamate and tert-butyl (3-(7-carbamoyl-1H-indol-4-yl)cyclopent-3-en-1-yl)carbamate

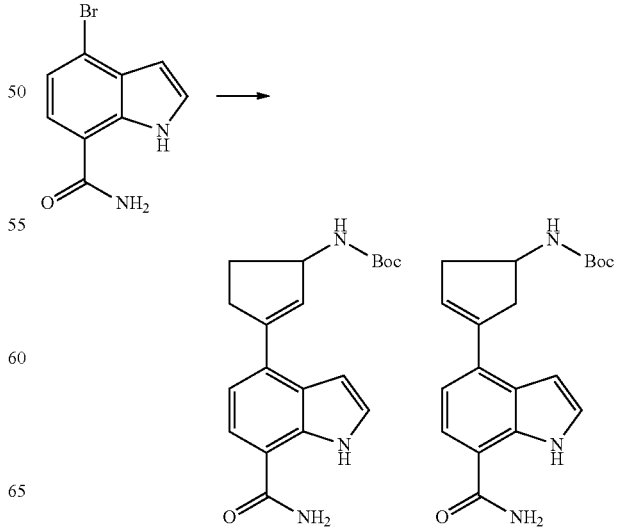

453

To a solution of 4-bromo-1H-indole-7-carboxamide (325 mg, 1.36 mmol, Preparation #2), tert-butyl (3-(4,4,5,5-tetramethyl-1,3,2-dioxaborolan-2-yl)cyclopent-2-en-1-yl)carbamate and tert-butyl (3-(4,4,5,5-tetramethyl-1,3,2-dioxaborolan-2-yl)cyclopent-3-en-1-yl)carbamate (420 mg, 1.36 mmol), $Na_2CO_3$ (360 mg, 3.4 mmol), $PdCl_2$(dppf)-DCM Adduct (111 mg, 0.136 mmol) in THF:MeOH:$H_2O$ (Ratio: 4:2:2, 15 mL) under $N_2$ atmosphere, the mixture was stirred at about 100° C. overnight. The reaction mixture was filtered to remove Pd complex. The resulting mixture was diluted with EtOAc (30 mL), washed with $H_2O$ (20 mL×2), dried with $Na_2SO_4$, concentrated and purified by prep-HPLC (Table 1, Method y) to provide a mixture of tert-butyl (3-(7-carbamoyl-1H-indol-4-yl)cyclopent-2-en-1-yl)carbamate and tert-butyl (3-(7-carbamoyl-1H-indol-4-yl)cyclopent -3-en-1-yl)carbamate (0.32 g, 69%): LC/MS (Table 1, Method I) $R_t$=1.65 min; MS m/z: 342 (M+H)⁺.

Step D: tert-Butyl (3-(7-carbamoyl-1H-indol-4-yl)cyclopentyl)carbamate

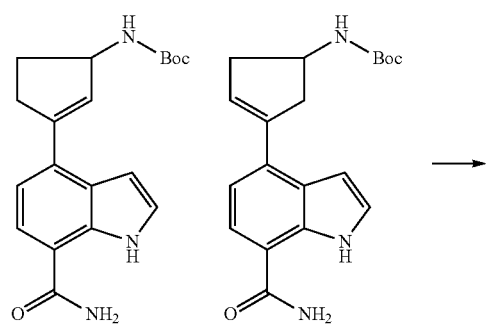

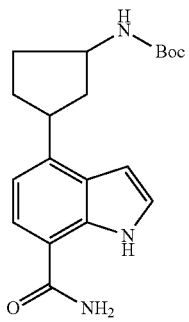

To a solution of tert-butyl (3-(7-carbamoyl-1H-indol-4-yl)cyclopent-2-en-1-yl)carbamate and tert-butyl (3-(7-carbamoyl-1H-indol-4-yl)cyclopent-3-en-1-yl)carbamate (300 mg, 0.844 mmol) in THF (20 mL), Pd/C (44.9 mg, 0.422 mmol) was added and the mixture was stirred for about 3 h at rt under $H_2$. The mixture was filtered and concentrated under reduced pressure to provide crude tert-butyl (3-(7-carbamoyl-1H-indol-4-yl)cyclopentyl)carbamate (0.29 g, 96%), which was used to next step directly without further purification. LC/MS (Table 1, Method I) $R_t$=1.50 min; MS m/z: 344 (M+H)⁺.

Step E: 4-(cis-3-Aminocyclopentyl)-1H-indole-7-carboxamide and 4-(trans-3-aminocyclopentyl)-1H-indole-7-carboxamide

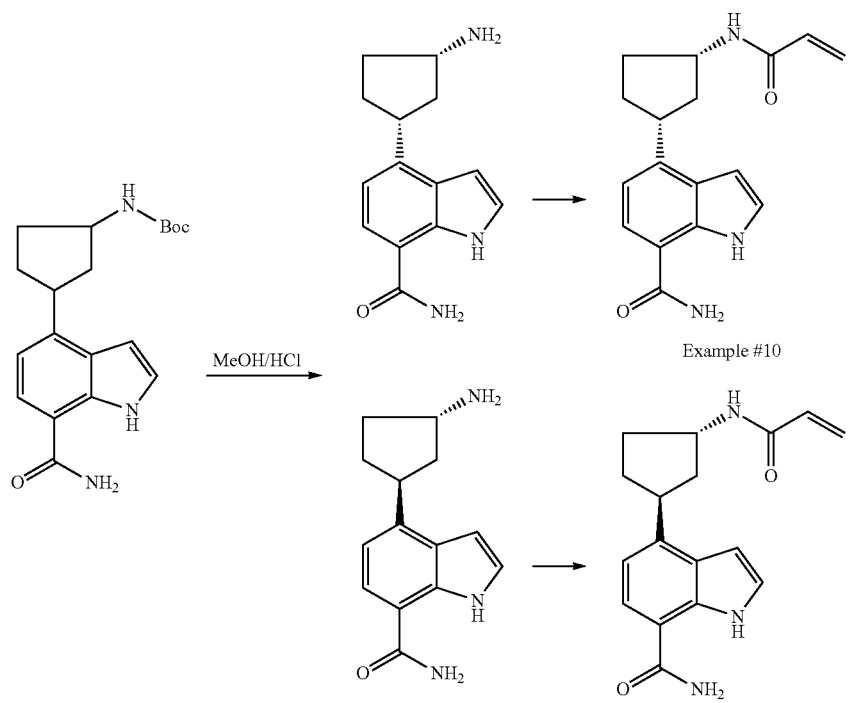

To a solution of tert-butyl (3-(7-carbamoyl-1H-indol-4-yl)cyclopentyl)carbamate (250 mg, 0.728 mmol) in MeOH (10 mL), MeOH/HCl (10 mL) was added at about 0° C. and the mixture was stirred for about 3 h at rt. The mixture was concentrated under reduced pressure and the residue was purified by prep-HPLC (Table 1, Method t) to provide 4-(trans-3-aminocyclopentyl)-1H-indole-7-carboxamide (10 mg, 6%) and 4-(cis-3-aminocyclopentyl)-1H-indole-7-carboxamide (50 mg, 28%). To a solution of 4-(cis-3-aminocyclopentyl)-1H-indole-7-carboxamide (50 mg, 0.206 mmol) in DCM (3 mL), DIEA (53 mg, 0.411 mmol) was added, then acryloyl chloride (18.60 mg, 0.206 mmol) was added dropwise at about 0° C., the mixture was stirred at about 0° C. for about 10 min, then concentrated under reduced pressure and the residue was purified by prep-HPLC (Table 1, Method z) to give 4-(cis-3-acrylamidocyclopentyl)-1H-indole-7-carboxamide (20 mg, 33%): $^1$H NMR (MeOD) δ 7.59 (d, J=7.2, 1H), 7.33 (s, 1H), 7.02 (d, J=8, 1H), 6.64 (s, 1H), 6.30-6.20 (m, 2H), 5.64 (d, J=8.8, 1H), 4.51-4.40 (m, 1H), 3.60-3.58 (m, 1H), 2.56-2.51 (m, 1H), 2.26-2.21 (m, 2H), 2.07-2.02 (m, 1H), 1.86-1.78 (m, 2H): LC/MS (Table 1, Method d) $R_t$=2.48 min; MS m/z: 298 (M+H)$^+$. (Btk IC$_{50}$=A) To a solution of 4-(trans-3-aminocyclopentyl)-1H-indole-7-carboxamide (10 mg, 0.041 mmol) in DCM (1 mL), DIEA (11 mg, 0.082 mmol) was added, then acryloyl chloride (3.72 mg, 0.041 mmol) was dropwise added, the mixture was stirred at about 0° C. for about 10 min, concentrated and purified by prep-HPLC (Table 1, Method z) to give 4-(trans-3-acrylamidocyclopentyl)-1H-indole-7-carboxamide (1.1 mg, 9%): $^1$H NMR (MeOD) δ 7.60 (d, J=7.6, 1H), 7.33 (d, J=2.8, 1H), 7.00 (d, J=7.6, 1H), 6.62 (d, J=3.2, 1H), 6.33-6.20 (m, 2H), 5.67-5.64 (m, 1H), 4.50-4.49 (m, 1H), 3.81-3.72 (m, 1H), 2.34-2.28 (m, 3H), 2.26-2.23 (m, 1H), 2.07-1.89 (m, 1H), 1.88-1.74 (m, 1H); LC/MS (Table 1, Method d) $R_t$=2.47 min; MS m/z: 298 (M+H)$^+$. (BtkIC$_{50}$=A)

Example #12*

(R)-2-(1-(Methylsulfonyl)-1,2,3,6-tetrahydropyridin-4-yl)-4-(2-oxo-1,3'-bipiperidin-1'-yl)-1H-indole-7-carboxamide

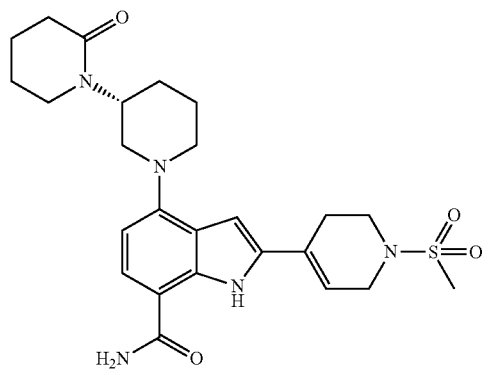 [SMILES: CS(=O)(=O)N1CC=C(c2cc3c(N4CCC[C@@H](N5CCCCC5=O)C4)ccc(C(N)=O)c3[nH]2)CC1]

Step A: (R)-2-(1-(Methylsulfonyl)-1,2,3,6-tetrahydropyridin-4-yl)-4-(2-oxo-1,3'-bipiperidin-1'-yl)-1-tosyl-1H-indole-7-carbonitrile

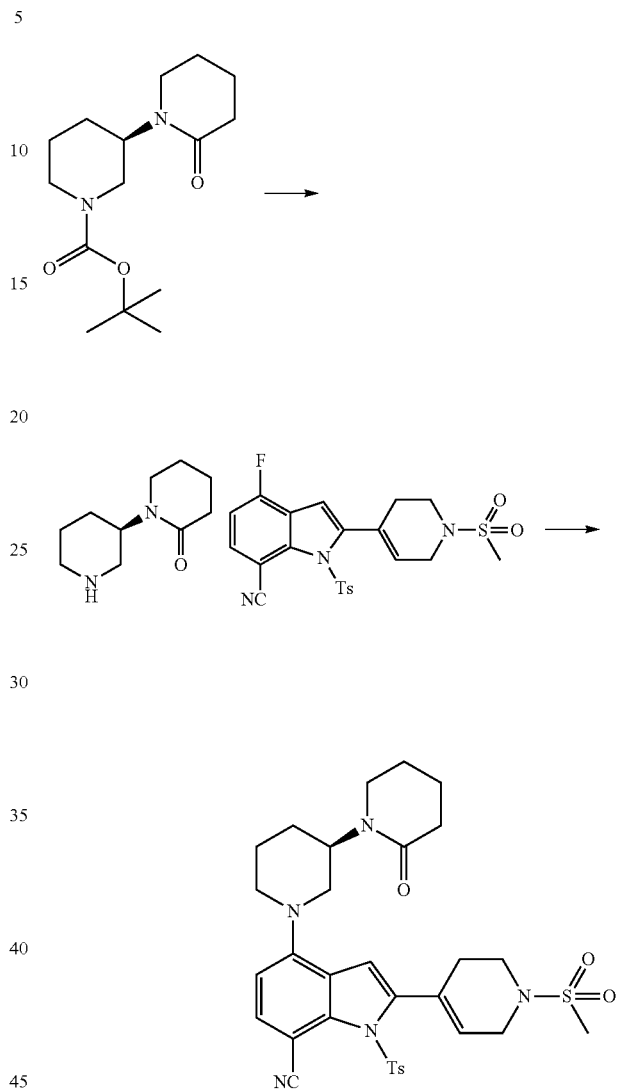

To a solution of (R)-tert-butyl 2-oxo-1,3'-bipiperidine-1'-carboxylate (100 mg, 0.354 mmol, WO 2011/029046) in DCM (4 mL) was added TFA (1.000 mL). The reaction was stirred for about 4 h at rt. The solvent was stripped off and a mixture of 4-fluoro-2-(1-(methylsulfonyl)-1,2,3,6-tetrahydropyridin-4-yl)-1-tosyl-1H-indole-7-carbonitrile (168 mg, 0.354 mmol, Preparation #27) and TEA (0.197 mL, 1.417 mmol) in DMSO (2 mL) was added. The vial was sealed and the reaction was heated in a microwave at about 120° C. for about 30 min. Water (20 mL) was added and extracted into DCM then washed with brine and passed through a phase separator to remove residual water. Evaporated and chromatographed on silica to eluting with a gradient of 0-100% EtOAc/hexane to provide crude (R)-2-(1-(methylsulfonyl)-1,2,3,6-tetrahydropyridin-4-yl) -4-(2-oxo-1,3'-bipiperidin-F-yl)-1-tosyl-1H-indole-7-carbonitrile (0.041 g, 18.21%).

457

Step B: (R)-2-(1-(methylsulfonyl)-1,2,3,6-tetrahydropyridin-4-yl)-4-(2-oxo-1,3'-bipiperidin-1'-yl)-1H-indole-7-carboxamide

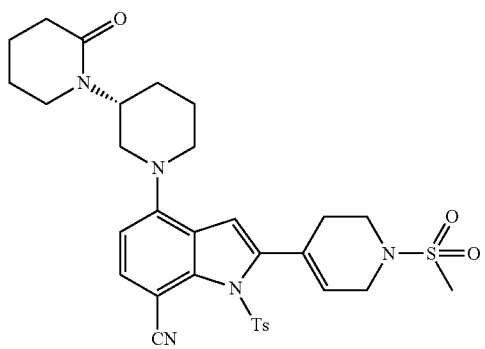

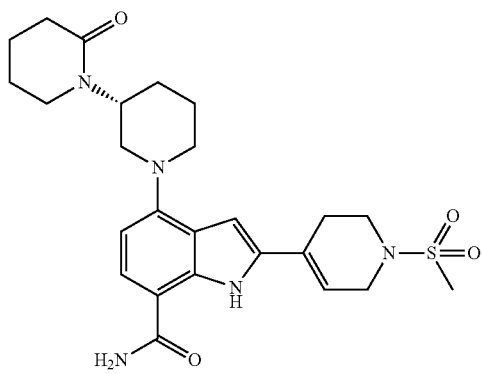

A mixture of Cs$_2$CO$_3$ (20.50 mg, 0.063 mmol) and (R)-2-(1-(methylsulfonyl)-1,2,3,6-tetrahydropyridin-4-yl)-4-(2-oxo-1,3'-bipiperidin-1'-yl)-1-tosyl-1H-indole-7-carbonitrile (40 mg, 0.063 mmol) in THF (2 mL) and MeOH (1.000 mL) were stirred at rt overnight. The solution was diluted with water (15 mL) and stirred for about 20 min DCM was added to dissolve the suspension and the mixture was filtered through a Biotage phase separator. The organics were collected and concentrated. The intermediate was dissolved in t-butanol (1 mL) and DMSO (0.500 mL) and NaOH (0.377 mL, 0.755 mmol) and hydrogen peroxide (0.175 mL, 1.699 mmol) were added. The mixture was stirred for about 20 min at rt and saturated NH$_4$Cl (1 mL) was added. The mixture was diluted with water (15 mL) and stirred for about 15 min. The solids were collected by filtration washing several times with water and dried under vacuum and purified by prep-HPLC (Table 1, Method aq). The samples were returned and dissolved in DCM. The organics were combined and washed with saturated sodium bicarbonate, filtered through a Biotage phase separator, and concentrated to provide (R)-2-(1-(methylsulfonyl)-1,2,3,6-tetrahydropyridin-4-yl)-4-(2-oxo-1,3'-bipiperidin-1'-yl)-1H-indole-7-carboxamide (3 mg, 9.54%): LC/MS (Table 1, Method f) R$_t$=1.37 min; MS m/z: 500 (M+H)$^+$. (Btk IC$_{50}$=B)

458

Example #13*

(R)-2-(1-(Methylsulfonyl)-1,2,3,6-tetrahydropyridin-4-yl)-4-(3-(1-oxo-3,4-dihydroisoquinolin-2(1H)-yl)piperidin-1-yl)-1H-indole-7-carboxamide

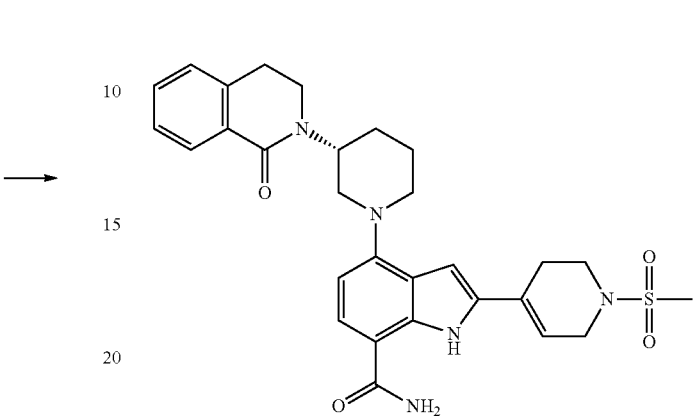

Step A: (R)-2-Methyl-N-(piperidin-3-yl)benzamide

A mixture of (R)-tert-butyl 3-(2-methylbenzamido)piperidine-1-carboxylate (19.0 g, 59.7 mmol, prepared using D from (R)-tert-butyl 3-aminopiperidine-1-carboxylate and 2-methylbenzoic acid) in HCl (2 N in MeOH, 300 mL, 600 mmol) was stirred at rt for about 4 h, then concentrated under reduced pressure to provide crude (R)-2-methyl-N-(piperidin-3-yl)benzamide (20.0 g), which was used directly for the next step without further purification.

Step B: (R)—N-(1-Benzylpiperidin-3-yl)-2-methylbenzamide

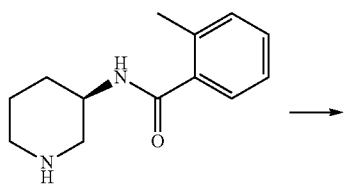

-continued

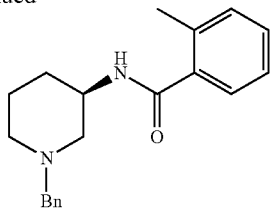

To a solution of (R)-2-methyl-N-(piperidin-3-yl)benzamide (20.0 g, crude) and TEA (30.1 g, 298.5 mmol) in DCM (260 mL) was added dropwise BnBr (11.2 g, 65.7 mmol) at rt over about 30 min. Then the mixture was stirred at rt overnight. After completion, DCM (1 L) was added, and the mixture was washed with H₂O (3×100 mL). The organic phase was dried over anhydrous Na₂SO₄ and concentrated under reduced pressure to provide (R)—N-(1-benzylpiperidin-3-yl)-2-methylbenzamide (12.0 g, 65% over two steps): LC/MS (Table 1, Method I) R$_t$=0.91 min; MS m/z: 309 (M+H)⁺.

Step C: (R)-2-(1-Benzylpiperidin-3-yl)isoquinolin-1(2H)-one

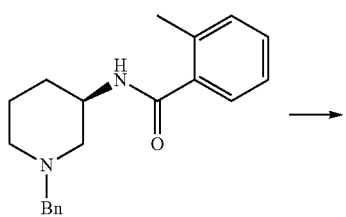

To the solution of (R)—N-(1-benzylpiperidin-3-yl)-2-methylbenzamide (12.0 g, 38.9 mmol) in THF was added dropwise n-BuLi (2.5 M, 32.7 mL) between −22 and −14° C., over about 30 min. The resulting deep red solution was stirred at about −22° C. for about 30 min and DMF was added below about −14° C. (internal). After the addition was completed, the solution was stirred at about −22° C. for about 30 min. Then HCl (6 N aqueous, 25 mL, 150 mmol) was slowly added, keeping the temperature below 5° C. The mixture was basified by addition of saturated NaOH at about 0° C. to pH 14 and extracted with DCM (3×500 mL). The organic phase was dried over Na₂SO₄ and concentrated under reduced pressure to provide (R)-2-(1-benzylpiperidin-3-yl)isoquinolin-1(2H)-one (12.0 g, 97%) as a solid: LC/MS (Table 1, Method I) R$_t$=1.35 min; MS m/z: 319 (M+H)⁺.

Step D: (R)-2-(Piperidin-3-yl)-3,4-dihydroisoquinolin-1(2H)-one

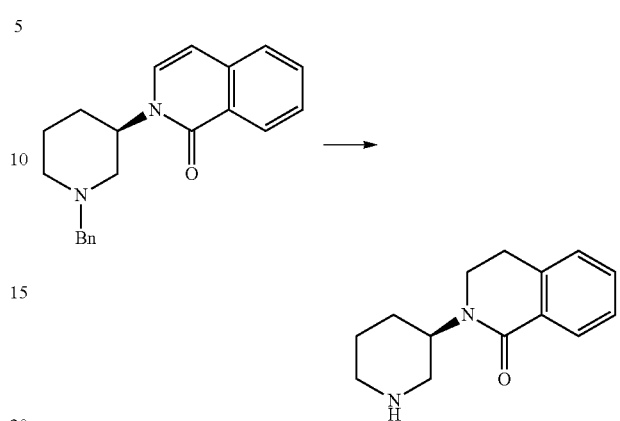

A mixture of (R)-2-(1-benzylpiperidin-3-yl)isoquinolin-1(2H)-one (12 g, 37.7 mmol) and Pd(OH)₂ (0.5 g) in MeOH was stirred at about 50° C. under H₂ atmosphere (50 psi) overnight. Then the mixture was filtrated through Celite®, and the filtrate was concentrated. The crude product was purified by flash chromatography to afford 6.3 g of the crude product which was recrystallized in a mixture of MTBE (15 mL) and HCl/MeOH (5 mL) to provide (R)-2-(piperidin-3-yl)-3,4-dihydroisoquinolin-1(2H)-one (HCl salt) as a solid (2.1 g, 21%): ¹H NMR (MeOD) 7.95 (d, J=8, 1H), 7.51-7.47 (m, 1H), 7.38-7.34 (m, 1H), 7.29 (d, J=7.6, 1H), 4.86-4.80 (m, 1H), 3.61-3.58 (m, 2H), 3.39-3.35 (m, 2H), 3.28-3.22 (m, 1H), 3.03-2.95 (m, 3H), 2.12-1.87 (m, 4H); LC/MS (Table 1, Method d) R$_t$=2.05 min; MS m/z: 231 (M+H)⁺.

Step E: (R)-2-(1-(Methylsulfonyl)-1,2,3,6-tetrahydropyridin-4-yl)-4-(3-(1-oxo-3,4-dihydroisoquinolin-2(1H)-yl)piperidin-1-yl)-1-tosyl-1H-indole-7-carbonitrile

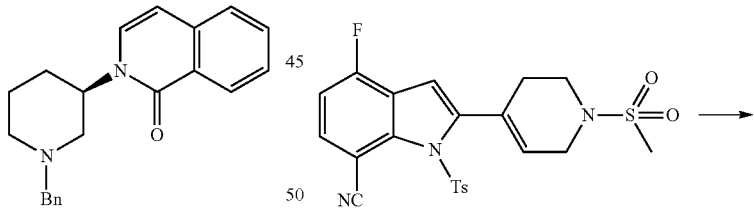

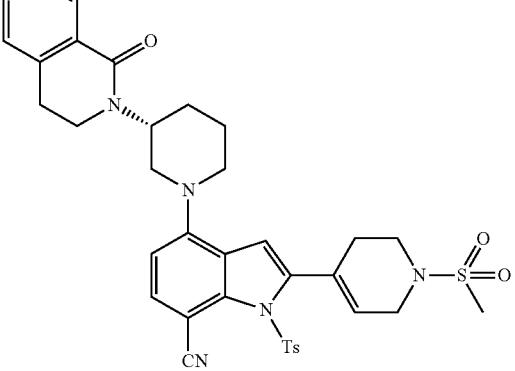

A mixture of 4-fluoro-2-(1-(methylsulfonyl)-1,2,3,6-tetrahydropyridin-4-yl)-1-tosyl-1H-indole-7-carbonitrile (318 mg, 0.672 mmol, Preparation #27), (R)-2-(piperidin-3-yl)-3,4-dihydroisoquinolin-1(2H)-one hydrochloride (179 mg, 0.672 mmol) and TEA (0.374 mL, 2.69 mmol) in DMSO (4 mL) were heated in a microwave at about 120° C. for about 20 min. The reaction was heated in a microwave at about 120° C. for an additional 30 min. Water (50 mL) was added and extracted into DCM. The solution was washed with brine and passed through a phase separator to remove residual water. The organics were concentrated and chromatographed on silica to eluting with a gradient of 0-100% EtOAc/hexane to provide crude (R)-2-(1-(methylsulfonyl)-1,2,3,6-tetrahydropyridin-4-yl)-4-(3-(1-oxo-3,4-dihydroisoquinolin-2(1H)-yl)piperidin-1-yl)-1-tosyl-1-indole-7-carbonitrile (110 mg, 24%). The material was used without further purification.

Step F: (R)-2-(1-(Methylsulfonyl)-1,2,3,6-tetrahydropyridin-4-yl)-4-(3-(1-oxo-3,4-dihydroisoquinolin-2(1H)-yl)piperidin-1-yl)-1H-indole-7-carboxamide

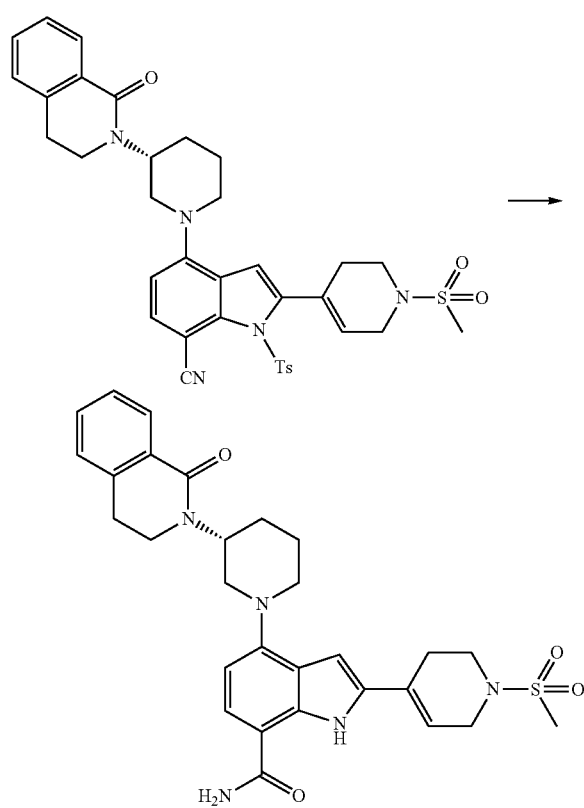

A mixture of Cs$_2$CO$_3$ (51.9 mg, 0.159 mmol) and (R)-2-(1-(methylsulfonyl)-1,2,3,6-tetrahydropyridin-4-yl)-4-(3-(1-oxo-3,4-dihydroisoquinolin-2(1H)-yl)piperidin-1-yl)-1-tosyl-1H-indole-7-carbonitrile (109 mg, 0.159 mmol) in THF (2 mL) and MeOH (1.000 mL) were stirred at rt overnight. The mixture was diluted with water (15 mL) and stirred for about 20 min. The precipitate was collected by filtration and the filter cake was washed with water. The filter cake was dissolved in t-butanol (1 mL) and DMSO (0.500 mL) was added NaOH (0.956 mL, 1.91 mmol) and hydrogen peroxide (0.444 mL, 4.30 mmol). The mixture was stirred for about 20 min at rt and saturated NH$_4$Cl (1 mL) was added. The mixture was diluted with water (15 mL) and stirred for about 15 min. The solids were collected by filtration washing several times with water and dried under vacuum. The resulting solids were purified by prep-HPLC (Table 1, Method ap). The samples were returned and dissolved in DCM. The organics were combined and washed with saturated sodium bicarbonate, filtered through a Biotage phase separator, and concentrated. The residue was further dried in a vacuum oven at about 50° C. for about 48 h to afford (R)-2-(1-(methylsulfonyl)-1,2,3,6-tetrahydropyridin-4-yl)-4-(3-(1-oxo-3,4-dihydroisoquinolin-2(1H)-yl)piperidin-1-yl)-1H-indole-7-carboxamide (30 mg, 34%): LC/MS (Table 1, Method f) R$_t$=1.63 min; MS m/z: 548 (M+H)$^+$. (Btk IC$_{50}$=A)

Example #13A*

(R)—N-(1-(7-Carbamoyl-2-(1-(methylsulfonyl)-1,2,3,6-tetrahydropyridin-4-yl)-1H-indol-4-yl)piperidin-3-yl)thiazole-2-carboxamide

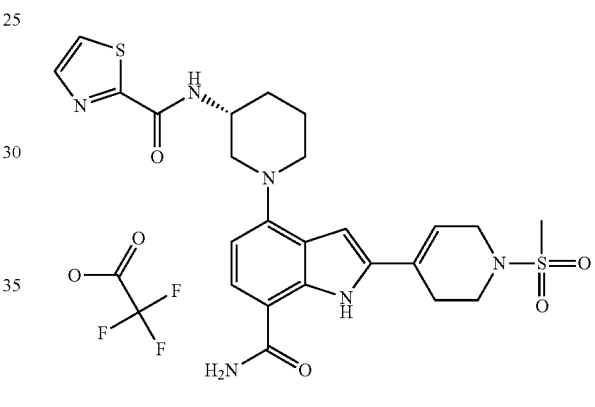

Step A: (R)-tert-Butyl 3-(thiazole-2-carboxamido)piperidine-1-carboxylate

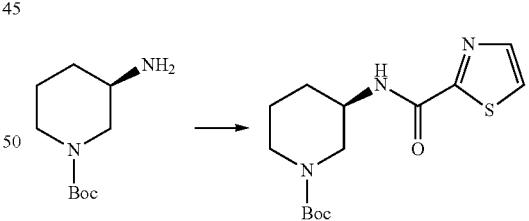

To a solution of (R)-tert-butyl 3-aminopiperidine-1-carboxylate (2 g, 9.99 mmol) and thiazole-2-carboxylic acid (1.29 g, 9.99 mmol) in DCM (40 mL) was added HATU (4.85, 12.5 mmol) and DIEA (3.87 g, 29.9 mmol) and the mixture was stirred at rt overnight. Then the mixture was poured into water and extracted with DCM (3×80 mL). The combined organic layers were washed with saturated aqueous NaHCO$_3$ (80 mL) and brine (80 mL), and dried over Na$_2$SO$_4$. The solvent was concentrated under reduced pressure to afford the crude product, which was purified by column chromatography on silica gel to provide (R)-tert-butyl 3-(thiazole-2-carboxamido)piperidine-1-carboxylate (2.2 g, 71%): $^1$H NMR (CDCl3) δ 1.45 (s, 9H), 1.78-1.73

(m, 2H), 1.94-1.91 (m, 1H), 2.80 (s, 2H), 3.42 (br, 2H), 3.66 (d, J=13.2 Hz, 1H), 4.11 (s, 1H), 7.36 (br, 1H), 7.57 (t, J=3.2 Hz, 1H), 7.84 (t, J=3.2 Hz, 1H).

Step B:
(R)—N-(Piperidin-3-yl)thiazole-2-carboxamide

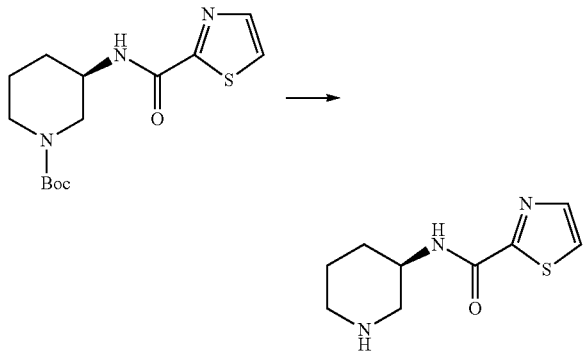

To a solution of (R)-tert-butyl 3-(thiazole-2-carboxamido)piperidine-1-carboxylate (1.9 g, 6.1 mmol) in EtOAc (20 mL) was added HCl/EtOAc (20 mL) dropwise at about 0° C., then the reaction was stirred at rt for about 3 h. The mixture was filtered and the filter cake was hygroscopic. The filter cake was dissolved into water and saturated aqueous NaHCO$_3$ solution. The mixture was extracted with DCM (3×50 mL) and the combined organic layers were washed with brine, dried over Na$_2$SO$_4$, filtered and concentrated to provide (R)—N-(piperidin-3-yl)thiazole-2-carboxamide (1.2 g, 5.68 mmol, 93%): $^1$H NMR (CDCl3) δ 1.79-1.66 (m, 3H), 1.92-1.86 (m, 1H), 2.04 (s, 1H), 2.87-2.70 (m, 3H), 3.15-2.88 (m, 1H), 4.12-4.06 (m, 1H), 7.54-7.53 (m, 2H), 7.84 (t, J=2.8 Hz, 1H).

Step C: (R)—N-(1-(7-Cyano-2-(1-(methylsulfonyl)-1,2,3,6-tetrahydropyridin-4-yl)-1-tosyl-1H-indol-4-yl)piperidin-3-yl)thiazole-2-carboxamide

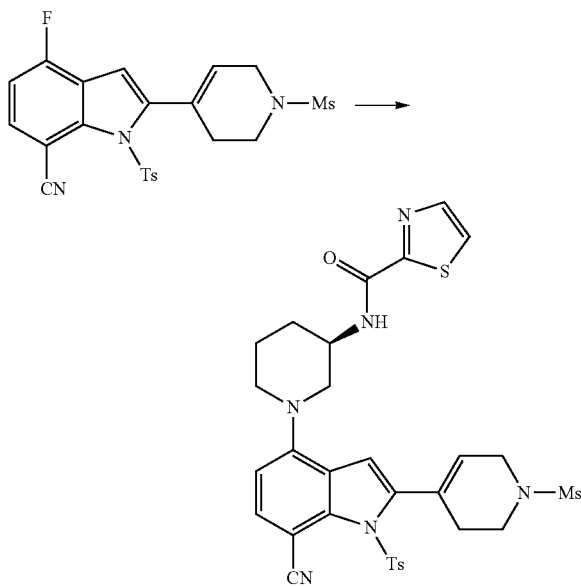

A mixture of 4-fluoro-2-(1-(methylsulfonyl)-1,2,3,6-tetrahydropyridin-4-yl)-1-tosyl-1H-indole-7-carbonitrile (200 mg, 0.422 mmol, Preparation #27), (R)—N-(piperidin-3-yl)thiazole-2-carboxamide (178 mg, 0.842 mmol) and TEA (170 mg, 1.680 mmol) in DMSO (2 mL) was heated under microwave condition at about 120° C. for about 1 h. Water (10 mL) was added to the mixture and extracted with DCM (3×20 mL). The organic layer was washed with brine, dried over Na$_2$SO$_4$, filtered and concentrated under reduced pressure to give the crude product which was purified by Prep-TLC (DCM:MeOH=75:1) to provide (R)—N-(1-(7-cyano-2-(1-(methylsulfonyl)-1,2,3,6-tetrahydropyridin-4-yl)-1-tosyl-1H-indol-4-yl)piperidin-3-yl)thiazole-2-carboxamide (20 mg, 7%): LC/MS (Table 1, Method m) R$_t$=2.24 min; MS m/z: 665 (M+H)$^+$.

Step D: (R)—N-(1-(7-Carbamoyl-2-(1-(methylsulfonyl)-1,2,3,6-tetrahydropyridin-4-yl)-1H-indol-4-yl)piperidin-3-yl)thiazole-2-carboxamide

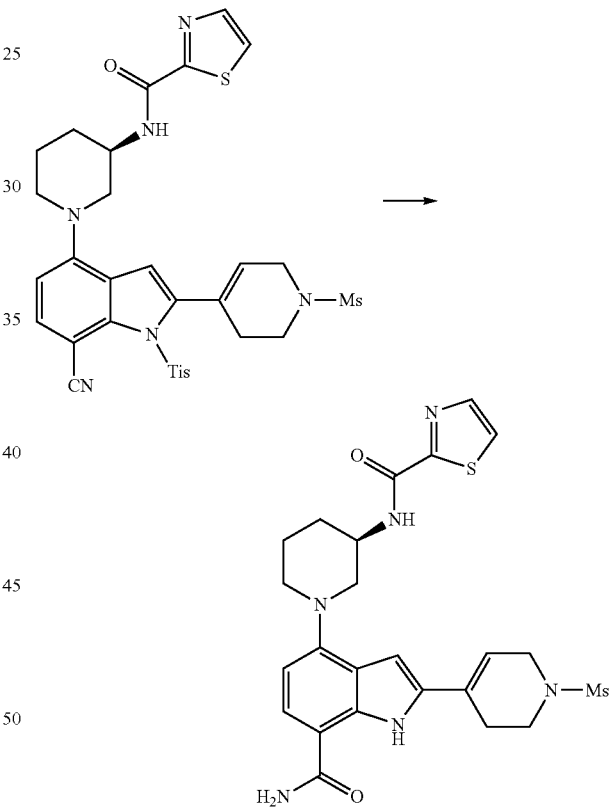

A mixture of (R)—N-(1-(7-cyano-2-(1-(methylsulfonyl)-1,2,3,6-tetrahydropyridin-4-yl)-1-tosyl-1H-indol-4-yl)piperidin-3-yl)thiazole-2-carboxamide (76 mg, 0.114 mmol), NaOH (54.9 mg, 1.37 mmol) and 30% H$_2$O$_2$ (350 mg, 3.09 mmol) in the mixture of DMSO (1 mL) and n-butanol (2 mL) was stirred at rt for about 24 h. Then saturated aqueous NH$_4$Cl (2 mL) was added and diluted with water (30 mL) and stirred for 30 min. The solid was collected by filtration and washed several times with water and the crude product was purified by Prep-TLC (50:1 DCM/MeOH) to provide (R)—N-(1-(7-carbamoyl-2-(1-(methylsulfonyl)-1,2,3,6-tetrahydropyridin-4-yl)-1H-indol-4-yl)piperidin-3-yl)thiazole- 2-carboxamide (32 mg, 53%): LC/MS (Table 1, Method d) $R_t$=2.90 min; MS m/z: 529 (M+H)$^+$. (Btk IC$_{50}$=A)

Example #14

2-(1-Methyl-1H-pyrazol-4-yl)-4-(2-methyl-3-(4-oxoquinazolin-3(4H)-yl)phenyl)-1H-benzo[d]imidazole-7-carboxamide

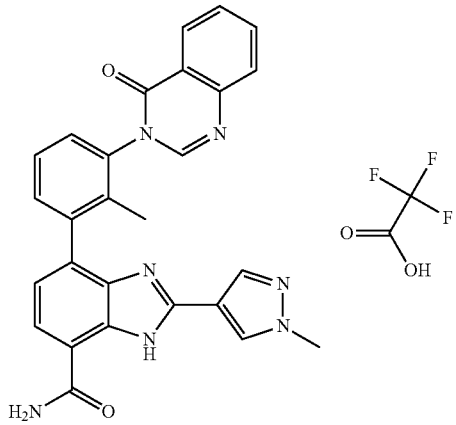 [SMILES: Cc1c(-c2ccc(C(N)=O)c3[nH]c(-c4cnn(C)c4)nc23)cccc1-n1cnc2ccccc2c1=O ; O=C(O)C(F)(F)F]

Step A: 3-(3-(7-Bromobenzo[c][1,2,5]thiadiazol-4-yl)-2-methylphenyl)quinazolin-4(3H)-one

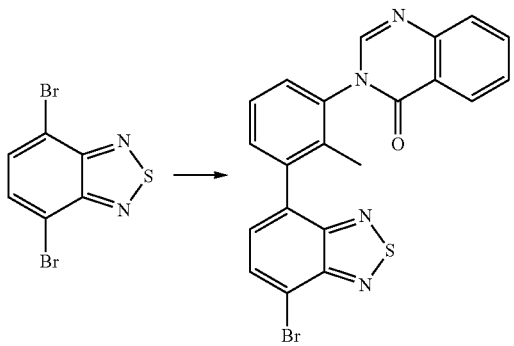 [SMILES: Brc1ccc(Br)c2nsnc12 ; Cc1c(-c2ccc(Br)c3nsnc23)cccc1-n1cnc2ccccc2c1=O]

To a solution of 4,7-dibromobenzo[c][1,2,5]thiadiazole (1.029 g, 3.5 mmol) and 3-(2-methyl-3-(4,4,5,5-tetramethyl-1,3,2-dioxaborolan-2-yl)phenyl)quinazolin-4(3H)-one (1.141 g, 3.15 mmol, WO 2011159857) in the mixture of toluene (40 mL), MeOH (10 mL) and water (10 mL) were added Na$_2$CO$_3$ (0.742 g, 7.00 mmol) and Pd(PPh$_3$)$_4$(0.081 g, 0.070 mmol). The mixture was heated to about 100° C. for 24 h. The resulting solution was cooled to rt and diluted with EtOAc, washed with water and brine, dried over Na$_2$SO$_4$, filtered and concentrated to give a crude product, which was purified by column chromatography on silica gel (eluted with Pet ether:EtOAc=5:1 to 1:1) to afford 3-(3-(7-bromobenzo[c][1,2,5]thiadiazol-4-yl)-2-methylphenyl)quinazolin-4(3H)-one (1.0 g, 64%): $^1$H NMR (CDCl$_3$) δ 8.40-8.38 (d, J=8.0 Hz, 1H), 8.13 (s, 1H), 7.95-7.93 (d, J=7.6 Hz, 1H), 7.82-7.80 (m, 2H), 7.58-7.56 (m, 1H), 7.51-7.46 (m, 3H), 7.41-7.39 (t, J=4.8 Hz, 1H), 1.95 (s, 3H).

Step B: 7-(2-Methyl-3-(4-oxoquinazolin-3(4H)-yl)phenyl)benzo[c][1,2,5]thiadiazole-4-carbonitrile

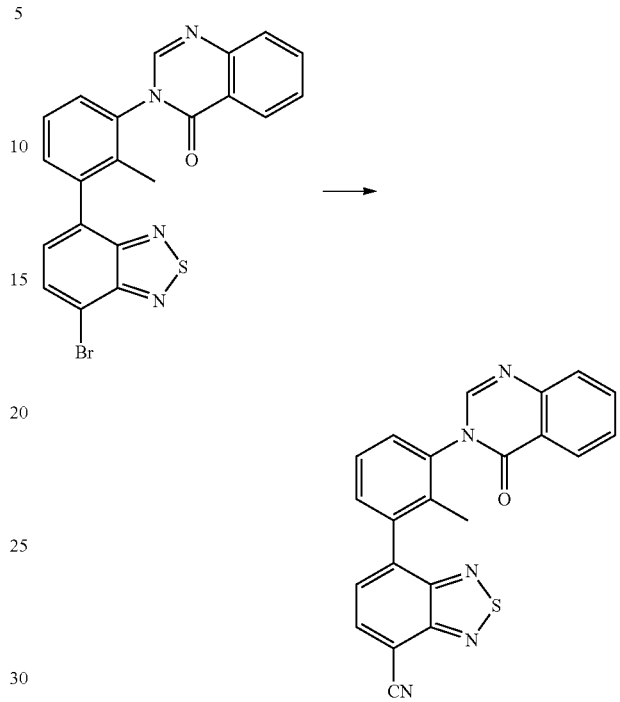

To a solution of 3-(3-(7-bromobenzo[c][1,2,5]thiadiazol-4-yl)-2-methylphenyl)quinazolin-4(3H)-one (0.449 g, 1 mmol) in DMF (12 mL) were added Zn(CN)$_2$ (0.076 g, 0.650 mmol) and Pd(PPh$_3$)$_4$ (0.046 g, 0.040 mmol). The mixture was heated to about 160° C. for about 15 min under N$_2$ atmosphere in a microwave reactor. The resulting solution was diluted with EtOAc, and washed with brine (4×). The organic phase was dried over Na$_2$SO$_4$, filtered and concentrated to give a crude product, which was purified by column chromatography on silica gel (eluted with Pet ether:EtOAc=5:1 to 1:1) to provide 7-(2-methyl-3-(4-oxoquinazolin-3(4H)-yl)phenyl)benzo[c][1,2,5]thiadiazole-4-carbonitrile (0.3 g, 76%): $^1$H NMR (CDCl$_3$) δ 8.33-8.03 (d, J=8.0 Hz, 1H), 8.10-8.06 (t, J=7.2 Hz, 2H), 7.77-7.74 (m, 2H), 7.63-7.61 (t, J=7.2 Hz, 1H), 7.53-7.45 (m, 3H), 7.39-7.37 (d, J=7.2 Hz, 1H), 1.90 (s, 3H).

Step C: 2,3-Diamino-2'-methyl-3'-(4-oxoquinazolin-3(4H)-yl)-[1,1'-biphenyl]-4-carbonitrile

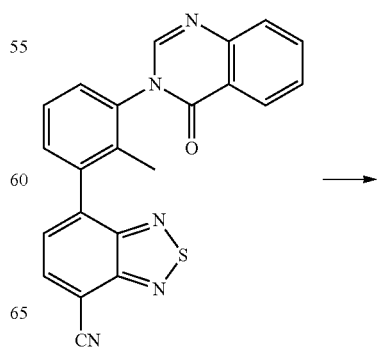

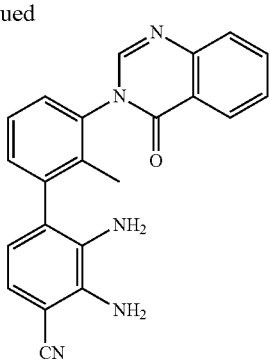

To a solution of 2,3-diamino-2'-methyl-3'-(4-oxoquinazolin-3(4H)-yl)-[1,1'-biphenyl]-4-carbonitrile (0.53 mg, 1.34 mmol) in AcOH (50 mL) was added zinc (1.75 g, 26.8 mmol), the mixture was heated to about 120° C. for about 2 h. The solvent was concentrated and the residue was taken up into EtOAc, washed with saturated aqueous NaHCO₃ solution and brine. The organic phase was dried over Na₂SO₄, filtered and concentrated to give a crude product, which was purified by column chromatography on silica gel (eluted with Pet ether:EtOAc=1:1 to 0:1) to provide 2,3-diamino-2'-methyl-3'-(4-oxoquinazolin-3(4H)-yl)-[1,1'-biphenyl]-4-carbonitrile (0.4 g, 81%): LC/MS (Table 1, Method I) R$_f$=1.33 min; MS m/z: 368 (M+H)⁺.

Step D: 2-(1-Methyl-1H-pyrazol-4-yl)-4-(2-methyl-3-(4-oxoquinazolin-3(4H)-yl)phenyl)-1H-benzo[d]imidazole-7-carbonitrile

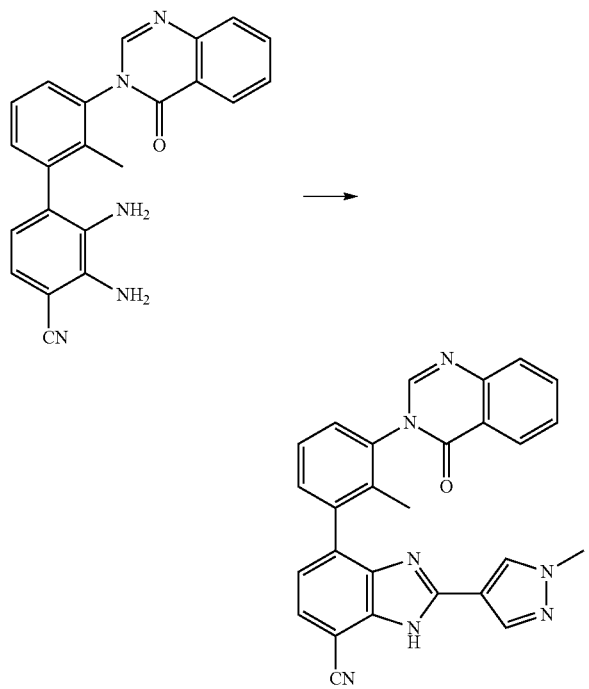

To a solution of 2,3-diamino-2'-methyl-3'-(4-oxoquinazolin-3(4H)-yl)-[1,1'-biphenyl]-4-carbonitrile (400 mg, 1.09 mmol) in DMF (15 mL) were added 1-methyl-1H-pyrazole-4-carbaldehyde (240 mg, 2.18 mmol) and TMSCl (0.417 mL, 3.27 mmol). The mixture was heated to about 100° C. for about 30 min in a microwave reactor. The resulting solution was diluted with EtOAc, and washed with brine (4×). The organic phase was dried over Na₂SO₄, filtered and concentrated to give a crude product, which was purified by column chromatography on silica gel (eluted with Pet ether:EtOAc=1:1 then EtOAc:MeOH=50:1) to provide 2-(1-methyl-1H-pyrazol-4-yl)-4-(2-methyl-3-(4-oxoquinazolin-3(4H)-yl)phenyl)-1H-benzo[d]imidazole-7-carbonitrile (200 mg, 40%): LC/MS (Table 1, Method m) R$_f$=1.78 min; MS m/z: 458 (M+H)⁺.

Step E: 2-(1-Methyl-1H-pyrazol-4-yl)-4-(2-methyl-3-(4-oxoquinazolin-3(4H)-yl)phenyl)-1H-benzo[d]imidazole-7-carboxamide

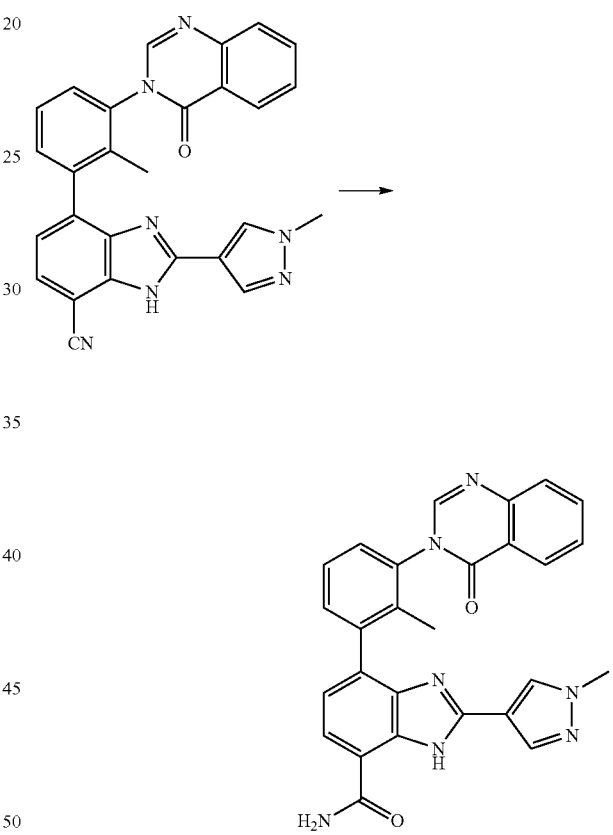

To a solution of 2-(1-methyl-1H-pyrazol-4-yl)-4-(2-methyl-3-(4-oxoquinazolin-3(4H)-yl)phenyl)-1H-benzo[d]imidazole-7-carbonitrile (278 mg, 0.608 mmol) in the mixture of butanol (6 mL) and DMSO (3 mL) were added NaOH (292 mg, 7.29 mmol) and H₂O₂ (1.68 mL, 16.4 mmol). The mixture was stirred for about 24 h at about 25° C. The resulting solution was quenched with saturated aqueous NH₄Cl solution, extracted with EtOAc. The organic phase was dried over Na₂SO₄, filtered and concentrated to give a crude product, which was purified by prep-HPLC (Table 1, Method n) to provide 2-(1-methyl-1H-pyrazol-4-yl)-4-(2-methyl-3-(4-oxoquinazolin-3(4H)-yl)phenyl)-1H-benzo[d]imidazole-7-carboxamide (140 mg, 48%): LCMS (Table 1, Method d) R$_f$32 2.53 min; MS m/z: 476 (M+H)⁺. (Btk IC$_{50}$=B)

Example #15

4-(3-Acrylamidophenyl)-1H-indazole-7-carboxamide

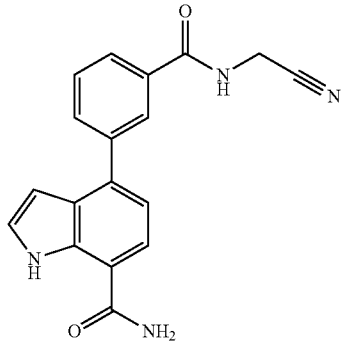 [SMILES: N#CCNC(=O)c1cccc(-c2ccc(C(N)=O)c3[nH]ccc23)c1]

Step A: 3-(7-Carbamoyl-1H-indol-4-yl)benzoic acid

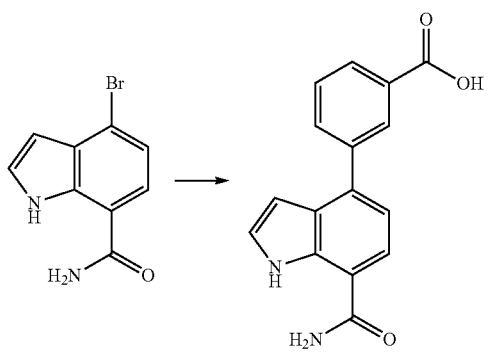 [SMILES: NC(=O)c1ccc(Br)c2cc[nH]c12 ; NC(=O)c1ccc(-c2cccc(C(=O)O)c2)c2cc[nH]c12]

A mixture of 4-bromo-1H-indole-7-carboxamide (0.5 g, 2.091 mmol, Preparation #2), (3-(methoxycarbonyl)phenyl)boronic acid (0.565 g, 3.14 mmol), sodium carbonate (2.61 mL, 5.23 mmol) in DME (10.00 mL) was degassed and purged with nitrogen for about 5 min, then tetrakis(triphenylphosphine)palladium(0) (0.121 g, 0.105 mmol) was added. The reaction vessel was sealed and heated with microwave (Biotage Initiator) at about 110° C. for about 45 min. The mixture was cooled to rt, followed by addition of about 50 mL of water. The precipitate is filtered, air-dried and used without further purification. This crude was then dissolved in THF (25 mL) and treated with lithium hydroxide (0.250 g, 10.46 mmol) solution in water (25 mL). The reaction mixture was stirred at rt overnight. THF was removed and the aqueous layer was extracted with DCM to remove triphenylphosphine oxide. The aqueous phase was then acidified with 1N HCl solution to about pH 2. The precipitate was filtered and dried to give 0.58 g of crude 3-(7-carbamoyl-1H-indol-4-yl)benzoic acid as a solid. LC/MS (Table 1, Method g) $R_t$=1.37 min; MS m/z 281 (M+H)$^+$.

Step B: 4-(3-(((Cyanomethyl)carbamoyl)phenyl)-1H-indole-7-carboxamide

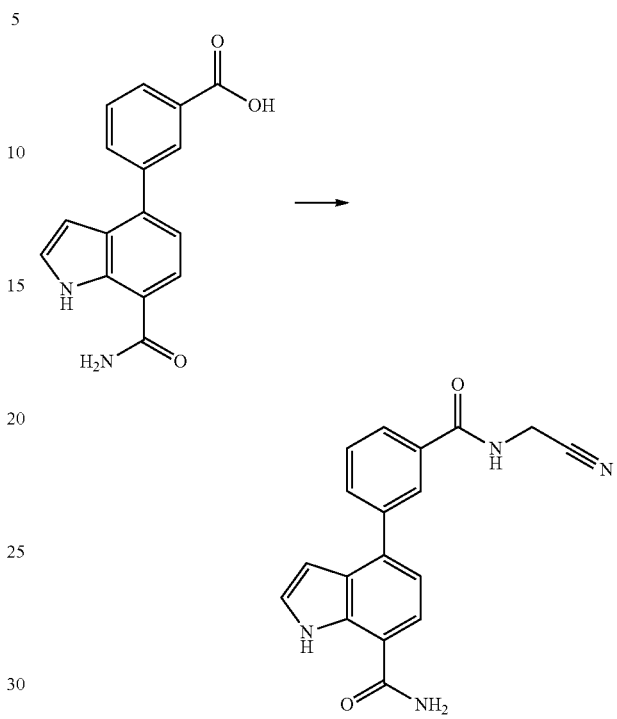

A mixture of 3-(7-carbamoyl-1H-indol-4-yl)benzoic acid (0.1 g, 0.357 mmol), TBTU (0.172 g, 0.535 mmol) and DIEA (0.249 mL, 1.43 mmol) in DMF (5.0 mL) was stirred at rt for about 5 min, followed by addition of 2-aminoacetonitrile, hydrochloric acid (0.040 g, 0.43 mmol). The reaction mixture was stirred at the same temperature overnight. Water was added and the aqueous phase was extracted with EtOAc. Organic layer was washed with brine, dried over magnesium sulfate and filtered. The filtrate was dried and the crude was purified by prep HPLC (Table 1, Method i) to give cyanomethyl)carbamoyl)phenyl)-1H-indole-7-carboxamide (0.065 g, 57%) as a solid. LC/MS (Table 1, Method g)$R_t$=1.30 min; MS m/z 319 (M+H)$^+$ (Btk IC$_{50}$=C)

Example #16

4-(3-Amino-2-methylphenyl)-1H-indole-7-carboxamide

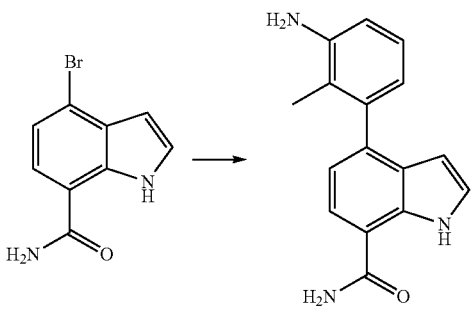 [SMILES: NC(=O)c1ccc(Br)c2cc[nH]c12 ; Cc1c(N)cccc1-c1ccc(C(N)=O)c2[nH]ccc12]

A mixture of 4-bromo-1H-indole-7-carboxamide (1.28 g, 5.35 mmol, Preparation #2), 2-methyl-3-(4,4,5,5-tetramethyl-1,3,2-dioxaborolan-2-yl)aniline (1.37 g, 5.89 mmol, Combi-Blocks), Na₂CO₃ (1.70 g, 16.06 mmol) and [1,1'-bis(diphenylphosphino)ferrocene]dichloropalladium(II) (0.392 g, 0.535 mmol) in THF (41.8 mL), MeOH (5.86 mL), and water (5.86 mL) was stirred at about 70° C. for about 16 h under a nitrogen atmosphere. The mixture was filtered through Celite® and concentrated under reduced pressure. The crude product was purified by silica gel column with 0-10% MeOH in DCM to provide the crude product. The residue was triturated with DCM (2× with sonication for about 5 min), filtered, was washed with DCM and dried under reduced pressure to provide 4-(3-amino-2-methylphenyl)-1H-indole-7-carboxamide (0.86 g, 61%): LC/MS (Table 1, Method g) R$_t$=1.03 min; MS m/z: 266 (M+H)⁺. (Btk IC$_{50}$=C)

Example #17

4-(3-Acrylamido-2-methylphenyl)-1H-pyrrolo[2,3-c]pyridine-7-carboxamide

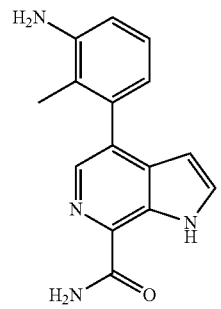

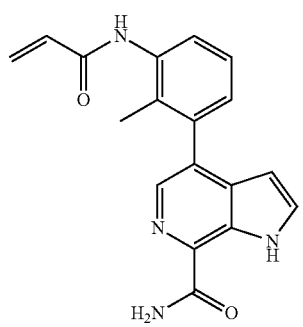

To a solution of 4-(3-amino-2-methylphenyl)-1H-pyrrolo[2,3-c]pyridine-7-carboxamide (3.0 g, 11.3 mmol, Example #2) and TEA (3.14 mL, 22.5 mmol) in THF (113 mL) was slowly added acryloyl chloride (1.01 mL, 12.4 mmol) at 0° C. The reaction was stirred at about 0° C. for about 20 min. The mixture was concentrated under reduced pressure and water (100 mL) was added and the suspension was sonicated for 30 min, filtered, washed with water (100 mL), ether (100 mL) and dried to give 4-(3-acrylamido-2-methylphenyl)-1H-pyrrolo[2,3-c]pyridine-7-carboxamide (3.05 g, 85%): LC/MS (Table 1, Method f) R$_t$=1.27 min; MS m/z: 321 (M+H)⁺. (Btk IC$_{50}$=A)

Example #18

4-(3-Acrylamidophenyl)-1H-indazole-7-carboxamide

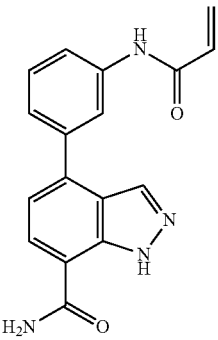 [SMILES: C=CC(=O)Nc1cccc(-c2ccc(C(N)=O)c3[nH]ncc23)c1]

Step A: Methyl 2-amino-4-chloro-3-methylbenzoate

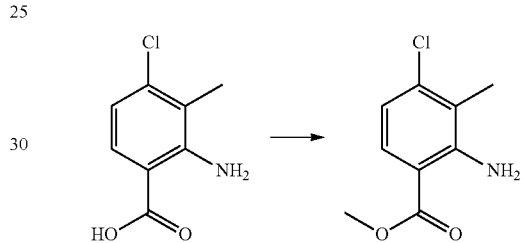

To a mixture of 2-amino-4-chloro-3-methylbenzoic acid (5.0 g, 26.9 mmol, Enamine) and cesium carbonate (13.2 g, 40.4 mmol) in DMF (100 mL) was added iodomethane (1.77 mL, 28.3 mmol). The mixture was then stirred at rt for about 16 h. Water was added and extracted with EtOAc. The organic layer was washed with brine, dried over magnesium sulfate and filtered. The filtrate was concentrated and purified by chromatography on silica gel (5-60% EtOAc in heptane) to provide methyl 2-amino-4-chloro-3-methylbenzoate (4.48 g) as a solid. LC/MS (Table 1, Method g) R$_t$=1.74 min; MS m/z 200 (M+H)⁺.

Step B: Methyl 4-chloro-1H-indazole-7-carboxylate

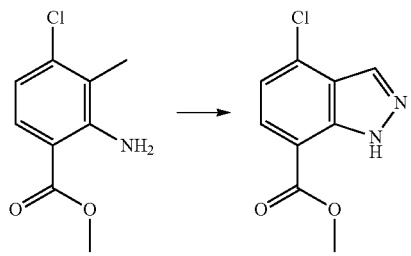

To a solution of methyl 2-amino-4-chloro-3-methylbenzoate (4.5 g, 22.5 mmol) in CHCl₃ (100 mL) was added acetic anhydride (4.89 mL, 51.8 mmol). The mixture was then stirred at rt for about 2 h, followed by addition of isopentyl nitrite (6.68 mL, 49.6 mmol) and potassium acetate (0.664 g, 6.76 mmol). The reaction mixture was heated at refluxed for about 18 h. The reaction was diluted with DCM and washed with saturated sodium bicarbonate and dried over magnesium sulfate. The filtrate is concentrate to provide crude methyl 4-chloro-1H-indazole-7-carboxylate (4.46 g); LC/MS (Table 1, Method g) $R_t$=1.47 min; MS m/z 211 (M+H)$^+$.

Step C: 4-Chloro-1H-indazole-7-carboxamide

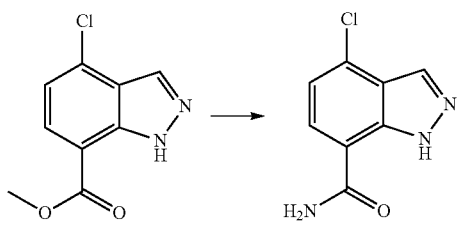

To a suspension of methyl 4-chloro-1H-indazole-7-carboxylate (4.3 g, 20.4 mmol) in 1,4-dioxane (75 mL) was added a solution of KOH (1.69 g, 26.5 mmol) in water (75 mL). The reaction mixture was then stirred at rt for about 16 h to give a clear solution. Solvent was removed and the residue was treated with 1N HCl to precipitate the crude acid, which was used without further purification. A mixture of this crude acid (0.5 g, 2.54 mmol), N1-((ethylimino)methylene)-N3,N3-dimethylpropane-1,3-diamine hydrochloride (0.731 g, 3.82 mmol) and HOBt (0.584 g, 3.82 mmol) in DMF (15 mL) was stirred at rt for about 60 min, then ammonia (0.5 N solution in 1,4-dioxane, 50.9 mL, 25.4 mmol) was added. The reaction mixture was stirred at rt for about 6 h. The suspension was filtered and washed with EtOAc. The filtrate was concentrated and treated with water. The precipitate was filtered, washed with water and air-dried to provide 4-chloro-1H-indazole-7-carboxamide (0.43 g) as a solid; LC/MS (Table 1, Method g) $R_t$=1.00 min; MS m/z 196 (M+H)$^+$.

Step D: 4-(3-Aminophenyl)-1H-indazole-7-carboxamide

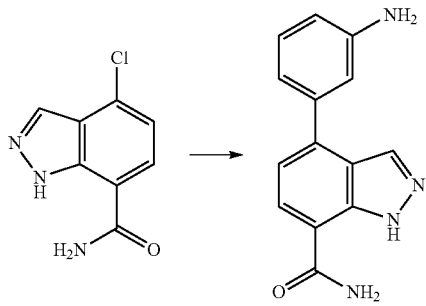 [SMILES: NC(=O)c1ccc(Cl)c2cn[nH]c12 ; NC(=O)c1ccc(-c2cccc(N)c2)c2cn[nH]c12]

A suspension of 4-chloro-1H-indazole-7-carboxamide (0.15 g, 0.767 mmol), tert-butyl (3-(4,4,5,5-tetramethyl-1,3,2-dioxaborolan-2-yl)phenyl)carbamate (0.367 g, 1.15 mmol), cesium carbonate (0.75 g, 2.3 mmol) in DME (4.0 mL) and water (2.0 mL) was degassed and purged with nitrogen for 5 min. Then tris(dibenzylideneacetone)dipalladium(0) (0.07 g, 0.077 mmol) and 2-(dicyclohexylphos-phino)-2',4',6'-triisopropylbiphenyl (0.037 g, 0.077 mmol) were added. The reaction vessel was sealed and heated using Biotage Initiator at about 140° C. for about 30 min. The mixture was cooled to rt and filtered through a pad of Celite®. The filtrate was partitioned between water and EtOAc. Organic layer was washed with brine, dried over magnesium sulfate and filtered. The filtrate was concentrated and purified by chromatography on silica gel (30-100% EtOAc/heptane). This product was then dissolved in DCM (2 mL) and treated with TFA (5 mL, 64.9 mmol). The reaction mixture was stirred at rt overnight. Excess TFA and solvent were removed to provide crude 4-(3-aminophenyl)-1H-indazole-7-carboxamide, trifluoroacetic acid (0.195 g) as a solid. LC/MS (Table 1, Method g) $R_t$=0.25 min; MS m/z 253(M+H)$^+$.

Step E: 4-(3-Acrylamidophenyl)-1H-indazole-7-carboxamide

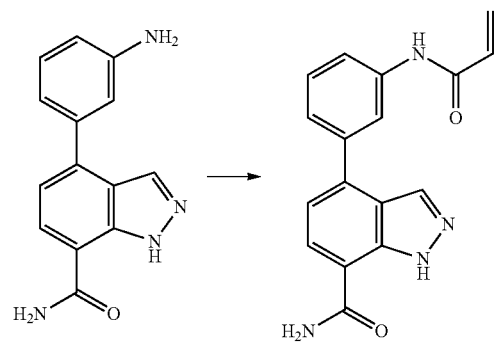 [SMILES: NC(=O)c1ccc(-c2cccc(N)c2)c2cn[nH]c12 ; C=CC(=O)Nc1cccc(-c2ccc(C(N)=O)c3[nH]ncc23)c1]

A suspension of 4-(3-aminophenyl)-1H-indazole-7-carboxamide, TFA (0.1 g, 0.27 mmol), DIEA (0.143 mL, 0.819 mmol) in THF (2.5 mL) was cooled in an ice bath and acryloyl chloride (0.026 mL, 0.31 mmol) is added slowly. After 30 min, the reaction was treated with MeOH and stirred for about 5 min Solvent was then removed under vacuum and the residue was triturated with DCM to provide 4-(3-acrylamidophenyl)-1H-indazole-7-carboxamide (56 mg) as a solid: $^1$H NMR (d-DMSO-d6) δ 13.17 (s, 1 H) 10.34 (s, 1 H) 8.28 (s, 1 H) 8.21 (s, 1 H) 8.17 (s, 1 H) 8.00 (d, J=7.48 Hz, 1 H) 7.73 (d, J=7.70 Hz, 1H) 7.40-7.59 (m, 3H) 7.30 (d, J=7.59 Hz, 1 H) 6.39-6.58 (m, 1 H) 6.17-6.36 (m, 1 H) 5.60-5.97 (m, 1 H). (Btk IC$_{50}$=A)

Example #19

4-(3-Acrylamidophenyl)-1H-indazole-7-carboxamide

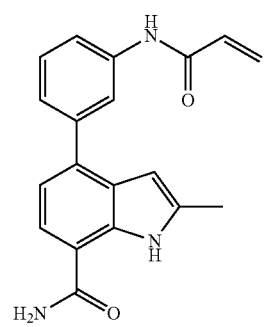 [SMILES: C=CC(=O)Nc1cccc(-c2ccc(C(N)=O)c3[nH]c(C)cc23)c1]

Step A: Methyl 4-bromo-2-methyl-1-((2-(trimethyl-silyl)ethoxy)methyl)-1H-indole-7-carboxylate

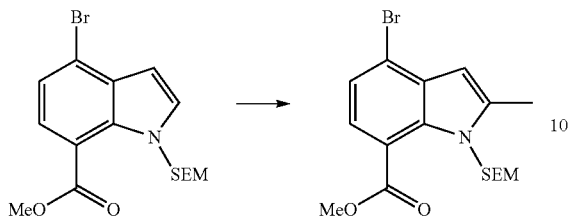

To a solution of diisopropylamine (1.45 mL 10.1 mmol) and anhydrous THF (30 mL), a solution of t-BuLi (11 mL, 11.7 mmol) in pentane was added at about −78° C. under nitrogen atmosphere reaction mixture was stirred for about 30 min. Then a solution of methyl 4-bromo-14(2-(trimethylsilyl)ethoxy)methyl)-1H-indole-7-carboxylate (3 g, 7.81 mmol, Preparation #10, step A) in anhydrous THF (10 mL) was added at about −78° C. After about 2 h, a solution of iodomethane (2.216 g, 15.61 mmol) in anhydrous THF (10 mL) was added at about −78° C. The mixture continued to stir for about 2 h at about −78° C. The reaction mixture was quenched with aqueous NH₄Cl, extracted with EtOAc (500 mL×3). The organic phase was dried over Na₂SO₄, concentrated under reduced pressure, and the residue was purified by prep-HPLC (Table 1, Method ao) to provide methyl 4-bromo-2-methyl-1-((2-(trimethylsilyl)ethoxy)methyl)-1H-indole-7-carboxylate (1 g, 32%) as a solid: ¹H NMR (CDCl₃) δ 7.51-7.49 (d, J=8.0, 1H), 7.39-7.37 (d, J=8, 1H), 6.55 (s, 1H), 5.77 (s, 2H), 4.06 (s, 3H), 3.31-3.27 (m, 2H), 2.60 (s, 3H), 0.87-0.83 (m, 2H), 0.00 (s, 9H).

Step B: 4-Bromo-2-methyl-1-((2-(trimethylsilyl)ethoxy)methyl)-1H-indole-7-carboxylic acid

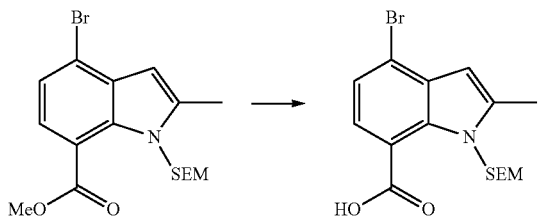 [SMILES: COC(=O)c1ccc(Br)c2cc(C)n(COCC[Si](C)(C)C)c12 ; Cc1cc2c(Br)ccc(C(=O)O)c2n1COCC[Si](C)(C)C]

To a solution of methyl 4-bromo-2-methyl-14(2-(trimethylsilyl)ethoxy)methyl)-1H-indole-7-carboxylate (0.6 g, 1.5 mmol) in MeOH (3 mL), THF (6 mL) and water (3 mL), LiOH (0.361 g, 15.1 mmol) was added and the reaction mixture was heated to about 45° C. for about 3 h. The reaction mixture was adjusted to pH<3 by the addition of 1N HCl, then extracted with EtOAc (300 mL×3), and the organic phase was concentrated under reduced pressure to provide 4-bromo-2-methyl-1-((2-(trimethylsilyl)ethoxy)methyl)-1H-indole-7-carboxylic acid (0.5 g, 86%) as a solid: ¹H NMR (DMSO-d6) δ 13.32 (s, 1H), 7.53-7.42 (m, 2H), 6.56 (s, 1H), 5.86 (s, 2H), 3.36-3.32 (m, 2H), 2.63 (s, 3H), 0.90-0.82 (m, 2H), 0.00 (s, 9H).

Step C: 4-Bromo-2-methyl-1-((2-(trimethylsilyl)ethoxy)methyl)-1H-indole-7-carboxamide

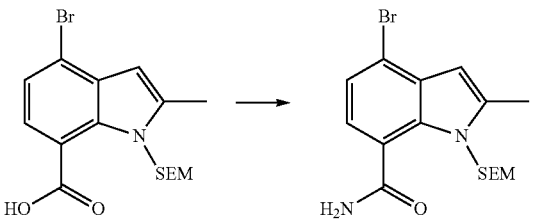 [SMILES: Cc1cc2c(Br)ccc(C(=O)O)c2n1COCC[Si](C)(C)C ; Cc1cc2c(Br)ccc(C(N)=O)c2n1COCC[Si](C)(C)C]

To a solution of 4-bromo-2-methyl-14(2-(trimethylsilyl)ethoxy)methyl)-1H-indole-7-carboxylic acid (0.5 g, 1.30 mmol) in THF (10 mL) and DCM (12 mL), HOBt (0.299 g, 1.95 mmol) and EDCI (0.374 g, 1.95 mmol) were added at about 0° C. Then the reaction mixture was stirred for about 1 hour at rt, then bubbled with NH₃ gas for about 20 min, and stirring continued overnight at rt. Aqueous NaHCO₃ was added and the mixture was extracted with EtOAc (200 mL×3), and the organic phase was dried over Na₂SO₄, concentrated under reduced pressure to provide 4-bromo-2-methyl-1-((2-(trimethylsilyl)ethoxy)methyl)-1H-indole-7-carboxamide (0.45 g, 90%) as a solid: ¹H NMR (DMSO-d6) δ 8.10 (s, 1H), 7.67 (s, 1H), 7.36-7.34 (d, J=8, 1H), 7.20-7.18 (d, J=8, 1H), 6.46 (s, 1H), 5.74 (s, 2H), 3.46-3.38 (m, 2H), 2.56 (s, 3H), 0.90-0.83 (m, 2H), 0.00 (s, 9H).

Step D: 4-Bromo-2-methyl-1H-indole-7-carboxamide

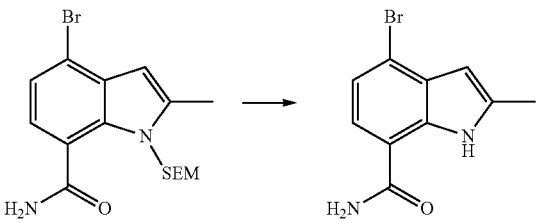 [SMILES: Cc1cc2c(Br)ccc(C(N)=O)c2n1COCC[Si](C)(C)C ; Cc1cc2c(Br)ccc(C(N)=O)c2[nH]1]

To a solution of 4-bromo-2-methyl-14(2-(trimethylsilyl)ethoxy)methyl)-1H-indole-7-carboxamide (350 mg, 0.913 mmol) in THF (15 mL) was added TBAF (2.4 g, 9.13 mmol) and ethane-1,2-diamine (1.1 g, 18.3 mmol). The mixture was refluxed overnight. The reaction mixture was concentrated under reduced pressure and the residue was purified by silica gel column to provide 4-bromo-2-methyl-1H-indole-7-carboxamide (180 mg, 78%) as a solid: ¹H NMR (DMSO-d6) δ 11.18 (s, 1H), 8.05 (s, 1H), 7.48-7.42 (m, 2H), 7.20-7.18 (d, J=8, 1H), 6.14 (s, 1H), 2.41 (s, 3H).

Step E: 4-(3-Aminophenyl)-2-methyl-1H-indole-7-carboxamide

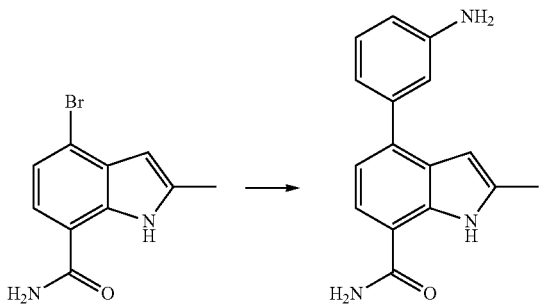 [SMILES: Cc1cc2c(Br)ccc(C(N)=O)c2[nH]1 ; Cc1cc2c(-c3cccc(N)c3)ccc(C(N)=O)c2[nH]1]

To a solution of 4-bromo-2-methyl-1H-indole-7-carboxamide (180 mg, 0.711 mmol) in THF (8 mL) and water (4 mL) and MeOH (4 mL) was added 3-(4,4,5,5-tetramethyl-1,3,2-dioxaborolan-2-yl)aniline (187 mg, 0.853 mmol), Pd(dppf)Cl$_2$ (104 mg, 0.142 mmol) and Na$_2$CO$_3$ (226 mg, 2.13 mmol), and the solution was heated at about 90° C. for about 2 h. The reaction mixture was concentrated under reduced pressure and purified by silica gel column to provide 4-(3-aminophenyl)-2-methyl-1H-indole-7-carboxamide (80 mg, 42%) as a solid: $^1$H NMR (MeOD) δ 10.92 (s, 1H), 7.99 (s, 1H), 7.66-7.63 (d, J=12, 2H), 7.61 (s, 1H), 7.13-7.09 (m, 1H), 6.99-6.97 (d, J=8, 1H), 6.88 (s, 1H), 6.78-6.73 (m, 2H), 6.58-6.56 (d, J=8, 1H), 6.29 (s, 1H), 2.42 (s, 3H).

Step F: 4-(3-Acrylamidophenyl)-2-methyl-1H-indole-7-carboxamide

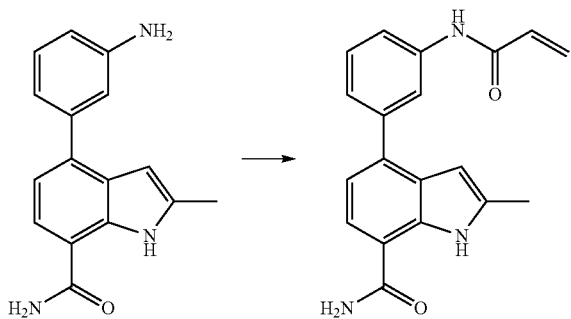 [SMILES: Cc1cc2c(-c3cccc(N)c3)ccc(C(N)=O)c2[nH]1 ; C=CC(=O)Nc1cccc(-c2ccc(C(N)=O)c3[nH]c(C)cc23)c1]

To a solution of 4-(3-aminophenyl)-2-methyl-1H-indole-7-carboxamide (80 mg, 0.302 mmol) in DCM (6 mL), acryloyl chloride (40.9 mg, 0.452 mmol) and DIEA (0.105 mL, 0.603 mmol) were added at about 0° C. The mixture was stirred for about 1 hour at rt. The reaction mixture was concentrated under reduced pressure and the residue was purified by prep-HPLC (Table 1, Method an) to give 4-(3-acrylamidophenyl)-2-methyl-1H-indole-7-carboxamide (10 mg, 11%) as a solid: LC/MS (Table 1, Method j) R$_t$=2.07 min; MS m/z: 320 (M+H)$^+$. (Btk IC$_{50}$=A)

Example #20

4-(3-Acrylamidophenyl)-2-ethyl-1H-indole-7-carboxamide

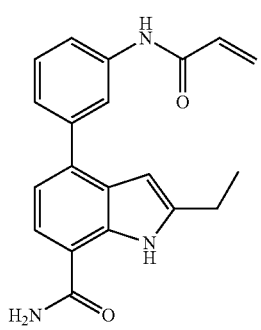 [SMILES: C=CC(=O)Nc1cccc(-c2ccc(C(N)=O)c3[nH]c(CC)cc23)c1]

Step A: 4-Bromo-2-iodo-1H-indole-7-carboxamide

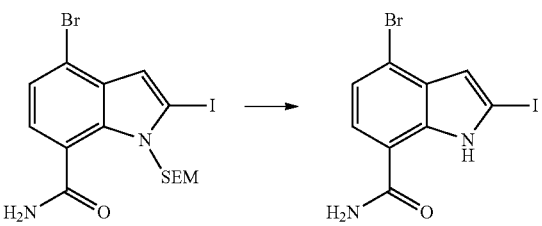 [SMILES: C[Si](C)(C)CCOCn1c(I)cc2c(Br)ccc(C(N)=O)c21 ; NC(=O)c1ccc(Br)c2cc(I)[nH]c12]

To a solution of 4-bromo-2-iodo-1-((2-(trimethylsilyl)ethoxy)methyl)-1H-indole-7-carboxamide ((1.5 g, 3.03 mmol, Preparation #24) in THF (20 mL), TBAF (15.84 g, 60.6 mmol) and ethane-1,2-diamine (1.82 g, 30.3 mmol) were added, and the solution was heated at reflux overnight. The solution was concentrated under reduced pressure and water (30 mL) and EtOAc (30 mL) were added, and the organic phase was dried and concentrated under reduced pressure. The residue was purified by column chromatography (Pet ether:EtOAc=10:1 to 1:1) to provide 4-bromo-2-iodo-1H-indole-7-carboxamide (700 mg, 63%): LC/MS (Table 1, Method k) R$_t$=1.91 min; MS m/z: 367 (M+H)$^+$.

Step B: 4-Bromo-2-vinyl-1H-indole-7-carboxamide

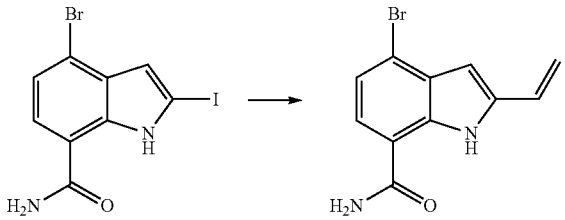

To a solution of 4-bromo-2-iodo-1H-indole-7-carboxamide (0.630 g, 1.726 mmol) in 1.4-dioxane (4.5 mL) and water (0.5 mL), CsF (0.787 g, 5.18 mmol), Pd(PPh$_3$)$_2$Cl$_2$ (0.242 g, 0.345 mmol) and potassium trifluoro(vinyl)borate (254 mg, 1.899 mmol) were added. The reaction mixture was heated to about 90° C. for about 2 h under N$_2$ atmosphere. The mixture was concentrated under reduced pressure, and the residue was purified by column chromatography to provide 4-bromo-2-vinyl-1H-indole-7-carboxamide (0.140 g, 31%): $^1$H NMR (CDCl3) δ 10.36 (s, 1H), 7.2-7.12 (m, 2H), 6.72-6.65 (m, 1H), 6.50 (s, 1H), 6.25-5.78 (m, 2H), 5.69 (d, J=17.6, 1H), 5.33 (d, J=10.8, 1H).

Step C: 4-(3-Aminophenyl)-2-vinyl-1H-indole-7-carboxamide

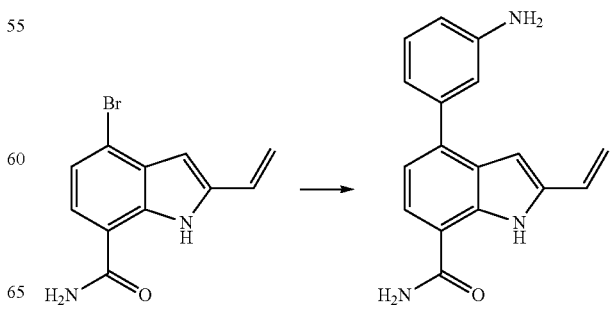

To a solution of 4-bromo-2-vinyl-1H-indole-7-carboxamide (0.12 g, 0.45 mmol) in THF (10 mL), water (5 mL) and MeOH (5 mL), 3-(4,4,5,5-tetramethyl-1,3,2-dioxaborolan-2-yl)aniline (119 mg, 0.543 mmol), PdCl$_2$(dppf) (66.2 mg, 0.091 mmol) and Na$_2$CO$_3$ (144 mg, 1.358 mmol) were added. The reaction mixture was heated at about 90° C. for about 2 h. The mixture was concentrated under reduced pressure and the residue was purified by column chromatography on silica gel to provide 4-(3-aminophenyl)-2-vinyl-1H-indole-7-carboxamide (80 mg, 75%): LC/MS (Table 1, Method I) R$_t$=1.06 min; MS m/z: 278 (M+H)$^+$.

Step C:
4-(3-Aminophenyl)-2-ethyl-1H-indole-7-carboxamide

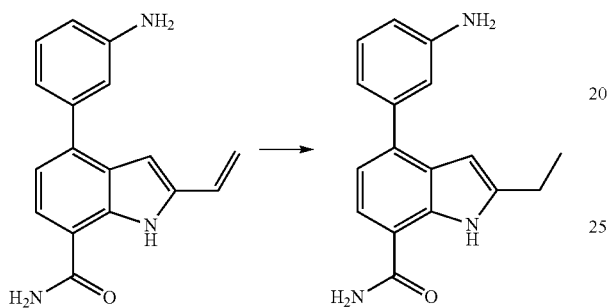

To a solution of 4-(3-aminophenyl)-2-vinyl-1H-indole-7-carboxamide (46 mg, 0.116 mmol) in THF (10 mL), Pd/C (10 mg, 0.094 mmol) was added. The mixture was stirred for about 1.5 h at rt. The mixture was filtered through a pad of Celite®, and the filtrate was concentrated under reduced pressure to provide 4-(3-aminophenyl)-2-ethyl-1H-indole-7-carboxamide (40 mg, 70%), which was used to next step directly: LC/MS (Table 1, Method I) R$_t$=1.21 min; MS m/z: 280 (M+H)$^+$.

Step D: 4-(3-Acrylamidophenyl)-2-ethyl-1H-indole-7-carboxamide

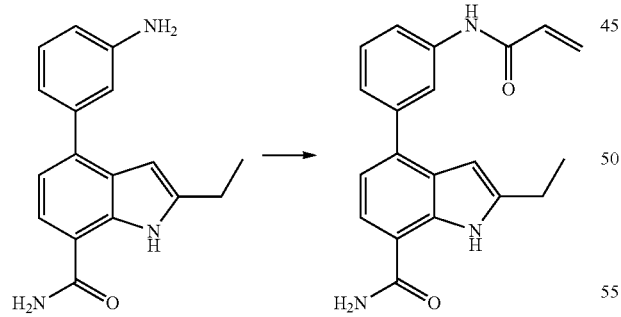

To a solution of 4-(3-aminophenyl)-2-ethyl-1H-indole-7-carboxamide (20 mg, 0.072 mmol) in DCM (15 mL), TEA (29 mg, 0.288 mmol) and acryloyl chloride (13.05 mg, 0.144 mmol) were added at about 0° C. The solution was stirred overnight at rt. The solution was concentrated under reduced pressure, and the residue was purified by pre-HPLC (Table 1, Method am) to provide 4-(3-acrylamidophenyl)-2-ethyl-1H-indole-7-carboxamide (9 mg, 38%): LC/MS (Table 1, Method d) R$_t$=2.91 min; MS m/z: 334 (M+H)$^+$. (Btk IC$_{50}$=A)

Example #21

4-(3-Amino-2-methylphenyl)-2-(4,4-difluorocyclohex-1-enyl)-1H-indole-7-carboxamide

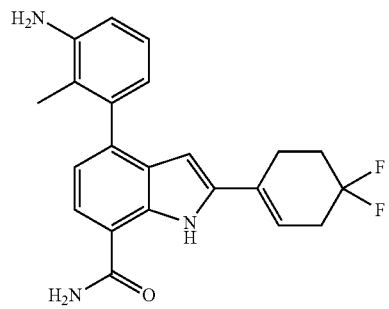 [SMILES: Cc1c(N)cccc1-c1ccc(C(N)=O)c2[nH]c(C3=CCC(F)(F)CC3)cc12]

Step A: 4-Bromo-2-(4,4-difluorocyclohex-1-en-1-yl)-1H-indole-7-carboxamide

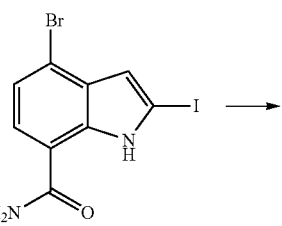

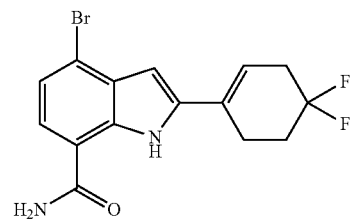

A mixture of 2-(4,4-difluorocyclohex-1-en-1-yl)-4,4,5,5-tetramethyl-1,3,2-dioxaborolane (0.267 g, 1.09 mmol, Syngene), 4-bromo-2-iodo-1H-indole-7-carboxamide (0.363 g, 0.995 mmol, Preparation #1), Na$_2$CO$_3$ (0.316 g, 2.98 mmol) in THF (7 mL), MeOH (0.98 mL), and water (0.98 mL) was added [1,1'-bis(diphenylphosphino)ferrocene]dichloropalladium(II) (0.073 g, 0.099 mmol). The mixture was bubbled with nitrogen and the vessel was sealed and heated at about 80° C. for about 4 h. The reaction was cooled to rt, filtered through Celite® and concentrated under reduced pressure. The residue was purified by silica gel column with EtOAc/hexanes (30-100%) to provide crude product which was further purified by silica gel column eluting with a gradient of 30-70% EtOAc/hexanes to provide 4-bromo-2-(4,4-difluoro cyclohex-1-en-1-yl)-1H-indole-7-carboxamide (0.25 g, 71%): LC/MS (Table 1, Method f) R$_t$=1.82 min; MS m/z: 357 (M+H)$^+$.

Step B: 4-(3-Amino-2-methylphenyl)-2-(4,4-difluorocyclohex-1-enyl)-1H-indole-7-carboxamide

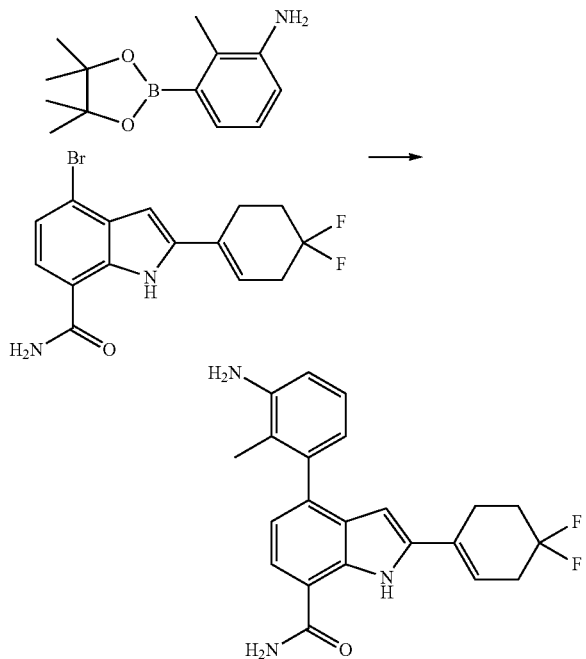

A mixture of 4-bromo-2-(4,4-difluorocyclohex-1-enyl)-1H-indole-7-carboxamide (0.48 g, 0.622 mmol), 2-methyl-3-(4,4,5,5-tetramethyl-1,3,2-dioxaborolan-2-yl)aniline (0.203 g, 0.870 mmol, Combi-Blocks), Na$_2$CO$_3$ (0.198 g, 1.865 mmol) and [1,1'-bis(diphenylphosphino)ferrocene]dichloropalladium(II) (0.045 g, 0.062 mmol) in THF (5 mL), MeOH (0.700 mL), and water (0.700 mL) was stirred at about 70° C. for about 16 h under a nitrogen atmosphere. The mixture was filtered through Celite® and concentrated under reduced pressure. The residue was passed through a silica gel column with EtOAc/heptane (50-75%) to provide the crude product. The crude product was triturated with DCM (2× with sonication for about 5 min), filtered, washed with DCM and dried under reduced pressure to provide 4-(3-amino-2-methylphenyl)-2-(4,4-difluorocyclohex-1-enyl)-1H-indole-7-carboxamide (134 mg, 57%): LC/MS (Table 1, Method f) R$_t$=1.36 min; MS m/z: 382 (M+H)$^+$. (Btk IC$_{50}$=A)

Example #22

4-(3-Acrylamidophenyl)-2-(2-ethoxyethyl)-1H-indole-7-carboxamide

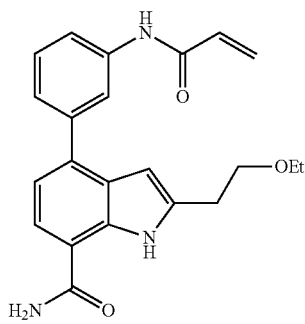 [SMILES: C=CC(=O)Nc1cccc(-c2ccc(C(N)=O)c3[nH]c(CCOCC)cc23)c1]

Step A: (E)-4-Bromo-2-(2-ethoxyvinyl)-1-((2-(trimethylsilyl)ethoxy)methyl)-1H-indole-7-carboxamide

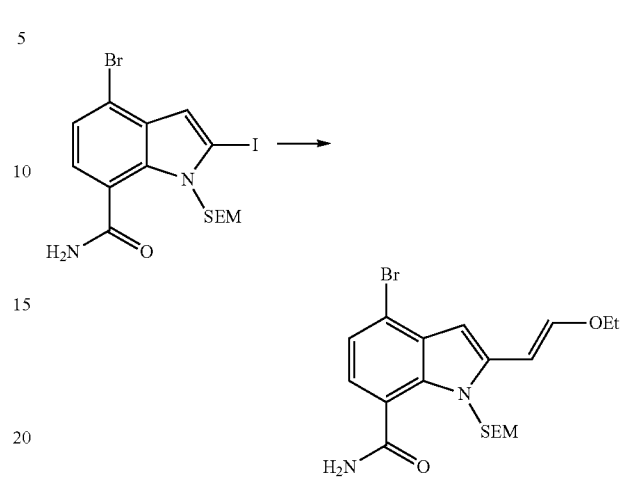

Five reaction vessels were charged with a solution of 4-bromo-2-iodo-1-((2-(trimethylsilyl)ethoxy)methyl)-1H-indole-7-carboxamide (1 g, 2.02 mmol, Preparation #24) in toluene (100 mL) was added (E)-tributyl(2-ethoxyvinyl)stannane (1.09 g, 3.03 mmol), Pd(PPh$_3$)$_2$Cl$_2$ (0.142 g, 0.202 mmol) and LiCl (0.428 g, 10.1 mmol). The mixtures were heated at about 90° C. overnight under N$_2$ atmosphere. All five reaction mixtures were combined, concentrated under reduced pressure, and the residue was purified by silica gel column to provide (E)-4-bromo-2-(2-ethoxyvinyl)-1-((2-(trimethylsilyl)ethoxy)methyl)-1H-indole-7-carboxamide (2 g, 45%) as a yellow solid: $^1$H NMR (DMSO-d6) δ 8.11 (s, 1H), 7.69 (s, 1H), 7.37-7.35 (d, J=8, 1H), 7.17-7.15 (d, J=8, 1H), 6.96 (s, 1H), 6.78-6.76 (d, J=8, 1H), 5.80-5.78 (d, J=8, 2H), 5.69-5.68 (d, J=4, 1H), 4.24-4.08 (m, 2H), 3.42-3.36 (m, 2H), 1.43-1.34 (m, 3H), 0.86-0.82 (m, 2H), 0.00 (s, 9H).

Step B: (E)-4-(3-Aminophenyl)-2-(2-ethoxyvinyl)-1-((2-(trimethylsilyl)ethoxy)methyl)-1H-indole-7-carboxamide

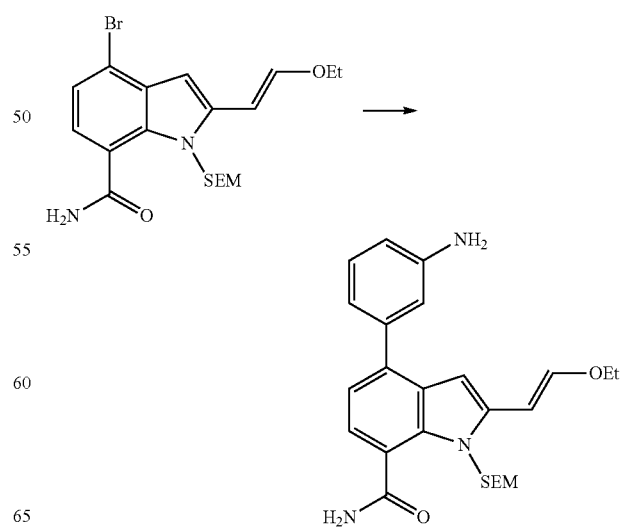

To a solution of (E)-4-bromo-2-(2-ethoxyvinyl)-14(2-(trimethylsilyl)ethoxy)methyl)-1H-indole-7-carboxamide (1.5 g, 3.41 mmol) in THF (20 mL), water (10 mL) and MeOH (10 mL) was added 3-(4,4,5,5-tetramethyl-1,3,2-dioxaborolan-2-yl)aniline (0.897 g, 4.10 mmol), Pd(dppf) Cl₂ (0.5 g, 0.683 mmol) and Na₂CO₃ (1.085 g, 10.24 mmol). The solution was heated at about 90° C. for about 2 h. The reaction mixture was concentrated under reduced pressure and purified by silica gel column to provide (E)-4-(3-aminophenyl)-2-(2-ethoxyvinyl)-1-((2-(trimethylsilyl)ethoxy)methyl)-1H-indole-7-carboxamide (0.80 g, 52%): ¹H NMR (DMSO-d6) δ 8.06 (s, 1H), 7.62 (s, 1H), 7.30-7.22 (m, 2H), 7.15 (s, 1H), 7.10-7.08 (d, J=8, 1H), 6.93 (s, 1H), 6.83-6.81 (d, J=8, 1H), 6.68-6.65 (m, 2H), 5.82-5.80 (d, J=8, 2H), 5.67-5.66 (d, J=4, 1H), 5.28 (s, 2H), 4.18-4.06 (m, 2H), 3.43-3.37 (m, 2H), 1.39-1.33 (m, 3H), 0.86-0.82 (m, 2H), 0.00 (s, 9H).

Step C: 4-(3-Aminophenyl)-2-(2-ethoxyethyl)-1-((2-(trimethylsilyl)ethoxy)methyl)-1H-indole-7-carboxamide

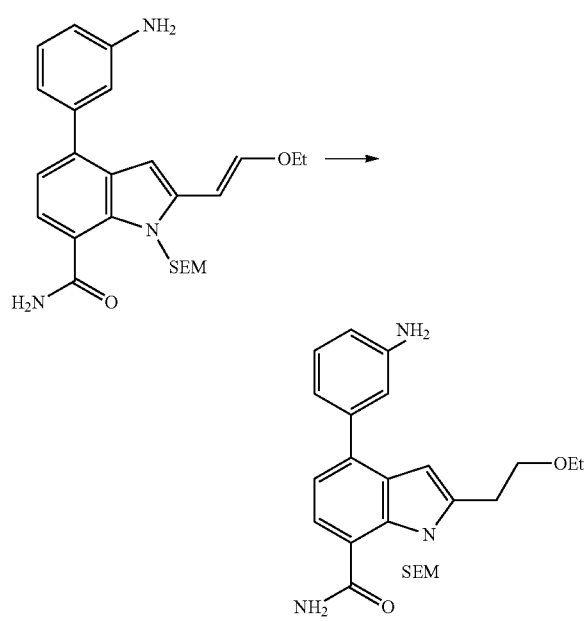

Two reaction vessels were charged with a solution of (E)-4-(3-aminophenyl)-2-(2-ethoxyvinyl)-1-((2-(trimethylsilyl)ethoxy)methyl)-1H-indole-7-carboxamide (400 mg, 0.886 mmol) in MeOH (60 mL), and Pd/C (400 mg, 10%). The mixtures were stirred for about 1 h at rt under H₂ (14 psi) atmosphere. The two reaction mixtures were combined, filtered and concentrated under reduced pressure to provide 4-(3-aminophenyl)-2-(2-ethoxyethyl)-1-((2-(trimethylsilyl)ethoxy)methyl)-1H-indole-7-carboxamide (600 mg, 75%) as a solid, which was used directly for the next step: ¹H NMR (DMSO-d6) δ 8.05 (s, 1H), 7.61 (s, 1H), 7.32-7.31 (d, J=4, 1H), 7.23-7.09 (m, 2H), 6.90 (s, 1H), 6.81-6.79 (d, J=8, 1H), 6.68-6.66 (d, J=8, 1H), 6.58 (s, 1H), 5.78 (s, 2H), 5.26 (s, 2H), 3.79-3.76 (m, 2H), 3.55-3.52 (m, 2H), 3.45-3.41 (m, 2H), 3.15-3.12 (m, 2H), 1.26-1.15 (m, 3H), 0.87-0.83 (m, 2H), 0.01 (s, 9H).

Step D: 4-(3-Aminophenyl)-2-(2-ethoxyethyl)-1H-indole-7-carboxamide

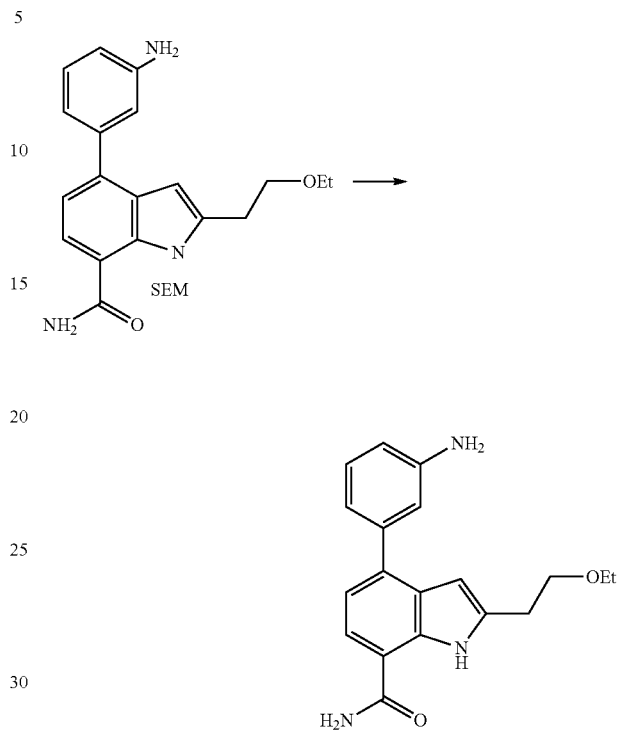

To a solution of 4-(3-aminophenyl)-2-(2-ethoxyethyl)-1-((2-(trimethylsilyl)ethoxy)methyl)-1H-indole-7-carboxamide (500 mg, 1.10 mmol) in THF (20 mL) was added TBAF (2.88 g, 11.0 mmol) and ethane-1,2-diamine (1.33 g, 22.0 mmol). The mixture was stirred for about 5 h at about 80° C. The reaction mixture was concentrated under reduced pressure, and the residue was purified by silica gel column to provide 4-(3-aminophenyl)-2-(2-ethoxyethyl)-1H-indole-7-carboxamide (267 mg, 75%) as a solid: ¹H NMR (DMSO-d6) δ 11.09 (s, 1H), 8.12 (s, 1H), 7.76-7.74 (d, J=8, 1H), 7.46-7.44 (d, J=8, 1H), 7.24-7.19 (m, 1H), 7.09-7.07 (d, J=8, 1H), 6.96 (s, 1H), 6.87-6.85 (d, J=8, 1H), 6.67-6.66 (d, J=4, 1H), 6.45 (s, 1H), 5.25 (s, 2H), 3.76-3.73 (m, 2H), 3.59-3.54 (m, 2H), 3.13-3.09 (m, 2H), 1.27-1.23 (m, 3H).

Step E: 4-(3-Acrylamidophenyl)-2-(2-ethoxyethyl)-1H-indole-7-carboxamide

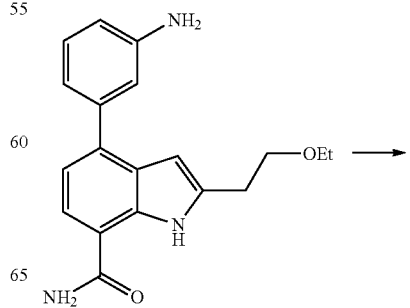

485
-continued

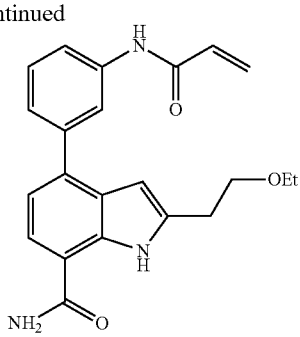

Two reaction vessels were charged with a solution of 4-(3-aminophenyl)-2-(2-ethoxyethyl)-1H-indole-7-carboxamide (60 mg, 0.186 mmol) in DCM (2 mL). DIEA (0.065 mL, 0.371 mmol) and acryloyl chloride (25.2 mg, 0.278 mmol) were added and the mixtures were stirred for about 1 h at rt. The two reaction mixtures were combined, concentrated under reduced pressure, and the residue was purified by prep-HPLC (Table 1, Method w) to provide 4-(3-acrylamidophenyl)-2-(2-ethoxyethyl)-1H-indole-7-carboxamide (21.6 mg, 26.4%) as a solid: LC/MS (Table 1, Method d) R$_f$=2.95 min; MS m/z: 378 (M–H). (Btk IC$_{50}$=A).

Example #23

4-(3-Acrylamidophenyl)-2-(2-hydroxyethyl)-1H-indole-7-carboxamide

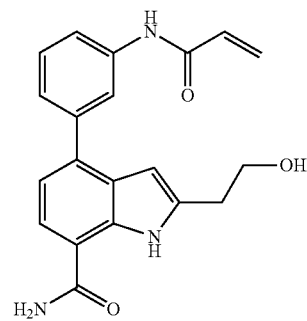 [SMILES: C=CC(=O)Nc1cccc(-c2ccc(C(N)=O)c3[nH]c(CCO)cc23)c1]

Step A: 4-(3-Aminophenyl)-2-(2-hydroxyethyl)-1H-indole-7-carboxamide

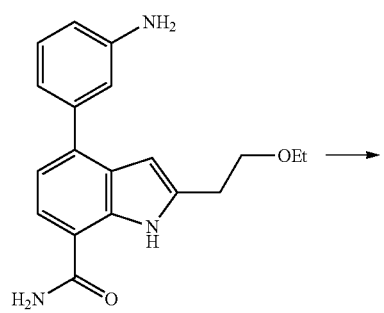

486
-continued

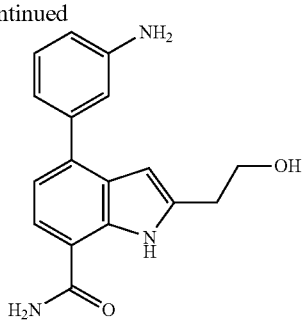

Two reaction vessels were charged with a solution of 4-(3-aminophenyl)-2-(2-ethoxyethyl)-1H-indole-7-carboxamide (100 mg, 0.309 mmol, Example #22, Step D) in DCM (10 mL) was added dropwise tribromoborane (387 mg, 1.55 mmol) at about –78° C. The mixtures were stirred for about 2 h at about 0° C. The two reaction mixtures were combined and aqueous NaHCO$_3$ was added and the mixture was extracted with DCM (100 mL×3). The organic phase was dried over Na$_2$SO$_4$, concentrated under reduced pressure to give 4-(3-aminophenyl)-2-(2-hydroxyethyl)-1H-indole-7-carboxamide (160 mg, 88%) as a yellow solid: $^1$H NMR (DMSO-d6) δ 10.96 (s, 1H), 8.04 (s, 1H), 7.67-7.65 (d, J=8, 1H), 7.38-7.34 (d, J=16, 1H), 7.16-7.12 (m, 1H), 7.01-6.99 (d, J=8, 1H), 6.91 (s, 1H), 6.81-6.80 (d, J=4, 1H), 6.62-6.59 (d, J=12, 1H), 6.36 (s, 1H), 5.33 (s, 2H), 4.87 (s, 1H), 3.73-3.70 (m, 2H), 2.96-2.93 (m, 2H).

Step B: 4-(3-Aminophenyl)-2-(2-hydroxyethyl)-1H-indole-7-carboxamide

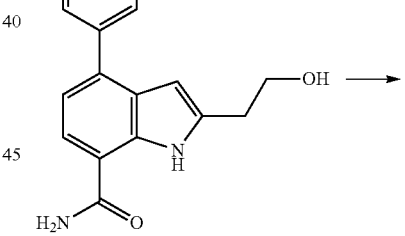

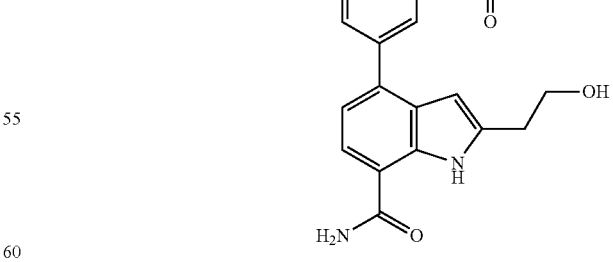

To a solution of 4-(3-aminophenyl)-2-(2-hydroxyethyl)-1H-indole-7-carboxamide (40 mg, 0.135 mmol) in pyridine (4 mL) was added EDCI (31 mg, 0.163 mmol) and acrylic acid (9.8 mg, 0.135 mmol). The mixture was stirred for about 3 h at about 110° C. The reaction mixture was concentrated under reduced pressure and the residue was purified by prep-HPLC (Table 1, Method al) to provide 4-(3-acrylamidophenyl)-2-(2-hydroxyethyl)-1H-indole-7-carboxamide (4.5 mg, 10%) as a solid: LC/MS (Table 1, Method j) $R_t$=2.46 min; MS m/z: 350 (M+H)$^+$. (Btk IC$_{50}$=A)

Example #24

4-((1-Acryloylazetidin-3-yl)(methyl)amino)-1H-indole-7-carboxamide

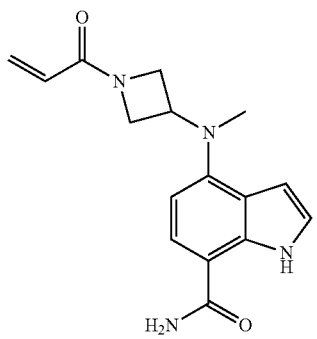 [SMILES: C=CC(=O)N1CC(N(C)c2ccc(C(N)=O)c3[nH]ccc23)C1]

Step A: tert-Butyl-3-((7-cyano-1H-indol-4-yl)amino)azetidine-1-carboxylate

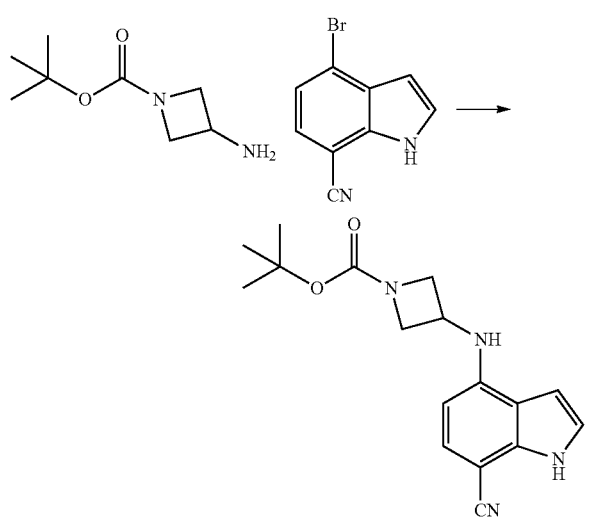

In a 4 mL reaction vial, 4-bromo-1H-indole-7-carbonitrile (200 mg, 0.905 mmol, Sinova), chloro[2-(dicyclohexylphosphino)-3,6-dimethoxy-2',4',6'-triisopropyl-1,1'-biphenyl][2-(2-amino-ethyl)phenyl]palladium(II) (9.03 mg, 0.011 mmol), and dicyclohexyl(2',4',6'-triisopropyl-3,6-dimethoxy-[1,1'-biphenyl]-2-yl)phosphine (6.07 mg, 0.011 mmol) were added. The solid mixture was evacuated and backfilled with nitrogen. Lithium bis(trimethylsilyl)amide (2.17 mL, 2.17 mmol) was added followed by tert-butyl-3-aminoazetidine-1-carboxylate (170 µl, 1.09 mmol). The reaction mixture was heated at about 65° C. for about 2.5 h.

The reaction mixture was quenched with a few drops of 1N HCl and diluted with EtOAc (10 mL). The EtOAc layer was washed with a saturated aqueous solution of NaHCO$_3$ and dried over MgSO$_4$, filtered and concentrated under vacuum. The crude material was purified via flash chromatography, using a gradient of 5-40% EtOAc in heptane to give tert-butyl-3-((7-cyano-1H-indol-4-yl)amino)azetidine-1-carboxylate (160 mg, 57%); LC/MS (Table 1, Method as) $R_t$=2.13 min.; MS m/z: 311 (M–H).

Step B: tert-Butyl 4-((1-(tert-butoxycarbonyl)azetidin-3-yl)amino)-7-cyano-1H-indole-1-carboxylate

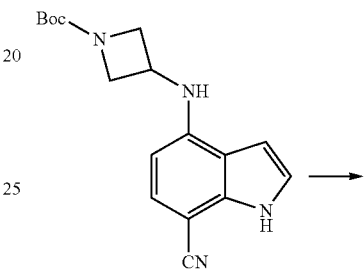

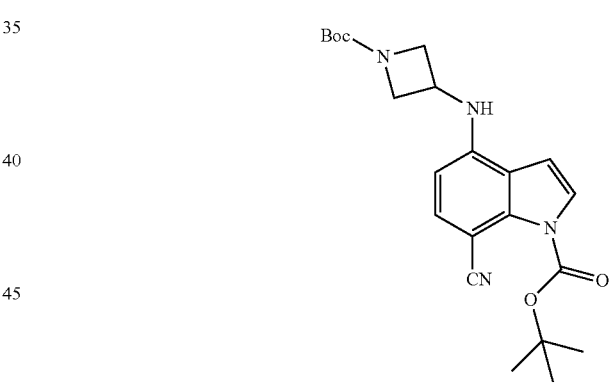

In a 100 mL round-bottomed flask, tert-butyl 3-((7-cyano-1H-indol-4-yl)amino)azetidine-1-carboxylate (200 mg, 0.640 mmol) in MeCN (5 mL) was added to give a brown solution. DMAP (15.6 mg, 0.128 mmol) and BOC$_2$O (419 mg, 1.92 mmol) were added. Reaction mixture was stirred for about 18 h at rt. Reaction mixture was diluted with water (2 mL) and EtOAC (3 mL). The entire suspension was filtered and washed with EtOAc (5 mL). The white precipitate collected was dried in a vacuum oven at about 70° C. for about 2 h to give tert-Butyl 4-((1-(tert-butoxycarbonyl)azetidin-3-yl)amino)-7-cyano-1H-indole-1-carboxylate (154 mg, 58.3%). LC/MS (Table 1, Method as) $R_t$=2.54 min; MS m/z: 411 (M–H).

Step C: tert-Butyl-44(1-(tert-butoxycarbonyl)azetidin-3-yl)(methyl)amino)-7-cyano-1H-indole-1-carboxylate

Step D: tert-Butyl 3-((7-carbamoyl-1H-indol-4-yl)(methyl)amino)azetidine-1-carboxylate

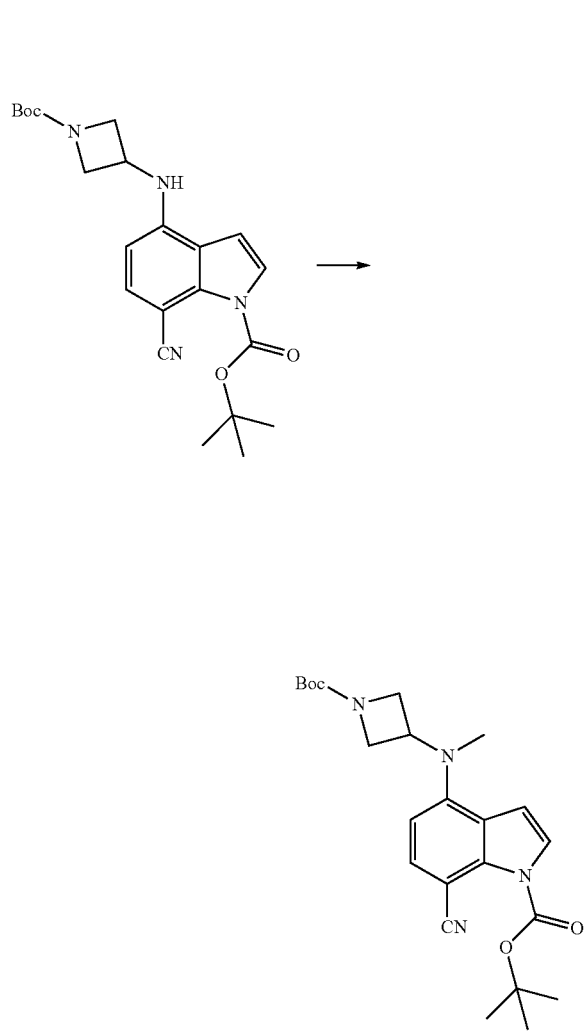

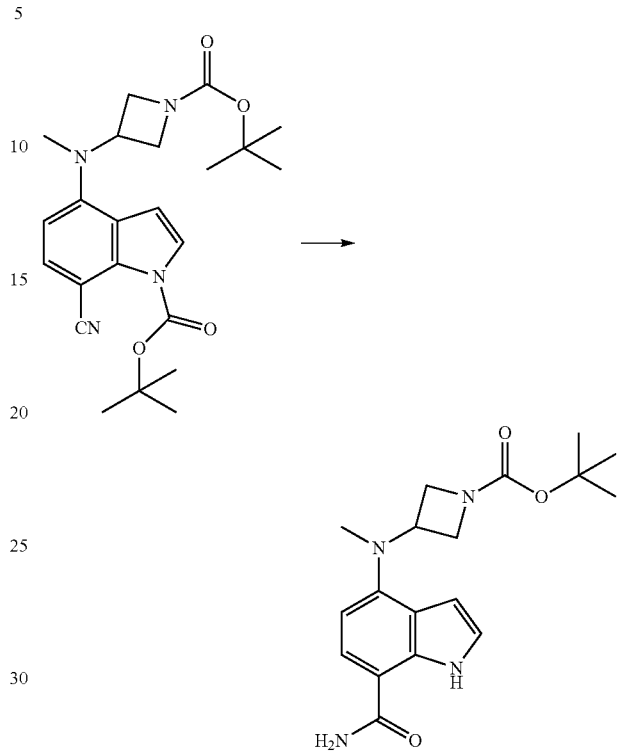

In a 4 mL reaction vial, sodium hydride (23.9 mg, 0.598 mmol, 60% disp in mineral oil) in DMF (1 mL) was added to give a white suspension. Reaction mixture was cooled to about 0° C. and tert-butyl 4-((1-(tert-butoxycarbonyl)azetidin-3-yl)amino)-7-cyano-1H-indole-1-carboxylate (145 mg, 0.352 mmol) was added as a solution in DMF (4 mL). After about 30 min, iodomethane (33 μl, 0.528 mmol) was added. Stirring was continued at 0° C. for about 1 h. The reaction was quenched with water (15 mL) and extracted with EtOAc (20 mL). The organic layer was dried over MgSO4, filtered and concentrated. The material was purified via flash chromatography using a gradient of 0-25% EtOAc/heptane over 5 min, then held at 25% EtOAc/heptane for 5 min, to give crude tert-Butyl-4-((1-(tert-butoxycarbonyl)azetidin-3-yl)(methyl)amino)-7-cyano-1H-indole-1-carboxylate (148 mg, 71.1%); LC/MS (Table 1, Method as) $R_t$=2.71 min; MS m/z: 427 (M+H)$^+$.

To a solution of tert-butyl 4-((1-(tert-butoxycarbonyl)azetidin-3-yl)(methyl)amino)-7-cyano-1H-indole-1-carboxylate (148 mg, 0.250 mmol) in ethanol (2 mL)/DMSO (0.500 mL) was added hydrogen peroxide (0.515 mL, 5.04 mmol) and NaOH (1M, 0.515 mL, 0.515 mmol). The reaction mixture was stirred at rt for about 2 h. To the reaction mixture was added water (5 mL) and the precipitate was collected via filtration, washed with water (5 mL) and dried in a vacuum oven at about 70° C. for about 2 h to give tert-Butyl 3-((7-carbamoyl-1H-indol-4-yl)(methyl)amino)azetidine-1-carboxylate (60 mg, 52%); LC/MS (Table 1, Method as) $R_t$=1.97 min; MS m/z: 345 (M+H)$^+$.

Step E: 4-(Azetidin-3-yl(methyl)amino)-1H-indole-7-carboxamide

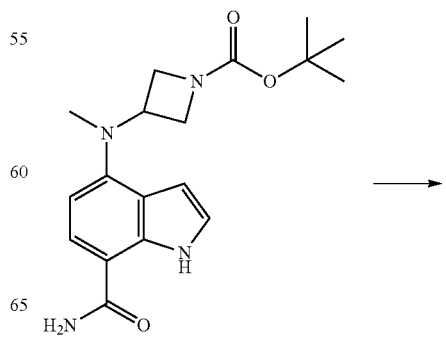

-continued

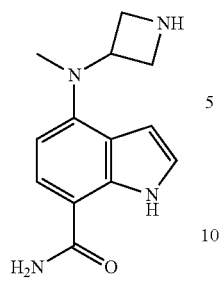

In a 4 mL reaction vial, tert-butyl 3-((7-carbamoyl-1H-indol-4-yl)(methyl)amino)azetidine-1-carboxylate (60 mg, 0.129 mmol) in 1,4-dioxane (2 mL) was added to give an off-white solution. 4M HCl in dioxane (0.129 mL, 0.516 mmol) was added. Reaction was stirred at rt for about 2 h. It was the warmed to about 50° C. for about 2 h. Additional 4M HCl in dioxane (0.129 mL, 0.516 mmol) was added and stirring was continued at about 50° C. for about 45 min Reaction mixture was filtered and washed with DCM to give a precipitate. The precipitate was dissolved in water (2 mL) and basified with a few drops of 5N aqueous NaOH solution. The aqueous layer was then extracted with DCM (2×7 mL) and EtOAC (2×8 mL). The organic layers were combined and dried over MgSO$_4$, filtered and concentrated to give 4-(azetidin-3-yl(methyl)amino)-1H-indole-7-carboxamide (29 mg, 66%); LC/MS (Table 1, Method as) R$_t$=0.73 min; MS m/z: 245 (M+H)$^+$.

Step F: 4-((1-Acryloylazetidin-3-yl)(methyl)amino)-1H-indole-7-carboxamide

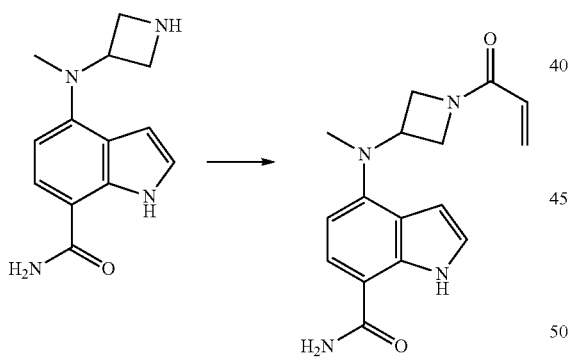

A flask was charged with 4-(azetidin-3-yl(methyl)amino)-1H-indole-7-carboxamide (28 mg, 0.083 mmol) and N-ethyl-N-isopropylpropan-2-amine (65 µl, 0.373 mmol) in DCM (5 mL). The mixture was cooled to 0° C. on an ice-bath. Acryloyl chloride (7.38 µl, 0.091 mmol) was added and the mixture stirred to about 20 min. Reaction mixture was concentrated. The material was purified via flash chromatography using a gradient of 1.0-3.3% MeOH/DCM over 7 min then held at 3.3% for 5 min to give 4-((1-Acryloylazetidin-3-yl)(methyl)amino)-1H-indole-7-carboxamide (10.5 mg, 43%); LC/MS (Table 1, Method a) R$_t$=1.31 min; MS m/z: 299 (M+H)$^+$. (Btk IC$_{50}$=A)

Example #25

4-(1-Acryloylpiperidin-3-yl)-1H-indole-7-carboxamide

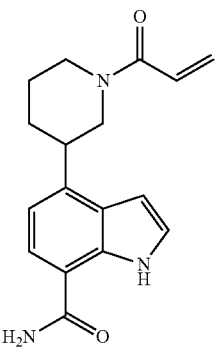

Step A: tert-Butyl 3-(7-carbamoyl-1H-indol-4-yl)-5,6-dihydropyridine-1(2H)-carboxylate

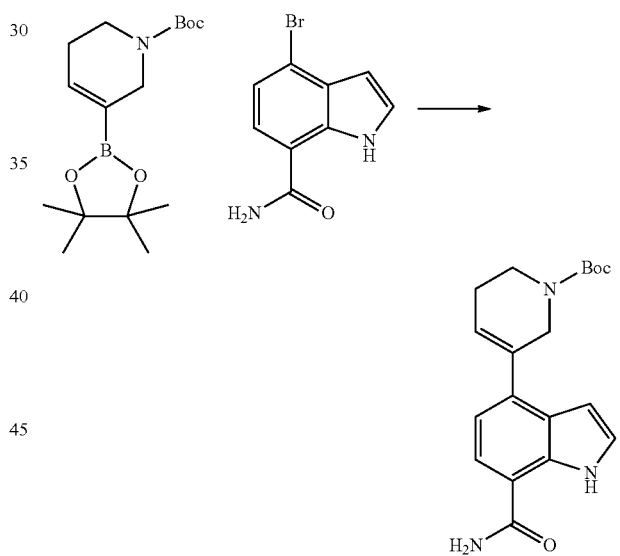

A 20 mL vial was charged with 4-bromo-1H-indole-7-carboxamide (300 mg, 1.255 mmol), tert-butyl 3-(4,4,5,5-tetramethyl-1,3,2-dioxaborolan-2-yl)-5,6-dihydropyridine-1(2H)-carboxylate (466 mg, 1.506 mmol), (1,1-bis(diphenylphosphino)ferrocene)dichloropalladium (92 mg, 0.125 mmol) and sodium carbonate (399 mg, 3.76 mmol). To the solid mixture was added THF (6 mL):MeOH (0.840 mL):Water (0.840 mL). The suspension was sparged with nitrogen for about 5 min. The reaction mixture was heated at about 70° C. overnight. Reaction mixture was filtered over a pad of Celite®, concentrated and purified by silica gel column (30-60% EtOAc/heptane) to give tert-butyl 3-(7-carbamoyl-1H-indol-4-yl)-5,6-dihydropyridine-1(2H)-carboxylate (355 mg, 83%); LC/MS (Table 1, Method as) R$_t$=2.14 min; MS m/z: 340 (M−H).

Step B: tert-Butyl 3-(7-carbamoyl-1H-indol-4-yl)piperidine-1-carboxylate

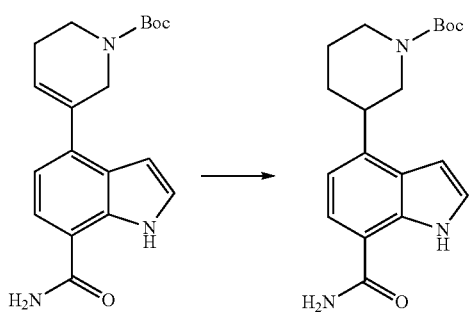 [SMILES: CC(C)(C)OC(=O)N1CCC=C(c2ccc(C(N)=O)c3[nH]ccc23)C1 ; CC(C)(C)OC(=O)N1CCCC(c2ccc(C(N)=O)c3[nH]ccc23)C1]

A flask was charged tert-butyl 3-(7-carbamoyl-1H-indol-4-yl)-5,6-dihydropyridine-1(2H)-carboxylate (355 mg, 1.04 mmol) and palladium (55.3 mg, 0.520 mmol). Ethyl acetate (10 mL) was added under vacuum and the mixture was stirred under $H_2$ balloon at rt for about 5 h. The reaction mixture was filtered over a pad of Celite® and washed with MeOH (20 mL) and EtOAc (30 mL). The filtrate was concentrated under reduced pressure to give tert-Butyl 3-(7-carbamoyl-1H-indol-4-yl)piperidine-1-carboxylate (357 mg, 100%); LC/MS (Table 1, Method as) $R_t$=2.14 min; MS m/z: 342 (M−H).

Step C: 4-(Piperidin-3-yl)-1H-indole-7-carboxamide

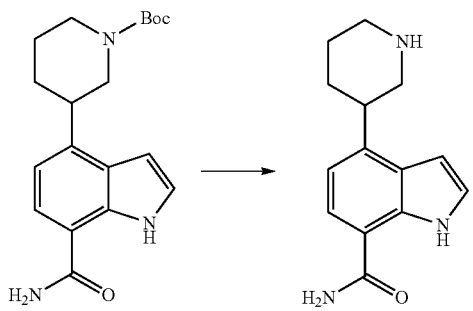 [SMILES: CC(C)(C)OC(=O)N1CCCC(c2ccc(C(N)=O)c3[nH]ccc23)C1 ; NC(=O)c1ccc(C2CCCNC2)c2cc[nH]c12]

A flask was charged with Methanol (5 mL) and cooled to 0° C. Acetyl chloride (0.828 mL, 11.6 mmol) was added drop wise, and the ice bath was removed. The mixture was stirred at rt for about 25 min. The solution was then added to tert-butyl 3-(7-carbamoyl-1H-indol-4-yl)piperidine-1-carboxylate (100 mg, 0.291 mmol) and the reaction mixture was stirred at rt for about 4 h. The mixture was concentrated under vacuum. The residue was dissolved in water (10 mL) and washed with EtOAc (7 mL). The aqueous layer was basified with a few of drops of 50% w/w NaOH solution and extracted with EtOAC (12 mL). The EtOAc layer was dried over MgSO4, filtered and concentrated to give 4-(Piperidin-3-yl)-1H-indole-7-carboxamide (40 mg, 56%); the material was used crude in the next step without further characterization.

Step D: 4-(1-Acryloylpiperidin-3-yl)-1H-indole-7-carboxamide

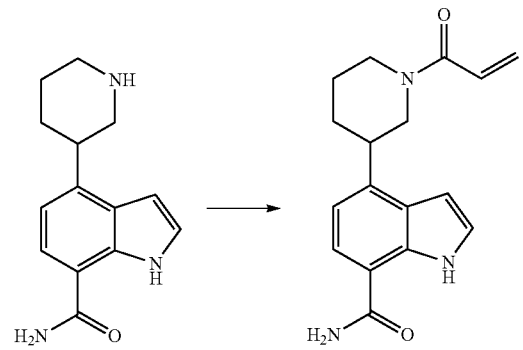 [SMILES: NC(=O)c1ccc(C2CCCNC2)c2cc[nH]c12 ; C=CC(=O)N1CCCC(c2ccc(C(N)=O)c3[nH]ccc23)C1]

A flask was charged with 4-(piperidin-3-yl)-1H-indole-7-carboxamide (40 mg, 0.164 mmol) and N-ethyl-N-isopropylpropan-2-amine (43 μL, 0.247 mmol) in DCM (5 mL). The mixture was cooled to 0° C. Acryloyl chloride (14.69 μL, 0.181 mmol) was added and the mixture stirred for about 20 min Reaction mixture was concentrated. The material was purified by silica gel column using a gradient of 1.0-5.5% MeOH/$CH_2Cl_2$ over 10 min; to give 4-(1-Acryloylpiperidin-3-yl)-1H-indole-7-carboxamide (41 mg, 84%); LC/MS (Table 1, Method a) $R_t$=1.53 min; MS m/z: 298 (M+H)⁺. (Btk $IC_{50}$=B)

Example #26

4-(1-Acryloylpiperidin 3-yl)-2-(1-methyl-1H-pyrazol-4-yl)-1H-indole-7-carboxamide

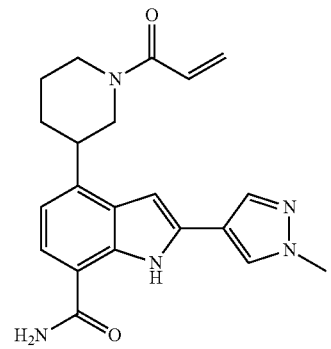

Step A: tert-Butyl 3-(7-carbamoyl-2-(1-methyl-1H-pyrazol-4-yl)-1H-indol-4-yl)-5,6-dihydropyridine-1(2H)-carboxylate

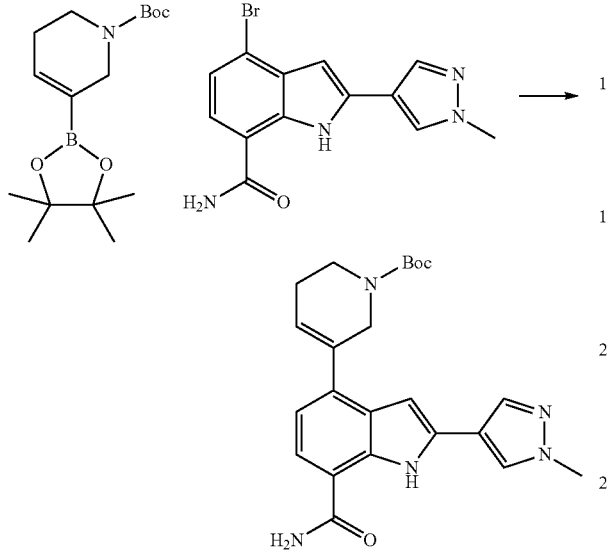

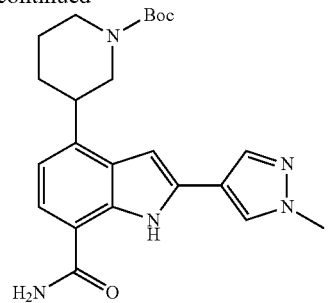

A 20 mL vial was charged with 4-bromo-2-(1-methyl-1H-pyrazol-4-yl)-1H-indole-7-carboxamide (216 mg, 0.677 mmol, Preparation #10), tert-butyl 3-(4,4,5,5-tetramethyl-1,3,2-dioxaborolan-2-yl)-5,6-dihydropyridine-1(2H)-carboxylate (251 mg, 0.812 mmol), (1,1-Bis(diphenylphosphino)ferrocene)dichloropalladium(1:1) complex with DCM (55.3 mg, 0.068 mmol) and sodium carbonate (215 mg, 2.03 mmol). To the solid mixture was added THF (3 mL):MeOH (0.420 mL):Water (0.420 mL). The suspension was sparged with N₂ for about 5 min. The reaction mixture was heated at about 70° C. overnight. Reaction mixture was filtered over a pad of celite, concentrated and was purified by silica gel column (0-2% MeOH/DCM) to give tert-butyl 3-(7-carbamoyl-2-(1-methyl-1H-pyrazol-4-yl)-1H-indol-4-yl)-5,6-dihydropyridine-1(2H)-carboxylate (227 mg, 80%); LC/MS (Table 1, Method as) $R_t$=2.09 min; MS m/z: 422 (M+H)⁺.

Step B: tert-butyl 3-(7-carbamoyl-2-(1-methyl-1H-pyrazol-4-yl)-1H-indol-4-yl)piperidine-1-carboxylate

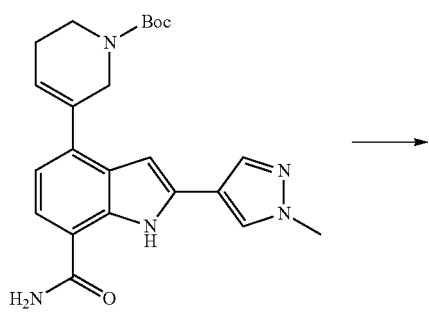

A flask was charged with tert-butyl 3-(7-carbamoyl-2-(1-methyl-1H-pyrazol-4-yl)-1H-indol-4-yl)-5,6-dihydropyridine-1(2H)-carboxylate (227 mg, 0.539 mmol) and 10% palladium on carbon (28.7 mg, 0.027 mmol). Ethyl acetate (5 mL) was added under vacuum and the mixture was stirred under H₂ balloon at rt for about 5 h. The reaction mixture was filtered over a pad of Celite® and washed with MeOH (20 mL) and EtOAc (30 mL). The filtrate was concentrated under reduced pressure to give the title compound (177 mg, 78%); LC/MS (Method as) $R_t$=2.08 min; MS m/z: 424 (M+H)⁺.

Step C: 2-(1-Methyl-1H-pyrazol-4-yl)-4-(piperidin-3-yl)-1H-indole-7-carboxamide

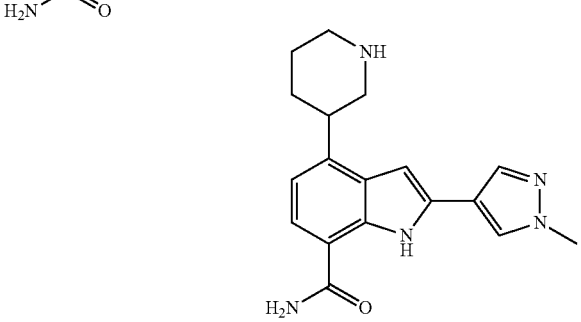

A flask was charged with MeOH (2 mL) and cooled to 0° C. Acetyl chloride (0.151 mL, 2.12 mmol) was added drop wise, and the ice bath was removed. The mixture was stirred at rt for about 25 min. The solution was then added to tert-butyl 3-(7-carbamoyl-2-(1-methyl-1H-pyrazol-4-yl)-1H-indol-4-yl)piperidine-1-carboxylate (30 mg, 0.071 mmol) and the reaction mixture was stirred at rt overnight. The mixture was concentrated under vacuum. The residue was dissolved in water (3 mL) and washed with DCM (3 mL). The aqueous layer was basified with a few drops of 5N NaOH to give a suspension, to which was added DCM. The DCM layer was separated. The aqueous layer formed a precipitate which was collected via filtration and washed with a mixture of DCM/EtOAC/MeOH (1:1:1) (6 mL). This filtrate was combined with the DCM layer and concentrated under vacuum to give 2-(1-methyl-1H-pyrazol-4-yl)-4-(piperidin-3-yl)-1H-indole-7-carboxamide (18 mg, 79%); LC/MS (Table 1, Method as) R$_t$=1.03 min; MS m/z: 324 (M+H)$^+$.

Step D: 4-(1-Acryloylpiperidin 3-yl)-2-(1-methyl-1H-pyrazol-4-yl)-1H-indole-7-carboxamide

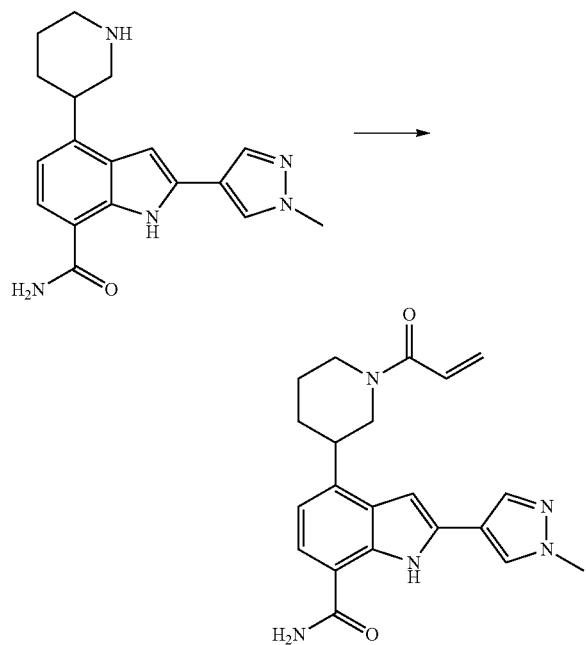

A flask was charged with 2-(1-methyl-1H-pyrazol-4-yl)-4-(piperidin-3-yl)-1H-indole-7-carboxamide (18 mg, 0.056 mmol) and N-ethyl-N-isopropylpropan-2-amine (0.044 mL, 0.250 mmol) in DCM (5 mL). The mixture was cooled to 0° C. on an ice-bath. Acryloyl chloride (4.97 µl, 0.061 mmol) was added and the mixture stirred for about 20 min Reaction mixture was concentrated. The material was purified by silica gel column (2.0-6.5% MeOH/DCM) to give 4-(1-acryloylpiperidin 3-yl)-2-(1-methyl-1H-pyrazol-4-yl)-1H-indole-7-carboxamide (9 mg, 43%); LC/MS (Table 1, Method a) R$_t$=1.56 min; MS m/z: 378 (M+H)$^+$. (Btk IC$_{50}$=A)

Example #27

4-((1-Acryloylazetidin-3-yl)oxy)-1H-indole-7-carboxamide

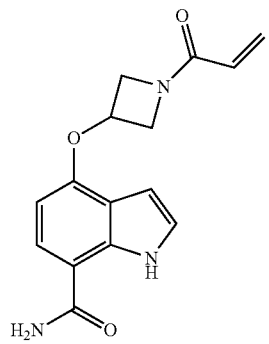 [SMILES: C=CC(=O)N1CC(Oc2ccc(C(N)=O)c3[nH]ccc23)C1]

Step A: tert-butyl 3-(4-bromo-3-nitrophenoxy)azetidine-1-carboxylate

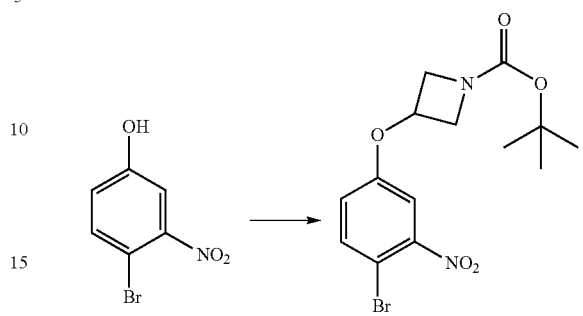

Cesium carbonate (2.038 g, 6.26 mmol) was added in DMF (12 mL) to give a white suspension. Molecular sieves (4 Å, 8-12 mesh, beads, 100 mg) 4-bromo-3-nitrophenol (1 g, 4.59 mmol) and tert-butyl 3-((methylsulfonyl)oxy)azetidine-1-carboxylate (1.048 g, 4.17 mmol) were added, and the mixture was heated at about 85° C. for about 18 h. The crude mixture was partitioned between EtOAc (50 mL) and saturated aqueous ammonium chloride solution (30 mL). The organic layer was washed by brine (30 mL), dried over sodium sulfate, filtered and concentrated to afford tert-butyl 3-(4-bromo-3-nitrophenoxy)azetidine-1-carboxylate (0.799 g, 2.14 mmol, 46.7% yield): LC/MS (Table 1, Method a) R$_t$=2.62 min; MS m/z 373, 375 (M+H)$^+$.

Step B: tert-butyl 3-((7-bromo-1H-indol-4-yl)oxy)azetidine-1-carboxylate

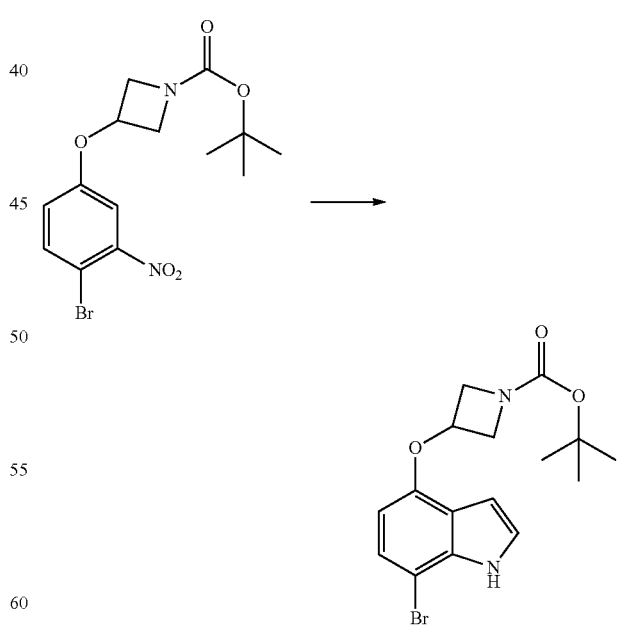

A 100 mL round-bottom flask was degassed with nitrogen and cooled to about −70° C. in a dry-ice/acetone bath. A solution of vinylmagnesium bromide in THF (1.0 M, 21.59 mL, 21.59 mmol) was added into the flask. Then a solution of tert-butyl 3-(4-bromo-3-nitrophenoxy)azetidine-1-carboxylate (2.65 g, 5.40 mmol) in 2-methyl-THF (18 mL) was added dropwise over 8 min, the mixture was stirred at about −70° C. for about 1 h, and the reaction mixture was quenched by saturated aqueous ammonium chloride solution (22 mL) at about −60° C. The resulting mixture was warmed to rt and EtOAc (50 mL) and water (40 mL) were added. The layers were separated, the aqueous layer was extracted with EtOAc (50 mL), the combined organic layers were washed with brine (50 mL), dried over sodium sulfate, filtered and concentrated to afford an orange oil, which was purified by silica gel chromatography eluting with a gradient of 0 to 40% EtOAc/heptane to afford tert-butyl 3-((7-bromo-1H-indol-4-yl)oxy)azetidine-1-carboxylate (0.87 g, 2.37 mmol, 43.9% yield): LC/MS (Table 1, Method a) $R_t$=2.52 min; MS m/z 367, 369 (M+H)⁺.

Step C: tert-butyl 3-((7-cyano-1H-indol-4-yl)oxy)azetidine-1-carboxylate

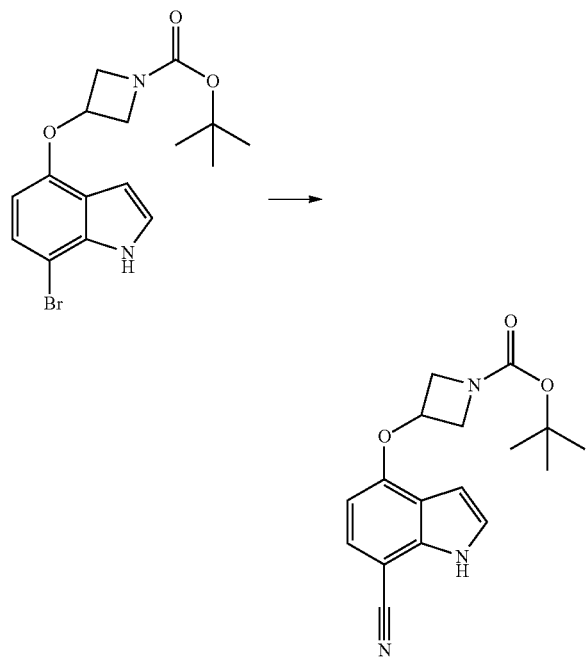

In a 20 mL microwave reaction vial, tert-butyl 3-((7-bromo-1H-indol-4-yl)oxy)azetidine-1-carboxylate (0.8 g, 2.178 mmol), zinc cyanide (0.512 g, 4.36 mmol) and DMF (12 mL) were added to give a yellow suspension. The vial was degassed with nitrogen, tetrakis(triphenylphosphine)palladium(0) (0.755 g, 0.654 mmol) was added. The mixture was degassed with nitrogen, and then the reaction mixture was heated in a Biotage® microwave reactor at about 160° C. for about 30 min (2 psi maximum pressure, 235 max watts). The resulting orange suspension was filtered through Celite®, washed with DMF (10 mL) and 2-methyl-THF (3×10 mL), the filtrate was concentrated in vacuo to remove most DMF, then it was partitioned between 2-methyl-THF (50 mL) and saturated aqueous ammonium chloride solution (50 mL). The organic layer was washed with water (30 mL) and brine (30 mL), dried over sodium sulfate, filtered and concentrated to afford an orange oil, which was purified by silica gel chromatography eluting with a gradient of 0 to 50% EtOAc/heptane to afford tert-butyl 3-((7-cyano-1H-indol-4-yl)oxy)azetidine-1-carboxylate (0.28 g, 0.894 mmol, 41.0% yield): LC/MS (Table 1, Method a) $R_t$=2.29 min; MS m/z 314 (M+H)⁺.

Step D: 4-((1-acryloylazetidin-3-yl)oxy)-1H-indole-7-carboxamide

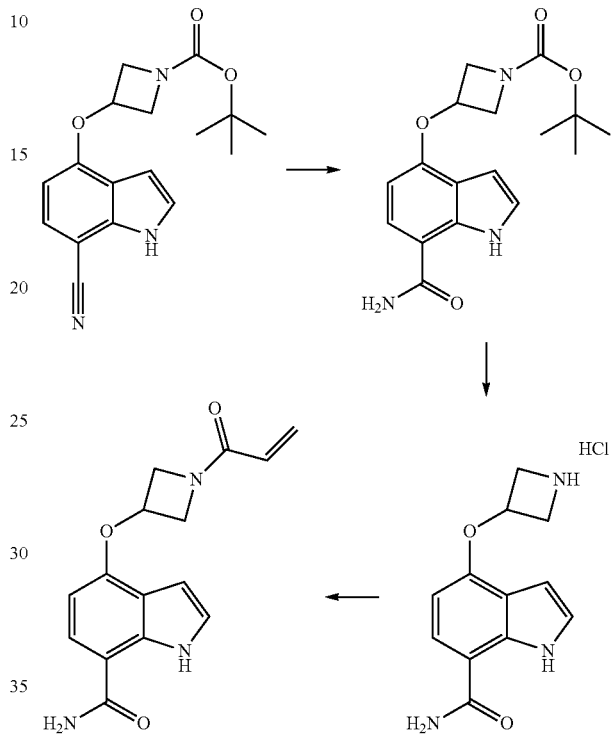

A mixture of tert-butyl 3-((7-cyano-1H-indol-4-yl)oxy)azetidine-1-carboxylate (0.28 g, 0.894 mmol) and potassium carbonate (0.309 g, 2.234 mmol) in DMSO (2.98 mL) was cooled to about 10° C. by ice-cold water bath, then hydrogen peroxide (0.091 ml, 0.894 mmol) was added dropwise. The reaction mixture was stirred at rt for about 18 h, hydrogen peroxide (0.023 mL, 0.225 mmol) was added. The reaction mixture was stirred at rt for about an additional 9 h. Water (30 mL) was added to the reaction mixture and the mixture was extracted with EtOAc (2×30 mL) and the combined organic layers were dried over sodium sulfate, filtered and concentrated to afford the crude tert-butyl 34(7-carbamoyl-1H-indol-4-yl)oxy)azetidine-1-carboxylate, which was used directly in the next step. To a suspension of tert-butyl 3((7-carbamoyl-1H-indol-4-yl)oxy)azetidine-1-carboxylate (0.27 g, 0.815 mmol) in MeOH (4.45 mL) was added hydrogen chloride (4.0 M in dioxane, 4.07 mL, 16.30 mmol) dropwise, the mixture was stirred at rt for about 30 min, then the mixture was concentrated in vacuo to afford the crude 4-(azetidin-3-yloxy)-1H-indole-7-carboxamide hydrochloride, which was used directly in the next step.

The suspension of 4-(azetidin-3-yloxy)-1H-indole-7-carboxamide hydrochloride (0.218 g, 0.815 mmol) in DCM (13.0 mL) was cooled to about −10° C. in an ice/sodium chloride bath, TEA (0.568 mL, 4.08 mmol) was added dropwise; then a solution of acryloyl chloride (0.075 mL, 0.897 mmol) in DCM (3.26 mL) was added dropwise via syringe and the reaction mixture was stirred for about 30 min. The reaction mixture was concentrated in vacuo, the crude material was purified by silica gel chromatography eluting with a gradient of 0 to 10% MeOH/DCM to afford 4-((1-acryloylazetidin-3-yl)oxy)-1H-indole-7-carboxamide (0.16 g, 0.555 mmol, 68.1% yield): LC/MS (Table 1, Method a) $R_t$=1.37 min; MS m/z 286 (M+H)$^+$. (Btk IC$_{50}$=A)

Example #28*

(S)-4-(1-(1-Acryloylazetidin-3-yl)ethyl)-1H-indole-7-carboxamide and (R)-4-(1-(1-acryloylazetidin-3-yl)ethyl)-1H-indole-7-carboxamide

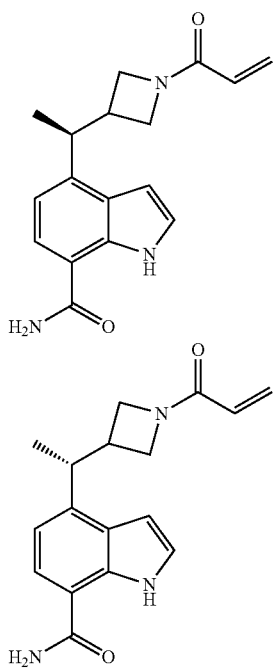

Step A: tert-butyl 3-(1-(((trifluoromethyl)sulfonyl)oxy)vinyl)azetidine-1-carboxylate and tert-butyl 3-(1-(((trifluoromethyl)sulfonyl)oxy)ethylidene)azetidine-1-carboxylate

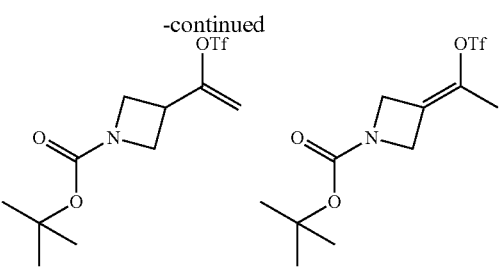

To a solution of diisopropylamine (0.646 mL, 4.57 mmol) in THF (3.8 mL) at about 0° C. was added a solution of n-butyllithium (2 M in hexanes) (2.28 mL, 4.57 mmol) dropwise (internal temperature maintained below about 3° C.). The reaction mixture was stirred at about 0° C. for about 30 min, and was cooled down to about −78° C. A solution of tert-butyl 3-acetylazetidine-1-carboxylate (0.758 g, 3.81 mmol) in THF (7.6 mL) was added dropwise (keeping the internal temperature below about −70° C.), and reaction mixture was then stirred at about −78° C. for about 30 min. A solution of 1,1,1-trifluoro-N-phenyl-N-fitrifluoromethyl-isulfonyfimethanesulfonamide (1.42 g, 4.00 mmol) in THF (7.6 mL) was added dropwise (keeping the internal temperature below about −70° C.). After addition, the mixture was allowed to warm to about 0° C. over about 4 h, and the reaction mixture was quenched with saturated NH$_4$Cl and extracted with EtOAc (3×50 mL), concentrated and purified by silica gel chromatography eluting with a gradient of 0-15% EtOAc/heptane to afford a mixture of tert-butyl 3-(1-(((trifluoromethyl)sulfonyl)oxy)vinyl)azetidine-1-carboxylate and tert-butyl 3-(1-(((trifluoromethyl)sulfonyl)oxy)ethylidene)azetidine-1-carboxylate as a yellow oil (0.398 g, 31%): $^1$H NMR (400 MHz, CDCl$_3$) tert-butyl 3-(1-(((trifluoromethyl)sulfonyl)oxy)vinyl)azetidine-1-carboxylate: δ 5.32 (d, J=4.2 Hz, 1H), 5.16 (dd, J=4.2, 1.0 Hz, 1H), 4.15 (t, J=8.8 Hz, 2H), 3.93 (dd, J=8.8, 6.1 Hz, 2H), 3.49-3.37 (m, 1H), 1.44 (s, 9H); tert-butyl 3-(1-(((trifluoromethyl)sulfonyl)oxy)ethylidene)azetidine-1-carboxylate: δ 4.58-4.53 (m, 2H), 4.52-4.49 (m, 2H), 1.98-1.94 (m, 3H), 1.45 (s, 9H)

Step B: tert-butyl 3-(1-(7-carbamoyl-1H-indol-4-yl)vinyl)azetidine-1-carboxylate and tert-butyl 3-(1-(7-carbamoyl-1H-indol-4-yl)ethylidene)azetidine-1-carboxylate

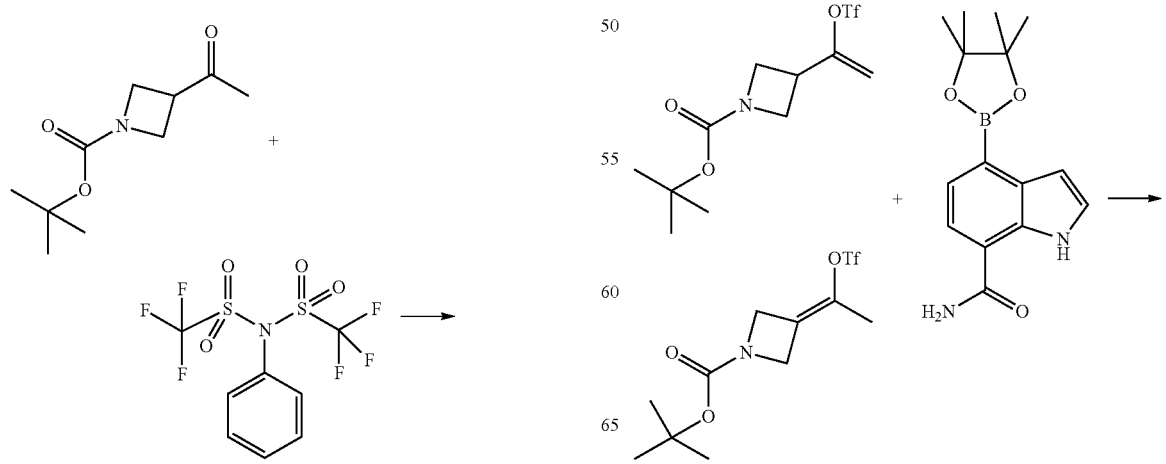

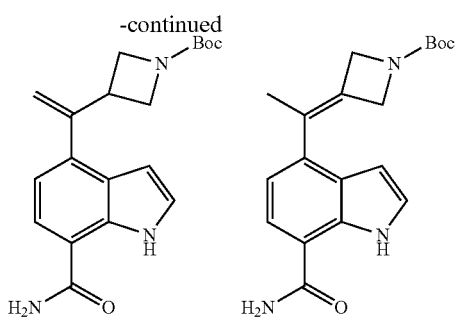

To a vial charged with a mixture of tert-butyl 3-(1-(((trifluoromethyl)sulfonyl)oxy)vinyl)azetidine-1-carboxylate and tert-butyl 3-(1-(((trifluoromethyl)sulfonyl)oxy)ethylidene)azetidine-1-carboxylate (0.388 g, 1.17 mmol), 4-(4,4,5,5-tetramethyl-1,3,2-dioxaborolan-2-yl)-1H-indole-7-carboxamide (0.279 g, 0.975 mmol), Pd(dppf)Cl$_2$ (0.043 g, 0.059 mmol) and sodium carbonate (0.31 g, 2.93 mmol) was added 1,4-dioxane (3 mL) and water (1 mL). The reaction mixture was evacuated and filled with nitrogen (repeated 3 times). The mixture was then heated at about 80° C. for about 1 h. The reaction mixture was concentrated and diluted with MeOH/DCM. The mixture was filtered and washed with MeOH/DCM and the filtrate was concentrated to dryness. The crude product was purified by silica gel chromatography eluting with a gradient of 0-3% MeOH/DCM to give a mixture of tert-butyl 3-(1-(7-carbamoyl-1H-indol-4-yl)vinyl)azetidine-1-carboxylate and tert-butyl 3-(1-(7-carbamoyl-1H-indol-4-yl)ethylidene)azetidine-1-carboxylate (0.277 g, 83%) as a yellow oil: LC/MS (Table 1, Method a) R$_t$=2.08, 2.13 min; MS m/z: 340 (M−H)⁻.

Step C: tert-butyl 3-(1-(7-carbamoyl-1H-indol-4-yl)ethyl)azetidine-1-carboxylate

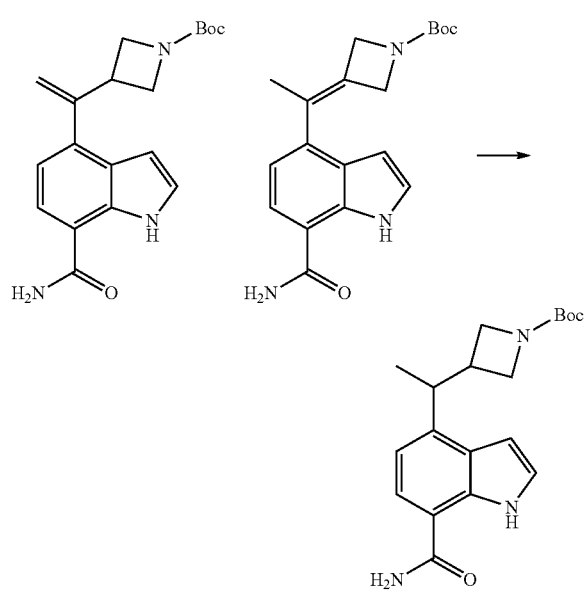

To a flask charged with 10 wt % Pd/C (0.026 g, 0.024 mmol) was added a solution of tert-butyl 3-(1-(7-carbamoyl-1H-indol-4-yl)vinyl)azetidine-1-carboxylate and tert-butyl 3-(1-(7-carbamoyl-1H-indol-4-yl)ethylidene)azetidine-1-carboxylate (0.26 g, 0.76 mmol) in EtOAc (10 mL) and about 2 drops of MeOH. The mixture was hydrogenated with a hydrogen balloon at about rt for about 2 h. The reaction mixture was filtered through a pad of Celite® and washed with EtOAc. The filtrate was concentrated to dryness to give tert-butyl 3-(1-(7-carbamoyl-1H-indol-4-yl)ethyl)azetidine-1-carboxylate (0.212 g, 81%) as a light yellow foam: LC/MS (Table 1, Method a) R$_t$=2.08 min; MS m/z: 342 (M−H)⁻.

Step D: (S)-4-(1-(1-acryloylazetidin-3-yl)ethyl)-1H-indole-7-carboxamide and (R)-4-(1-(1-acryloylazetidin-3-yl)ethyl)-1H-indole-7-carboxamide

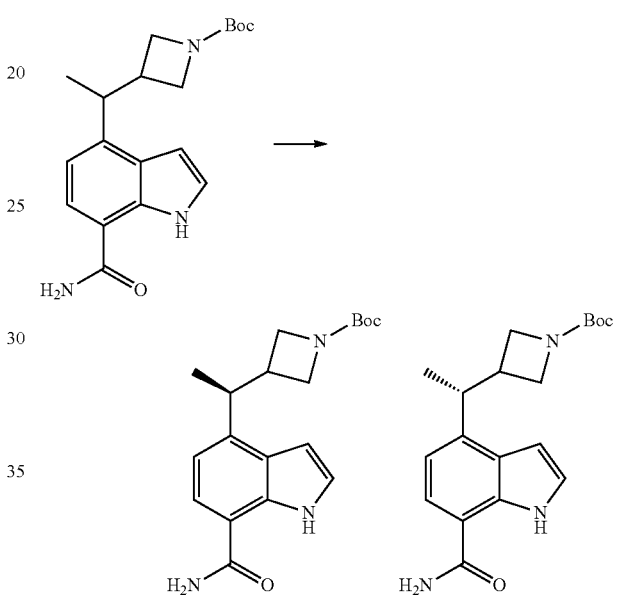

tert-Butyl 3-(1-(7-carbamoyl-1H-indol-4-yl)ethyl)azetidine-1-carboxylate (0.17 g, 0.495 mmol) was purified by preparative chiral HPLC (Table 2, Method 1) to give (S)-4-(1-(1-acryloylazetidin-3-yl)ethyl)-1H-indole-7-carboxamide (0.063 g, 37%) (R$_t$=12.339 min, or =positive) and (R)-4-(1-(1-acryloylazetidin-3-yl)ethyl)-1H-indole-7-carboxamide (0.066 g, 39%) (R$_t$=18.959 min, or =negative).

Step E.1: (S)-4-(1-(1-acryloylazetidin-3-yl)ethyl)-1H-indole-7-carboxamide

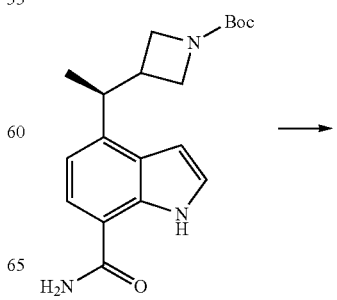

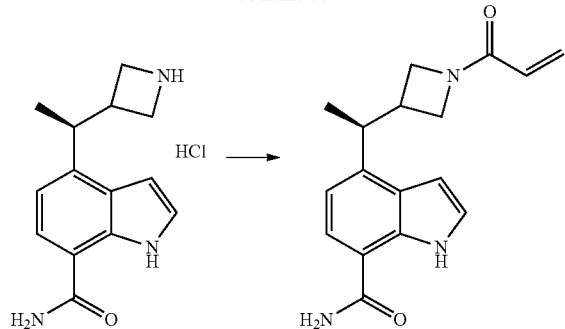

To a vial charged with (S)-tert-butyl 3-(1-(7-carbamoyl-1H-indol-4-yl)ethyl) azetidine-1-carboxylate (0.063 g, 0.183 mmol) and MeOH (1 mL) was added hydrogen chloride (4 M in dioxane, 0.92 mL, 3.67 mmol) at about rt. The mixture was stirred for about 30 min, then the mixture was concentrated in vacuo to afford the crude (S)-tert-butyl 3-(1-(7-carbamoyl-1H-indol-4-yl)ethyl) azetidine-1-carboxylate hydrochloride that was used without additional purification.

To a suspension of (S)-4-(1-(azetidin-3-yl)ethyl)-1H-indole-7-carboxamide hydrochloride (0.051, 0.183 mmol) in THF (2 mL) and DCM (1 mL) at about 0° C. was added N-ethyl-N-isopropylpropan-2-amine (0.096 mL, 0.550 mmol) followed by acryloyl chloride (0.017 mL, 0.202 mmol). The mixture was stirred at about 0° C. for about 30 min. The mixture was quenched with MeOH, and the volatiles were removed under reduced pressure. The residue was partitioned between DCM and saturated aqueous NaHCO₃. The organic layer was concentrated, and the crude product was purified by silica gel chromatography eluting with a gradient of 0-5% MeOH/DCM to afford (S)-4-(1-(1-acryloylazetidin-3-yl)ethyl)-1H-indole-7-carboxamide (0.039 g, 69.9%) as a white solid: LC/MS (Table 1, Method a) R$_f$=1.50 min.; MS m/z: 298 (M+H)⁺. (Btk IC$_{50}$=B)

Step E.2: (R)-4-(1-(1-acryloylazetidin-3-yl)ethyl)-1H-indole-7-carboxamide

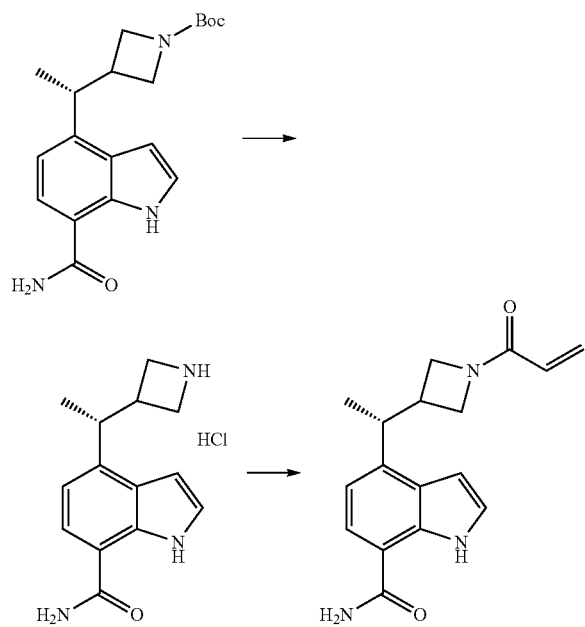

To a vial charged with (R)-tert-butyl 3-(1-(7-carbamoyl-1H-indol-4-yl)ethyl)azetidine-1-carboxylate (0.066 g, 0.192 mmol) and MeOH (1 mL) was added hydrogen chloride (4 M in dioxane, 0.96 mL, 3.84 mmol) at about rt. The mixture was stirred at rt for about 1 h, then the mixture was concentrated in vacuo to afford the crude (R)-tert-butyl 3-(1-(7-carbamoyl-1H-indol-4-yl)ethyl) azetidine-1-carboxylate hydrochloride that was used without additional purification.

To a suspension of (R)-4-(1-(azetidin-3-yl)ethyl)-1H-indole-7-carboxamide hydrochloride (0.054 g, 0.192 mmol) in THF (2 mL) and DCM (1 mL) at about 0° C. was added N-ethyl-N-isopropylpropan-2-amine (0.1 mL, 0.577 mmol) followed by dropwise addition of acryloyl chloride (0.018 mL, 0.212 mmol). The mixture was stirred at about 0° C. for about 30 min. The mixture was quenched with MeOH, and the volatiles were removed under reduce pressure. The residue was partitioned between DCM and saturated aqueous NaHCO₃. The organic layer was concentrated, and the crude product was purified by silica gel chromatography eluting with a gradient of 0-5% MeOH/DCM to afford (R)-4-(1-(1-acryloylazetidin-3-yl)ethyl)-1H-indole-7-carboxamide (0.042 g, 73.2%) as a white solid. LC/MS (Table 1, Method a) R$_f$=1.50 min; MS m/z: 298 (M+H)⁺. (Btk IC$_{50}$=A)

Example #29

4-((1-Acryloylazetidin-3-yl)(methyl)amino)-1H-pyrrolo[2,3-c]pyridine-7-carboxamide Step A:
4-bromo-1H-pyrrolo[2,3-c]pyridine-7-carbonitrile

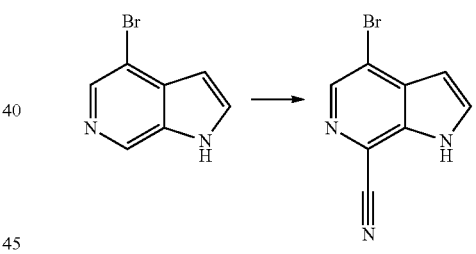

To a solution of 4-bromo-1H-pyrrolo[2,3-c]pyridine [ChemTec] (10.4 g, 52.8 mmol) in DCM (66.0 mL) and DME (66.0 mL) was added 3-chlorobenzoperoxoic acid (21.29 g, 95 mmol, 77% by weight) in one portion and the mixture was allowed to stir for about 16 h. The organic solvents were removed under reduced pressure, the solid triturated with DCM and the solid filtered to yield a mixture of both product and benzoic acid. The filtrate still contained additional product and it was concentrated further under reduced pressure to enable a second filtration. The combined filtercakes were dried and transferred to a 1 L round bottom flask containing a magnetic stir bar. MeCN (264 mL) and TEA (14.8 mL, 106 mmol) were added to give an off-white slurry. Trimethylsilyl cyanide (24.64 mL, 185 mmol) was added in one portion via syringe and the mixture was heated to reflux. After about 2 h of heating the mixture was allowed to cool to rt. The reaction was quenched by the addition of 100 mL of 1 M NaOH, diluted with 100 mL of EtOAc, transferred to a separatory funnel and further diluted with 100 mL of 1 M NaOH and 100 mL of EtOAc. The layers were separated and the aqueous phase was extracted with EtOAc (3×150 mL). The combined organic extracts were washed with at 1:1 mixture of brine and 1 M NaOH (2×50 mL), dried over Na₂SO₄, filtered and the solvent was removed to afford 4-bromo-1H-pyrrolo[2,3-c]pyridine-7-carbonitrile as a brown-yellow solid (10.28 g, 80%). ¹H NMR (400 MHz, DMSO) δ 8.44 (s, 1H), 7.96 (d, J=3.1 Hz, 1H), 6.71 (d, J=3.1 Hz, 1H).

Step B:
4-bromo-1H-pyrrolo[2,3-c]pyridine-7-carboxamide

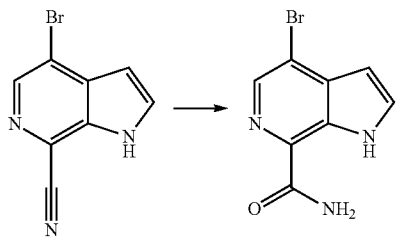 [SMILES: N#Cc1ncc(Br)c2cc[nH]c12 ; NC(=O)c1ncc(Br)c2cc[nH]c12]

To a solution of 4-bromo-1H-pyrrolo[2,3-c]pyridine-7-carbonitrile (10.2 g, 45.9 mmol) in EtOH (104 mL) were added a 1 M aqueous solution of NaOH (115 mL, 115 mmol) and 30% hydrogen peroxide (80 mL, 781 mmol) and the reaction mixture was heated to about 45° C. and stirred for about 30 min. The organic solvent was removed under reduced pressure. The mixture was diluted with 30 mL of water and filtered to afford 4-bromo-1H-pyrrolo[2,3-c]pyridine-7-carboxamide as a light yellow solid (9.87 g, 83%). LC/MS (Table 1, Method as): =1.81 min; MS m/z: 240, 242 (M+H)⁺.

Step C: tert-butyl 3-((7-carbamoyl-1H-pyrrolo[2,3-e]pyridin-4-yl)(methyl)amino)azetidine-1-carboxylate

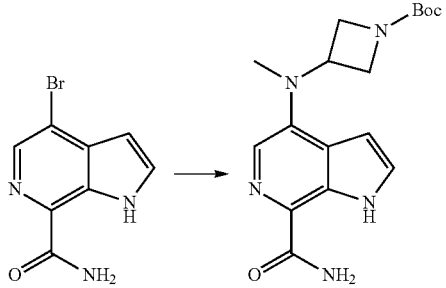 [SMILES: NC(=O)c1ncc(Br)c2cc[nH]c12 ; CN(c1cnc(C(N)=O)c2[nH]ccc12)C1CN(C(=O)OC(C)(C)C)C1]

4-Bromo-1H-pyrrolo[2,3-c]pyridine-7-carboxamide (580 mg, 2.416 mmol) was dissolved in 12 mL of anhydrous dioxane and dried for about 1 h over Na₂SO₄. The solution was then filtered into an oven-dried 75 mL pressure vessel and the drying agent washed using 3 mL of dioxane. The solution was degassed using a stream of argon and tert-butyl 3-(methylamino)azetidine-1-carboxylate hydrochloride (0.969 g, 4.35 mmol, Synthonix) was added followed by chloro(2-dicyclohexylphosphino-2',4',6'-triisopropyl-1,1'-biphenyl) [2-(2-aminoethyl)phenyl)]palladium(II) (0.089 g, 0.12 mmol) and X-Phos (0.057 g, 0.12 mmol). The mixture was degassed for about 10 min and LiHMDS (1 M in THF, 10.87 mL, 10.87 mmol) was added dropwise via syringe, the vial sealed and heated to about 90° C. for about 19 h. The reaction was cooled to rt and quenched by addition of aqueous NaHCO₃ (20 mL) and diluted with EtOAc (50 mL). Further dilution using water (10 mL) and brine (10 mL) led to complete dissolution and the layers were separated. The aqueous phase was extracted with EtOAc (3×20 mL). The combined organic extracts were washed with 1:1 brine and aqueous NaHCO₃ (20 mL), dried over Na₂SO₄, filtered and the solvent was removed under reduced pressure. The crude material was deposited onto silica and purified using a silica column (40 g), eluting with 0-5% of MeOH/DCM. The fractions containing product were concentrated under reduced pressure to afford tert-butyl 3-((7-carbamoyl-1H-pyrrolo[2,3-c]pyridin-4-yl)(methyl)amino)azetidine-1-carboxylate as a light-yellow solid (0.61 g, 69%). ¹H NMR (400 MHz, DMSO) δ 11.41 (bs, 1H), 7.90 (bs, 1H), 7.48-7.43 (m, 1H), 7.43-7.39 (m, 2H), 6.60 (dd, J=3.1, 2.0 Hz, 1H), 4.61-4.51 (m, 1H), 4.23-4.14 (m, 2H), 3.86 (dd, J=8.9, 5.2 Hz, 2H), 3.06 (s, 3H), 1.38 (s, 9H).

Step D: 4-(azetidin-3-yl(methyl)amino)-1H-pyrrolo[2,3-e]pyridine-7-carboxamide hydrochloride

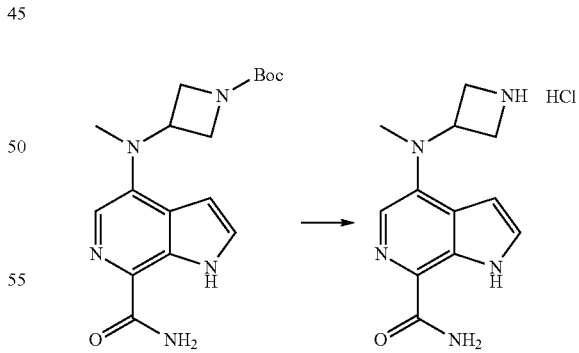

To a 50 mL round bottom flask containing a magnetic stir bar and MeOH (1.97 mL) was added acetyl chloride (1307 µl, 18.38 mmol) at about 0° C. via syringe. After about 10 min, the mixture was warmed to rt and stirred for about 1 h. Then, a solution of tert-butyl 34(7-carbamoyl-1H-pyrrolo[2, 3-c]pyridin-4-yl)(methyl)amino)azetidine-1-carboxylate (127 mg, 0.368 mmol) in MeOH (1970 µL) and DCM (657

μL) was added dropwise via syringe and the reaction stirred for about 5 h at rt. The solvents were removed under reduced pressure to afford 4-(azetidin-3-yl(methyl)amino)-1H-pyrrolo[2,3-c]pyridine-7-carboxamide hydrochloride (128 mg, 99%).LC/MS (Table 1, Method at): $R_t$=0.93 min; MS m/z: 246 (M+H)$^+$.

Example #30*

(R)-4-(1-Acryloylpiperidin-3-yl)-1H-indole-7-carboxamide and (S)-4-(1-acryloylpiperidin-3-yl)-1H-indole-7-carboxamide

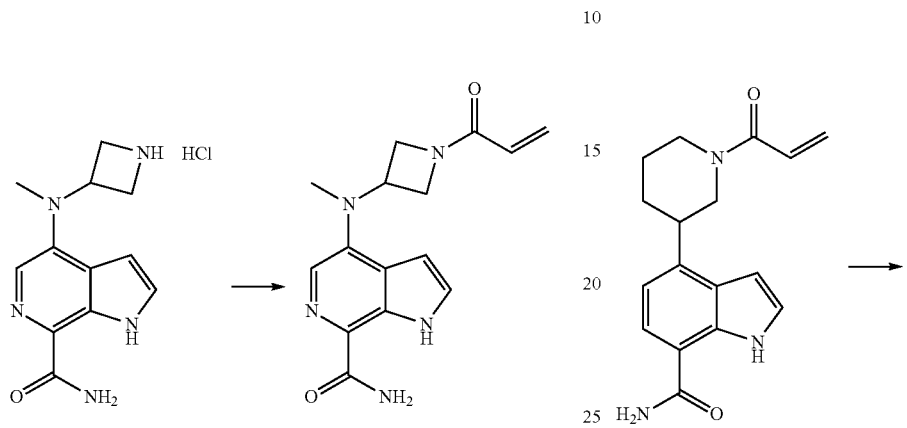

Step E: 4-((1-acryloylazetidin-3-yl)(methyl)amino)-1H-pyrrolo[2,3-c]pyridine-7-carboxamide To a cooled solution of the 4-(azetidin-3-yl(methyl) amino)-1H-pyrrolo[2,3-c]pyridine-7-carboxamide hydrochloride (101 mg, 0.36 mL) in DCM (5760 μL) and ethyldiisopropylamine (258 μL, 1.440 mmol) was added a solution of acryloyl chloride (50 mg, 0.552 mmol) in DCM (1440 μL) dropwise via syringe keeping the internal temperature at or below at −4° C. The mixture was allowed to stir for 15 min. The reaction was quenched by addition of 0.3 mL of water, the solvent volume reduced to 1.5 mL and the mixture loaded onto 4 g of silica. The material was purified using a 24 g silica column, 0-10% MeOH/DCM. The fractions containing product were concentrated under reduced pressure to afford 4-((1-acryloylazetidin-3-yl) (methyl)amino)-1,1-pyrrolo[2,3-c]pyridine-7-carboxamide as a white solid (89 mg, 78%). $^1$H NMR (400 MHz, DMSO) δ 11.43 (bs, 1H), 7.98-7.88 (m, 1H), 7.49-7.44 (m, 2H), 7.42 (s, 1H), 6.64-6.58 (m, 1H), 6.40-6.29 (m, 1H), 6.11 (dd, J=17.0, 2.2 Hz, 1H), 5.68 (dd, J=10.2, 2.2 Hz, 1H), 4.72-4.62 (m, 1H), 4.60-4.52 (m, 1H), 4.31-4.18 (m, 2H), 3.97 (dd, J=10.5, 5.2 Hz, 1H), 3.08 (s, 3H); MS m/z: 300 (M+H)$^+$. (Btk IC$_{50}$=A)

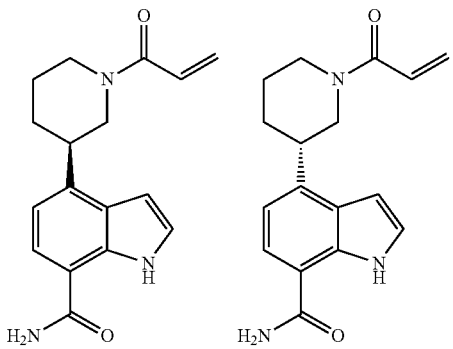

A sample of 4-(1-acryloylpiperidin-3-yl)-1H-indole-7-carboxamide (0.03 g, 0.10 mmol) was purified via preparative chiral HPLC (Table 2, Method 2) to give (R)-4-(1-acryloylpiperidin-3-yl)-1H-indole-7-carboxamide (0.012 g, 40%) (R$_t$=17.14 min, or =positive) (Btk IC$_{50}$=B) and (S)-4-(1-acryloylpiperidin-3-yl)-1H-indole-7-carboxamide (0.013 g, 43%) (R$_t$=20.46 min, or =negative) (Btk IC$_{50}$=A): LC/MS (Table 1, Method a) R$_t$=1.47 min; MS m/z: 298 (M+H)$^+$.

TABLE 3

Examples prepared from an acryloyl amide using chiral method: Table 2, Method 4

| Acryloyl Amide | Product | Example # | R$_t$ min (Table 1, Method) | m/z ESI+ (M + H)$^+$ | Btk IC$_{50}$ |
|---|---|---|---|---|---|
| 4-(Azetidin-3-yl)(methyl)amino)-2-(tetrahydrofuran-3-yl)-1H-indole-7-carboxamide (Example #E.9.21) | | 5.1 | 1.37 (ax) | 369 | A |
| 4-(Azetidin-3-yl)(methyl)amino)-2-(tetrahydrofuran-3-yl)-1H-indole-7-carboxamide (Example #E.9.21) | | 5.2 | 1.37 (ax) | 369 | A |

TABLE 4

Examples prepared from an acryloyl amide using chiral method: Table 2, Method 15

| Acryloyl Amide | Product | Example # | R$_t$ min (Table 1, Method) | m/z ESI+ (M + H)$^+$ | Btk IC$_{50}$ |
|---|---|---|---|---|---|
| 4-(1,4-Oxazepan-6-yl)-1H-pyrrolo[2,3-c]pyridine-7-carboxamide (Prepared using L with Preparation #49 and Pd(OH)$_2$, G with HCl and E with acryloyl chloride) | | 3.1 | 1.27 (as) | 315 | B |

TABLE 4-continued

Examples prepared from an acryloyl amide using chiral method: Table 2, Method 15

| Acryloyl Amide | Product | Example # | R$_t$ min (Table 1, Method) | m/z ESI+ (M + H)$^+$ | Btk IC$_{50}$ |
|---|---|---|---|---|---|
| 4-(1,4-Oxazepan-6-yl)-1H-pyrrolo[2,3-c]pyridine-7-carboxamide (Prepared using L with Preparation #49 and Pd(OH)$_2$, G with HCl and E with acryloyl chloride) | | 3.2 | 1.26 (as) | 315 | B |

TABLE 5

Examples prepared from an acryloyl amide using chiral method: Table 2, Method 16

| Acryloyl Amide | Product | Example # | R$_t$ min (Table 1, Method) | m/z ESI+ (M + H)$^+$ | Btk IC$_{50}$ |
|---|---|---|---|---|---|
| 2-(1-Methyl-1H-pyrazol-4-yl)-4-(piperidin-3-yl)-1H-indole-7-carboxamide hydrochloride (Prepared using A from Preparation #10 with tert-butyl 5-(4,4,5,5-tetramethyl-1,3,2-dioxaborolan-2-yl)-3,4-dihydropyridine-1(2H)-carboxylate [Anisyn], L with Pd/C, G with acetyl chloride, E with acryloyl chloride) | | 4.1 | 1.54 (ba) | 378 | A |
| 2-(1-Methyl-1H-pyrazol-4-yl)-4-(piperidin-3-yl)-1H-indole-7-carboxamide hydrochloride (Prepared using A from Preparation #10 with tert-butyl 5-(4,4,5,5-tetramethyl-1,3,2-dioxaborolan-2-yl)-3,4-dihydropyridine-1(2H)-carboxylate [Anisyn], L with Pd/C, G with acetyl chloride, E with acryloyl chloride) | | 4.2 | 1.58 (ba) | 378 | A |

What is claimed:
1. A compound of Formula (I):

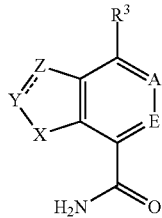

Formula (I)

or a pharmaceutically acceptable salt thereof, wherein:
X is NR²;
Y is CR¹, and Z is CR¹;
A is CR⁴;
E is CR⁵;
R¹ is independently H, deuterium, CN, halogen, CF₃, —NR$^c$R$^c$, —N(R$^a$)C(O)R$^b$, optionally substituted (C₁-C₆)alkyl, optionally substituted (C₂-C₆)alkenyl, optionally substituted (C₃-C₆)cycloalkyl, optionally substituted (C₃-C₆)cycloalkenyl, optionally substituted heteroaryl, or optionally substituted saturated or partially saturated heterocyclyl;
R² is independently H, deuterium, or optionally substituted (C₁-C₃)alkyl;
R³ is —R³⁰¹-L-R³⁰² wherein
R³⁰¹ is a bond, and
L is optionally substituted phenyl, optionally substituted (C₃-C₆)cycloalkyl, optionally substituted heteroaryl or a saturated or partially saturated heterocyclyl containing one or more heteroatoms, at least one of which is nitrogen; or
L is -L¹-L² wherein L¹ is attached to R³⁰¹ and
L¹ is optionally substituted phenyl, optionally substituted heteroaryl or optionally substituted saturated or partially saturated carbocycle or a saturated or partially saturated heterocyclyl; and
L² is a bond, CH₂, NR$^d$, CH₂N(H), S(O)₂N(H), or —O—;
R³⁰² is —C(O)CH=CH₂, —C(O)C≡CH, —C(O)CH=CHCl, —C(O)CH=CHCH₃, —C(O)C(=CH₂)CH₃, —C(O)C(CH₂CH₃)=CH₂, —C(O)CH=CHCH(CH₃)₂, —C(O)CH=CHC(O)OH, —C(O)CH=CHC(O)N(H)CH₂CH₃, —C(O)CH=CHCH₂N(CH₃)₂C(O)CH=CHC(O)OCH₃, —C(O)CH=CHC(O)OCH₂CH₃, —C(O)CH=CHC(O)N(H)CH₃, —C(O)CH=CHC(O)CH₂CH₂OCH₃, —C(O)CH=CHC(O)N(CH₃)₂, —C(O)CH=CHC(O)N(H)CH₂CH₃, —C(O)CH=CHC(O)N(H)CH₂CH₂OCH₃, —C(O)CH=CHCH₂N(H)CH₂CH₂OCH₃, —C(O)C(CN)=C(OH)(CH₃), —C(O)CH=CH-pyrazolyl, —C(O)CH=CHCH₂N(H)-cyclopropyl, —C(O)CH=CHCH₂N(H)CH₂-tetrahydrofuranyl, —C(O)CH=CHC(O)NH₂, —C(O)CH=CHC(O)N(H)-cyclopropyl, —C(O)C(CH₃)=CHCH₃, —C(O)C(CH₃)=CHCH₂CH₃, —C(O)C(=CH₂)CH₂N(CH₃)₂, —C(O)C(=CH₂)CH₂NH₂, —C(O)C(=CH₂)CH₂N(H)(CH₃), —C(O)C(=CH₂)CH₃, —C(O)C(=CH₂)CH₂-morpholinyl, —C(O)C(=CH₂)-phenyl, —C(O)CH=CH cyclopropyl, -C(O)CH=CHCH₂-morpholinyl, —C(O)CH=CHCH₂-piperidinyl, —C(O)CH=CH -pyrazolyl, —C(O)CH=CH-pyridinyl, or —C(O)CH=CH-thiazolyl;
R⁴ is H, deuterium, CN, optionally substituted (C₁-C₃)alkyl, optionally substituted (C₃-C₆) cycloalkyl or optionally substituted saturated or partially saturated heterocyclyl , or optionally substituted heteroaryl;
wherein the optionally substituted saturated or partially saturated heterocyclyl;
and optionally substituted heteroaryl contain at least one nitrogen atom;
R⁵ is H, deuterium, halogen, or optionally substituted (C₁-C₃)alkyl;
R$^a$ is independently selected from H, —C(O)-optionally substituted (C₂-C₆)alkenyl, optionally substituted (C₁-C₆)alkyl, —(CH₂)$_n$-optionally substituted (C₃-C₆)cycloalkyl, —(CH₂)$_n$-optionally substituted heterocyclyl, or —(CH₂)$_n$-optionally substituted heteroaryl;
R$^b$ is H, optionally substituted (C₁-C₆)alkyl, optionally substituted (C₂-C₆)alkenyl, optionally substituted (C₂-C₆)alkynyl, —CH₂—O-optionally substituted aryl, or —CH₂—O-optionally substituted heteroaryl;
R$^c$ is independently H, optionally substituted (C₁-C₆) alkyl, optionally substituted (C₃-C₆)cycloalkyl, optionally substituted saturated or partially saturated heterocyclyl, optionally substituted aryl or optionally substituted heteroaryl;
R$^d$ is H, optionally substituted heterocyclyl, —(CH₂)-optionally substituted (C₃-C₆)cycloalkyl, —(CH₂)-optionally substituted heteroaryl or optionally substituted (C₁-C₃)alkyl; and
n is independently 0 or 1,
wherein the optional substituent is one or more groups independently selected from (C₁-C₈)alkyl groups, (C₂-C₈)alkenyl groups, (C₂-C₈)alkynyl groups, (C₃-C₁₀) cycloalkyl groups, halogen, halogenated (C₁-C₈)alkyl groups, —CF₃, —O—(C₁—C₈)alkyl groups, =O, =CH₂, —OH, —CH₂OH, —CH₂NH₂, (C₁-C₄)alkyl-OH, —CH₂CH(OH)CH₂OH, —CH₂CH₂OCH₂CH₃, —S—(C₁-C₈)alkyl groups, —SH, —NH(C₁-C₈)alkyl groups, —N((C₁-C₈)alkyl)₂ groups, —NH₂, —C(O)NH₂, —CH₂NHC(O)(C₁-C₄)alkyl, —CH₂NHC(O)CH₂Cl, —CH₂NHC(O)CH₂CN, —CH₂NHC(O)CH₂CH₂N(CH₃)₂, —CH₂NHC(O)C(=CH₂)CH₃, —CH₂NHC(O)CH=CH₂, —CH₂NHC(O)CH=CHCH₃, —CH₂NHC(O)(C₂-C₄)alkynyl, —CH₂NHC(O)CH₂CH₂-piperidinyl, —(C₁-C₄)alkyl-morpholinyl, (C₁-C₄)alkoxy, —C(O)(C₁-C₄)alkyl, —C(O)(C₁-C₄)alkoxy, —C(O)N(H)₂, —C(O)N(CH₃)₂, —C(O)(C₁-C₆)heteroaryl, —C(O)-morpholinyl, —C(O)-pyrrolidinyl, —N(CH₃)₂, —NHC(O)(C₁-C₄)alkyl, —NHC(O)(C₂-C₄)alkenyl, —NHC(O)CH₂CN, —S(O)₂(C₁-C₄)alkyl, —S(O)₂(C₁-C₆) heteroaryl, —S(O)₂(C₁-C₆)heterocyclyl, 4-methylpiperazinecarbonyl, -(C₁-—C₄)alkylCN, —(C₁- C₄)alkylC(O)NH₂, —C(O)NH(C₁-C₈)alkyl groups, —C(O)N((C₁-C₈)alkyl)₂, —C(O)N(H)(C₃-C₈) cycloalkyl groups, —C(O)(C₁-C₄)alkoxy, —NHC(O) H, —NHC(O)(C₁-C₈)alkyl groups, —NHC(O)(C₃-C₈) cycloalkyl groups, —N((C₁-C₈)alkyl)C(O)H, —N((C₁-C₈)alkyl)C(O)(C₁-C₈)alkyl groups, —NHC(O)NH₂, —NHC(O)NH(C₁-C₈)alkyl groups, —N((C₁-C₈)alkyl)C(O)NH₂ groups, —NHC(O)N((C₁-C₈) alkyl)₂ groups, —N((C₁-C₈)alkyl)C(O)N((C₁-C₈) alkyl)₂ groups, —N((C₁-C₈)alkyl)C(O)NH((C₁-C₈) alkyl), —NHCH₂-heteroaryl, benzyl, —OCH₂-heteroaryl, benzyloxy, —C(O)H, —C(O)(C₁-C₈)alkyl groups, —CN, —NO₂, —S(O)(C₁-C₈)alkyl groups, —S(O)₂(C₁-C₈)alkyl groups,

517

—S(O)$_2$N((C$_1$-C$_8$)alkyl)$_2$ groups, —S(O)$_2$NH(C$_1$-C$_8$) alkyl groups, —S(O)$_2$NH(C$_3$-C$_8$)cycloalkyl groups, —S(O)$_2$NH$_2$ groups, —NHS(O)$_2$(C$_1$-C$_8$)alkyl groups, —N((C$_1$-C$_8$)alkyl)S(O)$_2$(C$_1$-C$_8$)alkyl groups, —(C$_1$-C$_8$)alkyl-O—(C$_1$-C$_8$)alkyl groups, —O—(C$_1$-C$_8$) alkyl-O—(C$_1$-C$_8$)alkyl groups, —C(O)OH, —C(O)O (C$_1$-C$_8$)alkyl groups, NHOH, NHO(C$_1$-C$_8$)alkyl groups, —O-halogenated (C$_1$-C$_8$)alkyl groups, —OCF$_3$, —S(O)$_2$-halogenated (C$_1$-C$_8$)alkyl groups, —S(O)$_2$CF$_3$, —S-halogenated C$_1$-C$_8$)alkyl groups, —SCF$_3$, (C$_1$-C$_6$)heterocyclyl, pyrrolidine, tetrahydrofuran, pyran, morpholine, —(C$_1$-C$_6$)heteroaryl, tetrazole, imidazole, furan, pyrazine, pyrazole, -phenyl, benzyl, —NHC(O)O—(C$_1$-C$_6$)alkyl groups, —N((C$_1$-C$_6$)alkyl)C(O)O—(C$_1$-C$_6$)alkyl groups, —C(=NH)—(C$_1$-C$_6$)alkyl groups, —C(=NOH)—(C$_1$-C$_6$)alkyl groups, —C(=N—O—(C$_1$-C$_6$)alkyl)-(C$_1$-C$_6$)alkyl groups, C(O)-heterocyclyl, or —CH$_2$NHC(O)CH$_2$O-phenyl wherein the phenyl is optionally substituted with halogen.

2. The compound according to claim 1 wherein
L is optionally substituted azetidinyl, optionally substituted cyclopentyl, optionally substituted 3,6-diazabicyclo[3.2.0]heptanyl, optioinally substituted 1,4-dioxanyl, optionally substituted morpholinyl, optionally substituted[1.4]oxepanyl, optionally substituted phenyl, optionally substituted piperidinyl, or optionally substituted pyrrolidinyl; or
L is L$^1$-L$^2$ wherein
L$^1$ is optionally substituted cyclohexyl, optionally substituted cyclopentyl, optionally substituted phenyl, optionally substituted piperidinyl, optionally substituted pyridinyl;
L$^2$ is N(H), N(CH$_3$), N(CH$_2$CH$_2$OH), N(CH$_2$CH(CH$_3$)$_2$), N(oxetanyl), N(CH$_2$-cyclopentyl), N(CH$_2$-thiazolyl), O, S(O)$_2$N(H), or CH$_2$N(H).

3. The compound according to claim 2, wherein L or L$^1$ is optionally substituted with one or more substituents independently selected from halogen, CN, OH, (C$_1$-C$_4$) alkoxy, (C$_1$-C$_4$)alkyl, —CH$_2$OH, —N(H)CH$_2$-heteroaryl, benzyloxy, and —OCH$_2$-heteroaryl.

4. The compound according to claim 3, wherein X is NR$^2$ and R$^2$ is H.

5. The compound according to claim 4, wherein Y is CR$^1$ and R$^1$ of Y is optionally substituted with one or more substituents independently selected from halogen, CN, =O, (C$_1$-C$_4$)alkyl, (C$_2$-C$_4$)alkenyl, —CH$_2$NH$_2$, —CH$_2$CH$_2$OH, —CH$_2$CH(OH)CH$_2$CH$_3$, —CH$_2$CH(OH)CH$_2$OH, —CH$_2$CH$_2$OCH$_2$CH$_3$, —CH$_2$C(OH)(CH$_3$)$_2$, —CH$_2$NHC(O)(C$_1$-C$_4$)alkyl, —CH$_2$NHC(O)CH$_2$Cl, —CH$_2$NHC(O)CH$_2$CN, —CH$_2$NHC(O)CH$_2$CH$_2$N(CH$_3$)$_2$, —CH$_2$NHC(O)C(=CH$_2$)CH$_3$, —CH$_2$NHC(O)(C$_2$-C$_4$)alkynyl, —CH$_2$NHC(O)CH$_2$CH$_2$-piperidinyl, —(C$_1$-C$_4$)alkyl-morpholinyl, —CH$_2$NHC(O)CH$_2$O-phenyl wherein the phenyl is optionally substituted with halogen, (C$_1$-C$_4$)alkoxy, —C(O)(C$_1$-C$_4$)alkyl, —C(O)(C$_1$-C$_4$)alkoxy, —C(O)N(H)$_2$, —C(O)N(CH$_3$)$_2$, —C(O)-morpholinyl, —C(O)-pyrrolidinyl, —N(CH$_3$)$_2$, —NHC(O)(C$_1$-C$_4$)alkyl, —NHC(O)(C$_2$-C$_4$)alkenyl, —NHC(O)CH$_2$CN, —S(O)$_2$(C$_1$-C$_4$)alkyl, —S(O)$_2$-pyrrolidinyl, morpholinyl, tetrahydropyranyl, or 4-methylpiperazinecarbonyl.

6. The compound according to claim 5, wherein Z is CR$^1$ and R$^1$ of Z is H, (C$_1$-C$_4$)alkyl, —NHC(O)CH$_2$Cl, —NHC(O)CH$_2$CN, —NHC(O)(C$_2$-C$_4$)alkenyl, —NHC(O)(C$_2$-C$_4$) alkynyl, —NHC(O)C(=CH$_2$)CH$_3$, —NHC(O)CH$_2$-phenyl, or pyrazolyl substituted with CH$_3$.

518

7. The compound according to claim 1, wherein
X is NR$^2$ wherein R$^2$ is H;
Y is CR$^1$ wherein R$^1$ is H, CH$_3$, substituted pyrazolyl, 6,7-dihydro-4H-pyrazolo[5,1-c][1,4]oxazinyl or tetrahydrofuranyl;
Z is CR$^1$ wherein R$^1$ is H;
E is CR$^5$ wherein R$^5$ is H;
R$^3$ is —R$^{301}$-L—R$^{302}$ wherein
R$^{301}$ is a bond;
L is azetidinyl, 3,6-diazabicyclo[3.2.0]heptanyl, morpholinyl, [1,4]oxepanyl, piperidinyl, or pyrrolidinyl; wherein the azetidinyl is optionally substituted with CH$_3$, and
wherein the piperidinyl is optionally substituted with —CH$_2$OH; and
R$^{302}$ is —C(O)CH=CH$_2$ or —C(O)C≡CH.

8. A compound selected from
4-((1-acryloylazetidin-3-yl)(methyl)amino)-1H-indole-7-carboxamide;
4-(3-acrylamido-2-methylphenyl)-2(1-(methylsulfonyl)-1,2,3,6-tetrahydropyridin-4-yl)-1H-indole-7-carboxamide;
(R)-4-(3-acrylamidopiperidin-1-yl)-2-(1-(methylsulfonyl)-1,2,3,6-tetrahydropyridin-4-yl)-1H-indole-7-carboxamide;
4-(2-methyl-3-(N-(thiazol-2-ylmethyl)acrylamido)phenyl)-2-(1-(methylsulfonyl)-1,2,3,6-tetrahydropyridin-4-yl)-1H-indole-7-carboxamide;
4-(3-methacrylamido-2-methylphenyl)-2-(1-(methylsulfonyl)-1,2,3,6-tetrahydropyridin-4-yl)-1H-indole-7-carboxamidel;
(Z)-4-(3-(3-chloroacrylamido)-2-methylphenyl)-2-(1-(methylsulfonyl)-1,2,3,6-tetrahydropyridin-4-yl)-1H-indole-7-carboxamide;
4-(3-acrylamido-2-methylphenyl)-2-(4,4-difluorocyclohex-1-enyl)-1H-indole-7-carboxamide;
4-(2-(acrylamidomethyl)phenyl)-2-(1-(methylsulfonyl)-1,2,3,6-tetrahydropyridin-4-yl)-1H-indole-7-carboxamide;
4-(2-acrylamidophenyl)-2-(1-(methylsulfonyl)-1,2,3,6-tetrahydropyridin-4-yl)-1H-indole-7-carboxamide;
4-(3-(acrylamidomethyl)phenyl)-2-(1-(methylsulfonyl)-1,2,3,6-tetrahydropyridin-4-yl)-1H-indole-7-carboxamide;
4-(3-acrylamidophenyl)-1H-indole-7-carboxamide;
4-(3-acrylamido-2-methylphenyl)-1H-indole-7-carboxamide;
4-(3-acrylamido-2-methylphenyl)-2-(2-methoxypyridin-3-yl)-1H-indole-7-carboxamide;
methyl 3-(4-(3-acrylamido-2-methylphenyl)-7-carbamoyl-1H-indol-2-yl)benzoate;
4-(3-acrylamido-2-methylphenyl)-2-(3-methoxyphenyl)-1H-indole-7-carboxamide;
4-(3-acrylamido-2-methylphenyl)-2-(4-methoxyphenyl)-1H-indole-7-carboxamide;
4-(3-acrylamido-2-methylphenyl)-2-6-methylpyridin-3-yl)-1H-indole7-carboxamide;
4-(3-acrylamido-2-methylphenyl)-2-(3-carbamoylphenyl)-1H-indole-7-carboxamide;
4-(3-acrylamido-2-methylphenyl)-2-(3,5-dimethylisoxazol-4-yl)-1H-indole-7-carboxamide;
4-(3-acrylamido-2-methylphenyl)-2-(1-(tetrahydro-2H-pyran-2-yl)-1H-pyrazol-5-yl)-1H-indole-7-carboxamide;
4-(3-acrylamido-2-methylphenyl)-2-(3,5-dimethyl-1H-pyrazol-4-yl)-1H-indole-7-carboxamide;

4-(3-acrylamido-2-methylphenyl)-2-(1-isopropyl-1H-pyrazol-4-yl)-1H-indole-7-carboxamide;
4-(3-acrylamido-2-methylphenyl)-2-(1,3-dimethyl-1H-pyrazol-4-yl)-1H-indole-7-carboxamide;
4-(3-acrylamido-2-methylphenyl)-2-(1-ethyl-1H-pyrazol-4-yl)-1H-indole-7-carboxamide;
4-(3-acrylamido-2-methylphenyl)-2-(1-isobutyl-1H-pyrazol-4-yl)-1H-indole-7-carboxamide;
N-(3-(7-carbamoyl-3-methacrylamido-1H-indol-4-yl)-2-methylphenyl)thiazole-2-carboxamide;
4-(3-acrylamido-2-methylphenyl)-2-(2-fluoropyridin-3-yl)-1H-indole-7-carboxamide;
4-(3-acrylamido-2-methylphenyl)-2-(1-ethyl-1H-pyrazol-4-yl)-1H-indole-7-carboxamide;
2-(3-acetamidophenyl)-4-(3-acrylamido-2-methylphenyl)-1H-indole7-carboxamide;
4-(3-acrylamido-2-methylphenyl)-2-(2-methoxypyridin-4-yl)-1H-indole-7-carboxamide;
4-(3-acrylamido-2-methylphenyl)-2-(3-cyanophenyl)-1H-indole-7-carboxamide;
methyl 4-(4-(3-acrylamido-2-methylphenyl)-7-carbamoyl-1H-indol-2-yl)benzoate;
4-(3-acrylamido-2-methylphenyl)-2-(2,3-dihydrobenzofuran-5-yl)-1H-indole-7-carboxamide;
4-(3-acrylamido-2-methylphenyl)-2-(3-fluorophenyl)-1H-indole-7-carboxamide;
4-(3-acrylamido-2-methylphenyl)-2-(3-(dimethylamino)phenyl)-1H-indole-7-carboxamide;
4-(3-acrylamido-2-methylphenyl)-2-(2-methyl-5-(pyrrolidin-1-ylsulfonyl)phenyl)-1H-indole-7-carboxamide;
4-(3-acrylamido-2-methylphenyl)-2-(2-fluorophenyl)-1H-indole-7-carboxamide;
N-(3-(3-acrylamido-7-carbamoyl-1H-indol-4-yl)-2-methylphenyl)thiazole-2-carboxamide;
4-(3-acrylamido-2-methylphenyl)-2-(1-methyl-1H-pyrazol-5-yl)-1H-indole-7-carboxamide;
4-(3-acrylamido-2-methylphenyl)-2-(pyridin-4-yl)-1H-indole-7-carboxamide;
4-(3-acrylamido-2-methylphenyl)-2-(1-(2-morpholinoethyl)-1H-pyrazol-4-yl)-1H-indole-7-carboxamide;
4-(3-acrylamido-2-methylphenyl)-2-(6-morpholinopyridin-3-yl)-1H-indole-7-carboxamide;
4-(3-acrylamido-2-methylphenyl)-2-(3-(4-methylpiperazine-1-carbonyl)phenyl)-1H-indole-7-carboxamide;
N-(3-(2-(2-(acrylamidomethyl)phenyl)-7-carbamoyl-1H-indol-4-yl)-2-methylphenyl)thiazole-2-carboxamide;
N-(3-(7-carbamoyl-2-(2-(methacrylamidomethyl)phenyl)-1H-indol-4-yl)-2-methylphenyl)thiazole-2-carboxamide;
4-(3-acrylamido-2-methylphenyl)-2-(4-fluorophenyl)-1H-indole-7-carboxamide;
4-(3-acrylamido-2-methylphenyl)-2-phenyl-1H-indole-7-carboxamide;
4-(3-acrylamido-2-methylphenyl)-2-(2-(methylsulfonyl)phenyl)-1H-indole-7-carboxamide;
4-(3-acrylamido-2-methylphenyl)-2-(4-(dimethylcarbamoyl)phenyl)-1H-indole-7-carboxamide;
4-(3-acrylamido-2-methylphenyl)-2-(pyrimidin-5-yl)-1H-indole-7-carboxamide;
4-(3-acrylamido-2-methylphenyl)-2-(pyridin-3-yl)-1H-indole-7-carboxamide;
4-(3-acrylamido-2-methylphenyl)-2-(4-(morpholine-4-carbonyl)phenyl)-1H-indole-7-carboxamide;
4-(3-acrylamido-2-methylphenyl)-2-(4-(pyrrolidine-1-carbonyl)phenyl)-1H-indole-7-carboxamide;
4-(3-acrylamido-2-methylphenyl)-2-(4-(4-methylpiperazine-1-carbonyl)phenyl)-1H-indole-7-carboxamide;
4-(3-acrylamido-2-methylphenyl)-2-(4-(methylsulfonyl)phenyl)-1H-indole-7-carboxamide;
4-(3-acrylamido-2-methylphenyl)-2-6-methoxypyridin-3-yl)-1H-indole-7-carboxamide;
4-(3-acrylamido-2-methylphenyl)-2-(4-cyanophenyl)-1H-indole-7-carboxamide;
4-(3acrylamido-2-methylphenyl)-2-(2-methoxyphenyl)-1H-indole-7-carboxamide;
4-(2-acrylamidophenyl)-1H-indole-7-carboxamide;
4-(3-acrylamido-2-methylphenyl)-2-(4-(morpholinomethyl)phenyl)-1H-indole-7-carboxamide;
4-(3-acrylamido-2-methylphenyl)-2-(4-carbamoylphenyl)-1H-indole-7-carboxamide;
4-(3-acrylamido-5-(thiazol-2-ylmethylamino)phenyl)-2-(1-(methylsulfonyl)-1,2,3,6-tetrahydropyridin-4-yl)-1H-indole-7-carboxamide;
4-(2methyl-3-(N-methylacrylamido)phenyl)-1H-indole-7-carboxamide;
4-(3-(N-methylacrylamido)phenyl)-1H-indole-7-carboxamide;
4-(3-methacrylamido-2-methylphenyl)-1H-indole-7-carboxamide;
(E)-4-(3-(3-cyclopropylacrylamido)-2-methylphenyl)-1H-indole-7-carboxamide;
(E)-4-(2-methyl-3-(3-(pyridin-2-yl)acrylamido)phenyl)-1H-indole-7-carboxamide;
(E)-4-(2-methyl-3-(3-(1-methyl-1H-pyrazol-4-yl)acrylamido)phenyl)-1H-indole-7-carboxamide;
(E)-4-(2-methyl-3-(3-(pyridin-3-yl)acrylamido)phenyl)-1H-indole-7-carboxamide;
(E)-4-(2-methyl-3-(3-(thiazol-2-yl)acrylamido)phenyl)-1H-indole-7-carboxamide;
4-(2-methyl-3-(2-phenylacrylamido)phenyl)-1H-indole-7-carboxamide;
4-(3-acrylamido-4-(benzyloxy)phenyl)-1H-indole-7-carboxamide;
4-(3-acrylamido-5-(benzyloxy)phenyl)-1H-indole-7-carboxamide;
4-(3-acrylamido-4-(thiazol-2-ylmethoxy)phenyl)-1H-indole-7-carboxamide;
4-(3-acrylamido-5-(thiazol-2-ylmethoxy)phenyl)-1H-indole-7-carboxamide;
4-(2-acrylamido-4-(thiazol-2-ylmethoxy)phenyl)-1H-indole-7-carboxamide;
4-(2-acrylamido-4-(benzyloxy)phenyl)-1H-indole-7-carboxamide;
4-(5-acrylamidopyridin-3-yl)-1H-indole-7-carboxamide;
4-(2-acrylamidopyridin-4-yl)-1H-indole-7-carboxamide;
4-(3-(N-isobutylacrylamido)phenyl)-1H-indole-7-carboxamide;
1-Acryloyl-1,2,3,6-tetrahydro-pyrrolo[2,3-e]indole-5-carboxylic acid amide;
4-acrylamido-1H-indole-7-carboxamide;
4-(3-acrylamido-2-methoxyphenyl)-1H-indole-7-carboxamide;
4-(3-acrylamido-2-fluorophenyl)-1H-indole-7-carboxamide;
4-(5-acrylamido-2-fluorophenyl)-1H-indole-7-carboxamide;
4-(3-acrylamido-4-fluorophenyl)-1H-indole-7-carboxamide;
4-(5-acrylamido-2-chlorophenyl)-1H-indole-7-carboxamide;
4-(5-acrylamido-2,4-difluorophenyl)-1H-indole-7-carboxamide;
4-(3-acrylamido-4-cyanophenyl)-1H-indole-7-carboxamide;

4-(3-acrylamido-2,6-difluorophenyl)-1H-indole-7-carboxamide;
4-(3-acrylamido-5-methylphenyl)-1H-indole-7-carboxamide;
4-(3-acrylamido-4-methylphenyl)-1H-indole-7-carboxamide;
4-(3-acrylamido-4-methoxyphenyl)-1H-indole-7-carboxamide;
4-(3-acrylamido-5-methoxyphenyl)-1H-indole-7-carboxamide;
4-(3-acrylamido-4-chlorophenyl)-1H-indole-7-carboxamide;
4-(5-acrylamido-2,3-difluorophenyl)-1H-indole-7-carboxamide;
4-(3-acrylamido-5-cyanophenyl)-1H-indole-7-carboxamide;
4-(3-acrylamido-2-cyanophenyl)-1H-indole-7-carboxamide;
4-(3-acrylamidophenyl)-2-vinyl-1H-indole-7-carboxamide;
4-(3-acrylamidophenyl)-2-ethyl-1H-indole-7-carboxamide;
4-(3-(2-(morpholinomethyl)acrylamido)phenyl)-1H-indole-7-carboxamide;
4-(3-(2-((dimethylamino)methyl)acrylamido)phenyl)-1H-indole-7-carboxamide;
4-(1R,3S)-3-acrylamidocyclohexyl)-1H-indole-7-carboxamide;
4-(cis-3-acrylamidocyclohexyl)-1H-indole-7-carboxamide;
4-((1S,3S)-3-acrylamidocyclohexyl)-1H-indole-7-carboxamide;
4-(trans-3-acrylamidocyclohexyl)-1H-indole-7-carboxamide;
4-(cis-3-acrylamidocyclohexyl)-1H-indole-7-carboxamide;
4-(3-(2-(aminomethyl)acrylamido)phenyl)-1H-indole-7-carboxamide;
4-(1R,3S)-3-acrylamidocyclopentyl)-1H-indole-7-carboxamide;
4-(3-(2-((methylamino)methyl)acrylamido)phenyl)-1H-indole-7-carboxamide;
4-(3-acrylamidophenyl)-2-methyl-1H-indole-7-carboxamide;
4-((1S,3S)-3-acrylamidocyclopentyl)-1H-indole-7-carboxamide;
4-(3-acrylamidophenyl)-2-(2-ethoxyethyl)-1H-indole-7-carboxamide;
4-(3-acrylamidophenyl)-2-(2-hydroxyethyl)-1H-indole-7-carboxamide;
4-(1-acryloylpiperidin 3-yl)-2-(1-methyl-1H-pyrazol-4-yl)-1H-indole-7-carboxamide;
4-(3-acrylamido-2-methylphenyl)-2-(1-isopropyl-1H-pyrazol-4-yl)-1H-indole-7-carboxamide;
4-(3-(N-(cyclopentylmethyl)acrylamido)phenyl)-1H-indole-7-carboxamide;
4-(cis-3-acrylamidocyclopentyl)-1H-indole-7-carboxamide;
4-(trans-3-acrylamidocyclopentyl)-1H-indole-7-carboxamide;
4-(trans-3-acrylamidocyclopentyl)-1H-indole-7-carboxamide;
(S)-4-(1-(1-acryloylazetidin-3-yl)ethyl)-1H-indole-7-carboxamide;
(R)-4-(1-(1-acryloylazetidin-3-yl)ethyl)-1H-indole-7-carboxamide;
(R)-4-(1-acryloylpiperidin-3-yl)-1H-indole-7-carboxamide;
(S)-4-(1-acryloylpiperidin-3-yl)-1H-indole-7-carboxamide;
(S)-4-(1-acryloylpiperidin-3-yl)-2-methyl-1H-indole-7-carboxamide;
(R)-4-(1-acryloylpiperidin-3-yl)-2-methyl-1H-indole-7-carboxamide;
(R)-4-(4-acryloylmorpholin-2-yl)-2-(1-methyl-1H-pyrazol-4-yl)-1H-indole-7-carboxamide;
(S)-4-(4-acryloylmorpholin-2-yl)-2-(1-methyl-1H-pyrazol-4-yl)-1H-indole-7-carboxamide;
(R)-4-(1 -acryloylpyrrolidin-3-yl)-2-(6,7-dihydro-4H-pyrazolo-[5,1-c][1,4]oxazin-2-yl)-1H-indole-7-carboxamide;
2-methyl-4-(methyl(1-propioloylazetidin-3-yl)amino)-1H-indole-7-carboxamide;
(S)-4-(1-acryloylpyrrolidin-3-yl)-2-(6,7-dihydro-4H-pyrazolo[5,1-c][1,4-]oxazin-2-yl)-1H-indole-7-carboxamide;
(S)-4-(4-acryloyl-1,4-oxazepan-6-yl)-1H-indole-7-carboxamide;
4-((3S,5R)-1-acryloyl-5-(hydroxymethyl)piperidin-3-yl)-1H-indole-7-carboxamide;
4-((3S,5S)-1-acryloyl-5-(hydroxymethyl)piperidin-3-yl)-1H-indole-7-carboxamide;
4-((3R,5S)-1-acryloyl-5-(hydroxymethyl)piperidin-3-yl)-1H-indole-7-carboxamide;
4-((3R,5R)-1-acryloyl-5-(hydroxymethyl)piperidin-3-yl)-1H-indole-7-carboxamide;
(R)-4-(1-acryloylpyrrolidin-3-yl)-2-(1-methyl-1H-pyrazol-4-yl)-1H-indole-7-carboxamide;
(S)-4-(1-acryloylpyrrolidin-3-yl)-2-(1-methyl-1H-pyrazol-4-yl)-1H-indole-7-carboxamide;
4-((1R,3R)-3-acrylamidocyclopentyl)-1H-indole-7-carboxamide;
4-((1-acryloylazetidin-3-yl)(methyl)amino)-2-(isochroman-7-yl)-1H-indole-7-carboxamide;
4-((1-acryloylazetidin-3-yl)(methyl)amino)-2-(6,7-dihydro-4H-pyrazolo[5,1-c][1,4]oxazin-2-yl)- 1H -indole-7-carboxamide;
4-((1-acryloylazetidin-3-yl)(methyl)amino)-2-(4,4-difluorocyclohex-1-en-1-yl)-1H-indole-7-carboxamide;
4-((1-acryloylazetidin-3-yl)(methyl)amino)-2-(4-(methylsulfonyl)cyclohex-1-en-1-yl)-1H-indole-7-carboxamide;
4-((1-acryloylazetidin-3-yl)(methyl)amino)-2-(6-morpholinopyridin-3-yl)-1H-indole-7-carboxamide;
4-((1-acryloylazetidin-3-yl)(methyl)amino)-2-(7,8-dihydro-5H-pyrano[4,3]pyridin-3-yl)-1H-indole-7-carboxamide;
4-((1-acryloylazetidin-3-yl)(methyl)amino)-2-(chroman-7-yl)-1H-indole-7-carboxamide;
4-((1-acryloylazetidin-3-yl)(methyl)amino)-2-(5-(morpholinomethyl)pyridin-2-yl)-1H-indole-7-carboxamide;
4-((1-acryloylazetidin-3-yl)(methyl)amino)-2-(1-methyl-1H-pyrazol-4-yl)-1H-indole-7-carboxamide;
4-((1-acryloylazetidin-3-yl)(methyl)amino)-2-(3,4-dihydro-2H-benzo[b][1,4]oxazin-6-yl)-1H-indole-7-carboxamide;
4-((1-acryloylazetidin-3-yl)(methyl)amino)-2-(1-methyl-1H-pyrazol-5-yl)-1H-indole-7-carboxamide;
4-((1-acryloylazetidin-3-yl)(methyl)amino)-2-(2-ethyl-1,2,3,4-tetrahydroisoquinolin-6-yl)-1H-indole-7-carboxamide;

4-((1-acryloylazetidin-3-yl)(methyl)amino)-2(1,3-dimethyl-1H-pyrazol-4-yl)-1H-indole-7-carboxamide;

4-((1-acryloylazetidin-3-yl)(methyl)amino)-2-(1,1-dioxidotetrahydro-2H-thiopyran-4-yl)-1H-indole-7-carboxamide;

4-((1-acryloylazetidin-3-yl)(methyl)amino)-2-(1-propylpiperidin-4-yl)-1H-indole-7-carboxamide;

4-((1-acryloylazetidin-3-yl)(methyl)amino)-2-(tetrahydrofuran-3-yl)-1H-indole-7-carboxamide;

4-((1-acryloylazetidin-3-yl)(methyl)amino)-2-(3-hydroxyoxetan-3-yl)-1H-indole-7-carboxamide;

4-((1-acryloylazetidin-3-yl)(methyl)amino)-2-methyl-1H-indole-7-carboxamide;

(R)-4-(4-acryloyl-1,4-oxazepan-6-yl)-1H-indole-7-carboxamide;

(S)-4-(1-acryloylpyrrolidin-3-yl)-2-methyl-1H-indole-7-carboxamide;

(R)-4-(1-acryloylpyrrolidin-3-yl)-2-methyl-1H-indole-7-carboxamide;

4-((1R,5S)-6-acryloyl-3,6-diazabicyclo[3.2.0]heptan-3-yl)-1H-indole-7-carboxamide;

4-((1S,5R)-6-acryloyl-3,6-diazabicyclo[3.2.0]heptan-3-yl)-1H-indole-7-carboxamide;

4-((1-acryloyl-3-methylazetidin-3-yl)(methyl)amino)-1H-indole-7-carboxamide;

(S)-4-((1-acryloylazetidin-3-yl)(methyl)amino)-2-(tetrahydrofuran-3-yl)-1H-indole-7-carboxamide;

(R)-4-((1-acryloylazetidin-3-yl)(methyl)amino)-2-(tetrahydrofuran-3-yl)-1H-indole-7-carboxamide;

(S)-4-(1-acryloylpiperidin-3-yl)-2-(1-methyl-1H-pyrazol-4-yl)-1H-indole-7-carboxamide;

(R)-4-(1-acryloylpiperidin-3-yl)-2-(1-methyl-1H-pyrazol-4-yl)-1H-indole-7-carboxamide, or a pharmaceutically acceptable salt thereof.

9. A method of treating a disease comprising administering a therapeutically effective amount of a compound of claim 1 to a patient in need thereof, wherein the disease is mantle cell lymphoma, chronic lymphocytic leukemia, small lymphocytic lymphoma, follicular lymphoma, diffuse large B-cell lymphoma, or multiple myeloma.

10. A kit comprising a packaged product comprising components with which to administer a compound of claim 1 for treatment of a disease, wherein the disease is mantle cell lymphoma, chronic lymphocytic leukemia, small lymphocytic lymphoma, follicular lymphoma, diffuse large B-cell lymphoma, or multiple myeloma.

11. A pharmaceutical composition comprising a compound according to claim 1 and one or more pharmaceutically acceptable excipients.

12. A pharmaceutical composition comprising a compound according to claim 8 and one or more pharmaceutically acceptable excipients.

13. A method of treating a disease comprising administering a therapeutically effective amount of a compound of claim 8 to a patient in need thereof, wherein the disease is mantle cell lymphoma, chronic lymphocytic leukemia, small lymphocytic lymphoma, follicular lymphoma, diffuse large B-cell lymphoma, or multiple myeloma.

14. A kit comprising a packaged product comprising components with which to administer a compound of claim 8 for treatment of a disease, wherein the disease is mantle cell lymphoma, chronic lymphocytic leukemia, small lymphocytic lymphoma, follicular lymphoma, diffuse large B-cell lymphoma, or multiple myeloma.

15. A compound or a pharmaceutically acceptable salt thereof, wherein the compound is (S)-4-(1-acryloylpiperidin-3-yl)-1H-indole-7-carboxamide.

16. A compound or a pharmaceutically acceptable salt thereof, wherein the compound is (R)-4-(1-acryloylpiperidin-3-yl)-1H-indole-7-carboxamide.

17. A compound or a pharmaceutically acceptable salt thereof, wherein the compound is 4-(1-acryloylpiperidin 3-yl)-2-(1-methyl-1H-pyrazol-4-yl)-1H-indole-7-carboxamide.

18. A compound or a pharmaceutically acceptable salt thereof, wherein the compound is 4-((1-acryloylazetidin-3-yl)(methyl)amino)-1H-indole-7-carboxamide.

19. A compound or a pharmaceutically acceptable salt thereof, wherein the compound is 4-(3-acrylamidophenyl)-2-(2-hydroxyethyl)-1H-indole-7-carboxamide.

20. A compound or a pharmaceutically acceptable salt thereof, wherein the compound is 4-(3-acrylamidophenyl)-2-ethyl-1H-indole-7-carboxamide.

* * * * *

UNITED STATES PATENT AND TRADEMARK OFFICE
CERTIFICATE OF CORRECTION

PATENT NO. : 9,567,339 B2
APPLICATION NO. : 14/315504
DATED : February 14, 2017
INVENTOR(S) : Bonafoux et al.

It is certified that error appears in the above-identified patent and that said Letters Patent is hereby corrected as shown below:

In the Claims

Claim 1, Column 515, Lines 49 and 50, replace "-C(O)CH=CHC(O)N(H)CH$_2$CH$_3$, -C(O)CH=CHCH$_2$N(CH$_3$)$_2$C(O)CH=CHC(O)OCH$_3$," with -- -C(O)CH=CHC(O)N(H)CH$_2$CH$_3$, -C(O)CH=CHCH$_2$N(CH$_3$)$_2$, -C(O)CH=CHC(O)OCH$_3$, --.

Signed and Sealed this
Thirtieth Day of May, 2017

Michelle K. Lee
*Director of the United States Patent and Trademark Office*